US012291529B2

(12) United States Patent
Huang et al.

(10) Patent No.: US 12,291,529 B2
(45) Date of Patent: May 6, 2025

(54) HETEROCYCLIC GLP-1 AGONISTS

(71) Applicant: Gasherbrum Bio, Inc., South San Francisco, CA (US)

(72) Inventors: Wei Huang, Shanghai (CN); Hui Lei, Shanghai (CN); Chunliang Lu, Shanghai (CN); Haizhen Zhang, Shanghai (CN)

(73) Assignee: Gasherbrum Bio, Inc., South San Francisco, CA (US)

( * ) Notice: Subject to any disclaimer, the term of this patent is extended or adjusted under 35 U.S.C. 154(b) by 0 days.

(21) Appl. No.: 18/762,532

(22) Filed: Jul. 2, 2024

(65) Prior Publication Data

US 2024/0376105 A1    Nov. 14, 2024

Related U.S. Application Data

(63) Continuation of application No. 18/628,545, filed on Apr. 5, 2024, which is a continuation of application No. PCT/CN2024/077096, filed on Feb. 9, 2024.

(30) Foreign Application Priority Data

Feb. 16, 2023  (WO) ................ PCT/CN2023/076495
Aug. 17, 2023  (WO) ................ PCT/CN2023/113565
Dec. 22, 2023  (WO) ................ PCT/CN2023/141034

(51) Int. Cl.
C07D 471/04        (2006.01)
A61K 31/437        (2006.01)

(52) U.S. Cl.
CPC .......... *C07D 471/04* (2013.01); *A61K 31/437* (2013.01)

(58) Field of Classification Search
CPC ........................... C07D 471/04; A61K 31/437
USPC ........................................ 546/120; 514/303
See application file for complete search history.

(56) References Cited

U.S. PATENT DOCUMENTS

| | | | |
|---|---|---|---|
| 10,858,356 | B2 | 12/2020 | Yoshino et al. |
| 11,492,365 | B2 | 11/2022 | Meng et al. |
| 2004/0009573 | A1 | 1/2004 | Strobel et al. |
| 2007/0015812 | A1 | 1/2007 | Boehringer et al. |
| 2009/0197863 | A1 | 8/2009 | Chu et al. |
| 2011/0190343 | A1 | 8/2011 | Gochin et al. |
| 2016/0141517 | A1 | 5/2016 | Yang |
| 2018/0092908 | A1 | 4/2018 | Stockwell et al. |
| 2019/0300526 | A1 | 10/2019 | Fan et al. |
| 2020/0017505 | A1 | 1/2020 | Maeba et al. |
| 2022/0213130 | A1 | 7/2022 | Meng et al. |
| 2023/0174565 | A1 | 6/2023 | Meng et al. |
| 2023/0032271 | A1 | 10/2023 | Meng et al. |
| 2023/0331732 | A1 | 10/2023 | Meng et al. |

FOREIGN PATENT DOCUMENTS

| | | |
|---|---|---|
| CN | 103421006 | 12/2013 |
| CN | 110325530 | 10/2019 |
| CN | 110804059 | 2/2020 |
| CN | 111217796 | 6/2020 |
| CN | 111217842 | 6/2020 |
| CN | 109790161 | 3/2022 |
| EP | 461079 | 12/1991 |
| EP | 3539948 | 9/2019 |
| EP | 3539950 | 9/2019 |
| JP | 08295646 | 11/1996 |
| JP | 2012223714 | 11/2012 |
| JP | 2012224760 | 11/2012 |
| JP | 2019099571 | 6/2019 |
| KR | 2013088577 | 8/2013 |
| TW | 201827426 A | 8/2018 |
| WO | WO-95/01961 | 1/1995 |
| WO | WO-97/32848 | 9/1997 |
| WO | WO-98/30569 | 7/1998 |
| WO | WO-99/01457 | 1/1999 |
| WO | WO-2001/003680 | 1/2001 |
| WO | WO-2002/046164 | 6/2002 |
| WO | WO-2002/046183 | 6/2002 |
| WO | WO-2002/096888 | 12/2002 |
| WO | WO-2003/000682 | 1/2003 |
| WO | WO-2004/026836 | 4/2004 |
| WO | WO-2004/107958 | 12/2004 |
| WO | WO-2005/037800 | 4/2005 |
| WO | WO-2005/040169 | 5/2005 |
| WO | WO-2005/066136 | 7/2005 |
| WO | WO-2005/112932 | 12/2005 |
| WO | WO-2005/121138 | 12/2005 |
| WO | WO-2006/024837 | 3/2006 |
| WO | WO-2006/034419 | 3/2006 |
| WO | WO-2006/083869 | 8/2006 |
| WO | WO-2006/111169 | 10/2006 |
| WO | WO-2007/054453 | 5/2007 |
| WO | WO-2007/091107 | 8/2007 |
| WO | WO-2008/014219 | 1/2008 |

(Continued)

OTHER PUBLICATIONS

Kawai et al., "Structural basis for GLP-1 receptor activation by LY3502970, an orally active nonpeptide agonist", Proceedings of the National Academy of Sciences of the United States of America (2020), 117(47), 29959-29967.

Finkbeiner et al.,"Phosphine Oxides from a Medicinal Chemist's Perspective: Physicochemical and in Vitro Parameters Relevant for Drug Discovery", Journal of Medicinal Chemistry (2020), 63(13), 7081-7107.

(Continued)

*Primary Examiner* — Charanjit Aulakh
(74) *Attorney, Agent, or Firm* — Sheppard Mullin Richter & Hampton LLP

(57) ABSTRACT

The present disclosure relates generally to GLP-1 agonists and pharmaceutical compositions comprising the same, as well as methods for treating a GLP-1 associated disease, disorder, or condition.

28 Claims, No Drawings

(56) References Cited

FOREIGN PATENT DOCUMENTS

| | | |
|---|---|---|
| WO | WO-2008/053341 | 5/2008 |
| WO | WO-2008/077597 | 7/2008 |
| WO | WO-2008/117061 | 10/2008 |
| WO | WO-2009/019505 | 2/2009 |
| WO | WO-2009/036275 | 3/2009 |
| WO | WO-2009/126691 | 10/2009 |
| WO | WO-2010/037050 | 4/2010 |
| WO | WO-2010/091176 | 8/2010 |
| WO | WO-2011/044181 | 4/2011 |
| WO | WO-2012/038411 | 3/2012 |
| WO | WO-2012/065065 | 5/2012 |
| WO | WO-2013/151975 | 10/2013 |
| WO | WO-2014/055634 | 4/2014 |
| WO | WO-2014/101120 | 7/2014 |
| WO | WO-2014/105666 | 7/2014 |
| WO | WO-2014/122067 | 8/2014 |
| WO | WO-2014/150331 | 9/2014 |
| WO | WO-2015/007669 | 1/2015 |
| WO | WO-2015/049624 | 4/2015 |
| WO | WO-2016/038045 | 3/2016 |
| WO | WO-2017/025491 | 2/2017 |
| WO | WO-2017/182983 | 10/2017 |
| WO | WO-2017/182984 | 10/2017 |
| WO | WO-2017/182986 | 10/2017 |
| WO | WO-2018/056453 | 3/2018 |
| WO | WO-2018/109607 | 6/2018 |
| WO | WO-2018/178947 | 10/2018 |
| WO | WO-2019/013311 | 1/2019 |
| WO | WO-2019/126424 | 6/2019 |
| WO | WO-2019/158731 | 8/2019 |
| WO | WO-2019/166951 | 9/2019 |
| WO | WO-2019/239319 | 12/2019 |
| WO | WO-2019/239371 | 12/2019 |
| WO | WO-2020/001321 | 1/2020 |
| WO | WO-2020/024232 | 1/2020 |
| WO | WO-2020/089453 | 5/2020 |
| WO | WO-2020/089455 | 5/2020 |
| WO | WO-2020/103815 | 5/2020 |
| WO | WO-2020/127208 | 6/2020 |
| WO | WO-2020/135513 | 7/2020 |
| WO | WO-2020/163236 | 8/2020 |
| WO | WO-2020/207474 | 10/2020 |
| WO | WO-2020/263695 | 12/2020 |
| WO | WO-2021/018023 | 2/2021 |
| WO | WO-2021/081207 | 4/2021 |
| WO | WO-2021/096284 | 5/2021 |
| WO | WO-2021/096304 | 5/2021 |
| WO | WO-2021/155841 | 8/2021 |
| WO | WO-2021/160127 | 8/2021 |
| WO | WO-2021/219019 | 11/2021 |
| WO | WO-2022/017338 | 1/2022 |
| WO | WO-2022/048665 | 3/2022 |
| WO | WO-2022/052958 | 3/2022 |
| WO | WO-2023/016546 | 2/2023 |
| WO | WO-2023/169456 | 9/2023 |

OTHER PUBLICATIONS

Huang et al., "Discovery of Brigatinib (AP26113), a Phosphine Oxide-Containing, Potent, Orally Active Inhibitor of Anaplastic Lymphoma Kinase", Journal of Medicinal Chemistry (2016), 59(10), 4948-4964.

Paternoster, et al. Dissecting the Physiology and Pathophysiology of Glucagon-Like Peptide-1. Frontiers in Endocrinology. Oct. 2018; vol. 9, Article 584. pp. 1-26.

Taing, et al. GLP-1 (28-36) amide, the Glucagon-like peptide-1 metabolite: friend, foe, or pharmacological folly? Drug Design, Development and Therapy 2014, 8, 677-688.

Montrose-Rafizadeh, et al. Pancreatic Glucagon-Like Peptide-1 Receptor Couples to Multiple G Proteins and Activates Mitogen-Activated Protein Kinase Pathways in Chinese Hamster Ovary Cells. Endocrinology 1999, 40(3), 1132-1140.

Tomas, et al. New Insights into Beta-Cell GLP-1 Receptor and cAMP Signaling. Journal of Molecular Biology. (2020) 432, 1347-1366.

Bavec, et al. Different role of intracellular loops of glucagon-like peptide-1 receptor in G-protein coupling. Regul Pept. 2003, 111:137-144.

Hallbrink, et al. Different domains in the third intracellular loop of the GLP-1 receptor are responsible for Galpha(s) and Galpha(i)/Galpha (o) activation. Biochim Biophys Acta. 2001, 1546:79-86.

Walsh, et al. Eating Disorders. in Harrison's Principles of Internal Medicine (McGraw-Hill Book Company, New York, 2005 Kasper, Dennis L., Harrison, Tinsley Randolph. Eds. pp. 430-433.

Ramos, et al. Designing drugs that combat kidney damage. Expert Opinion on Drug Discovery. (2015), 10(5), 541-556.

Nauck, et al. GLP-1 receptor agonists in type 1 diabetes: a MAGIC bullet? The Lancet Diabetes & Endocrinology. vol. 8, Issue 4, Apr. 2020, p. 262.

Petit-Demouliere, et. al. Forced swimming test in mice: a review of antidepressant activity. Psychopharmacology. 2005, 177, 245-255.

Miyamoto "Pharmacological treatment of schizophrenia: a critical review of the pharmacology and clinical effects of current and future therapeutic agents" Molecular Psychiatry (2012) 17, 1206-1227.

Marcotte, et al. Animal models of schizophrenia: a critical review. Psychiatry Neurosci. 2001; 26(5):395-410.

DeWeerdt. Parkinson's disease 4 Big Questions. Nature. vol. 538, Oct. 2016, S17.

Bergman et al. Safety, Tolerability, Pharmacokinetics, and Pharmacodynamics of a Liver-Targeting Acetyl-CoA Carbonxylase Inhibitor (PF-05221304): A Three-Part Randomized Phase 1 Study, Clinical Pharmacology in Drug Development, 2020, 9(4) 514-526 (with Supporting Information, Figure S1, 1 page).

International Search Report for PCT Patent Application No. PCT/CN2024/077096 dated May 7, 2024, 15 pgs.

Bolm et al. "Rhodium-Catalyzed Imination of Sulfoxides and Sulfides: Efficient Preparation of N-Unsubstituted Sulfoximines and Sulfilimines" Institute of Organic Chemistry, 2004, vol. 6, No. 8, pp. 1305-1307.

Frings, Marcus et al. "Sulfoximines from a Medicinal Chemist's Perspective: Physicochemical and in vitro Parameters Relevant for Drug Discovery" European Journal of Medicinal Chemistry, 126, 2017, pp. 225-245.

Graham, Mark et al. "Development and Scale-Up of an Improved Manufacturing Route to the ATR Inhibitor Ceralasertib" American Chemical Society, Organic Process Research & Development 2021, 25 (1), 14 pgs.

Lucking, U. et al. The Lab Oddity Prevails: Discovery of Pan-CDK Inhibitor (R)-S-Cyclopropyl-S-(4-{[4-{[(1R,2R)-2-hydroxy-1-methylpropyl]oxy}-5-(trifluoromethyl)pyrimidin-2-yl]amino}phenyl)sulfoximide (BAY 1000394) for the Treatment of Cancer, ChemMedChem, 2013, 8, pp. 1-20.

Ulrich Lucking "Sulfoximines in Medicinal Chemistry: Emerging Trends and Opportunities from the Drug Designer's Perspective" May 18, 2022, pp. 1-11.

Yu Han, "Application of Sulfoximines in medicinal chemistry from 2013 to 2020" European Journal of Medicinal Chemistry, vol. 209, Jan. 1, 2021, 1 pg.

Zenzola et al. "Transfer of Electrophilic NH Using Convenient Sources of Ammonia: Direct Synthesis of NH sulfoximines from Sulfoxides", Angewandte Chemie Int Ed (2016) 55, pp. 7203-7207.

HETEROCYCLIC GLP-1 AGONISTS

CROSS REFERENCE TO RELATED APPLICATIONS

This application is a continuation of U.S. application Ser. No. 18/628,545, filed Apr. 5, 2024, which is a continuation of International Patent Application Number PCT/CN2024/077096, filed Feb. 9, 2024, which claims the benefit of International Patent Application Number PCT/CN2023/076495, filed on Feb. 16, 2023, International Patent Application Number PCT/CN2023/113565, filed on Aug. 17, 2023, and International Patent Application Number PCT/CN2023/141034, filed Dec. 22, 2023, each of which is incorporated herein by reference in its entirety.

FIELD

This disclosure relates to GLP-1 agonists, pharmaceutical compositions, and methods of use thereof.

BACKGROUND

Incretin metabolic hormones, including glucagon-like peptide-1 (GLP-1) and glucose-dependent insulinotropic polypeptide (GIP), are important in the regulation of glucose homeostasis. Medicaments targeting this family of intestinal peptides, such as GLP-1 agonists, have been shown to suppress glucagon production, decrease gastric motility, and increase satiety.

Diabetes mellitus refers to a group of metabolic disorders characterized by persistent hyperglycemia. The most common form, type 2 diabetes mellitus (T2DM) is an acquired condition that accounts for more than 90% of diabetes cases. Typical onset occurs in obese or otherwise sedentary adults and begins with insulin resistance. Though lifestyle changes can be useful in management of this disorder, patients with T2DM may be required to take antidiabetic medications, including dipeptidyl peptidase-4 inhibitors, SGLT2 inhibitors, and sulfonylureas, among others.

In healthy individuals, the incretin hormones glucose-dependent insulinotropic polypeptide (GIP) and glucagon-like peptide 1 (GLP-1) provide tandem modulation of insulin secretory response to glucose ingestion. While this incretin effect is significantly diminished (if at all present) in cases of T2DM, GLP-1 retains insulinotropic properties, even as endocrine pancreatic response to GIP is effectively halted. As such, incretin mimetics and other GLP-1-based therapies can help stimulate insulin production in T2DM patients.

SUMMARY

The present application describes heterocyclic GLP-1 agonists, as well as pharmaceutical compositions comprising the compounds disclosed herein. Also provided are methods for treating GLP-1-associated diseases, disorders, and conditions.

In one aspect, provided are compounds of Formula I.

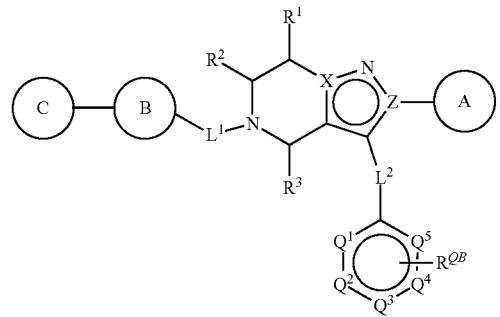

or a pharmaceutically acceptable salt, isotopically enriched analog, stereoisomer, mixture of stereoisomers, or prodrug thereof, wherein ring A, ring B, ring C, X, Z, $Q^1$, $Q^2$, $Q^3$, $Q^4$, $Q^5$, $L^1$, $L^2$, $R^1$, $R^2$, $R^3$, and $R^{QB}$ are each independently as defined herein.

This disclosure also provides pharmaceutical compositions comprising one or more compounds of Formula I, or a pharmaceutically acceptable salt, isotopically enriched analog, stereoisomer, mixture of stereoisomers, or prodrug thereof, and a pharmaceutically acceptable excipient.

Also provided herein are pharmaceutical compositions comprising a compound of Formula I, or a pharmaceutically acceptable salt, isotopically enriched analog, stereoisomer, mixture of stereoisomers, or prodrug thereof, and a pharmaceutically acceptable excipient.

Also provided herein are methods for treating type 2 diabetes mellitus in a patient in need thereof, the methods comprising administering to the patient a therapeutically effective amount of a compound of Formula I, or a pharmaceutically acceptable salt, isotopically enriched analog, stereoisomer, mixture of stereoisomers, or prodrug thereof, or a pharmaceutical composition thereof.

Also provided herein are methods for treating type 2 diabetes mellitus in a patient, the methods comprising administering to a patient identified or diagnosed as having type 2 diabetes mellitus a therapeutically effective amount of a compound of Formula I, or a pharmaceutically acceptable salt, isotopically enriched analog, stereoisomer, mixture of stereoisomers, or prodrug thereof, or a pharmaceutical composition thereof.

Also provided herein are methods for treating diabetes mellitus in a patient, the methods comprising determining that the patient has type 2 diabetes mellitus; and administering to the patient a therapeutically effective amount of a compound of Formula I, or a pharmaceutically acceptable salt, isotopically enriched analog, stereoisomer, mixture of stereoisomers, or prodrug thereof, or a pharmaceutical composition thereof. In some embodiments, the step of determining that the patient has type 2 diabetes mellitus includes performing an assay to determine the level of an analyte in a sample from the patient, wherein the analyte is selected from the group consisting of hemoglobin A1c (HbA1c), fasting plasma glucose, non-fasting plasma glucose, or any combination thereof. In some embodiments, the level of HbA1c is greater than or about 6.5%. In some embodiments, the level of fasting plasma glucose is greater than or about 126 mg/dL. In some embodiments, the level of non-fasting plasma glucose is greater than or about 200 mg/dL.

In some embodiments, the methods further comprise obtaining a sample from the patient. In some embodiments, the sample is a body fluid sample. In some embodiments, the patient is about 40 to about 70 years old and is overweight or obese. In some embodiments, the patient has a body mass index (BMI) greater than or about 22 kg/m$^2$. In some embodiments, the patient has a BMI greater than or about 30 kg/m$^2$.

In some embodiments, the methods for the treatment of type 2 diabetes mellitus comprise a reduction in fasting plasma glucose levels. In some embodiments, the fasting plasma glucose levels are reduced to about or below 100 mg/dL.

In some embodiments, the methods for the treatment of type 2 diabetes mellitus comprise a reduction in HbA1c levels. In some embodiments, the HbA1c levels are reduced to about or below 5.7%.

In some embodiments, the methods for the treatment of type 2 diabetes mellitus comprise a reduction in glucagon levels.

In some embodiments, the methods for the treatment of type 2 diabetes mellitus comprise an increase in insulin levels.

In some embodiments, the methods for the treatment of type 2 diabetes mellitus comprise a decrease in BMI. In some embodiments, the BMI is decreased to about or below 25 kg/m$^2$.

In some embodiments, the compound of Formula I, or a pharmaceutically acceptable salt, isotopically enriched analog, stereoisomer, mixture of stereoisomers, or prodrug thereof, or a pharmaceutical composition thereof, is administered orally.

In some embodiments, the methods of treatment for type 2 diabetes mellitus further comprise administering an additional therapy or therapeutic agent to the patient. In some embodiments, the additional therapy or therapeutic agent is selected from the group consisting of an antidiabetic agent, an anti-obesity agent, a GLP-1 receptor agonist, an agent to treat non-alcoholic steatohepatitis (NASH), anti-emetic agent, gastric electrical stimulation, dietary monitoring, physical activity, or any combinations thereof. In some embodiments, the antidiabetic agent is selected from the group consisting of a biguanide, a sulfonylurea, a glitazar, a thiazolidinedione, a dipeptidyl peptidase 4 (DPP-4) inhibitor, a meglitinide, a sodium-glucose linked transporter 2 (SGLT2) inhibitor, a glitazone, a GRP40 agonist, a glucose-dependent insulinotropic peptide (GIP), an insulin or insulin analogue, an alpha glucosidase inhibitor, a sodium-glucose linked transporter 1 (SGLT1) inhibitor, or any combinations thereof. In some embodiments, the biguanide is metformin. In some embodiments, the anti-obesity agent is selected from the group consisting of neuropeptide Y receptor type 2 (NPYR2) agonist, a NPYR1 or NPYR5 antagonist, a human proislet peptide (HIP), a cannabinoid receptor type 1 (CB1R) antagonist, a lipase inhibitor, a melanocortin receptor 4 agonist, a farnesoid X receptor (FXR) agonist, phentermine, zonisamide, a norepinephrine/dopamine reuptake inhibitor, a GDF-15 analog, an opioid receptor antagonist, a cholecystokinin agonist, a serotonergic agent, a methionine aminopeptidase 2 (MetAP2) inhibitor, diethylpropion, phendimetrazine, benzphetamine, a fibroblast growth factor receptor (FGFR) modulator, an AMP-activated protein kinase (AMPK) activator, or any combinations thereof. In some embodiments, the GLP-1 receptor agonist is selected from the group consisting of liraglutide, exenatide, dulaglutide, albiglutide, taspoglutide, lixisenatide, semaglutide, or any combinations thereof. In some embodiments, the agent to treat NASH is selected from the group consisting of an FXR agonist, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21) agonist, a niacin analogue, a leukotriene D4 (LTD4) receptor antagonist, an acetyl-CoA carboxylase (ACC) inhibitor, a ketohexokinase (KHK) inhibitor, an ileal bile acid transporter (IBAT) inhibitor, an apoptosis signal-regulating kinase 1 (ASK1) inhibitor, or any combinations thereof. In some embodiments, the compound of Formula I, or a pharmaceutically acceptable salt, isotopically enriched analog, stereoisomer, mixture of stereoisomers, or prodrug thereof, or a pharmaceutical composition thereof, and the additional therapeutic agent are administered as separate dosages sequentially in any order.

Also provided herein are methods for modulating insulin levels in a patient in need of such modulating, the method comprising administering to the patient an effective amount of a compound of Formula I, or a pharmaceutically acceptable salt, isotopically enriched analog, stereoisomer, mixture of stereoisomers, or prodrug thereof, or a pharmaceutical composition thereof. In some embodiments, the modulation results in an increase of insulin levels.

Also provided herein are methods for modulating glucose levels in a patient in need of such modulating, the method comprising administering to the patient an effective amount of a compound of Formula I, or a pharmaceutically acceptable salt, isotopically enriched analog, stereoisomer, mixture of stereoisomers, or prodrug thereof, or a pharmaceutical composition thereof. In some embodiments, the modulation results in a decrease of glucose levels.

Also provided herein are methods for treating a GLP-1 associated disease, disorder, or condition, the method comprising administering to a patient in need thereof an effective amount of a compound of Formula I, or a pharmaceutically acceptable salt, isotopically enriched analog, stereoisomer, mixture of stereoisomers, or prodrug thereof, or a pharmaceutical composition thereof. In some embodiments, the disease, disorder, or condition is selected from the group consisting of type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, Polycystic Ovary Syndrome (PCOS), or any combination thereof. In some embodiments, the disease, disorder, or condition is selected from the group consisting of type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof. In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DESCRIPTION

Before the present compounds and methods are described, it is to be understood that the disclosure is not limited to the methodologies, protocols, cell lines, assays, and reagents described, as these may vary. It is also to be understood that the terminology used herein is intended to describe embodiments of the present disclosure, and is in no way intended to limit the scope of the present disclosure as set forth in the appended claims.

Definitions

Provided herein are heterocyclic GLP-1 agonists for use in the management of T2DM and other conditions where activation of GLP-1 activity is useful.

Before the present compounds and methods are described, it is to be understood that the disclosure is not limited to the methodologies, protocols, cell lines, assays, and reagents described, as these may vary. It is also to be understood that the terminology used herein is intended to describe embodiments of the present disclosure, and is in no way intended to limit the scope of the present disclosure as set forth in the appended claims.

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%.

In certain other embodiments, the term "about" includes the indicated amount ±1%. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH ($CH_3$)$_2$), and tert-butyl (i.e., —C($CH_3$)$_3$), and "propyl" includes n-propyl (i.e., —($CH_2$)$_2$$CH_3$), and isopropyl (i.e., —CH($CH_3$)$_2$).

"Alkenyl" refers to an alkyl group containing at least one (e.g., 1-3, or 1) carbon-carbon double bond and having from 2 to 20 carbon atoms (i.e., $C_{2-20}$ alkenyl), 2 to 12 carbon atoms (i.e., $C_{2-12}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include, e.g., ethenyl, propenyl, butadienyl (including 1,2-butadienyl, and 1,3-butadienyl).

"Alkynyl" refers to an alkyl group containing at least one (e.g., 1-3, or 1) carbon-carbon triple bond and having from 2 to 20 carbon atoms (i.e., $C_{2-20}$ alkynyl), 2 to 12 carbon atoms (i.e., $C_{2-12}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively.

"Alkoxy" refers to the group "alkyl-O-". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Thioalkoxy" refers to the group "alkyl-S-".

"Haloalkyl" refers to an unbranched or branched alkyl group as defined above, wherein one or more (e.g., 1 to 6 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Haloalkoxy" refers to an alkoxy group as defined above, wherein one or more (e.g., 1 to 6, or 1 to 3) hydrogen atoms are replaced by a halogen.

"Hydroxyalkyl" refers to an alkyl group as defined above, wherein one or more (e.g., 1 to 6, or 1 to 3) hydrogen atoms are replaced by a hydroxy group.

"Cyanoalkyl" refers to an alkyl group as defined above, wherein one, or one or more (e.g., 1 to 6, or 1 to 3) hydrogen atoms are replaced by a hydroxy group.

"Alkylthio" refers to the group "alkyl-S-".

"Acyl" refers to a group —C(O)R, wherein $R^a$ is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(O)$NR^yR^z$ and an "N-amido" group which refers to the group —$NR^y$C(O)$R^z$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to the group —$NR^yR^z$ wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Amidino" refers to —C($NR^y$)($NR^z_2$), wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl, and anthryl. Aryl, however, does not encompass or overlap in any way with heteroaryl defined below. If one or more aryl groups are fused with a heteroaryl, the resulting ring system is heteroaryl regardless of point of attachment. If one or more aryl groups are fused with a heterocyclyl, the resulting ring system is heterocyclyl regardless of point of attachment. If one or more aryl groups are fused with a cycloalkyl, the resulting ring system is cycloalkyl regardless of point of attachment.

"Carbamoyl" refers to both an "O-carbamoyl" group which refers to the group —O—C(O)$NR^yR^z$ and an "N-carbamoyl" group which refers to the group —$NR^y$C(O)$OR^z$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl ester" or "ester" refer to both —OC(O)$R^x$ and —C(O)$OR^x$, wherein $R^x$ is alkyl, alkenyl, alkynyl, cycloalkyl, heterocyclyl, aryl, heteroalkyl, or heteroaryl; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{3-20}$ cycloalkyl), 3 to 14 ring carbon atoms (i.e., $C_{3-12}$ cycloalkyl), 3 to 12 ring carbon atoms (i.e., $C_{3-12}$ cycloalkyl), 3 to 10 ring carbon atoms (i.e., $C_3$-10 cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl, and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl, and the like.

Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Imino" refers to a group —C($NR^y$)$R^z$, wherein $R^y$ and $R^z$ are each independently hydrogen, alkyl, alkenyl, alkynyl, cycloalkyl, heterocyclyl, aryl, heteroalkyl, or heteroaryl; each of which may be optionally substituted, as defined herein.

"Halogen" or "halo" refers to atoms occupying group VIIA of the periodic table, such as fluoro, chloro, bromo, or iodo.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R$^a$ is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroalkylene" refers to a divalent heteroalkyl group. "Heteroalkylene" groups must have at least one carbon and at least one heteroatomic group within the chain. The term "heteroalkylene" includes unbranched or branched saturated chain having carbon and heteroatoms. By way of example, 1, 2, or 3 carbon atoms may be independently replaced with the same or different heteroatomic group.

Heteroatomic groups include, but are not limited to, —NR$^y$—, —O—, —S—, —S(O)—, —S(O)$_2$—, and the like, wherein R$^a$ is hydrogen, alkyl, alkenyl, alkynyl, cycloalkyl, heterocyclyl, aryl, heteroalkyl or heteroaryl; each of which may be optionally substituted, as defined herein. Examples of heteroalkylene groups include, e.g., —CH$_2$OCH$_2$—, —CH(CH$_3$)OCH$_2$—, —CH$_2$CH$_2$OCH$_2$—, —OCH$_2$—, —CH(CH$_3$)O—, —CH$_2$CH$_2$O—, —CH$_2$CH$_2$OCH$_2$CH$_2$OCH$_2$—, —CH$_2$CH$_2$OCH$_2$CH$_2$O—, —CH$_2$SCH$_2$—, —CH(CH$_3$)SCH$_2$—, —CH$_2$CH$_2$SCH$_2$—, —CH$_2$CH$_2$SCH$_2$CH$_2$SCH$_2$—, —SCH$_2$—, —CH(CH$_3$)S—, —CH$_2$CH$_2$S—, —CH$_2$CH$_2$SCH$_2$CH$_2$S—, —CH$_2$S(O)$_2$CH$_2$—, —CH(CH$_3$)S(O)$_2$CH$_2$—, —CH$_2$CH$_2$S(O)$_2$CH$_2$—, —CH$_2$CH$_2$S(O)$_2$CH$_2$CH$_2$OCH$_2$—, —CH$_2$NR$^y$CH$_2$—, —CH(CH$_3$)NR$^y$CH$_2$—, —CH$_2$CH$_2$NR$^y$CH$_2$—, —CH$_2$CH$_2$NR$^y$CH$_2$CH$_2$NR$^y$CH$_2$—, etc., where R$^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkylene includes 1 to 10 carbon atoms, 1 to 8 carbon atoms, or 1 to 4 carbon atoms; and 1 to 3 heteroatoms, 1 to 2 heteroatoms, or 1 heteroatom.

As used herein, the term "heteroalkylene" does not include groups such as amides or other functional groups having an oxo present on one or more carbon atoms.

"Heteroaryl" refers to an aromatic group having a single ring or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl, benzotriazolyl, benzo[4,6]imidazo[1,2-a]pyridyl, carbazolyl, cinnolinyl, dibenzofuranyl, dibenzothienyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, thienyl, triazolyl, tetrazolyl, and triazinyl. Examples of the fused-heteroaryl rings include, but are not limited to, benzo[d]thiazolyl, quinolinyl, isoquinolinyl, benzo[b]thienyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or partially unsaturated cyclic alkyl group, with one or more ring heteroatoms independently selected from nitrogen, oxygen, and sulfur. The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro, and may comprise one or more (e.g., 1 to 3) oxo (=O) or N-oxide (—O—) moieties. Any non-aromatic ring or fused ring system containing at least one heteroatom and one non-aromatic ring is considered a heterocyclyl, regardless of the attachment to the remainder of the molecule. For example, fused ring systems such as decahydroquinazolinyl, 1,2,3,4-tetrahydroquinazolinyl, and 5,6,7,8-tetrahydroquinazolinyl are heterocyclyl, regardless of the attachment (i.e., can be bound through a carbon atom or a heteroatom). Further, the term heterocyclyl is intended to encompass any non-aromatic ring containing at least one heteroatom, which ring may be fused to a cycloalkyl, an aryl, or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur, or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiomorpholinyl, thiamorpholinyl, 1-oxo-thiomorpholinyl, and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system. The term "heterocyclyl" also includes rings comprising the sulfoximine moiety of $R^{QB}$ (e.g., when $R^a$ and $R^b$ of $R^{QB}$ is fused to the ring comprising $Q^1$-$Q^5$, e.g., when $R^a$ and $R^{QA}$, or R and $R^{QA}$, form a ring), such as, but not limited to, 3,4-dihydro-1$\lambda^6$,2-thiazine 1-oxide, 1$\lambda^6$,2-thiazine 1-oxide, 4,5-dihydro-3H-1$\lambda^6$-isothiazole 1-oxide, 1-(imino)tetrahydro-1H-1$\lambda^6$-thiophene 1-oxide, 4,5-dihydro-3H-1$\lambda^6$,2-thiazepine 1-oxide, and the like. See, e.g., Cram, et. al., *J. Org. Chem.*, 1973, 38(1), 20-26.

"Sulfonyl" refers to the group $—S(O)_2R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl, and toluenesulfonyl.

"Alkylsulfonyl" refers to the group $—S(O)_2R$, where R is alkyl.

"Alkylsulfinyl" refers to the group $—S(O)R$, where R is alkyl.

The terms "optional" or "optionally" means that the subsequently described event or circumstance may or may not occur, and that the description includes instances where said event or circumstance occurs and instances in which it does not. Also, the term "optionally substituted" refers to any one or more (e.g., 1 to 5, or 1 to 3) hydrogen atoms on the designated atom or group may or may not be replaced by a moiety other than hydrogen.

As used herein, the term "compound," is meant to include any or all stereoisomers, geometric isomers, tautomers, and isotopically enriched analogs (e.g., deuterated analogs) of the structures depicted.

Compounds herein identified by name or structure as one particular tautomeric form are intended to include other tautomeric forms unless otherwise specified.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number.

Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$ $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^3H$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life, reduced dosage requirements, and/or an improvement in therapeutic index. An $^{18}F$, $^3H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, aluminum, ammonium, calcium, and magnesium salts. Salts derived from organic bases include, but are not limited to, salts of $NH_3$, or primary, secondary, tertiary amines, such as salts derived from a N-containing heterocycle, a N-containing heteroaryl, or derived from an amine of formula $N(R^N)_3$ (e.g., $HN^+(R^N)_3$ or $(alkyl)N^+(R^N)_3$) where each $R^N$ is independently hydrogen, alkyl, alkenyl, alkynyl, haloalkyl, cycloalkyl, heterocyclyl, aryl, or heteroaryl, wherein each is optionally substituted, such as by one or more (e.g., 1-5 or 1-3) substituents (e.g., halo, cyano, hydroxy, amino, alkyl, alkenyl, alkynyl, haloalkyl, alkoxy, or haloalkoxy).

Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. In some embodiments, the one or more substituents include, but are not limited to, alkyl, alkenyl, alkynyl, alkoxy, alkoxyalkyl, acyl, amino, amido, amidino, aryl, azido, carbamoyl, carboxyl, carboxyl ester, cyano, cycloalkyl, cycloalkylalkyl, guanidino, halo, haloalkyl, hydroxyalkyl, haloalkoxy, haloalkoxyalkyl, heteroalkyl, heteroaryl, heterocyclyl, hydroxy, hydrazino, imino, imido, oxo, nitro, sulfinyl, sulfonic acid, sulfonyl, thiocyanate, thiol, thione, or combinations thereof.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms).

Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

As used herein, when a ring is described as being "aromatic," it means the ring has a continuous, delocalized π-electron system. Typically, the number of out of plane π-electrons corresponds to the Hückel rule (4n+2). Examples of such rings include: benzene, pyridine, pyrimidine, pyrazine, pyridazine, pyridone, pyrrole, pyrazole, oxazole, thiazole, isoxazole, isothiazole, and the like. When a ring system comprising at least two rings is described as "aromatic," it means the ring system comprises one or more aromatic ring(s). Accordingly, when a ring system comprising at least two rings is described as "non-aromatic," none of the constituent rings of the ring system is aromatic.

As used herein, when a ring is described as being "partially unsaturated," it means the ring has one or more additional degrees of unsaturation (in addition to the degree of unsaturation attributed to the ring itself; e.g., one or more double bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like. When a ring system comprising at least two rings is described as "partially unsaturated," it means the ring system comprises one or more partially unsaturated ring(s), provided that none of the constituent rings of the ring system is aromatic.

As used herein, the term "compound," is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the disclosure, and the naming of the compounds does not exclude any tautomer.

The term "GLP-1R" or "GLP-1 receptor" as used herein is meant to include, without limitation, nucleic acids, polynucleotides, oligonucleotides, sense and antisense polynucleotide strands, complementary sequences, peptides, polypeptides, proteins, homologous, and/or orthologous GLP-1R molecules, isoforms, precursors, mutants, variants, derivatives, splice variants, alleles, different species, and active fragments thereof.

The term "GLP-1 associated disease" as used herein is meant to include, without limitation, all those diseases, disorders, or conditions in which modulating glucagon-like peptide-1 (GLP-1) receptor signaling can alter the pathology and/or symptoms and/or progression of the disease, disorder, or condition.

The term "GLP-1 agonist" or "GLP-1 RA" as used herein refers to an agonist of the glucagon-like peptide-1 (GLP-1) receptor. GLP-1 RAs enhance glucose-dependent insulin secretion; suppress inappropriately elevated glucagon levels, both in fasting and postprandial states; and slow gastric emptying. Karla et al., Glucagon-like peptide-1 receptor agonists in the treatment of type 2 diabetes: Past, present, and future, Indian J Endocrinol Metab. 2016 Mar-Apr; 20(2): 254-267. GLP-1 RAs have been shown to treat type 2 diabetes. Examples of GLP-1 RAs include, but are not limited to, albiglutide (Tanzeum®), dulaglutide (LY2189265, Trulicity®), efpeglenatide, exenatide (Byetta®, Bydureon®, Exendin-4), liraglutide (Victoza®, NN2211), lixisenatide (Lyxumia®), semaglutide (Ozempic®), tirzepatide, ZP2929, NNC0113-0987, BPI-3016, and TT401.

The term "pharmaceutically acceptable" as used herein indicates that the compound, or salt or composition thereof is compatible chemically and/or toxicologically with the other ingredients comprising a formulation and/or the subject being treated therewith.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula I, or a pharmaceutically acceptable salt or solvate thereof) being administered which will relieve to some extent one or more of the symptoms of the disease or condition being treated, and can include curing the disease. "Curing" means that the symptoms of active disease are eliminated.

The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, F L, 2009.

The term "pharmaceutical composition" refers to a mixture of a compound of Formula I, or a pharmaceutically acceptable salt or solvate thereof as provided herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "preventing," as used herein, is the prevention of the onset, recurrence or spread, in whole or in part, of the disease or condition as described herein, or a symptom thereof.

The terms "subject," "patient," or "individual," as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the subject is a human. In some embodiments, the subject has experienced and/or exhibited at least one symptom of the disease, disorder, or condition to be treated and/or prevented.

The terms "treatment regimen" and "dosing regimen" are used interchangeably to refer to the dose and timing of administration of each therapeutic agent in a combination.

The term "pharmaceutical combination," as used herein, refers to a pharmaceutical treatment resulting from the mixing or combining of more than one active ingredient and includes both fixed and non-fixed combinations of the active ingredients.

The term "combination therapy" as used herein refers to a dosing regimen of two different therapeutically active agents (i.e., the components or combination partners of the combination), wherein the therapeutically active agents are administered together or separately in a manner prescribed by a medical care taker or according to a regulatory agency as defined herein.

The term "modulate," "modulating," or "modulation," as used herein, refers to a regulation or an adjustment (e.g., increase or decrease) and can include, for example agonism, partial agonism or antagonism.

Compounds

Provided herein are compounds of Formula I:

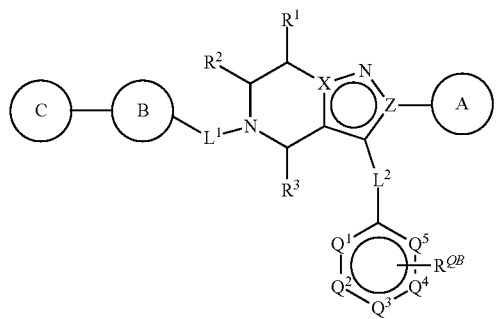

I or a pharmaceutically acceptable salt, isotopically enriched analog, stereoisomer, mixture of stereoisomers, or prodrug thereof, wherein ring A, ring B, ring C, X, Z, $Q^1$, $Q^2$, $Q^3$, $Q^4$, $Q^5$, $L^1$, $L^2$, $R^1$, $R^2$, $R^3$, and $R^{QB}$ are each independently as defined herein.

In one aspect, provided herein are compounds of Formula I:

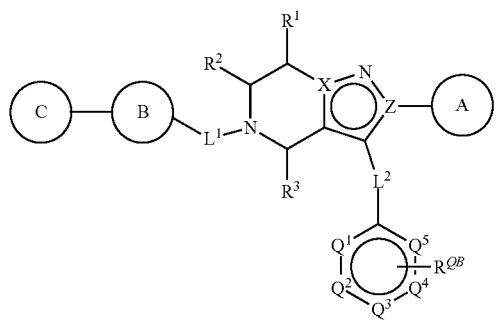

I or a pharmaceutically acceptable salt, isotopically enriched analog, stereoisomer, mixture of stereoisomers, or prodrug thereof, wherein:

X is C and Z is N, or X is N and Z is C;

$Q^1$ and $Q^5$ are each independently N or $CR^{QA}$; and $Q^2$, $Q^3$, and $Q^4$ are each independently N, $CR^{QA}$, or $CR^{QB}$, provided that at least one of $Q^2$, $Q^3$, and $Q^4$ is $CR^{QB}$; or $Q^1$ is a bond; and $Q^2$, $Q^3$, $Q^4$, and $Q^5$ are each independently O, S, N, NH, $NR^c$, $CR^{QA}$, or $CR^{QB}$, provided that at least one of $Q^2$, $Q^3$, $Q^4$, and $Q^5$ is $CR^{QB}$;

provided that the ring including $Q^1$-$Q^5$ is aromatic;

$R^{QB}$ is —S(O)(=$NR^a$)$R^b$, —($CR^iR^j$)$_n$—S(O)(=$NR^a$)$R^b$, —N=S(O)($R^{1a}$)$R^b$, or —O—($CR^iR^j$)$_n$—S(O)(=$NR^a$)$R^b$;

$R^{1a}$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

n is 1, 2, 3, 4, 5, or 6;

each $R^i$ is independently hydrogen, halo, or $C_{1-6}$ alkyl;

or $R^a$ and $R^i$, or $R^b$ and $R^i$, taken together with the atoms to which each is attached form a 5-8 membered heterocyclyl, wherein said heterocyclyl is optionally substituted with 1-3 independently selected $C_{1-6}$ alkyl;

each $R^j$ is independently hydrogen, halo, or $C_{1-6}$ alkyl;

or one $R^i$ and one $R^j$, taken together with the atom(s) to which each is attached, form a $C_{3-6}$ cycloalkyl, wherein said cycloalkyl is optionally substituted with 1-3 independently selected $C_{1-6}$ alkyl;

or one $R^i$ and one $R^j$ on adjacent carbon atoms taken together with the atom(s) to which each is attached form an alkene, wherein said alkene is optionally substituted with 1-3 independently selected $C_{1-6}$ alkyl;

each $R^{QA}$ is independently hydrogen, halo, cyano, hydroxy, —$NR^cR^d$, —C(O)$NR^cR^d$, —S(O)$_{0-2}R^e$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —C(O)($C_{1-6}$ alkyl), $C_{6-10}$ aryl optionally substituted with 1-3 independently selected —C(O)($C_{1-6}$ alkyl), and 5-10 membered heteroaryl optionally substituted with 1-6 independently selected $R^g$;

or two $R^{QA}$ on adjacent carbon atoms, taken together with the atom to which each is attached form a 5-8 membered heterocyclyl, wherein said ring is optionally substituted with 1-2 independently selected $R^h$;

or $R^a$ or $R^b$ and an adjacent $R^{QA}$ are taken together with the atom to which each is attached to form a 5-8 membered heterocyclyl, wherein said heterocyclyl is optionally substituted with 1-2 independently selected $R^h$.

$L^2$ is $C_{6-10}$ aryl optionally substituted with 1-2 independently selected $R^h$, 5-10 membered heteroaryl optionally substituted with 1-2 independently selected $R^h$

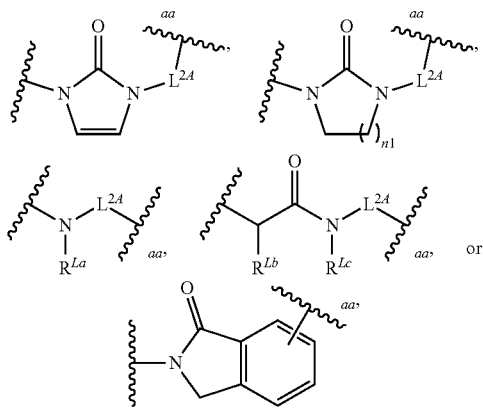

wherein aa represents the point of attachment to the ring containing $Q^1$-$Q^5$;

n1 is 1, 2, or 3;
$L^{2A}$ is a bond or $C_{1-10}$ alkylene;
$R^{La}$ is hydrogen, $C_{1-6}$ alkyl, or —C(O)($C_{1-6}$ alkyl);
each of $R^{Lb}$ and $R^{Lc}$ is independently hydrogen or $C_{1-6}$ alkyl;
Ring A is $C_{6-10}$ aryl, $C_{s7}$ cycloalkyl, 5-7 membered heterocyclyl, or 5-10 membered heteroaryl, each of which is optionally substituted with 1-5 independently selected $R^A$;
each $R^A$ is independently halo, $C_{1-6}$ alkyl, $C_{1-6}$ haloalkyl, $C_{1-6}$ alkoxy, or $C_{3-6}$ cycloalkyl;
$R^1$, $R^2$, and $R^3$ are each independently hydrogen or $C_{1-6}$ alkyl optionally substituted with 1-6 substituents independently selected from the group consisting of halo, hydroxy, and $C_{1-6}$ alkoxy;
$L^1$ is —C(O)—, —CH$_2$—, —CH($C_{1-6}$ alkyl)-, or —S(O)$_2$—;
Ring B is a 5,6-fused heteroaryl having from 5 to 8 carbon atoms and from 1 to 3 heteroatoms independently selected from O, S, and N, wherein Ring B is substituted with $R^8$ and optionally substituted with 1 to 4 substituents independently selected from halo, oxo, and $C_{1-6}$ alkyl;
$R^8$ is phenyl, 5-6 membered heteroaryl, or

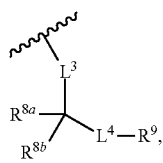

wherein the phenyl or 5-6 membered heteroaryl are substituted with $R^{8c}$, and are optionally further substituted with 1-3 independently selected $R^h$.
$L^3$ is a bond or $C_{1-3}$ alkylene;
$L^4$ is a bond or $C_{1-5}$ alkylene;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or
$R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;
each $R^{8c}$ is independently —C(O)OH, —S(O)$_2$OH, —S(O)$_2$NH$_2$, —$L^5$-$C_{1-6}$ alkyl, —$L^5$-$C_{3-6}$ cycloalkyl, —$L^5$-$C_{6-10}$ aryl, —$L^5$-5-6 membered heterocyclyl, —$L^5$-(5-6 membered heteroaryl), wherein each is optionally substituted with 1-6 substituents independently selected from the group consisting of hydroxy, halo, and $C_{1-6}$ alkoxy;
each $L^5$ is independently —C(O)—, —C(O)O—, —OC(O)—, —S(O)$_{1-2}$—, —S(O)$_2$O—, —S(O)$_2$NH—, or —NHS(O)$_2$—;
$R^9$ is —C(O)O$R^{9a}$, —C(O)N$R^{9a}R^{9b}$, 5-6 membered heteroaryl optionally substituted with 1-3 independently selected $R^{9c}$, 4-6 membered heterocyclyl optionally substituted with 1-3 independently selected $R^{9c}$, or;

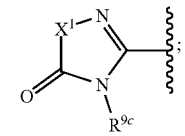

$X^1$ is O or S;
$R^{9a}$ is hydrogen or $C_{1-6}$ alkyl;
$R^{9b}$ is hydrogen, $C_{1-6}$ alkyl, —C(O)($C_{1-6}$ alkyl), —S(O)$_{0-2}$($C_{1-6}$ alkyl), or cyano;
each $R^{9c}$ is independently hydrogen, oxo, $C_{1-6}$ alkyl optionally substituted with 1-6 independently selected halo and $C_{1-6}$ alkoxy, or —C(O)($C_{1-6}$ alkyl);
Ring C is 3-12 membered heterocyclyl, $C_{3-15}$ cycloalkyl, or 5-10 membered heteroaryl, each of which is optionally substituted with 1-3 $R^{Ca}$;
each $R^{Ca}$ is independently halo, cyano, $C_{1-6}$ alkyl, $C_{1-6}$ haloalkyl, $C_{1-6}$ alkoxy, or $NR^cR^d$;
or a pair of $R^{Ca}$ on the same or different ring atoms, taken together with the ring atom(s) to which each is attached, forms a carbocyclic ring including 3-8 ring atoms;
each $R^c$ and $R^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;
$R^e$ is hydrogen, $C_{1-6}$ alkyl, or $C_{1-6}$ haloalkyl;
each $R^f$ is independently halo, hydroxy, —$NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;
each $R^g$ is independently $C_{1-6}$ alkyl, $C_{1-6}$ alkoxy, —$NR^cR^d$, or 3 to 12 membered heterocyclyl optionally substituted with one or more substituents each independently selected from the group consisting of $C_{1-6}$ alkyl and —C(O)$C_{1-6}$ alkyl; and each $R^h$ is independently halo, cyano, hydroxy, $C_{1-6}$ alkyl, $C_{1-6}$ haloalkyl, —$NH_2$, —NH($C_{1-3}$ alkyl), —N($C_{1-3}$ alkyl)$_2$, $C_{1-3}$ alkoxy, or $C_{1-3}$ haloalkoxy.

In one aspect, provided herein are compounds of Formula I:

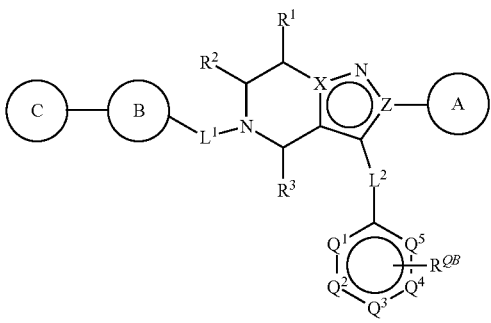

or a pharmaceutically acceptable salt, isotopically enriched analog, stereoisomer, mixture of stereoisomers, or prodrug thereof, wherein:

X is C and Z is N, or X is N and Z is C;

$Q^1$ and $Q^1$ are each independently N or $CR^{QA}$; and $Q^2$, $Q^3$, and $Q^4$ are each independently N, $CR^{QA}$, or $CR^{QB}$, provided that at least one of $Q^2$, $Q^3$, and $Q^4$ is $CR^{QB}$; or $Q^1$ is a bond; and $Q^2$, $Q^3$, $Q^4$, and $Q^5$ are each independently O, S, N, NH, $NR^c$, $CR^{QA}$, or $CR^{QB}$, provided that at least one of $Q^2$, $Q^3$, $Q^4$, and $Q^5$ is $CR^{QB}$;

provided that the ring including $Q^1$-$Q^5$ is aromatic;

$R^{QB}$ is —S(O)(=$NR^a$)$R^b$ or —(C$R^iR^j$)$_n$—S(O)(=$NR^a$)$R^b$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

n is 1, 2, 3, 4, 5, or 6;

each $R^i$ is independently hydrogen, halo, or $C_{1-6}$ alkyl;

or $R^a$ and $R^i$, or $R^b$ and $R^j$, taken together with the atoms to which each is attached form a 5-8 membered heterocyclyl, wherein said heterocyclyl is optionally substituted with 1-3 independently selected $C_{1-6}$ alkyl;

each $R^j$ is independently hydrogen, halo, or $C_{1-6}$ alkyl;

or one $R^i$ and one $R^j$, taken together with the atom(s) to which each is attached, form a $C_{3-6}$ cycloalkyl, wherein said cycloalkyl is optionally substituted with 1-3 independently selected $C_{1-6}$ alkyl;

each $R^{QA}$ is independently hydrogen, halo, cyano, hydroxy, —$NR^cR^d$, —C(O)$NR^cR^d$, —S(O)$_{0-2}$R, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —C(O)($C_{1-6}$ alkyl), $C_{6-10}$ aryl optionally substituted with 1-3 independently selected —C(O)($C_{1-6}$ alkyl), and 5-10 membered heteroaryl optionally substituted with 1-6 independently selected $R^g$;

or two $R^{QA}$ on adjacent carbon atoms, taken together with the atom to which each is attached form a 5-8 membered heterocyclyl, wherein said ring is optionally substituted with 1-2 independently selected $R^h$;

or $R^a$ or R and an adjacent $R^{QA}$ are taken together with the atom to which each is attached to form a 5-8 membered heterocyclyl, wherein said heterocyclyl is optionally substituted with 1-2 independently selected $R^h$;

$L^2$ is $C_{6-10}$ aryl optionally substituted with 1-2 independently selected $R^h$, 5-10 membered heteroaryl optionally substituted with 1-2 independently selected $R^h$

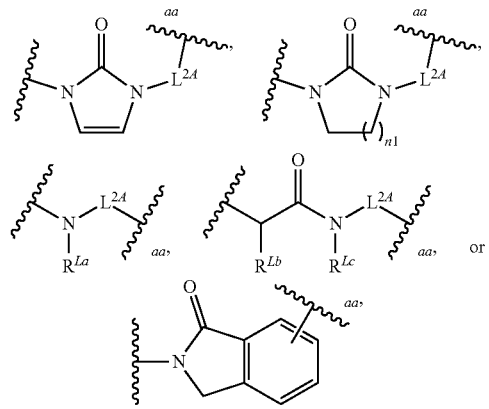

wherein aa represents the point of attachment to the ring containing $Q^1$-$Q^5$;

n1 is 1, 2, or 3;

$L^{2A}$ is a bond or $C_{1-10}$ alkylene;

$R^{La}$ is hydrogen, $C_{1-6}$ alkyl, or —C(O)($C_{1-6}$ alkyl);

each of $R^{Lb}$ and $R^{Lc}$ is independently hydrogen or $C_{1-6}$ alkyl;

Ring A is $C_{6-10}$ aryl, $C_{5-7}$ cycloalkyl, 5-7 membered heterocyclyl, or 5-10 membered heteroaryl, each of which is optionally substituted with 1-5 independently selected RA;

each $R^A$ is independently halo, $C_{1-6}$ alkyl, $C_{1-6}$ haloalkyl, $C_{1-6}$ alkoxy, or $C_{3-6}$ cycloalkyl;

$R^1$, $R^2$, and $R^3$ are each independently hydrogen or $C_{1-6}$ alkyl optionally substituted with 1-6 substituents independently selected from the group consisting of halo, hydroxy, and $C_{1-6}$ alkoxy;

$L^1$ is —C(O)—, —$CH_2$—, —CH($C_{1-6}$ alkyl)-, or —S(O)$_2$—;

Ring B is a 5,6-fused heteroaryl having from 5 to 8 carbon atoms and from 1 to 3 heteroatoms independently selected from O, S, and N, wherein Ring B is substituted with $R^8$ and optionally substituted with 1 to 4 substituents independently selected from halo, oxo, and $C_{1-6}$ alkyl;

$R^8$ is phenyl, 5-6 membered heteroaryl, or

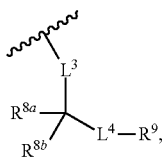

wherein the phenyl or 5-6 membered heteroaryl are substituted with $R^{8c}$, and are optionally further substituted with 1-3 independently selected $R^h$;

$L^3$ is a bond or $C_{1-3}$ alkylene;

$L^4$ is a bond or $C_{1-5}$ alkylene;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;

each $R^{8c}$ is independently —C(O)OH, —S(O)$_2$OH, —S(O)$_2$NH$_2$, —$L^5$-$C_{1-6}$ alkyl, —$L^5$-$C_{3-6}$ cycloalkyl, —$L^5$-$C_{6-10}$ aryl, —$L^5$-5-6 membered heterocyclyl, —$L^5$-(5-6 membered heteroaryl), wherein each is optionally substituted with 1-6 substituents independently selected from the group consisting of hydroxy, halo, and $C_{1-6}$ alkoxy;

each $L^5$ is independently —C(O)—, —C(O)O—, —OC(O)—, —S(O)$_{1-2}$—, —S(O)$_2$O—, —S(O)$_2$NH—, or —NHS(O)$_2$—;

$R^9$ is —C(O)OR$^{9a}$, —C(O)NR$^{9a}$R$^{9b}$, 5-6 membered heteroaryl optionally substituted with 1-3 independently selected $R^{9c}$, 4-6 membered heterocyclyl optionally substituted with 1-3 independently selected $R^{9c}$, or

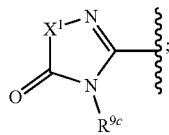

$X^1$ is O or S;

$R^{9a}$ is hydrogen or $C_{1-6}$ alkyl;

$R^{9b}$ is hydrogen, $C_{1-6}$ alkyl, —C(O)($C_{1-6}$ alkyl), —S(O)$_{0-2}$($C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or —C(O)($C_{1-6}$ alkyl);

Ring C is 3-12 membered heterocyclyl, $C_{3-15}$ cycloalkyl, or 5-10 membered heteroaryl, each of which is optionally substituted with 1-3 $R^{Ca}$;

each $R^{Ca}$ is independently halo, cyano, $C_{1-6}$ alkyl, $C_{1-6}$ haloalkyl, $C_{1-6}$ alkoxy, or NR$^c$R$^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;

$R^e$ is hydrogen, $C_{1-6}$ alkyl, or $C_{1-6}$ haloalkyl;

each $R^f$ is independently halo, hydroxy, —NR$^c$R$^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, —NR$^c$R$^d$, or 3 to 12 membered heterocyclyl optionally substituted with one or more substituents each independently selected from the group consisting of $C_{1-6}$ alkyl and —C(O)$C_{1-6}$ alkyl; and each $R^h$ is independently halo, cyano, hydroxy, $C_{1-6}$ alkyl, $C_{1-6}$ haloalkyl, —NH$_2$, —NH($C_{1-3}$ alkyl), —N($C_{1-3}$ alkyl)$_2$, $C_{1-3}$ alkoxy, or $C_{1-3}$ haloalkoxy.

In one aspect, provided herein are compounds of Formula I:

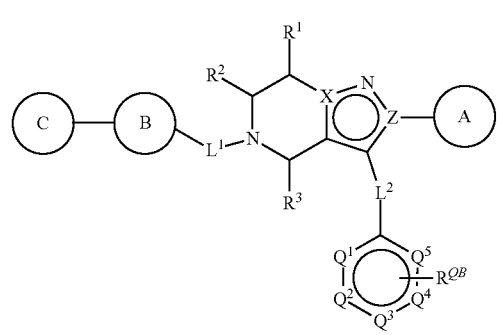

or a pharmaceutically acceptable salt or solvate thereof, wherein:

X is C and Z is N, or X is N and Z is C;

$Q^1$ and $Q^1$ are each independently N or CR$^{QA}$; and $Q^2$, $Q^3$, and $Q^4$ are each independently N, CR$^{QA}$, or CR$^{QB}$, provided that at least one of $Q^2$, $Q^3$, and $Q^4$ is CR$^{QB}$; or $Q^1$ is a bond; and $Q^2$, $Q^3$, $Q^4$, and $Q^5$ are each independently O, S, N, NH, NR$^c$, CR$^{QA}$, or CR$^{QB}$, provided that at least one of $Q^2$, $Q^3$, $Q^4$, and $Q^5$ is CR$^{QB}$;

provided that the ring including $Q^1$-$Q^5$ is aromatic;

$R^{QB}$ is —S(O)(=NR$^a$)R$^b$ or —(CR$^i$R$^j$)$_n$—S(O)(=NR$^a$)R$^b$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said ring is optionally substituted with 1-3 independently selected $C_{1-6}$ alkyl;

n is 1, 2, 3, 4, 5, or 6;

each $R^i$ is independently hydrogen, halo, or $C_{1-6}$ alkyl;

or $R^a$ and $R^i$, or $R^b$ and $R^j$, taken together with the atoms to which each is attached form a 5-8 membered heterocyclyl, wherein said ring is optionally substituted with 1-3 independently selected $C_{1-6}$ alkyl;

each $R^j$ is independently hydrogen, halo, or $C_{1-6}$ alkyl;

each $R^{QA}$ is independently hydrogen, halo, cyano, hydroxy, $-NR^cR^d$, $-C(O)NR^cR^d$, $-S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and $-C(O)(C_{1-6}$ alkyl), $C_{6-10}$ aryl optionally substituted with 1-3 independently selected $-C(O)(C_{1-6}$ alkyl), and 5-10 membered heteroaryl optionally substituted with 1-6 independently selected $R^g$;

or two $R^{QA}$ on adjacent carbon atoms, taken together with the atom to which each is attached form a 5-8 membered heterocyclyl, wherein said ring is optionally substituted with 1-2 independently selected $R^h$;

or $R^a$ or $R^b$ and an adjacent $R^{QA}$ are taken together with the atom to which each is attached to form a 5-8 membered heterocyclyl, wherein said ring is optionally substituted with 1-2 independently selected $R^h$;

$L^2$ is $C_{6-10}$ aryl optionally substituted with 1-2 independently selected $R^h$, 5-10 membered heteroaryl optionally substituted with 1-2 independently selected $R^h$

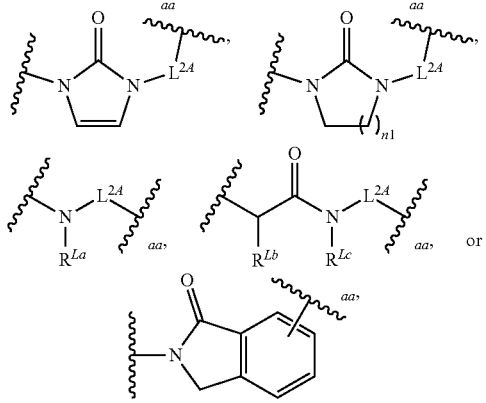

wherein aa represents the point of attachment to the ring containing $Q^1$-$Q^5$;

n1 is 1, 2, or 3;

$L^{2A}$ is a bond or $C_{1-10}$ alkylene;

$R^{La}$ is hydrogen, $C_{1-6}$ alkyl, or $-C(O)(C_{1-6}$ alkyl);

each of $R^{Lb}$ and $R^{Lc}$ is independently hydrogen or $C_{1-6}$ alkyl;

Ring A is $C_{6-10}$ aryl, $C_{5-7}$ cycloalkyl, 5-7 membered heterocyclyl, or 5-10 membered heteroaryl, each of which is optionally substituted with 1-5 independently selected $R^A$;

each $R^A$ is independently halo, $C_{1-6}$ alkyl, $C_{1-6}$ haloalkyl, $C_{1-6}$ alkoxy, or $C_{3-6}$ cycloalkyl;

$R^1$, $R^2$, and $R^3$ are each independently hydrogen or $C_{1-6}$ alkyl optionally substituted with 1-6 substituents independently selected from the group consisting of halo, hydroxy, and $C_{1-6}$ alkoxy;

$L^1$ is $-C(O)-$, $-CH_2-$, $-CH(C_{1-6}$ alkyl)-, or $-S(O)_2-$;

Ring B is a 5,6 fused heteroaryl having from 5 to 8 carbon atoms and from 1 to 3 heteroatoms independently selected from O, S, and N, wherein Ring B is substituted with $R^8$ and optionally substituted with 1 to 4 substituents independently selected from halo, oxo, and $C_{1-6}$ alkyl;

$R^8$ is phenyl, 5-6 membered heteroaryl, or

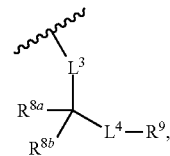

wherein the phenyl or 5-6 membered heteroaryl are substituted with $R^{8c}$ and are optionally further substituted with 1-3 independently selected $R^h$.

$L^3$ is a bond or $C_{1-3}$ alkylene;

$L^4$ is a bond or $C_{1-5}$ alkylene;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;

each $R^{8c}$ is independently $-C(O)OH$, $-S(O)_2OH$, $-S(O)_2NH_2$, $-L^5$-$C_{1-6}$ alkyl, $-L^5$-$C_{3-6}$ cycloalkyl, $-L^5$-$C_{6-10}$ aryl, $-L^5$-5-6 membered heterocyclyl, $-L^5$-(5-6 membered heteroaryl), wherein each is optionally substituted with 1-6 substituents independently selected from the group consisting of hydroxy, halo, and $C_{1-6}$ alkoxy;

each $L^5$ is independently $-C(O)-$, $-C(O)O-$, $-OC(O)-$, $-S(O)_{1-2}-$, $-S(O)_2O-$, $-S(O)_2NH-$, or $-NHS(O)_2-$;

$R^9$ is $-C(O)OR^{9a}$, $-C(O)NR^{9a}R^{9b}$, 5-6 membered heteroaryl optionally substituted with 1-3 independently selected $R^{9c}$, or

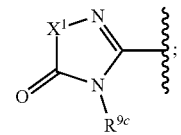

$X^1$ is O or S;

$R^{9a}$ is hydrogen or $C_{1-6}$ alkyl;

$R^{9b}$ is hydrogen, $C_{1-6}$ alkyl, $-C(O)(C_{1-6}$ alkyl), $-S(O)_{0-2}(C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or —C(O)($C_{1-6}$ alkyl);

Ring C is 3-12 membered heterocyclyl, $C_{3-15}$ cycloalkyl, or 5-10 membered heteroaryl, each of which is optionally substituted with 1-3 $R^{Ca}$;

each $R^{Ca}$ is independently halo, cyano, $C_{1-6}$ alkyl, $C_{1-6}$ haloalkyl, $C_{1-6}$ alkoxy, or $NR^cR^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;

$R^e$ is hydrogen, $C_{1-6}$ alkyl, or $C_{1-6}$ haloalkyl;

each $R^f$ is independently halo, hydroxy, $-NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, $-NR^cR^d$, or 3 to 12 membered heterocyclyl optionally substituted with one or more substituents each independently selected from the group consisting of $C_{1-6}$ alkyl and —C(O)$C_{1-6}$ alkyl; and each $R^h$ is independently halo, cyano, hydroxy, $C_{1-6}$ alkyl, $C_{1-6}$ haloalkyl, $-NH_2$, $-NH(C_{1-3}$ alkyl), $-N(C_{1-3}$ alkyl)$_2$, $C_{1-3}$ alkoxy, or $C_{1-3}$ haloalkoxy.

In one aspect, provided herein are compounds of Formula I:

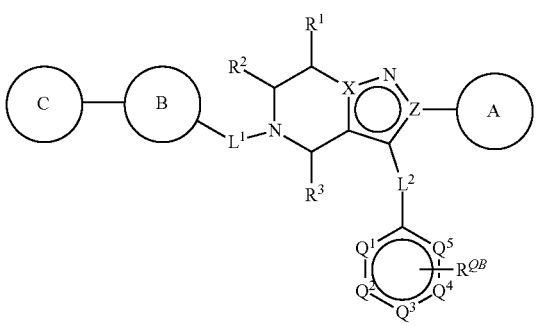

I or a pharmaceutically acceptable salt or solvate thereof, wherein:

X is C and Z is N, or X is N and Z is C;

$Q^1$ and $Q^1$ are each independently N or $CR^{QA}$; and $Q^2$, $Q^3$, and $Q^4$ are each independently N, $CR^{QA}$, or $CR^{QB}$, provided that at least one of $Q^2$, $Q^3$, and $Q^4$ is $CR^{QB}$; or $Q^1$ is a bond; and $Q^2$, $Q^3$, $Q^4$, and $Q^5$ are each independently O, S, N, NH, $NR^c$, $CR^{QA}$, or $CR^{QB}$, provided that at least one of $Q^2$, $Q^3$, $Q^4$, and $Q^5$ is $CR^{QB}$; provided that the ring including $Q^1$-$Q^5$ is aromatic;

$R^{QB}$ is $-S(O)(=NR^a)R^b$ or $-(CR^iR^j)_n-S(O)(=NR^a)R^b$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said ring is optionally substituted with 1-3 independently selected $C_{1-6}$ alkyl;

n is 1, 2, 3, 4, 5, or 6;

each $R^i$ is independently hydrogen, halo, or $C_{1-6}$ alkyl;

or $R^a$ and $R^i$, or $R^b$ and $R^j$, taken together with the atoms to which each is attached form a 5-8 membered heterocyclyl, wherein said ring is optionally substituted with 1-3 independently selected $C_{1-6}$ alkyl;

each $R^j$ is independently hydrogen, halo, or $C_{1-6}$ alkyl;

each $R^{QA}$ is independently hydrogen, halo, cyano, hydroxy, $-NR^cR^d$, $-C(O)NR^cR^d$, $-S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —C(O)($C_{1-6}$ alkyl), $C_{6-10}$ aryl optionally substituted with 1-3 independently selected —C(O)($C_{1-6}$ alkyl), and 5-10 membered heteroaryl optionally substituted with 1-6 independently selected $R^g$;

or two $R^{QA}$ on adjacent carbon atoms, taken together with the atom to which each is attached form a 5-8 membered heterocyclyl, wherein said ring is optionally substituted with 1-2 independently selected $R^h$;

or $R^a$ or $R^b$ and an adjacent $R^{QA}$ are taken together with the atom to which each is attached to form a 5-8 membered heterocyclyl, wherein said ring is optionally substituted with 1-2 independently selected $R^h$;

$L^2$ is $C_{6-10}$ aryl optionally substituted with 1-2 independently selected $R^h$, 5-10 membered heteroaryl optionally substituted with 1-2 independently selected $R^h$,

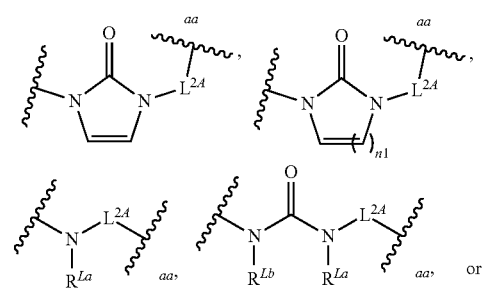

-continued

[structure showing isoindolinone with N, C=O, and attachment points]

wherein aa represents the point of attachment to the ring containing $Q^1$-$Q^5$;

n1 is 1, 2, or 3;

$L^{2A}$ is a bond or $C_{1-10}$ alkylene;

$R^{La}$ is hydrogen, $C_{1-6}$ alkyl, or —C(O)($C_{1-6}$ alkyl);

each of $R^{Lb}$ and $R^{LC}$ is independently hydrogen or $C_{1-6}$ alkyl;

Ring A is $C_{6-10}$ aryl, $C_{s7}$ cycloalkyl, 5-7 membered heterocyclyl, or 5-10 membered heteroaryl, each of which is optionally substituted with 1-5 independently selected $R^A$; each $R^A$ is independently halo, $C_{1-6}$ alkyl, $C_{1-6}$ haloalkyl, $C_{1-6}$ alkoxy, or $C_{3-6}$ cycloalkyl;

$R^1$, $R^2$, and $R^3$ are each independently hydrogen or $C_{1-6}$ alkyl optionally substituted with 1-6 substituents independently selected from the group consisting of halo, hydroxy, and $C_{1-6}$ alkoxy;

$L^1$ is —C(O)—, —$CH_2$—, —CH($C_{1-6}$ alkyl)-, or —S(O)$_2$—;

Ring B is a 5,6-fused heteroaryl having from 5 to 8 carbon atoms and from 1 to 3 heteroatoms independently selected from O, S, and N, wherein Ring B is optionally substituted with 1 to 4 substituents independently selected from halo, oxo, and $C_{1-6}$ alkyl;

wherein bb represents point of attachment to $L^1$;

$R^4$, $R^5$, $R^6$, and $R^7$ are each independently hydrogen, halo, or $C_{1-6}$ alkyl;

$R^8$ is phenyl, 5-6 membered heteroaryl, or

[structure with $R^{8a}$, $R^{8b}$, $L^3$, $L^4$—$R^9$]

wherein the phenyl or 5-6 membered heteroaryl are substituted with $R^{8c}$ and are optionally further substituted with 1-3 independently selected $R^h$.

$L^3$ is a bond or $C_{1-3}$ alkylene;

$L^4$ is a bond or $C_{1-5}$ alkylene;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;

each $R^{8c}$ is independently —C(O)OH, —S(O)$_2$OH, —S(O)$_2$NH$_2$, —$L^5$-$C_{1-6}$ alkyl, —$L^5$-$C_{3-6}$ cycloalkyl, —$L^5$-$C_{6-10}$ aryl, —$L^5$-5-6 membered heterocyclyl, —$L^5$-(5-6 membered heteroaryl), wherein each is optionally substituted with 1-6 substituents independently selected from the group consisting of hydroxy, halo, and $C_{1-6}$ alkoxy;

each $L^5$ is independently —C(O)—, —C(O)O—, —OC(O)—, —S(O)$_{1-2}$—, —S(O)$_2$O—, —S(O)$_2$NH—, or —NHS(O)$_2$—;

$R^9$ is —C(O)O$R^{9a}$, —C(O)N$R^{9a}R^{9b}$, 5-6 membered heteroaryl optionally substituted with 1-3 independently selected $R^{9c}$, or

[structure with $X^1$, N, C=O, N-$R^{9c}$ ring]

$X^1$ is O or S;

$R^{9a}$ is hydrogen or $C_{1-6}$ alkyl;

$R^{9b}$ is hydrogen, $C_{1-6}$ alkyl, —C(O)($C_{1-6}$ alkyl), —S(O)$_{0-2}$($C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or —C(O)($C_{1-6}$ alkyl);

Ring C is 3-12 membered heterocyclyl, $C_{3-15}$ cycloalkyl, or 5-10 membered heteroaryl, each of which is optionally substituted with 1-3 $R^{Ca}$;

each $R^{Ca}$ is independently halo, cyano, $C_{1-6}$ alkyl, $C_{1-6}$ haloalkyl, $C_{1-6}$ alkoxy, or N$R^cR^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;

$R^e$ is hydrogen, $C_{1-6}$ alkyl, or $C_{1-6}$ haloalkyl;

each $R^f$ is independently halo, hydroxy, —N$R^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, —N$R^cR^d$, or 3 to 12 membered heterocyclyl optionally substituted with one or more substituents each independently selected from the group consisting of $C_{1-6}$ alkyl and —C(O)$C_{1-6}$ alkyl; and each $R^h$ is independently halo, cyano, hydroxy, $C_{1-6}$ alkyl, $C_{1-6}$ haloalkyl, —NH$_2$, —NH($C_{1-3}$ alkyl), —N($C_{1-3}$ alkyl)$_2$, $C_{1-3}$ alkoxy, or $C_{1-3}$ haloalkoxy.

In some embodiments, provided herein is a compound of Formula II:

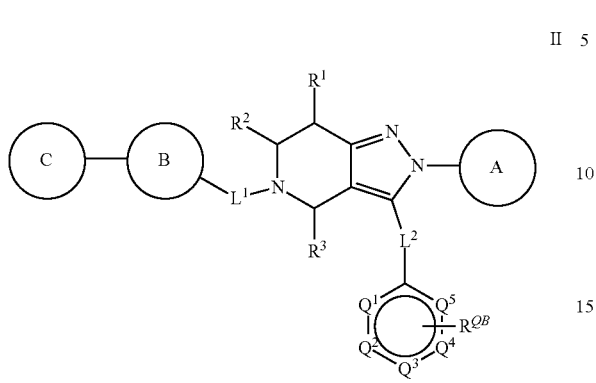

or a pharmaceutically acceptable salt, isotopically enriched analog, stereoisomer, mixture of stereoisomers, or prodrug thereof, wherein ring A, ring B, ring C, $Q^1$, $Q^2$, $Q^3$, $Q^4$, $Q^5$, $L^1$, $L^2$, $R^1$, $R^2$, $R^3$, and $R^{QB}$ are each independently as defined herein.

In some embodiments, provided herein is a compound of Formula III:

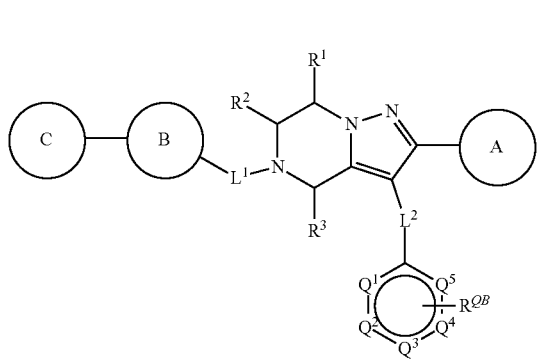

or a pharmaceutically acceptable salt, isotopically enriched analog, stereoisomer, mixture of stereoisomers, or prodrug thereof, wherein ring A, ring B, ring C, $Q^1$, $Q^2$, $Q^3$, $Q^4$, $Q^5$, L, $L^2$, $R^1$, $R^2$, $R^3$, and $R^{QB}$ are each independently as defined herein.

In some embodiments, $Q^1$ and $Q^5$ are each independently N or $CR^{QA}$; and $Q^2$, $Q^3$, and $Q^4$ are each independently N, $CR^{QA}$, or $CR^{QB}$, provided that at least one of $Q^2$, $Q^3$, and $Q^4$ is $CR^{QB}$.

In some embodiments, $Q^1$ and $Q^5$ are each independently N or $CR^{QA}$; and $Q^2$ and $Q^3$ are each independently N or $CR^{QA}$, and $Q^4$ is $CR^{QB}$. In some embodiments, $Q^1$ and $Q^5$ are each independently N or $CR^{QA}$; and $Q^2$ and $Q^4$ are each independently N or $CR^{QA}$, and $Q^3$ is $CR^{QB}$. In some embodiments, $Q^1$ and $Q^5$ are each independently N or $CR^{QA}$; and $Q^3$ and $Q^4$ are each independently N or $CR^{QA}$, and $Q^2$ is $CR^{QB}$.

In some embodiments, $Q^1$ and $Q^1$ are each independently $CR^{QA}$; and $Q^2$ and $Q^3$ are each independently N or $CR^{QA}$, and $Q^4$ is $CR^{QB}$. In some embodiments, $Q^5$ and $Q^1$ are each independently $CR^{QA}$; and $Q^2$ and $Q^4$ are each independently N or $CR^{QA}$, and $Q^3$ is $CR^{QB}$. In some embodiments, $Q^1$ and $Q^5$ are each independently $CR^{QA}$; and $Q^3$ and $Q^4$ are each independently N or $CR^{QA}$, and $Q^2$ is $CR^{QB}$.

In some embodiments, the moiety

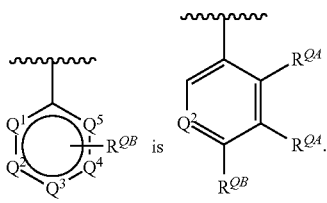

In some embodiments, each $R^{QA}$ is independently hydrogen, halo, $C_{1-6}$ alkyl, $C_{1-6}$ alkoxy, or —$NR^cR^d$.

In some embodiments, $R^c$ and $R^d$ are each independently hydrogen or $C_{1-6}$ alkyl.

In some embodiments, $Q^1$ and $Q^1$ are each independently $CR^{QA}$; where each $R^{QA}$ is independently hydrogen or halo.

In some embodiments, one of $Q^2$, $Q^3$, and $Q^4$ is N.

In some embodiments, $Q^2$, $Q^3$, and $Q^4$ are each independently $CR^{QA}$ or $CR^{QB}$, provided that at least one of $Q^2$, $Q^3$, and $Q^4$ is $CR^{QB}$.

In some embodiments, $R^{QB}$ is —S(O)(=$NR^a$)$R^b$.

In some embodiments, $R^{QB}$ is —S(O)(=$NR^a$)$R^b$; $R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl; and $R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl.

In some embodiments, $R^{QB}$ is —S(O)(=$NR^a$)$R^b$; and $R^a$ and $R^b$ taken together with the atoms to which each is attached form a 5-8 membered heterocyclyl, wherein said heterocyclyl is optionally substituted with 1-3 independently selected $C_{1-6}$ alkyl.

In some embodiments, $R^{QB}$ is —S(O)(=$NR^a$)$R^b$; and $R^a$ or R and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is —S(O)(=$NR^a$)$R^b$; and $R^a$ and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is —S(O)(=$NR^a$)$R^b$; and $R^b$ and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is —$(CR^iR^j)_n$—S(O)(=$NR^a$)$R^b$.

In some embodiments, $R^{QB}$ is —$(CR^iR^j)_n$—S(O)(=$NR^a$)$R^b$; n is 1, 2, 3, 4, 5, or 6; $R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl; and $R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl.

In some embodiments, $R^{QB}$ is $—(CR^iR^j)_n—S(O)(=NR^a)R^b$; and $R^a$ and $R^b$ taken together with the atoms to which each is attached form a 5-8 membered heterocyclyl, wherein said heterocyclyl is optionally substituted with 1-3 independently selected $C_{1-6}$ alkyl.

In some embodiments, $R^{QB}$ is $—(CR^iR^j)_n—S(O)(=NR^a)R^b$; n is 1, 2, 3, 4, 5, or 6; and each $R^1$ is independently hydrogen, halo, or $C_{1-6}$ alkyl; and each $R^j$ is independently hydrogen, halo, or $C_{1-6}$ alkyl.

In some embodiments, $R^{QB}$ is $—(CR^iR^j)_n—S(O)(=NR^a)R^b$; and one $R^1$ and one $R^j$, taken together with the atom(s) to which each is attached, form a $C_{3-6}$ cycloalkyl, wherein said cycloalkyl is optionally substituted with 1-3 independently selected $C_{1-6}$ alkyl.

In some embodiments, $R^{QB}$ is $—(CR^iR^j)_n—S(O)(=NR^a)R^b$; n is 1, 2, 3, 4, 5, or 6; and $R^a$ and $R^i$, or $R^b$ and $R^j$, taken together with the atoms to which each is attached form a 5-8 membered heterocyclyl, wherein said heterocyclyl is optionally substituted with 1-3 independently selected $C_{1-6}$ alkyl.

In some embodiments, $R^{QB}$ is $—(CR^iR^j)_n—S(O)(=NR^a)R^b$; and $R^a$ or R and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is $—(CR^iR^j)_n—S(O)(=NR^a)R^b$; $R^a$ or $R^b$ and an adjacent $R^{QA}$ are taken together with the atom to which each is attached to form a 5-8 membered heterocyclyl, wherein said heterocyclyl is optionally substituted with 1-2 independently selected $R^h$; and one $R^1$ and one $R^j$ on adjacent carbon atoms taken together with the atom(s) to which each is attached form an alkene, wherein said alkene is optionally substituted with 1-3 independently selected $C_{1-6}$ alkyl.

In some embodiments, $R^{QB}$ is $—(CR^iR^j)_n—S(O)(=NR^a)R^b$; and $R^a$ and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is $—(CR^iR^j)_n—S(O)(=NR^a)R^b$; and $R^b$ and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is $—N=S(O)(R^{1a})R^b$.

In some embodiments, $R^{QB}$ is $—N=S(O)(R^{1a})R^b$; $R^{1a}$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_60.1o$ aryl optionally substituted with 1-3 independently selected $C_{1-3}$ alkyl; and $R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl.

In some embodiments, $R^{QB}$ is $—O—(CR^iR^j)_n—S(O)(=NR^a)R^b$.

In some embodiments, $R^{QB}$ is $—O—(CR^iR^j)_n—S(O)(=NR^a)R^b$; n is 1, 2, 3, 4, 5, or 6; $R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl; and $R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl.

In some embodiments, $R^{QB}$ is $—O—(CR^iR^j)_n—S(O)(=NR^a)R^b$; and $R^a$ and $R^b$ taken together with the atoms to which each is attached form a 5-8 membered heterocyclyl, wherein said heterocyclyl is optionally substituted with 1-3 independently selected $C_{1-6}$ alkyl.

In some embodiments, $R^{QB}$ is $—O—(CR^iR^j)_n—S(O)(=NR^a)R^b$; n is 1, 2, 3, 4, 5, or 6; and each $R^1$ is independently hydrogen, halo, or $C_{1-6}$ alkyl; and each $R^j$ is independently hydrogen, halo, or $C_{1-6}$ alkyl.

In some embodiments, $R^{QB}$ is $—O—(CR^iR^j)_n—S(O)(=NR^a)R^b$; and one $R^1$ and one $R^j$, taken together with the atom(s) to which each is attached, form a $C_{3-6}$ cycloalkyl, wherein said cycloalkyl is optionally substituted with 1-3 independently selected $C_{1-6}$ alkyl.

In some embodiments, $R^{QB}$ is $—O—(CR^iR^j)—S(O)(=NR^a)R^b$; n is 1, 2, 3, 4, 5, or 6; and $R^a$ and $R^i$, or $R^b$ and $R^j$, taken together with the atoms to which each is attached form a 5-8 membered heterocyclyl, wherein said heterocyclyl is optionally substituted with 1-3 independently selected $C_{1-6}$ alkyl.

In some embodiments, $R^{QB}$ is $—O—(CR^iR^j)_n—S(O)(=NR^a)R^b$; and $R^a$ or R and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is $—O—(CR^iR^j)_n—S(O)(=NR^a)R^b$; and $R^a$ and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is $—O—(CR^iR^j)_n—S(O)(=NR^a)R^b$; and $R^b$ and an adjacent $R^{QA}$ are taken together with the atom to which each is attached to form a 5-8 membered heterocyclyl, wherein said heterocyclyl is optionally substituted with 1-2 independently selected $R^h$.

In some embodiments, $R^{QB}$ is $—S(O)(=NR^a)R^b$ or $—C_{1-6}$ alkyl-$S(O)(=NR^a)R^b$.

In some embodiments, $R^{QB}$ is $—C_{1-6}$ alkyl-$S(O)(=NR^a)R^b$.

In some embodiments, $R^{QB}$ is $—S(O)(=NR^a)R^b$ or $—CH_2—S(O)(=NR^a)R^b$.

In some embodiments, $R^{QB}$ is $—CH_2—S(O)(=NR^a)R^b$.

In some embodiments, the moiety is
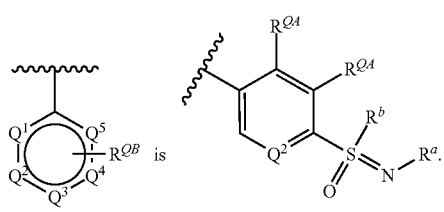
In some embodiments, the moiety
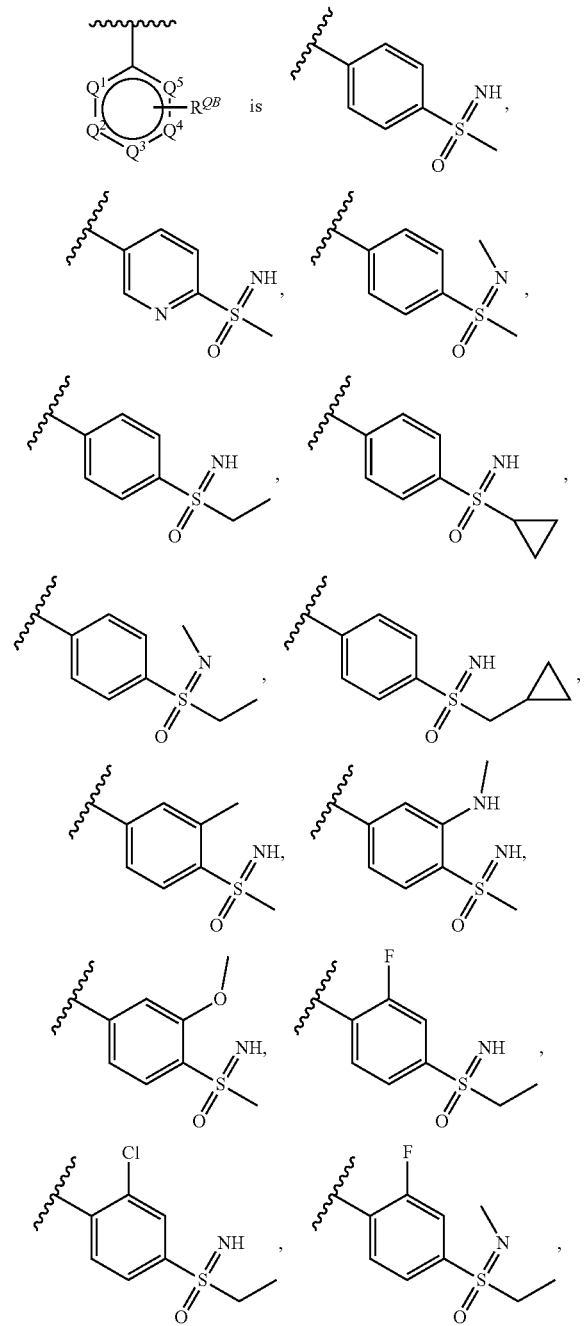

-continued
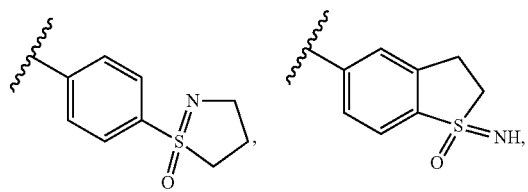
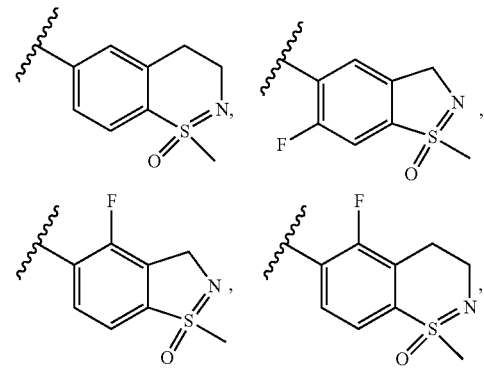
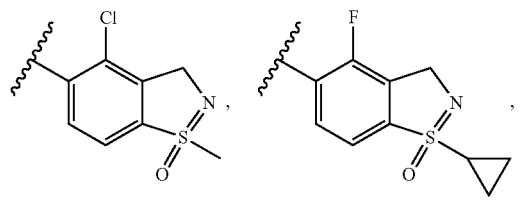
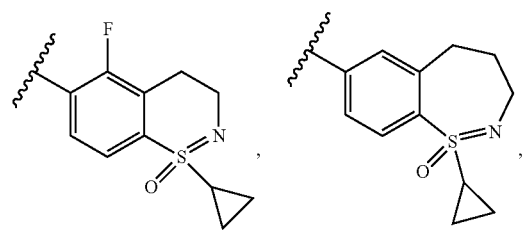
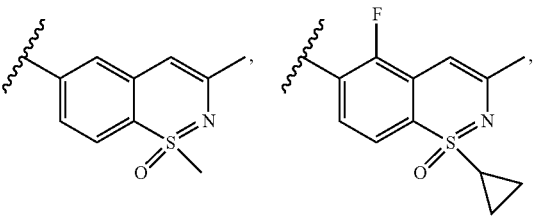
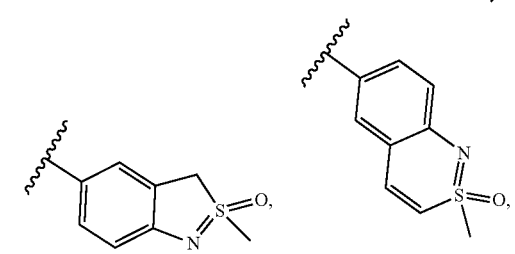
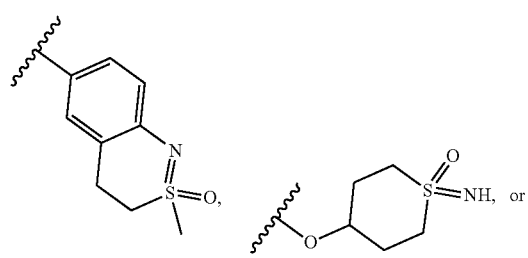
-continued
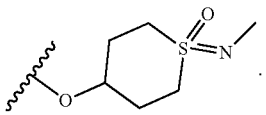
In some embodiments, the moiety
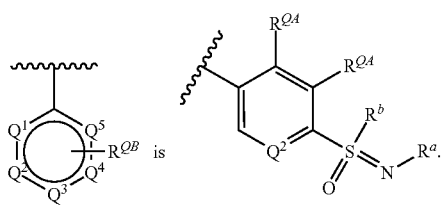
In some embodiments, the moiety
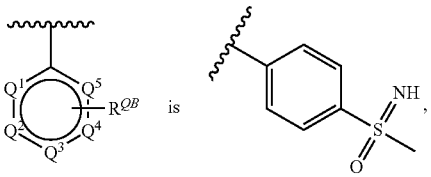
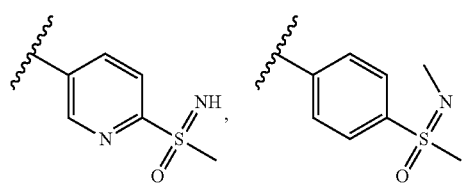
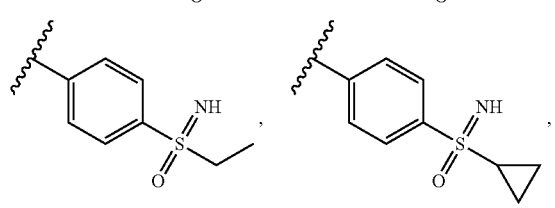
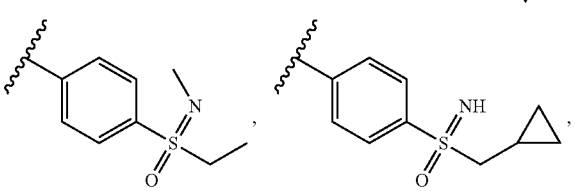
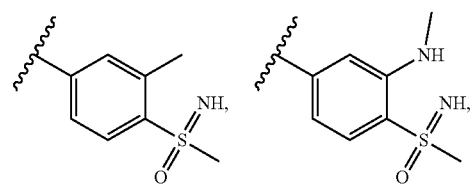
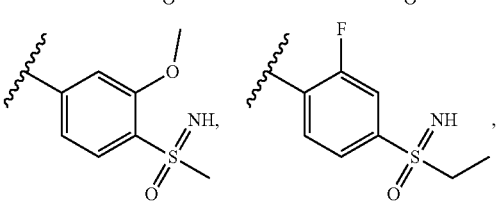

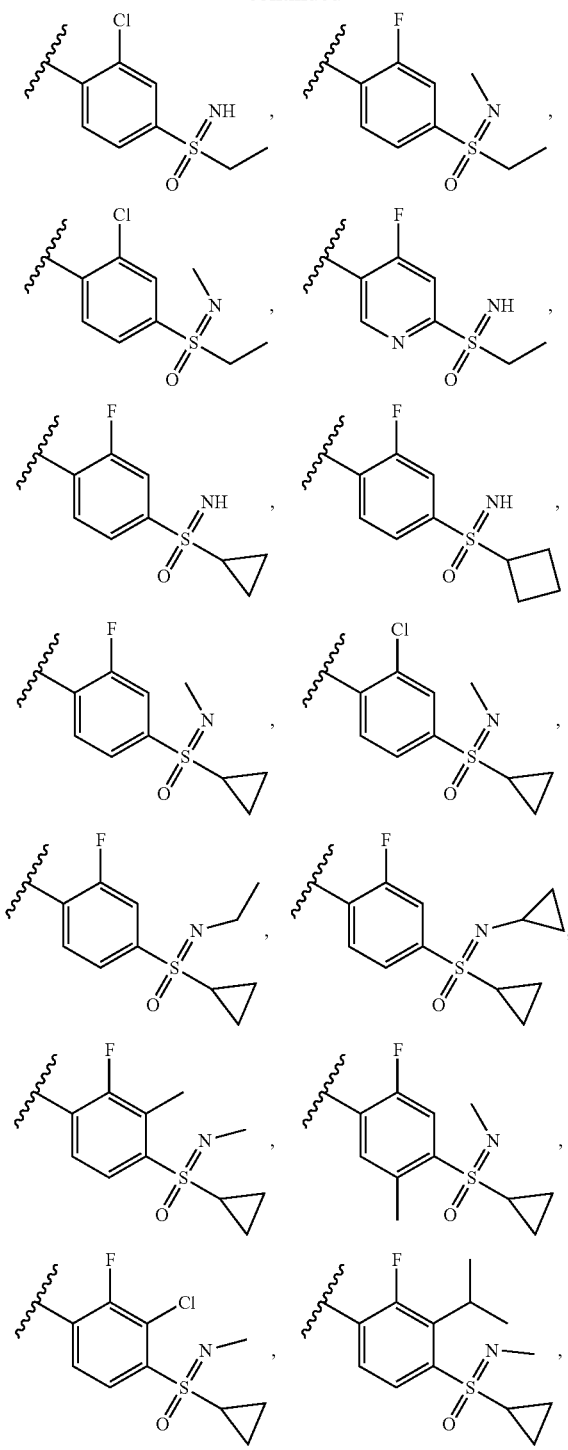
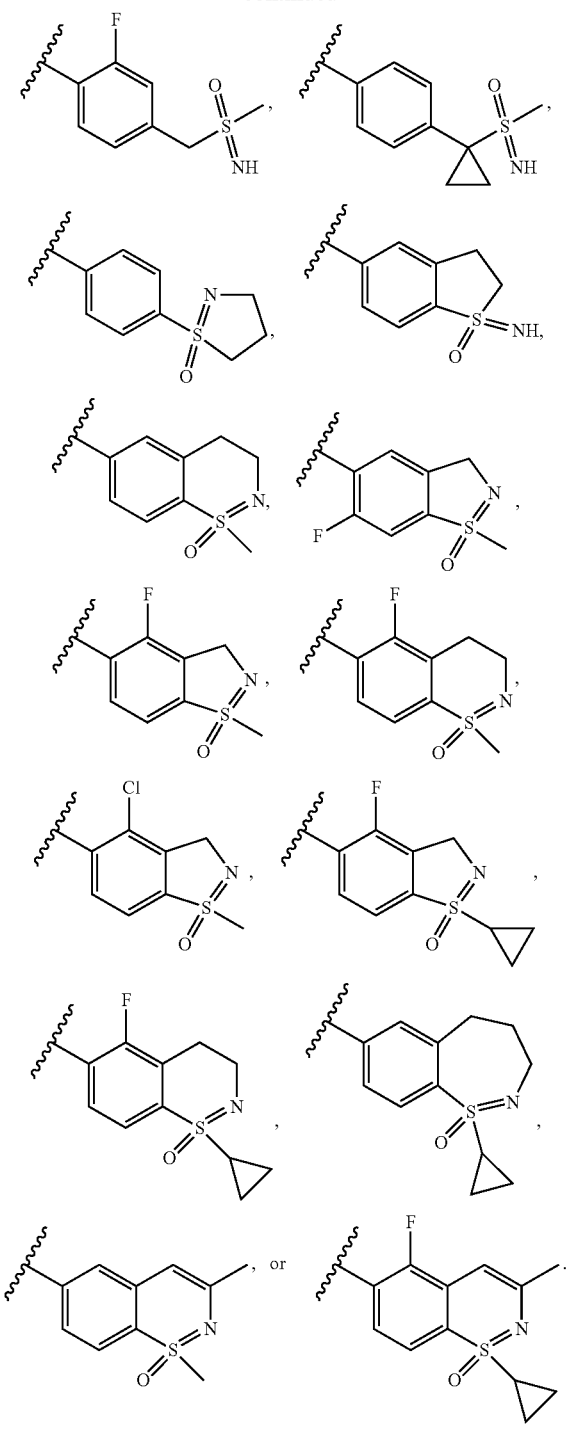
In some embodiments, the moiety
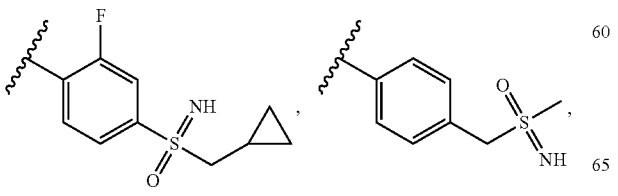
is
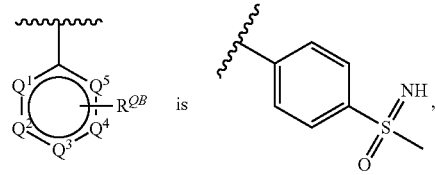

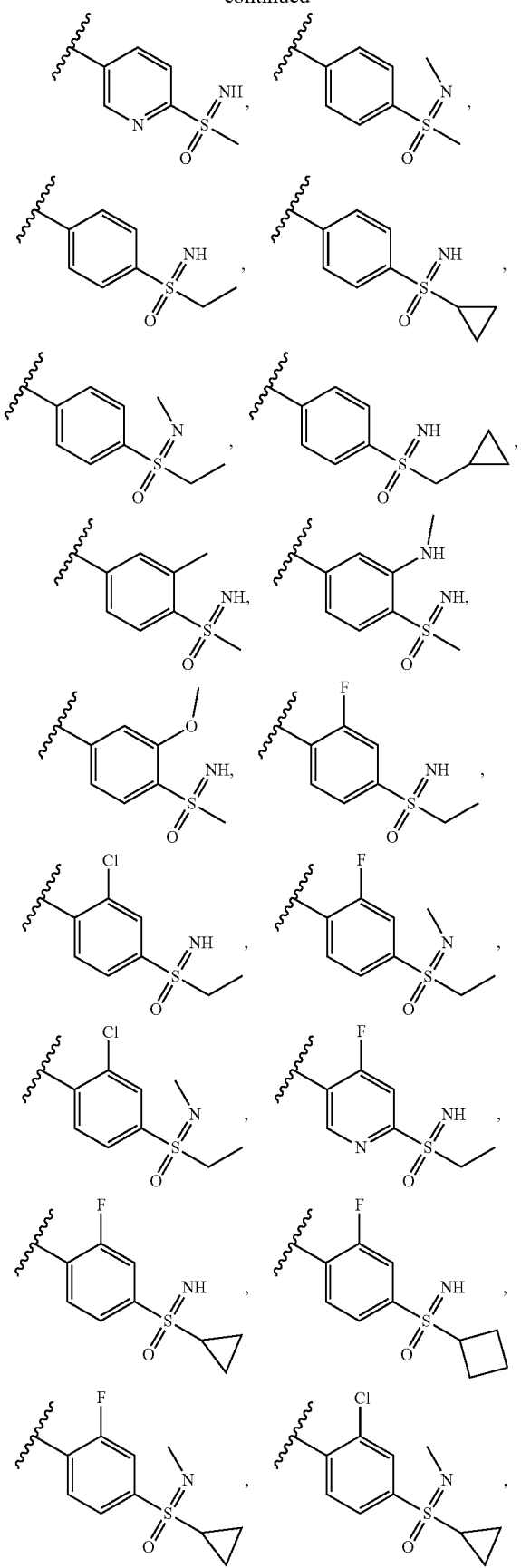
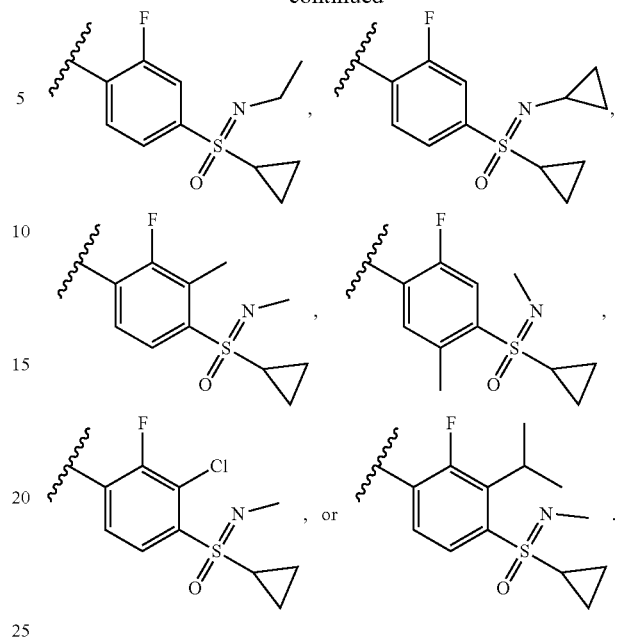
In some embodiments, the moiety
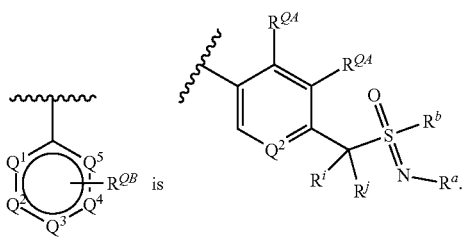
In some embodiments, the moiety
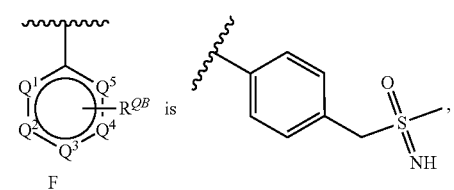
In some embodiments, the moiety
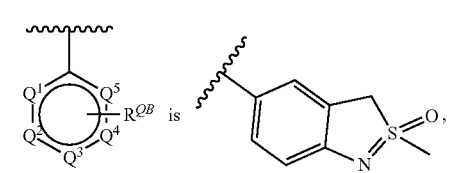

In some embodiments, the moiety

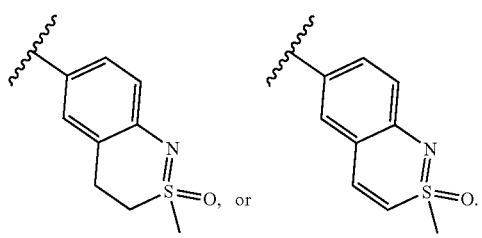

In some embodiments, the moiety

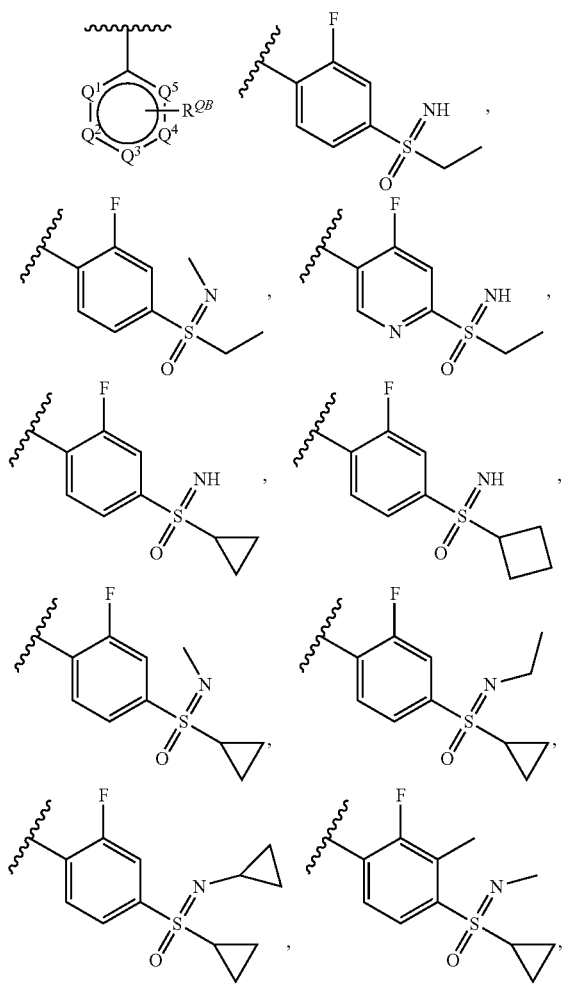

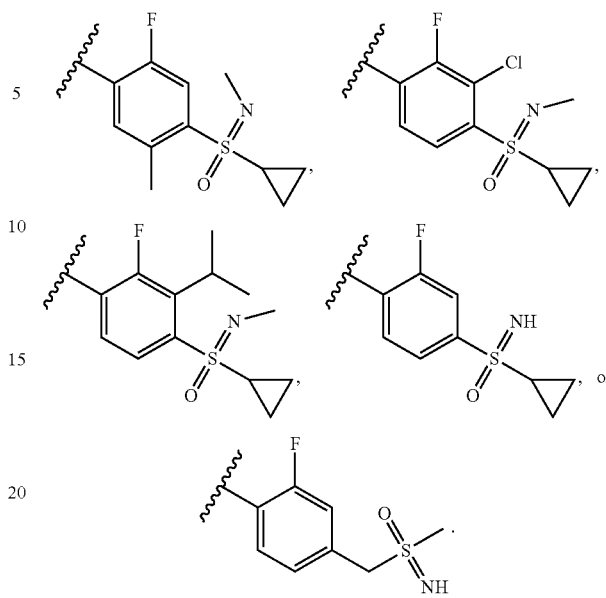

In some embodiments, $R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl.

In some embodiments, $R^b$ is $C_{1-6}$ alkyl which is optionally substituted with 1-6 substituents each independently selected from the group consisting of $C_{1-6}$ alkoxy, $C_{3-6}$ cycloalkyl, and halo, or $C_{3-6}$ cycloalkyl.

In some embodiments, $R^a$ and $R^b$ taken together with the atoms to which each is attached form a 5-8 membered heterocyclyl. In some embodiments, $R^a$ and $R^b$ taken together with the atoms to which each is attached form a 5 membered heterocyclyl. In some embodiments, the moiety

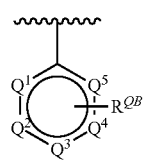

is

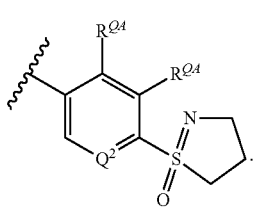

In some embodiments, $R^a$ or $R^b$ and an adjacent $R^{QA}$ are taken together with the atom to which each is attached to form a 5-8 membered heterocyclyl, wherein said ring is optionally substituted with 1-2 independently selected $R^h$. In some embodiments, the moiety

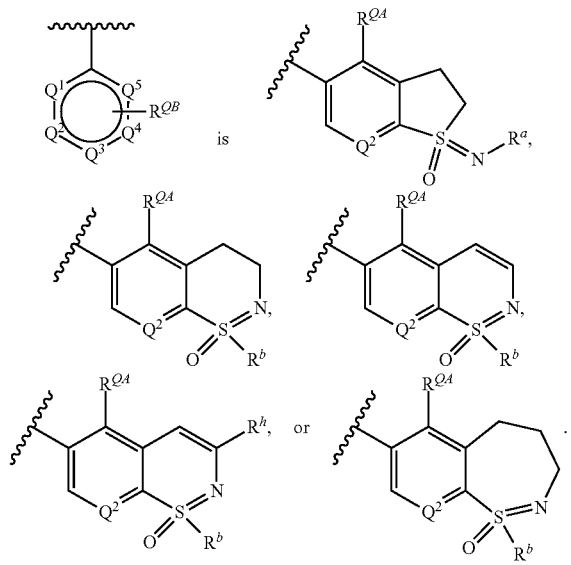

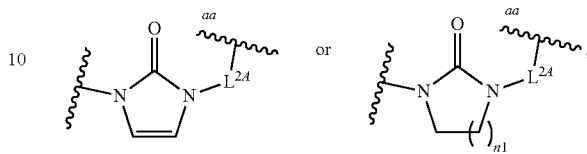

In some embodiments, $R^a$ and $R^i$, or $R^b$ and $R^j$, taken together with the atoms to which each is attached form a 5-8 membered heterocyclyl, wherein said ring is optionally substituted with 1-3 independently selected $C_{1-6}$ alkyl.

In some embodiments, $L^2$ is $C_6$0.1o aryl optionally substituted with 1-2 independently selected $R^h$, 5-10 membered heteroaryl optionally substituted with 1-2 independently selected $R^h$,

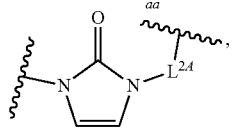

or

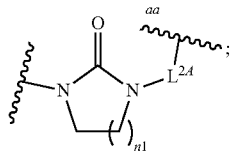

wherein aa represents the point of attachment to the ring containing $Q^1$-$Q^5$.

In some embodiments, $L^2$ is $C_6$0.1o aryl optionally substituted with 1-2 independently selected $R^h$,

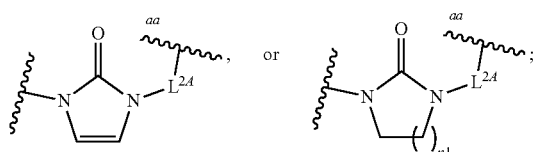

wherein aa represents the point of attachment to the ring containing $Q^1$-$Q^5$.

In some embodiments, $L^2$ is $C_6$0.1o aryl optionally substituted with 1-2 independently selected $R^h$.

In some embodiments, $L^2$ is 5-10 membered heteroaryl optionally substituted with 1-2 independently selected $R^h$.

In some embodiments, $L^2$ is

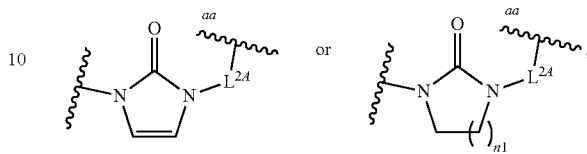

wherein aa represents the point of attachment to the ring containing $Q^1$-$Q^5$. In some embodiments, $L^2$ is

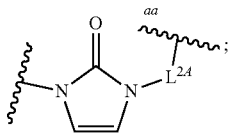

wherein aa represents the point of attachment to the ring containing $Q^1$-$Q^5$. In some embodiments, $L^2$ is

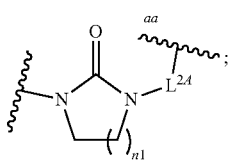

wherein aa represents the point of attachment to the ring containing $Q^1$-$Q^5$.

In some embodiments, $L^{2A}$ is a bond.

In some embodiments, $R^1$ is hydrogen. In some embodiments, $R^2$ is hydrogen. In some embodiments, $R^1$ and $R^2$ are each hydrogen.

In some embodiments, $R^3$ is hydrogen or $C_{1-6}$ alkyl. In some embodiments, $R^3$ is hydrogen. In some embodiments, $R^3$ is $C_{1-6}$ alkyl. In some embodiments, $R^3$ is hydrogen or methyl. In some embodiments, $R^3$ is methyl. In some embodiments, $R^3$ is methyl and is connected to the ring to which it is attached in the (S)—configuration. In some embodiments, $R^3$ is hydrogen or methyl, where the methyl is connected to the ring to which it is attached in the (S)—configuration.

In some embodiments, $L^1$ is —C(O)—,

In some embodiments, Ring A is $C_{6-10}$ aryl optionally substituted with 1-5 independently selected $R^4$. In some embodiments, Ring A is $C_{5-7}$ cycloalkyl optionally substituted with 1-5 independently selected $R^4$. In some embodiments, Ring A is 5-7 membered heterocyclyl optionally substituted with 1-5 independently selected $R^4$. In some embodiments, Ring A is 5-10 membered heteroaryl optionally substituted with 1-5 independently selected $R^4$.

In some embodiments, each $R^4$ is independently halo, $C_{1-6}$ alkyl, or $C_{3-6}$ cycloalkyl.

In some embodiments, Ring A is $C_{6-10}$ aryl which is optionally substituted with 1-5 substituents independently selected from the group consisting of halo, $C_{1-6}$ alkyl, $C_{1-6}$ haloalkyl, $C_{1-6}$ alkoxy, and $C_{3-6}$ cycloalkyl.

In some embodiments, Ring A is phenyl substituted with 2-3 substituents independently selected from the group consisting of halo, $C_{1-6}$ alkyl, and $C_{3-6}$ cycloalkyl.

In some embodiments, Ring B is a 5,6-fused heteroaryl having from 5 to 8 carbon atoms and from 1 to 3 heteroatoms independently selected from O, S, and N, wherein Ring B is substituted with $R^8$ and optionally substituted with 1 to 4 substituents independently selected from halo, oxo, and $C_{1-6}$ alkyl; and the 5-membered ring of the 5,6-fused heteroaryl is bonded to $L^1$. In some embodiments, Ring B is a 5,6-fused heteroaryl having from 5 to 8 carbon atoms and from 1 to 3 heteroatoms independently selected from O, S, and N, wherein Ring B is substituted with $R^8$ and optionally substituted with 1 to 4 substituents independently selected from halo, oxo, and $C_{1-6}$ alkyl; the 5-membered ring of the 5,6-fused heteroaryl is bonded to $L^1$; and ring C is bonded to the 6-membered ring of the 5,6-fused heteroaryl.

In some embodiments, Ring B is a 5,6-fused heteroaryl having from 5 to 8 carbon atoms and from 1 to 3 heteroatoms independently selected from O, S, and N, wherein Ring B is optionally substituted with 1 to 4 substituents independently selected from halo, oxo, and $C_{1-6}$ alkyl; and the 5-membered ring of the 5,6-fused heteroaryl is bonded to $L^1$. In some embodiments, Ring B is a 5,6-fused heteroaryl having from 5 to 8 carbon atoms and from 1 to 3 heteroatoms independently selected from O, S, and N, wherein Ring B is optionally substituted with 1 to 4 substituents independently selected from halo, oxo, and $C_{1-6}$ alkyl; the 5-membered ring of the 5,6-fused heteroaryl is bonded to $L^1$; and ring C is bonded to the 6-membered ring of the 5,6-fused heteroaryl.

In some embodiments, Ring B is:

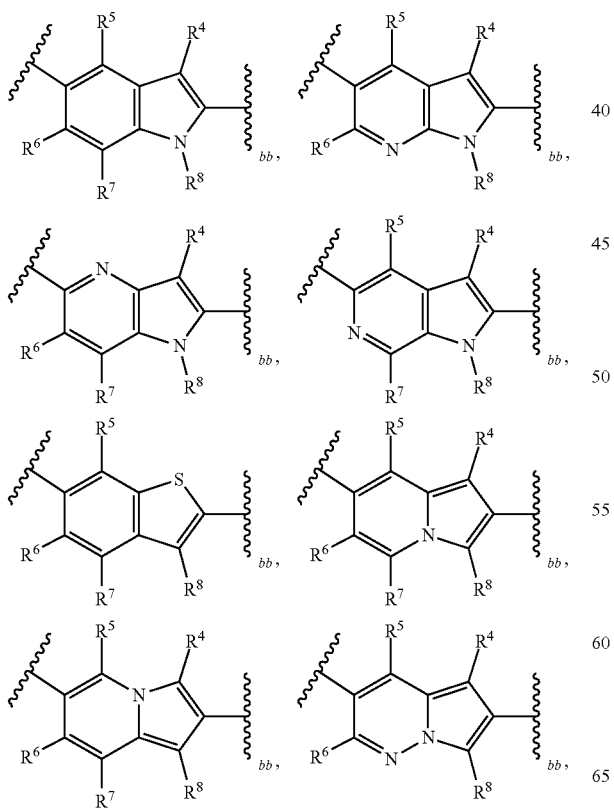

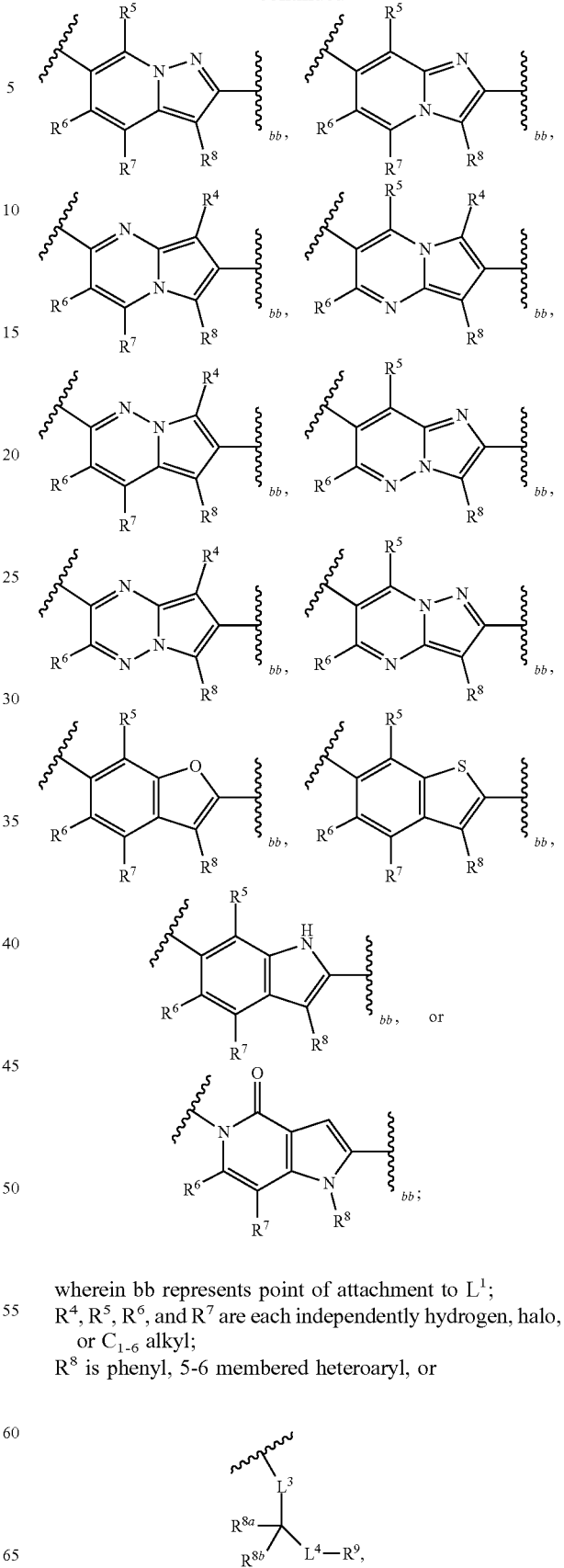

wherein bb represents point of attachment to $L^1$;

$R^4$, $R^5$, $R^6$, and $R^7$ are each independently hydrogen, halo, or $C_{1-6}$ alkyl;

$R^8$ is phenyl, 5-6 membered heteroaryl, or wherein the phenyl or 5-6 membered heteroaryl are substituted with $R^{8c}$ and are optionally further substituted with 1-3 independently selected $R^h$.

$L^3$ is a bond or $C_{1-3}$ alkylene;
$L^4$ is a bond or $C_{1-5}$ alkylene;
$R^{8a}$ and $R^{8b}$ are each independently hydrogen or $C_{1-6}$ alkyl optionally substituted with one or more substituents independently selected from the group consisting of halo and $C_{3-15}$ cycloalkyl; or
$R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;
each $R^{8c}$ is independently —C(O)OH, —S(O)$_2$OH, —S(O)$_2$NH$_2$, —L$^5$-C$_{1-6}$ alkyl, —L$^5$-C$_{3-6}$ cycloalkyl, —L$^5$-C$_{6-10}$ aryl, —L$^5$-5-6 membered heterocyclyl, —L$^5$-(5-6 membered heteroaryl), wherein each is optionally substituted with 1-6 substituents independently selected from the group consisting of hydroxy, halo, and $C_{1-6}$ alkoxy;
each $L^5$ is independently —C(O)—, —C(O)O—, —OC(O)—, —S(O)$_{1-2}$—, —S(O)$_2$O—, —S(O)$_2$NH—, or —NHS(O)$_2$—;
$R^9$ is —C(O)OR$^{9a}$, —C(O)NR$^{9a}$R$^{9b}$, 5-6 membered heteroaryl optionally substituted with 1-3 independently selected $R^{9c}$, or

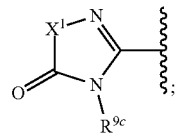

$X^1$ is O or S;
$R^{9a}$ is hydrogen or $C_{1-6}$ alkyl;
$R^{9b}$ is hydrogen, $C_{1-6}$ alkyl, —C(O)(C$_{1-6}$ alkyl), —S(O)$_{0-2}$(C$_{1-6}$ alkyl), or cyano;
each $R^{9c}$ is independently hydrogen, oxo, $C_{1-6}$ alkyl optionally substituted with 1-6 independently selected halo and $C_{1-6}$ alkoxy, or —C(O)(C$_{1-6}$ alkyl).

In some embodiments, Ring B is

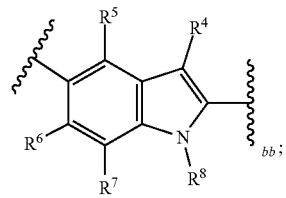

wherein bb represents point of attachment to $L^1$.
In some embodiments, Ring B is

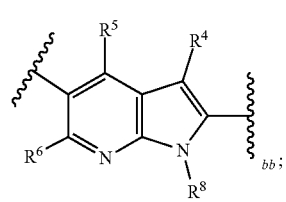

wherein bb represents point of attachment to $L^1$.
In some embodiments, Ring B is

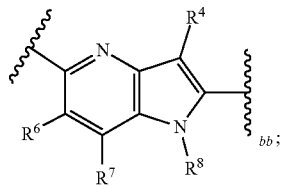

wherein bb represents point of attachment to $L^1$.
In some embodiments, Ring B is

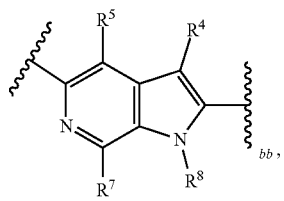

wherein bb represents point of attachment to $L^1$.
In some embodiments, Ring B is

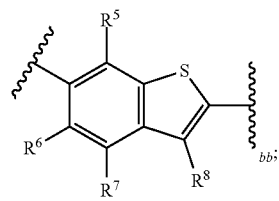

wherein bb represents point of attachment to $L^1$.
In some embodiments, Ring B is

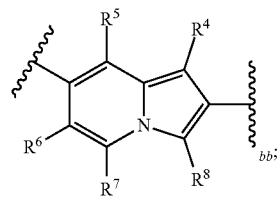

wherein bb represents point of attachment to $L^1$.
In some embodiments, Ring B is

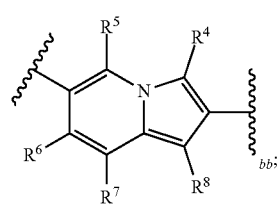

wherein bb represents point of attachment to $L^1$.

In some embodiments, Ring B is

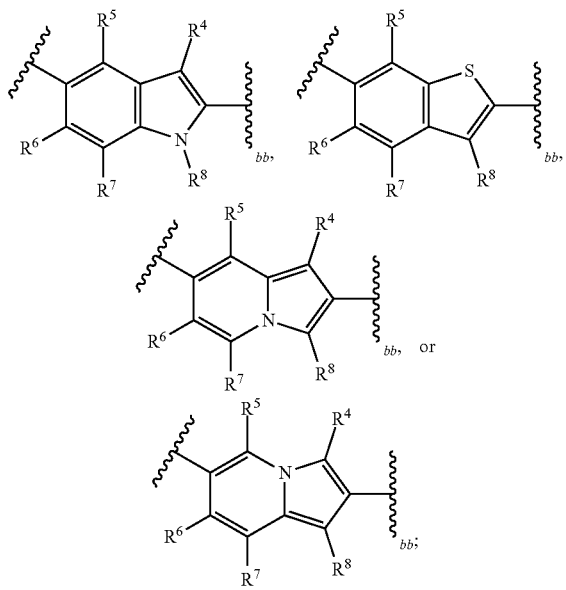

bb represents point of attachment to $L^1$;

In some embodiments, $R^8$ is phenyl substituted with $R^{8c}$. In some embodiments, $R^8$ is 5-6 membered heteroaryl substituted with $R^{8c}$. In some embodiments, $R^8$ is pyridyl substituted with $R^{8c}$. In some embodiments, $R^8$ is phenyl substituted with $R^{8c}$ or pyridyl substituted with $R^{8c}$.

In some embodiments, $R^8$ is

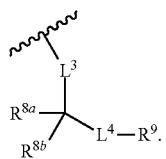

In some embodiments, Ring B is:

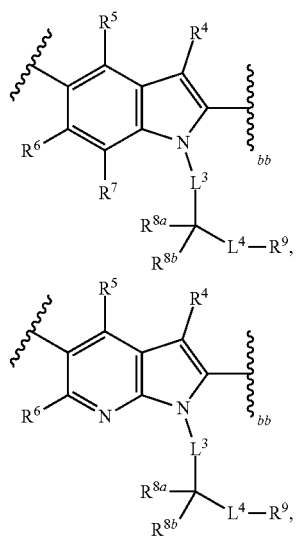

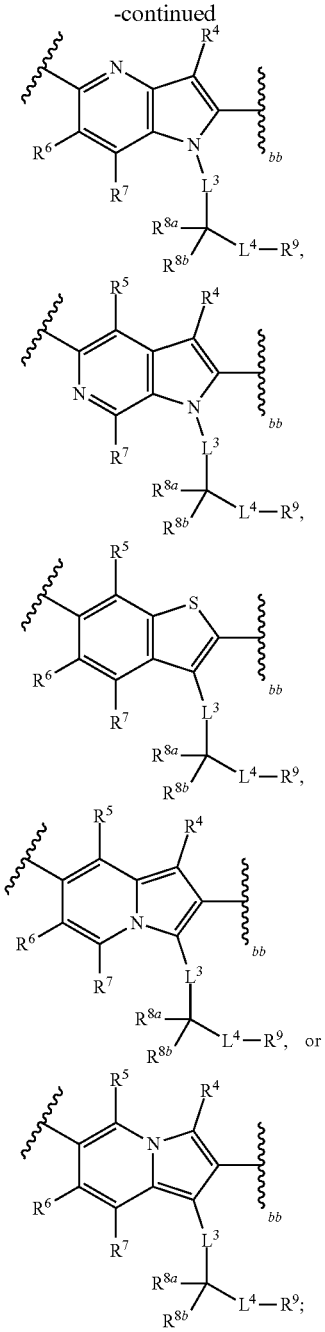

wherein bb represents point of attachment to $L^1$.

In some embodiments, Ring B is:

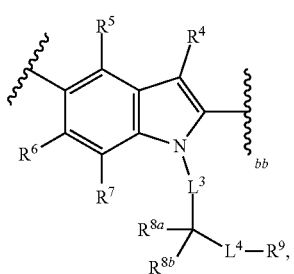

-continued

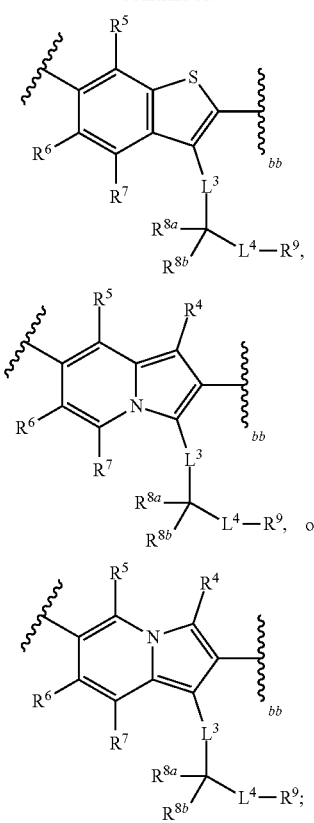

wherein bb represents point of attachment to L¹.

In some embodiments, Ring B is

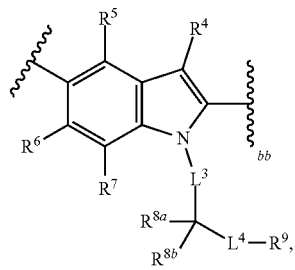

wherein bb represents point of attachment to L¹.

In some embodiments, Ring B is

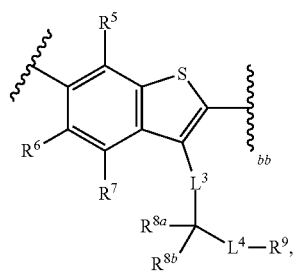

wherein bb represents point of attachment to L¹.

In some embodiments, Ring B is

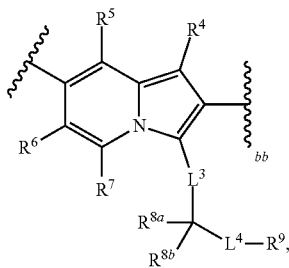

wherein bb represents point of attachment to L¹.

In some embodiments, Ring B is

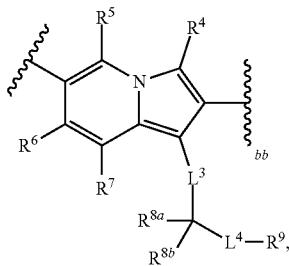

wherein bb represents point of attachment to L¹.

In some embodiments, L³ is a bond.
In some embodiments, L⁴ is a bond.
In some embodiments, L³ is a bond and L⁴ is a bond.
In some embodiments, R⁸ is phenyl substituted with R⁸, 5-6 membered heteroaryl substituted with $R^{8c}$, or

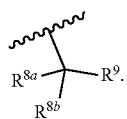

In some embodiments, provided herein is a compound of Formula IIA:

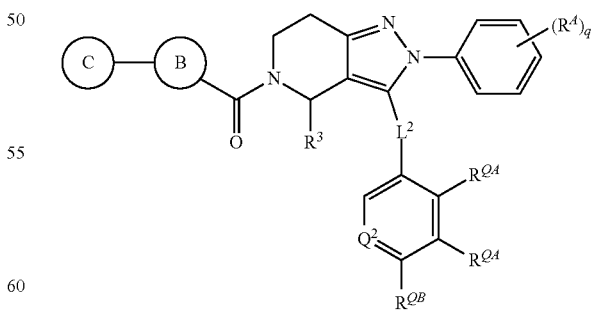

IIA or a pharmaceutically acceptable salt, isotopically enriched analog, stereoisomer, mixture of stereoisomers, or prodrug thereof, wherein q is 0, 1, 2, 3, 4, or 5; and ring B, ring C, $Q^2$, $L^2$, $R^A$, $R^3$, $R^{QA}$, and $R^{QB}$ are each independently as defined herein.

In some embodiments, provided herein is a compound of Formula IIB:

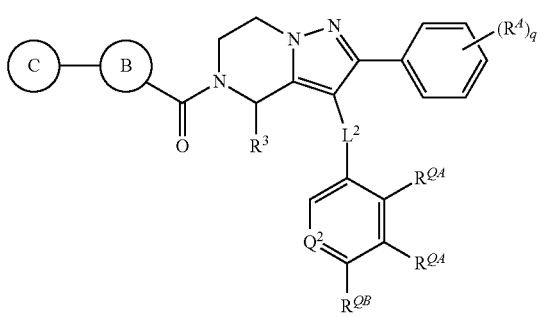

IIB or a pharmaceutically acceptable salt, isotopically enriched analog, stereoisomer, mixture of stereoisomers, or prodrug thereof, wherein q is 0, 1, 2, 3, 4, or 5; and ring B, ring C, $Q^2$, $L^2$, $R^A$, $R^3$, $R^{QA}$, and $R^{QB}$ are each independently as defined herein.

In some embodiments, provided herein is a compound of Formula IIA-(S):

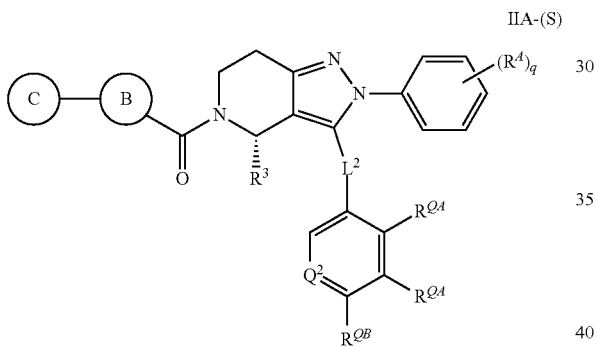

IIA-(S)

or a pharmaceutically acceptable salt, isotopically enriched analog, stereoisomer, mixture of stereoisomers, or prodrug thereof, wherein q is 0, 1, 2, 3, 4, or 5; and ring B, ring C, $Q^2$, $L^2$, $R^A$, $R^3$, $R^{QA}$, and $R^{QB}$ are each independently as defined herein.

In some embodiments, provided herein is a compound of Formula IIB-(S):

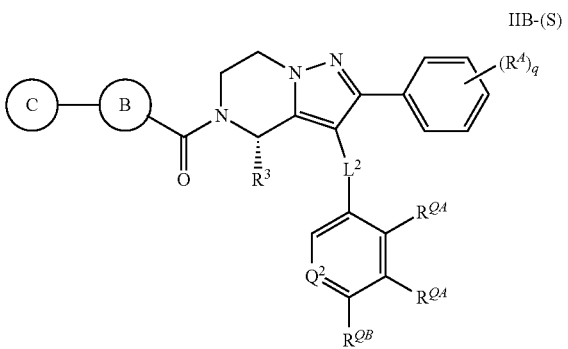

IIB-(S)

or a pharmaceutically acceptable salt, isotopically enriched analog, stereoisomer, mixture of stereoisomers, or prodrug thereof, wherein q is 0, 1, 2, 3, 4, or 5; and ring B, ring C, $Q^2$, $L^2$, $R^A$, $R^3$, $R^{QA}$, and $R^{QB}$ are each independently as defined herein.

In some embodiments, Ring B is

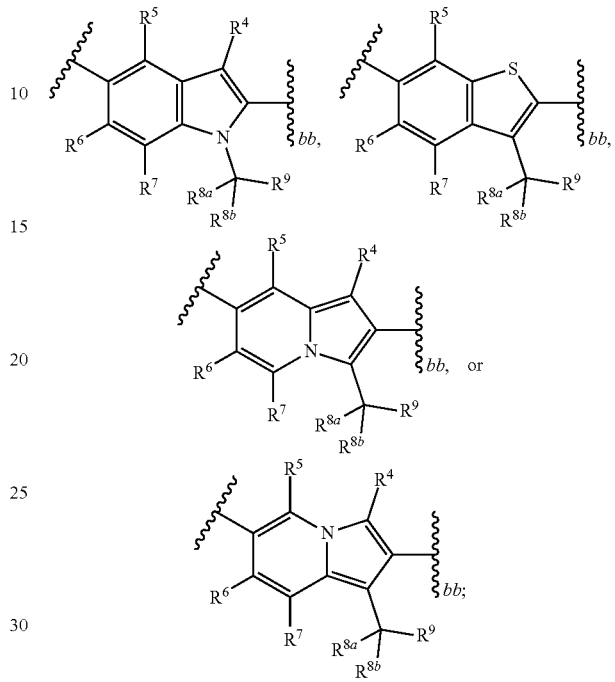

wherein bb represents point of attachment to $L^1$.

In some embodiments, $R^4$ is hydrogen or halo.

In some embodiments, $R^5$, $R^6$, and $R^7$ are each hydrogen.

In some embodiments, $R^{8a}$ and $R^{8b}$ are each independently hydrogen.

In some embodiments, $R^{8a}$ and $R^{8b}$ taken together with the carbon atom to which each is attached forms a $C_{3-15}$ cycloalkyl ring which is optionally substituted $C_{1-6}$ alkyl.

In some embodiments, $R^9$ is a 5-6 membered heteroaryl optionally substituted with 1-3 independently selected $R^{9c}$, or

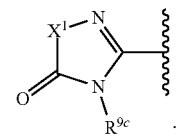

In some embodiments, $R^9$ is a 5-6 membered heteroaryl optionally substituted with 1-3 independently selected $R^{9c}$.

In some embodiments, $R^9$ is

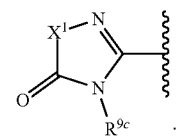

In some embodiments, $R^9$ is a 6 membered heteroaryl.

In some embodiments, R⁹ is

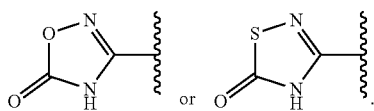 [SMILES: *c1noc(=O)[nH]1 ; *c1nsc(=O)[nH]1]

or .

In some embodiments, Ring C is 3-12 membered heterocyclyl optionally substituted with 1-3 $R^{Ca}$. In some embodiments, Ring C is a 6 membered heterocyclyl optionally substituted with 1-3 $R^{Ca}$ In some embodiments, each $R^{Ca}$ is $C_{1-6}$ alkyl.

In some embodiments, Ring C is

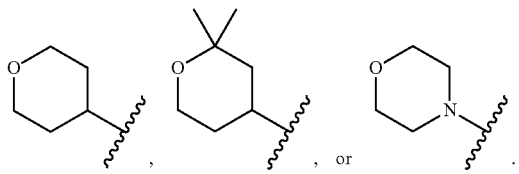

, or .

In some embodiments, Ring C is

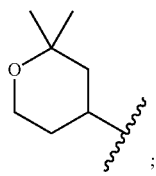

;

and the moiety

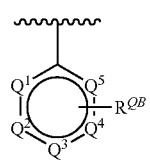

is

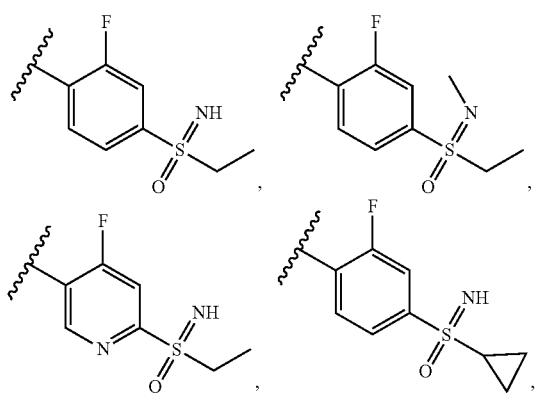

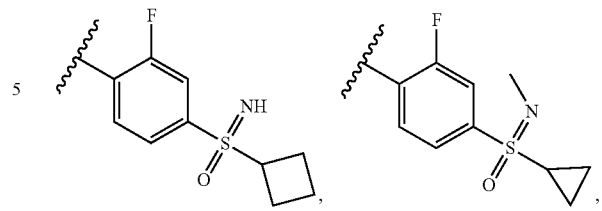

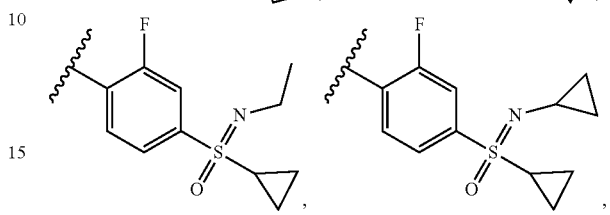

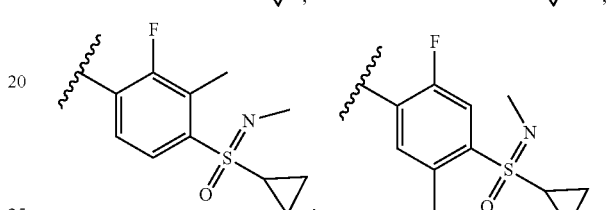

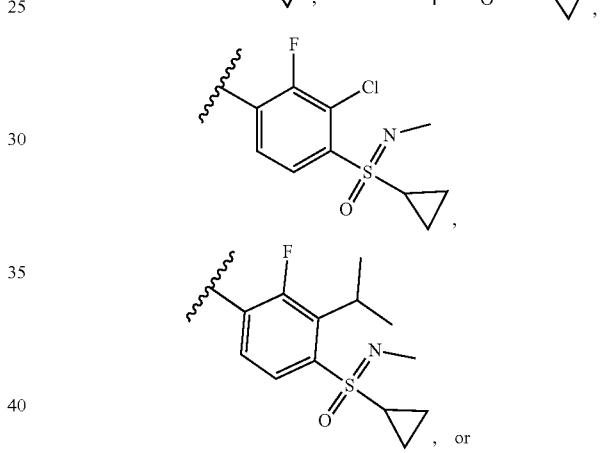

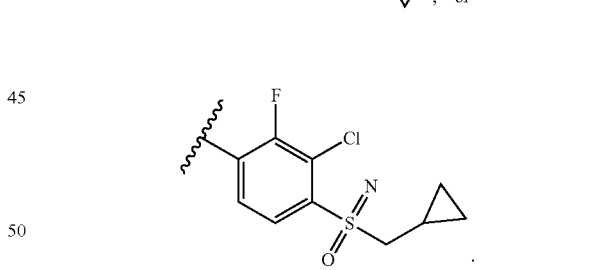

, or

In some embodiments, Ring C is

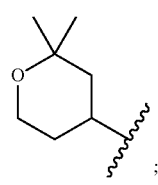

;

and the moiety

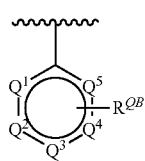

is:

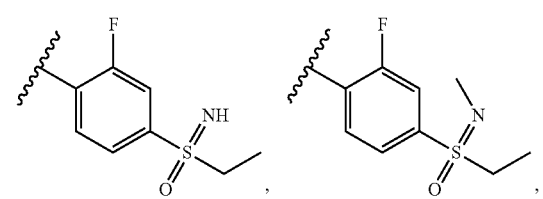
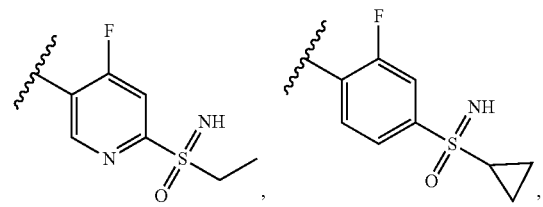
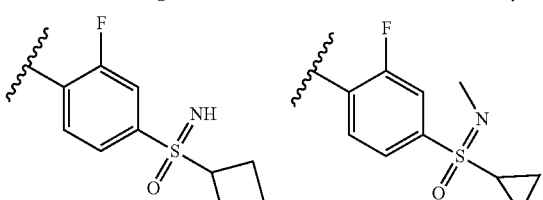
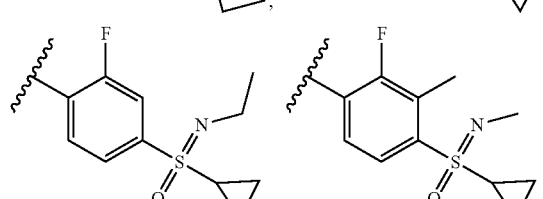
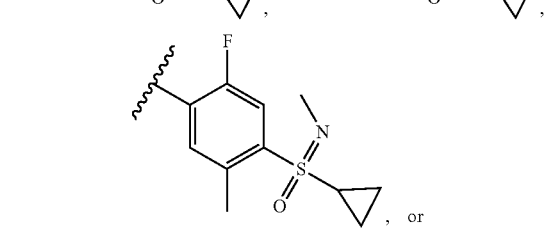

, or

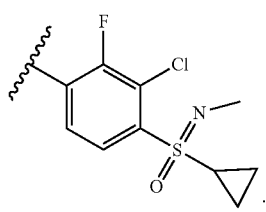.

In some embodiments, provided herein is a compound of Formula IIC:

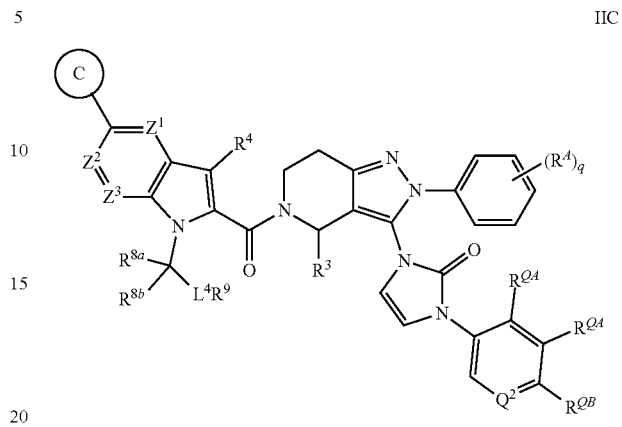

IIC or a pharmaceutically acceptable salt, isotopically enriched analog, stereoisomer, mixture of stereoisomers, or prodrug thereof, wherein q is 0, 1, 2, 3, 4, or 5; $Z^1$ is N or $CR^5$; $Z^2$ is N or $CR^6$; $Z^3$ is N or $CR^7$; $R^4$, $R^5$, $R^6$, and $R^7$ are each independently hydrogen, halo, or $C_{1-6}$ alkyl; and ring C, $R^{8a}$, $R^{8b}$, $L^4$, $R^9$, $R^A$, $R^3$, $Q^2$, $R^{QA}$, and $R^{QB}$ are each independently as defined herein.

In some embodiments, provided herein is a compound of Formula IIC-(S):

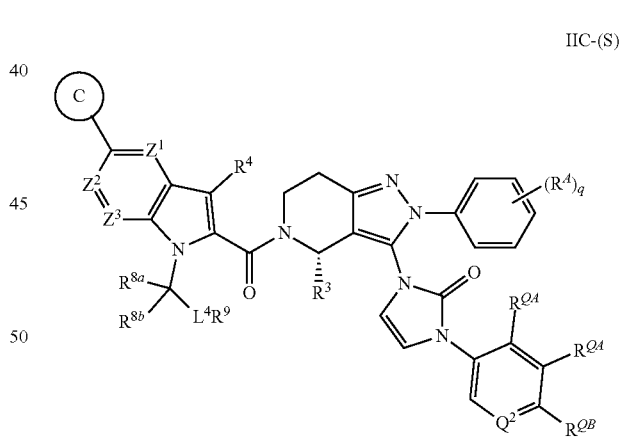

IIC-(S)

or a pharmaceutically acceptable salt, isotopically enriched analog, stereoisomer, mixture of stereoisomers, or prodrug thereof, wherein q is 0, 1, 2, 3, 4, or 5; $Z^1$ is N or $CR^5$; $Z^2$ is N or $CR^6$; $Z^3$ is N or $CR^7$; $R^4$, $R^5$, $R^6$, and $R^7$ are each independently hydrogen, halo, or $C_{1-6}$ alkyl; and ring C, $R^{8a}$, $R^{8b}$, $L^4$, $R^9$, $R^A$, $R^3$, $Q^2$, $R^{QA}$, and $R^{QB}$ are each independently as defined herein.

In one aspect, provided herein are compounds of Formula IIC-(S):

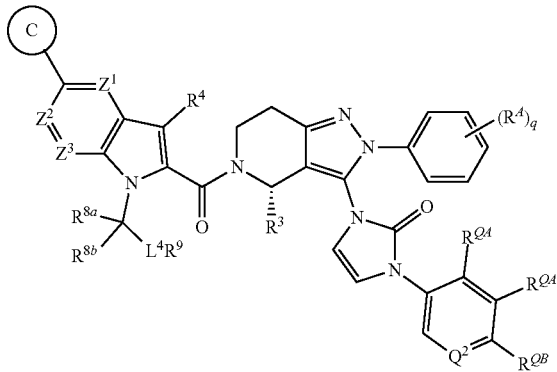

IIC-(S)

or a pharmaceutically acceptable salt, isotopically enriched analog, stereoisomer, mixture of stereoisomers, or prodrug thereof, wherein:

$Q^2$ is N or $CR^{QA}$;

$R^{QB}$ is —S(O)(=$NR^a$)$R^b$, —($CR^iR^j$)$_n$—S(O)(=$NR^a$)$R^b$, —N=S(O)($R^{1a}$)$R^b$, or —O—($CR^iR^j$)$_n$—S(O)(=$NR^a$)$R^b$;

$R^{1a}$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

n is 1, 2, 3, 4, 5, or 6;

each $R^i$ is independently hydrogen, halo, or $C_{1-6}$ alkyl;

or $R^a$ and $R^i$, or $R^b$ and $R^j$, taken together with the atoms to which each is attached form a 5-8 membered heterocyclyl, wherein said heterocyclyl is optionally substituted with 1-3 independently selected $C_{1-6}$ alkyl;

each $R^j$ is independently hydrogen, halo, or $C_{1-6}$ alkyl;

or one $R^i$ and one $R^j$, taken together with the atom(s) to which each is attached, form a $C_{3-6}$ cycloalkyl, wherein said cycloalkyl is optionally substituted with 1-3 independently selected $C_{1-6}$ alkyl;

each $R^{QA}$ is independently hydrogen, halo, cyano, hydroxy, —$NR^cR^d$, —C(O)$NR^cR^d$, —S(O)$_{0-2}$R, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —C(O)($C_{1-6}$ alkyl), $C_{6-10}$ aryl optionally substituted with 1-3 independently selected —C(O)($C_{1-6}$ alkyl), and 5-10 membered heteroaryl optionally substituted with 1-6 independently selected $R^g$;

or $R^a$ or $R^b$ and an adjacent $R^{QA}$ are taken together with the atom to which each is attached to form a 5-8 membered heterocyclyl, wherein said heterocyclyl is optionally substituted with 1-2 independently selected $R^h$;

q is 0, 1, 2, 3, 4, or 5;

each $R^4$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$Z^1$ is N or $CR^5$;

$Z^2$ is N or $CR^6$;

$Z^3$ is N or $CR^7$;

$R^4$, $R^5$, $R^6$, and $R^7$ are each independently hydrogen, halo, or $C_{1-6}$ alkyl;

$L^4$ is a bond or $C_{1-5}$ alkylene;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;

$R^9$ is —C(O)$OR^{9a}$, —C(O)$NR^{9a}R^{9b}$, 5-6 membered heteroaryl optionally substituted with 1-3 independently selected $R^{9c}$, 4-6 membered heterocyclyl optionally substituted with 1-3 independently selected $R^{9c}$, or

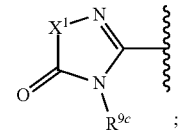

$X^1$ is O or S;

$R^{9a}$ is hydrogen or $C_{1-6}$ alkyl;

$R^{9b}$ is hydrogen, $C_{1-6}$ alkyl, —C(O)($C_{1-6}$ alkyl), —S(O)$_{0-2}$($C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or —C(O)($C_{1-6}$ alkyl);

Ring C is 3-12 membered heterocyclyl, $C_{3-15}$ cycloalkyl, or 5-10 membered heteroaryl, each of which is optionally substituted with 1-3 $R^{Ca}$;

each $R^{Ca}$ is independently halo, cyano, $C_{1-6}$ alkyl, $C_{1-6}$ haloalkyl, $C_{1-6}$ alkoxy, or $NR^cR^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

each $R^f$ is independently halo, hydroxy, —NR$^c$R$^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, —NR$^c$R$^d$, or 3 to 12 membered heterocyclyl optionally substituted with one or more substituents each independently selected from the group consisting of $C_{1-6}$ alkyl and —C(O)$C_{1-6}$ alkyl; and each $R^h$ is independently halo, cyano, hydroxy, $C_{1-6}$ alkyl, $C_{1-6}$ haloalkyl, —NH$_2$, —NH($C_{1-3}$ alkyl), —N($C_{1-3}$ alkyl)$_2$, $C_{1-3}$ alkoxy, or $C_{1-3}$ haloalkoxy.

In one aspect, provided herein are compounds of Formula IIC-(S):

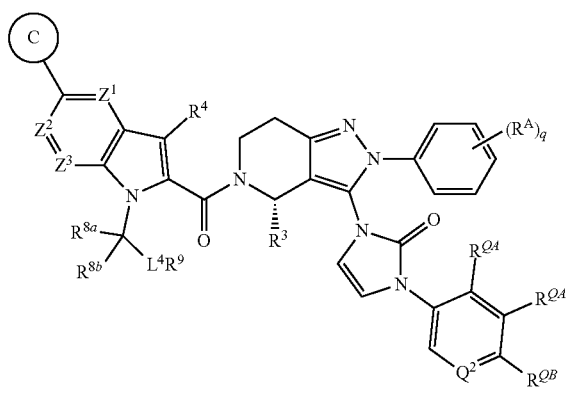

IIC-(S)

or a pharmaceutically acceptable salt, isotopically enriched analog, stereoisomer, mixture of stereoisomers, or prodrug thereof, wherein:

$Q^2$ is N or CR$^{QA}$;

$R^{QB}$ is —S(O)(=NR$^a$)R$^b$ or —(CR$^i$R$^j$)$_n$—S(O)(=NR$^a$)R$^b$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

n is 1, 2, 3, 4, 5, or 6;

each $R^i$ is independently hydrogen, halo, or $C_{1-6}$ alkyl;

or $R^a$ and $R^i$, or $R^b$ and $R^j$, taken together with the atoms to which each is attached form a 5-8 membered heterocyclyl, wherein said heterocyclyl is optionally substituted with 1-3 independently selected $C_{1-6}$ alkyl;

each $R^j$ is independently hydrogen, halo, or $C_{1-6}$ alkyl;

or one $R^i$ and one $R^j$, taken together with the atom(s) to which each is attached, form a $C_{3-6}$ cycloalkyl, wherein said cycloalkyl is optionally substituted with 1-3 independently selected $C_{1-6}$ alkyl;

each $R^{QA}$ is independently hydrogen, halo, cyano, hydroxy, —NR$^c$R$^d$, —C(O)NR$^c$R$^d$, —S(O)$_{0-2}$R, $C_{1-6}$ alkyl optionally substituted with 1-6 independently selected R$^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —C(O)($C_{1-6}$ alkyl), $C_{6-10}$ aryl optionally substituted with 1-3 independently selected —C(O)($C_{1-6}$ alkyl), and 5-10 membered heteroaryl optionally substituted with 1-6 independently selected R$^g$;

or $R^a$ or R and an adjacent $R^{QA}$ are taken together with the atom to which each is attached to form a 5-8 membered heterocyclyl, wherein said heterocyclyl is optionally substituted with 1-2 independently selected R$^h$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$Z^1$ is N or CR$^5$;

$Z^2$ is N or CR$^6$;

$Z^3$ is N or CR$^7$;

$R^4$, $R^5$, $R^6$, and $R^7$ are each independently hydrogen, halo, or $C_{1-6}$ alkyl;

$L^4$ is a bond or $C_{1-5}$ alkylene;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected R$^f$;

$R^9$ is —C(O)OR$^{9a}$, —C(O)NR$^{9a}$R$^{9b}$, 5-6 membered heteroaryl optionally substituted with 1-3 independently selected R$^{9c}$, 4-6 membered heterocyclyl optionally substituted with 1-3 independently selected R$^{9c}$, or

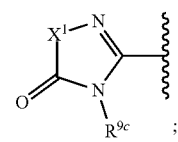

$X^1$ is O or S;

$R^{9a}$ is hydrogen or $C_{1-6}$ alkyl;

$R^{9b}$ is hydrogen, $C_{1-6}$ alkyl, —C(O)($C_{1-6}$ alkyl), —S(O)$_{0-2}$($C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or —C(O)($C_{1-6}$ alkyl);

Ring C is 3-12 membered heterocyclyl, $C_{3-15}$ cycloalkyl, or 5-10 membered heteroaryl, each of which is optionally substituted with 1-3 $R^{Ca}$;

each $R^{Ca}$ is independently halo, cyano, $C_{1-6}$ alkyl, $C_{1-6}$ haloalkyl, $C_{1-6}$ alkoxy, or $NR^cR^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

each $R^f$ is independently halo, hydroxy, —$NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, —$NR^cR^d$, or 3 to 12 membered heterocyclyl optionally substituted with one or more substituents each independently selected from the group consisting of $C_{1-6}$ alkyl and —C(O)$C_{1-6}$ alkyl; and each $R^h$ is independently halo, cyano, hydroxy, $C_{1-6}$ alkyl, $C_{1-6}$ haloalkyl, —$NH_2$, —$NH(C_{1-3}$ alkyl), —$N(C_{1-3}$ alkyl)$_2$, $C_{1-3}$ alkoxy, or $C_{1-3}$ haloalkoxy.

In some embodiments, $R^4$ is hydrogen. In some embodiments, $R^4$, $R^5$, $R^6$, and $R^b$ are each hydrogen.

In some embodiments, $Z^1$ is CH. In some embodiments, $Z^1$ is N.

In some embodiments, $Z^2$ is CH. In some embodiments, $Z^2$ is N.

In some embodiments, $Z^3$ is CH. In some embodiments, $Z^3$ is N.

In some embodiments, one of $Z^1$, $Z^2$, and $Z^3$ is N or CH, and the other two of $Z^1$, $Z^2$, and $Z^3$ are CH. In some embodiments, one of $Z^1$, $Z^2$, and $Z^3$ is N, and the other two of $Z^1$, $Z^2$, and $Z^3$ are CH. In some embodiments, $Z^1$, $Z^2$, and $Z^3$ are each CH.

In some embodiments, $R^4$ is hydrogen; and one of $Z^1$, $Z^2$, and $Z^3$ is N or CH, and the other two of $Z^1$, $Z^2$, and $Z^3$ are CH. In some embodiments, $R^4$ is hydrogen; and one of $Z^1$, $Z^2$, and $Z^3$ is N, and the other two of $Z^1$, $Z^2$, and $Z^3$ are CH.

In some embodiments, $R^4$ is hydrogen; and $Z^1$, $Z^2$, and $Z^3$ are each CH.

In some embodiments, $R^{QB}$ is —S(O)(=$NR^a$)$R^b$.

In some embodiments, provided herein is a compound of Formula IID:

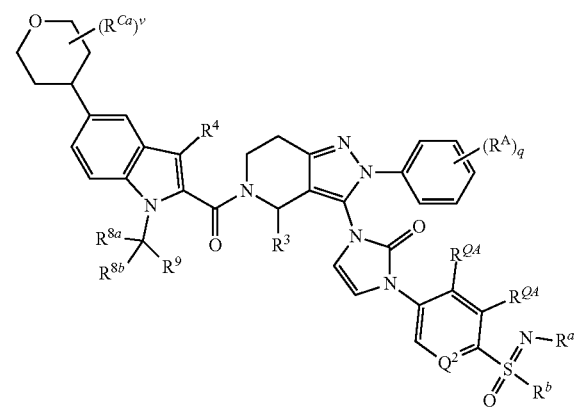

IID or a pharmaceutically acceptable salt, isotopically enriched analog, stereoisomer, mixture of stereoisomers, or prodrug thereof, wherein q is 0, 1, 2, 3, 4, or 5; v is 0, 1, 2, or 3; and $R^a$, $R^b$, $R^{Ca}$, $R^{8a}$, $R^{8b}$, $R^9$, $R^4$, $R^3$, $Q^2$, and $R^{QA}$ are each independently as defined herein.

In some embodiments, provided herein is a compound of Formula IID-(S):

IID-(S)

or a pharmaceutically acceptable salt, isotopically enriched analog, stereoisomer, mixture of stereoisomers, or prodrug thereof, wherein q is 0, 1, 2, 3, 4, or 5; v is 0, 1, 2, or 3; and $R^a$, $R^b$, $R^{Ca}$, $R^{8a}$, $R^{8b}$, $R^9$, $R^4$, $R^3$, $Q^2$, and $R^{QA}$ are each independently as defined herein.

In one aspect, provided herein are compounds of Formula IID-(S):

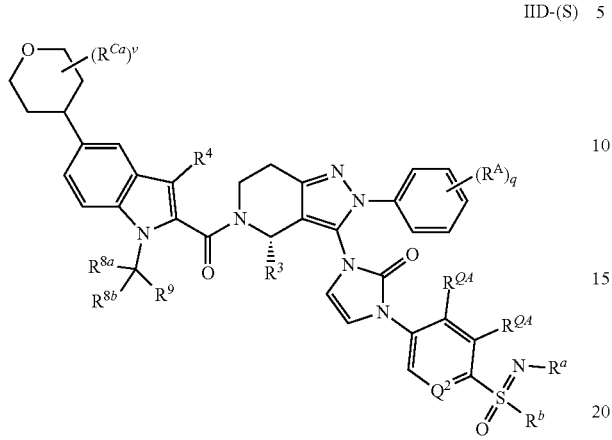

IID-(S)

or a pharmaceutically acceptable salt, isotopically enriched analog, stereoisomer, mixture of stereoisomers, or prodrug thereof, wherein:

$Q^2$ is N or $CR^{QA}$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

each $R^{QA}$ is independently hydrogen, halo, cyano, hydroxy, —$NR^cR^d$, —$C(O)NR^cR^d$, —$S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —$C(O)(C_{1-6}$ alkyl), $C_{6-10}$ aryl optionally substituted with 1-3 independently selected —$C(O)(C_{1-6}$ alkyl), and 5-10 membered heteroaryl optionally substituted with 1-6 independently selected $R^g$;

or $R^a$ or $R^b$ and an adjacent $R^{QA}$ are taken together with the atom to which each is attached to form a 5-8 membered heterocyclyl, wherein said heterocyclyl is optionally substituted with 1-2 independently selected $R^h$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;

$R^9$ is —$C(O)OR^{9a}$, —$C(O)NR^{9a}R^{9b}$, 5-6 membered heteroaryl optionally substituted with 1-3 independently selected $R^{9c}$, 4-6 membered heterocyclyl optionally substituted with 1-3 independently selected $R^{9c}$, or

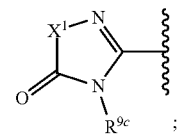

$X^1$ is O or S;

$R^{9a}$ is hydrogen or $C_{1-6}$ alkyl;

$R^{9b}$ is hydrogen, $C_{1-6}$ alkyl, —$C(O)(C_{1-6}$ alkyl), —$S(O)_{0-2}(C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or —$C(O)(C_{1-6}$ alkyl);

v is 0, 1, 2, or 3;

each $R^{Ca}$ is independently halo, cyano, $C_{1-6}$ alkyl, $C_{1-6}$ haloalkyl, $C_{1-6}$ alkoxy, or $NR^cR^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, —$C(O)(C_{1-6}$ alkyl), —$C(O)(C_{3-6}$ cycloalkyl), —$C(O)O(C_{1-6}$ alkyl), —$S(O)_{1-2}(C_{1-6}$ alkyl), or —$S(O)_{1-2}(C_{3-6}$ cycloalkyl), wherein the $C_{1-6}$ alkyl, —$C(O)(C_{1-6}$ alkyl), —$C(O)(C_{3-6}$ cycloalkyl), —$C(O)O(C_{1-6}$ alkyl), —$S(O)_{1-2}(C_{1-6}$ alkyl), and —$S(O)_{1-2}(C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

each $R^f$ is independently halo, hydroxy, —$NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, —$NR^cR^d$, or 3 to 12 membered heterocyclyl optionally substituted with one or more substituents each independently selected from the group consisting of $C_{1-6}$ alkyl and —$C(O)C_{1-6}$ alkyl; and each $R^h$ is independently halo, cyano, hydroxy, $C_{1-6}$ alkyl, $C_{1-6}$ haloalkyl, —$NH_2$, —$NH(C_{1-3}$ alkyl), —$N(C_{1-3}$ alkyl)$_2$, $C_{1-3}$ alkoxy, or $C_{1-3}$ haloalkoxy.

In some embodiments, provided herein is a compound of Formula IIE:

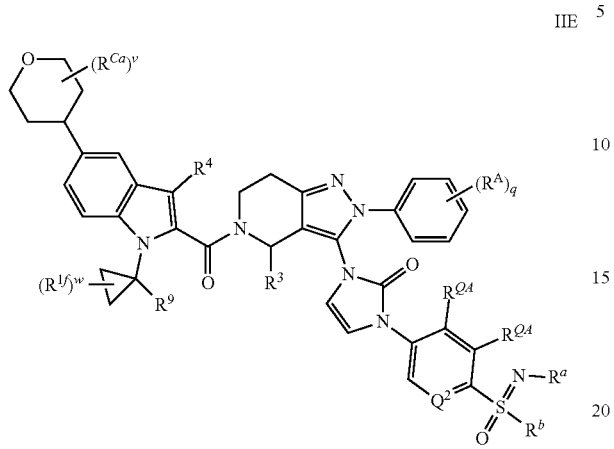

IIE or a pharmaceutically acceptable salt, isotopically enriched analog, stereoisomer, mixture of stereoisomers, or prodrug thereof, wherein q is 0, 1, 2, 3, 4, or 5; v is 0, 1, 2, or 3; w is 0, 1, 2, or 3; each $R^{1f}$ is independently $C_{1-6}$ alkyl, wherein each $C_{1-6}$ alkyl is independently optionally substituted with 1-6 independently selected $R^f$; and $R^a$, $R^b$, $R^{Ca}$, $R^9$, $R^4$, $R^3$, $Q^2$, and $R^{QA}$ are each independently as defined herein.

In some embodiments, provided herein is a compound of Formula IIE-(S):

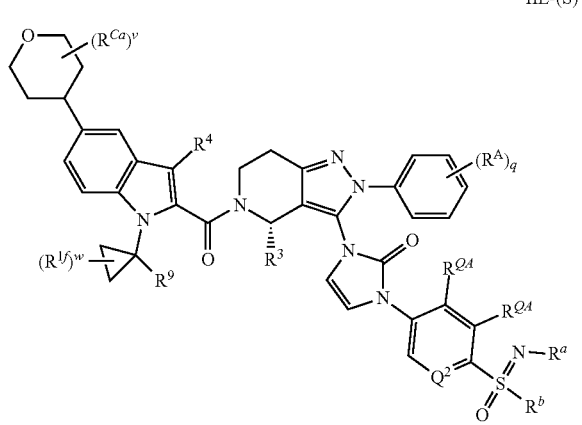

IIE-(S)

or a pharmaceutically acceptable salt, isotopically enriched analog, stereoisomer, mixture of stereoisomers, or prodrug thereof, wherein q is 0, 1, 2, 3, 4, or 5; v is 0, 1, 2, or 3; w is 0, 1, 2, or 3; $R^{1f}$ is independently $C_{1-6}$ alkyl, wherein each $C_{1-6}$ alkyl is independently optionally substituted with 1-6 independently selected $R^f$; and $R^a$, $R^b$, $R^{Ca}$, $R^9$, $R^4$, $R^3$, $Q^2$, and $R^{QA}$ are each independently as defined herein.

In one aspect, provided herein are compounds of Formula IIE-(S):

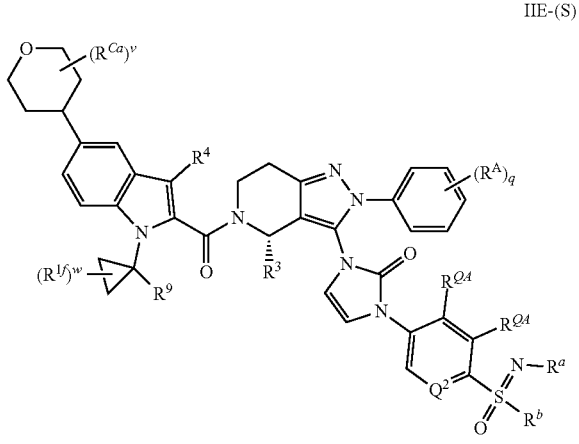

IIE-(S)

or a pharmaceutically acceptable salt, isotopically enriched analog, stereoisomer, mixture of stereoisomers, or prodrug thereof, wherein:

$Q^2$ is N or $CR^{QA}$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

each $R^{QA}$ is independently hydrogen, halo, cyano, hydroxy, —$NR^cR^d$, —$C(O)NR^cR^d$, —$S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —C(O)($C_{1-6}$ alkyl), $C_{6-10}$ aryl optionally substituted with 1-3 independently selected —C(O)($C_{1-6}$ alkyl), and 5-10 membered heteroaryl optionally substituted with 1-6 independently selected $R^g$;

or $R^a$ or $R^b$ and an adjacent $R^{QA}$ are taken together with the atom to which each is attached to form a 5-8 membered heterocyclyl, wherein said heterocyclyl is optionally substituted with 1-2 independently selected $R^h$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

R$^3$ is hydrogen or C$_{1-6}$ alkyl optionally substituted with 1-6 substituents independently selected from the group consisting of halo, hydroxy, and C$_{1-6}$ alkoxy;

R$^9$ is —C(O)OR$^{9a}$, —C(O)NR$^{9a}$R$^{9b}$, 5-6 membered heteroaryl optionally substituted with 1-3 independently selected R$^{9c}$, 4-6 membered heterocyclyl optionally substituted with 1-3 independently selected R$^{9c}$, or

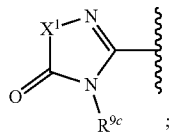

X$^1$ is O or S;

R$^{9a}$ is hydrogen or C$_{1-6}$ alkyl;

R$^{9b}$ is hydrogen, C$_{1-6}$ alkyl, —C(O)(C$_{1-6}$ alkyl), —S(O)$_{0-2}$(C$_{1-6}$ alkyl), or cyano;

each R$^{9c}$ is independently hydrogen, oxo, C$_{1-6}$ alkyl optionally substituted with 1-6 independently selected halo and C$_{1-6}$ alkoxy, or —C(O)(C$_{1-6}$ alkyl);

v is 0, 1, 2, or 3;

each R$^{Ca}$ is independently halo, cyano, C$_{1-6}$ alkyl, C$_{1-6}$ haloalkyl, C$_{1-6}$ alkoxy, or NR$^c$R$^d$;

or a pair of R$^{Ca}$ on the same or different ring atoms, taken together with the ring atom(s) to which each is attached, forms a carbocyclic ring including 3-8 ring atoms;

each R$^c$ and R$^d$ are each independently hydrogen, C$_{1-6}$ alkyl, —C(O)(C$_{1-6}$ alkyl), —C(O)(C$_{3-6}$ cycloalkyl), —C(O)O(C$_{1-6}$ alkyl), —S(O)$_{1-2}$(C$_{1-6}$ alkyl), or —S(O)$_{1-2}$(C$_{3-6}$ cycloalkyl), wherein the C$_{1-6}$ alkyl, —C(O)(C$_{1-6}$ alkyl), —C(O)(C$_{3-6}$ cycloalkyl), —C(O)O(C$_{1-6}$ alkyl), —S(O)$_{1-2}$(C$_{1-6}$ alkyl), and —S(O)$_{1-2}$(C$_{3-6}$ cycloalkyl) are each optionally substituted with 1-6 substituents independently selected from the group consisting of hydroxy, halo, and C$_{1-6}$ alkoxy;

each R$^e$ is independently hydrogen, C$_{1-6}$ alkyl, or C$_{1-6}$ haloalkyl;

w is 0, 1, 2, or 3;

each R$^1$ is independently C$_{1-6}$ alkyl, wherein each C$_{1-6}$ alkyl is independently optionally substituted with 1-6 independently selected R$^f$;

each R$^f$ is independently halo, hydroxy, —NR$^c$R$^d$, C$_{1-6}$ alkoxy, C$_{1-6}$ haloalkoxy, or 3-12 membered heterocyclyl which is optionally substituted with 1-4 substituents each independently selected from the group consisting of hydroxy, C$_{1-6}$ alkyl, and 3-12 membered heterocyclyl;

each R$^g$ is independently C$_{1-6}$ alkyl, C$_{1-6}$ alkoxy, —NR$^c$R$^d$, or 3 to 12 membered heterocyclyl optionally substituted with one or more substituents each independently selected from the group consisting of C$_{1-6}$ alkyl and —C(O)C$_{1-6}$ alkyl; and each R$^h$ is independently halo, cyano, hydroxy, C$_{1-6}$ alkyl, C$_{1-6}$ haloalkyl, —NH$_2$, —NH(C$_{1-3}$ alkyl), —N(C$_{1-3}$ alkyl)$_2$, C$_{1-3}$ alkoxy, or C$_{1-3}$ haloalkoxy.

In some embodiments, R$^{QB}$ is —(CR$^i$R$^j$)$_n$—S(O)(=NR$^a$)R$^b$. In some embodiments, n is 1 or 2. In some embodiments, n is 1. In some embodiments, n is 2.

In some embodiments, R$^a$ and an adjacent R$^{QA}$ are taken together with the atom to which each is attached to form a 5-8 membered heterocyclyl, wherein said heterocyclyl is optionally substituted with 1-2 independently selected R$^h$.

In some embodiments, provided herein is a compound of Formula IIF:

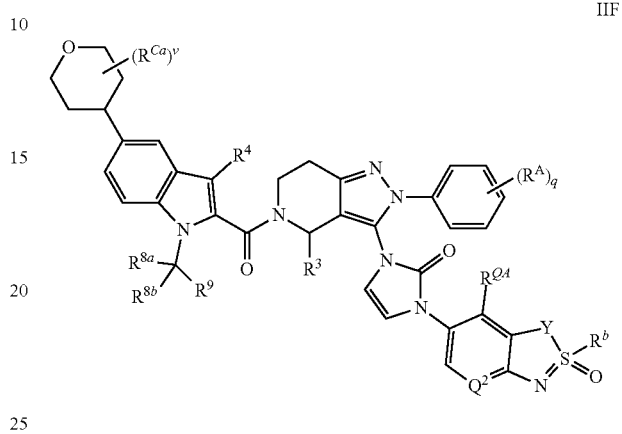

IIF or a pharmaceutically acceptable salt, isotopically enriched analog, stereoisomer, mixture of stereoisomers, or prodrug thereof, wherein Y is —(CR$^i$R$^j$)$_n$—; q is 0, 1, 2, 3, 4, or 5; v is 0, 1, 2, or 3; and n, R$^b$, R$^i$, R$^j$, R$^{Ca}$, R$^{8a}$, R$^{8b}$, R$^9$, R$^A$, R$^3$, Q$^2$, and R$^{QA}$ are each independently as defined herein.

In some embodiments, provided herein is a compound of Formula IIF-(S):

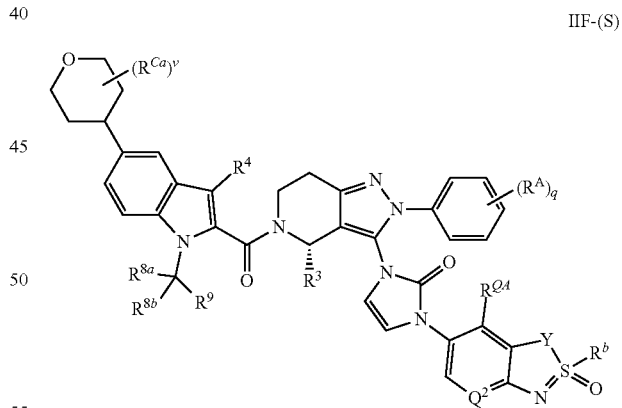

IIF-(S)

or a pharmaceutically acceptable salt, isotopically enriched analog, stereoisomer, mixture of stereoisomers, or prodrug thereof, wherein Y is —(CR$^i$R$^j$)$_n$—; q is 0, 1, 2, 3, 4, or 5; v is 0, 1, 2, or 3; and n, R$^b$, R$^i$, R$^j$, R$^{Ca}$, R$^{8a}$, R$^{8b}$, R$^9$, R$^A$, R, Q$^2$, and R$^{QA}$ are each independently as defined herein.

In one aspect, provided herein are compounds of Formula IIF-(S):

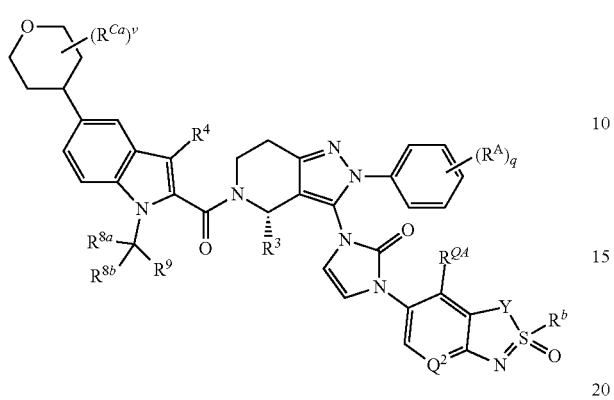

IIF-(S)

or a pharmaceutically acceptable salt, isotopically enriched analog, stereoisomer, mixture of stereoisomers, or prodrug thereof, wherein:

$Q^2$ is N or $CR^{QA}$;

Y is $-(CR^iR^j)_n-$;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

n is 1, 2, 3, 4, 5, or 6;

each $R^i$ is independently hydrogen, halo, or $C_{1-6}$ alkyl;

each $R^j$ is independently hydrogen, halo, or $C_{1-6}$ alkyl;

or one $R^i$ and one $R^j$ on adjacent carbon atoms taken together with the atom(s) to which each is attached form an alkene, wherein said alkene is optionally substituted with 1-3 independently selected $C_{1-6}$ alkyl;

each $R^{QA}$ is independently hydrogen, halo, cyano, hydroxy, $-NR^cR^d$, $-C(O)NR^cR^d$, $-S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and $-C(O)(C_{1-6}$ alkyl), $C_{6-10}$ aryl optionally substituted with 1-3 independently selected $-C(O)(C_{1-6}$ alkyl), and 5-10 membered heteroaryl optionally substituted with 1-6 independently selected $R^g$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;

$R^9$ is $-C(O)OR^{9a}$, $-C(O)NR^{9a}R^{9b}$, 5-6 membered heteroaryl optionally substituted with 1-3 independently selected $R^{9c}$, 4-6 membered heterocyclyl optionally substituted with 1-3 independently selected $R^{9c}$, or

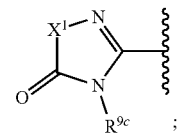

;

$X^1$ is O or S;

$R^{9a}$ is hydrogen or $C_{1-6}$ alkyl;

$R^{9b}$ is hydrogen, $C_{1-6}$ alkyl, $-C(O)(C_{1-6}$ alkyl), $-S(O)_{0-2}(C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or $-C(O)(C_{1-6}$ alkyl);

v is 0, 1, 2, or 3;

each $R^{Ca}$ is independently halo, cyano, $C_{1-6}$ alkyl, $C_{1-6}$ haloalkyl, $C_{1-6}$ alkoxy, or $NR^cR^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), or $-S(O)_{1-2}(C_{3-6}$ cycloalkyl), wherein the $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), and $-S(O)_{1-2}(C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

each $R^f$ is independently halo, hydroxy, $-NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, $-NR^cR^d$, or 3 to 12 membered heterocyclyl optionally substituted with one or more substituents each independently selected from the group consisting of $C_{1-6}$ alkyl and $-C(O)C_{1-6}$ alkyl; and each $R^h$ is independently halo, cyano, hydroxy, $C_{1-6}$ alkyl, $C_{1-6}$ haloalkyl, $-NH_2$, $-NH(C_{1-3}$ alkyl), $-N(C_{1-3}$ alkyl)$_2$, $C_{1-3}$ alkoxy, or $C_{1-3}$ haloalkoxy.

In some embodiments, provided herein is a compound of Formula IIG:

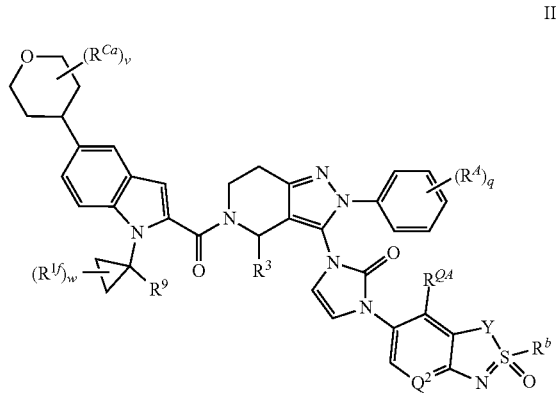

IIG or a pharmaceutically acceptable salt, isotopically enriched analog, stereoisomer, mixture of stereoisomers, or prodrug thereof, wherein Y is —(CR$^i$R$^j$)$_n$—; q is 0, 1, 2, 3, 4, or 5; w is 0, 1, 2, or 3; v is 0, 1, 2, or 3; each R$^{1f}$ is independently C$_{1-6}$ alkyl, wherein each C$_{1-6}$ alkyl is independently optionally substituted with 1-6 independently selected R$^f$; and n, R$^b$, R$^i$, R$^j$, R$^{Ca}$, R$^9$, R$^A$, R$^3$, Q$^2$, and R$^{QA}$ are each independently as defined herein.

In some embodiments, provided herein is a compound of Formula IIG-(S):

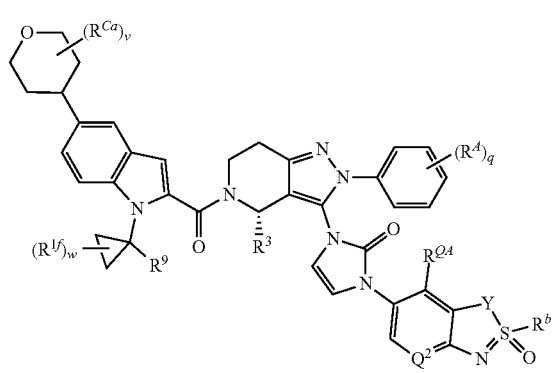

IIG-(S)

or a pharmaceutically acceptable salt, isotopically enriched analog, stereoisomer, mixture of stereoisomers, or prodrug thereof, wherein Y is —(CR$^i$R$^j$)$_n$—; q is 0, 1, 2, 3, 4, or 5; w is 0, 1, 2, or 3; v is 0, 1, 2, or 3; each R$^{1f}$ is independently C$_{1-6}$ alkyl, wherein each C$_{1-6}$ alkyl is independently optionally substituted with 1-6 independently selected R$^f$; and n, R$^b$, R$^i$, R$^j$, R$^{Ca}$, R$^9$, R$^A$, R$^3$, Q$^2$, and R$^{QA}$ are each independently as defined herein.

In one aspect, provided herein are compounds of Formula IIG-(S):

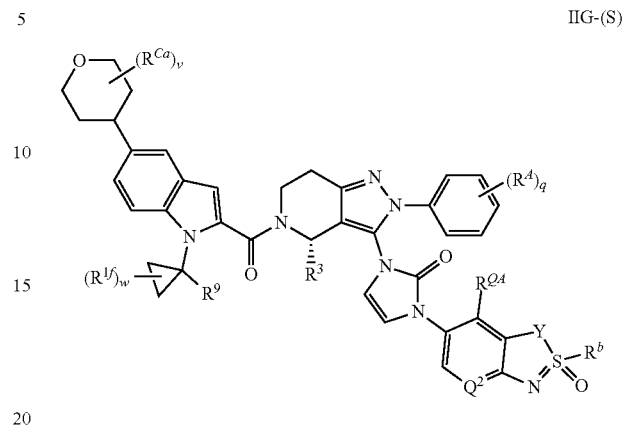

IIG-(S)

or a pharmaceutically acceptable salt, isotopically enriched analog, stereoisomer, mixture of stereoisomers, or prodrug thereof, wherein:

Q$^2$ is N or CR$^{QA}$;

Y is —(CR$^i$R$^j$)$_n$—;

R$^b$ is C$_{1-6}$ alkyl which is optionally substituted with 1-6 substituents each independently selected from the group consisting of C$_{1-6}$ alkoxy, C$_{3-6}$ cycloalkyl, and halo, C$_{3-6}$ cycloalkyl optionally substituted with 1-3 substituents each independently selected from the group consisting of C$_{1-3}$ alkyl and halo, or C$_{6-10}$ aryl optionally substituted with 1-3 independently selected C$_{1-3}$ alkyl;

n is 1, 2, 3, 4, 5, or 6;

each R$^i$ is independently hydrogen, halo, or C$_{1-6}$ alkyl;

each R$^j$ is independently hydrogen, halo, or C$_{1-6}$ alkyl;

or one R$^i$ and one R$^j$ on adjacent carbon atoms taken together with the atom(s) to which each is attached form an alkene, wherein said alkene is optionally substituted with 1-3 independently selected C$_{1-6}$ alkyl;

each R$^{QA}$ is independently hydrogen, halo, cyano, hydroxy, —NR$^c$R$^d$, —C(O)NR$^c$R$^d$, —S(O)$_{0-2}$R, C$_{1-6}$ alkyl optionally substituted with 1-6 independently selected R$^f$, C$_{1-6}$ alkoxy optionally substituted with 1-6 substituents each independently selected from the group consisting of hydroxy, halo, and C$_{1-6}$ alkoxy, 3-12 membered heterocyclyl optionally substituted with one or more substituents each independently selected from the group consisting of C$_{1-6}$ alkyl and —C(O)(C$_{1-6}$ alkyl), C$_{6-10}$ aryl optionally substituted with 1-3 independently selected —C(O)(C$_{1-6}$ alkyl), and 5-10 membered heteroaryl optionally substituted with 1-6 independently selected R$^g$;

q is 0, 1, 2, 3, 4, or 5;

each R$^A$ is independently halo, C$_{1-6}$ alkyl, C$_{1-6}$ haloalkyl, C$_{1-6}$ alkoxy, or C$_{3-6}$ cycloalkyl;

R$^3$ is hydrogen or C$_{1-6}$ alkyl optionally substituted with 1-6 substituents independently selected from the group consisting of halo, hydroxy, and C$_{1-6}$ alkoxy;

R⁹ is —C(O)OR⁹ᵃ, —C(O)NR⁹ᵃR⁹ᵇ, 5-6 membered heteroaryl optionally substituted with 1-3 independently selected R⁹ᶜ, 4-6 membered heterocyclyl optionally substituted with 1-3 independently selected R⁹ᶜ, or;

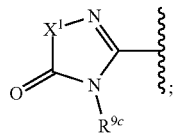

X¹ is O or S;

R⁹ᵃ is hydrogen or $C_{1-6}$ alkyl;

R⁹ᵇ is hydrogen, $C_{1-6}$ alkyl, —C(O)($C_{1-6}$ alkyl), —S(O)$_{0-2}$($C_{1-6}$ alkyl), or cyano;

each R⁹ᶜ is independently hydrogen, oxo, $C_{1-6}$ alkyl optionally substituted with 1-6 independently selected halo and $C_{1-6}$ alkoxy, or —C(O)($C_{1-6}$ alkyl);

v is 0, 1, 2, or 3;

each $R^{Ca}$ is independently halo, cyano, $C_{1-6}$ alkyl, $C_{1-6}$ haloalkyl, $C_{1-6}$ alkoxy, or NR$^c$R$^d$;

or a pair of $R^{Ca}$ on the same or different ring atoms, taken together with the ring atom(s) to which each is attached, forms a carbocyclic ring including 3-8 ring atoms;

each R$^c$ and R$^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;

each R$^e$ is independently hydrogen, $C_{1-6}$ alkyl, or $C_{1-6}$ haloalkyl;

w is 0, 1, 2, or 3;

each R¹ is independently $C_{1-6}$ alkyl, wherein each $C_{1-6}$ alkyl is independently optionally substituted with 1-6 independently selected R$^f$;

each R$^f$ is independently halo, hydroxy, —NR$^c$R$^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each R$^g$ is independently $C_{1-6}$ alkyl, $C_{1-6}$ alkoxy, —NR$^c$R$^d$, or 3 to 12 membered heterocyclyl optionally substituted with one or more substituents each independently selected from the group consisting of $C_{1-6}$ alkyl and —C(O)$C_{1-6}$ alkyl; and each R$^h$ is independently halo, cyano, hydroxy, $C_{1-6}$ alkyl, $C_{1-6}$ haloalkyl, —NH₂, —NH($C_{1-3}$ alkyl), —N($C_{1-3}$ alkyl)₂, $C_{1-3}$ alkoxy, or $C_{1-3}$ haloalkoxy.

In some embodiments, provided herein is a compound of Formula IIH:

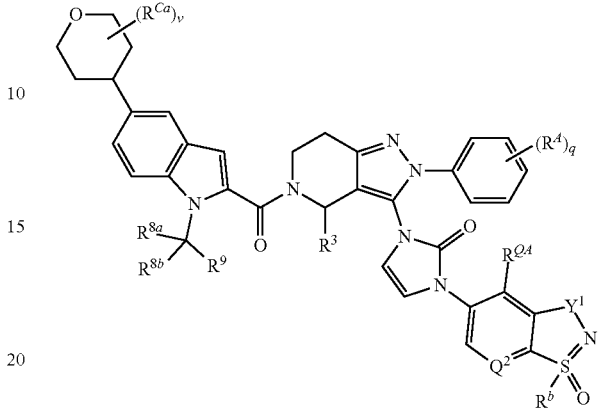

IIH or a pharmaceutically acceptable salt, isotopically enriched analog, stereoisomer, mixture of stereoisomers, or prodrug thereof, wherein Y¹ is $C_{1-3}$ alkylene or $C_2$ alkenylene, wherein the $C_{1-3}$ alkylene or $C_2$ alkenylene is optionally substituted with 1-2 independently selected R$^h$; q is 0, 1, 2, 3, 4, or 5; v is 0, 1, 2, or 3; and R$^b$, $R^{Ca}$, R⁸ᵃ, R⁸ᵇ, R⁹, R$^A$, R³, Q², and $R^{QA}$ are each independently as defined herein.

In some embodiments, provided herein is a compound of Formula IIH-(S):

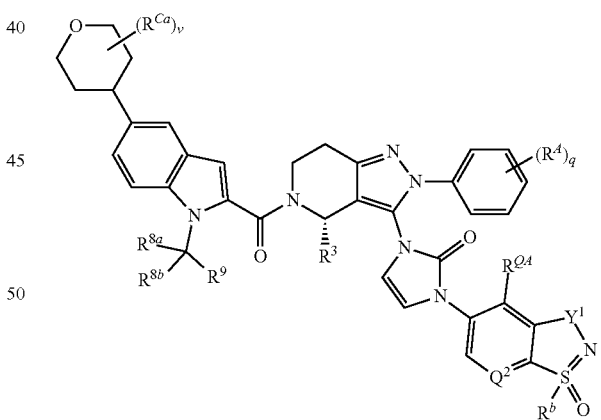

IIH-(S)

or a pharmaceutically acceptable salt, isotopically enriched analog, stereoisomer, mixture of stereoisomers, or prodrug thereof, wherein Y¹ is $C_{1-3}$ alkylene or $C_2$ alkenylene, wherein the $C_{1-3}$ alkylene or $C_2$ alkenylene is optionally substituted with 1-2 independently selected R$^h$; q is 0, 1, 2, 3, 4, or 5; v is 0, 1, 2, or 3; and R$^b$, $R^{Ca}$, R⁸ᵃ, R⁸ᵇ, R⁹, R$^A$, R³, Q², and $R^{QA}$ are each independently as defined herein.

In one aspect, provided herein are compounds of Formula IIH-(S):

IIH-(S)

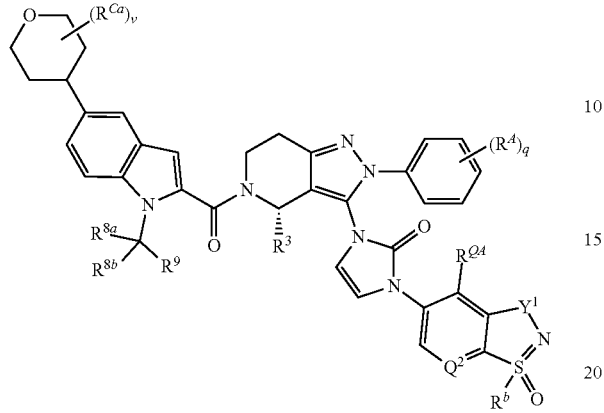

or a pharmaceutically acceptable salt, isotopically enriched analog, stereoisomer, mixture of stereoisomers, or prodrug thereof, wherein:

$Q^2$ is N or $CR^{QA}$;

$Y^1$ is $C_{1-3}$ alkylene or $C_2$ alkenylene, wherein the $C_{1-3}$ alkylene or $C_2$ alkenylene is optionally substituted with 1-2 independently selected $R^h$.

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

each $R^{QA}$ is independently hydrogen, halo, cyano, hydroxy, $-NR^cR^d$, $-C(O)NR^cR^d$, $-S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and $-C(O)(C_{1-6}$ alkyl), $C_{6-10}$ aryl optionally substituted with 1-3 independently selected $-C(O)(C_{1-6}$ alkyl), and 5-10 membered heteroaryl optionally substituted with 1-6 independently selected $R^g$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$R^{8a}$ and $R^{8b}$ are each independently hydrogen or $C_{1-6}$ alkyl optionally substituted with one or more substituents independently selected from the group consisting of halo and $C_{3-15}$ cycloalkyl; or $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;

$R^9$ is $-C(O)OR^{9a}$, $-C(O)NR^{9a}R^{9b}$, 5-6 membered heteroaryl optionally substituted with 1-3 independently selected $R^{9c}$, 4-6 membered heterocyclyl optionally substituted with 1-3 independently selected $R^{9c}$, or

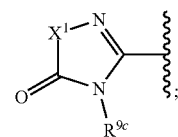

$X^1$ is O or S;

$R^{9a}$ is hydrogen or $C_{1-6}$ alkyl;

$R^{9b}$ is hydrogen, $C_{1-6}$ alkyl, $-C(O)(C_{1-6}$ alkyl), $-S(O)_{0-2}(C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or $-C(O)(C_{1-6}$ alkyl);

v is 0, 1, 2, or 3;

each $R^{Ca}$ is independently halo, cyano, $C_{1-6}$ alkyl, $C_{1-6}$ haloalkyl, $C_{1-6}$ alkoxy, or $NR^cR^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), or $-S(O)_{1-2}(C_{3-6}$ cycloalkyl), wherein the $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), and $-S(O)_{1-2}(C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

each $R^f$ is independently halo, hydroxy, $-NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, $-NR^cR^d$, or 3 to 12 membered heterocyclyl optionally substituted with one or more substituents each independently selected from the group consisting of $C_{1-6}$ alkyl and $-C(O)C_{1-6}$ alkyl; and each $R^h$ is independently halo, cyano, hydroxy, $C_{1-6}$ alkyl, $C_{1-6}$ haloalkyl, $-NH_2$, $-NH(C_{1-3}$ alkyl), $-N(C_{1-3}$ alkyl)$_2$, $C_{1-3}$ alkoxy, or $C_{1-3}$ haloalkoxy.

In some embodiments, provided herein is a compound of Formula III:

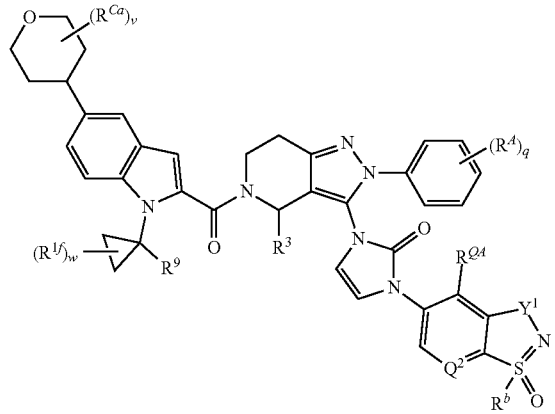

IIJ or a pharmaceutically acceptable salt, isotopically enriched analog, stereoisomer, mixture of stereoisomers, or prodrug thereof, wherein $Y^1$ is $C_{1-3}$ alkylene or $C_2$ alkenylene, wherein the $C_{1-3}$ alkylene or $C_2$ alkenylene is optionally substituted with 1-2 independently selected $R^h$; q is 0, 1, 2, 3, 4, or 5; w is 0, 1, 2, or 3; v is 0, 1, 2, or 3; each $R^{1f}$ is independently $C_{1-6}$ alkyl, wherein each $C_{1-6}$ alkyl is independently optionally substituted with 1-6 independently selected $R^f$; and R, $R^{Ca}$, $R^9$, $R^A$, $R^3$, $Q^2$, and $R^{QA}$ are each independently as defined herein.

In some embodiments, provided herein is a compound of Formula IIJ-(S):

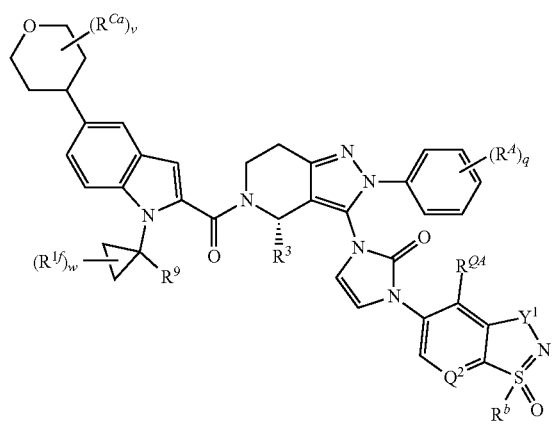

IIJ-(S)

or a pharmaceutically acceptable salt, isotopically enriched analog, stereoisomer, mixture of stereoisomers, or prodrug thereof, wherein $Y^1$ is $C_{1-3}$ alkylene or $C_2$ alkenylene, wherein the $C_{1-3}$ alkylene or $C_2$ alkenylene is optionally substituted with 1-2 independently selected $R^h$; q is 0, 1, 2, 3, 4, or 5; w is 0, 1, 2, or 3; v is 0, 1, 2, or 3; each $R^{1f}$ is independently $C_{1-6}$ alkyl, wherein each $C_{1-6}$ alkyl is independently optionally substituted with 1-6 independently selected $R^f$; and R, $R^{Ca}$, $R^9$, $R^A$, $R^3$, $Q^2$, and $R^{QA}$ are each independently as defined herein.

In one aspect, provided herein are compounds of Formula IIJ-(S):

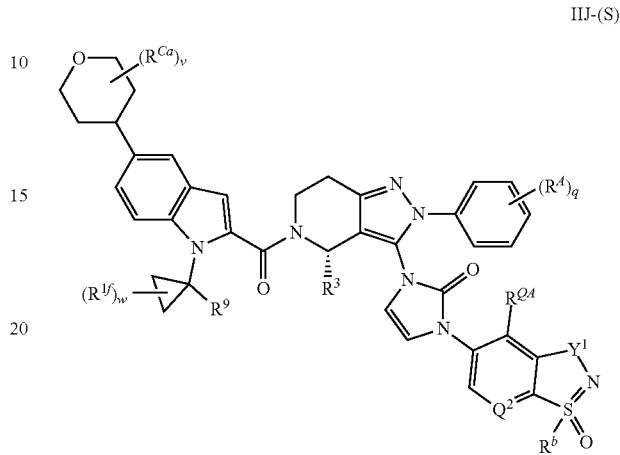

IIJ-(S)

or a pharmaceutically acceptable salt, isotopically enriched analog, stereoisomer, mixture of stereoisomers, or prodrug thereof, wherein:

$Q^2$ is N or $CR^{QA}$;

$Y^1$ is $C_{1-3}$ alkylene or $C_2$ alkenylene, wherein the $C_{1-3}$ alkylene or $C_2$ alkenylene is optionally substituted with 1-2 independently selected $R^h$.

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

n is 1, 2, 3, 4, 5, or 6;

each $R^1$ is independently hydrogen, halo, or $C_{1-6}$ alkyl;

each $R^j$ is independently hydrogen, halo, or $C_{1-6}$ alkyl;

or one $R^1$ and one $R^j$ on adjacent carbon atoms taken together with the atom(s) to which each is attached form an alkene, wherein said alkene is optionally substituted with 1-3 independently selected $C_{1-6}$ alkyl;

each $R^{QA}$ is independently hydrogen, halo, cyano, hydroxy, $-NR^cR^d$, $-C(O)NR^cR^d$, $-S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and $-C(O)(C_{1-6}$ alkyl), $C_{6-10}$ aryl optionally substituted with 1-3 independently selected $-C(O)(C_{1-6}$ alkyl), and 5-10 membered heteroaryl optionally substituted with 1-6 independently selected $R^g$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$R^9$ is —C(O)OR$^{9a}$, —C(O)NR$^{9a}$R$^{9b}$, 5-6 membered heteroaryl optionally substituted with 1-3 independently selected R$^{9c}$, 4-6 membered heterocyclyl optionally substituted with 1-3 independently selected R$^{9c}$, or

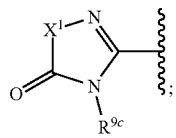

$X^1$ is O or S;

$R^{9a}$ is hydrogen or $C_{1-6}$ alkyl;

$R^{9b}$ is hydrogen, $C_{1-6}$ alkyl, —C(O)($C_{1-6}$ alkyl), —S(O)$_{0-2}$($C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or —C(O)($C_{1-6}$ alkyl);

v is 0, 1, 2, or 3;

each $R^{Ca}$ is independently halo, cyano, $C_{1-6}$ alkyl, $C_{1-6}$ haloalkyl, $C_{1-6}$ alkoxy, or NR$^c$R$^d$;

or a pair of R$^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

w is 0, 1, 2, or 3;

each $R^1$ is independently $C_{1-6}$ alkyl, wherein each $C_{1-6}$ alkyl is independently optionally substituted with 1-6 independently selected $R^f$;

each $R^f$ is independently halo, hydroxy, —NR$^c$R$^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, —NR$^c$R$^d$, or 3 to 12 membered heterocyclyl optionally substituted with one or more substituents each independently selected from the group consisting of $C_{1-6}$ alkyl and —C(O)$C_{1-6}$ alkyl; and each $R^h$ is independently halo, cyano, hydroxy, $C_{1-6}$ alkyl, $C_{1-6}$ haloalkyl, —NH$_2$, —NH($C_{1-3}$ alkyl), —N($C_{1-3}$ alkyl)$_2$, $C_{1-3}$ alkoxy, or $C_{1-3}$ haloalkoxy.

In some embodiments, $R^{QB}$ is —O—(CR$^i$R$^j$)$_n$—S(O)(=NR$^a$)R$^b$. In some embodiments, n is 3. In some embodiments, $R^b$ and $R^1$, taken together with the atoms to which each is attached, form a 5-8 membered heterocyclyl, wherein said heterocyclyl is optionally substituted with 1-3 independently selected $C_{1-6}$ alkyl.

In some embodiments, provided herein is a compound of Formula IIK:

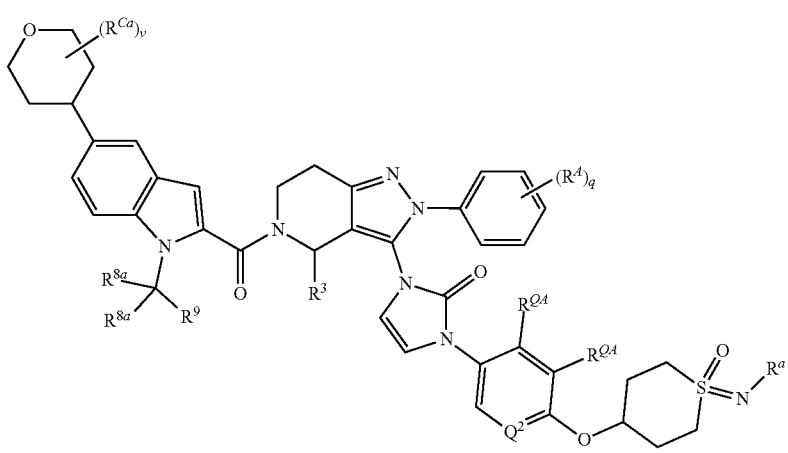

IIK or a pharmaceutically acceptable salt, isotopically enriched analog, stereoisomer, mixture of stereoisomers, or prodrug thereof, wherein q is 0, 1, 2, 3, 4, or 5; v is 0, 1, 2, or 3; and R$^a$, R$^{Ca}$, R$^{8a}$, R$^{8b}$, R$^9$, R$^A$, R$^3$, Q$^2$, and R$^{QA}$ are each independently as defined herein.

In some embodiments, provided herein is a compound of Formula IIK-(S):

IIK-(S)

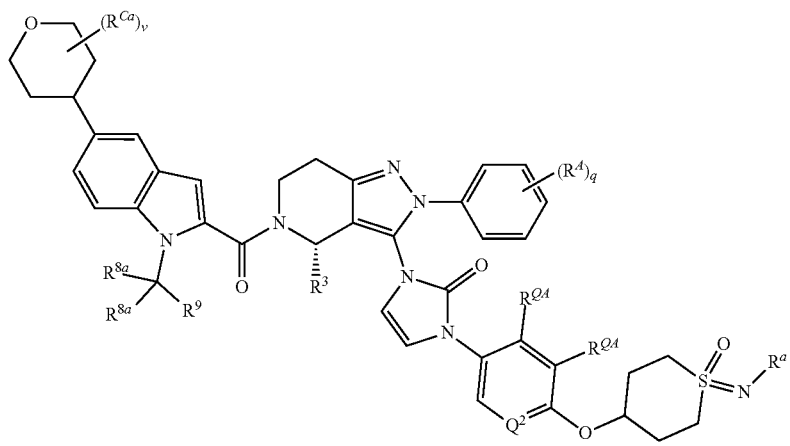

or a pharmaceutically acceptable salt, isotopically enriched analog, stereoisomer, mixture of stereoisomers, or prodrug thereof, wherein q is 0, 1, 2, 3, 4, or 5; v is 0, 1, 2, or 3; and $R^a$, $R^Ca$, $R^{8a}$, $R^{8b}$, $R^9$, $R^A$, $R^3$, $Q^2$, and $R^{QA}$ are each independently as defined herein.

In one aspect, provided herein are compounds of Formula IIF-(S):

IIK-(S)

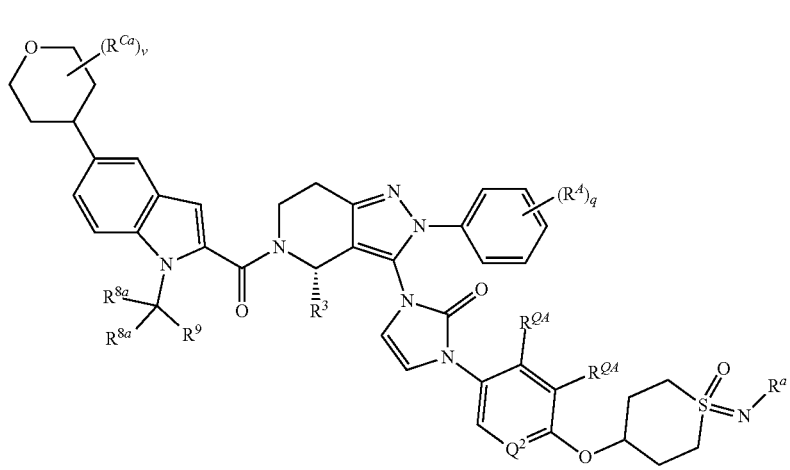

or a pharmaceutically acceptable salt, isotopically enriched analog, stereoisomer, mixture of stereoisomers, or prodrug thereof, wherein:
- $Q^2$ is N or $CR^{QA}$;
- $R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;
- each $R^{QA}$ is independently hydrogen, halo, cyano, hydroxy, $-NR^cR^d$, $-C(O)NR^cR^d$, $-S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and $-C(O)(C_{1-6}$ alkyl), $C_{6-10}$ aryl optionally substituted with 1-3 independently selected $-C(O)(C_{1-6}$ alkyl), and 5-10 membered heteroaryl optionally substituted with 1-6 independently selected $R^g$;
- q is 0, 1, 2, 3, 4, or 5;
- each $R^A$ is independently halo, $C_{1-6}$ alkyl, $C_{1-6}$ haloalkyl, $C_{1-6}$ alkoxy, or $C_{3-6}$ cycloalkyl;
- $R^3$ is hydrogen or $C_{1-6}$ alkyl optionally substituted with 1-6 substituents independently selected from the group consisting of halo, hydroxy, and $C_{1-6}$ alkoxy;
- $R^{8a}$ and $R^{8b}$ are each independently hydrogen or $C_{1-6}$ alkyl optionally substituted with one or more substituents independently selected from the group consisting of halo and $C_{3-15}$ cycloalkyl; or
- $R^{8a}$ and $R^{8b}$ taken together with the carbon atom to which each is attached forms a $C_{3-15}$ cycloalkyl ring which is optionally substituted with 1-3 independently selected $C_{1-6}$ alkyl, wherein the $C_{1-6}$ alkyl is optionally substituted with 1-6 independently selected $R^f$;

$R^9$ is —C(O)OR$^{9a}$, —C(O)NR$^{9a}$R$^{9b}$, 5-6 membered heteroaryl optionally substituted with 1-3 independently selected R$^{9c}$, 4-6 membered heterocyclyl optionally substituted with 1-3 independently selected R$^{9c}$, or

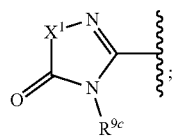

$X^1$ is O or S;

$R^{9a}$ is hydrogen or $C_{1-6}$ alkyl;

$R^{9b}$ is hydrogen, $C_{1-6}$ alkyl, —C(O)($C_{1-6}$ alkyl), —S(O)$_{0-2}$($C_{1-6}$ alkyl), or cyano;

each R$^{9c}$ is independently hydrogen, oxo, $C_{1-6}$ alkyl optionally substituted with 1-6 independently selected halo and $C_{1-6}$ alkoxy, or —C(O)($C_{1-6}$ alkyl);

v is 0, 1, 2, or 3;

each R$^{Ca}$ is independently halo, cyano, $C_{1-6}$ alkyl, $C_{1-6}$ haloalkyl, $C_{1-6}$ alkoxy, or NR$^c$R$^d$;

or a pair of R$^{Ca}$ on the same or different ring atoms, taken together with the ring atom(s) to which each is attached, forms a carbocyclic ring including 3-8 ring atoms;

each R$^c$ and R$^d$ are each independently hydrogen, $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), or —S(O)$_{1-2}$($C_{3-6}$ cycloalkyl), wherein the $C_{1-6}$ alkyl, —C(O)($C_{1-6}$ alkyl), —C(O)($C_{3-6}$ cycloalkyl), —C(O)O($C_{1-6}$ alkyl), —S(O)$_{1-2}$($C_{1-6}$ alkyl), and —S(O)$_{1-2}$($C_{3-6}$ cycloalkyl) are each optionally substituted with 1-6 substituents independently selected from the group consisting of hydroxy, halo, and $C_{1-6}$ alkoxy;

each R$^e$ is independently hydrogen, $C_{1-6}$ alkyl, or $C_{1-6}$ haloalkyl;

each R$^f$ is independently halo, hydroxy, —NR$^c$R$^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each R$^g$ is independently $C_{1-6}$ alkyl, $C_{1-6}$ alkoxy, —NR$^c$R$^d$, or 3 to 12 membered heterocyclyl optionally substituted with one or more substituents each independently selected from the group consisting of $C_{1-6}$ alkyl and —C(O)C$_{1-6}$ alkyl; and each R$^h$ is independently halo, cyano, hydroxy, $C_{1-6}$ alkyl, $C_{1-6}$ haloalkyl, —NH$_2$, —NH($C_{1-3}$ alkyl), —N($C_{1-3}$ alkyl)$_2$, $C_{1-3}$ alkoxy, or $C_{1-3}$ haloalkoxy.

In some embodiments, provided herein is a compound of Formula IIL:

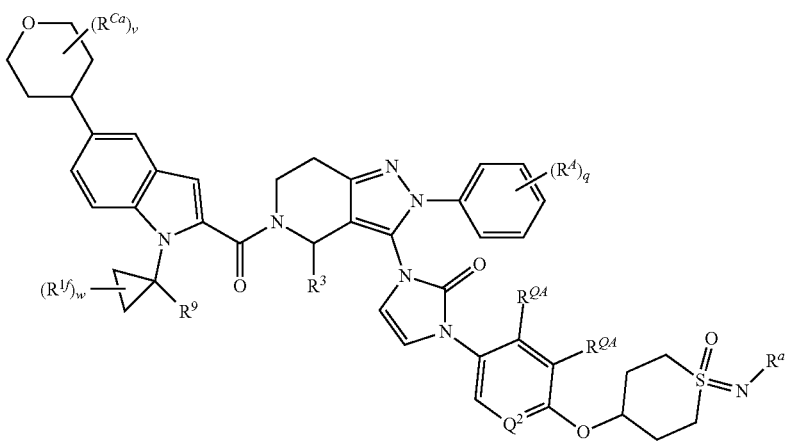

IIL or a pharmaceutically acceptable salt, isotopically enriched analog, stereoisomer, mixture of stereoisomers, or prodrug thereof, wherein each R$^{1f}$ is independently $C_{1-6}$ alkyl, wherein each $C_{1-6}$ alkyl is independently optionally substituted with 1-6 independently selected R$^f$; q is 0, 1, 2, 3, 4, or 5; v is 0, 1, 2, or 3; w is 0, 1, 2, or 3; and R$^a$, R$^{Ca}$, R$^f$, R$^9$, R$^A$, R, Q$^2$, and R$^{QA}$ are each independently as defined herein.

In some embodiments, provided herein is a compound of Formula IIL-(S):

IIL-(S)

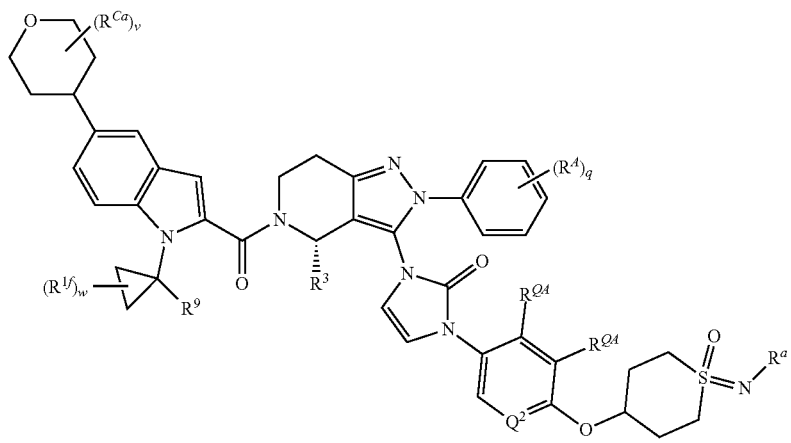

or a pharmaceutically acceptable salt, isotopically enriched analog, stereoisomer, mixture of stereoisomers, or prodrug thereof, wherein each $R^{1f}$ is independently $C_{1-6}$ alkyl, wherein each $C_{1-6}$ alkyl is independently optionally substituted with 1-6 independently selected $R^f$; q is 0, 1, 2, 3, 4, or 5; v is 0, 1, 2, or 3; w is 0, 1, 2, or 3; and $R^a$, $R^Ca$, $R^f$, $R^9$, $R^A$, $R^3$, $Q^2$, and $R^{QA}$ are each independently as defined herein.

In one aspect, provided herein are compounds of Formula IIL-(S):

IIL-(S)

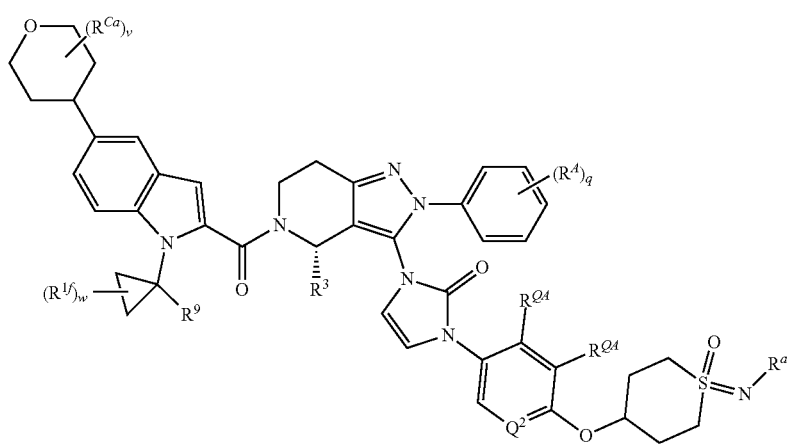

or a pharmaceutically acceptable salt, isotopically enriched analog, stereoisomer, mixture of stereoisomers, or prodrug thereof, wherein:

$Q^2$ is N or $CR^{QA}$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

each $R^{QA}$ is independently hydrogen, halo, cyano, hydroxy, —NR$^c$R$^d$, —C(O)NR$^c$R$^d$, —S(O)$_{0-2}$R, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —C(O)($C_{1-6}$ alkyl), $C_{6-10}$ aryl optionally substituted with 1-3 independently selected —C(O)($C_{1-6}$ alkyl), and 5-10 membered heteroaryl optionally substituted with 1-6 independently selected $R^g$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$R^9$ is —C(O)OR$^{9a}$, —C(O)NR$^{9a}$R$^{9b}$, 5-6 membered heteroaryl optionally substituted with 1-3 independently selected $R^{9c}$, 4-6 membered heterocyclyl optionally substituted with 1-3 independently selected $R^{9c}$, or

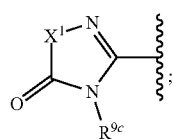

$X^1$ is O or S;

$R^{1a}$ is hydrogen or $C_{1-6}$ alkyl;

$R^{9b}$ is hydrogen, $C_{1-6}$ alkyl, $-C(O)(C_{1-6}$ alkyl), $-S(O)_{0-2}(C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or $-C(O)(C_{1-6}$ alkyl);

v is 0, 1, 2, or 3;

each $R^{Ca}$ is independently halo, cyano, $C_{1-6}$ alkyl, $C_{1-6}$ haloalkyl, $C_{1-6}$ alkoxy, or $NR^cR^d$;

or a pair of $R^{Ca}$ on the same or different ring atoms, taken together with the ring atom(s) to which each is attached, forms a carbocyclic ring including 3-8 ring atoms;

each $R^c$ and $R^d$ are each independently hydrogen, $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), or $-S(O)_{1-2}(C_{3-6}$ cycloalkyl), wherein the $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), and $-S(O)_{1-2}(C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

w is 0, 1, 2, or 3;

each $R^f$ is independently $C_{1-6}$ alkyl, wherein each $C_{1-6}$ alkyl is independently optionally substituted with 1-6 independently selected $R^{f'}$;

each $R^{f'}$ is independently halo, hydroxy, $-NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, $-NR^cR^d$, or 3 to 12 membered heterocyclyl optionally substituted with one or more substituents each independently selected from the group consisting of $C_{1-6}$ alkyl and $-C(O)C_{1-6}$ alkyl; and each $R^h$ is independently halo, cyano, hydroxy, $C_{1-6}$ alkyl, $C_{1-6}$ haloalkyl, $-NH_2$, $-NH(C_{1-3}$ alkyl), $-N(C_{1-3}$ alkyl)$_2$, $C_{1-3}$ alkoxy, or $C_{1-3}$ haloalkoxy.

In some embodiments, $R^3$ is methyl.

In some embodiments, q is 2 or 3.

In some embodiments, each $R^A$ is independently halo, $C_{1-6}$ alkyl, or $C_{3-6}$ cycloalkyl. In some embodiments, each $R^A$ is independently fluoro, chloro, methyl, or cyclopropyl.

In some embodiments, q is 2 or 3; and each $R^A$ is independently halo, $C_{1-6}$ alkyl, or $C_{3-6}$ cycloalkyl. In some embodiments, q is 2 or 3; and each $R^A$ is independently fluoro, chloro, methyl, or cyclopropyl.

In some embodiments, $Q^2$ is N. In some embodiments, $Q^2$ is $CR^{QA}$.

In some embodiments, each $R^{QA}$ is independently hydrogen, halo, $-NH(C_{1-6}$ alkyl), $C_{1-6}$ alkyl, or $C_{1-6}$ alkoxy. In some embodiments, each $R^{QA}$ is independently hydrogen, fluoro, chloro, $-NHCH_3$, methyl, isopropyl, or $-OCH_3$.

In some embodiments, $Q^2$ is $CR^{QA}$; and each $R^{QA}$ is independently hydrogen, halo, $-NH(C_{1-6}$ alkyl), $C_{1-6}$ alkyl, or $C_{1-6}$ alkoxy.

In some embodiments, $Q^2$ is $CR^{QA}$; and $R^a$ or R and $R^{QA}$ are taken together with the atom to which each is attached to form a 5-7 membered heterocyclyl, wherein said heterocyclyl is optionally substituted with 1-2 independently selected $R^h$.

In some embodiments, $R^a$ is hydrogen, cyano, $C_{1-6}$ alkyl, or $C_{3-6}$ cycloalkyl.

In some embodiments, $R^b$ is $C_{1-6}$ alkyl optionally substituted with $C_{3-6}$ cycloalkyl, or $C_{3-6}$ cycloalkyl. In some embodiments, $R^b$ is $C_{1-6}$ alkyl. In some embodiments, $R^b$ is $C_{1-6}$ alkyl substituted with $C_{3-6}$ cycloalkyl. In some embodiments, $R^b$ is $C_{3-6}$ cycloalkyl.

In some embodiments, $R^a$ is hydrogen, cyano, $C_{1-6}$ alkyl, or $C_{3-6}$ cycloalkyl; and $R^b$ is $C_{1-6}$ alkyl optionally substituted with $C_{3-6}$ cycloalkyl, or $C_{3-6}$ cycloalkyl. In some embodiments, $R^a$ is hydrogen, cyano, methyl, or cyclopropyl; and $R^b$ is methyl, ethyl, $-CH_2$-cyclopropyl, cyclopropyl, or cyclobutyl.

In some embodiments, $R^a$ and $R^b$ are taken together with the atoms to which each is attached form a 5-8 membered heterocyclyl.

In some embodiments, $R^a$ or R and an adjacent $R^{QA}$ are taken together with the atom to which each is attached to form a 5-7 membered heterocyclyl, wherein said heterocyclyl is optionally substituted with 1-2 independently selected $R^h$.

In some embodiments, w is 0 or 1. In some embodiments, w is 0. In some embodiments, w is 1. In some embodiments, each $R^f$ is independently $C_{1-6}$ alkyl.

In some embodiments, w is 0 or 1; and $R^b$ is methyl.

In some embodiments, $R^a$ is hydrogen, cyano, $C_{1-6}$ alkyl, or $C_{3-6}$ cycloalkyl; and $R^b$ is $C_{1-6}$ alkyl optionally substituted with $C_{3-6}$ cycloalkyl, or $C_{3-6}$ cycloalkyl; or $R^a$ and $R^b$ are taken together with the atoms to which each is attached form a 5-8 membered heterocyclyl; or $R^a$ is hydrogen, cyano, $C_{1-6}$ alkyl, or $C_{3-6}$ cycloalkyl; and $R^b$ and an adjacent $R^{QA}$ are taken together with the atom to which each is attached to form a 5-7 membered heterocyclyl, wherein said heterocyclyl is optionally substituted with 1-2 independently selected $R^h$; or $R^a$ and an adjacent $R^{QA}$ are taken together with the atom to which each is attached to form a 5-7 membered heterocyclyl, wherein said heterocyclyl is optionally substituted with 1-2 independently selected $R^h$; and $R^b$ is $C_{1-6}$ alkyl optionally substituted with $C_{3-6}$ cycloalkyl, or $C_{3-6}$ cycloalkyl.

In some embodiments, each $R^h$ is independently $C_{1-6}$ alkyl. In some embodiments, each $R^h$ is independently methyl.

In some embodiments, each $R^i$ and each $R^j$ are hydrogen; or $R^a$ or $R^b$ and $R^j$, taken together with the atoms to which each is attached form a 5-8 membered heterocyclyl; or one $R^i$ and one $R^j$, taken together with the atom(s) to which each is attached, form a $C_{3-6}$ cycloalkyl.

In some embodiments, $R^3$ is methyl;

q is 2 or 3;

each $R^A$ is independently halo, $C_{1-6}$ alkyl, or $C_{3-6}$ cycloalkyl;

each $R^{QA}$ is independently hydrogen, halo, $-NH(C_{1-6}$ alkyl), $C_{1-6}$ alkyl, or $C_{1-6}$ alkoxy;

$R^a$ is hydrogen, cyano, $C_{1-6}$ alkyl, or $C_{3-6}$ cycloalkyl; and $R^b$ is $C_{1-6}$ alkyl optionally substituted with $C_{3-6}$ cycloalkyl, or $C_{3-6}$ cycloalkyl; or $R^a$ and $R^b$ are taken together with the atoms to which each is attached form a 5-8 membered heterocyclyl; or $R^a$ is hydrogen, cyano, $C_{1-6}$ alkyl, or $C_{3-6}$ cycloalkyl; and $R^b$ and an adjacent $R^{QA}$ are taken together with the atom to which each is attached to form a 5-7 membered heterocyclyl, wherein said heterocyclyl is optionally substituted with 1-2 independently selected $R^h$; or $R^a$ and an adjacent $R^{QA}$ are taken together with the atom to which each is attached to form a 5-7 membered heterocyclyl, wherein said heterocyclyl is optionally substituted with 1-2 independently selected $R^h$; and $R^b$ is $C_{1-6}$ alkyl optionally substituted with $C_{3-6}$ cycloalkyl, or $C_{3-6}$ cycloalkyl;

each $R^h$ is independently $C_{1-6}$ alkyl; and each $R^1$ and each $R^j$ are hydrogen; or $R^a$ and $R^i$, or $R^b$ and $R^j$, taken together with the atoms to which each is attached form a 5-8 membered heterocyclyl; or one $R^1$ and one $R^j$, taken together with the atom(s) to which each is attached, form a $C_{3-6}$ cycloalkyl.

In one aspect, provided herein are compounds of Formula IIIA:

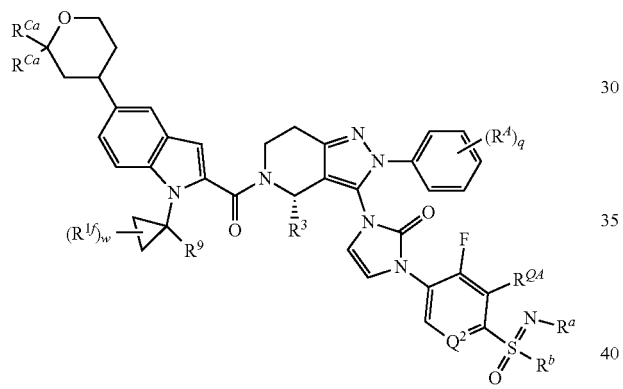

IIIA or a pharmaceutically acceptable salt, isotopically enriched analog, stereoisomer, mixture of stereoisomers, or prodrug thereof, wherein:

$Q^2$ is N or $CR^{QA}$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

each $R^{QA}$ is independently hydrogen, halo, cyano, hydroxy, $-NR^cR^d$, $-C(O)NR^cR^d$, $-S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and $-C(O)(C_{1-6}$ alkyl), $C_{6-10}$ aryl optionally substituted with 1-3 independently selected $-C(O)(C_{1-6}$ alkyl), and 5-10 membered heteroaryl optionally substituted with 1-6 independently selected $R^g$;

or $R^a$ or $R^b$ and an adjacent $R^{QA}$ are taken together with the atom to which each is attached to form a 5-8 membered heterocyclyl, wherein said heterocyclyl is optionally substituted with 1-2 independently selected $R^h$;

each $R^{Ca}$ is independently $C_{1-6}$ alkyl;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$R^9$ is $-C(O)OR^{9a}$, $-C(O)NR^{9a}R^{9b}$, 5-6 membered heteroaryl optionally substituted with 1-3 independently selected $R^{9c}$, 4-6 membered heterocyclyl optionally substituted with 1-3 independently selected $R^{9c}$, or

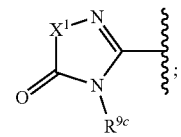

$X^1$ is O or S;

$R^{9a}$ is hydrogen or $C_{1-6}$ alkyl;

$R^{9b}$ is hydrogen, $C_{1-6}$ alkyl, $-C(O)(C_{1-6}$ alkyl), $-S(O)_{0-2}(C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or $-C(O)(C_{1-6}$ alkyl);

each $R^c$ and $R^d$ are each independently hydrogen, $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), or $-S(O)_{1-2}(C_{3-6}$ cycloalkyl), wherein the $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), and $-S(O)_{1-2}(C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

w is 0, 1, 2, or 3;

each $R^1$ is independently $C_{1-6}$ alkyl, wherein each $C_{1-6}$ alkyl is independently optionally substituted with 1-6 independently selected $R^f$;

each $R^f$ is independently halo, hydroxy, $-NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, —$NR^cR^d$, or 3 to 12 membered heterocyclyl optionally substituted with one or more substituents each independently selected from the group consisting of $C_{1-6}$ alkyl and —$C(O)C_{1-6}$ alkyl; and each $R^h$ is independently halo, cyano, hydroxy, $C_{1-6}$ alkyl, $C_{1-6}$ haloalkyl, —$NH_2$, —$NH(C_{1-3}$ alkyl), —$N(C_{1-3}$ alkyl)$_2$, $C_{1-3}$ alkoxy, or $C_{1-3}$ haloalkoxy.

In one aspect, provided herein are compounds of Formula IIIB:

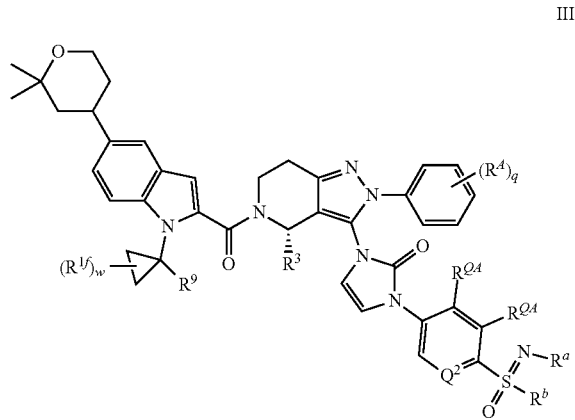

IIIB or a pharmaceutically acceptable salt, isotopically enriched analog, stereoisomer, mixture of stereoisomers, or prodrug thereof, wherein:

$Q^2$ is N or $CR^{QA}$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

each $R^{QA}$ is independently hydrogen, halo, cyano, hydroxy, —$NR^cR^d$, —$C(O)NR^cR^d$, —$S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and —$C(O)(C_{1-6}$ alkyl), $C_{6-10}$ aryl optionally substituted with 1-3 independently selected —$C(O)(C_{1-6}$ alkyl), and 5-10 membered heteroaryl optionally substituted with 1-6 independently selected $R^g$;

or $R^a$ or $R^b$ and an adjacent $R^{QA}$ are taken together with the atom to which each is attached to form a 5-8 membered heterocyclyl, wherein said heterocyclyl is optionally substituted with 1-2 independently selected $R^h$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$R^9$ is —$C(O)OR^{9a}$, —$C(O)NR^{9a}R^{9b}$, 5-6 membered heteroaryl optionally substituted with 1-3 independently selected $R^{9c}$, 4-6 membered heterocyclyl optionally substituted with 1-3 independently selected $R^{9c}$, or

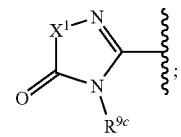

$X^1$ is O or S;

$R^{9a}$ is hydrogen or $C_{1-6}$ alkyl;

$R^{9b}$ is hydrogen, $C_{1-6}$ alkyl, —$C(O)(C_{1-6}$ alkyl), —$S(O)_{0-2}(C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or —$C(O)(C_{1-6}$ alkyl);

each $R^c$ and $R^d$ are each independently hydrogen, $C_{1-6}$ alkyl, —$C(O)(C_{1-6}$ alkyl), —$C(O)(C_{3-6}$ cycloalkyl), —$C(O)O(C_{1-6}$ alkyl), —$S(O)_{1-2}(C_{1-6}$ alkyl), or —$S(O)_{1-2}(C_{3-6}$ cycloalkyl), wherein the $C_{1-6}$ alkyl, —$C(O)(C_{1-6}$ alkyl), —$C(O)(C_{3-6}$ cycloalkyl), —$C(O)O(C_{1-6}$ alkyl), —$S(O)_{1-2}(C_{1-6}$ alkyl), and —$S(O)_{1-2}(C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

w is 0, 1, 2, or 3;

each $R^1$ is independently $C_{1-6}$ alkyl, wherein each $C_{1-6}$ alkyl is independently optionally substituted with 1-6 independently selected $R^f$;

each $R^f$ is independently halo, hydroxy, —$NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl;

each $R^g$ is independently $C_{1-6}$ alkyl, $C_{1-6}$ alkoxy, —$NR^cR^d$, or 3 to 12 membered heterocyclyl optionally substituted with one or more substituents each independently selected from the group consisting of $C_{1-6}$ alkyl and —$C(O)C_{1-6}$ alkyl; and each $R^h$ is independently halo, cyano, hydroxy, $C_{1-6}$ alkyl, $C_{1-6}$ haloalkyl, —$NH_2$, —$NH(C_{1-3}$ alkyl), —$N(C_{1-3}$ alkyl)$_2$, $C_{1-3}$ alkoxy, or $C_{1-3}$ haloalkoxy.

In one aspect, provided herein are compounds of Formula IIIC:

IIIC

[Chemical structure of Formula IIIC]

or a pharmaceutically acceptable salt, isotopically enriched analog, stereoisomer, mixture of stereoisomers, or prodrug thereof, wherein:

$Q^2$ is N or $CR^{QA}$;

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

or $R^a$ and $R^b$ taken together with the atoms to which each is attached form a 5-8 membered heterocyclyl, wherein said heterocyclyl is optionally substituted with 1-3 independently selected $C_{1-6}$ alkyl;

each $R^{QA}$ is independently hydrogen, halo, cyano, hydroxy, $-NR^cR^d$, $-C(O)NR^cR^d$, $-S(O)_{0-2}R$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and $-C(O)(C_{1-6}$ alkyl), $C_{6-10}$ aryl optionally substituted with 1-3 independently selected $-C(O)(C_{1-6}$ alkyl), and 5-10 membered heteroaryl optionally substituted with 1-6 independently selected $R^g$;

q is 0, 1, 2, 3, 4, or 5;

each $R^A$ is independently halo, $C_{1-6}$ alkyl, $C_{1-6}$ haloalkyl, $C_{1-6}$ alkoxy, or $C_{3-6}$ cycloalkyl;

$R^3$ is hydrogen or $C_{1-6}$ alkyl optionally substituted with 1-6 substituents independently selected from the group consisting of halo, hydroxy, and $C_{1-6}$ alkoxy;

$R^9$ is $-C(O)OR^{9a}$, $-C(O)NR^{9a}R^{9b}$, 5-6 membered heteroaryl optionally substituted with 1-3 independently selected $R^{9c}$, 4-6 membered heterocyclyl optionally substituted with 1-3 independently selected $R^{9c}$, or

[Chemical structure]

$X^1$ is O or S;

$R^{9a}$ is hydrogen or $C_{1-6}$ alkyl;

$R^{9b}$ is hydrogen, $C_{1-6}$ alkyl, $-C(O)(C_{1-6}$ alkyl), $-S(O)_{0-2}(C_{1-6}$ alkyl), or cyano;

each $R^{9c}$ is independently hydrogen, oxo, $C_{1-6}$ alkyl optionally substituted with 1-6 independently selected halo and $C_{1-6}$ alkoxy, or $-C(O)(C_{1-6}$ alkyl);

each $R^c$ and $R^d$ are each independently hydrogen, $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), or $-S(O)_{1-2}(C_{3-6}$ cycloalkyl), wherein the $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), and $-S(O)_{1-2}(C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl;

w is 0, 1, 2, or 3;

each $R^1$ is independently $C_{1-6}$ alkyl, wherein each $C_{1-6}$ alkyl is independently optionally substituted with 1-6 independently selected $R^f$;

each $R^f$ is independently halo, hydroxy, $-NR^cR^d$, $C_{1-6}$ alkoxy, $C_{1-6}$ haloalkoxy, or 3-12 membered heterocyclyl which is optionally substituted with 1-4 substituents each independently selected from the group consisting of hydroxy, $C_{1-6}$ alkyl, and 3-12 membered heterocyclyl; and each $R^g$ is independently $C_{1-6}$ alkyl, $C_{1-6}$ alkoxy, $-NR^cR^d$, or 3 to 12 membered heterocyclyl optionally substituted with one or more substituents each independently selected from the group consisting of $C_{1-6}$ alkyl and $-C(O)C_{1-6}$ alkyl.

In certain embodiments, such as of Formula IIIA or IIIB, $R^3$ is $C_{1-6}$ alkyl. In certain embodiments, such as of Formula IIIA or IIIB, $R^3$ is methyl.

In certain embodiments, such as of Formula IIIA or IIIB, $Q^2$ is CH. such as of Formula IIIA or IIIB, $R^3$ is methyl.

In certain embodiments, such as of Formula IIIA or IIIB, q is 2 or 3.

In certain embodiments, such as of Formula IIIA or IIIB, $R^9$

[Chemical structure]

In one aspect, provided herein are compounds of Formula IIID:

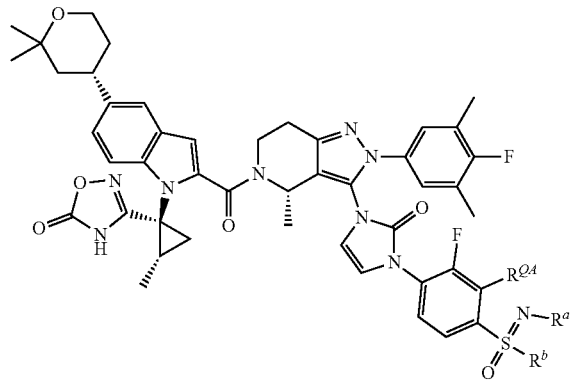

IIID or a pharmaceutically acceptable salt, isotopically enriched analog, stereoisomer, mixture of stereoisomers, or prodrug thereof, wherein:

$R^a$ is hydrogen, cyano, $C_{1-6}$ alkyl which is optionally substituted with 1-6 substituents each independently selected from the group consisting of halo, oxo, $C_{1-6}$ alkoxy, $C_{3-6}$ cycloalkyl, and heteroaryl, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^b$ is $C_{1-6}$ alkyl which is optionally substituted with 1-6 substituents each independently selected from the group consisting of $C_{1-6}$ alkoxy, $C_{3-6}$ cycloalkyl, and halo, $C_{3-6}$ cycloalkyl optionally substituted with 1-3 substituents each independently selected from the group consisting of $C_{1-3}$ alkyl and halo, or $C_{6-10}$ aryl optionally substituted with 1-3 independently selected $C_{1-3}$ alkyl;

$R^{QA}$ is hydrogen, halo, cyano, hydroxy, $-NR^cR^d$, $-C(O)NR^cR^d$, $-S(O)_{0-2}R^e$, $C_{1-6}$ alkyl optionally substituted with 1-6 independently selected $R^f$, $C_{1-6}$ alkoxy optionally substituted with 1-6 substituents each independently selected from the group consisting of hydroxy, halo, and $C_{1-6}$ alkoxy, 3-12 membered heterocyclyl optionally substituted with one or more substituents each independently selected from the group consisting of $C_{1-6}$ alkyl and $-C(O)(C_{1-6}$ alkyl), $C_{6-10}$ aryl optionally substituted with 1-3 independently selected -C(O)$(C_{1-6}$ alkyl), and 5-10 membered heteroaryl optionally substituted with 1-6 independently selected $R^g$;

each $R^c$ and $R^d$ are each independently hydrogen, $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), or $-S(O)_{1-2}(C_{3-6}$ cycloalkyl), wherein the $C_{1-6}$ alkyl, $-C(O)(C_{1-6}$ alkyl), $-C(O)(C_{3-6}$ cycloalkyl), $-C(O)O(C_{1-6}$ alkyl), $-S(O)_{1-2}(C_{1-6}$ alkyl), and $-S(O)_{1-2}(C_{3-6}$ cycloalkyl) are each optionally substituted with 1-6 substituents independently selected from the group consisting of hydroxy, halo, and $C_{1-6}$ alkoxy;

each $R^e$ is independently hydrogen, $C_{1-6}$ alkyl, or $C_{1-6}$ haloalkyl; and each $R^g$ is independently $C_{1-6}$ alkyl, $C_{1-6}$ alkoxy, $-NR^cR^d$, or 3 to 12 membered heterocyclyl optionally substituted with one or more substituents each independently selected from the group consisting of $C_{1-6}$ alkyl and $-C(O)C_{1-6}$ alkyl.

In certain embodiments, such as of Formula IIIA, IIIB, or IIIC, $R^{QA}$ is hydrogen, halo, $-NR^cR^d$, or $C_{1-6}$ alkyl. In certain embodiments, such as of Formula IIIA, IIIB, or IIIC, $R^{QA}$ is hydrogen, halo, $-NHCH_3$, or methyl.

In certain embodiments, such as of Formula IIIA, IIIB, or IIIC, $R^a$ is hydrogen or $C_{1-6}$ alkyl. In certain embodiments, such as of Formula IIIA, IIIB, or IIIC, $R^a$ is hydrogen, methyl, or ethyl.

In certain embodiments, such as of Formula IIIA, IIIB, or IIIC, $R^b$ is $C_{1-6}$ alkyl or $C_{3-6}$ cycloalkyl.

In certain embodiments, such as of Formula IIIA, IIIB, or IIIC, $R^b$ is methyl, ethyl, cyclopropyl, or cyclobutyl.

In certain embodiments, such as of Formula IIIA, IIIB, or IIIC, $R^a$ is hydrogen or $C_{1-6}$ alkyl; and $R^b$ is $C_{1-6}$ alkyl or $C_{3-6}$ cycloalkyl.

In certain embodiments, such as of Formula IIIA, IIIB, or IIIC, $R^a$ is hydrogen, methyl, or ethyl; and $R^b$ is methyl, ethyl, cyclopropyl, or cyclobutyl.

In one aspect, provided herein are compounds of Formula IIID:

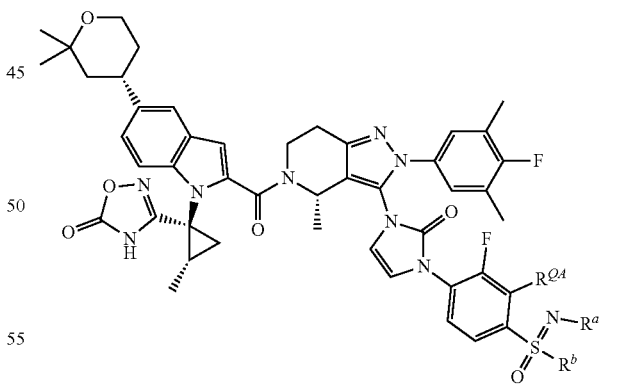

IIID or a pharmaceutically acceptable salt, isotopically enriched analog, stereoisomer, mixture of stereoisomers, or prodrug thereof, wherein: $R^{QA}$ is hydrogen, halo, $-NR^cR^d$, or $C_{1-6}$ alkyl; $R^a$ is hydrogen or $C_{1-6}$ alkyl; and $R^b$ is $C_{1-6}$ alkyl or $C_{3-6}$ cycloalkyl.

In one aspect, provided herein are compounds of Formula IIID:

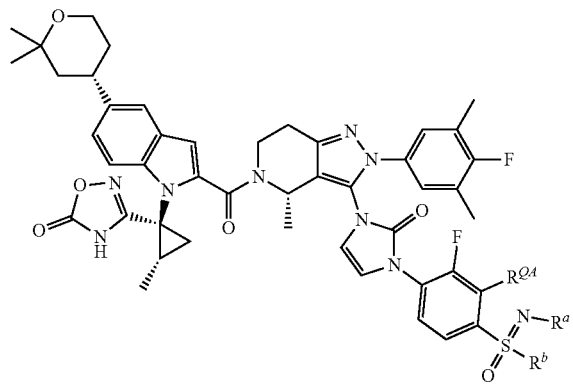

IIID or a pharmaceutically acceptable salt, isotopically enriched analog, stereoisomer, mixture of stereoisomers, or prodrug thereof, wherein: $R^{QA}$ is hydrogen, halo, —NHCH$_3$, or methyl; $R^a$ is hydrogen, methyl, or ethyl; and $R^b$ is methyl, ethyl, cyclopropyl, or cyclobutyl.

In one aspect, provided herein are compounds of Formula IIID:

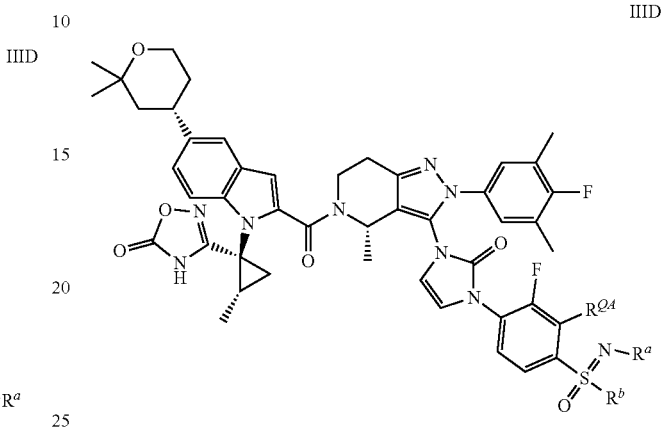

IIID or a pharmaceutically acceptable salt, isotopically enriched analog, stereoisomer, mixture of stereoisomers, or prodrug thereof, wherein: $R^{QA}$ is hydrogen, halo, —NHCH$_3$, or methyl; $R^a$ is methyl or ethyl; and $R^b$ is ethyl or cyclopropyl or cyclobutyl.

In certain embodiments, provided is a compound selected from Table 1, or a pharmaceutically acceptable salt, isotopically enriched analog, stereoisomer, mixture of stereoisomers, or prodrug thereof:

TABLE 1

| Compound No. | Structure |
|---|---|
| 101 | 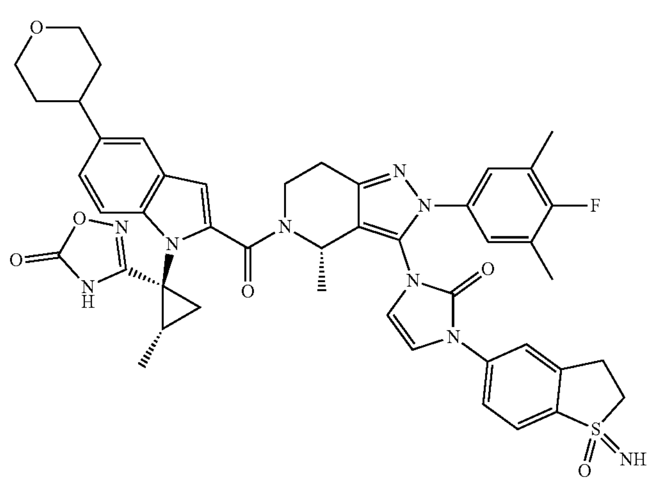 [SMILES: Cc1cc(-n2nc3c(c2-n2ccn(-c4ccc5c(c4)CCS5(=N)=O)c2=O)[C@H](C)N(C(=O)c2cc4cc(C5CCOCC5)ccc4n2[C@@]2(c4noc(=O)[nH]4)C[C@@H]2C)CC3)cc(C)c1F] |

TABLE 1-continued

| Compound No. | Structure |
| --- | --- |
| 102 | 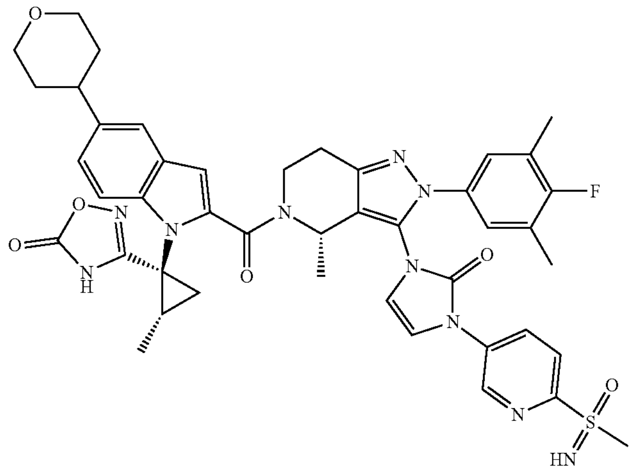 [SMILES: Cc1cc(-n2nc3c(c2-n2ccn(-c4ccc(S(C)(=N)=O)nc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 103 | 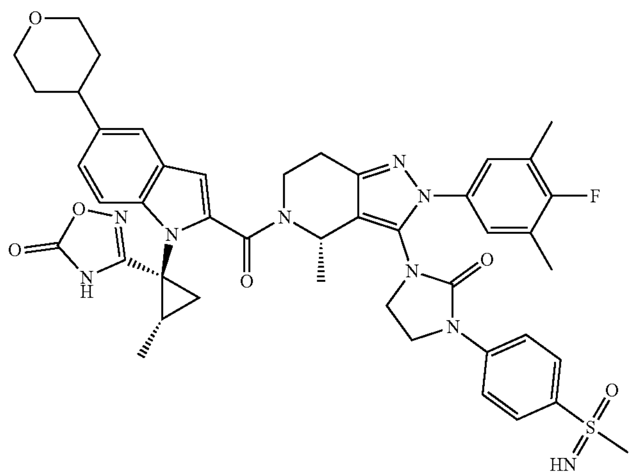 [SMILES: Cc1cc(-n2nc3c(c2N2CCN(c4ccc(S(C)(=N)=O)cc4)C2=O)[C@H](C)N(C(=O)c2cc4cc(C5CCOCC5)ccc4n2[C@@]2(c4noc(=O)[nH]4)C[C@@H]2C)CC3)cc(C)c1F] |
| 104 | 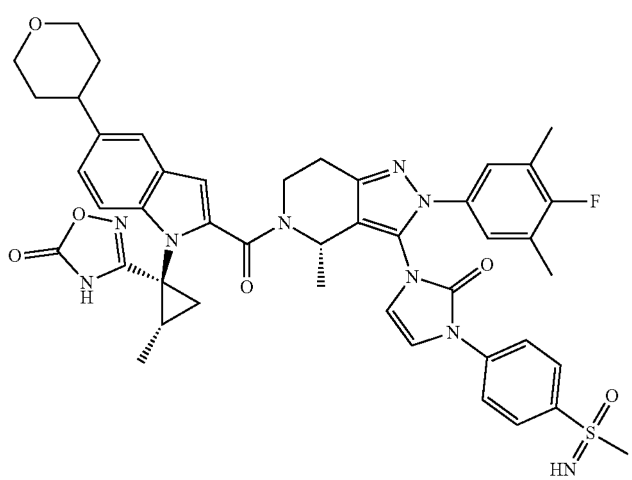 [SMILES: Cc1cc(-n2nc3c(c2-n2ccn(-c4ccc(S(C)(=N)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |

TABLE 1-continued

| Compound No. | Structure |
|---|---|
| 105 | 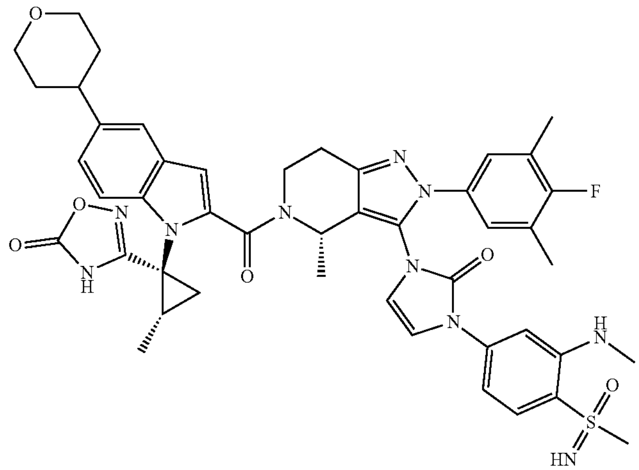 [SMILES: CNc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1S(C)(=N)=O] |
| 106 | 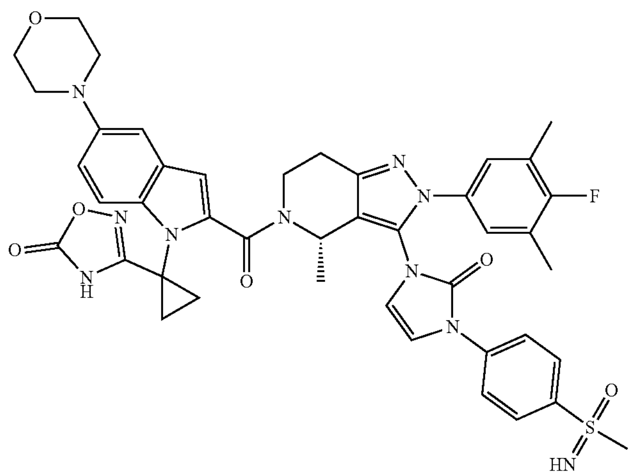 [SMILES: Cc1cc(-n2nc3c(c2-n2ccn(-c4ccc(S(C)(=N)=O)cc4)c2=O)[C@H](C)N(C(=O)c2cc4cc(N5CCOCC5)ccc4n2C2(c4noc(=O)[nH]4)CC2)CC3)cc(C)c1F] |
| 107 | 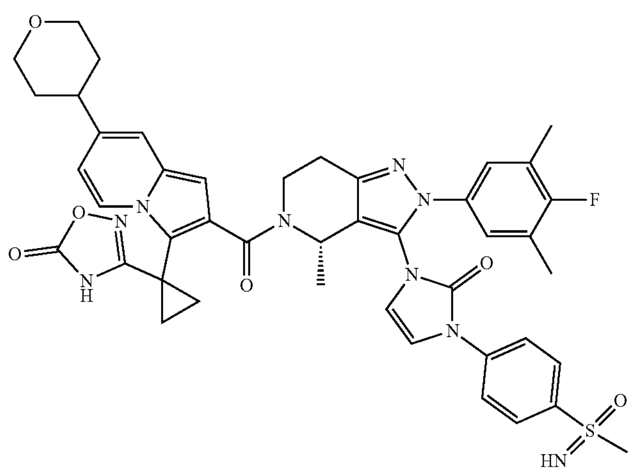 [SMILES: Cc1cc(-n2nc3c(c2-n2ccn(-c4ccc(S(C)(=N)=O)cc4)c2=O)[C@H](C)N(C(=O)c2cc4cc(C5CCOCC5)ccn4c2C2(c4noc(=O)[nH]4)CC2)CC3)cc(C)c1F] |

TABLE 1-continued

| Compound No. | Structure |
| --- | --- |
| 108 | 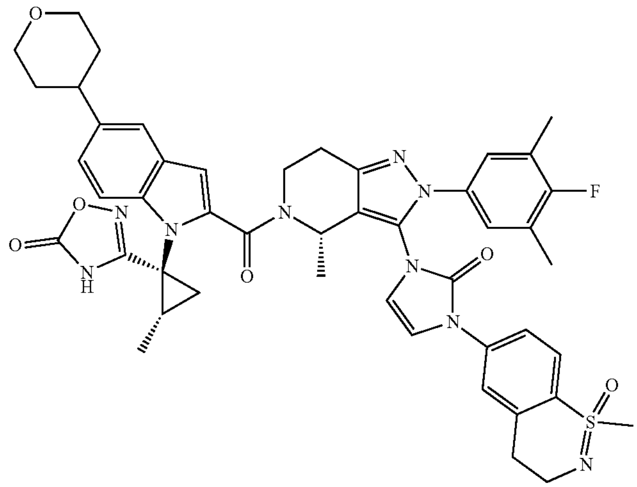 [SMILES: Cc1cc(-n2nc3c(c2-n2ccn(-c4ccc5c(c4)CCN=S5(C)=O)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 109 | 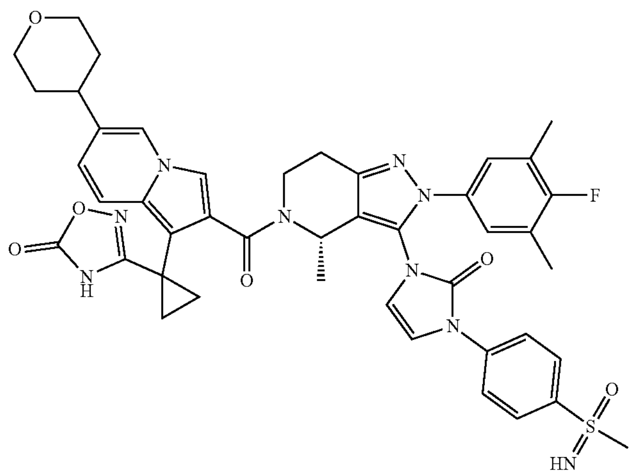 [SMILES: Cc1cc(-n2nc3c(c2-n2ccn(-c4ccc(S(C)(=N)=O)cc4)c2=O)[C@H](C)N(C(=O)c2cn4cc(C5CCOCC5)ccc4c2C2(c4noc(=O)[nH]4)CC2)CC3)cc(C)c1F] |
| 110 | 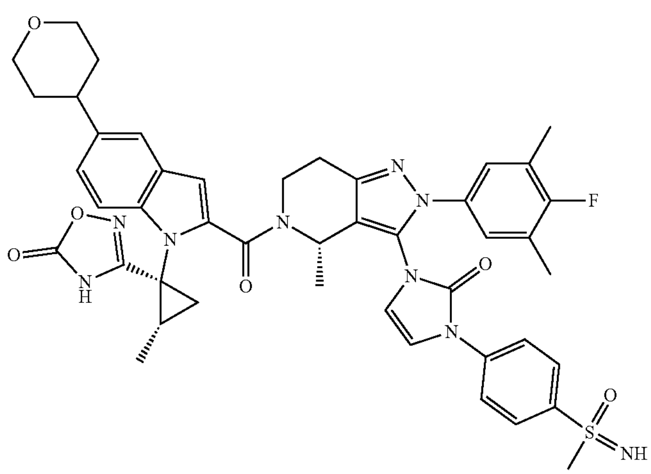 [SMILES: Cc1cc(-n2nc3c(c2-n2ccn(-c4ccc(S(C)(=N)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |

TABLE 1-continued
| Compound No. | Structure |
|---|---|
| 111 | 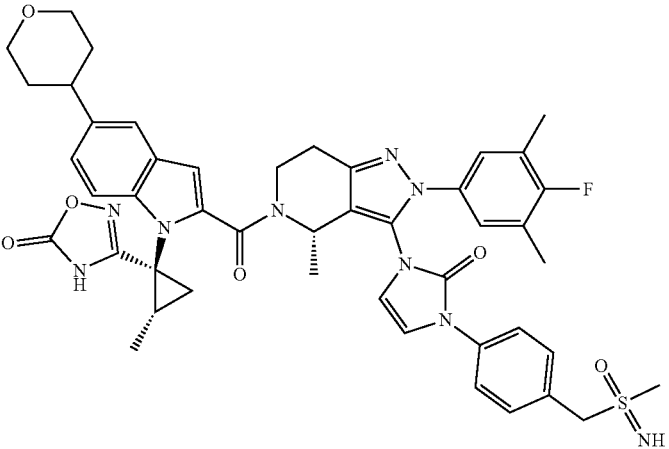 [SMILES: Cc1cc(-n2nc3c(c2-n2ccn(-c4ccc(CS(C)(=N)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 112 | 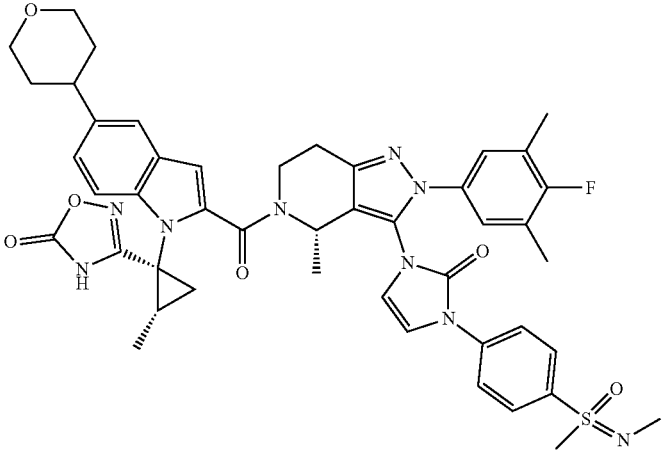 [SMILES: CN=S(C)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]
Enantiomer 1 |
| 113 | 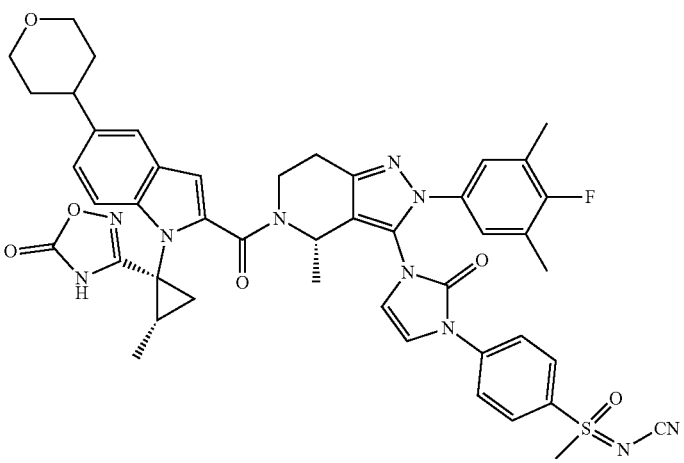 [SMILES: Cc1cc(-n2nc3c(c2-n2ccn(-c4ccc(S(C)(=O)=NC#N)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
Enantiomer 1 |

TABLE 1-continued
| Compound No. | Structure |
|---|---|
| 114 | 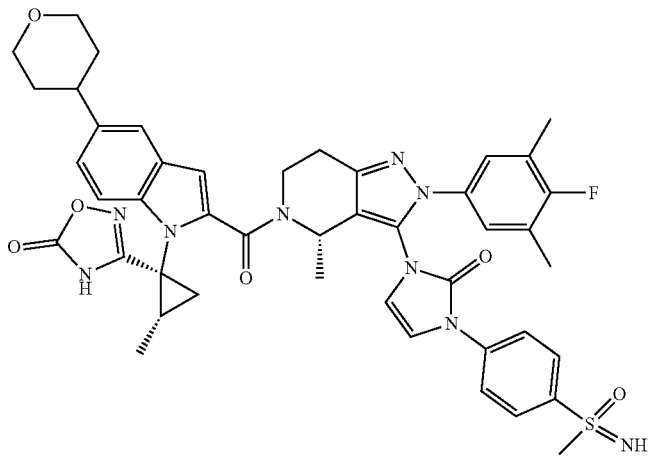 [SMILES: Cc1cc(-n2nc3c(c2-n2ccn(-c4ccc(S(C)(=N)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]<br>Enantiomer 1 |
| 115 | 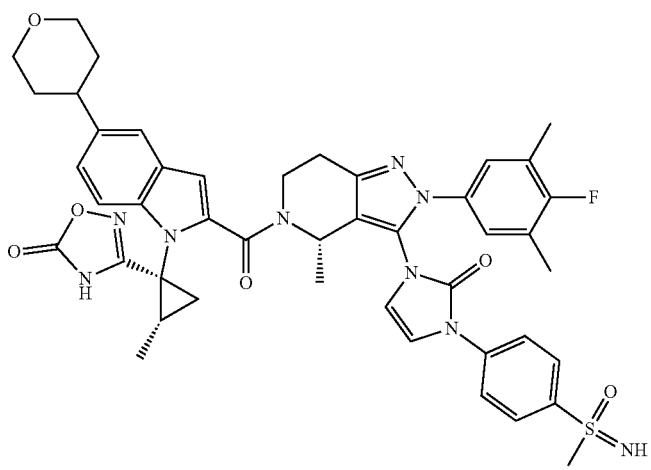 [SMILES: Cc1cc(-n2nc3c(c2-n2ccn(-c4ccc(S(C)(=N)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]<br>Enantiomer 2 |
| 116 | 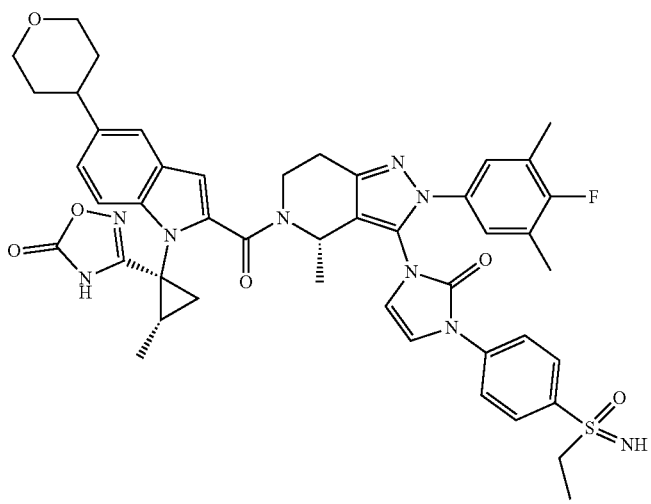 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]<br>Enantiomer 1 |

TABLE 1-continued
| Compound No. | Structure |
|---|---|
| 117 | 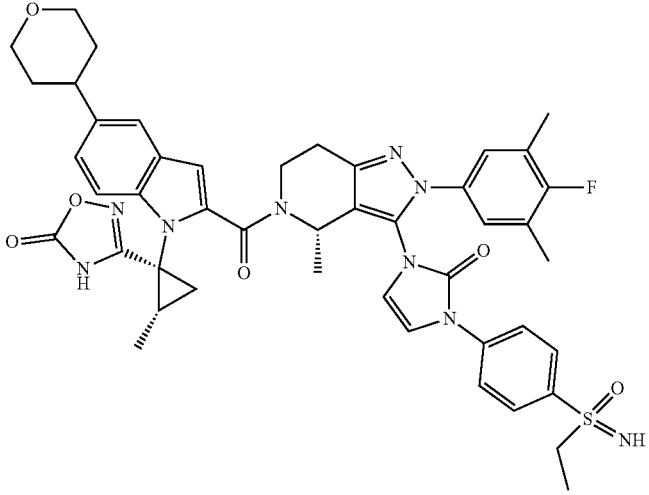 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]<br>Enantiomer 2 |
| 118 | 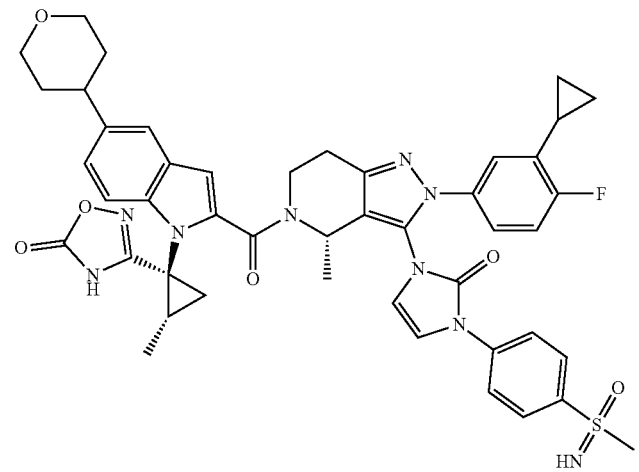 [SMILES: C[C@H]1c2c(nn(-c3ccc(F)c(C4CC4)c3)c2-n2ccn(-c3ccc(S(C)(=N)=O)cc3)c2=O)CCN1C(=O)c1cc2cc(C3CCOCC3)ccc2n1[C@@]1(c2noc(=O)[nH]2)C[C@@H]1C] |
| 119 | 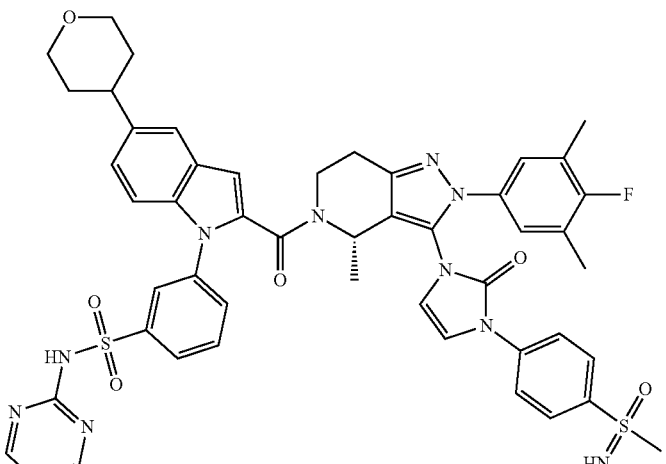 |

TABLE 1-continued

| Compound No. | Structure |
|---|---|
| 120 | 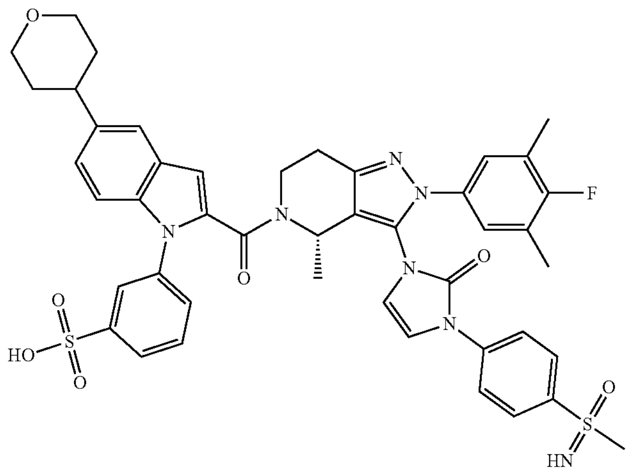 [SMILES: Cc1cc(-n2nc3c(c2-n2ccn(-c4ccc(S(C)(=N)=O)cc4)c2=O)[C@H](C)N(C(=O)c2cc4cc(C5CCOCC5)ccc4n2-c2cccc(S(=O)(=O)O)c2)CC3)cc(C)c1F] |
| 121 | Enantiomer 2 |
| 122 | Enantiomer 2 |

TABLE 1-continued

| Compound No. | Structure |
| --- | --- |
| 123 | 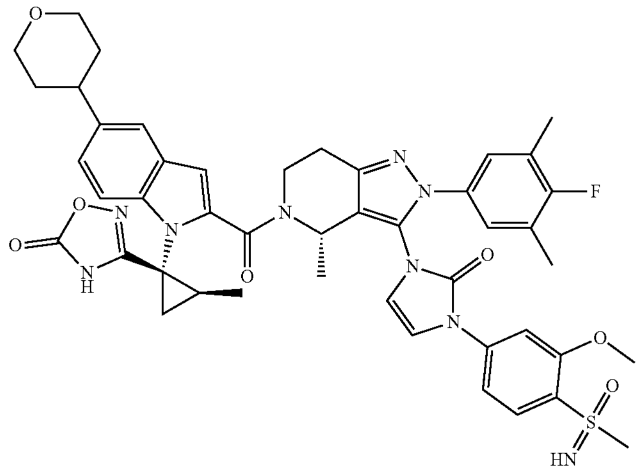 [SMILES: COc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1S(C)(=N)=O] |
| 124 | 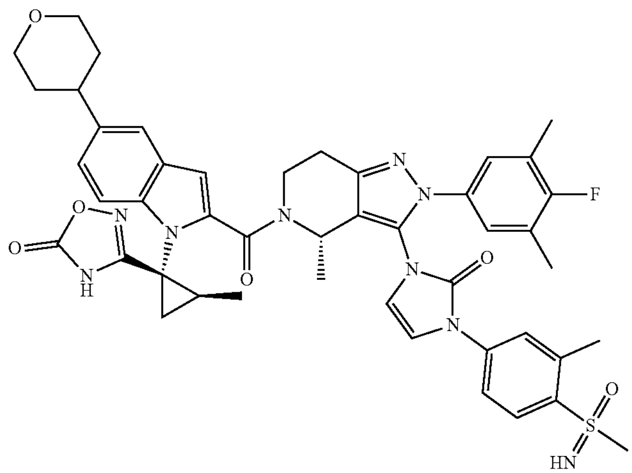 [SMILES: Cc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1S(C)(=N)=O] |
| 125 | 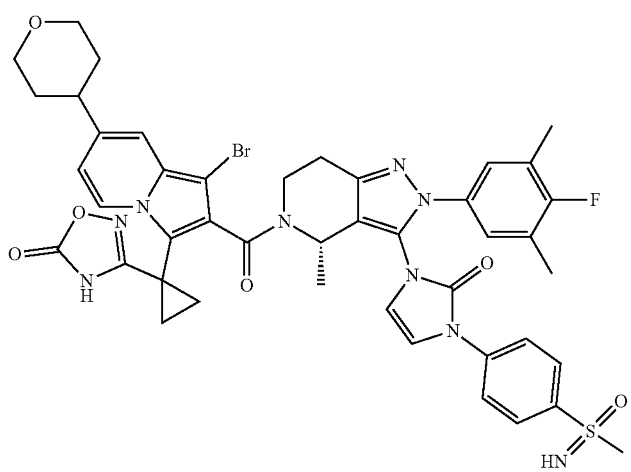 [SMILES: Cc1cc(-n2nc3c(c2-n2ccn(-c4ccc(S(C)(=N)=O)cc4)c2=O)[C@H](C)N(C(=O)c2c(Br)c4cc(C5CCOCC5)ccn4c2C2(c4noc(=O)[nH]4)CC2)CC3)cc(C)c1F] |

TABLE 1-continued

| Compound No. | Structure |
| --- | --- |
| 126 | 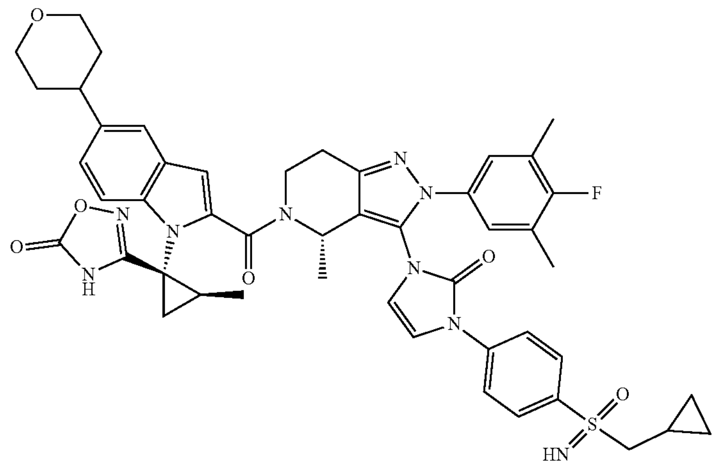 [SMILES: Cc1cc(-n2nc3c(c2-n2ccn(-c4ccc(S(=N)(=O)CC5CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 127 | 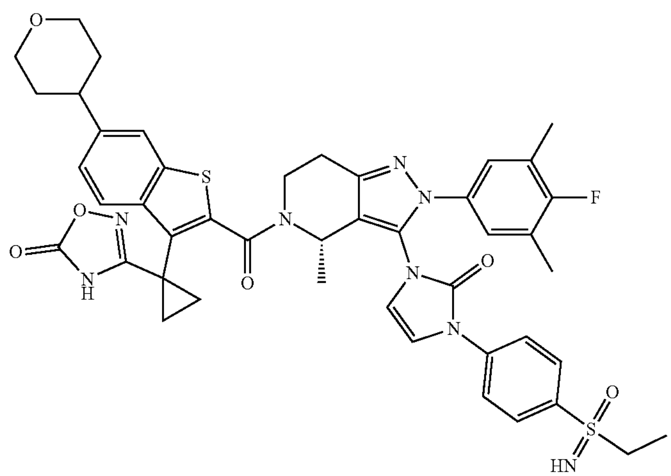 [SMILES: CCS(=N)(=O)c1ccc(-n2ccn(-c3c4c(nn3-c3cc(C)c(F)c(C)c3)CCN(C(=O)c3sc5cc(C6CCOCC6)ccc5c3C3(c5noc(=O)[nH]5)CC3)[C@H]4C)c2=O)cc1] |
| 128 | 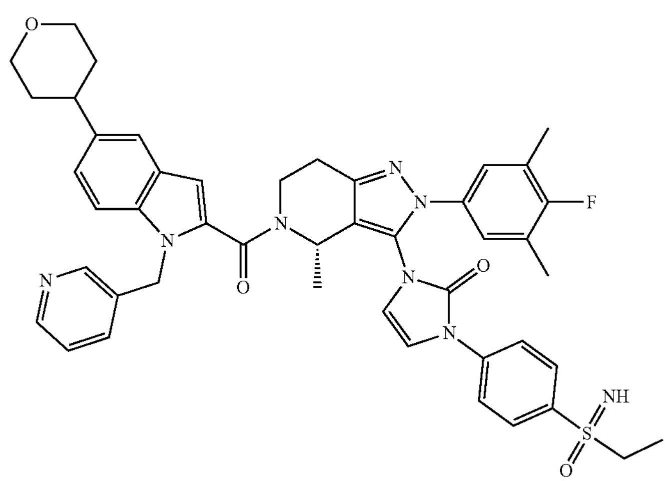 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3Cc3cccnc3)[C@H]4C)c2=O)cc1] |

TABLE 1-continued

| Compound No. | Structure |
|---|---|
| 129 | *(structure)* |
| 130 | *(structure)* Enantiomer 1 |
| 131 | *(structure)* Enantiomer 2 |

TABLE 1-continued

| Compound No. | Structure |
|---|---|
| 132 | Enantiomer 1 |
| 133 | Enantiomer 2 |
| 134 | Enantiomer 1 |

TABLE 1-continued
| Compound No. | Structure |
|---|---|
| 135 | 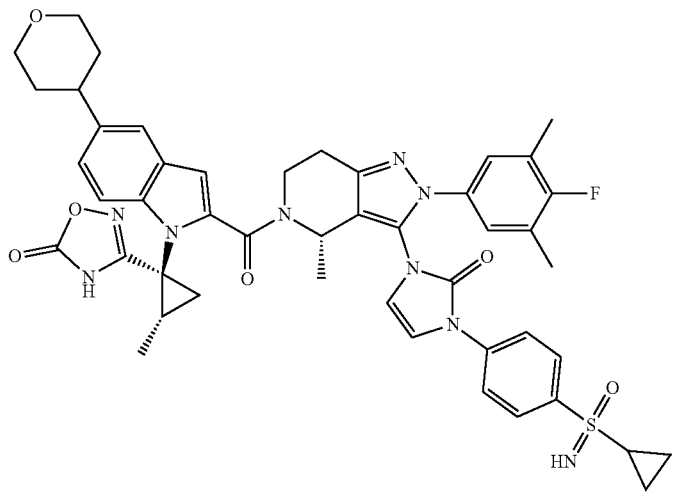 [SMILES: Cc1cc(-n2nc3c(c2-n2ccn(-c4ccc(S(=N)(=O)C5CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]<br>Enantiomer 2 |
| 136 | 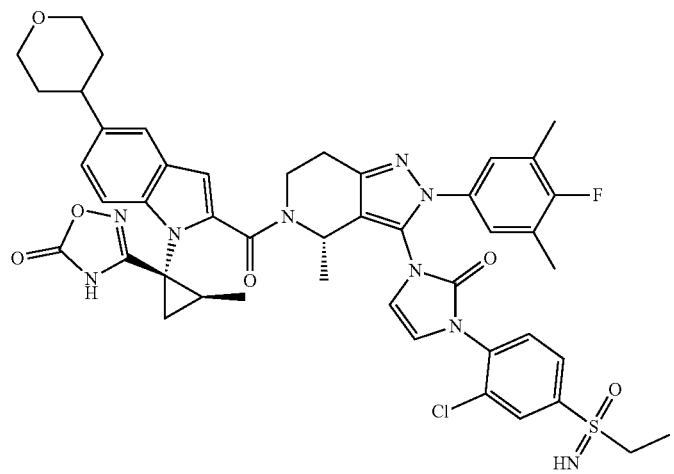 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(Cl)c1]<br>Enantiomer 1 |
| 137 | 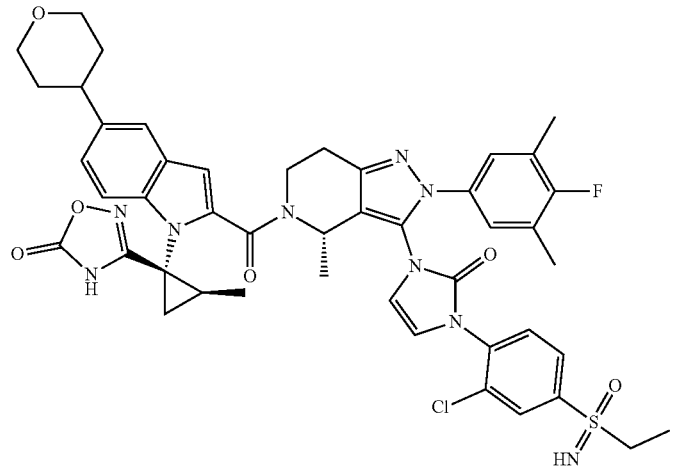 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(Cl)c1]<br>Enantiomer 2 |

TABLE 1-continued
| Compound No. | Structure |
|---|---|
| 138 | 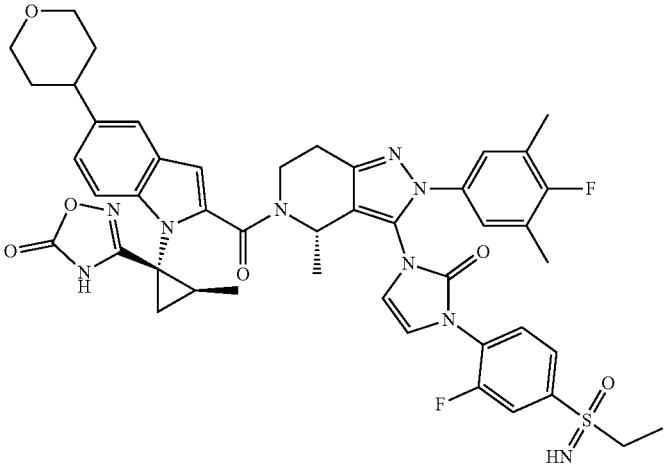 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(F)c1] |
| 139 | 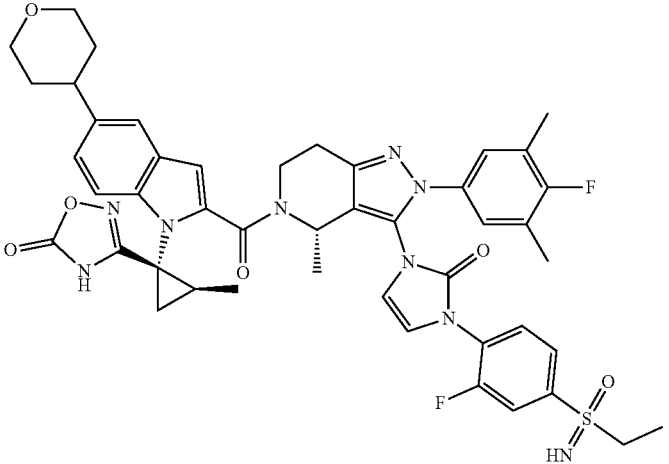 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(F)c1]
Enantiomer 2 |
| 140 | 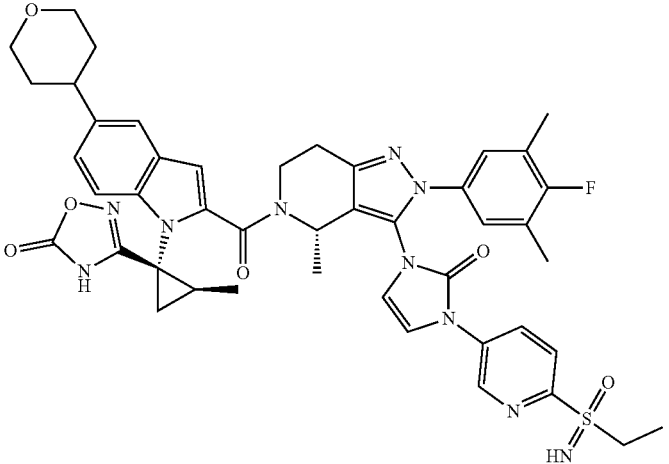 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cn1]
Enantiomer 1 |

TABLE 1-continued
| Compound No. | Structure |
|---|---|
| 141 | 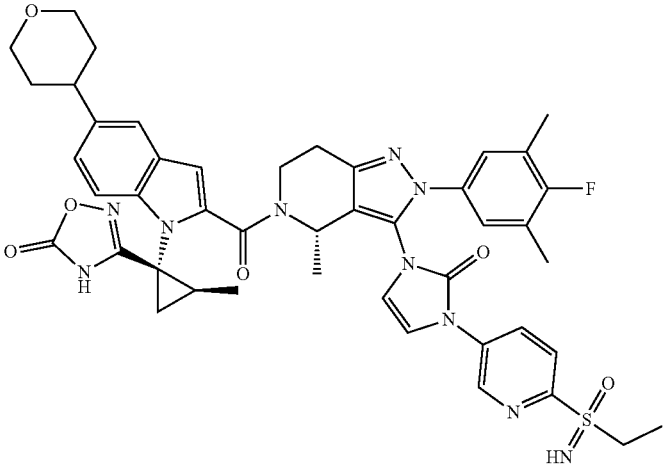 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cn1]<br>Enantiomer 2 |
| 142 | 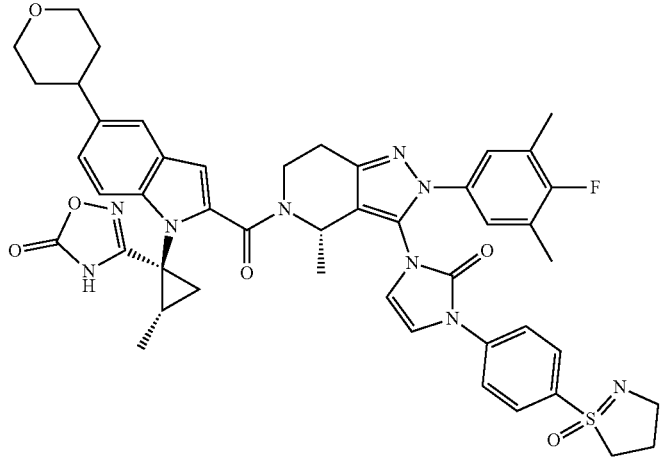 [SMILES: Cc1cc(-n2nc3c(c2-n2ccn(-c4ccc(S5(=O)=NCCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]<br>Enantiomer 1 |
| 143 | 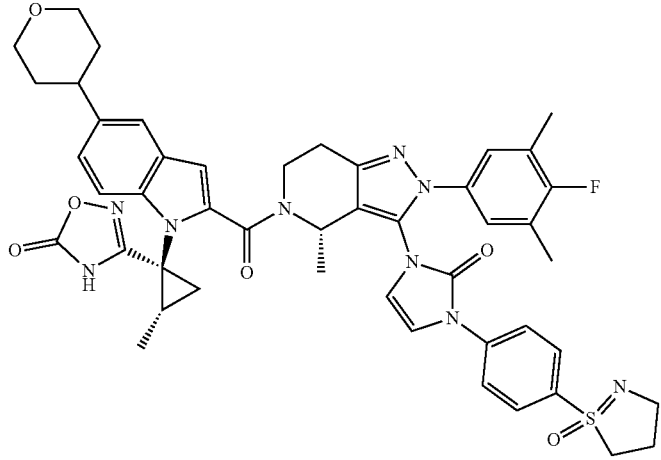 [SMILES: Cc1cc(-n2nc3c(c2-n2ccn(-c4ccc(S5(=O)=NCCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]<br>Enantiomer 2 |

| Compound No. | Structure |
|---|---|
| 144 | 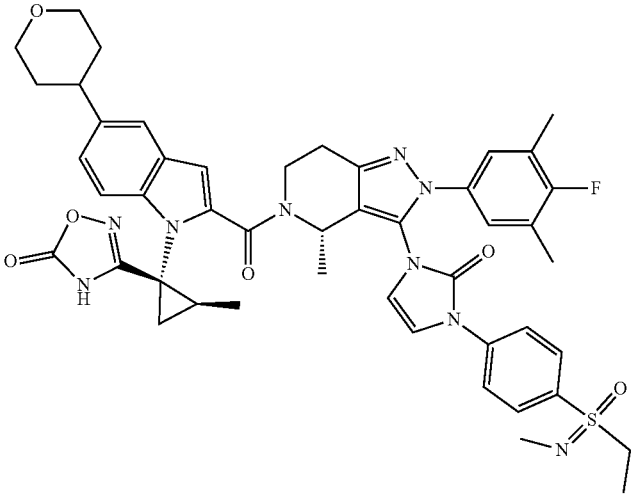<br>Single unknown enantiomer |
| 145 | 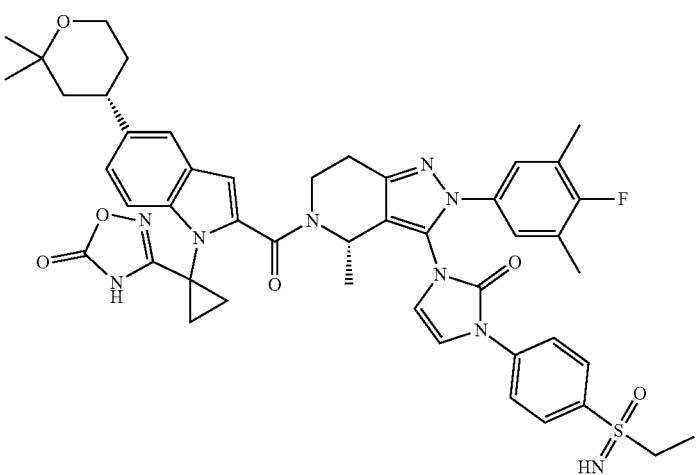 [SMILES: CCS(=N)(=O)c1ccc(-n2ccn(-c3c4c(nn3-c3cc(C)c(F)c(C)c3)CCN(C(=O)c3cc5cc([C@H]6CCOC(C)(C)C6)ccc5n3C3(c5noc(=O)[nH]5)CC3)[C@H]4C)c2=O)cc1]<br>Single unknown enantiomer |
| 146 | 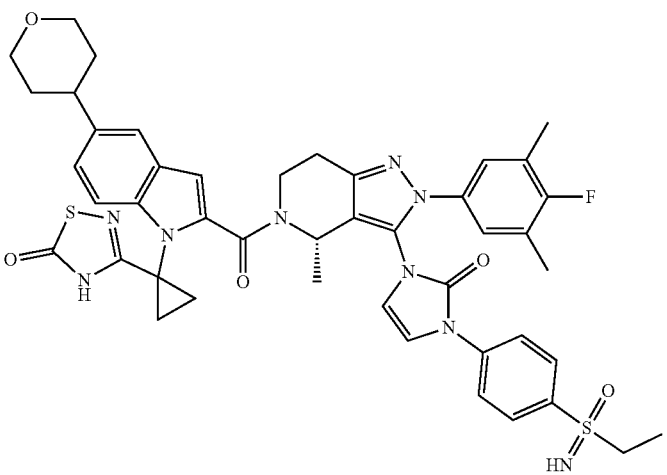 [SMILES: CCS(=N)(=O)c1ccc(-n2ccn(-c3c4c(nn3-c3cc(C)c(F)c(C)c3)CCN(C(=O)c3cc5cc(C6CCOCC6)ccc5n3C3(c5nsc(=O)[nH]5)CC3)[C@H]4C)c2=O)cc1]<br>Single unknown enantiomer |

TABLE 1-continued
| Compound No. | Structure |
|---|---|
| 147 | 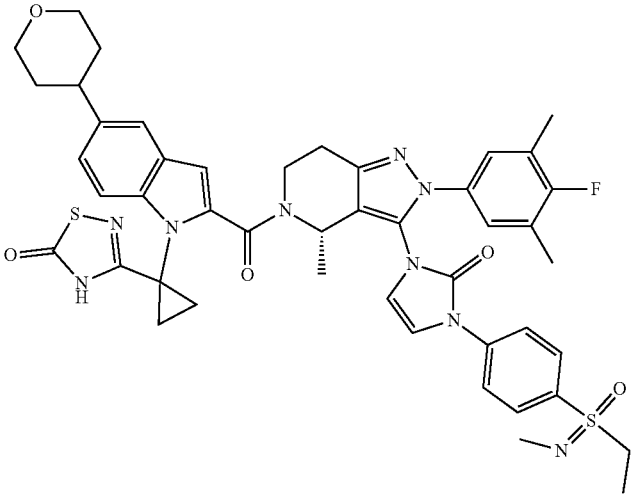<br>Single unknown enantiomer |
| 148 | 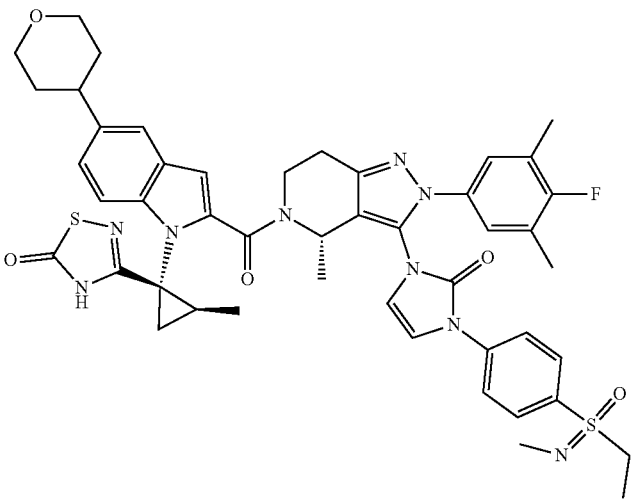<br>Single unknown enantiomer |

TABLE 1-continued
| Compound No. | Structure |
| --- | --- |
| 149 | 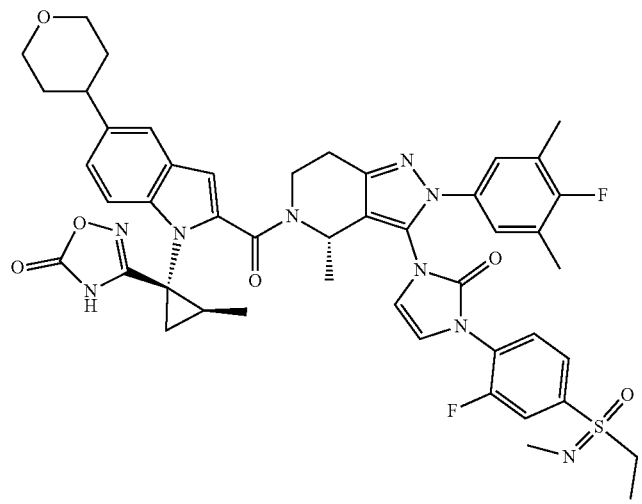<br>Enantiomer 1 |
| 150 | 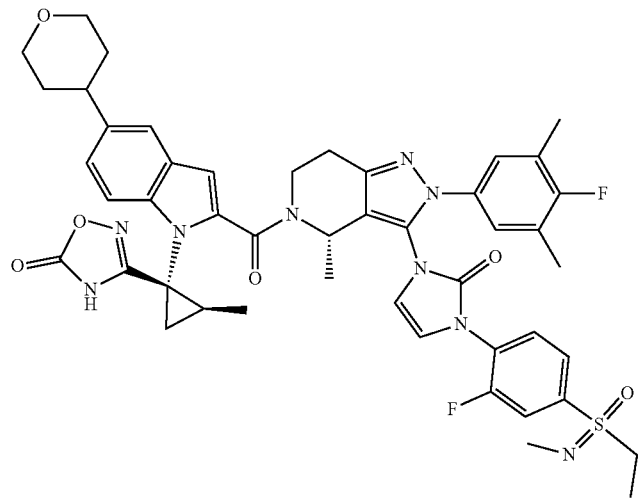<br>Enantiomer 2 |

TABLE 1-continued
| Compound No. | Structure |
|---|---|
| 151 | 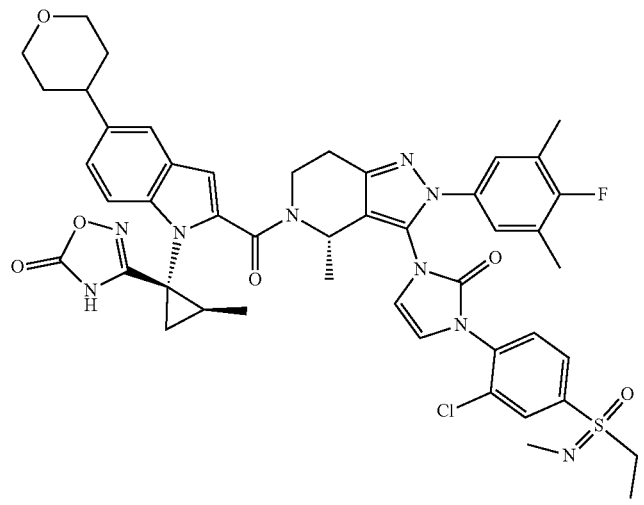<br>Enantiomer 1 |
| 152 | 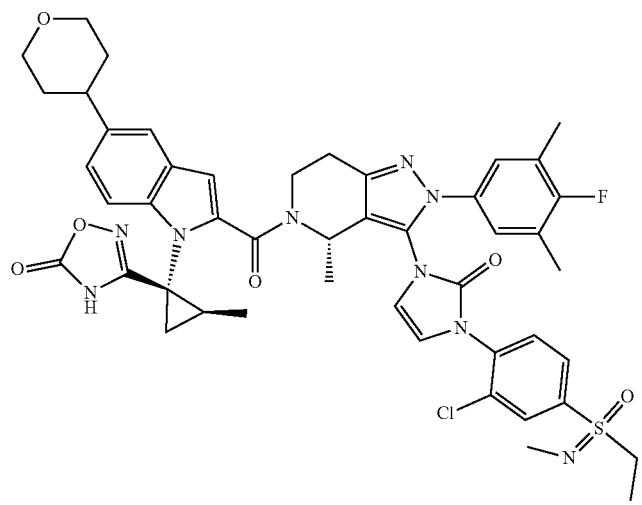<br>Enantiomer 2 |
| 153 | 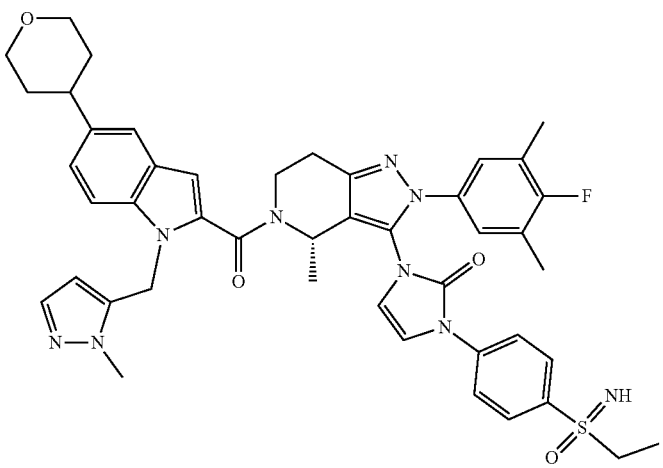<br>Enantiomer 1 |

TABLE 1-continued

| Compound No. | Structure |
|---|---|
| 154 | Enantiomer 2 |
| 155 | Enantiomer 2 |
| 156 | Enantiomer 1 |

TABLE 1-continued

| Compound No. | Structure |
|---|---|
| 157 | *(chemical structure)* <br> Enantiomer 1 |
| 158 | *(chemical structure)* <br> Enantiomer 2 |
| 159 | *(chemical structure)* <br> Single unknown enantiomer <br> Single unknown enantiomer |

TABLE 1-continued
| Compound No. | Structure |
|---|---|
| 160 | 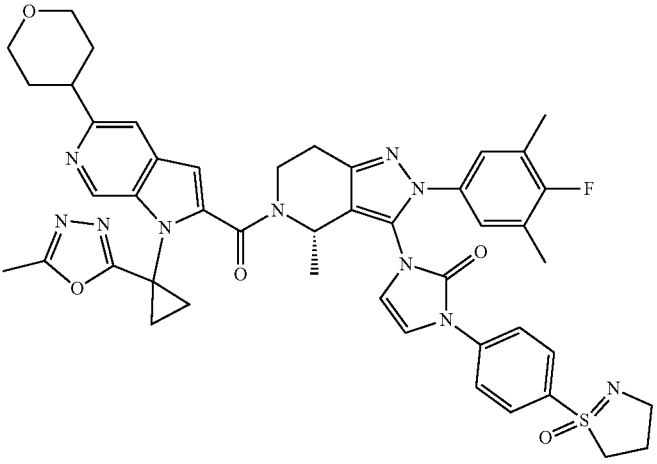<br>Single unknown enantiomer |
| 161 | 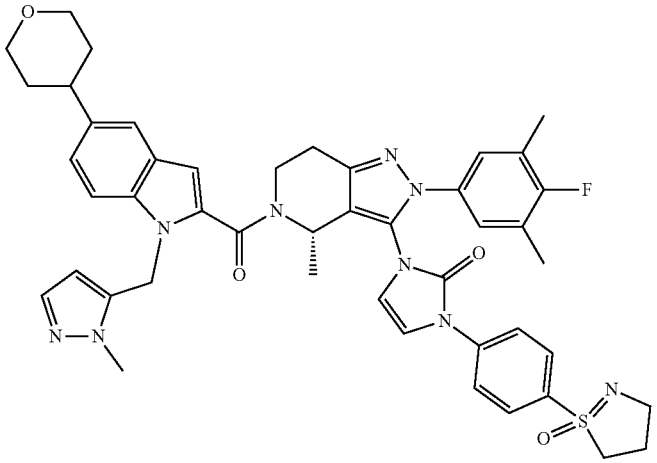<br>Single unknown enantiomer |
| 162 | 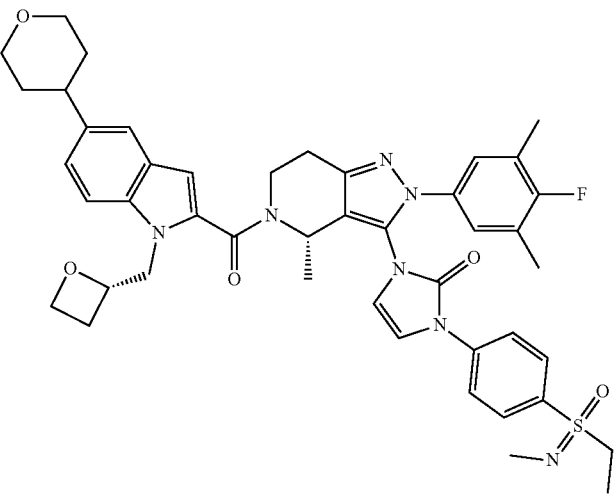<br>Single unknown enantiomer |

TABLE 1-continued

| Compound No. | Structure |
|---|---|
| 163 | 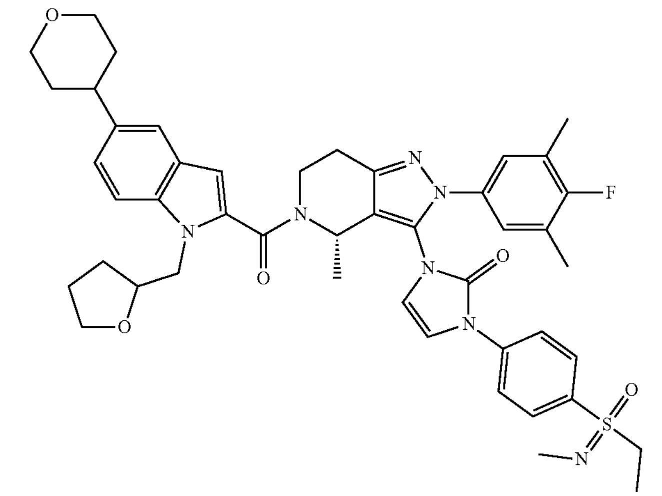 [SMILES: CCS(=O)(=NC)c1ccc(-n2ccn(-c3c4c(nn3-c3cc(C)c(F)c(C)c3)CCN(C(=O)c3cc5cc(C6CCOCC6)ccc5n3CC3CCCO3)[C@H]4C)c2=O)cc1] |
| 164 | Single unknown enantiomer |
| 165 | Single unknown enantiomer |

TABLE 1-continued

| Compound No. | Structure |
|---|---|
| 166 | Enantiomer 1 |
| 167 | Enantiomer 2 |
| 168 | Enantiomer 1 |

TABLE 1-continued
| Compound No. | Structure |
|---|---|
| 169 | 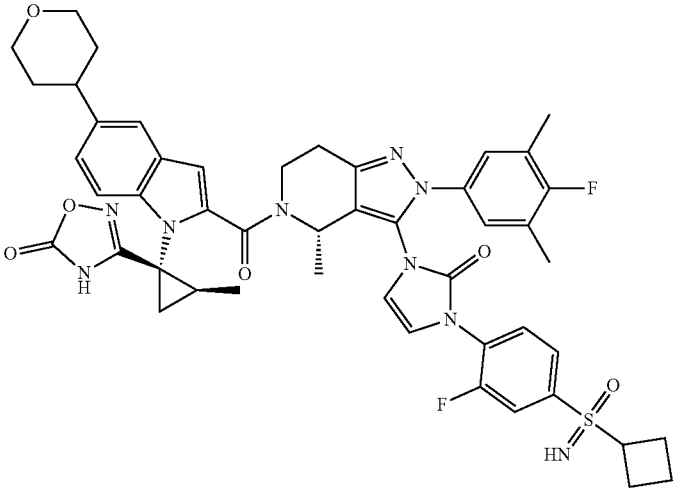<br>Enantiomer 2 |
| 170 | 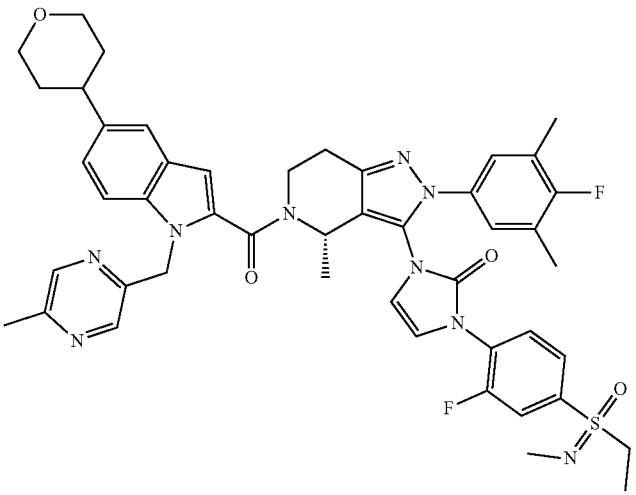<br>Single unknown enantiomer |
| 171 | 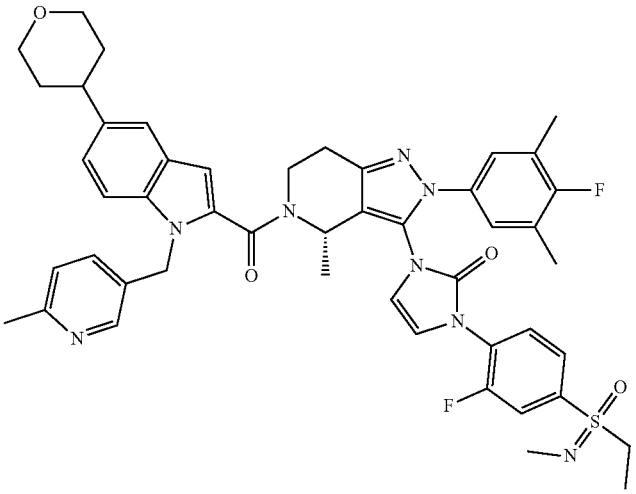<br>Single unknown enantiomer |

TABLE 1-continued
| Compound No. | Structure |
|---|---|
| 172 | 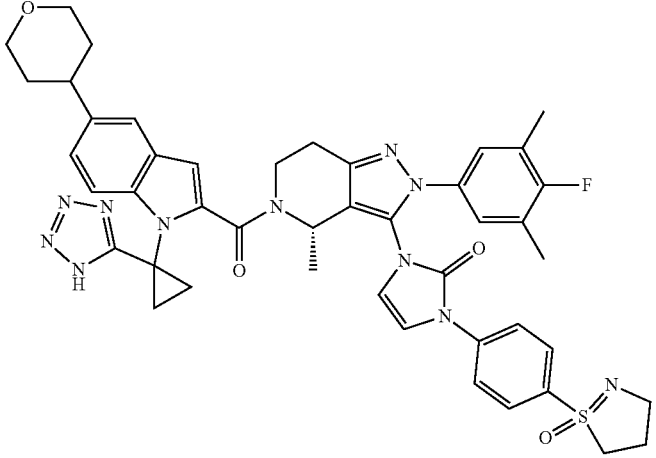<br>Single unknown enantiomer |
| 173 | 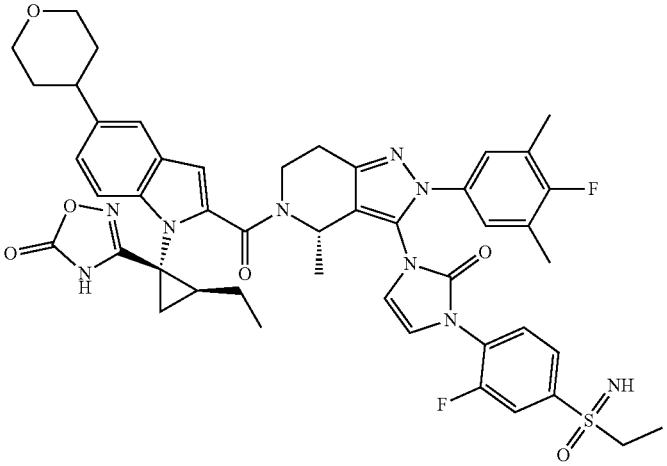<br>Single unknown enantiomer |
| 174 | 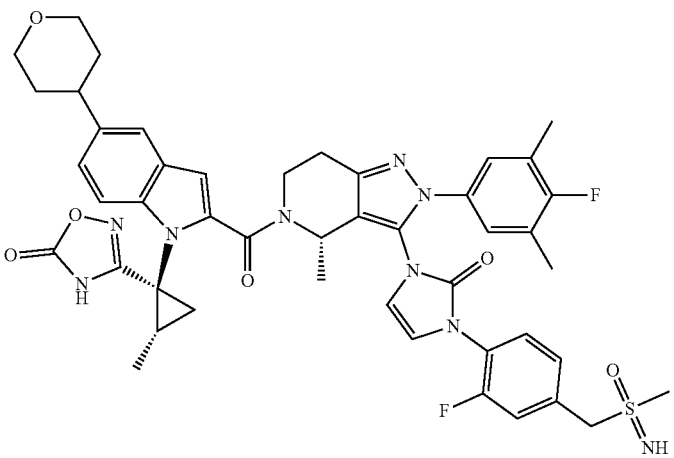 |

TABLE 1-continued
| Compound No. | Structure |
|---|---|
| 175 | 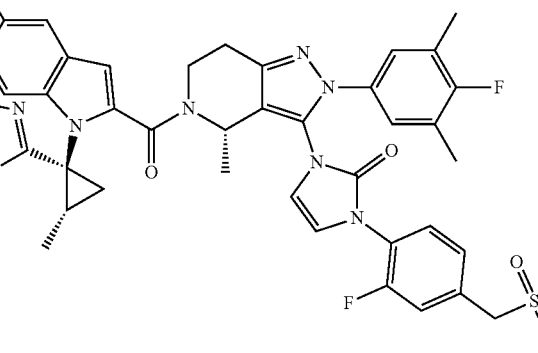  Enantiomer 2 |
| 176 | 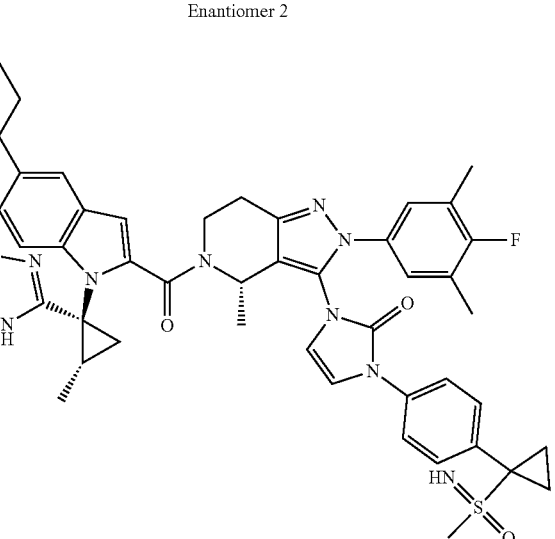  Enantiomer 1 |
| 177 | 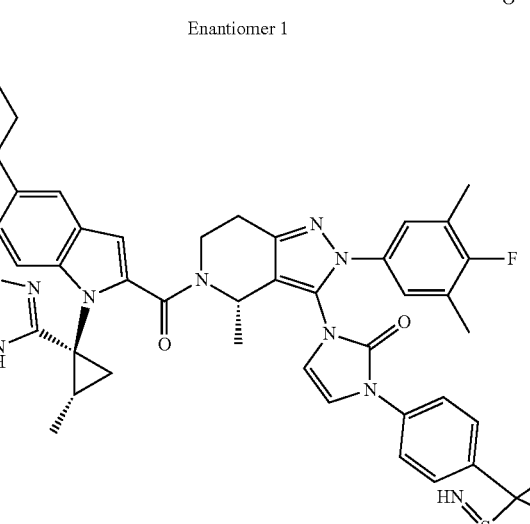  Enantiomer 2 |

TABLE 1-continued
| Compound No. | Structure |
|---|---|
| 178 | 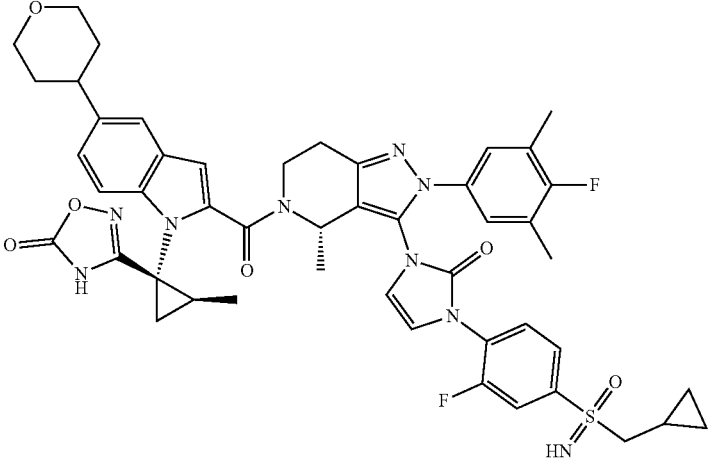<br>Single unknown enantiomer |
| 179 | 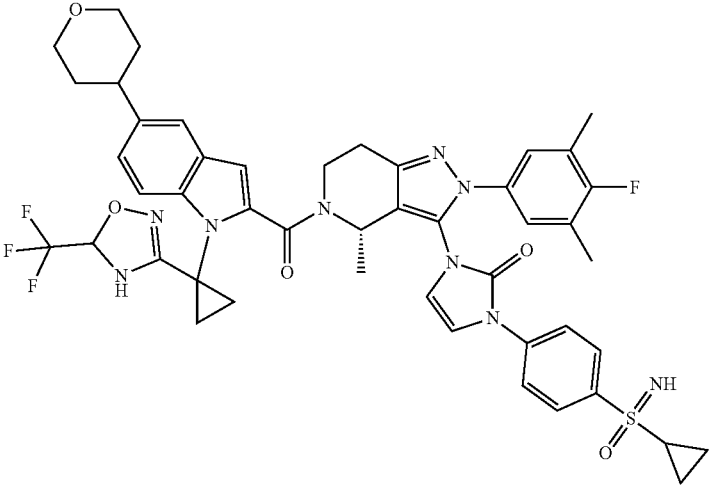<br>Single unknown enantiomer |
| 180 | 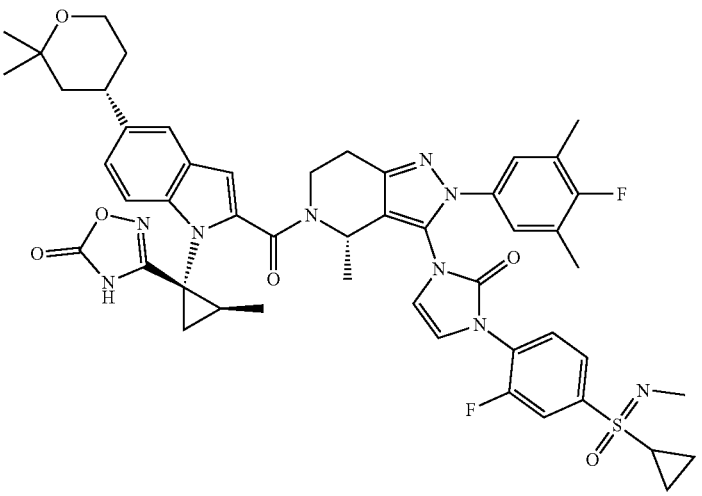<br>Single unknown enantiomer |

TABLE 1-continued
| Compound No. | Structure |
|---|---|
| 181 | 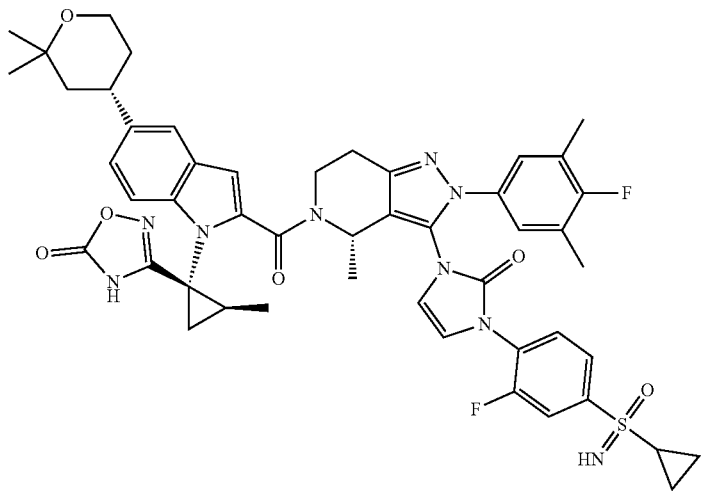<br>Single unknown enantiomer |
| 182 | 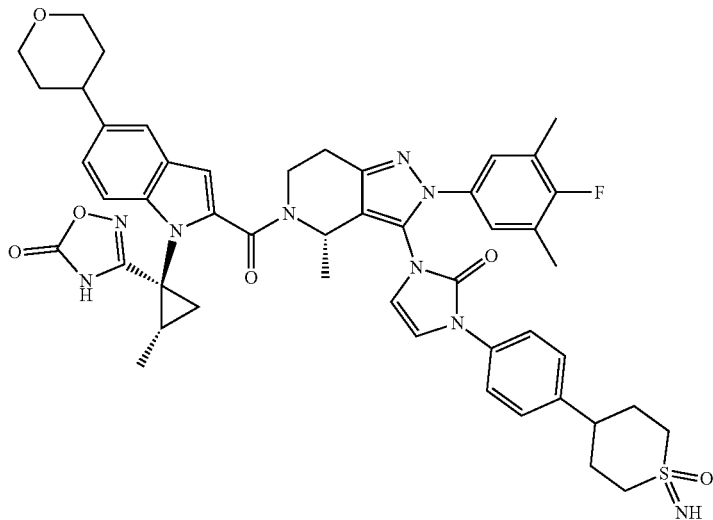<br>Single unknown enantiomer |

TABLE 1-continued
| Compound No. | Structure |
|---|---|
| 183 | 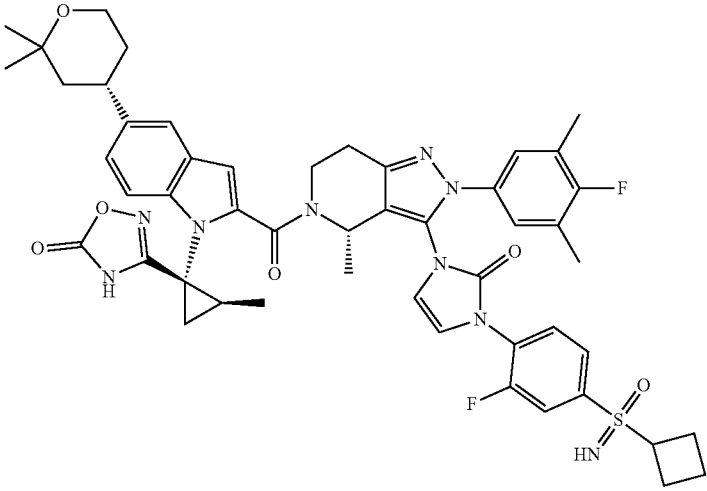<br>Single unknown enantiomer |
| 184 | 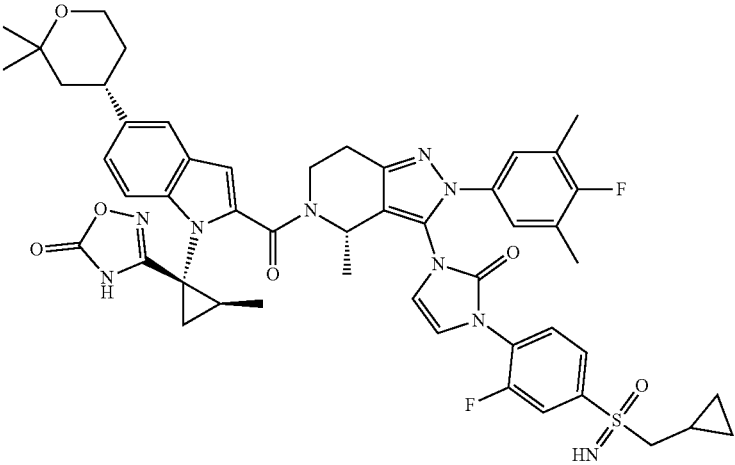<br>Single unknown enantiomer |
| 185 | 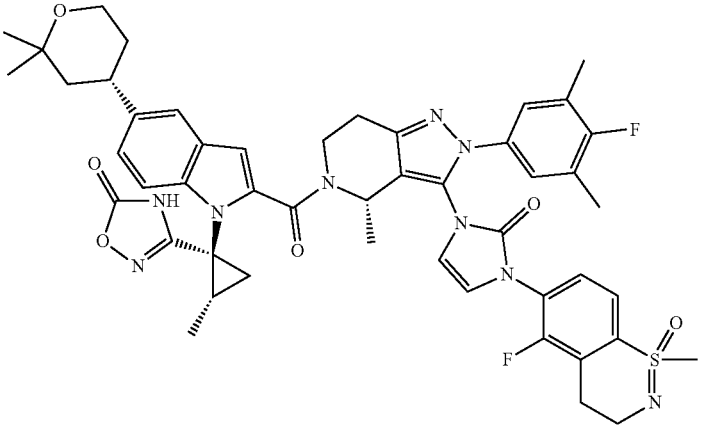<br>Enantiomer 1 |

TABLE 1-continued
| Compound No. | Structure |
|---|---|
| 186 | 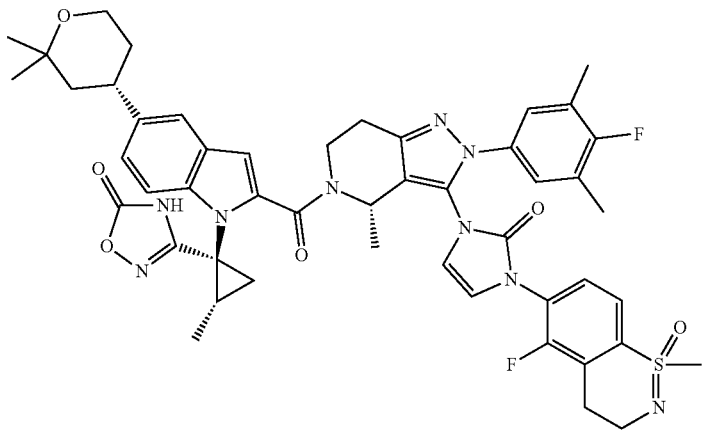<br>Enantiomer 2 |
| 187 | 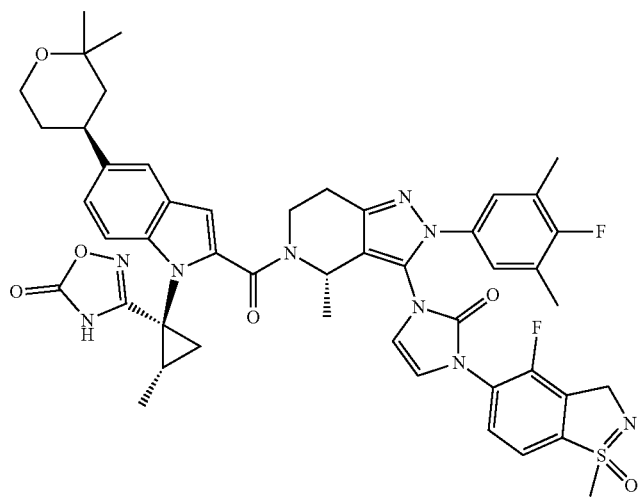<br>Enantiomer 1 |
| 188 | 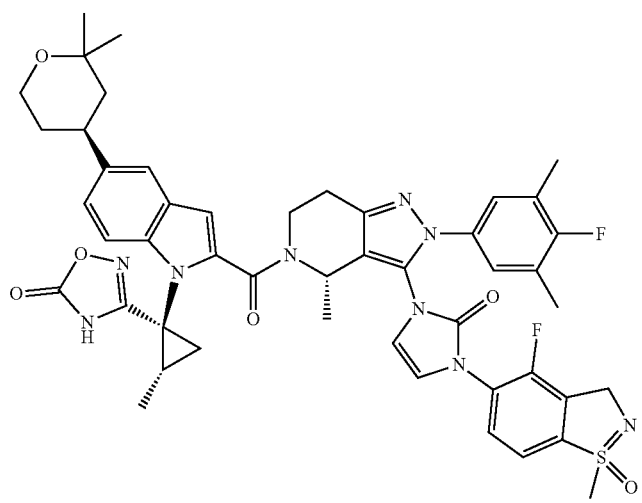<br>Enantiomer 2 |

TABLE 1-continued
| Compound No. | Structure |
|---|---|
| 189 | 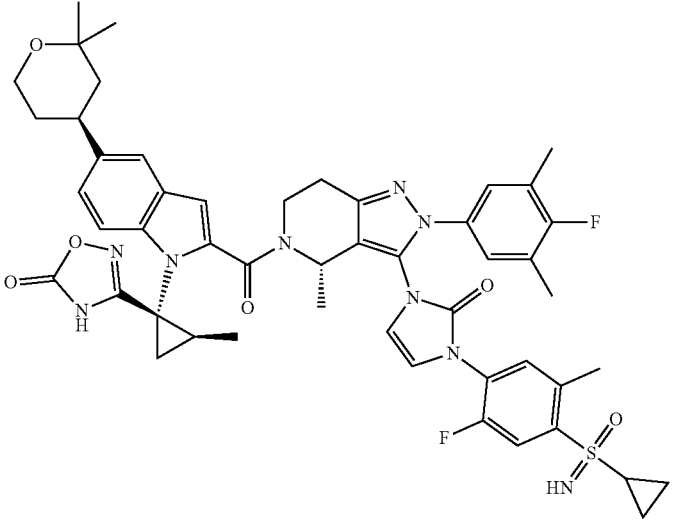<br>Enantiomer 1 |
| 190 | 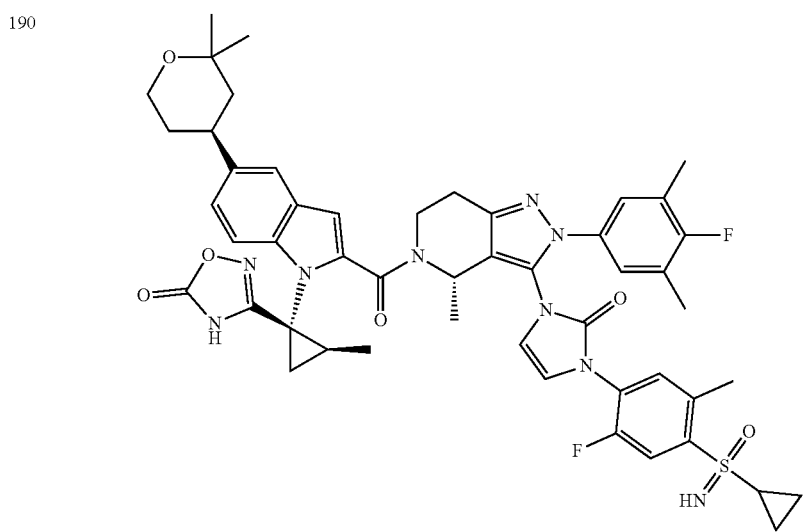<br>Enantiomer 2 |

TABLE 1-continued
| Compound No. | Structure |
|---|---|
| 191 | 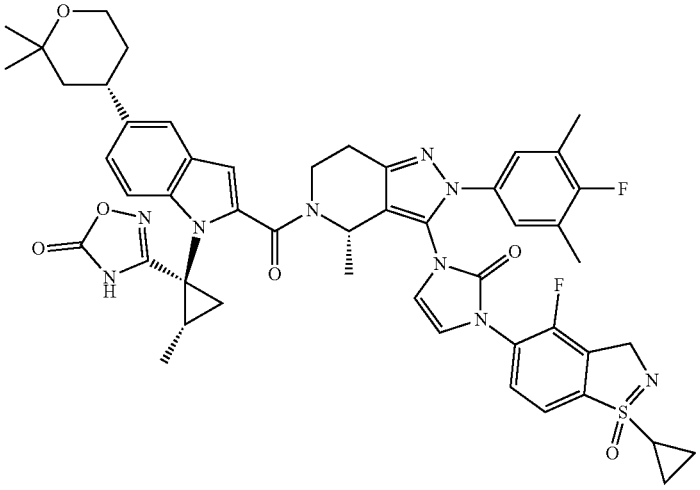
Enantiomer 1 |
| 192 | 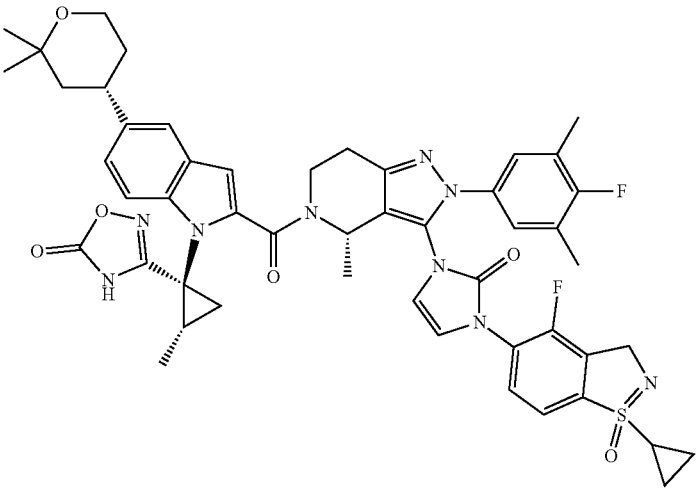
Enantiomer 2 |

TABLE 1-continued

| Compound No. | Structure |
|---|---|
| 193 | Enantiomer 1 |
| 194 | Enantiomer 2 |

TABLE 1-continued
| Compound No. | Structure |
|---|---|
| 195 | 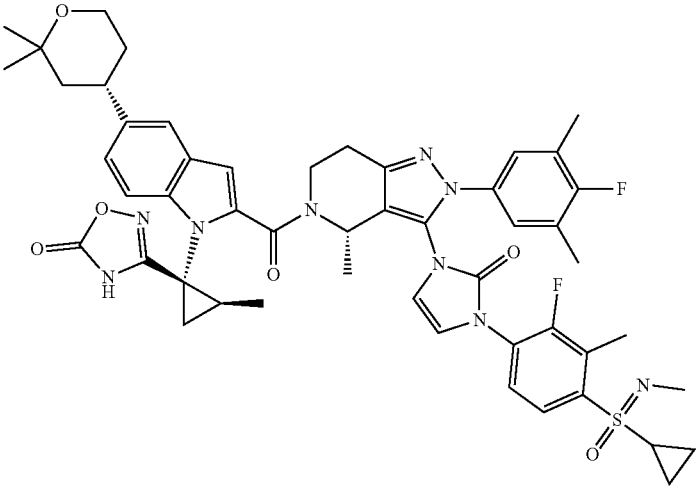
Enantiomer 1 |
| 196 | 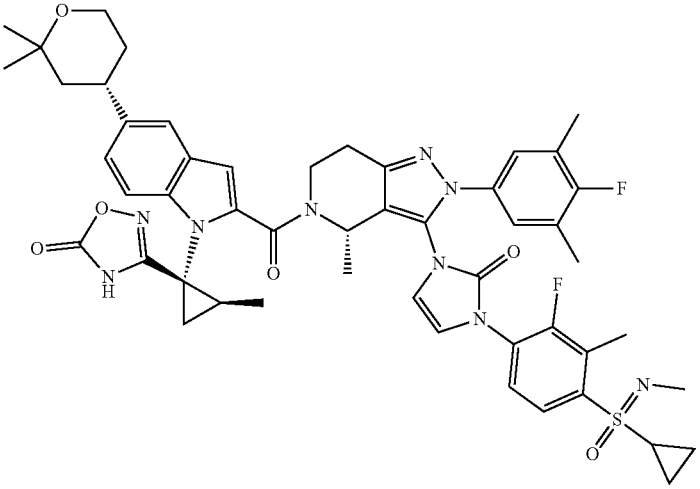
Enantiomer 2 |
| 197 | 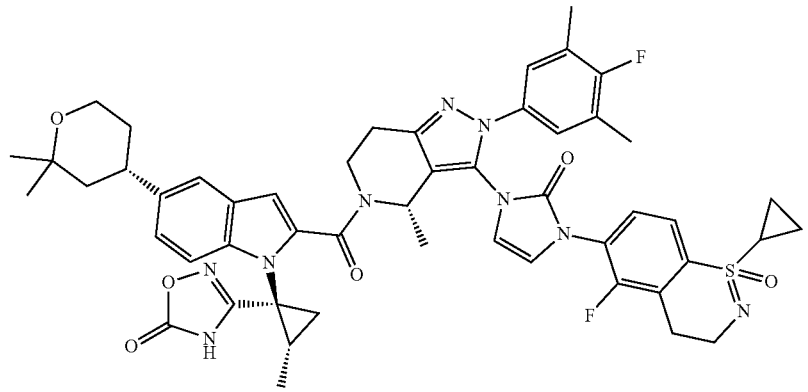
Enantiomer 1 |

TABLE 1-continued
| Compound No. | Structure |
|---|---|
| 198 | 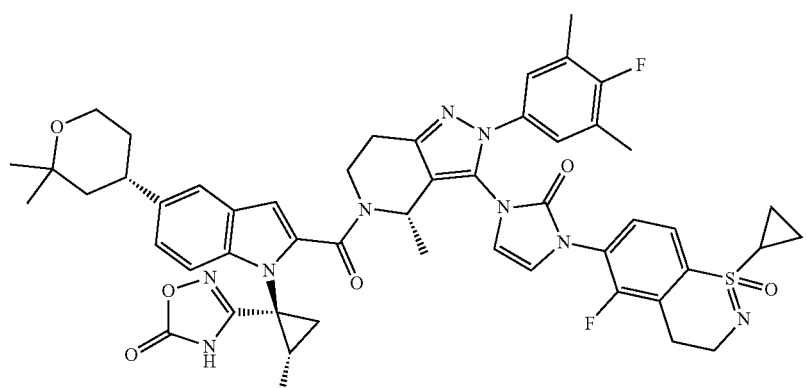<br>Enantiomer 2 |
| 199 | 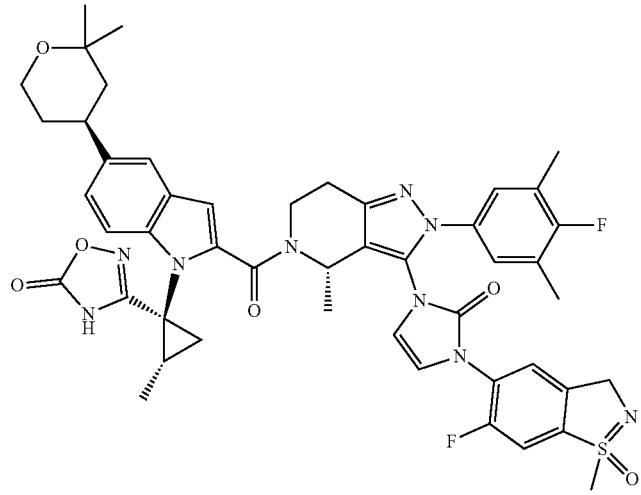<br>Enantiomer 1 |
| 200 | 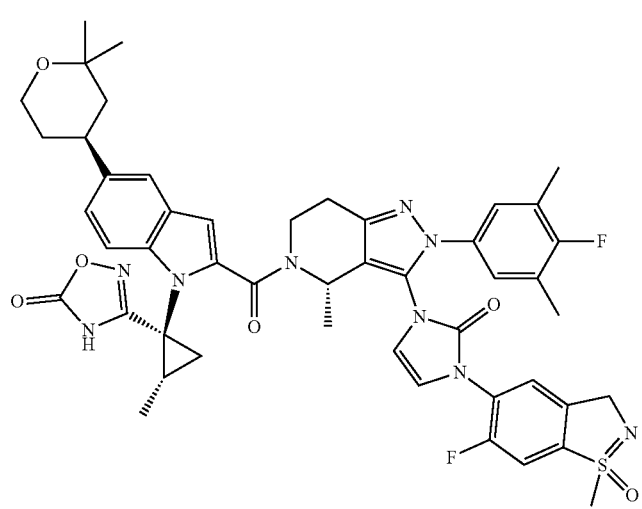<br>Enantiomer 2 |

TABLE 1-continued
| Compound No. | Structure |
|---|---|
| 201 | 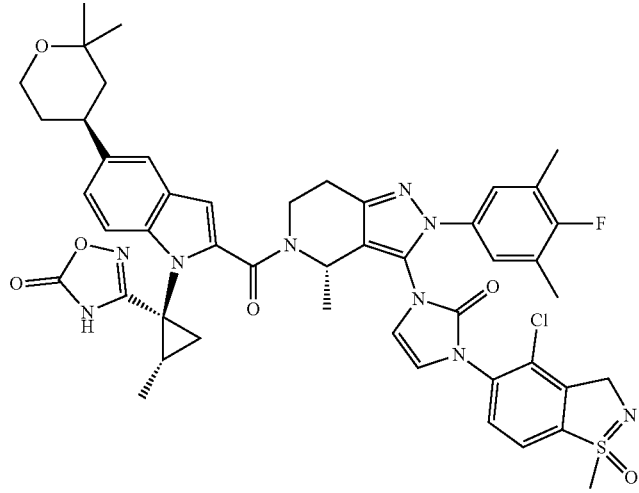<br>Enantiomer 1 |
| 202 | 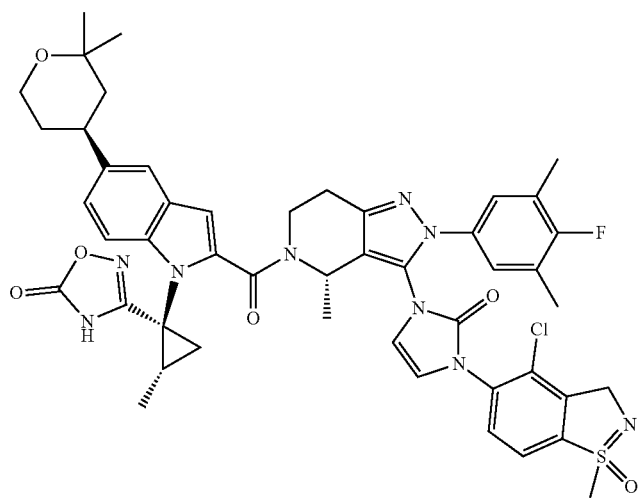<br>Enantiomer 2 |
| 203 | 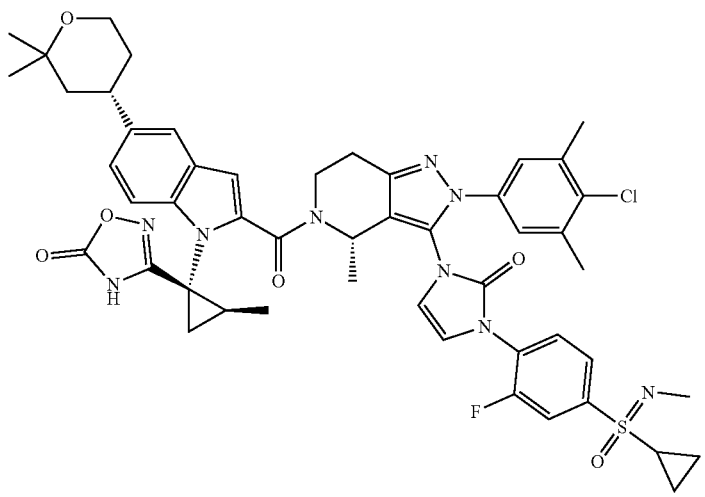<br>Single unknown enantiomer |

TABLE 1-continued
| Compound No. | Structure |
|---|---|
| 204 | 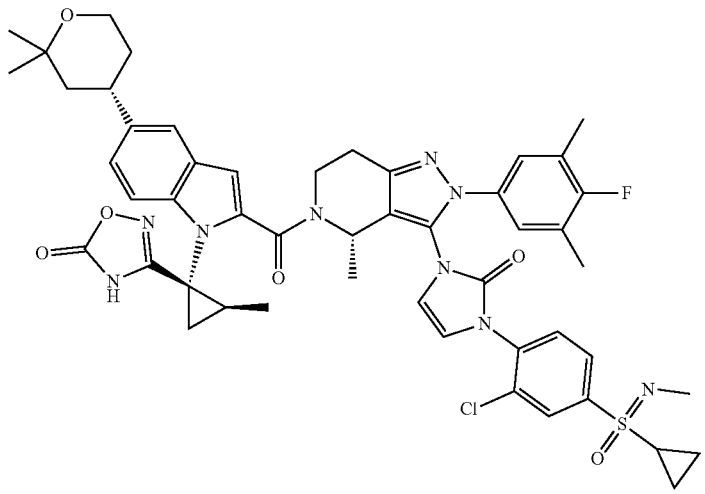<br>Enantiomer 1 |
| 205 | 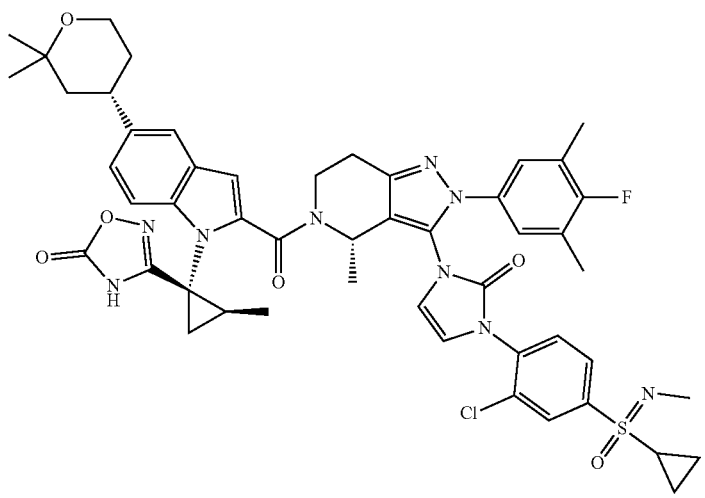<br>Enantiomer 2 |
| 206 | 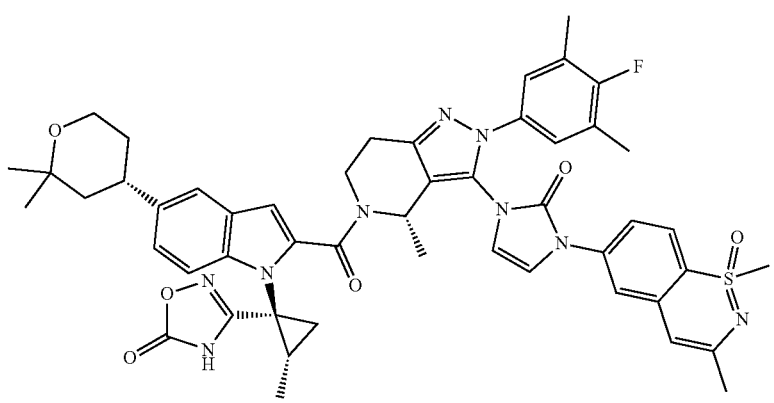<br>Enantiomer 1 |

TABLE 1-continued
| Compound No. | Structure |
|---|---|
| 207 | 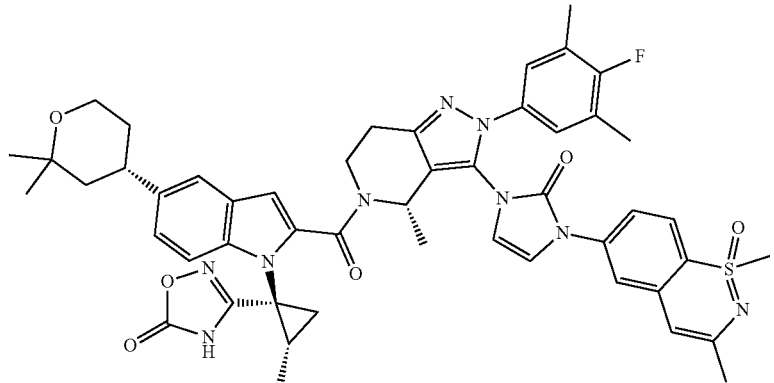<br>Enantiomer 2 |
| 208 | 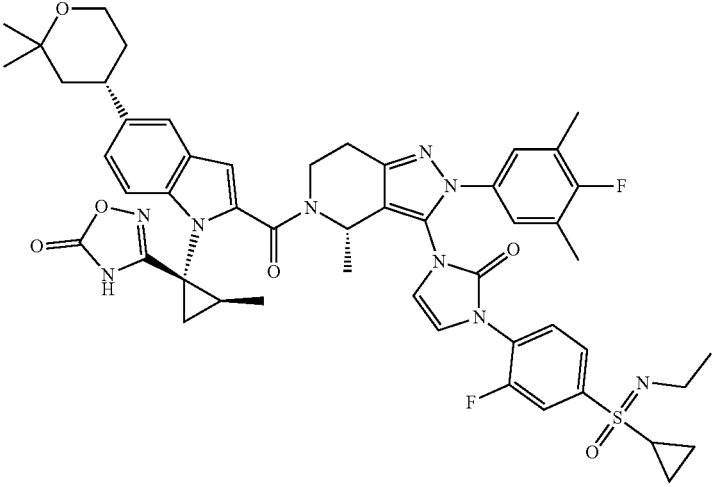<br>Single unknown enantiomer |
| 209 | 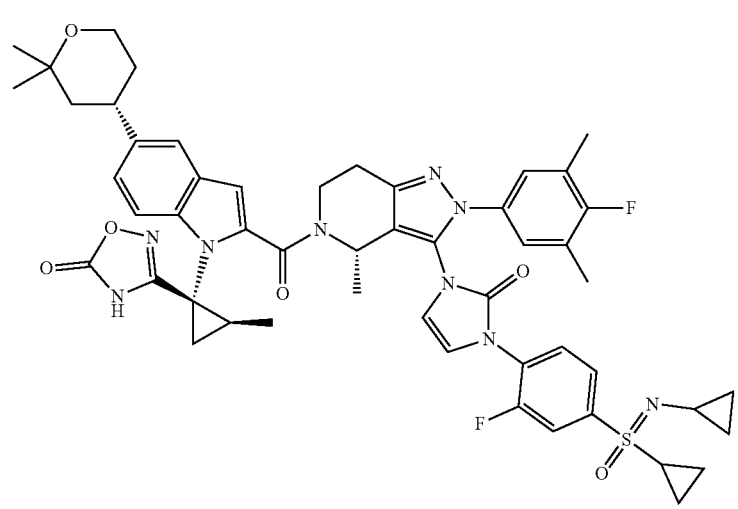<br>Single unknown enantiomer |

TABLE 1-continued
| Compound No. | Structure |
|---|---|
| 210 | 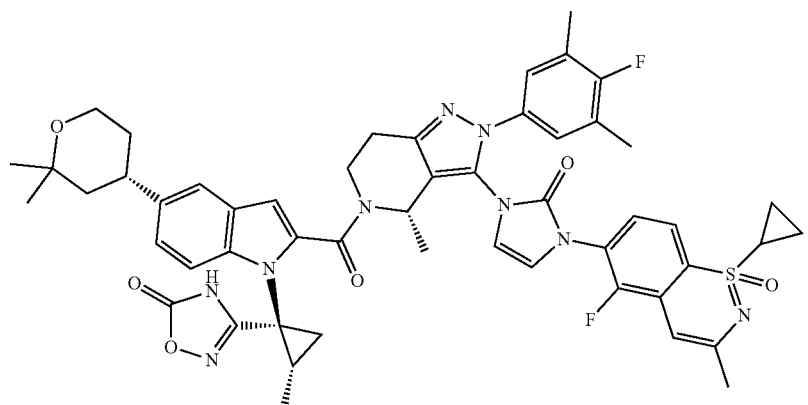<br>Enantiomer 1 |
| 211 | 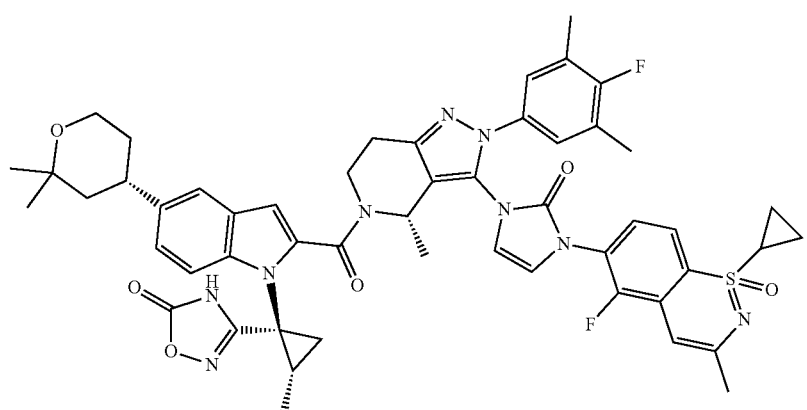<br>Enantiomer 2 |
| 212 | 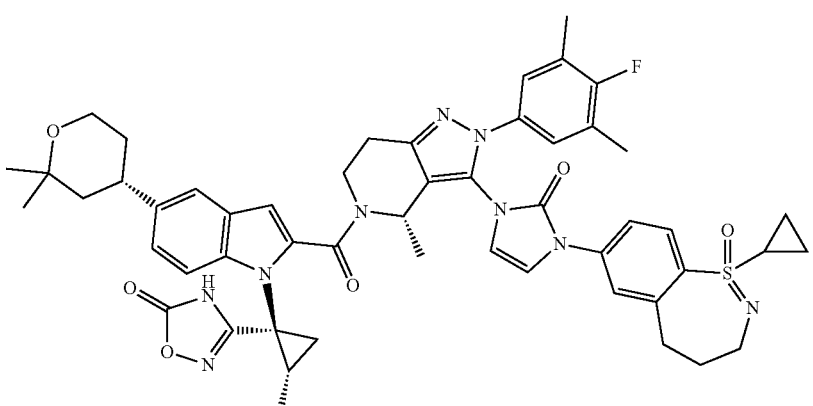<br>Enantiomer 1 |

TABLE 1-continued

| Compound No. | Structure |
|---|---|
| 213 | Enantiomer 2 |
| 214 | Enantiomer 1 |
| 215 | Enantiomer 2 |

TABLE 1-continued

| Compound No. | Structure |
|---|---|
| 216 | *(chemical structure)* <br> Single unknown enantiomer |
| 217 | *(chemical structure)* <br> Single unknown enantiomer |
| 218 | *(chemical structure)* <br> Single unknown enantiomer |

TABLE 1-continued
| Compound No. | Structure |
|---|---|
| 219 | 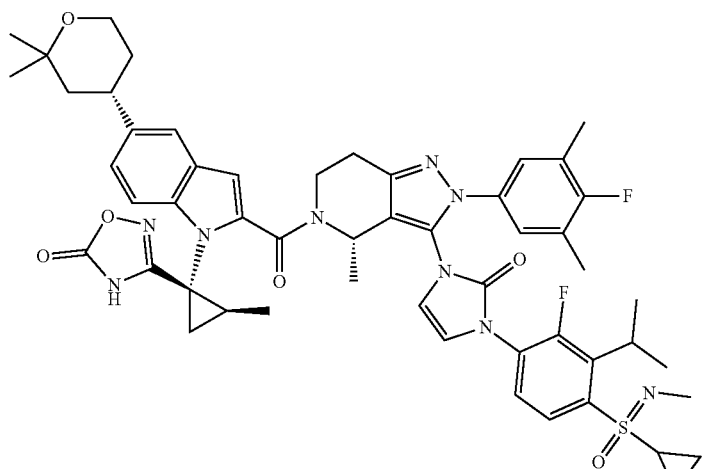<br>Enantiomer 1 |
| 220 | Enantiomer 2 |

TABLE 1-continued
| Compound No. | Structure |
|---|---|
| 221 | 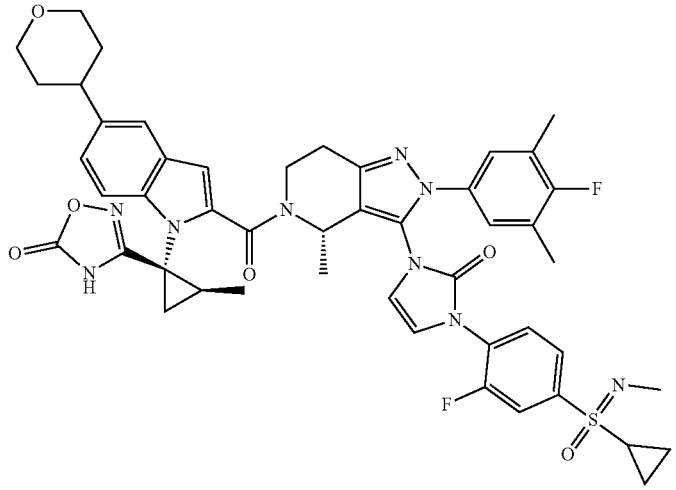 Enantiomer 1 |
| 222 | 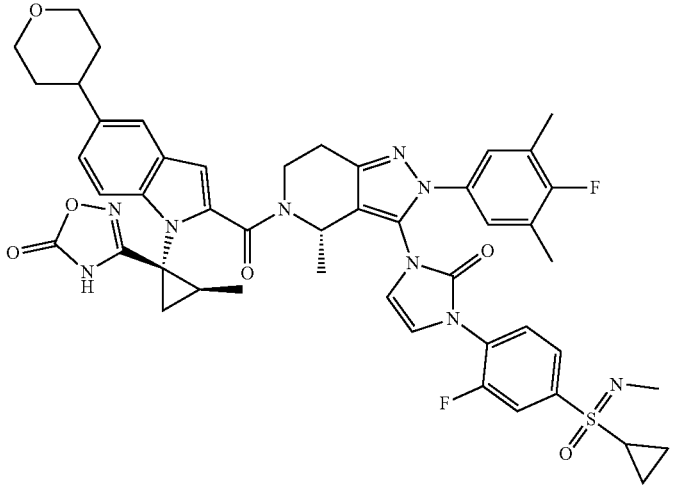 Enantiomer 2 |
| 225 | 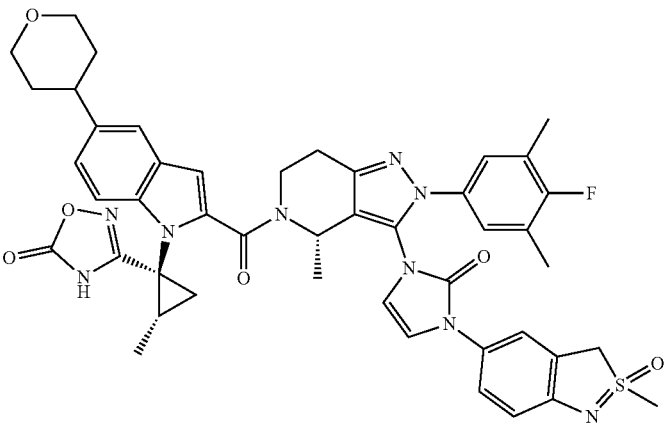 [SMILES: Cc1cc(-n2nc3c(c2-n2ccn(-c4ccc5c(c4)CS(C)(=O)=N5)c2=O)[C@H](C)N(C(=O)c2cc4cc(C5CCOCC5)ccc4n2[C@@]2(c4noc(=O)[nH]4)C[C@@H]2C)CC3)cc(C)c1F] |

TABLE 1-continued
| Compound No. | Structure |
|---|---|
| 226 | 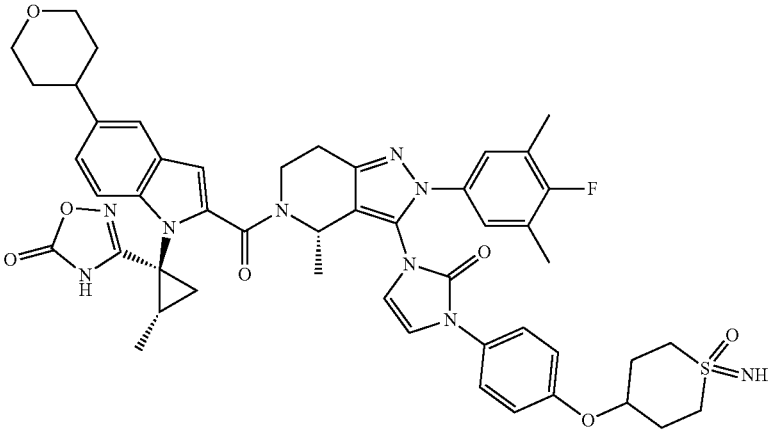 [SMILES: Cc1cc(-n2nc3c(c2-n2ccn(-c4ccc(OC5CCS(=N)(=O)CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 227 | 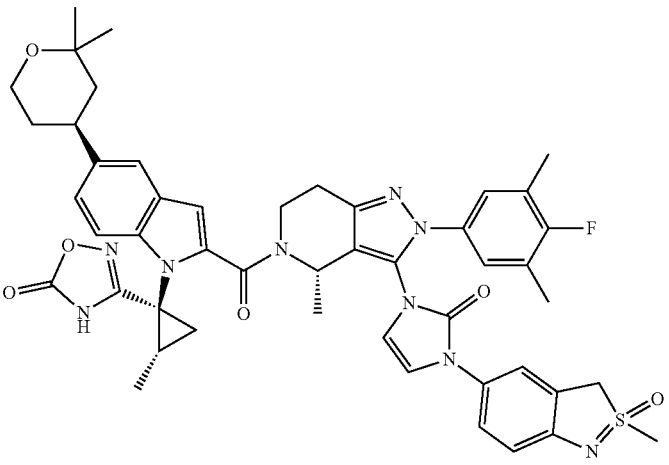 [SMILES: Cc1cc(-n2nc3c(c2-n2ccn(-c4ccc5c(c4)CS(C)(=O)=N5)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F] |
| 228 | 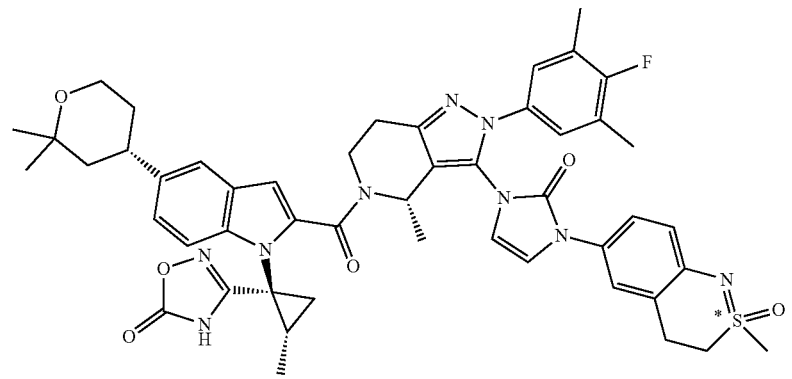<br>Enantiomer 1 |

TABLE 1-continued

| Compound No. | Structure |
|---|---|
| 229 | Enantiomer 2 |
| 230 | Enantiomer 1 |
| 231 | Enantiomer 2 |

TABLE 1-continued
| Compound No. | Structure |
|---|---|
| 232 | 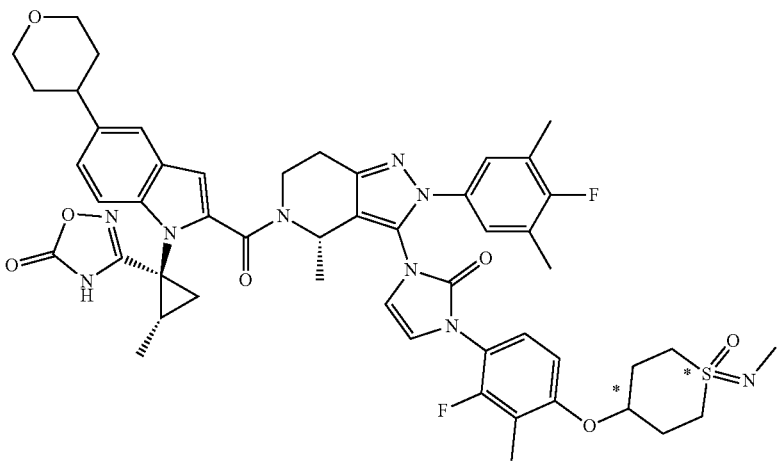<br>Enantiomer 1 |
| 233 | 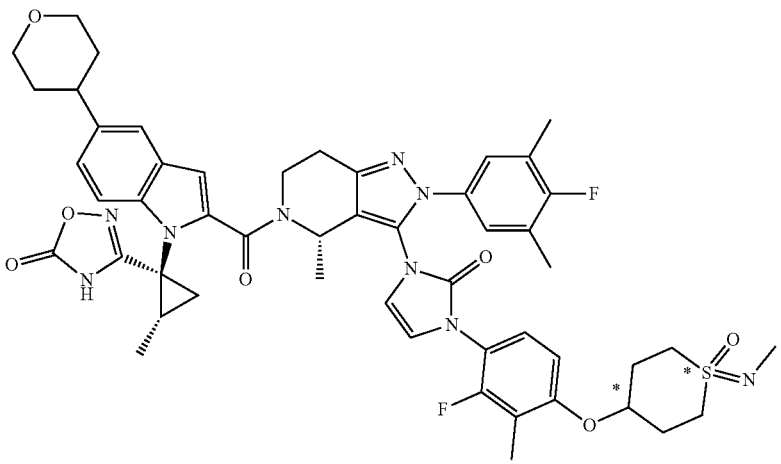<br>Enantiomer 2 |
| 234 | 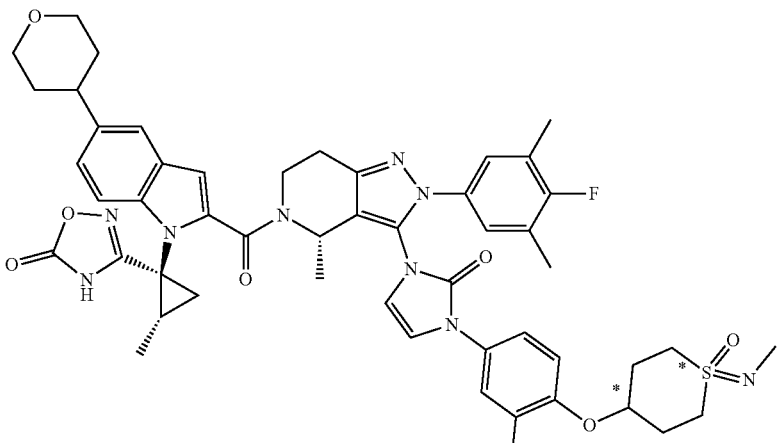<br>Enantiomer 1 |

TABLE 1-continued

| Compound No. | Structure |
|---|---|
| 235 | (chemical structure) Enantiomer 2 |
| 236 | (chemical structure) Enantiomer 1 |

TABLE 1-continued

| Compound No. | Structure |
|---|---|
| 237 | 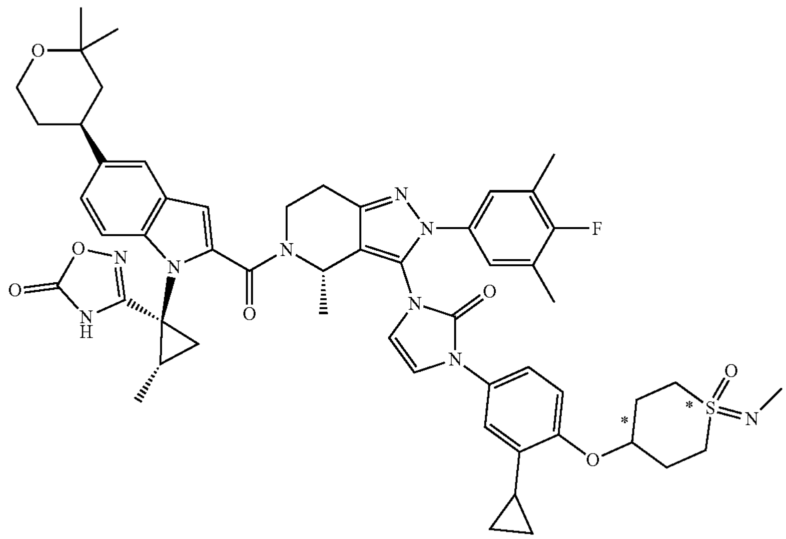 [SMILES: CN=S1(=O)CCC(Oc2ccc(-n3ccn(-c4c5c(nn4-c4cc(C)c(F)c(C)c4)CCN(C(=O)c4cc6cc([C@H]7CCOC(C)(C)C7)ccc6n4[C@@]4(c6noc(=O)[nH]6)C[C@@H]4C)[C@H]5C)c3=O)cc2C2CC2)CC1] |
| 238 | 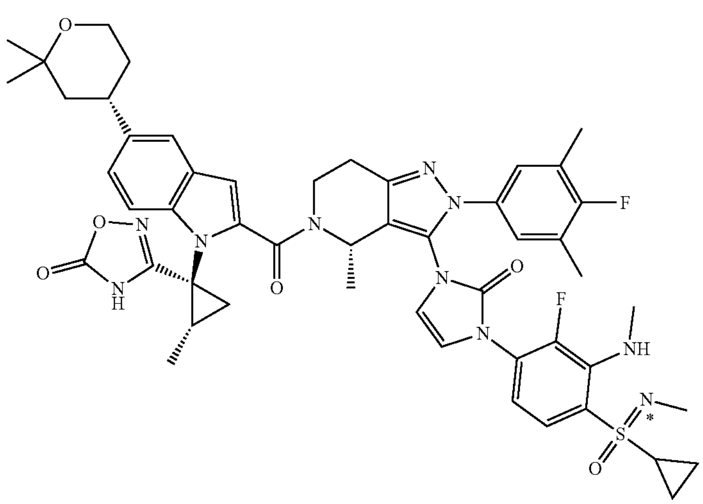 [SMILES: CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1NC)C1CC1] |

In certain embodiments, provided is a compound selected from Table 2, or a pharmaceutically acceptable salt, isotopically enriched analog, stereoisomer, mixture of stereoisomers, or prodrug thereof:

TABLE 2

Structure

TABLE 2-continued
Structure
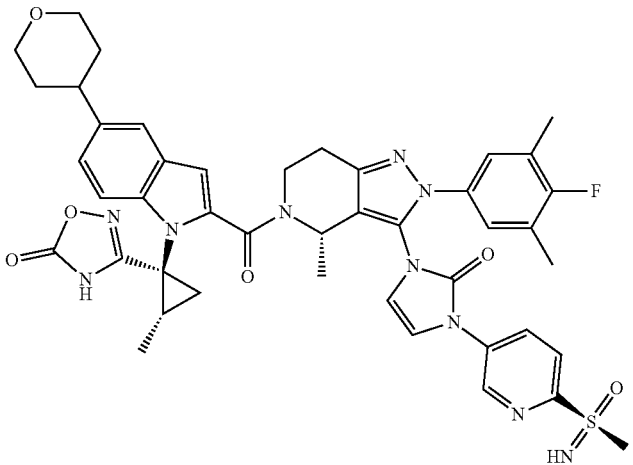 [SMILES: Cc1cc(-n2nc3c(c2-n2ccn(-c4ccc([S@@](C)(=N)=O)nc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
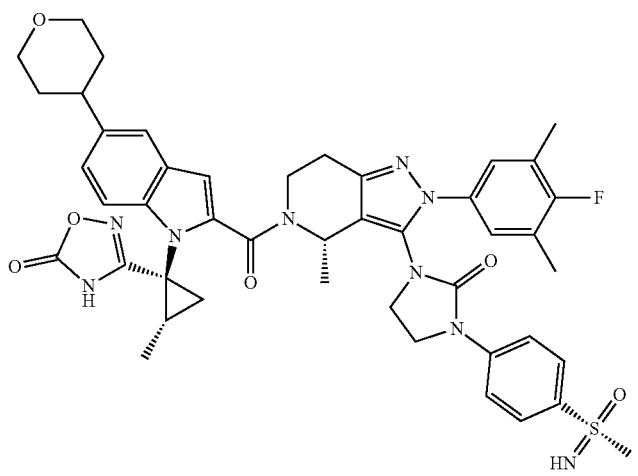 [SMILES: Cc1cc(-n2nc3c(c2N2CCN(c4ccc([S@](C)(=N)=O)cc4)C2=O)[C@H](C)N(C(=O)c2cc4cc(C5CCOCC5)ccc4n2[C@@]2(c4noc(=O)[nH]4)C[C@@H]2C)CC3)cc(C)c1F]
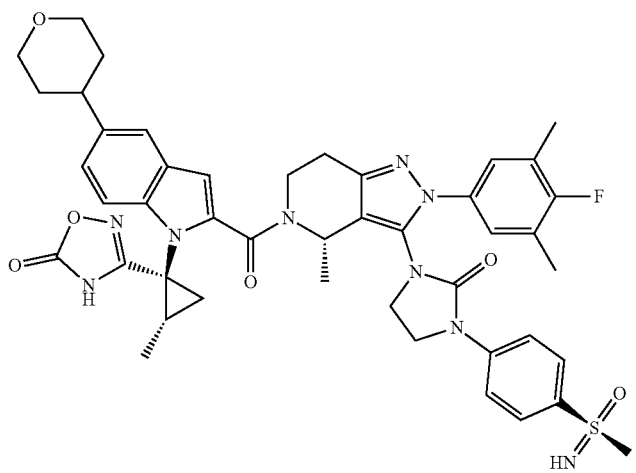 [SMILES: Cc1cc(-n2nc3c(c2N2CCN(c4ccc([S@@](C)(=N)=O)cc4)C2=O)[C@H](C)N(C(=O)c2cc4cc(C5CCOCC5)ccc4n2[C@@]2(c4noc(=O)[nH]4)C[C@@H]2C)CC3)cc(C)c1F]

TABLE 2-continued

Structure

TABLE 2-continued
Structure
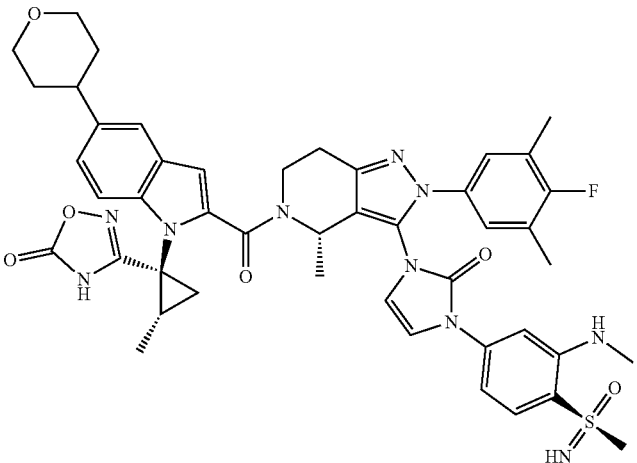 [SMILES: CNc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1[S@@](C)(=N)=O]
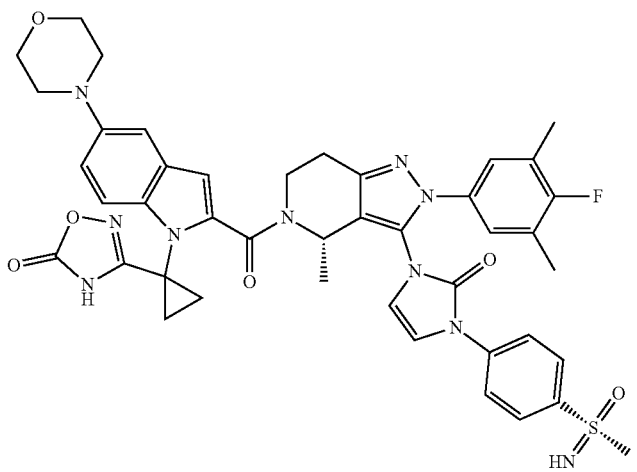 [SMILES: Cc1cc(-n2nc3c(c2-n2ccn(-c4ccc([S@](C)(=N)=O)cc4)c2=O)[C@H](C)N(C(=O)c2cc4cc(N5CCOCC5)ccc4n2C2(c4noc(=O)[nH]4)CC2)CC3)cc(C)c1F]
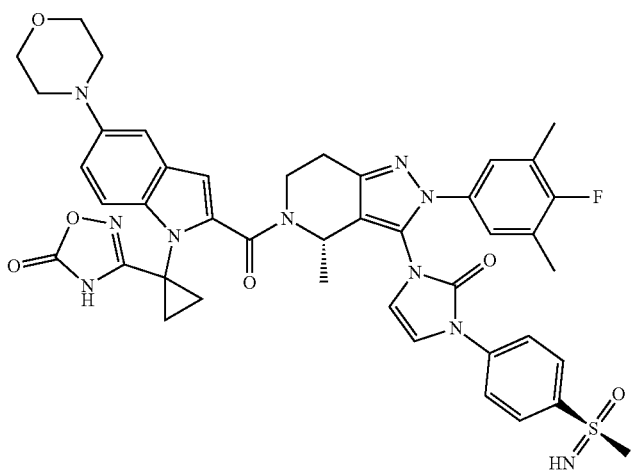 [SMILES: Cc1cc(-n2nc3c(c2-n2ccn(-c4ccc([S@@](C)(=N)=O)cc4)c2=O)[C@H](C)N(C(=O)c2cc4cc(N5CCOCC5)ccc4n2C2(c4noc(=O)[nH]4)CC2)CC3)cc(C)c1F]

TABLE 2-continued

Structure

TABLE 2-continued
Structure
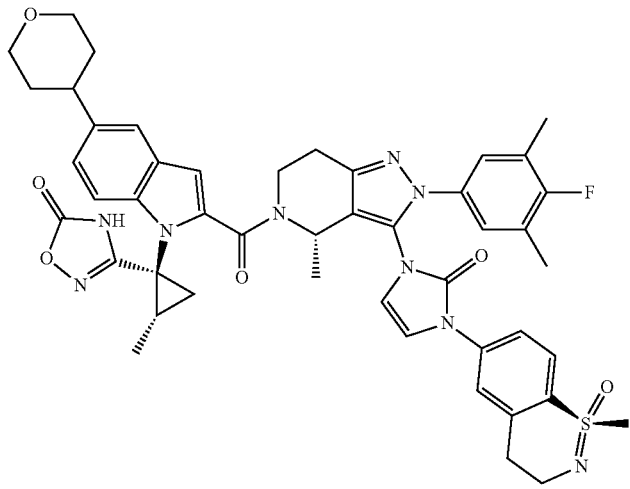 [SMILES: Cc1cc(-n2nc3c(c2-n2ccn(-c4ccc5c(c4)CCN=[S@@]5(C)=O)c2=O)[C@H](C)N(C(=O)c2cc4cc(C5CCOCC5)ccc4n2[C@@]2(c4noc(=O)[nH]4)C[C@@H]2C)CC3)cc(C)c1F]
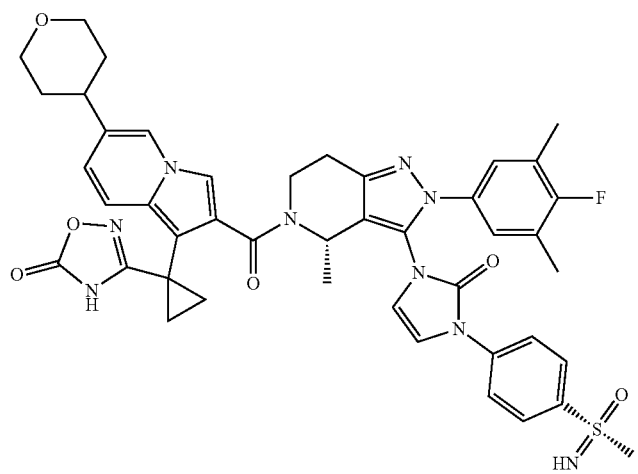 [SMILES: Cc1cc(-n2nc3c(c2-n2ccn(-c4ccc([S@](C)(=N)=O)cc4)c2=O)[C@H](C)N(C(=O)c2cn4cc(C5CCOCC5)ccc4c2C2(c4noc(=O)[nH]4)CC2)CC3)cc(C)c1F]
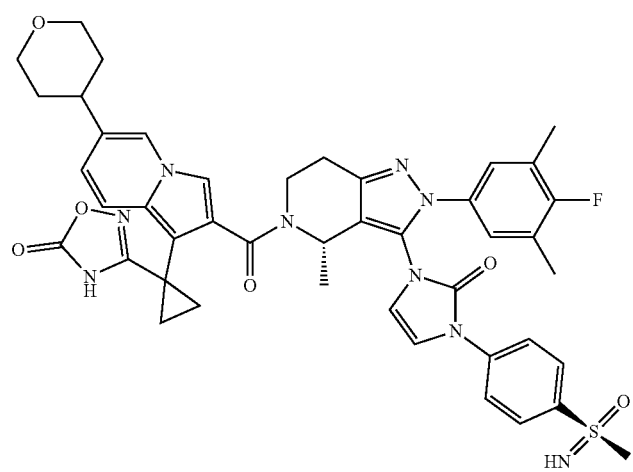 [SMILES: Cc1cc(-n2nc3c(c2-n2ccn(-c4ccc([S@@](C)(=N)=O)cc4)c2=O)[C@H](C)N(C(=O)c2cn4cc(C5CCOCC5)ccc4c2C2(c4noc(=O)[nH]4)CC2)CC3)cc(C)c1F]

TABLE 2-continued

Structure

TABLE 2-continued
Structure
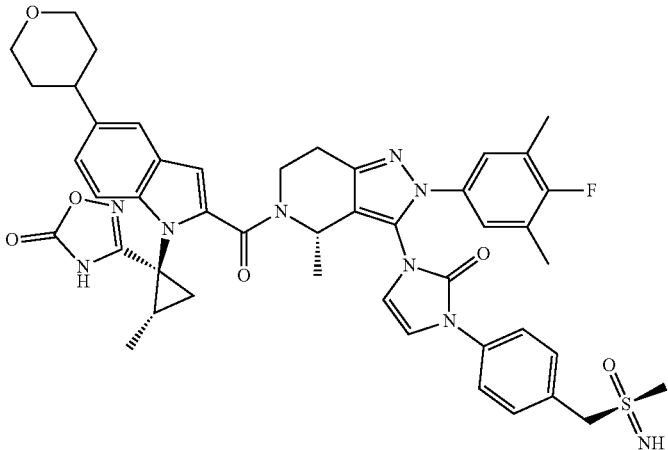 [SMILES: Cc1cc(-n2nc3c(c2-n2ccn(-c4ccc(C[S@@](C)(=N)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
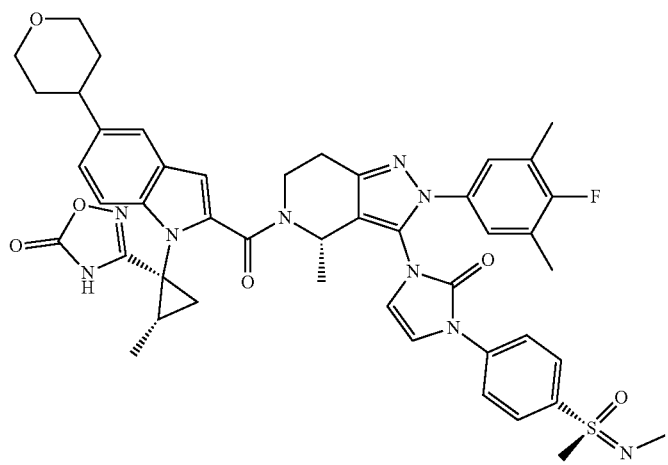 [SMILES: CN=[S@@](C)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]
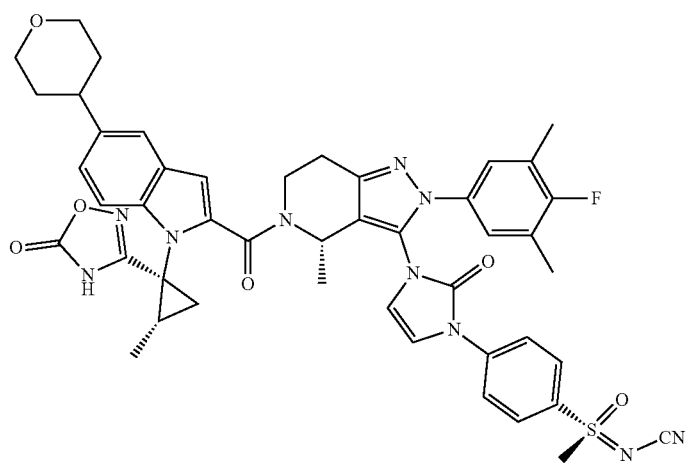 [SMILES: Cc1cc(-n2nc3c(c2-n2ccn(-c4ccc([S@](C)(=O)=NC#N)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]

TABLE 2-continued
Structure
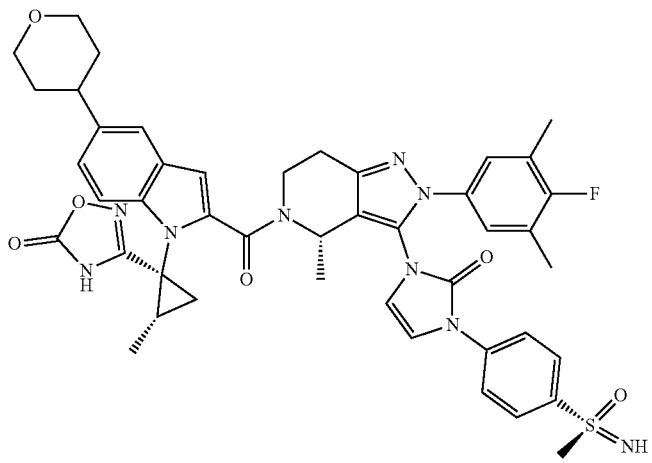 [SMILES: Cc1cc(-n2nc3c(c2-n2ccn(-c4ccc([S@@](C)(=N)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
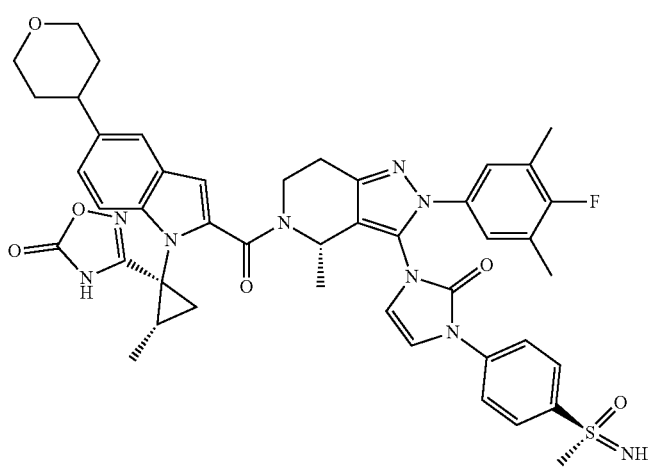 [SMILES: Cc1cc(-n2nc3c(c2-n2ccn(-c4ccc([S@](C)(=N)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
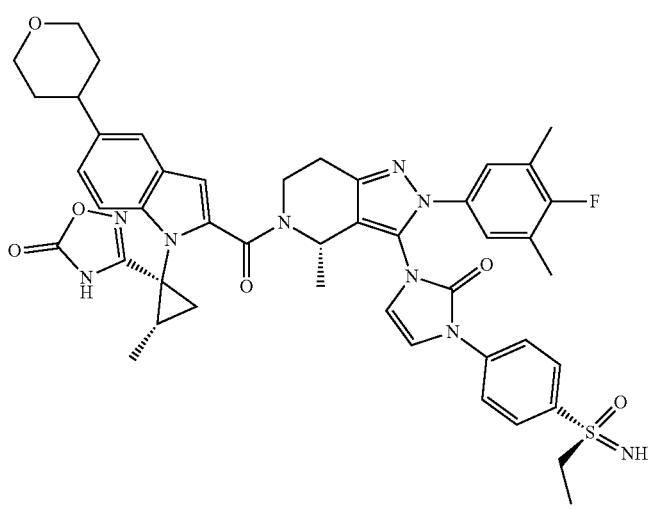 [SMILES: CC[S@](=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]

TABLE 2-continued

Structure

TABLE 2-continued

Structure

TABLE 2-continued
Structure
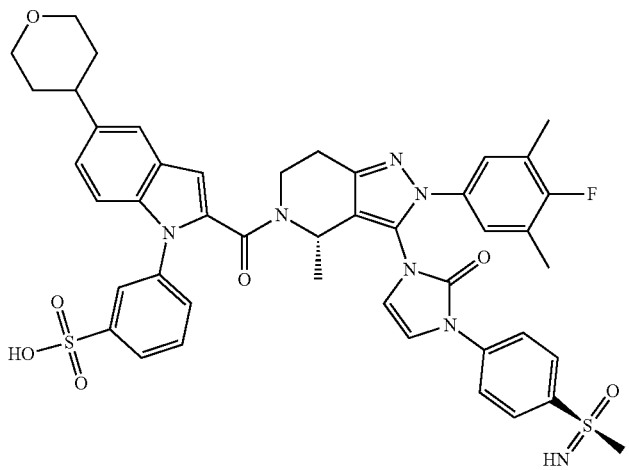 [SMILES: Cc1cc(-n2nc3c(c2-n2ccn(-c4ccc([S@](C)(=N)=O)cc4)c2=O)[C@H](C)N(C(=O)c2cc4cc(C5CCOCC5)ccc4n2-c2cccc(S(=O)(=O)O)c2)CC3)cc(C)c1F]
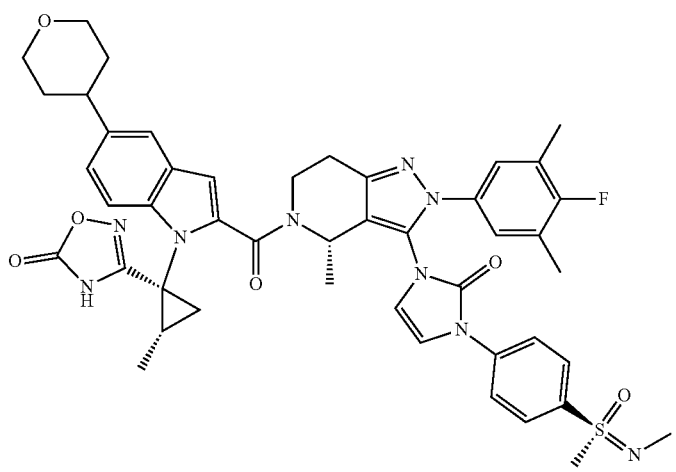 [SMILES: CN=[S@](C)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]
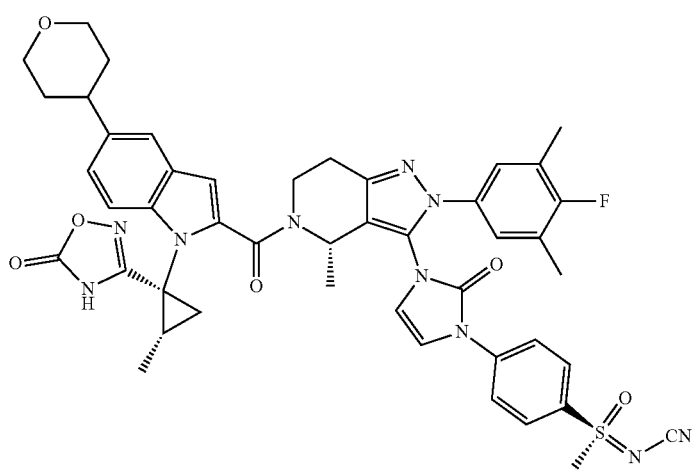 [SMILES: Cc1cc(-n2nc3c(c2-n2ccn(-c4ccc([S@@](C)(=O)=NC#N)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]

TABLE 2-continued

Structure

TABLE 2-continued

Structure

TABLE 2-continued
Structure
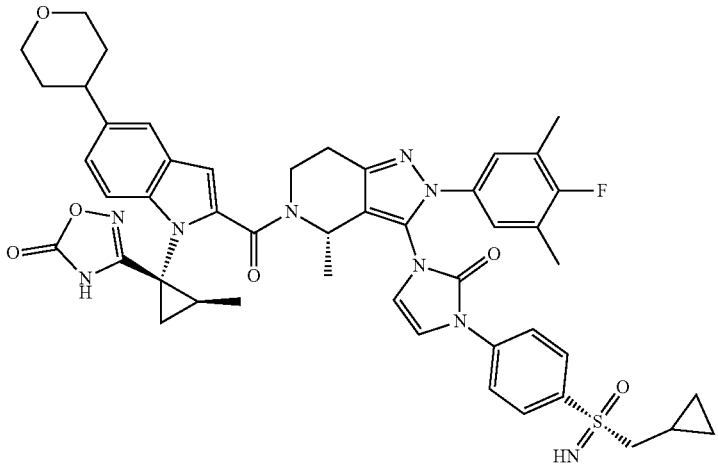 [SMILES: Cc1cc(-n2nc3c(c2-n2ccn(-c4ccc([S@](=N)(=O)CC5CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
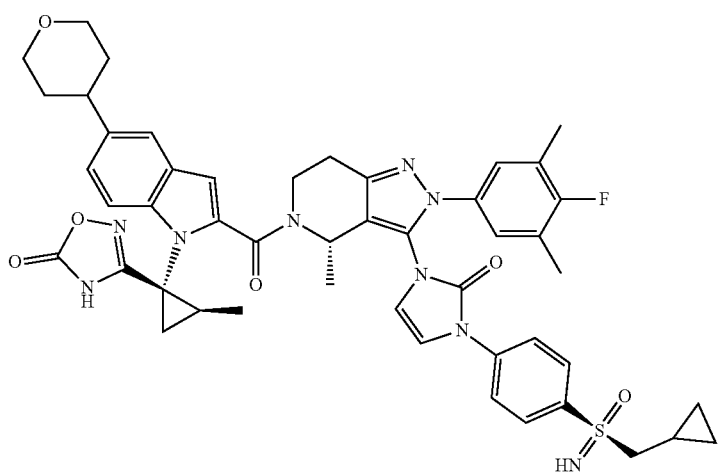 [SMILES: Cc1cc(-n2nc3c(c2-n2ccn(-c4ccc([S@@](=N)(=O)CC5CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
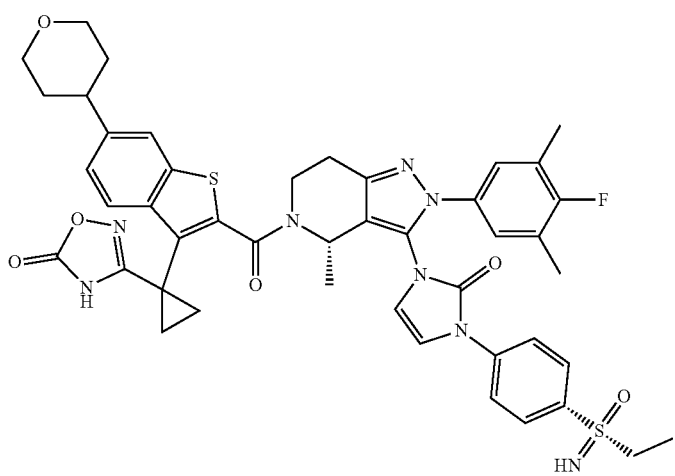

TABLE 2-continued
Structure
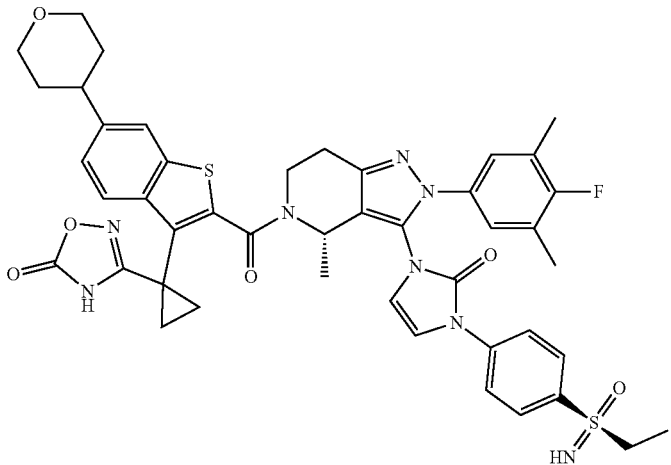
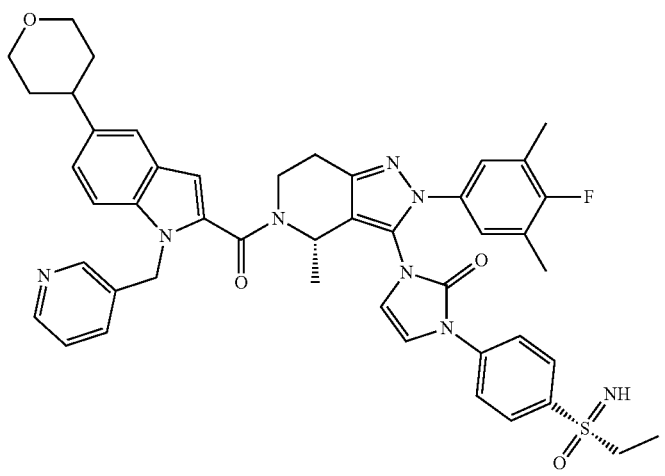
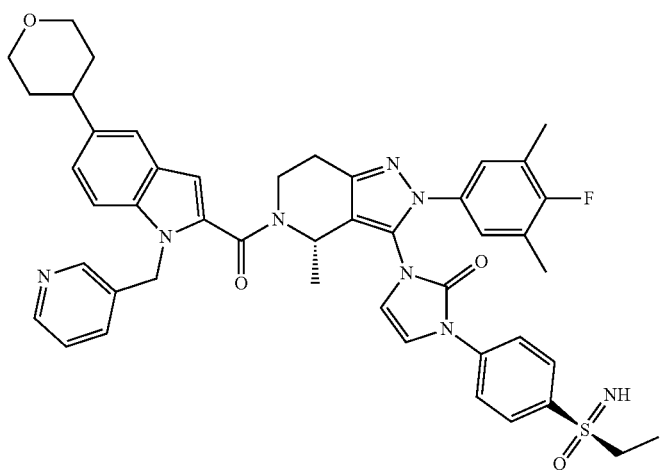

TABLE 2-continued
Structure
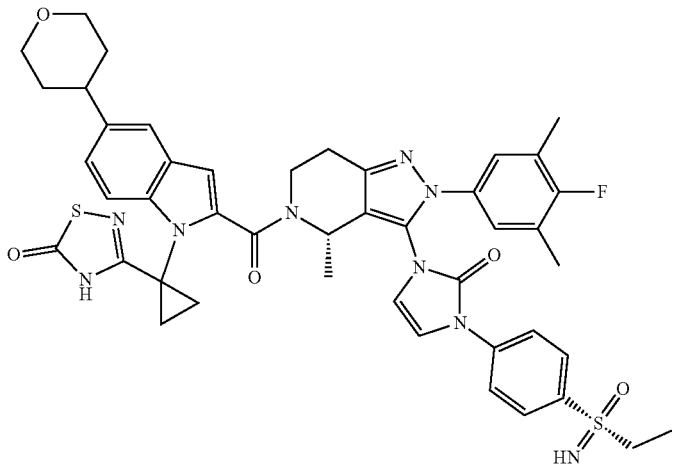 [SMILES: CC[S@@](=N)(=O)c1ccc(-n2ccn(-c3c4c(nn3-c3cc(C)c(F)c(C)c3)CCN(C(=O)c3cc5cc(C6CCOCC6)ccc5n3C3(c5nsc(=O)[nH]5)CC3)[C@H]4C)c2=O)cc1]
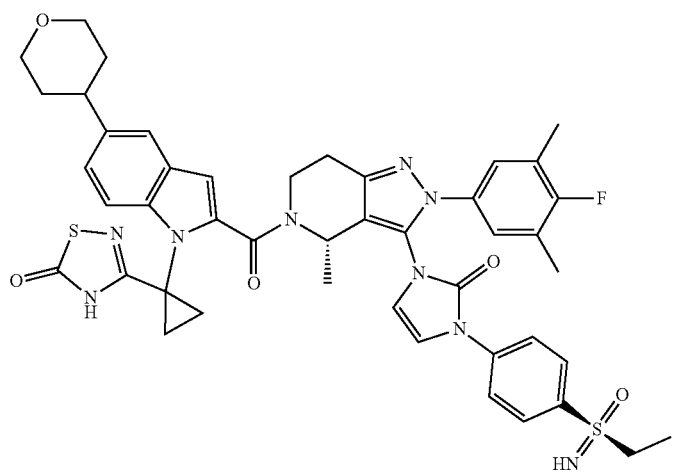
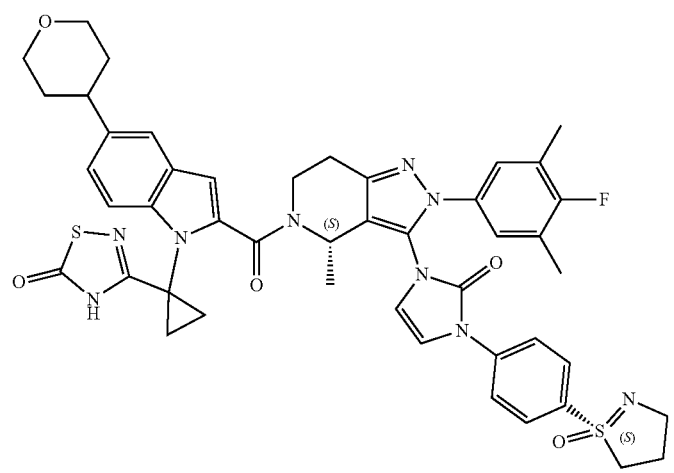

TABLE 2-continued
Structure
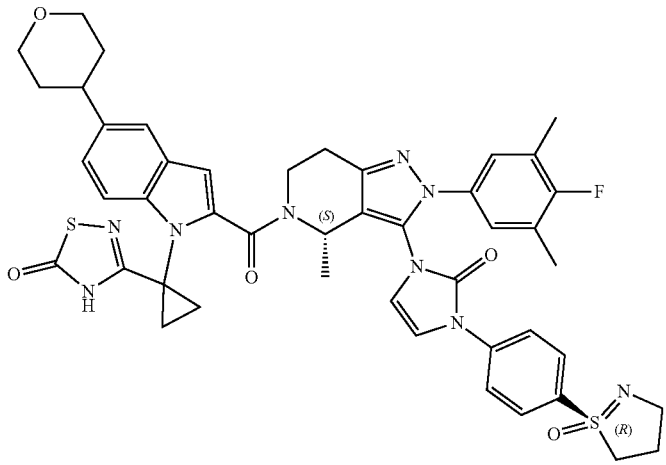
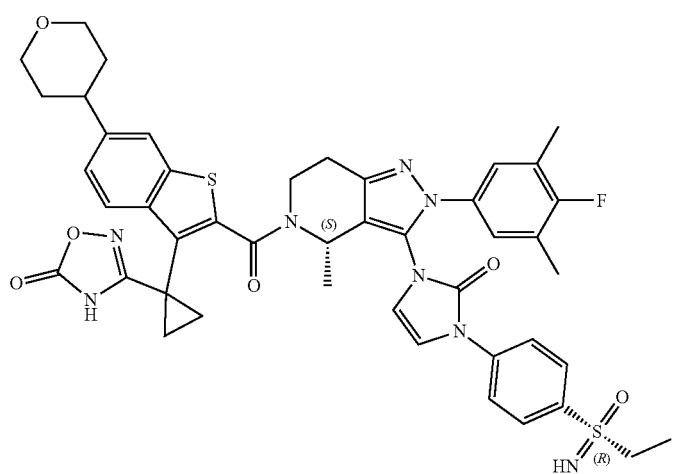
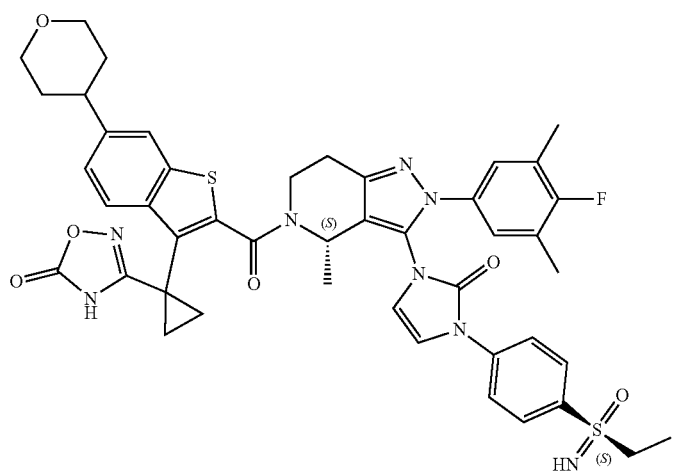

TABLE 2-continued
Structure
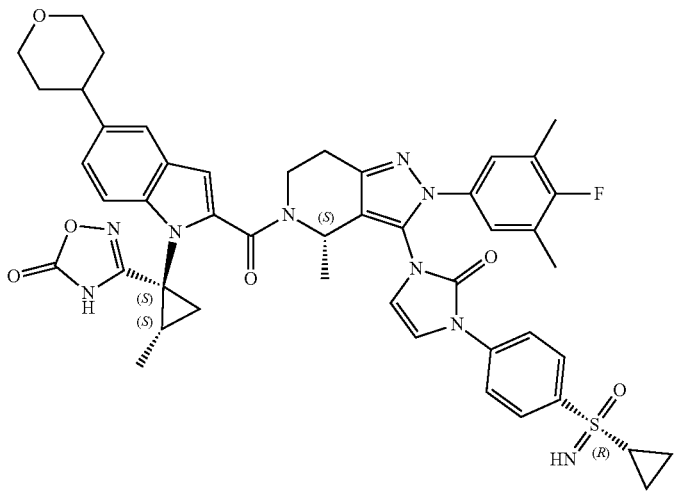
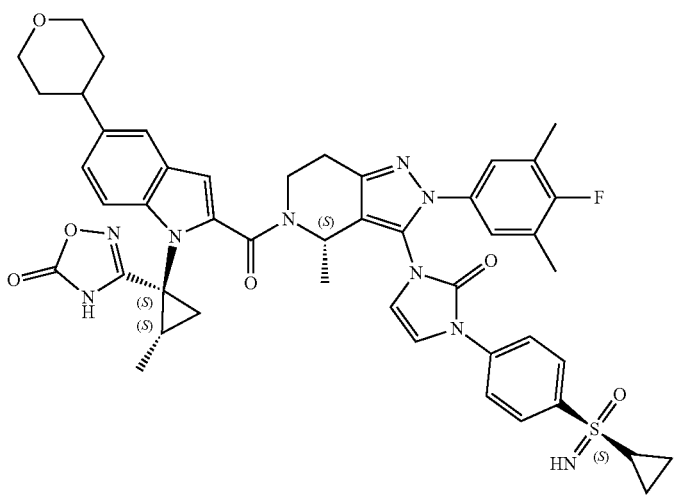
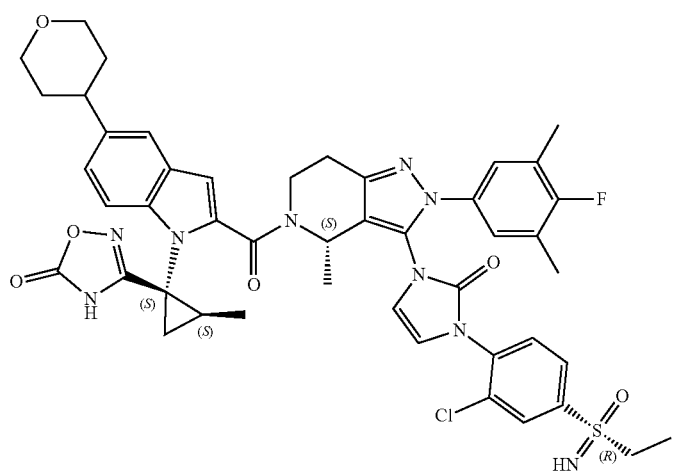

TABLE 2-continued
Structure
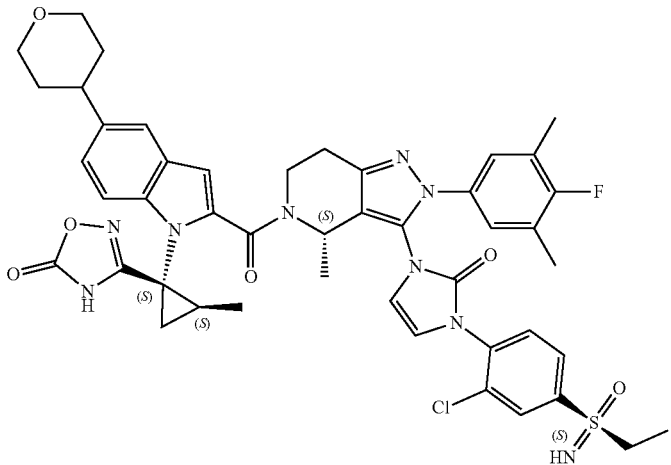
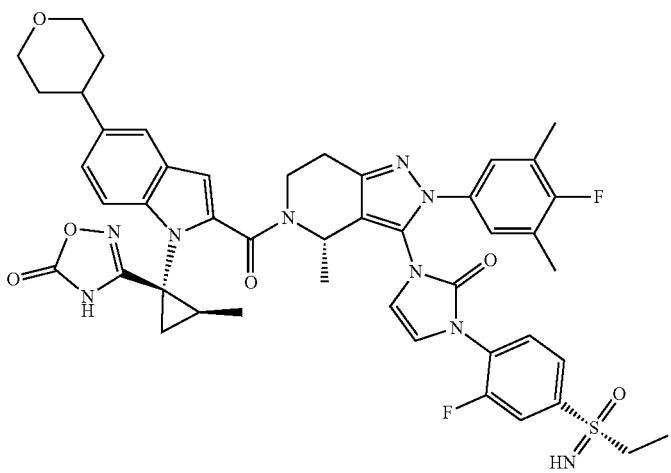
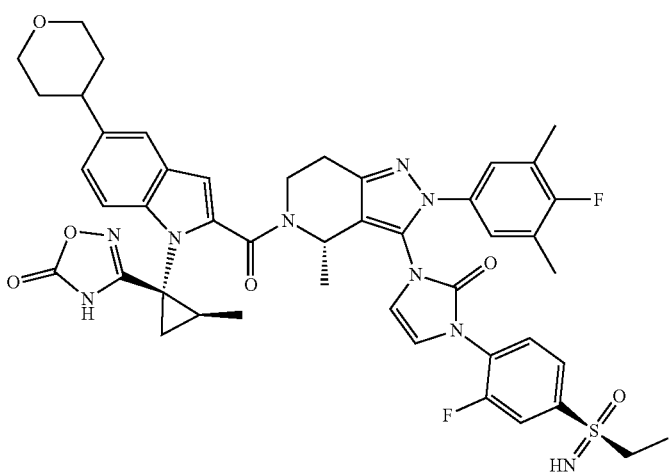

TABLE 2-continued
Structure
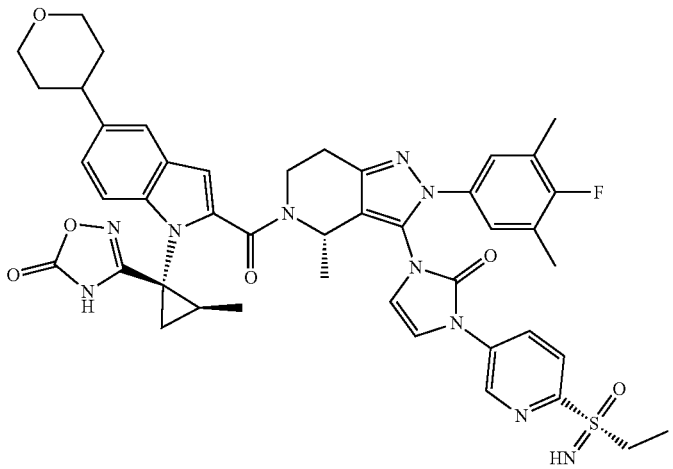
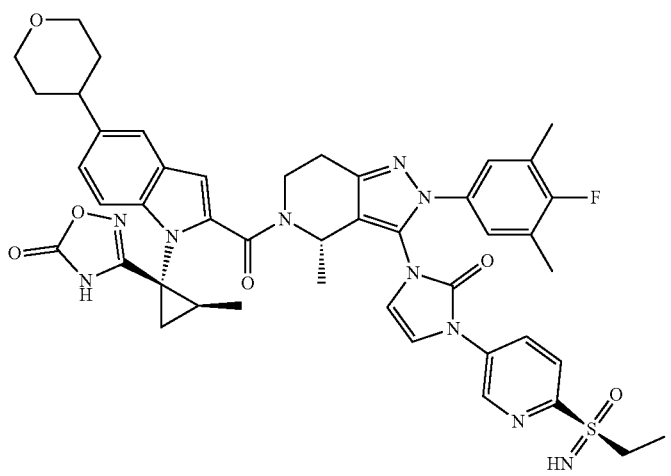 [SMILES: CC[S@](=N)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cn1]
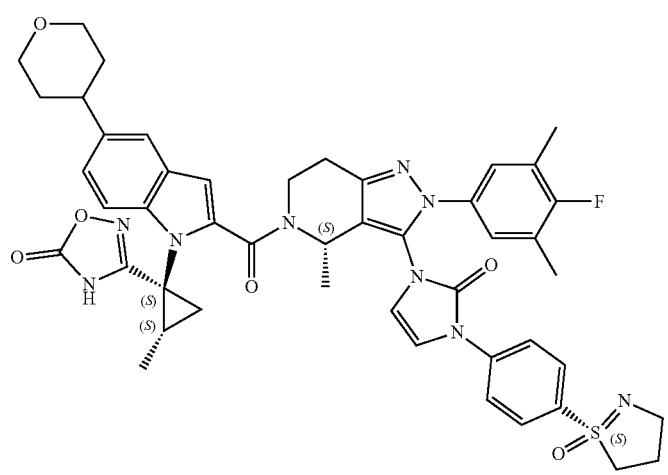

TABLE 2-continued
Structure
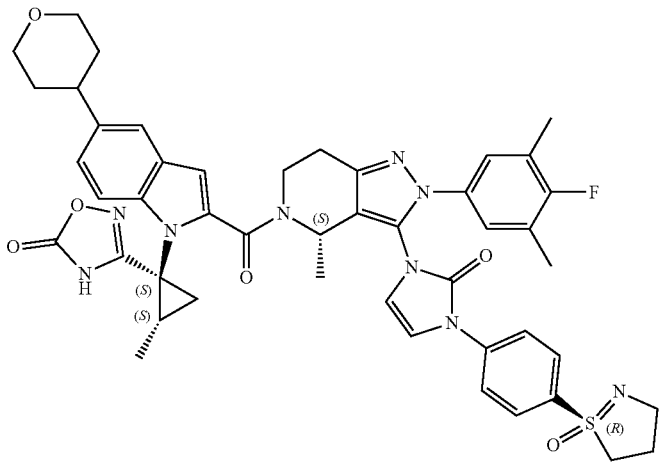
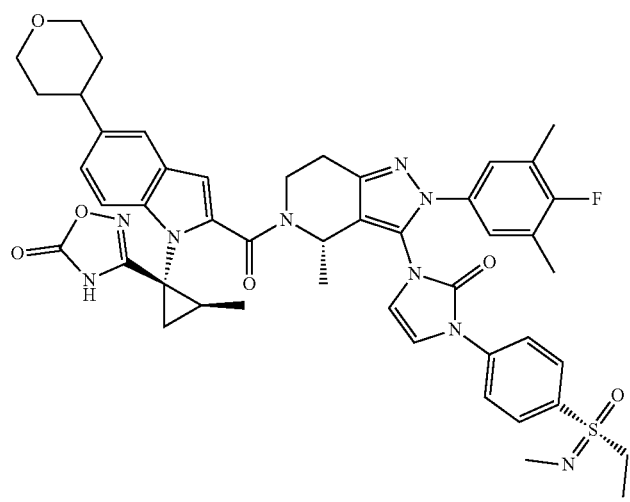 [SMILES: CC[S@](=O)(=NC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]
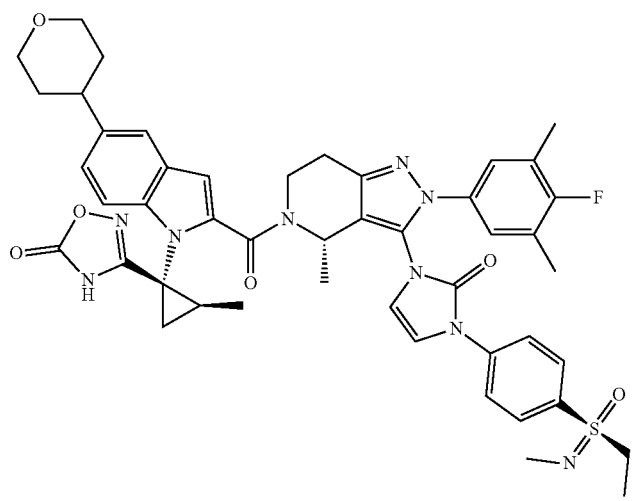 [SMILES: CC[S@@](=O)(=NC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]

TABLE 2-continued
Structure
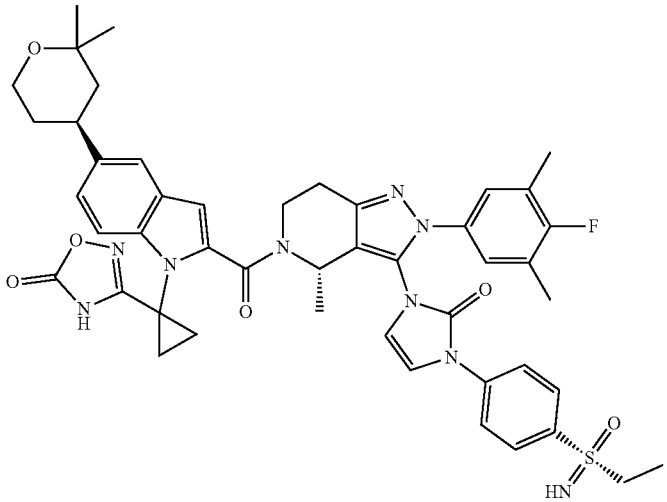 [SMILES: CC[S@@](=N)(=O)c1ccc(-n2ccn(-c3c4c(nn3-c3cc(C)c(F)c(C)c3)CCN(C(=O)c3cc5cc([C@H]6CCOC(C)(C)C6)ccc5n3C3(c5noc(=O)[nH]5)CC3)[C@H]4C)c2=O)cc1]
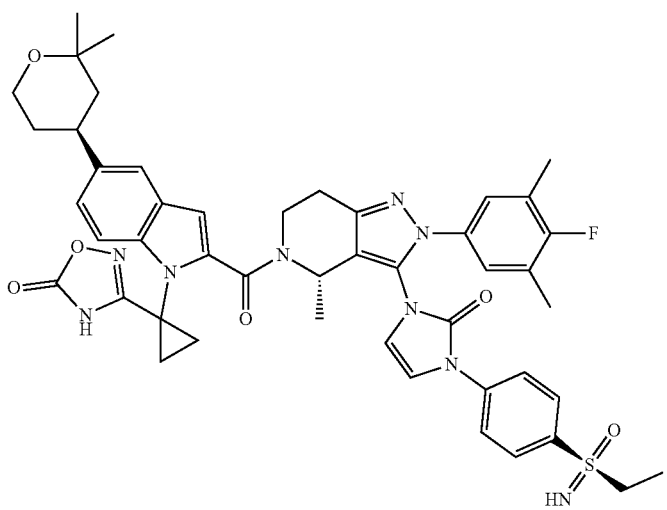 [SMILES: CC[S@](=N)(=O)c1ccc(-n2ccn(-c3c4c(nn3-c3cc(C)c(F)c(C)c3)CCN(C(=O)c3cc5cc([C@H]6CCOC(C)(C)C6)ccc5n3C3(c5noc(=O)[nH]5)CC3)[C@H]4C)c2=O)cc1]
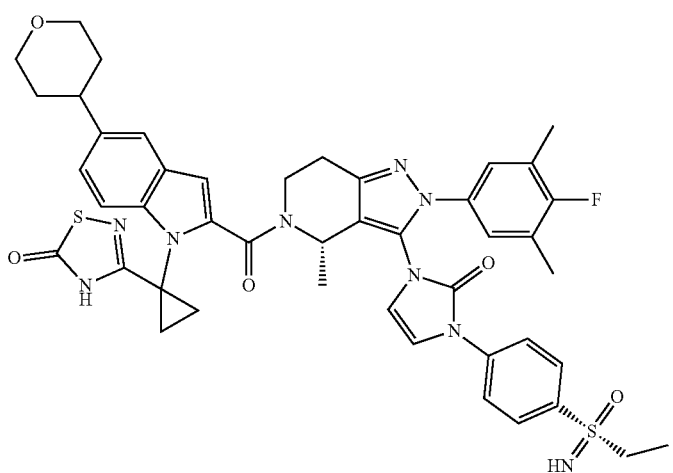 [SMILES: CC[S@@](=N)(=O)c1ccc(-n2ccn(-c3c4c(nn3-c3cc(C)c(F)c(C)c3)CCN(C(=O)c3cc5cc(C6CCOCC6)ccc5n3C3(c5nsc(=O)[nH]5)CC3)[C@H]4C)c2=O)cc1]

TABLE 2-continued

Structure

TABLE 2-continued
Structure
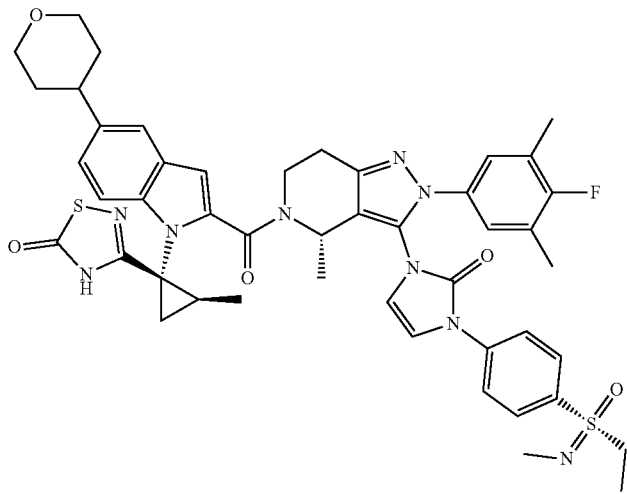 [SMILES: CC[S@](=O)(=NC)c1ccc(-n2ccn(-c3c4c(nn3-c3cc(C)c(F)c(C)c3)CCN(C(=O)c3cc5cc(C6CCOCC6)ccc5n3[C@@]3(c5nsc(=O)[nH]5)C[C@@H]3C)[C@H]4C)c2=O)cc1]
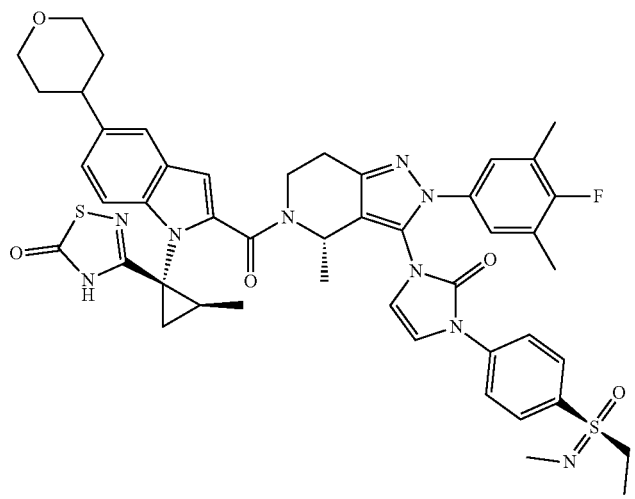
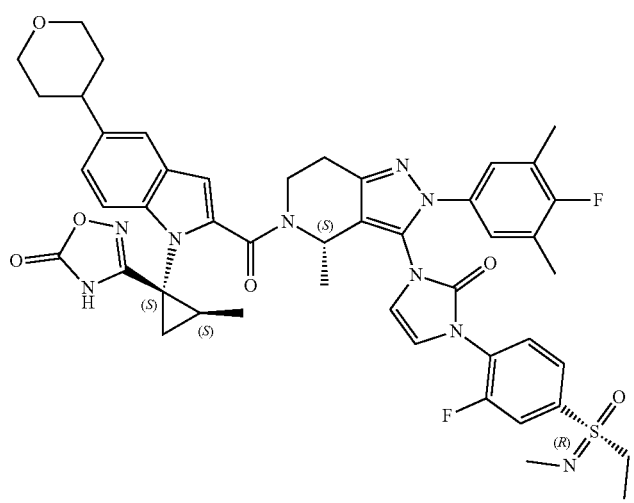

TABLE 2-continued
Structure
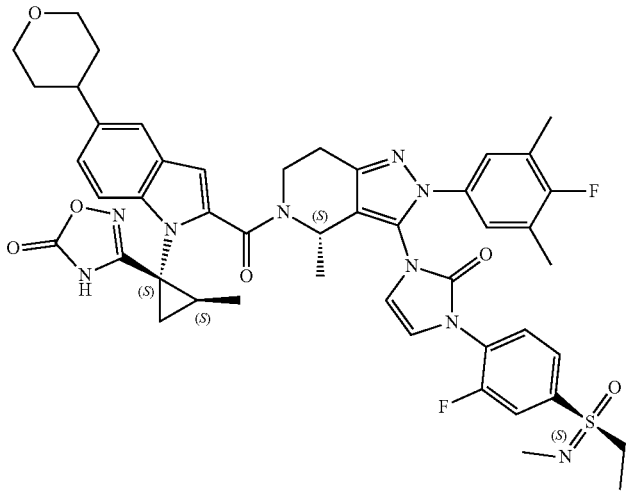
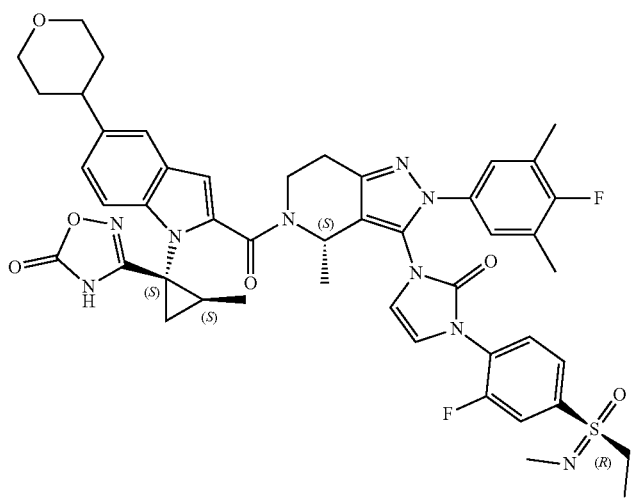
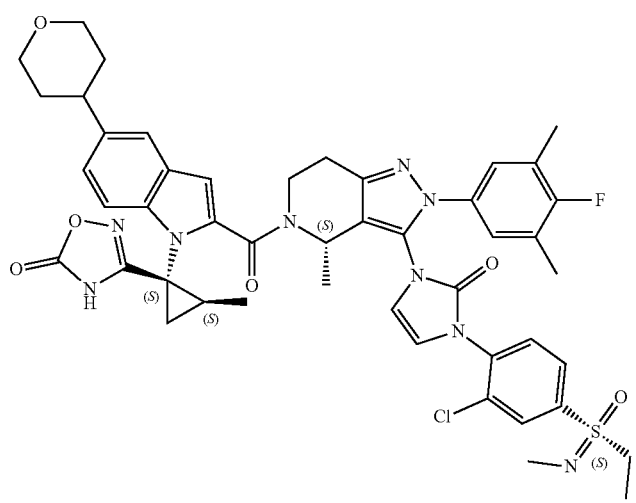

TABLE 2-continued
Structure
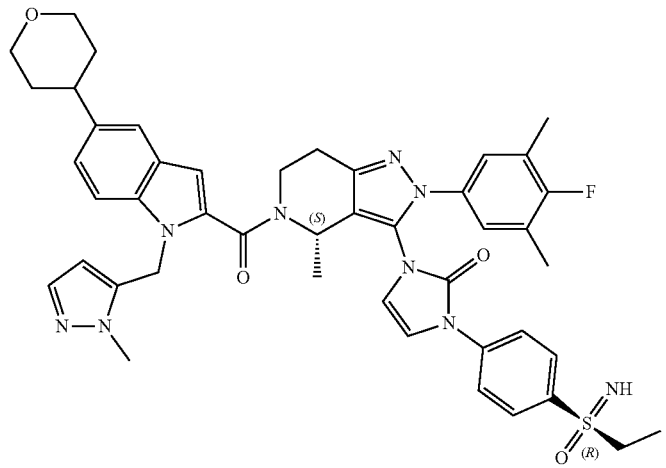
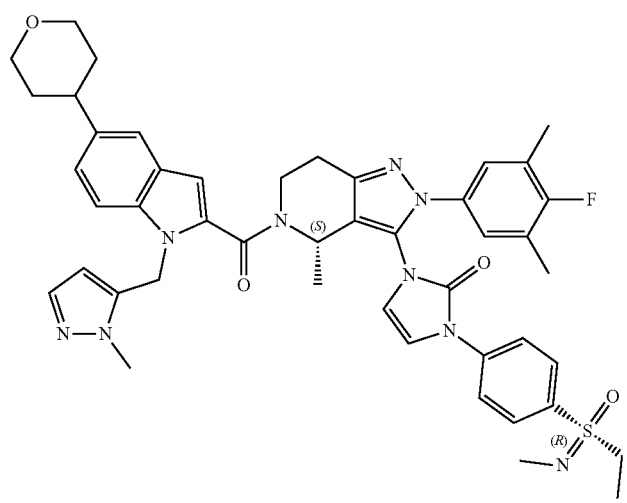
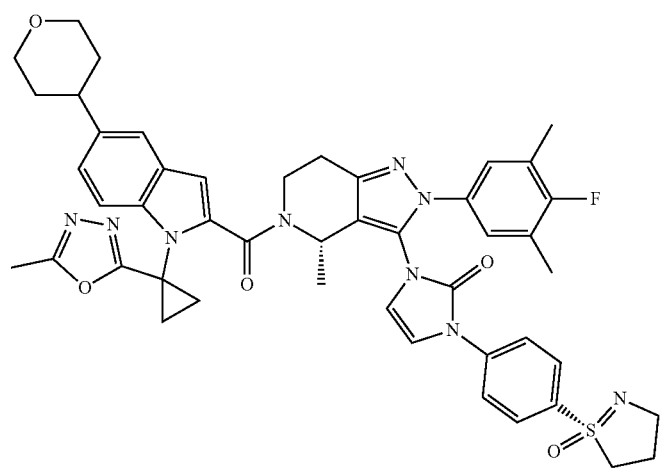 [SMILES: Cc1nnc(C2(n3c(C(=O)N4CCc5nn(-c6cc(C)c(F)c(C)c6)c(-n6ccn(-c7ccc([S@]8(=O)=NCCC8)cc7)c6=O)c5[C@@H]4C)cc4cc(C5CCOCC5)ccc43)CC2)o1]

TABLE 2-continued
Structure
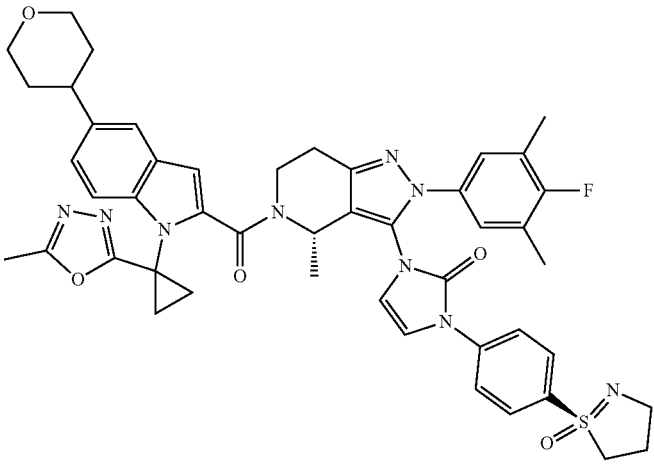 [SMILES: Cc1nnc(C2(n3c(C(=O)N4CCc5nn(-c6cc(C)c(F)c(C)c6)c(-n6ccn(-c7ccc([S@@]8(=O)=NCCC8)cc7)c6=O)c5[C@@H]4C)cc4cc(C5CCOCC5)ccc43)CC2)o1]
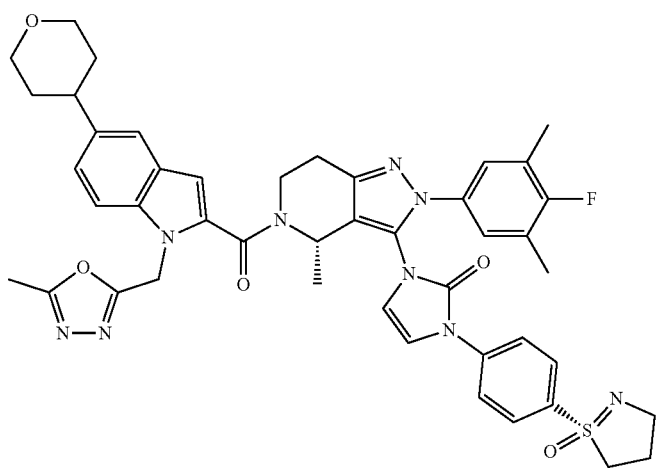 [SMILES: Cc1nnc(Cn2c(C(=O)N3CCc4nn(-c5cc(C)c(F)c(C)c5)c(-n5ccn(-c6ccc([S@]7(=O)=NCCC7)cc6)c5=O)c4[C@@H]3C)cc3cc(C4CCOCC4)ccc32)o1]
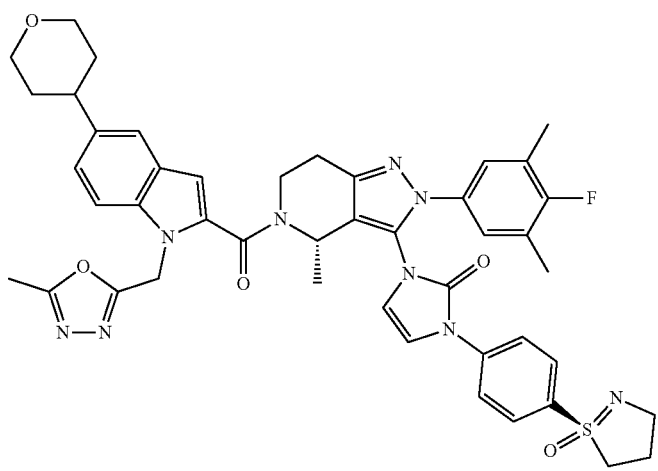 [SMILES: Cc1nnc(Cn2c(C(=O)N3CCc4nn(-c5cc(C)c(F)c(C)c5)c(-n5ccn(-c6ccc([S@@]7(=O)=NCCC7)cc6)c5=O)c4[C@@H]3C)cc3cc(C4CCOCC4)ccc32)o1]

TABLE 2-continued
Structure
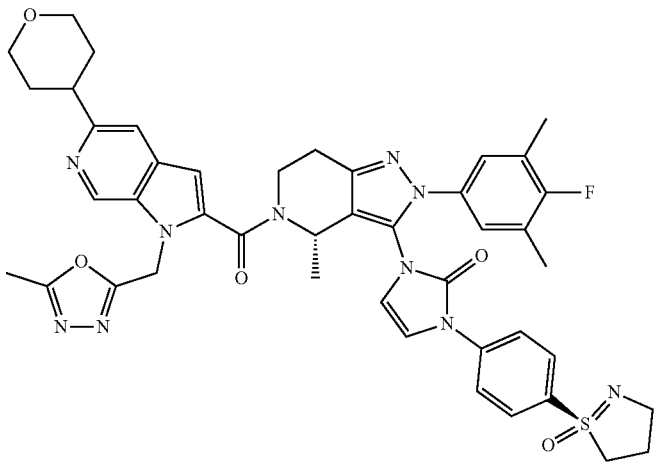 [SMILES: Cc1nnc(Cn2c(C(=O)N3CCc4nn(-c5cc(C)c(F)c(C)c5)c(-n5ccn(-c6ccc([S@@]7(=O)=NCCC7)cc6)c5=O)c4[C@@H]3C)cc3cc(C4CCOCC4)ncc32)o1]
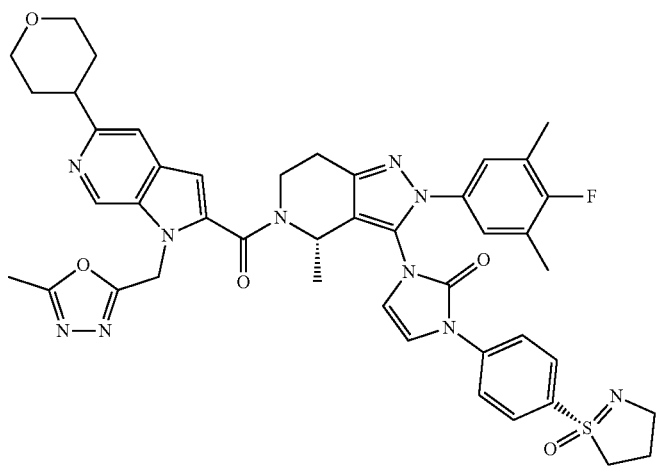 [SMILES: Cc1nnc(Cn2c(C(=O)N3CCc4nn(-c5cc(C)c(F)c(C)c5)c(-n5ccn(-c6ccc([S@]7(=O)=NCCC7)cc6)c5=O)c4[C@@H]3C)cc3cc(C4CCOCC4)ncc32)o1]
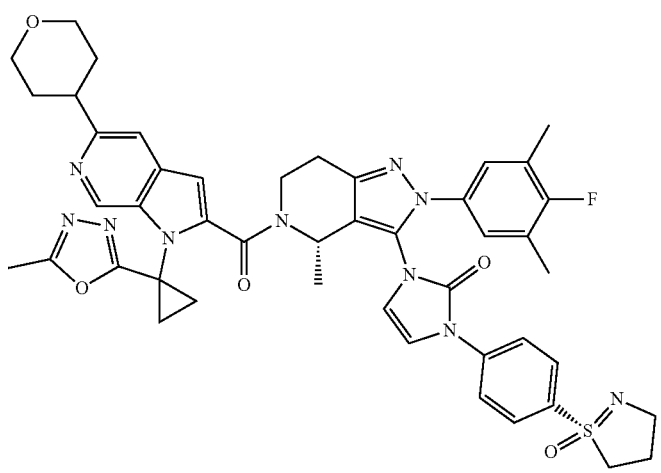 [SMILES: Cc1nnc(C2(n3c(C(=O)N4CCc5nn(-c6cc(C)c(F)c(C)c6)c(-n6ccn(-c7ccc([S@]8(=O)=NCCC8)cc7)c6=O)c5[C@@H]4C)cc4cc(C5CCOCC5)ncc43)CC2)o1]

TABLE 2-continued

Structure

TABLE 2-continued
Structure
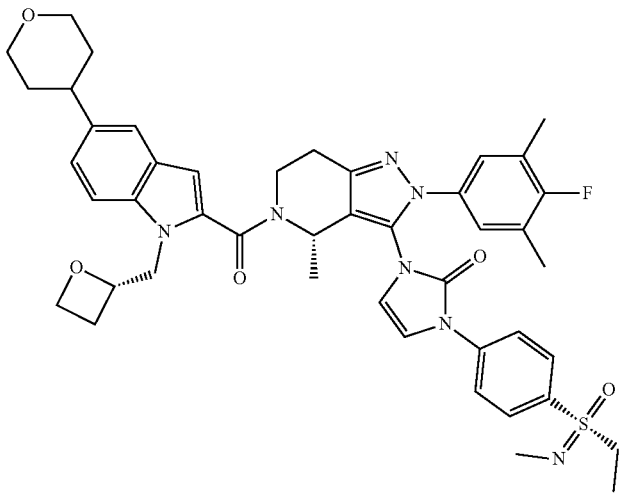
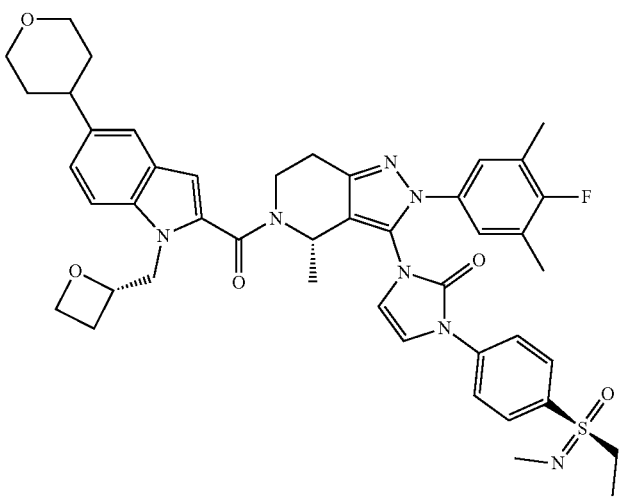
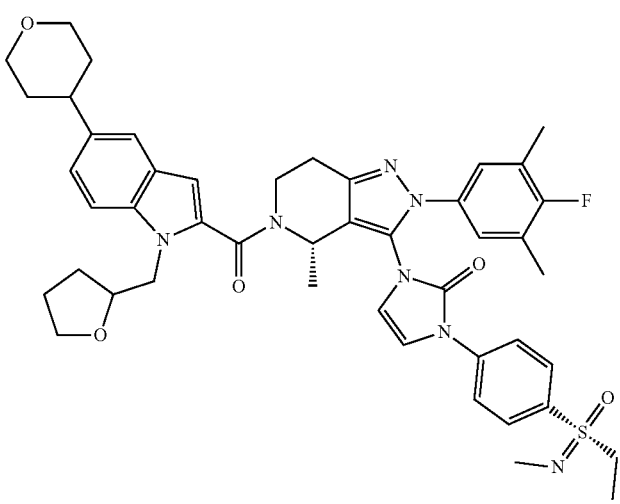

TABLE 2-continued
Structure
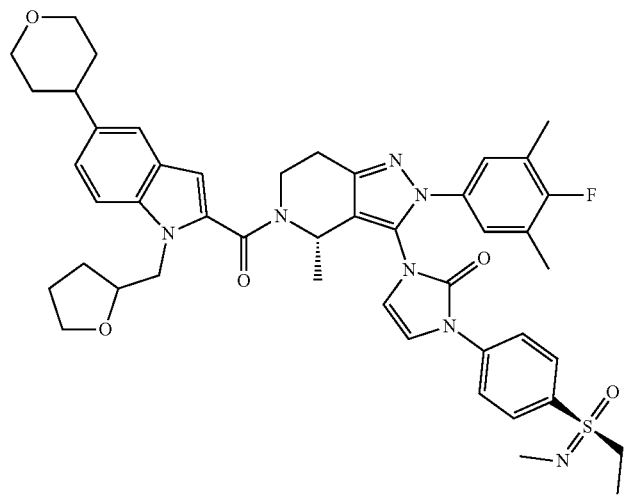
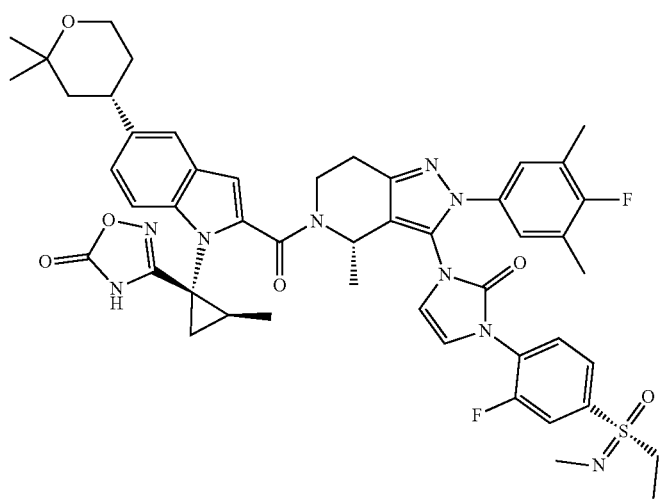
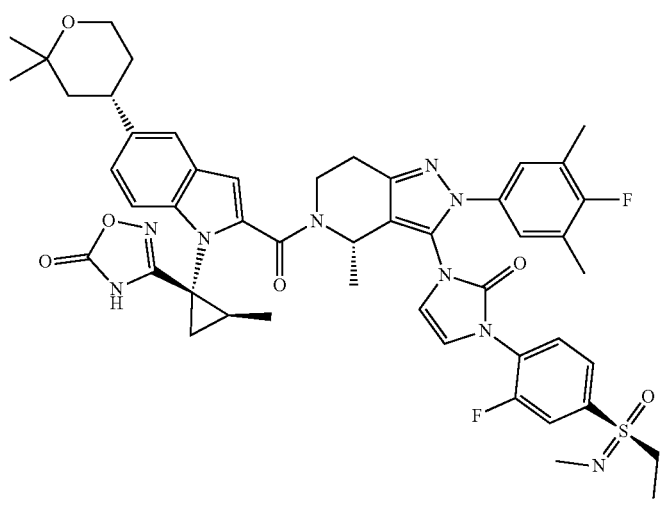

TABLE 2-continued

Structure

TABLE 2-continued
Structure
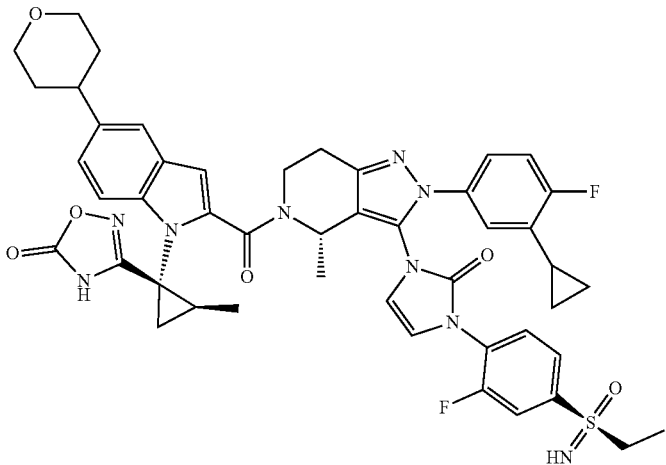
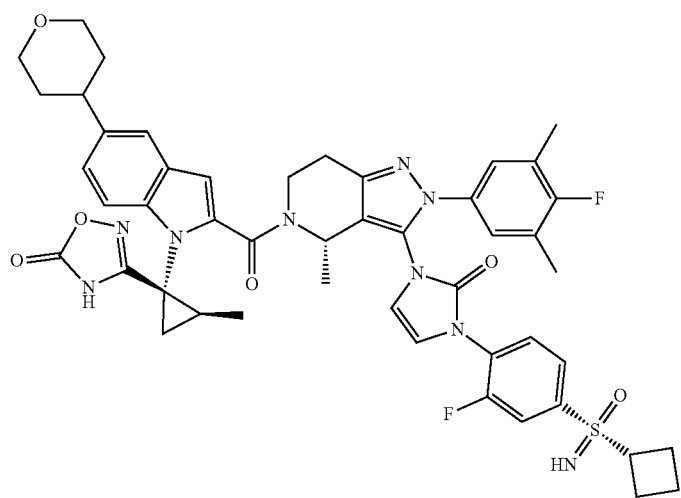
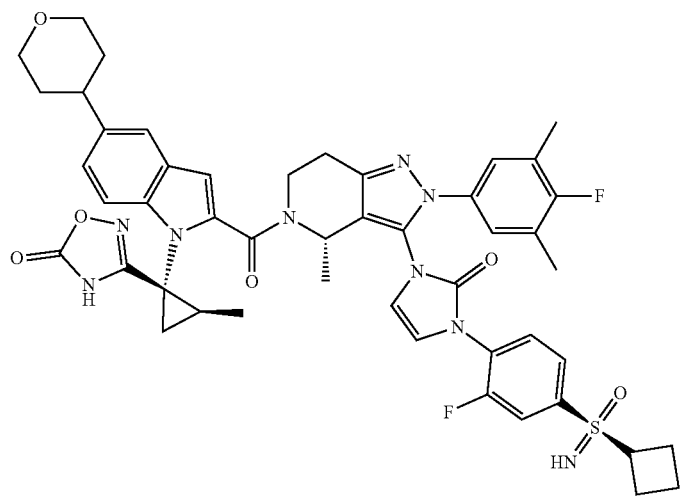

TABLE 2-continued
Structure
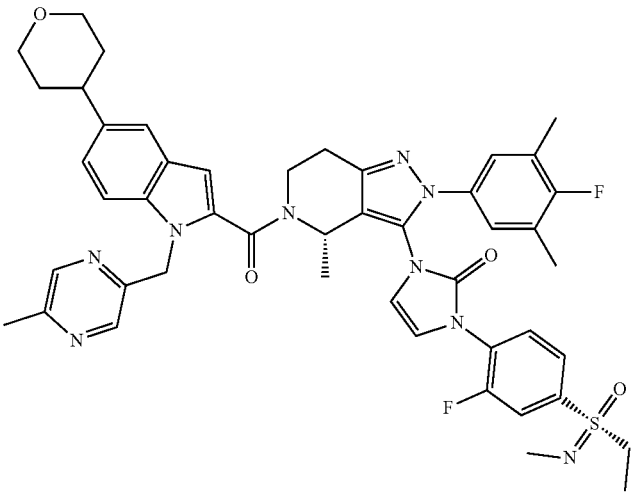
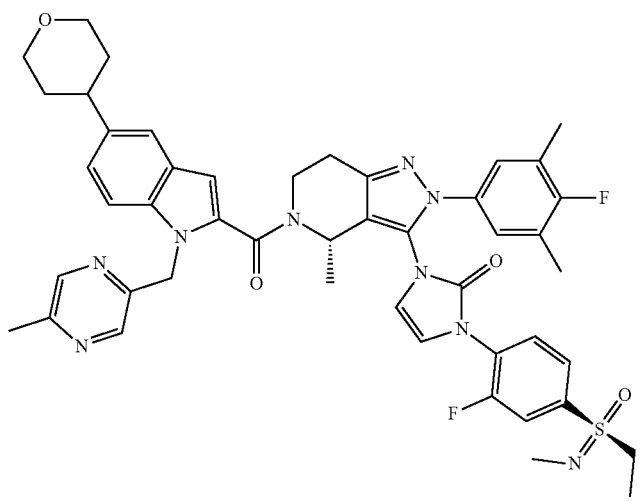
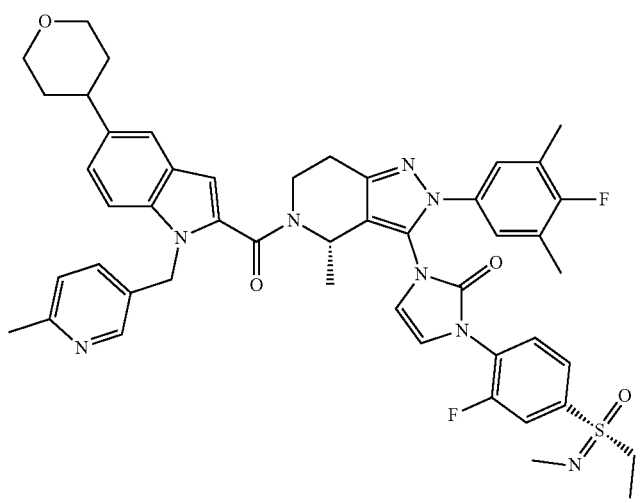

TABLE 2-continued
Structure
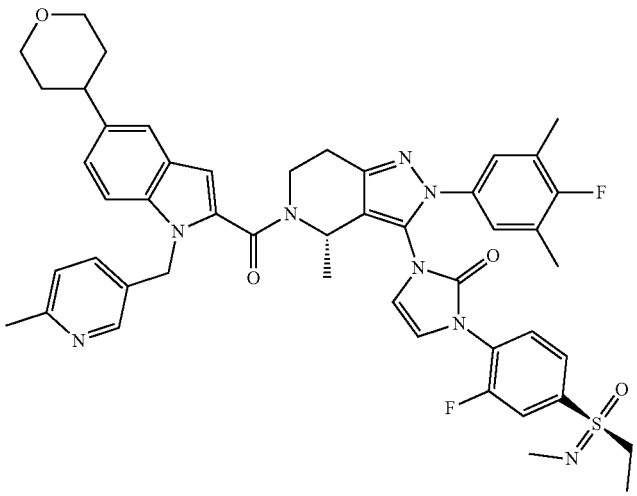 [SMILES: CC[S@@](=O)(=NC)c1ccc(-n2ccn(-c3c4c(nn3-c3cc(C)c(F)c(C)c3)CCN(C(=O)c3cc5cc(C6CCOCC6)ccc5n3Cc3ccc(C)nc3)[C@H]4C)c2=O)c(F)c1]
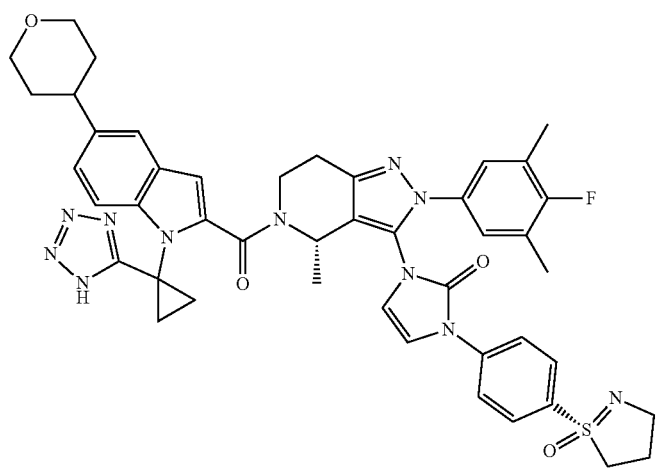 [SMILES: Cc1cc(-n2nc3c(c2-n2ccn(-c4ccc([S@]5(=O)=NCCC5)cc4)c2=O)[C@H](C)N(C(=O)c2cc4cc(C5CCOCC5)ccc4n2C2(c4nnn[nH]4)CC2)CC3)cc(C)c1F]
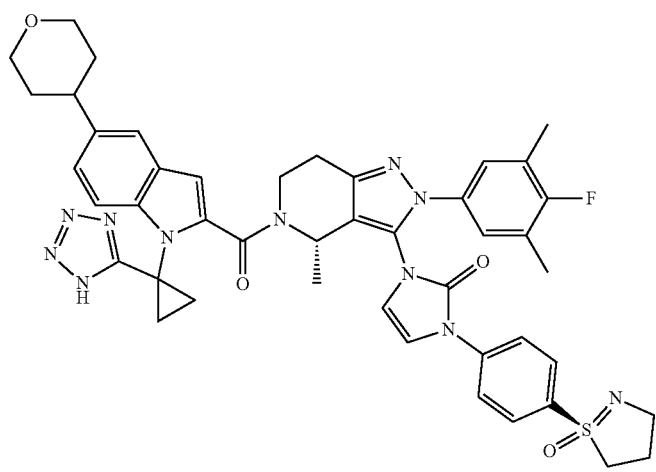 [SMILES: Cc1cc(-n2nc3c(c2-n2ccn(-c4ccc([S@@]5(=O)=NCCC5)cc4)c2=O)[C@H](C)N(C(=O)c2cc4cc(C5CCOCC5)ccc4n2C2(c4nnn[nH]4)CC2)CC3)cc(C)c1F]

TABLE 2-continued

Structure

TABLE 2-continued
Structure
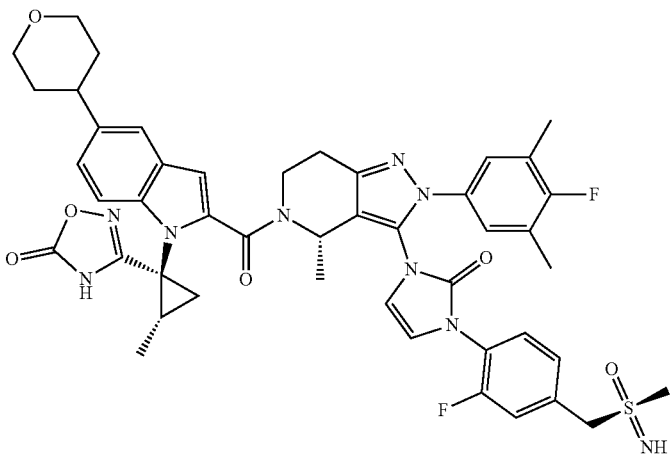 [SMILES: Cc1cc(-n2nc3c(c2-n2ccn(-c4ccc(C[S@@](C)(=N)=O)cc4F)c2=O)[C@H](C)N(C(=O)c2cc4cc(C5CCOCC5)ccc4n2[C@@]2(c4noc(=O)[nH]4)C[C@@H]2C)CC3)cc(C)c1F]
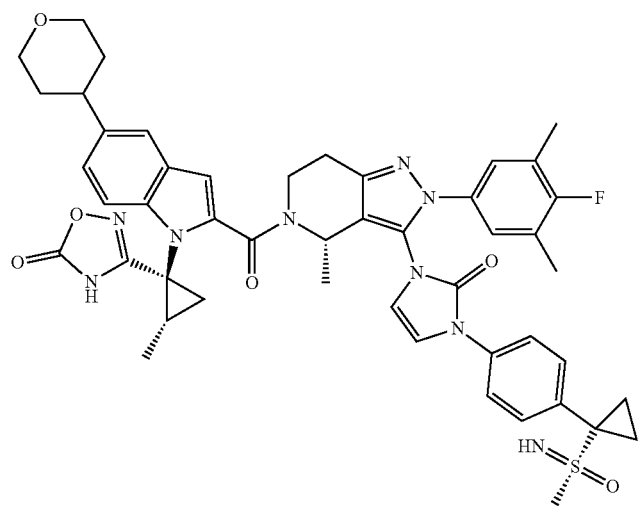 [SMILES: Cc1cc(-n2nc3c(c2-n2ccn(-c4ccc(C5([S@](C)(=N)=O)CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
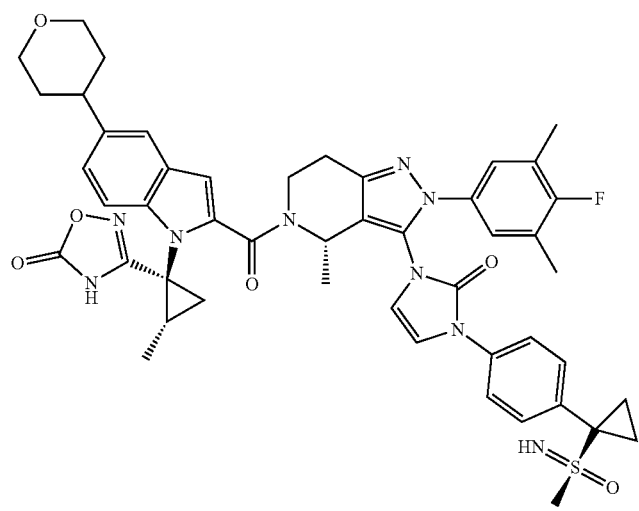 [SMILES: Cc1cc(-n2nc3c(c2-n2ccn(-c4ccc(C5([S@@](C)(=N)=O)CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]

TABLE 2-continued
Structure
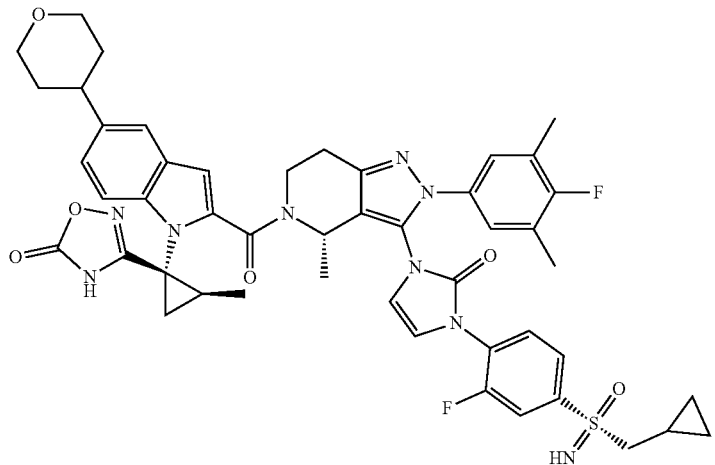 [SMILES: Cc1cc(-n2nc3c(c2-n2ccn(-c4ccc([S@](=N)(=O)CC5CC5)cc4F)c2=O)[C@H](C)N(C(=O)c2cc4cc(C5CCOCC5)ccc4n2[C@@]2(c4noc(=O)[nH]4)C[C@@H]2C)CC3)cc(C)c1F]
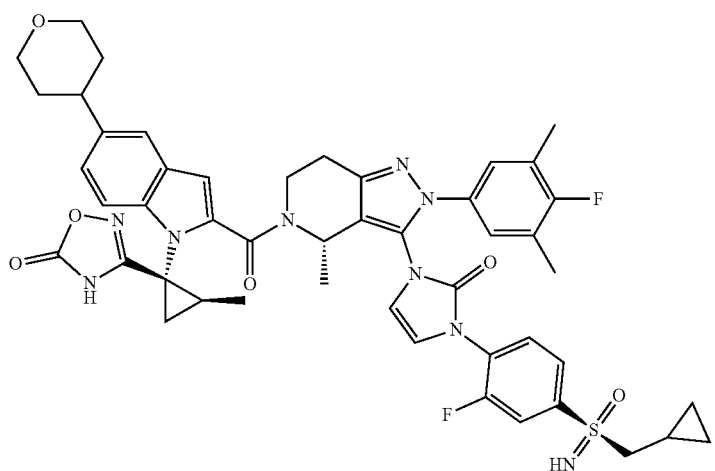 [SMILES: Cc1cc(-n2nc3c(c2-n2ccn(-c4ccc([S@@](=N)(=O)CC5CC5)cc4F)c2=O)[C@H](C)N(C(=O)c2cc4cc(C5CCOCC5)ccc4n2[C@@]2(c4noc(=O)[nH]4)C[C@@H]2C)CC3)cc(C)c1F]
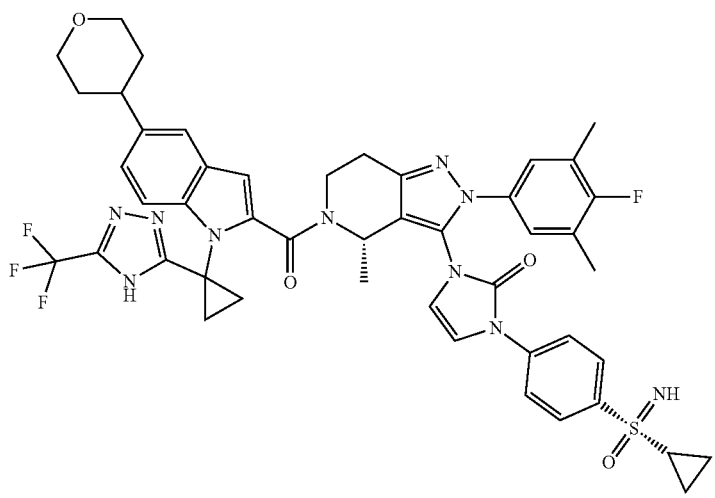 [SMILES: Cc1cc(-n2nc3c(c2-n2ccn(-c4ccc([S@@](=N)(=O)C5CC5)cc4)c2=O)[C@H](C)N(C(=O)c2cc4cc(C5CCOCC5)ccc4n2C2(c4nnc(C(F)(F)F)[nH]4)CC2)CC3)cc(C)c1F]

TABLE 2-continued
Structure
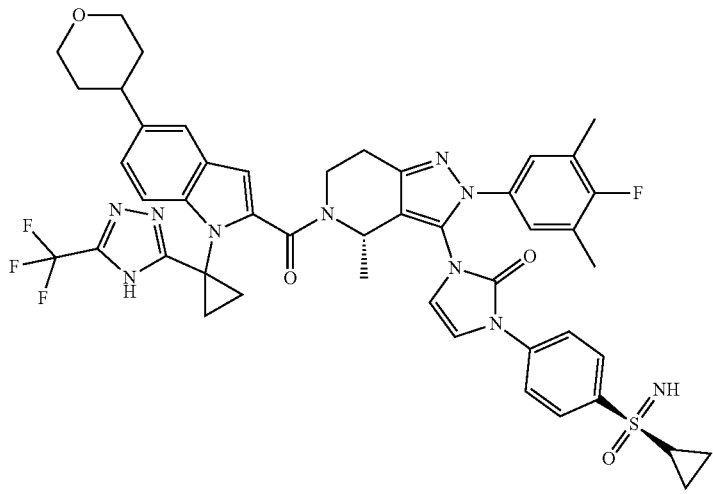 [SMILES: Cc1cc(-n2nc3c(c2-n2ccn(-c4ccc([S@](=N)(=O)C5CC5)cc4)c2=O)[C@H](C)N(C(=O)c2cc4cc(C5CCOCC5)ccc4n2C2(c4nnc(C(F)(F)F)[nH]4)CC2)CC3)cc(C)c1F]
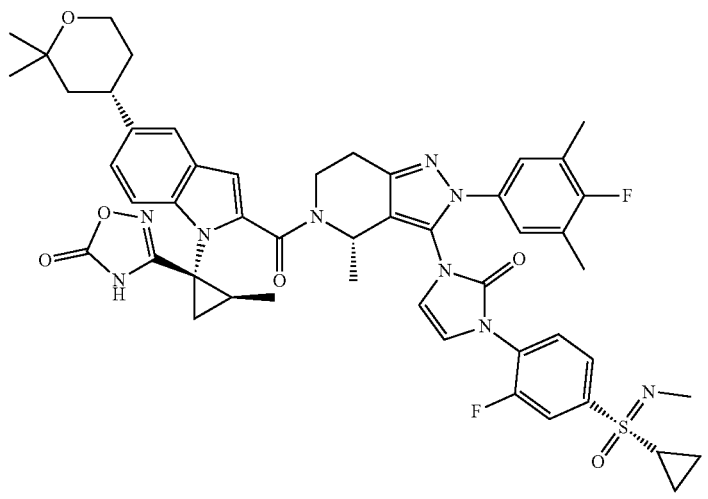 [SMILES: CN=[S@@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1)C1CC1]
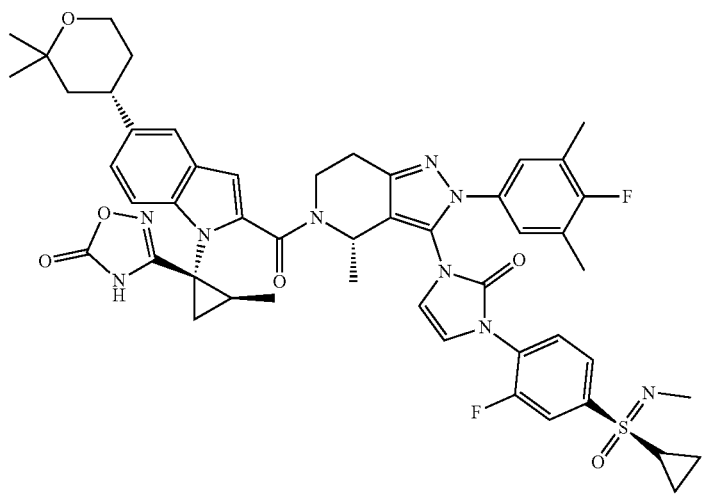 [SMILES: CN=[S@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1)C1CC1]

TABLE 2-continued
Structure
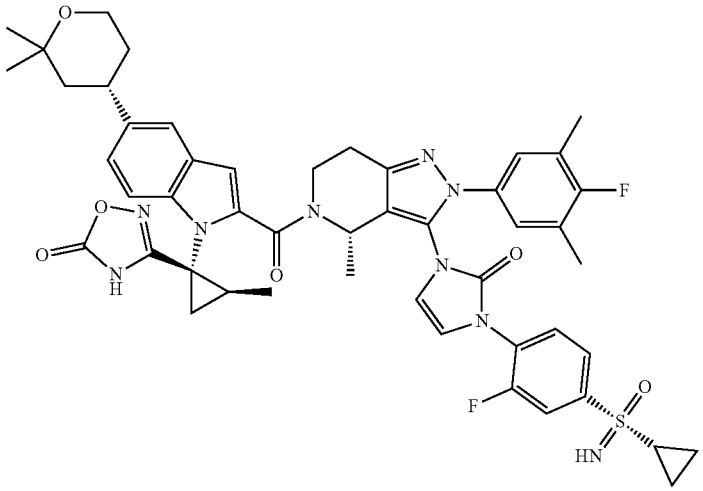 [SMILES: Cc1cc(-n2nc3c(c2-n2ccn(-c4ccc([S@](=N)(=O)C5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
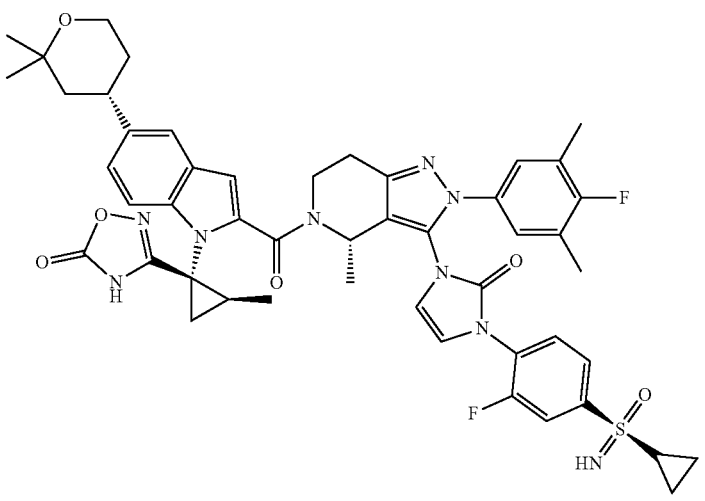 [SMILES: Cc1cc(-n2nc3c(c2-n2ccn(-c4ccc([S@@](=N)(=O)C5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
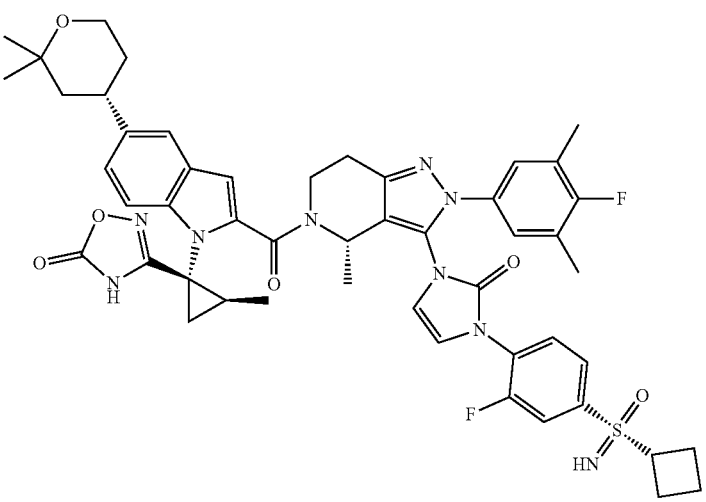 [SMILES: Cc1cc(-n2nc3c(c2-n2ccn(-c4ccc([S@](=N)(=O)C5CCC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

TABLE 2-continued
Structure
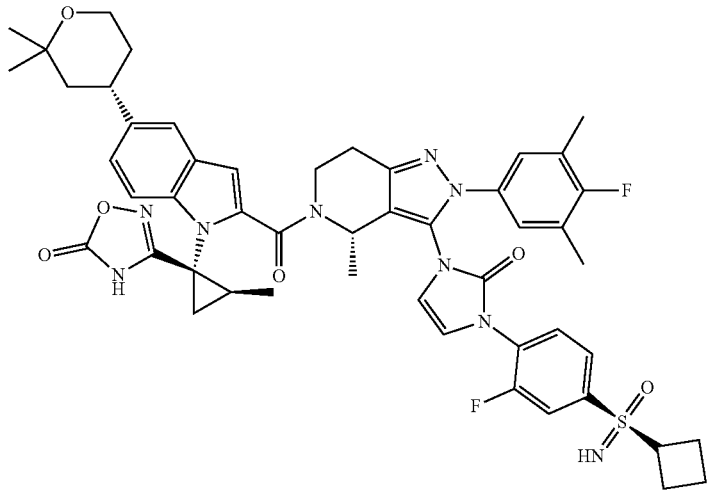 [SMILES: Cc1cc(-n2nc3c(c2-n2ccn(-c4ccc([S@@](=N)(=O)C5CCC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
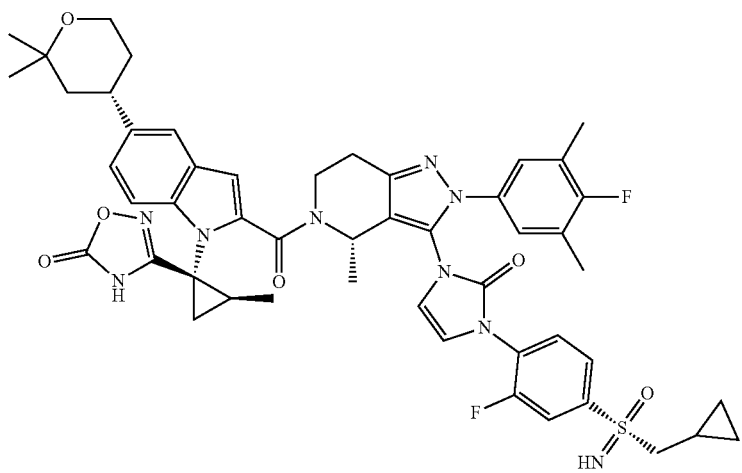 [SMILES: Cc1cc(-n2nc3c(c2-n2ccn(-c4ccc([S@](=N)(=O)CC5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
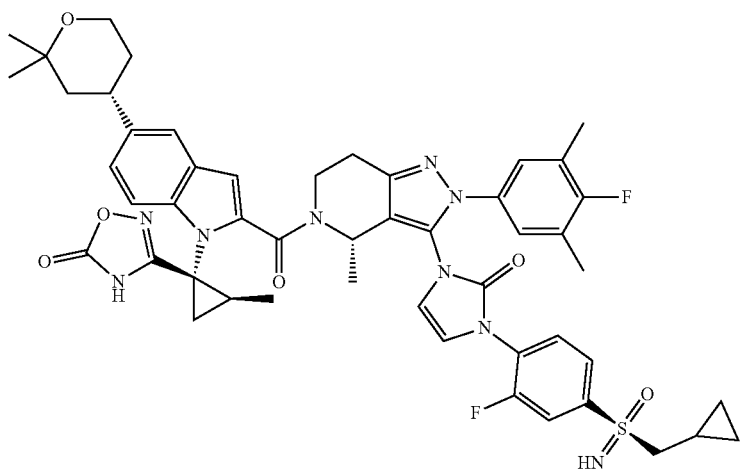 [SMILES: Cc1cc(-n2nc3c(c2-n2ccn(-c4ccc([S@@](=N)(=O)CC5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

TABLE 2-continued
Structure
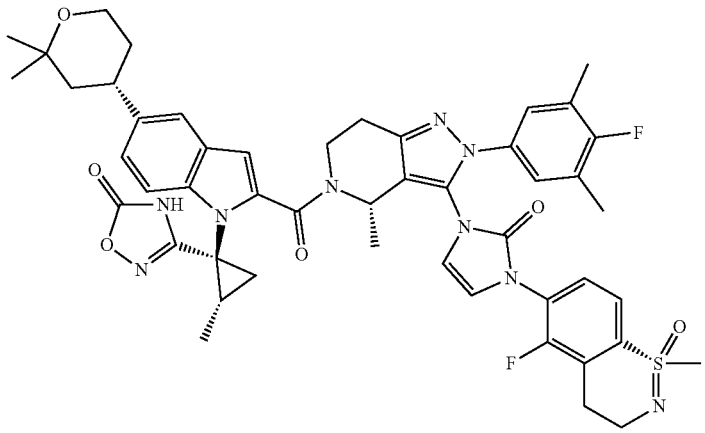
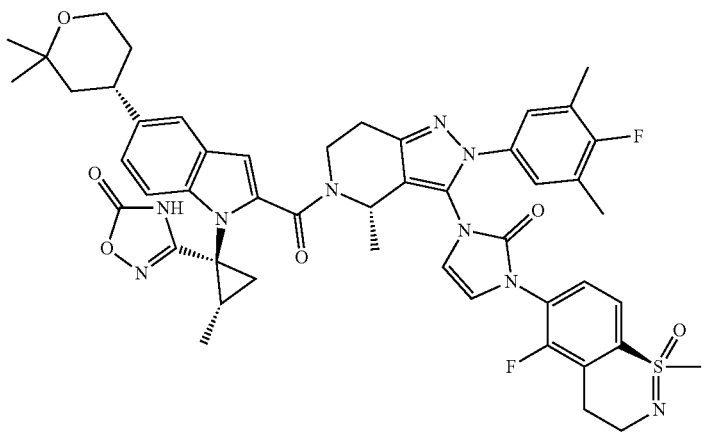
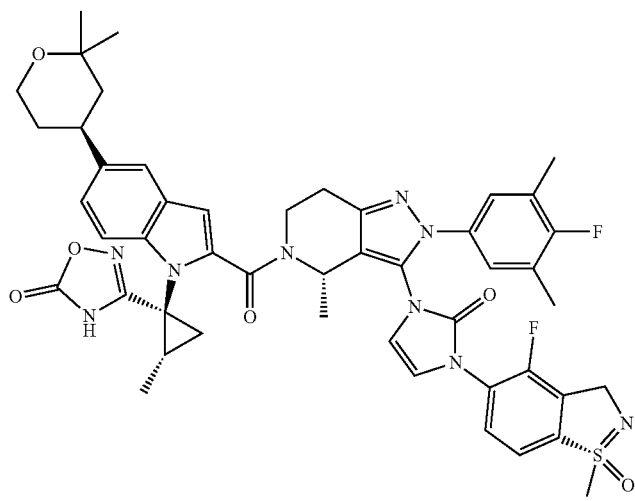 [SMILES: Cc1cc(-n2nc3c(c2-n2ccn(-c4ccc5c(c4F)CN=[S@]5(C)=O)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

TABLE 2-continued
Structure
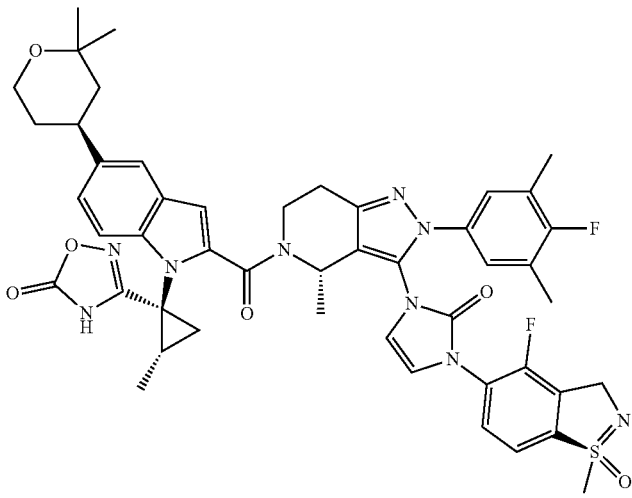 [SMILES: Cc1cc(-n2nc3c(c2-n2ccn(-c4ccc5c(c4F)CN=[S@@]5(C)=O)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
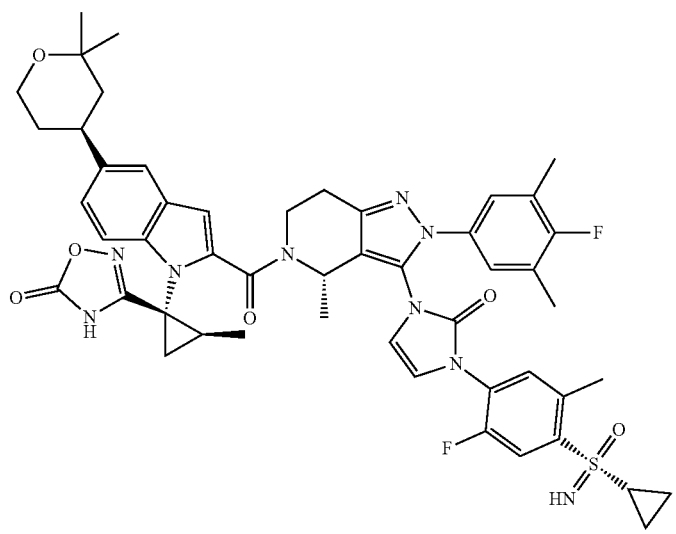 [SMILES: Cc1cc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)cc1[S@](=N)(=O)C1CC1]
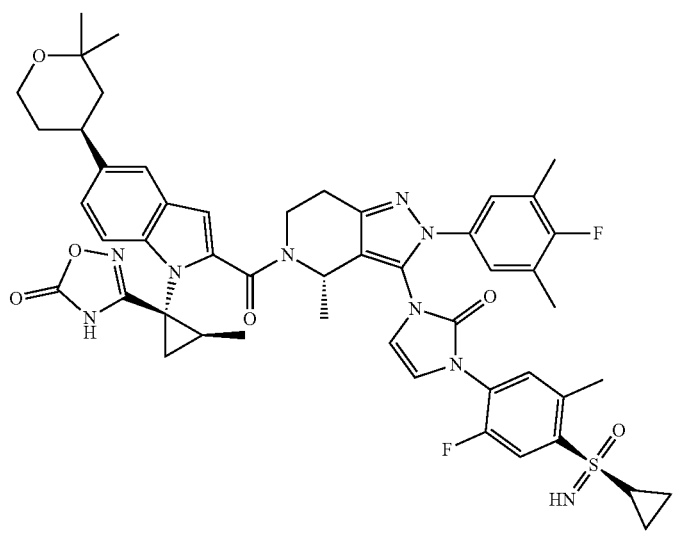 [SMILES: Cc1cc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)cc1[S@@](=N)(=O)C1CC1]

TABLE 2-continued
Structure
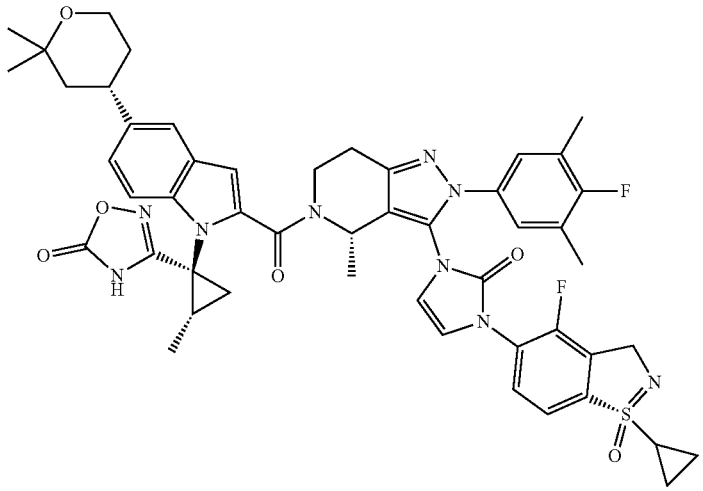 [SMILES: Cc1cc(-n2nc3c(c2-n2ccn(-c4ccc5c(c4F)CN=[S@]5(=O)C4CC4)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
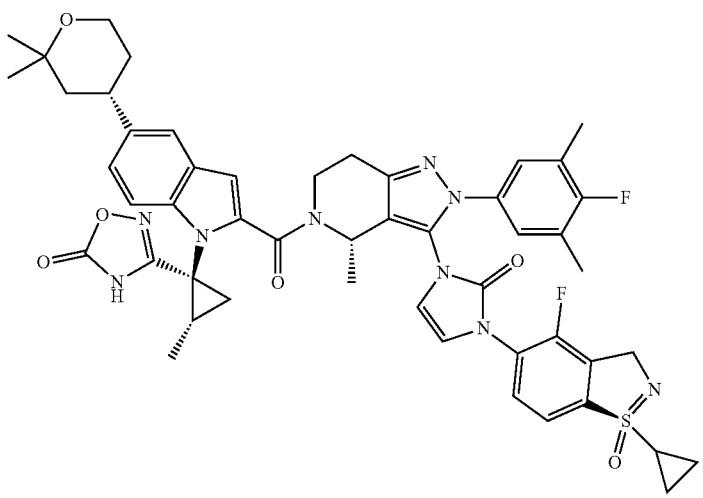 [SMILES: Cc1cc(-n2nc3c(c2-n2ccn(-c4ccc5c(c4F)CN=[S@@]5(=O)C4CC4)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
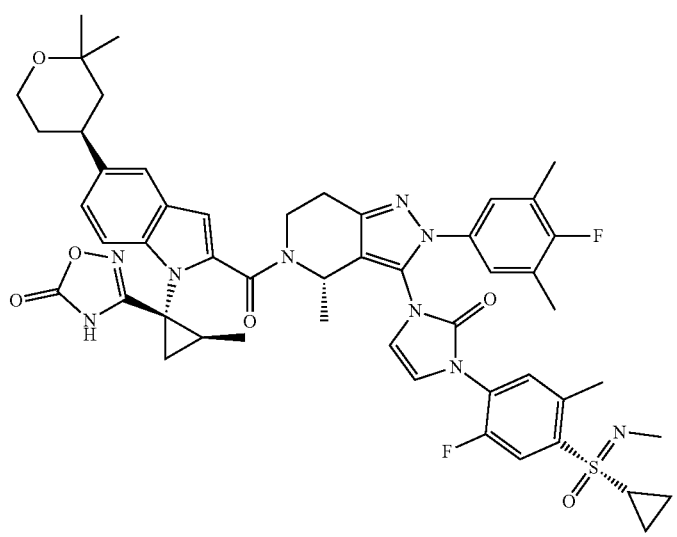 [SMILES: CN=[S@@](=O)(c1cc(F)c(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)cc1C)C1CC1]

TABLE 2-continued
Structure
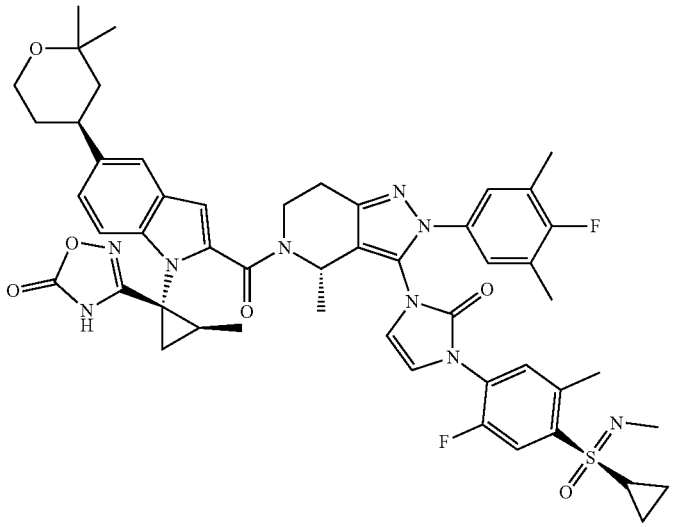 [SMILES: CN=[S@](=O)(c1cc(F)c(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)cc1C)C1CC1]
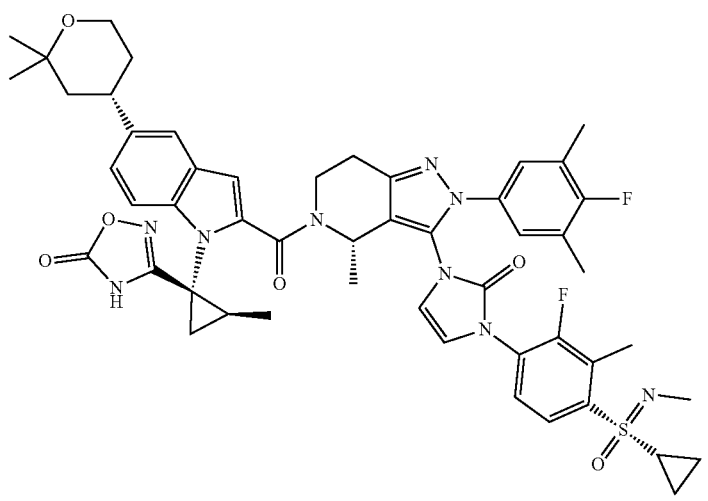
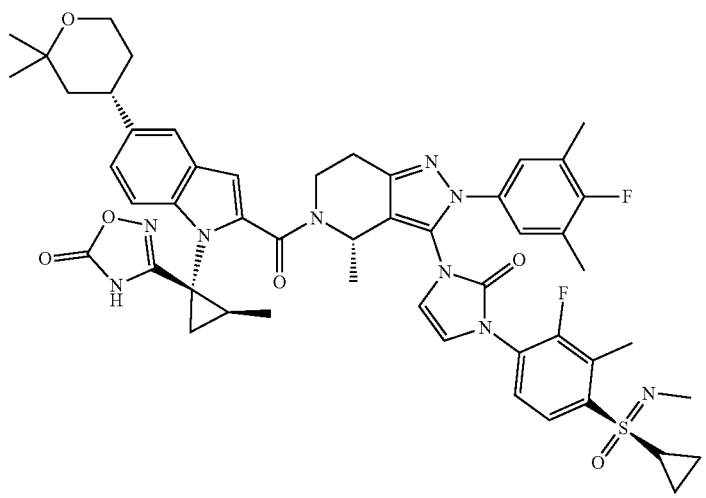

TABLE 2-continued
Structure
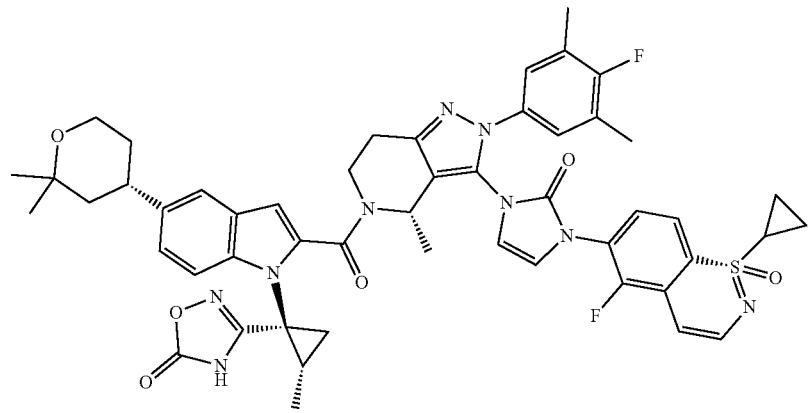 [SMILES: Cc1cc(-n2nc3c(c2-n2ccn(-c4ccc5c(c4F)C=CN=[S@]5(=O)C4CC4)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
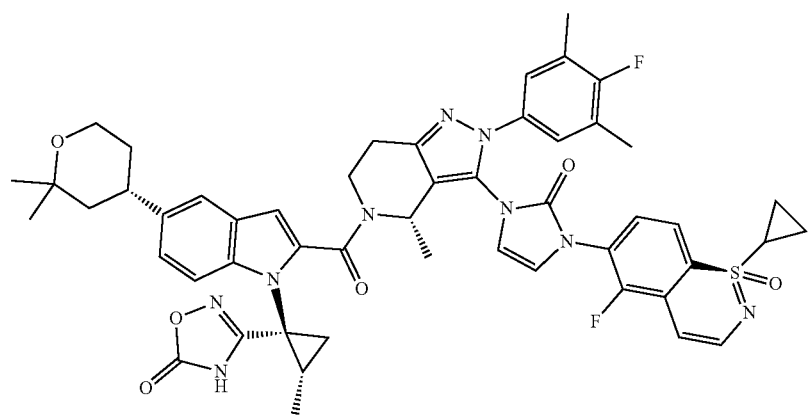 [SMILES: Cc1cc(-n2nc3c(c2-n2ccn(-c4ccc5c(c4F)C=CN=[S@@]5(=O)C4CC4)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
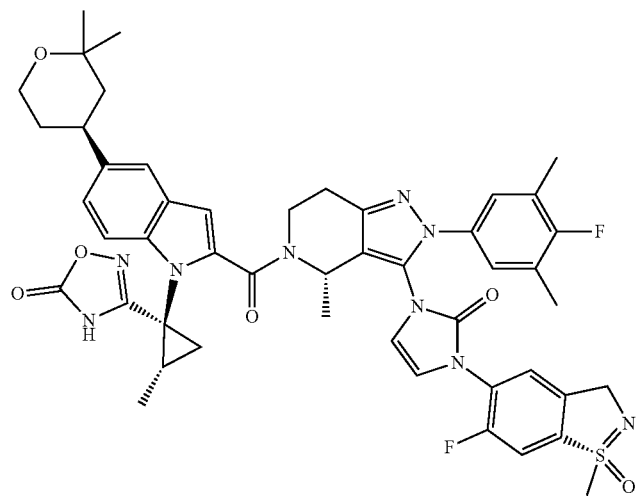

TABLE 2-continued
Structure
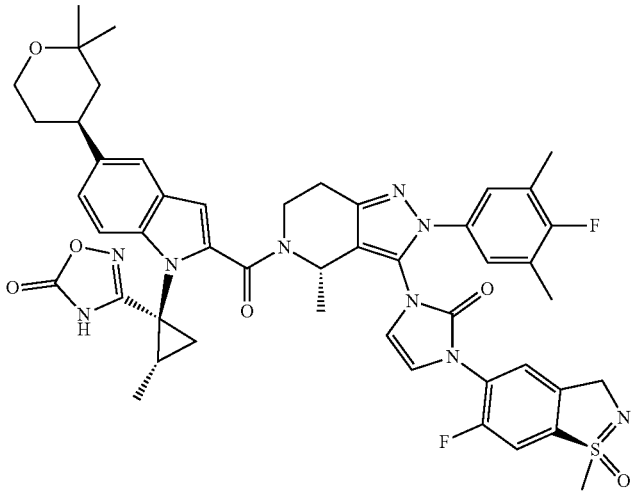
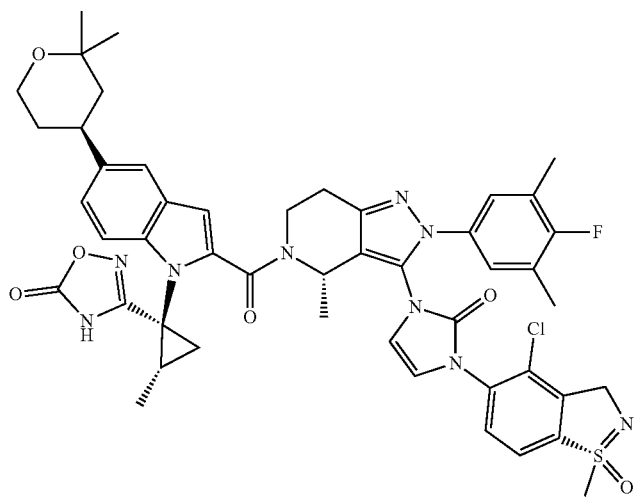
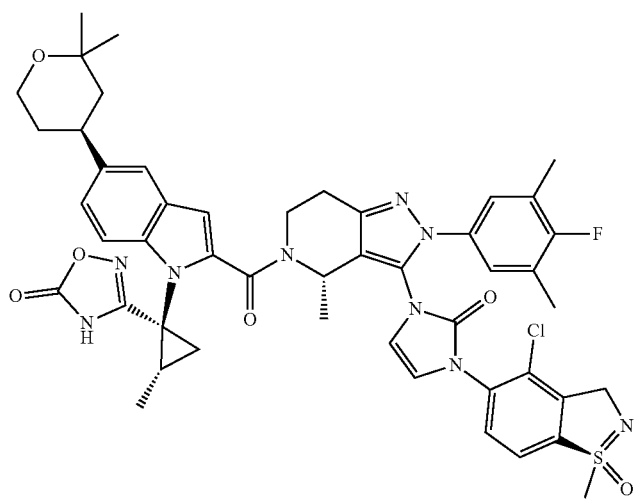

295 296
TABLE 2-continued
Structure
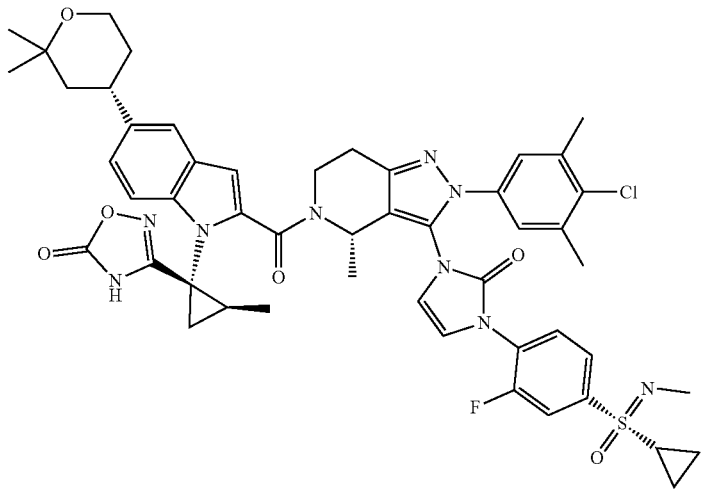
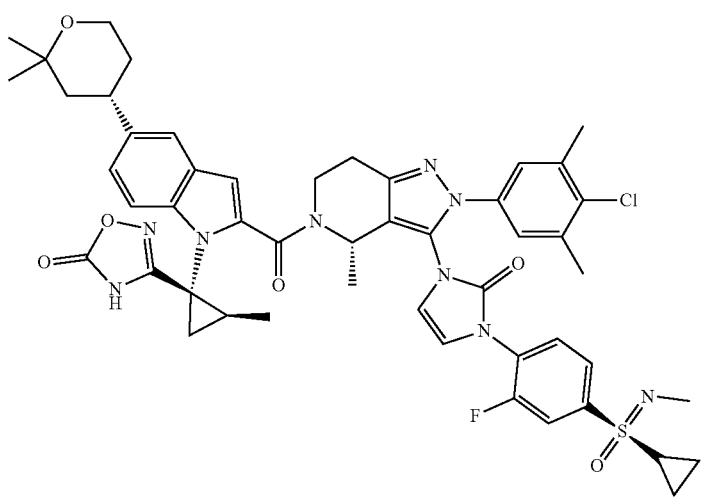
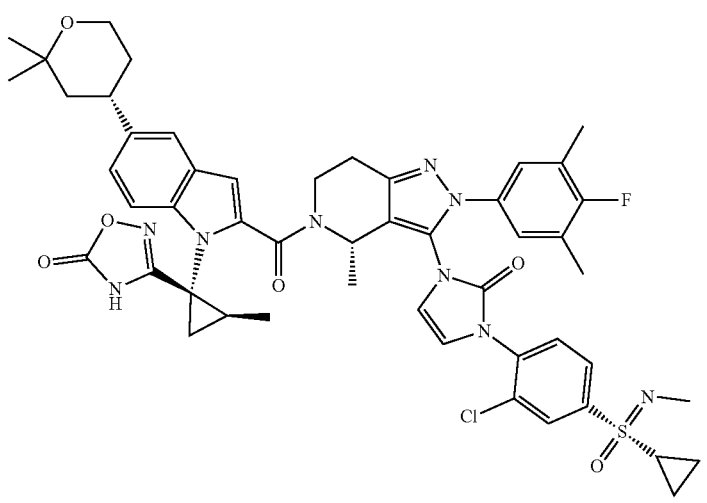

297 298
TABLE 2-continued
Structure
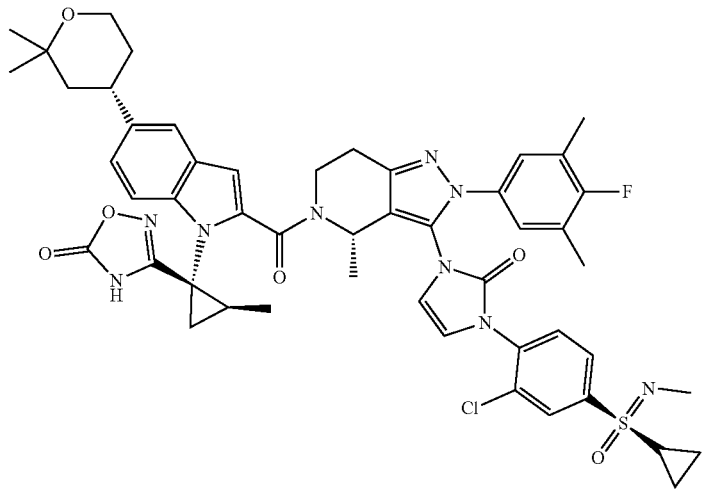
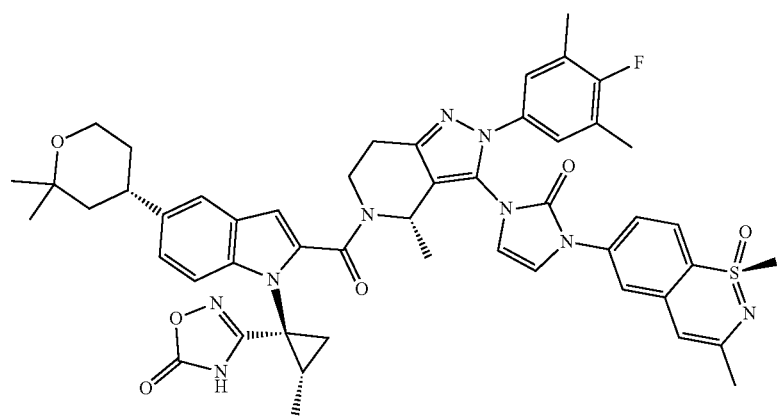
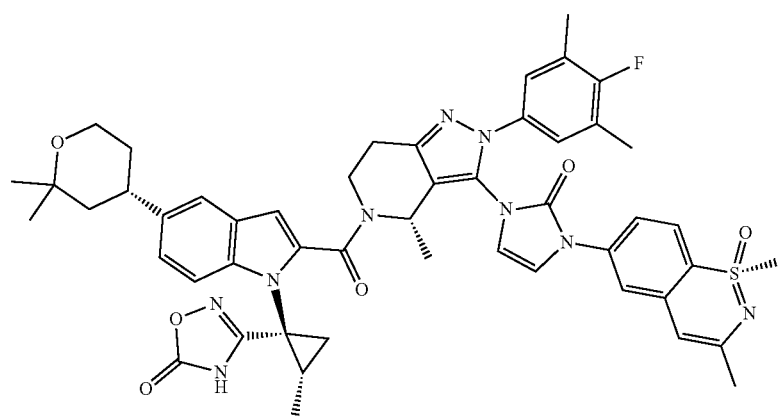

TABLE 2-continued
Structure
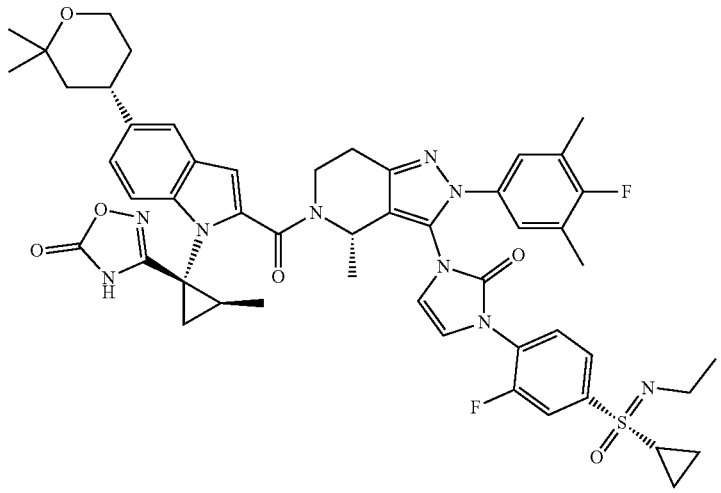 [SMILES: CCN=[S@@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1)C1CC1]
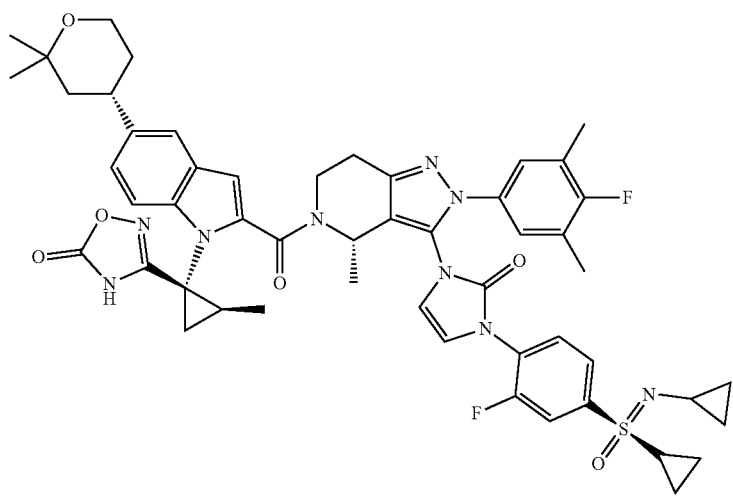 [SMILES: Cc1cc(-n2nc3c(c2-n2ccn(-c4ccc([S@@](=O)(=NC5CC5)C5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
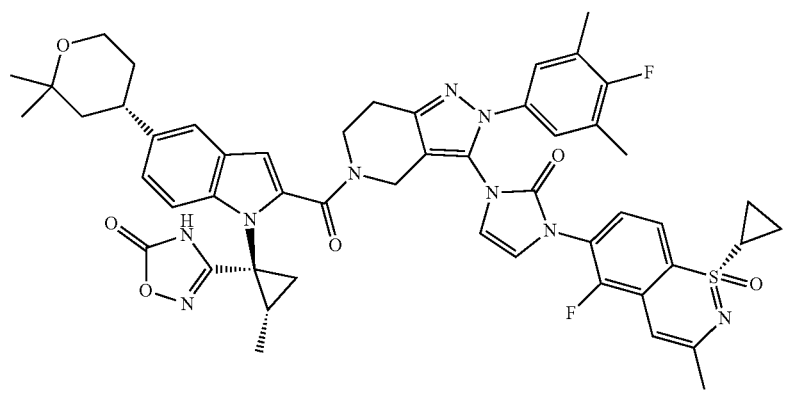 [SMILES: CC1=Cc2c(ccc(-n3ccn(-c4c5c(nn4-c4cc(C)c(F)c(C)c4)CCN(C(=O)c4cc6cc([C@H]7CCOC(C)(C)C7)ccc6n4[C@@]4(c6noc(=O)[nH]6)C[C@@H]4C)C5)c3=O)c2F)[S@](=O)(C2CC2)=N1]

TABLE 2-continued
Structure
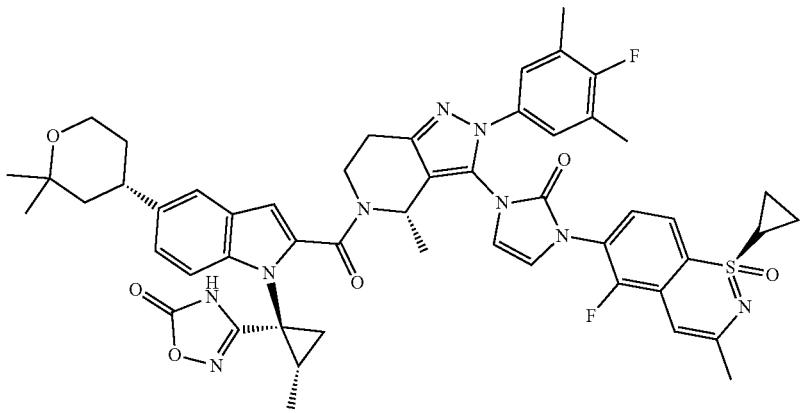 [SMILES: CC1=Cc2c(ccc(-n3ccn(-c4c5c(nn4-c4cc(C)c(F)c(C)c4)CCN(C(=O)c4cc6cc([C@H]7CCOC(C)(C)C7)ccc6n4[C@@]4(c6noc(=O)[nH]6)C[C@@H]4C)[C@H]5C)c3=O)c2F)[S@@](=O)(C2CC2)=N1]
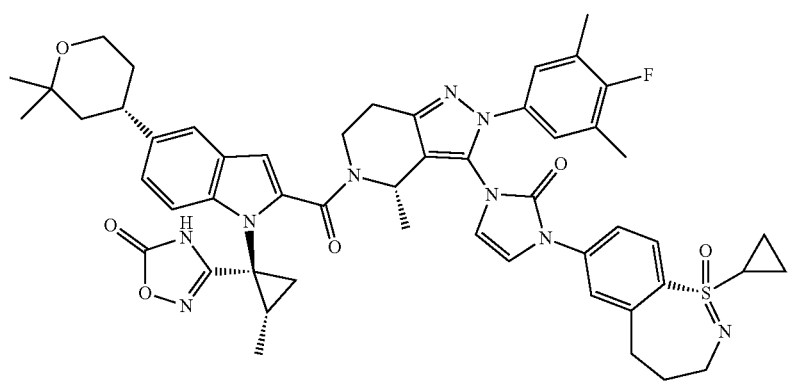 [SMILES: Cc1cc(-n2nc3c(c2-n2ccn(-c4ccc5c(c4)CCCN=[S@@]5(=O)C4CC4)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
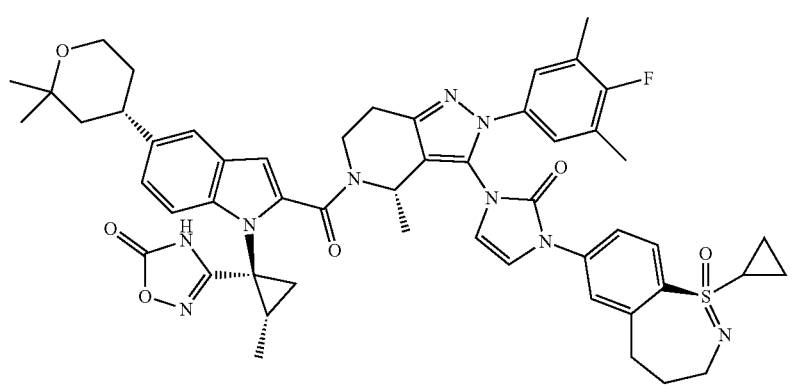 [SMILES: Cc1cc(-n2nc3c(c2-n2ccn(-c4ccc5c(c4)CCCN=[S@]5(=O)C4CC4)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

TABLE 2-continued
Structure
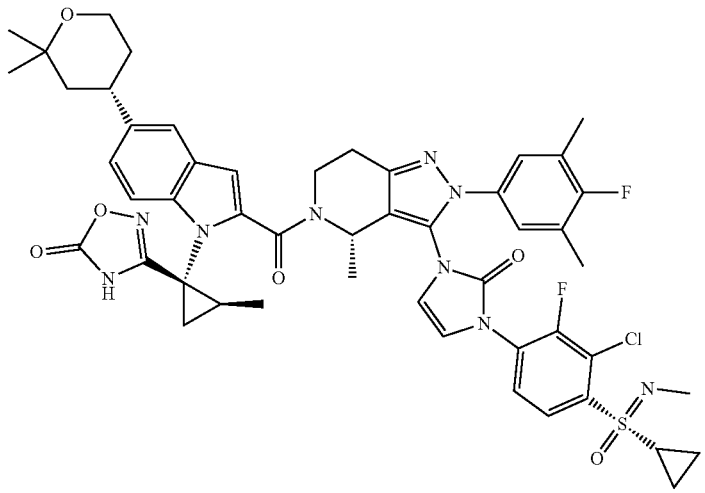 [SMILES: CN=[S@@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1Cl)C1CC1]
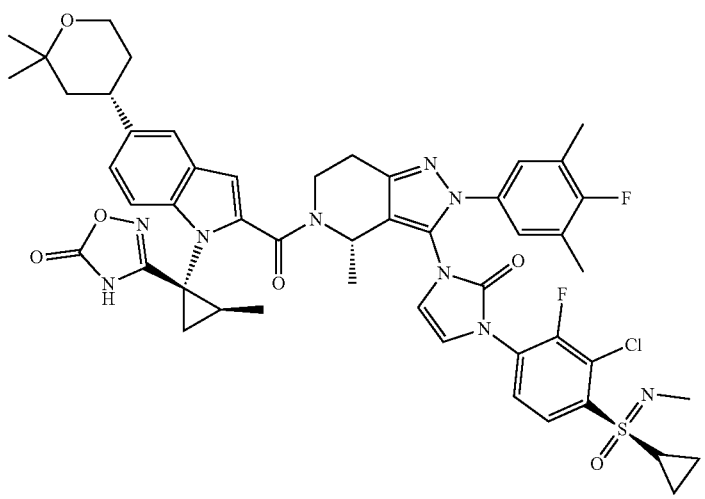 [SMILES: CN=[S@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1Cl)C1CC1]
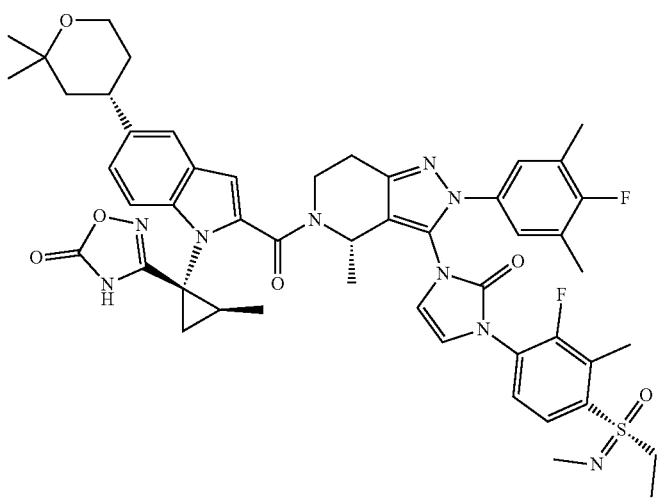 [SMILES: CC[S@](=O)(=NC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1C]

TABLE 2-continued

Structure

TABLE 2-continued
Structure
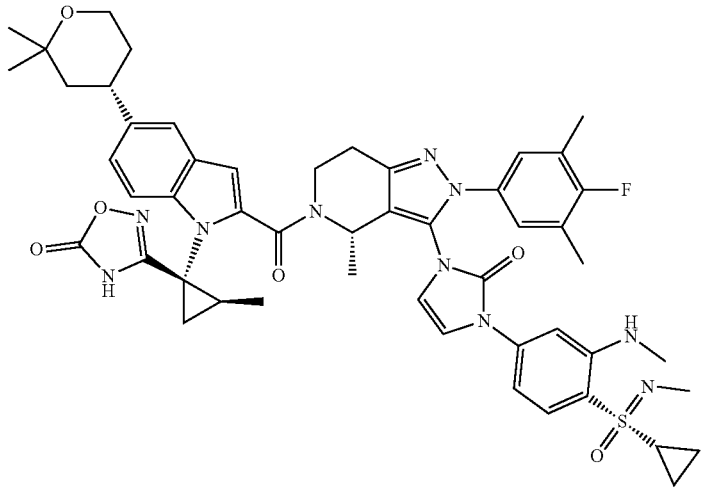 [SMILES: CN=[S@@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)cc1NC)C1CC1]
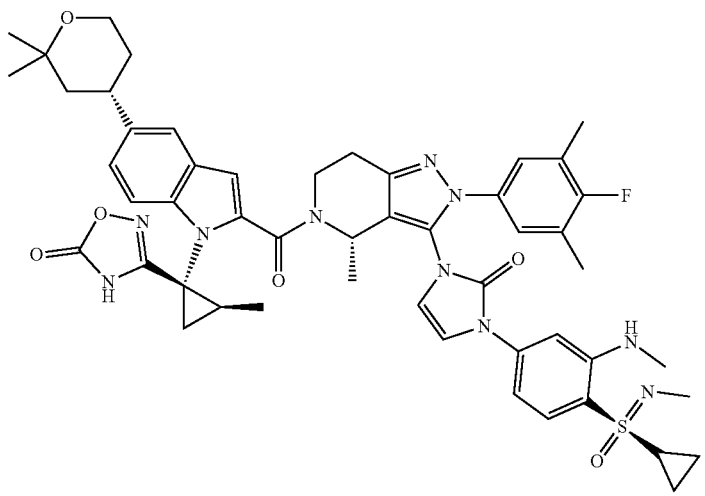 [SMILES: CN=[S@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)cc1NC)C1CC1]
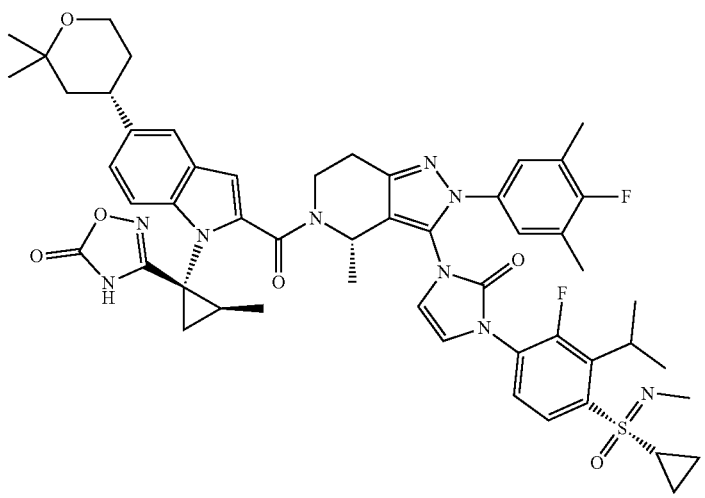 [SMILES: CN=[S@@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1C(C)C)C1CC1]

TABLE 2-continued
Structure
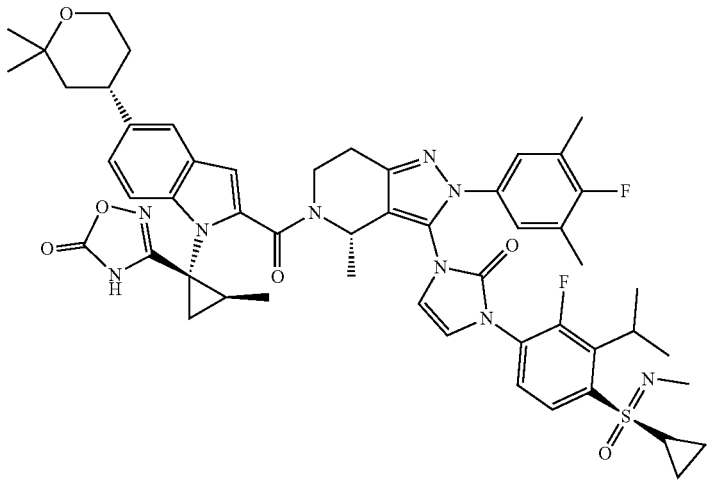 [SMILES: CN=[S@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1C(C)C)C1CC1]
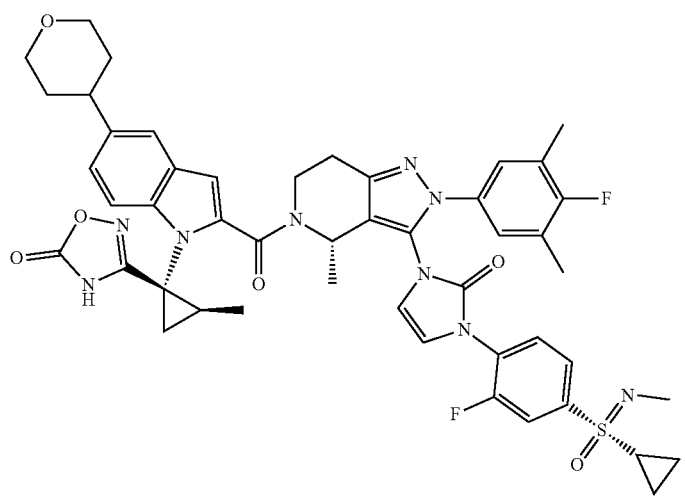 [SMILES: CN=[S@@](=O)(c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(F)c1)C1CC1]
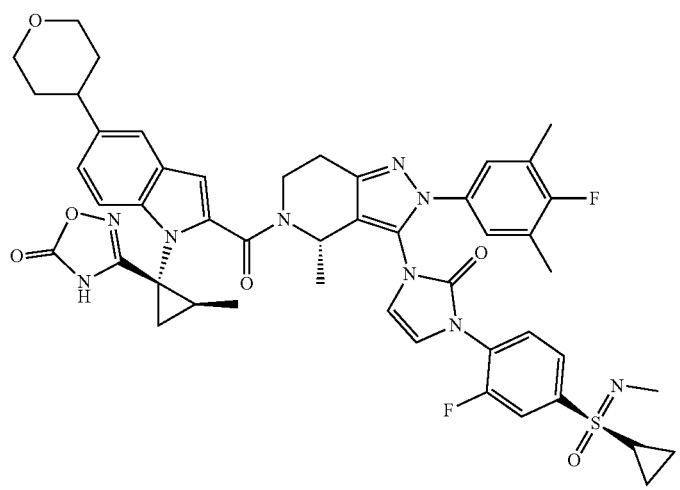 [SMILES: CN=[S@](=O)(c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(F)c1)C1CC1]

TABLE 2-continued

Structure

TABLE 2-continued
Structure
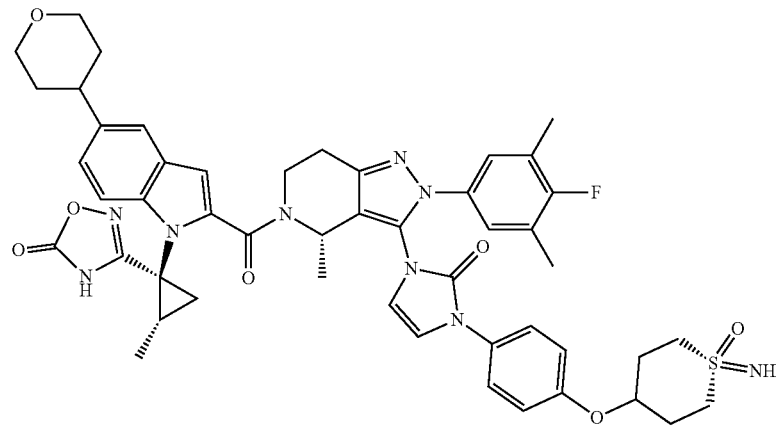
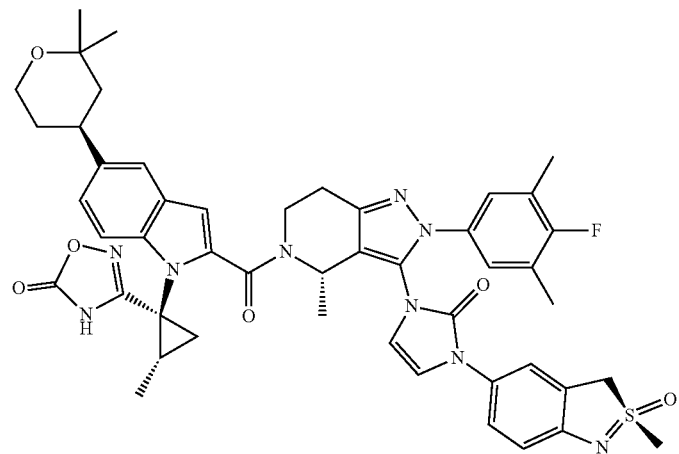 [SMILES: Cc1cc(-n2nc3c(c2-n2ccn(-c4ccc5c(c4)C[S@](C)(=O)=N5)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
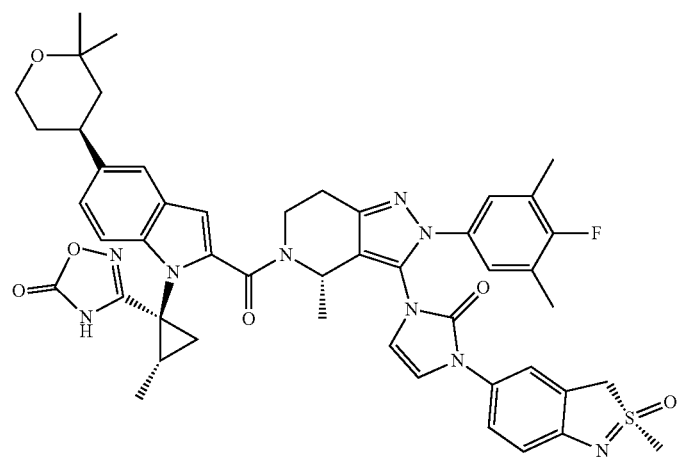 [SMILES: Cc1cc(-n2nc3c(c2-n2ccn(-c4ccc5c(c4)C[S@@](C)(=O)=N5)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

TABLE 2-continued

Structure

TABLE 2-continued
Structure
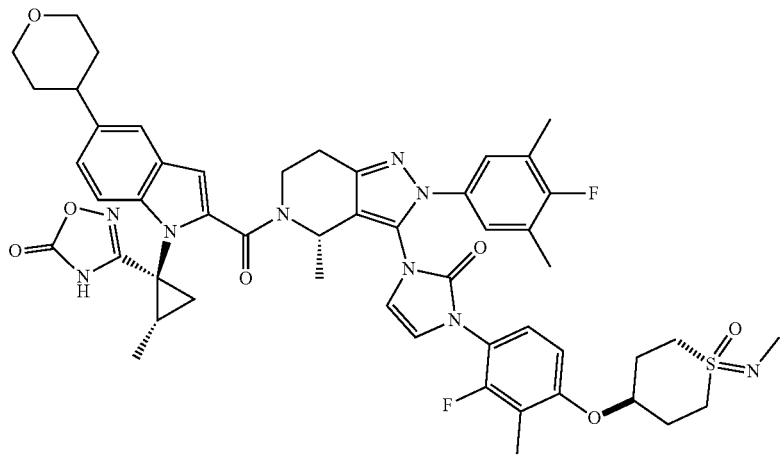
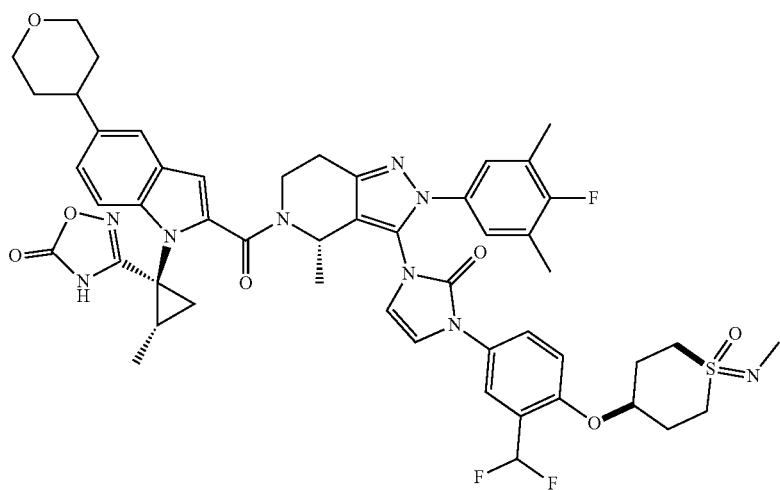
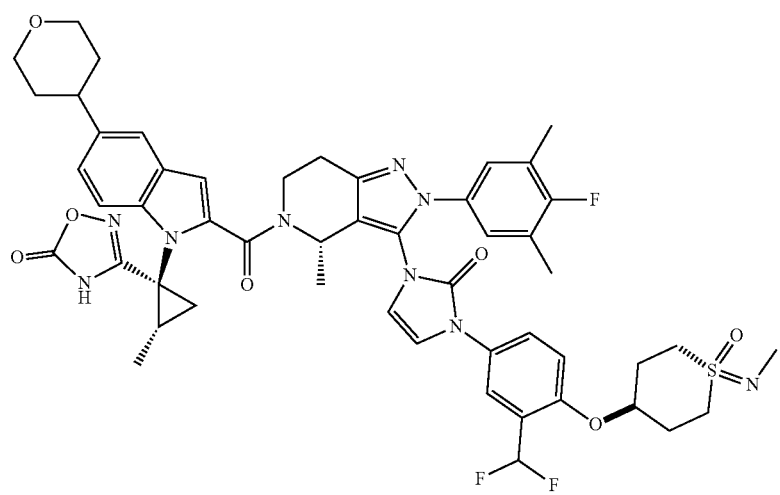

TABLE 2-continued
Structure
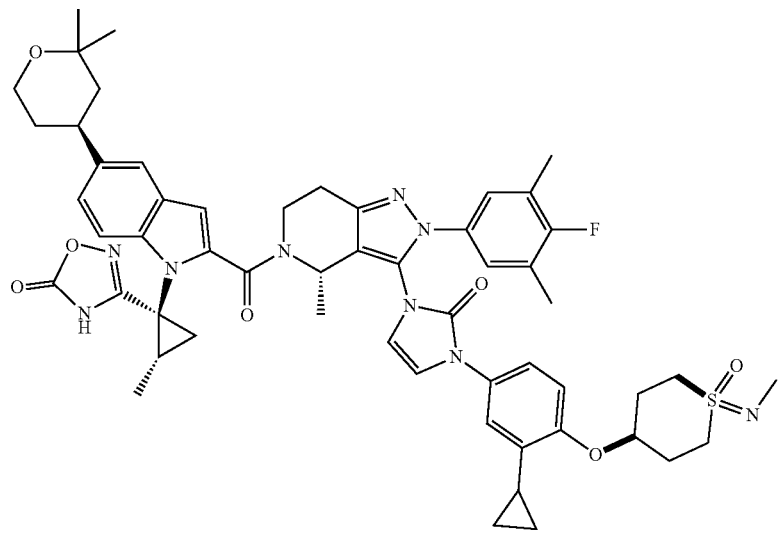
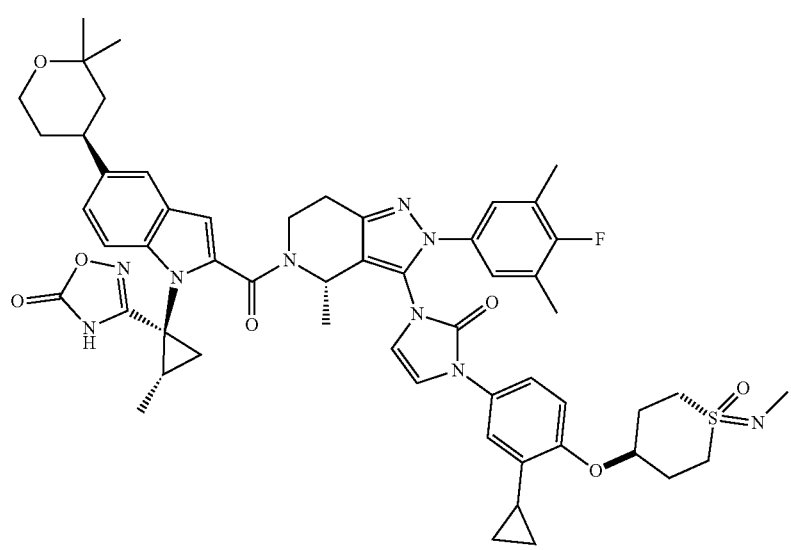
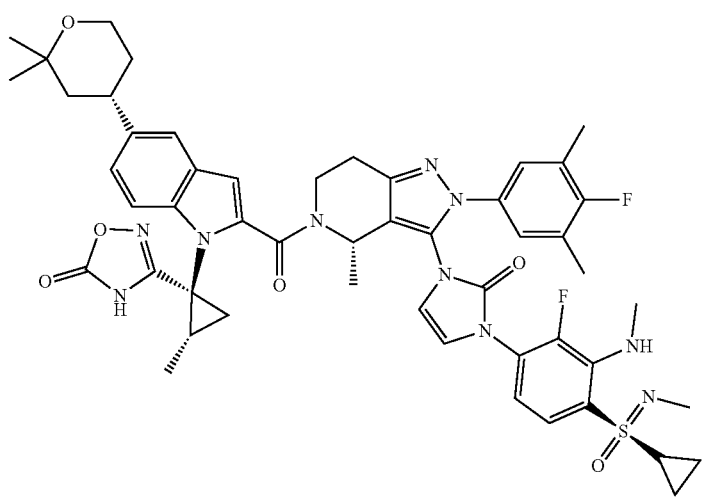

TABLE 2-continued

Structure

[Chemical structure]

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include trifluoroacetic acid salts.

It will further be appreciated that the compounds of Formula I or their salts may be isolated in the form of solvates, and accordingly that any such solvate is included within the scope of the present disclosure. For example, compounds of Formula I and salts thereof can exist in unsolvated as well as solvated forms with pharmaceutically acceptable solvents such as water, ethanol, and the like.

Pharmaceutical Compositions and Administration

When employed as pharmaceuticals, compounds as described herein (e.g., a compound of Formula I, or a pharmaceutically acceptable salt, isotopically enriched analog, stereoisomer, mixture of stereoisomers, or prodrug thereof) can be administered in the form of a pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula I, or a pharmaceutically acceptable salt, isotopically enriched analog, stereoisomer, mixture of stereoisomers, or prodrug thereof, in combination with one or more pharmaceutically acceptable excipients (carriers). For example, a pharmaceutical composition prepared using a compound of Formula I, or a pharmaceutically acceptable salt, isotopically enriched analog, stereoisomer, mixture of stereoisomers, or prodrug thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient.

Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula I, or a pharmaceutically acceptable salt, isotopically enriched analog, stereoisomer, mixture of stereoisomers, or prodrug thereof with a pharmaceutically acceptable excipient. Pharmaceutical compositions containing a compound of Formula I, or a pharmaceutically acceptable salt, isotopically enriched analog, stereoisomer, mixture of stereoisomers, or prodrug thereof as the active ingredient can be prepared by intimately mixing the compound of Formula I, or a pharmaceutically acceptable salt, isotopically enriched analog, stereoisomer, mixture of stereoisomers, or prodrug thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

In some embodiments, the compound or pharmaceutical composition can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2—and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22nd Edition (Pharmaceutical Press, London, U K. 2012).

In some embodiments, the compounds and pharmaceutical compositions described herein or a pharmaceutical composition thereof can be administered to patient in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intramenangeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal (e.g., intranasal), nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In some embodiments, a route of administration is parenteral (e.g., intratumoral).

In some embodiments, a compound of Formula I, or a pharmaceutically acceptable salt, isotopically enriched analog, stereoisomer, mixture of stereoisomers, or prodrug thereof as described herein or pharmaceutical compositions thereof can be formulated for parenteral administration, e.g., formulated for injection via the intraarterial, intrasternal, intracranial, intravenous, intramuscular, sub-cutaneous, or intraperitoneal routes. For example, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure. In some embodiments, devices are used for parenteral administration. For example, such devices may include needle injectors, microneedle injectors, needle-free injectors, and infusion techniques.

In some embodiments, the pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In some embodiments, the form must be sterile and must be fluid to the extent that it may be easily injected. In some embodiments, the form should be stable under the conditions of manufacture and storage and must be preserved against the contaminating action of microorganisms, such as bacteria and fungi.

In some embodiments, the carrier also can be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity can be maintained, for example, by the use of a coating, such as lecithin, by the maintenance of the required particle size in the case of dispersion, and by the use of surfactants. In some embodiments, the prevention of the action of microorganisms can be brought about by various antibacterial and antifungal agents, for example, parabens, chlorobutanol, phenol, sorbic acid, thimerosal, and the like. In some embodiments, isotonic agents, for example, sugars or sodium chloride are included. In some embodiments, prolonged absorption of the injectable compositions can be brought about by the use in the compositions of agents delaying absorption, for example, aluminum monostearate and gelatin.

In some embodiments, sterile injectable solutions are prepared by incorporating a compound of Formula I, or a pharmaceutically acceptable salt, isotopically enriched analog, stereoisomer, mixture of stereoisomers, or prodrug thereof in the required amount in the appropriate solvent with various of the other ingredients enumerated above, as required, followed by filtered sterilization. In some embodiments, dispersions are prepared by incorporating the various sterilized active ingredients into a sterile vehicle which contains the basic dispersion medium and the required other ingredients from those enumerated above. In some embodiments, sterile powders are used for the preparation of sterile injectable solutions.

In some embodiments, the methods of preparation are vacuum-drying and freeze-drying techniques, which yield a powder of the active ingredient, plus any additional desired ingredient from a previously sterile-filtered solution thereof.

In some embodiments, pharmacologically acceptable excipients usable in a rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol, Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In some embodiments, suppositories can be prepared by mixing a compound of Formula I, or a pharmaceutically acceptable salt, isotopically enriched analog, stereoisomer, mixture of stereoisomers, or prodrug thereof, or pharmaceutical compositions as described herein with suitable non-irritating excipients or carriers such as cocoa butter, polyethylene glycol or a suppository wax which are solid at ambient temperature but liquid at body temperature and therefore melt in the rectum and release the active compound. In some embodiments, compositions for rectal administration are in the form of an enema.

In some embodiments, a compound of Formula I, or a pharmaceutically acceptable salt, isotopically enriched analog, stereoisomer, mixture of stereoisomers, or prodrug thereof, as described herein or a pharmaceutical composition thereof is formulated for local delivery to the digestive or GI tract by way of oral administration (e.g., solid or liquid dosage forms).

In some embodiments, solid dosage forms for oral administration include capsules, tablets, pills, powders, and granules. In some embodiments, a compound of Formula I, or a pharmaceutically acceptable salt, isotopically enriched analog, stereoisomer, mixture of stereoisomers, or prodrug thereof, is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For example, in the case of capsules, tablets and pills, the dosage form may also comprise buffering agents. In some embodiments, solid compositions of a similar type may also be employed as fillers in soft and hard-filled gelatin capsules using such excipients as lactose or milk sugar as well as high molecular weight polyethylene glycols and the like.

In some embodiments, the pharmaceutical compositions will take the form of a unit dosage form such as a pill or tablet and thus the composition may contain, along with a compound of Formula I, or a pharmaceutically acceptable salt, isotopically enriched analog, stereoisomer, mixture of stereoisomers, or prodrug thereof as provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In some embodiments, another solid dosage form, a powder, marume, solution or suspension (e.g., in propylene carbonate, vegetable oils, PEG's, poloxamer 124 or triglycerides) is encapsulated in a capsule (gelatin or cellulose base capsule). In some embodiments, unit dosage forms in which one or more compounds and pharmaceutical compositions as provided herein or additional active agents are physically separated are also contemplated; e.g., capsules with granules (or tablets in a capsule) of each drug; two-layer tablets; two-compartment gel caps, etc. In some embodiments, enteric coated or delayed release oral dosage forms are also contemplated.

In some embodiments, other physiologically acceptable compounds may include wetting agents, emulsifying agents, dispersing agents or preservatives that are particularly useful for preventing the growth or action of microorganisms. For example, various preservatives are well known and include, for example, phenol and ascorbic acid.

In some embodiments, the excipients are sterile and generally free of undesirable matter. For example, these compositions can be sterilized by conventional, well-known sterilization techniques. In some embodiments, for various oral dosage form excipients such as tablets and capsules, sterility is not required. For example, the United States Pharmacopeia/National Formulary (USP/NF) standard can be sufficient.

In some embodiments, a compound of Formula I, or a pharmaceutically acceptable salt, isotopically enriched analog, stereoisomer, mixture of stereoisomers, or prodrug thereof as described herein or a pharmaceutical composition thereof is formulated for ocular administration. In some embodiments, ocular compositions can include, without limitation, one or more of any of the following: viscogens (e.g., carboxymethylcellulose, glycerin, polyvinylpyrrolidone, polyethylene glycol); stabilizers (e.g., Pluronic (tri-block copolymers), cyclodextrins); preservatives (e.g., benzalkonium chloride, EDTA, SofZia (boric acid, propylene glycol, sorbitol, and zinc chloride; Alcon Laboratories, Inc.), Purite (stabilized oxychloro complex; Allergan, Inc.)).

In some embodiments, a compound of Formula I, or a pharmaceutically acceptable salt, isotopically enriched analog, stereoisomer, mixture of stereoisomers, or prodrug thereof as described herein or a pharmaceutical composition thereof is formulated for topical administration to the skin or mucosa (e.g., dermally ortransdermally). In some embodiments, topical compositions can include ointments and creams. In some embodiments, ointments are semisolid preparations that are typically based on petrolatum or other petroleum derivatives. In some embodiments, creams containing the selected active agent are typically viscous liquid or semisolid emulsions, often either oil-in-water or water-in-oil. For example, cream bases are typically water-washable, and contain an oil phase, an emulsifier and an aqueous phase. For example, the oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. In some embodiments, the emulsifier in a cream formulation is generally a nonionic, anionic, cationic or amphoteric surfactant. In some embodiments, as with other carriers or vehicles, an ointment base should be inert, stable, nonirritating and non-sensitizing.

In any of the foregoing embodiments, pharmaceutical compositions as described herein can include one or more one or more of the following: lipids, interbilayer crosslinked multilamellar vesicles, biodegradable poly(D,L-lactic-co-glycolic acid) (PLGA)-based or poly anhydride-based nanoparticles or microparticles, and nanoporous particle-supported lipid bilayers.

The amount of the compound in a pharmaceutical composition or formulation can vary within the full range employed by those skilled in the art. Typically, the formulation will contain, on a weight percent (wt %) basis, from about 0.01-99.99 wt % of a compound of this disclosure based on the total formulation, with the balance being one or more suitable pharmaceutical excipients. In one embodiment, the compound is present at a level of about 1-80 wt %. Representative pharmaceutical formulations are described below.

Formulation Example 1—Tablet Formulation

The following ingredients are mixed intimately and pressed into single scored tablets.

| Ingredient | Quantity per tablet, mg |
| --- | --- |
| compound of this disclosure | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule

| Ingredient | Quantity per capsule, mg |
| --- | --- |
| compound of this disclosure | 200 |
| lactose, spray-dried | 148 |
| magnesium stearate | 2 |

Formulation Example 3—Suspension Formulation

The following ingredients are mixed to form a suspension for oral administration.

| Ingredient | Amount |
| --- | --- |
| compound of this disclosure | 1.0 g |
| fumaric acid | 0.5 g |
| sodium chloride | 2.0 g |
| methyl paraben | 0.15 g |

-continued

| Ingredient | Amount |
| --- | --- |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| coloring | 0.5 mg |
| distilled water | q.s. to 100 mL |

Formulation Example 4—Injectable Formulation

The following ingredients are mixed to form an injectable formulation.

| Ingredient | Amount |
| --- | --- |
| compound of this disclosure | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5 Suppository Formulation

A suppository of total weight 2.5 g is prepared by mixing the compound of this disclosure with Witepsol® H-15 (triglycerides of saturated vegetable fatty acid; Riches-Nelson, Inc., New York), and has the following composition:

| Ingredient | Amount |
| --- | --- |
| compound of this disclosure | 500 mg |
| Witepsol ® H-15 | balance |

In some embodiments, the dosage for a compound of Formula I, or a pharmaceutically acceptable salt, isotopically enriched analog, stereoisomer, mixture of stereoisomers, or prodrug thereof, is determined based on a multiple factors including, but not limited to, type, age, weight, sex, medical condition of the patient, severity of the medical condition of the patient, route of administration, and activity of the compound or pharmaceutically acceptable salt, isotopically enriched analog, stereoisomer, mixture of stereoisomers, or prodrug thereof. In some embodiments, proper dosage for a particular situation can be determined by one skilled in the medical arts. In some embodiments, the total daily dosage may be divided and administered in portions throughout the day or by means providing continuous delivery.

In some embodiments, a compound of Formula I, or a pharmaceutically acceptable salt, isotopically enriched analog, stereoisomer, mixture of stereoisomers, or prodrug thereof, is administered at a dose from about 0.01 to about 1000 mg. For example, from about 0.1 to about 30 mg, about 10 to about 80 mg, about 0.5 to about 15 mg, about 50 mg to about 200 mg, about 100 mg to about 300 mg, about 200 to about 400 mg, about 300 mg to about 500 mg, about 400 mg to about 600 mg, about 500 mg to about 800 mg, about 600 mg to about 900 mg, or about 700 mg to about 1000 mg. In some embodiments, the dose is a therapeutically effective amount.

In some embodiments, a compound of Formula I, or a pharmaceutically acceptable salt, isotopically enriched analog, stereoisomer, mixture of stereoisomers, or prodrug thereof as described herein is administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg). In some embodiments, a compound of Formula I, or a pharmaceutically acceptable salt, isotopically enriched analog, stereoisomer, mixture of stereoisomers, or prodrug thereof as described herein is administered as a dosage of about 100 mg/Kg.

In some embodiments, the foregoing dosages of a compound of Formula I, or a pharmaceutically acceptable salt, isotopically enriched analog, stereoisomer, mixture of stereoisomers, or prodrug thereof, can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound of Formula I, or a pharmaceutically acceptable salt, isotopically enriched analog, stereoisomer, mixture of stereoisomers, or prodrug thereof as described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a compound of Formula I, or a pharmaceutically acceptable salt, isotopically enriched analog, stereoisomer, mixture of stereoisomers, or prodrug thereof is administered to a patient for a period of time followed by a separate period of time where administration of the compound of Formula I, or a pharmaceutically acceptable salt, isotopically enriched analog, stereoisomer, mixture of stereoisomers, or prodrug thereof is stopped. In some embodiments, a compound of Formula I, or a pharmaceutically acceptable salt, isotopically enriched analog, stereoisomer, mixture of stereoisomers, or prodrug thereof is administered for a first period and a second period following the first period, with administration stopped during the second period, followed by a third period where administration of the compound of Formula I, or a pharmaceutically acceptable salt, isotopically enriched analog, stereoisomer, mixture of stereoisomers, or prodrug thereof is started and then a fourth period following the third period where administration is stopped. For example, the period of administration of a compound of Formula I, or a pharmaceutically acceptable salt, isotopically enriched analog, stereoisomer, mixture of stereoisomers, or prodrug thereof followed by a period where administration is stopped is repeated for a determined or undetermined period of time. In some embodiments, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In some embodiments, a compound of Formula I, or a pharmaceutically acceptable salt, isotopically enriched analog, stereoisomer, mixture of stereoisomers, or prodrug thereof, is orally administered to the patient one or more times per day (e.g., one time per day, two times per day, three times per day, four times per day per day or a single daily dose).

In some embodiments, a compound of Formula I, or a pharmaceutically acceptable salt, isotopically enriched analog, stereoisomer, mixture of stereoisomers, or prodrug thereof, is administered by parenteral administration to the patient one or more times per day (e.g., 1 to 4 times, one time per day, two times per day, three times per day, four times per day or a single daily dose).

In some embodiments, a compound of Formula I, or a pharmaceutically acceptable salt, isotopically enriched analog, stereoisomer, mixture of stereoisomers, or prodrug thereof, is administered by parenteral administration to the patient weekly.

Methods of Treatment

In some embodiments, this disclosure features methods for treating a patient (e.g., a human) having a disease, disorder, or condition in which modulation of GLP-1R (e.g., repressed or impaired and/or elevated or unwanted GLP-1R) is beneficial for the treatment of the underlying pathology and/or symptoms and/or progression of the disease, disorder, or condition. In some embodiments, the methods described herein can include or further include treating one or more conditions associated, co-morbid or sequela with any one or more of the conditions described herein.

Provided herein is a method for treating a GLP-1 associated disease, disorder, or condition, the method comprising administering to a patient in need thereof an effective amount of a compound of Formula I, or a pharmaceutically acceptable salt, isotopically enriched analog, stereoisomer, mixture of stereoisomers, or prodrug thereof, or a pharmaceutical composition as disclosed herein.

In some embodiments, the disease, disorder, or condition includes, but is not limited to type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, and Polycystic Ovary Syndrome (PCOS).

In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof.

In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

In some embodiments, the compounds and pharmaceutical compositions and methods for treating a patient described herein induce one or more of blood glucose reduction (e.g., reduce blood glucose levels), reduce blood hemoglobin A1c (HbA1c) levels, promote insulin synthesis, stimulate insulin secretion, increase the mass of β-cells, modulate gastric acid secretion, modulate gastric emptying, decrease the body mass index (BMI), and/or decrease glucagon production (e.g., level). In certain embodiments, the compounds and pharmaceutical compositions and methods for treating a patient described herein stabilize serum glucose and serum insulin levels (e.g., serum glucose and serum insulin concentrations). Also provided herein are methods for modulating glucose or insulin levels in a patient in need of such modulating, the method comprising administering to the patient an effective amount of a compound of Formula I, or a pharmaceutically acceptable salt, isotopically enriched analog, stereoisomer, mixture of stereoisomers, or prodrug thereof, or a pharmaceutical composition as disclosed herein.

In some embodiments, provided herein is a method for reducing the risk (e.g., by about at least 20%, at least 30%, at least 40%, at least 50%, at least 60%, at least 70%, or at least 80%) of major adverse cardiovascular events (MACE) in a patient in need thereof, the method comprising administering to the patient an effective amount of a compound of Formula I, or a pharmaceutically acceptable salt, isotopically enriched analog, stereoisomer, mixture of stereoisomers, or prodrug thereof, or a pharmaceutical composition as disclosed herein. In certain of these embodiments, the patient is an adult that has been diagnosed with type 2 diabetes (T2D). In certain embodiments, the patient is an adult that has been diagnosed with a heart disease. In certain embodiments, the patient is an adult that has been diagnosed with type 2 diabetes (T2D) and a heart disease. In certain embodiments, the patient is an adult that has type 2 diabetes (T2D). In certain embodiments, the patient is an adult that has a heart disease. In certain embodiments, the patient has type 2 diabetes (T2D) and a heart disease.

Indications

Obesity

In some embodiments, the condition, disease, or disorder is obesity and conditions, diseases or disorders that are associated with or related to obesity. Non-limiting examples of obesity and obesity related conditions include symptomatic obesity, simple obesity, childhood obesity, morbid obesity, and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudohypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or 0-blocker-induced obesity).

In some embodiments, the condition, disease, or disorder is associated with obesity. Examples of such conditions, diseases or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catemenial symptom), visceral obesity syndrome, and metabolic syndrome. In some embodiments, the chemical compound and pharmaceutical compositions described herein can be used to treat patients exhibiting symptoms of both obesity and insulin deficiency.

Diabetes

In some embodiments, the condition, disease, or disorder is diabetes. Non-limiting examples of diabetes include type 1 diabetes mellitus, type 2 diabetes mellitus (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes. In some embodiments, the condition, disease, or disorder is type 2 diabetes mellitus (e.g., diet-treated type 2-diabetes, sulfonylurea-treated type 2-diabetes, a far-advanced stage type 2-diabetes, long-term insulin-treated type 2-diabetes).

Provided herein is a method of treating a diabetes mellitus in a patient, the method comprising (a) determining that the patient has type 2 diabetes mellitus, and (b) administering to the patient a therapeutically effective amount of a compound of Formula I, or a pharmaceutically acceptable salt, isotopically enriched analog, stereoisomer, mixture of stereoisomers, or prodrug thereof, or a pharmaceutical composition as disclosed herein.

Provided herein is a method for treating type 2 diabetes mellitus in a patient, the method comprising administering to a patient identified or diagnosed as having type 2 diabetes mellitus a therapeutically effective amount of a compound of Formula I, or a pharmaceutically acceptable salt, isotopically enriched analog, stereoisomer, mixture of stereoisomers, or prodrug thereof, or a pharmaceutical composition as disclosed herein.

Also provided herein is a method of treating type 2 diabetes mellitus in a patient in need thereof, the method comprising administering to the patient a therapeutically effective amount of a compound of Formula I, or a pharmaceutically acceptable salt, isotopically enriched analog, stereoisomer, mixture of stereoisomers, or prodrug thereof, or a pharmaceutical composition as disclosed herein.

In some embodiments, the compounds and pharmaceutical compositions and methods for treating a patient with a condition, disease, or disorder (e.g., type 2 diabetes mellitus) described herein reduce fasting plasma glucose levels. In some embodiments, the compounds and pharmaceutical compositions and methods for treating a patient with a condition, disease, or disorder (e.g., type 2 diabetes mellitus) described herein reduce non-fasting plasma glucose levels. In some embodiments, the compounds and pharmaceutical compositions and methods for treating a patient with a condition, disease, or disorder (e.g., type 2 diabetes mellitus) described herein reduce HbA1c levels. In some embodiments, the compounds and pharmaceutical compositions and methods for treating a patient with a condition, disease, or disorder (e.g., type 2 diabetes mellitus) described herein reduce glucagon levels. In some embodiments, the compounds and pharmaceutical compositions and methods for treating a patient with a condition, disease, or disorder (e.g., type 2 diabetes mellitus) described herein increase insulin levels. In some embodiments, the compounds and pharmaceutical compositions and methods for treating a patient with a condition, disease, or disorder (e.g., type 2 diabetes mellitus) described herein reduce BMI.

In some embodiments, a reduction in fasting plasma glucose levels of about 5% to about 95% indicates treatment of type 2 diabetes mellitus. In some embodiments, a reduction in fasting plasma glucose levels of about 15% to about 80% indicates treatment of type 2 diabetes mellitus. In some embodiments, a reduction in fasting plasma glucose levels of about 25% to about 60% indicates treatment of type 2 diabetes mellitus. In some embodiments, a reduction in fasting plasma glucose levels to about or below 126 mg/dL, about or below 110 mg/dL, or about or below 90 mg/dL indicates treatment of the type 2 diabetes mellitus.

In some embodiments, a reduction in non-fasting plasma glucose levels of about 5% to about 95% indicates treatment of type 2 diabetes mellitus. In some embodiments, a reduction in non-fasting plasma glucose levels of about 15% to about 80% indicates treatment of type 2 diabetes mellitus. In some embodiments, a reduction in non-fasting plasma glucose levels of about 25% to about 60% indicates treatment of type 2 diabetes mellitus. In some embodiments, a reduction in non-fasting plasma glucose levels to about or below 200 mg/dL, about or below 150 mg/dL, or about or below 130 mg/dL indicates treatment of type 2 diabetes mellitus.

In some embodiments, a reduction in HbA1c levels of about 5% to about 95% indicates treatment of type 2 diabetes mellitus. In some embodiments, a reduction in HbA1c levels of about 15% to about 80% indicates treatment of type 2 diabetes mellitus. In some embodiments, a reduction in HbA1c levels of about 25% to about 60% indicates treatment of type 2 diabetes mellitus. In some embodiments, reduction in HbA1c levels to about or below 6.5%, about or below 6.0%, or about or below 5.0% indicates treatment of type 2 diabetes mellitus.

In some embodiments, a reduction in glucagon levels of about 5% to about 95% indicates treatment of type 2 diabetes mellitus. In some embodiments, a reduction in glucagon levels of about 15% to about 80% indicates treatment of type 2 diabetes mellitus. In some embodiments, a reduction in glucagon levels of about 25% to about 60% indicates treatment of type 2 diabetes mellitus. In some embodiments, an increase in insulin levels of about 5% to about 95% indicates treatment of type 2 diabetes mellitus. In some embodiments, an increase in insulin levels of about 15% to about 80% indicates treatment of type 2 diabetes mellitus. In some embodiments, an increase in insulin levels of about 25% to about 60% indicates treatment of type 2 diabetes mellitus.

In some embodiments, a reduction in BMI of about 5% to about 95% indicates treatment of type 2 diabetes mellitus. In some embodiments, a reduction in BMI of about 15% to about 80% indicates treatment of the type 2 diabetes mellitus. In some embodiments, a reduction in BMI of about 25% to about 60% indicates treatment of type 2 diabetes mellitus. In some embodiments, a reduction in BMI of about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of type 2 diabetes mellitus. In some embodiments, a reduction in BMI to about or below 40, about or below 30, or about or below 20 indicates treatment of type 2 diabetes mellitus.

In some embodiments, the condition, disease, or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture, and cognitive dysfunction Other non-limiting examples of disorders related to diabetes include pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease, or disorder is diabetes and obesity (diabesity). In some embodiments, the compounds described herein are also useful in improving the therapeutic effectiveness of metformin.

Disorders of Metabolically Important Tissues

In some embodiments, the condition, disease, or disorder is a disorder of a metabolically important tissue. Non-limiting examples of metabolically important tissues include liver, fat, pancreas, kidney, and gut.

In some embodiments, the condition, disease, or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolman's disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and may ultimately lead to cirrhosis (Skelly et al., J Hepatol 2001; 35: 195-9; Chitturi et al., Hepatology 2002; 35(2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 Suppl:S186-90). In some embodiments, the patient is a pediatric patient. The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W. B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age. In some embodiments, the patient is an adult patient.

Other non-limiting examples of disorders in metabolically important tissues include joint disorders (e.g., osteoarthritis, secondary osteoarthritis), steatosis (e.g., in the liver); gall stones; gallbladder disorders; gastroesophageal reflux; sleep apnea; hepatitis; fatty liver; bone disorder characterized by altered bone metabolism, such as osteoporosis, including post-menopausal osteoporosis, poor bone strength, osteopenia, Paget's disease, osteolytic metastasis in cancer patients, osteodistrophy in liver disease and the altered bone metabolism caused by renal failure or hemodialysis, bone fracture, bone surgery, aging, pregnancy, protection against bone fractures, and malnutrition polycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction), and geriatric syndrome. In some embodiments, the compounds and pharmaceutical compositions described herein can be used for treating surgical trauma by improving recovery after surgery and/or by preventing the catabolic reaction caused by surgical trauma.

Cardiovascular and Vascular Diseases

In some embodiments, the condition, disease, or disorder is a cardiovascular disease. Non-limiting examples of cardiovascular disease include congestive heart failure, atherosclerosis, arteriosclerosis, coronary heart disease, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

In some embodiments, the condition, disease, or disorder is related to a vascular disease. Non-limiting examples of vascular diseases include peripheral vascular disease, macrovascular complications (e.g., stroke), vascular dysfunction, peripheral artery disease, abdominal aortic aneurysm, carotid artery disease, cerebrovascular disorder (e.g., cerebral infarction), pulmonary embolism, chronic venous insufficiency, critical limb ischemia, retinopathy, nephropathy, and neuropathy.

Neurological Diseases

In some embodiments, the condition, disease, or disorder is a neurological disorder (e.g., neurodegenerative disorder) or a psychiatric disorder. Non-limiting examples of neurological disorders include brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), and chronic wasting syndrome). See, e.g., US2006/0275288A1.

Non-limiting examples of psychiatric disorders include drug dependence/addiction (narcotics and amphetamines and attention deficit/hyperactivity disorder (ADHD). The compounds and pharmaceutical compositions described herein can be useful in improving behavioral response to addictive drugs, decreasing drug dependence, prevention drug abuse relapse, and relieving anxiety caused by the absence of a given addictive substance. See, e.g., US2012/0021979A1.

In some embodiments, the compounds and pharmaceutical compositions described herein are useful in improving learning and memory by enhancing neuronal plasticity and facilitation of cellular differentiation, and also in preserving dopamine neurons and motor function in Morbus Parkinson.

Insulin-Related Conditions and Disorders

In some embodiments, the condition, disease, or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperprolactinemia, hypoglycemia (e.g., nighttime hypoglycemia), and concomitant comatose endpoint associated with insulin.

In some embodiments, the compounds and pharmaceutical compositions described herein can reduce or slow down the progression of borderline type, impaired fasting glucose or impaired fasting glycemia into diabetes.

Autoimmune Disorders

In some embodiments, the condition, disease, or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves' disease.

See, e.g., US20120148586A1.

Stomach and Intestine-Related Disorders

In some embodiments, the condition, disease, or disorder is a stomach or intestine related disorder. Non-limiting examples of these disorders include ulcers of any etiology (e.g., peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, and cachexia caused by acquired immunodeficiency syndrome).

Body Weight

In some embodiments, the compounds and pharmaceutical compositions described herein can be used to reduce body weight (e.g., excess body weight), prevent body weight gain, induce weight loss, decrease body fat, or reduce food intake in a patient (e.g., a patient in need thereof). In some embodiments, the weight increase in a patient may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). In some embodiments, the weight increase may be weight increase before reaching obesity, or may be weight increase in an obese patient. In some embodiments, the weight increase may also be medication-induced weight gain or weight gain subsequent to cessation of smoking.

In some embodiments, the condition, disease, or disorder is an eating disorder, such as hyperphagia, binge eating, bulimia, or compulsive eating.

Inflammatory Diseases

In some embodiments, the condition, disease, or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like C-reactive protein in the blood).

Cancer

In some embodiments, the condition, disease, or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Hypothalamic-Pituitary Disorders

In some embodiments, the condition, disease, or disorder is related to the hypothalamic-pituitary-gonadal axis. For example, the condition, disease, or disorder is related to the hypothalamus-pituitary-ovary axis. In another example, the condition, disease, or disorder is related to the hypothalamus-pituitary-testis axis. Hypothalamic-pituitary-gonadal axis diseases include, but are not limited to, hypogonadism, polycystic ovary syndrome, hypothyroidism, hypopituitarism, sexual dysfunction, and Cushing's disease.

In some embodiments, the condition, disease, or disorder associated with diabetes is related to the hypothalamic-pituitary-gonadal axis.

Pulmonary Disease

In some embodiments, the condition, disease, or disorder is related to a pulmonary disease. Pulmonary diseases include, but are not limited to, asthma, idiopathic pulmonary fibrosis, pulmonary hypertension, obstructive sleep apnoea-hypopnoea syndrome, and chronic obstructive pulmonary disease (COPD) (e.g., emphysema, chronic bronchitis, and refractory (non-reversible) asthma).

In some embodiments, the condition, disease, or disorder associated with diabetes is a pulmonary disease.

Combination Therapy

In some embodiments, this disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., dietary monitoring, diet therapy for diabetes), an exercise therapy (e.g., physical activity), blood sugar monitoring, gastric electrical stimulation (e.g., TANTALUS®), and diet modifications.

In some embodiments, the compounds of Formula I, or a pharmaceutically acceptable salt, isotopically enriched analog, stereoisomer, mixture of stereoisomers, or prodrug thereof as described herein can be administered in combination with one or more additional therapeutic agents.

Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, therapeutic agents for NASH, therapeutic agents for dysuria and anti-emetic agents.

In some embodiments, the one or more additional therapeutic agents include those useful, for example, as anti-obesity agents. Non-limiting examples include monoamine uptake inhibitors (e.g., tramadol, phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), including GABA receptor agonists (e.g., gabapentin, pregabalin), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017, BVT-3498, INCB-13739), pancreatic lipase inhibitors (e.g., orlistat, cetilistat), 03 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), sodium-glucose cotransporter 2 (SGLT-2) inhibitors (e.g., JNJ-28431754, dapagliflozin, AVE2268, TS-033, YM543, TA-7284, ASP1941, remogliflozin), NFK inhibitors (e.g., HE-3286), PPAR agonists (e.g., GFT-505, DRF-11605, gemfibrozil and fenofibrate), phosphotyrosine phosphatase inhibitors (e.g., sodium vanadate, trodusquemin), GPR119 agonists (e.g., PSN-821, MBX-2982, APD597), glucokinase activators (e.g., piragliatin, AZD-1656, AZD6370, TTP-355, compounds described in W0006/112549, W0007/028135, W0008/047821, W0008/050821, W0008/136428 and W0008/156757), leptin, leptin derivatives (e.g., metreleptin), leptin resistance improving drugs, CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin (OXM) preparations, appetite suppressants (e.g., ephedrine), FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57), human proislet peptide (HIP), farnesoid X receptor (FXR) agonist, phentermine, zonisamide, norepinephrine/dopamine reuptake inhibitor, GDF-15 analog, methionine aminopeptidase 2 (MetAP2) inhibitor, diethylpropion, phendimetrazine, benzphetamine, fibroblast growth factor receptor (FGFR) modulator, and AMP-activated protein kinase (AMPK) activator.

In some embodiments, the one or more additional therapeutic agents include those useful, for example, as anti-diabetic agents. Non-limiting examples include insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin), insulin sensitizers (e.g., pioglitazone or a salt thereof), biguanides (e.g., metformin, buformin or a salt thereof (e.g., hydrochloride, fumarate, succinate)), glucagon analogs (e.g., any of glucagon analogs described, e.g., in WO 2010/011439), agents which antagonize the actions of or reduce secretion of glucagon, sulfonylurea agents (e.g., chlorpropamide, tolazamide, gliclazide, glimepiride, tolbutamide, glibenclamide, gliclazide, acetohexamide, glyclopyramide, glybuzole, glyburide), thiazolidinedione agents (e.g., rosiglitazone or pioglitazone), α-glucosidase inhibitors (e.g., voglibose, acarbose, miglitol, emiglitate), insulin secretagogues, such as prandial glucose regulators (sometimes called "short-acting secretagogues"), e.g., meglitinides (e.g., repaglinide and nateglinide), cholinesterase inhibitors (e.g., donepezil, galantamine, rivastigmine, tacrine), NMDA receptor antagonists, dual GLP-1/GIP receptor agonists (e.g., LBT-2000, ZPD1-70), GLP-1R agonists (e.g., exenatide, liraglutide, albiglutide, dulaglutide, abiglutide, taspoglutide, lixisenatide, semaglutide, AVE-0010, S4P and Boc5), and dipeptidyl peptidase IV (DPP-4) inhibitors (e.g., vildagliptin, dutogliptin, gemigliptin, alogliptin, saxagliptin, sitagliptin, linagliptin, berberine, adogliptin, BI1356, GRC8200, MP-513, PF-00734200, PHX1149, SK-0403, ALS2-0426, TA-6666, TS-021, KRP-104, trelagliptin).

In some embodiments, the one or more additional therapeutic agents include those useful, for example, for treating NAFL and NASH. Non-limiting examples include FXR agonists, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21), a niacin analogue, a leukotriene D4 (LTD4) receptor antagonist, an acetyl-CoA carboxylase (ACC) inhibitor, a ketohexokinase (KHK) inhibitor, an apoptosis signal-regulating kinase 1 (ASK1) inhibitor, an ileal bile acid transporter (IBAT) inhibitor, glycyrrhizin, Schisandra extract, ascorbic acid, glutathione, silymarin, lipoic acid, and d-alpha-tocopherol, ascorbic acid, glutathione, vitamin B-complex, glitazones/thiazolidinediones (e.g., troglitazone, rosiglitazone, pioglitazone), metformin, cysteamine, sulfonylureas, alpha-glucosidase inhibitors, meglitinides, vitamin E, tetrahydrolipstatin, milk thistle protein, anti-virals, and antioxidants.

In some embodiments, the one or more additional therapeutic agents include those useful, for example, for treating diabetic complications. Non-limiting examples include aldose reductase inhibitors (e.g., tolrestat, epalrestat, zopolrestat, fidarestat, CT-112, ranirestat, lidorestat), neurotrophic factor and increasing agents thereof (e.g., NGF, NT-3, BDNF, neurotrophic production/secretion promoting agents described in WO01/14372 (e.g., 4-(4-chlorophenyl)-2-(2-methyl-1-imidazolyl)-5-[3-(2-methylphenoxy)propyl]oxazole), compounds described in WO2004/039365), PKC inhibitors (e.g., ruboxistaurin mesylate), AGE inhibitors (e.g., ALT946, N-phenacylthiazolium bromide (ALT766), EXO-226, pyridorin, pyridoxamine), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

In some embodiments, the one or more additional therapeutic agents include those useful, for example, for treating hyperlipidemia. Non-limiting examples include HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), nicotinic acid drugs (e.g., nicomol, niceritrol, niaspan), phytosterols (e.g., soysterol, gamma oryzanol (γ-oryzanol)), cholesterol absorption inhibitors (e.g., zechia), CETP inhibitors (e.g., dalcetrapib, anacetrapib) and ω-3 fatty acid preparations (e.g., ω-3-fatty acid ethyl esters 90).

In some embodiments, the one or more additional therapeutic agents include those useful, for example, as antihypertensive agents. Non-limiting examples include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine) and β-blockers (e.g., metoprolol, atenolol, propranolol, carvedilol, pindolol).

In some embodiments, the one or more additional therapeutic agents include those useful, for example, as diuretics. Non-limiting examples include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide), antialdosterone preparations (e.g., spironolactone, triamterene), carbonic anhydrase inhibitors (e.g., acetazolamide) and chlorobenzenesulfonamide agents (e.g., chlortalidone, mefruside, indapamide).

In some embodiments, the one or more additional therapeutic agents include those useful, for example, as immunotherapeutic agents. Non-limiting examples include microbial or bacterial compounds (e.g., muramyl dipeptide derivative, picibanil), polysaccharides having immunoenhancing activity (e.g., lentinan, sizofiran, krestin), cytokines obtained by genetic engineering approaches (e.g., interferon, interleukin (IL) such as IL-1, IL-2, IL-12), and colony-stimulating factors (e.g., granulocyte colony-stimulating factor, erythropoietin).

In some embodiments, the one or more additional therapeutic agents include those useful, for example, as antithrombotic agents. Non-limiting examples include heparins (e.g., heparin sodium, heparin calcium, enoxaparin sodium, dalteparin sodium) warfarin (e.g., warfarin potassium); antithrombin drugs (e.g., aragatroban, dabigatran) FXa inhibitors (e.g., rivaroxaban, apixaban, edoxaban, betrixaban, YM150, compounds described in WO02/06234, WO2004/048363, WO2005/030740, WO2005/058823, and WO2005/113504) thrombolytic agents (e.g., urokinase, tisokinase, alteplase, nateplase, monteplase, pamiteplase), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

In some embodiments, the one or more additional therapeutic agents include those useful, for example, for treating osteoporosis. Non-limiting examples include alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin B1 and vitamin B12. Suitable examples of erectile dysfunction drugs include apomorphine and sildenafil citrate. Suitable examples of therapeutic agents for urinary frequency or urinary incontinence include flavorxate hydrochloride, oxybutynin hydrochloride and propiverine hydrochloride. Suitable examples of therapeutic agents for dysuria include acetylcholine esterase inhibitors (e.g., distigmine). Suitable examples of anti-inflammatory agents include nonsteroidal anti-inflammatory drugs such as aspirin, acetaminophen, indomethacin.

Other exemplary additional therapeutic agents include agents that modulate hepatic glucose balance (e.g., fructose 1,6-bisphosphatase inhibitors, glycogen phosphorylase inhibitors, glycogen synthase kinase inhibitors, glucokinase activators), agents designed to treat the complications of prolonged hyperglycemia, such as aldose reductase inhibitors (e.g., epalrestat and ranirestat), agents used to treat complications related to micro-angiopathies, anti-dyslipidemia agents, such as HMG-CoA reductase inhibitors (statins, e.g., rosuvastatin), cholesterol-lowering agents, bile acid sequestrants (e.g., cholestyramine), cholesterol absorption inhibitors (e.g., plant sterols such as phytosterols), cholesteryl ester transfer protein (CETP) inhibitors, inhibitors of the ileal bile acid transport system (IBAT inhibitors), bile acid binding resins, nicotinic acid (niacin) and analogues thereof, anti-oxidants (e.g., probucol), omega-3 fatty acids, antihypertensive agents, including adrenergic receptor antagonists, such as beta blockers (e.g., atenolol), alpha blockers (e.g., doxazosin), and mixed alpha/beta blockers (e.g., labetalol), adrenergic receptor agonists, including alpha-2 agonists (e.g., clonidine), angiotensin converting enzyme (ACE) inhibitors (e.g., lisinopril), calcium channel blockers, such as dihydropyridines (e.g., nifedipine), phenylalkylamines (e.g., verapamil), and benzothiazepines (e.g., diltiazem), angiotensin II receptor antagonists (e.g., candesartan), aldosterone receptor antagonists (e.g., eplerenone), centrally acting adrenergic drugs, such as central alpha agonists (e.g., clonidine), diuretic agents (e.g., furosemide), haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g., argatroban), antiplatelet agents (e.g., cyclooxygenase inhibitors (e.g., aspirin)), adenosine diphosphate (ADP) receptor inhibitors (e.g., clopidogrel), phosphodiesterase inhibitors (e.g., cilostazol), glycoprotein IIB/IIA inhibitors (e.g., tirofiban), adenosine reuptake inhibitors (e.g., dipyridamole), noradrenergic agents (e.g., phentermine), serotonergic agents (e.g., sibutramine), diacyl glycerolacyltransferase (DGAT) inhibitors, feeding behavior modifying agents, pyruvate dehydrogenase kinase (PDK) modulators, serotonin receptor modulators, monoamine transmission-modulating agents, such as selective serotonin reuptake inhibitors (SSRI) (e.g., fluoxetine), noradrenaline reuptake inhibitors (NARI), noradrenaline-serotonin reuptake inhibitors (SNRI), and monoamine oxidase inhibitors (MAOI) (e.g., toloxatone and amiflamine), compounds described in W0007/013694, WO2007/018314, WO2008/093639 and WO2008/099794, GPR40 agonists (e.g., fasiglifam or a hydrate thereof, compounds described in WO2004/041266, WO2004/106276, WO2005/063729, WO2005/063725, WO2005/087710, WO2005/095338, WO2007/013689 and WO2008/001931), SGLT1 inhibitors, adiponectin or agonist thereof, IKK inhibitors (e.g., AS-2868), somatostatin receptor agonists, ACC2 inhibitors, cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-α, LIF, IL-6, and oncostatin M, metabolism-modifying proteins or peptides such as glucokinase (GK), glucokinase regulatory protein (GKRP), uncoupling proteins 2 and 3 (UCP2 and UCP3), peroxisome proliferator-activated receptor a (PPARa), MC4r agonists, insulin receptor agonist, PDE 5 inhibitors, glycation inhibitors (e.g., ALT-711), nerve regeneration-promoting drugs (e.g., Y-128, VX853, prosaptide), antidepressants (e.g., desipramine, amitriptyline, imipramine), antiepileptic drugs (e.g., lamotrigine, trileptal, keppra, zonegran, pregabalin, harkoseride, carbamazepine), antiarrhythmic drugs (e.g., mexiletine), acetylcholine receptor ligands (e.g., ABT-594), endothelin receptor antagonists (e.g., ABT-627), narcotic analgesics (e.g., morphine), a2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine), cytotoxic antibodies (e.g., T-cell receptor and IL-2 receptor-specific antibodies), B cell depleting therapies (e.g., anti-CD20 antibody (e.g., rituxan), i-BLyS antibody), drugs affecting T cell migration (e.g., anti-integrin alpha 4/beta 1 antibody (e.g., tysabri), drugs that act on immunophilins (e.g., cyclosporine, tacrolimus, sirolimus, rapamicin), interferons (e.g., IFN-β), immunomodulators (e.g., glatiramer), TNF-binding proteins (e.g., circulating receptors), immunosupressants (e.g., mycophenolate), and metaglidasen, AMG-131, balaglitazone, MBX-2044, rivoglitazone, aleglitazar, chiglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide, piroxicam, NO donating agents (e.g., organonitrates), and NO promoting agents (e.g., phosphodiesterase inhibitors).

In some embodiments, the one or more additional therapeutic agents include those useful, for example, as anti-emetic agents. As used herein, an "anti-emetic" agent refers to any agent that counteracts (e.g., reduces or removes) nausea or emesis (vomiting). It is to be understood that when referring to a therapeutically effective amount of an anti-emetic agent, the amount administered is an amount needed to counteract (e.g., reduce or remove) nausea or emesis (vomiting). While not wishing to be bound by theory, it is believed that administering one or more anti-emetic agents in combination with the formula (I) compounds described herein may allow higher dosages of the formula (I) compounds to be administered, e.g., because the patient may be able to have a normal food intake and thereby respond faster to the treatment.

Non-limiting examples of anti-emetic agents include 5HT3-receptor antagonists (serotonin receptor antagonists), neuroleptics/anti-psychotics, antihistamines, anticholinergic agents, steroids (e.g., corticosteroids), NK1-receptor antagonists (e.g., Neurokinin 1 substance P receptor antagonists), antidopaminergic agents/dopamine receptor antagonists, benzodiazepines, cannabinoids.

For example, the antiemetic agent can be selected from the group consisting of; neuroleptics, antihistamines, anticholinergic agents, steroids, 5HT-3-receptor antagonists, NK1-receptor antagonists, anti-dopaminergic agents/dopamine receptor antagonists, benzodiazepines and non-psychoactive cannabinoids.

In some embodiments, the anti-emetic agent is a 5HT3-receptor antagonist (serotonin receptor antagonist). Non-limiting examples of 5HT3-receptor antagonists (serotonin receptor antagonists) include: Granisetron (Kytril), Dolasetron, Ondansetron (Zofran), Tropisetron, Ramosetron, Palonosetron, Alosetron, azasetron, Bemesetron, Zatisetron, Batanopirde, MDL-73147EF; Metoclopramide, N-3389 (endo-3,9-dimethyl-3,9-diazabicyclo[3,3,1]non-7-yl-1 H-indazole-3-carboxamide dihydrochloride), Y-25130 hydrochloride, MDL 72222, Tropanyl-3,5-dimethylbenzoate, 3-(4-Allylpiperazin-1-yl)-2-quinoxalinecarbonitrile maleate, Zacopride hydrochloride, and Mirtazepine.

Other non-limiting examples of 5HT3-receptor antagonists (serotonin receptor antagonists) include: cilansetron, clozapine, cyproheptadine, dazopride, hydroxyzine, lerisetron, metoclopramide, mianserin, olanzapine, palonosetron (+netupitant), quetiapine, qamosetron, ramosteron, ricasetron, risperidone, ziprasidone, and zatosetron.

In certain embodiments, the 5HT-3-receptor antagonist is Granisetron, Dolasetron, Ondansetron hydrochloride, Tropisetron, Ramosetron, Palonosetron, Alosetron, Bemesetron, Zatisetron, Batanopirde, MDL-73147EF, Metoclopramide, N-3389, Y-25130 hydrochloride, MDL 72222, Tropanyl-3,5-dimethylbenzoate 3-(4-AIIyI-piperazin-1-yl)-2-quinoxalinecarbonitrile maleate, Zacopride hydrochloride and Mirtazepine.

In certain embodiments, the 5HT-3-receptor antagonist is Granisetron, Dolasetron, Ondansetron hydrochloride, Tropisetron, Ramosetron, Palonosetron, Alosetron, Bemesetron, and Zatisetron.

In certain embodiments, the 5HT-3-receptor antagonist is Granisetron, Dolasetron and Ondansetron.

In certain embodiments, the 5HT-3-receptor antagonist is Granisetron.

In certain embodiments, the 5HT-3-receptor antagonist is Ondansetron.

In some embodiments, the anti-emetic agent is an antihistamine. Non-limiting examples of antihistamines include: piperazine derivatives (e.g., cyclizine, meclizine, and cinnarizine); Promethazine; Dimenhydrinate (Dramamine, Gravol); Diphenhydramine; Hydroxyzine; Buclizine; and Meclizine hydrochloride (Bonine, Antivert), doxylamine, and mirtazapine.

In some embodiments, the anti-emetic agent is an anticholinergic agent (Inhibitors of the acetylcholine receptors). Non-limiting examples of anticholinergic agents include: atropine, Scopolamine, Glycopyrron, Hyoscine, Artane (Trihexy-5 trihexyphenidyl hydrochloride), Cogentin (benztropine mesylate), Akineton (biperiden hydrochloride), Disipal (Norflex orphenadrine citrate), diphenhydramine, hydroxyzine, hyoscyamine, and Kemadrin (procyclidine hydrochloride).

In some embodiments, the anti-emetic agent is a steroid (e.g., a corticosteroid). Non-limiting examples of steroids include: betamethasone, Dexamethasone, Methylprednisolone, Prednisone®, and Trimethobenzamide (Tigan).

In some embodiments, the anti-emetic agent is an NK1-receptor antagonists (e.g., Neurokinin 1 substance P receptor antagonists). Non-limiting examples of NK1-receptor antagonists include: aprepitant, casopitant, ezlopitant, fosaprepitant, maropitant, netupitant, rolapitant, and vestipitant.

Other non-limiting examples of NK1-receptor antagonists include: MPC-4505, GW597599, MPC-4505, GR205171, L-759274, SR 140333, CP-96,345, BIIF 1149, NKP 608C, NKP 608A, CGP 60829, SR 140333 (Nolpitantium besilate/chloride), LY 303870 (Lanepitant), MDL-105172A, MDL-103896, MEN-11149, MEN-11467, DNK 333A, YM-49244, YM-44778, ZM-274773, MEN-10930, S-19752, Neuronorm, YM-35375, DA-5018, MK-869, L-754030, CJ-11974, L-758298, DNK-33A, 6b-1, CJ-11974 j. Benserazide and carbidopa k. TAK-637 [(aR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6,13-dione], PD 154075, ([(2-benzofuran)-CH2O CO]-(R)-alpha-MeTrp-(S)-NHCH(CH$_3$) Ph), FK888, and (D-Pro4, D-Trp7,9,10, Phe11)SP4-11.

In some embodiments, the anti-emetic agent is an anti-dopaminergic agents/dopamine receptor antagonist (e.g., dopamine receptor antagonist, e.g., D2 or D3 antagonists). Non-limiting examples include phenothiazines (e.g., promethazine, chlorpromazine, prochlorperazine, perphenazine, hydroxyzine, thiethylperazine, metopimazine); benzamides (e.g., Metoclopramide, domperidone), butyrophenones (e.g., haloperidol, droperidol); alizapride, bromopride, clebopride, domperidone, itopride, metoclopramide, trimethobenzamide, and amisulpride.

In some embodiments, the anti-emetic agent is a non-psychoactive cannabinoids (e.g., Cannabidiol (CBD), Cannabidiol dimethylheptyl (CBD-DMH), Tetra-hydro-cannabinol (THC), Cannabinoid agonists such as WIN 55-212 (a CBi and CB2 receptor agonist), Dronabinol (Marinol®), and Nabilone (Cesamet)).

Other exemplary anti-emetic agents include: c-9280 (Merck); benzodiazepines (diazepam, midazolam, lorazepam); neuroleptics/anti-psychotics (e.g., dixyrazine, haloperidol, and Prochlorperazine (Compazine®)); cerium oxalate; propofol; sodium citrate; dextrose; fructose (Nauzene); orthophosphoric acid; fructose; glucose (Emetrol); bismuth subsalicylate (Pepto Bismol); ephedrine; vitamin B6; peppermint, lavender, and lemon essential oils; and ginger.

Still other exemplary anti-emetic agents include those disclosed in US 20120101089A1; U.S. Pat. No. 10,071,088 B2; U.S. Pat. No. 6,673,792 B1; U.S. Pat. No. 6,197,329 B1; U.S. Pat. No. 10,828,297 B2; U.S. Pat. No. 10,322,106 B2; U.S. Pat. No. 10,525,033 B2; WO 2009080351 A1; WO 2019203753 A2; WO 2002020001 A2; U.S. Pat. No. 8,119,697 B2; U.S. Pat. No. 5,039,528; US20090305964A1; and WO 2006/111169, each of which is incorporated by reference in its entirety.

In some embodiments, the additional therapeutic agent or regimen is administered to the patient prior to contacting with or administering the compounds and pharmaceutical compositions (e.g., about one hour prior, or about 6 hours prior, or about 12 hours prior, or about 24 hours prior, or about 48 hours prior, or about 1 week prior, or about 1 month prior).

In some embodiments, the additional therapeutic agent or regimen is administered to the patient at about the same time as contacting with or administering the compounds and pharmaceutical compositions. By way of example, the additional therapeutic agent or regimen and the compounds and pharmaceutical compositions are provided to the patient simultaneously in the same dosage form. As another example, the additional therapeutic agent or regimen and the compounds and pharmaceutical compositions are provided to the patient concurrently in separate dosage forms.

Patient Selection

In some embodiments, the methods described herein further include the step of identifying a patient (e.g., a subject) in need of such treatment (e.g., by way of blood assay, body mass index, or other conventional method known in the art).

In some embodiments, the methods described herein further include the step of identifying a patient (e.g., patient) that has a disease, disorder, or condition as provided here (e.g., a GLP-1 associated disease, disorder, or condition).

In some embodiments, the methods described herein further include the step of identifying a patient (e.g., patient) that has type 2 diabetes mellitus. In some embodiments, determining if the patient has type 2 diabetes mellitus includes performing an assay to determine the level of hemoglobin Alc (HbAlc), fasting plasma glucose, non-fasting plasma glucose, or any combination thereof. In some embodiments, the level of HbAlc is about 6.5% to about 24.0%. In some embodiments, the level of HbA1c is greater than or about 6.5%. In some embodiments, the level of HbA1c is greater than or about 8.0%. In some embodiments, the level of HbA1c is greater than or about 10.0%. In some embodiments, the level of HbA1c is greater than or about 12.0%. In some embodiments, the level of HbA1c is greater than or about 14.0%. In some embodiments, the level of HbA1c is greater than or about 16.0%. In some embodiments, the level of HbA1c is greater than or about 18.0%. In some embodiments, the level of HbA1c is greater than or about 20.0%. In some embodiments, the level of HbA1c is greater than or about 22.0%. In some embodiments, the level of HbA1c is greater than or about 24.0%.

In some embodiments, the level of fasting plasma glucose is greater than or about 120 mg/dL to greater than or about 750 mg/dL. In some embodiments, the level of fasting plasma glucose is greater than or about 200 mg/dL to greater than or about 500 mg/dL. In some embodiments, the level of fasting plasma glucose is greater than or about 300 mg/dL to greater than or about 700 mg/dL.

In some embodiments, the level of non-fasting plasma glucose is greater than or about 190 mg/dL to greater than or about 750 mg/dL. In some embodiments, the level of non-fasting plasma glucose is greater than or about 250 mg/dL to greater than or about 450 mg/dL. In some embodiments, the level of non-fasting plasma glucose is greater than or about 400 mg/dL to greater than or about 700 mg/dL.

In some embodiments, determining if the patient has type 2 diabetes mellitus further includes determining the patient's BMI. In some embodiments, the BMI of the patient is greater than or about 22 kg/m2 to greater than or about 100 kg/m2. In some embodiments, the BMI of the patient is greater than or about 30 kg/m2 to greater than or about 90 kg/m2. In some embodiments, the BMI of the patient is greater than or about 40 kg/m2 to greater than or about 80 kg/m2. In some embodiments, the BMI of the patient is greater than or about 50 kg/m2 to greater than or about 70 kg/m2.

In some embodiments, additional factors (e.g., risk factors) used for determining if the patient has type 2 diabetes mellitus further includes age and ethnicity of the patient. In some embodiments, the patient's age is greater than or about 10 years. In some embodiments, the patient's age is greater than or about 15 years. In some embodiments, the patient's age is greater than or about 20 years. In some embodiments, the patient's age is greater than or about 25 years. In some embodiments, the patient's age is greater than or about 30 years. In some embodiments, the patient's age is greater than or about 35 years. In some embodiments, the patient's age is greater than or about 40 years. In some embodiments, the patient's age is greater than or about 42 years. In some embodiments, the patient's age is greater than or about 44 years. In some embodiments, the patient's age is greater than or about 46 years. In some embodiments, the patient's age is greater than or about 48 years. In some embodiments, the patient's age is greater than or about 50 years. In some embodiments, the patient's age is greater than or about 52 years. In some embodiments, the patient's age is greater than or about 54 years. In some embodiments, the patient's age is greater than or about 56 years. In some embodiments, the patient's age is greater than or about 58 years. In some embodiments, the patient's age is greater than or about 60 years. In some embodiments, the patient's age is greater than or about 62 years. In some embodiments, the patient's age is greater than or about 64 years. In some embodiments, the patient's age is greater than or about 66 years. In some embodiments, the patient's age is greater than or about 68 years. In some embodiments, the patient's age is greater than or about 70 years. In some embodiments, the patient's age is greater than or about 72 years. In some embodiments, the patient's age is greater than or about 74 years. In some embodiments, the patient's age is greater than or about 76 years. In some embodiments, the patient's age is greater than or about 78 years. In some embodiments, the patient's age is greater than or about 80 years. In some embodiments, the patient's age is greater than or about 85 years. In some embodiments, the patient's age is greater than or about 90 years. In some embodiments, the patient's age is greater than or about 95 years. In some embodiments, the ethnicity of the patient may be African American, American Indian or Alaska Native, Asian American, Hispanics or Latinos, or Native Hawaiian or Pacific Islander.

General Synthetic Methods

The compounds of this disclosure can be prepared from readily available starting materials using, for example, the following general methods, and procedures. It will be appreciated that where certain process conditions (i.e., reaction temperatures, times, mole ratios of reactants, solvents, pressures, etc.) are given, other process conditions can also be used unless otherwise stated. Optimum reaction conditions may vary with the reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting certain functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance CA USA), EMKA-Chemie Gmbh & Co. K G (Eching Germany), or Millipore Sigma (Burlington MA USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

Scheme I illustrates a general method which can be employed for the synthesis of compounds described herein, where ring A, ring B, ring C, X, Z, $Q^1$, $Q^2$, $Q^3$, $Q^4$, $Q^5$, $L^1$, $L^2$, $R^1$, $R^2$, $R^3$, and $R^{QB}$ are each independently as defined herein, and LG is a leaving group, such as halo (e.g., hydroxy, alkoxy, halo, etc.).

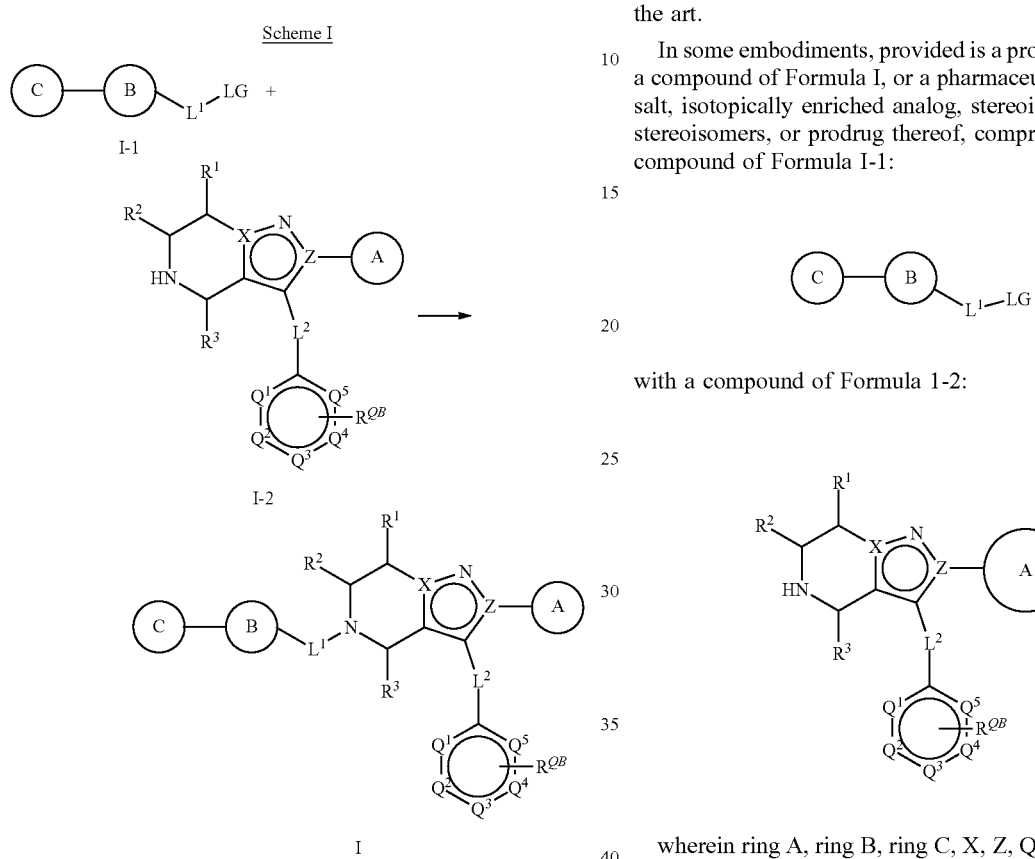

Compounds of Formula I can be provided by coupling compound I-1 with compound I-2 under suitable coupling reaction conditions, such as amide bond forming reaction conditions or nucleophilic substitution reaction conditions reaction conditions. Further derivatization can be performed of the resulting product via methods and chemical transformations which are known to those of skill in the art can provide alternative compounds of Formula I. For example, when the leaving group is an electrophile, such as an aldehyde, the coupling reaction conditions may comprise reductive amination reaction conditions. Thus, the conversion may comprise more than one reaction or set of reactants.

Upon reaction completion, compounds of Formula I can be recovered by conventional techniques such as neutralization, extraction, precipitation, chromatography, filtration and the like. In certain embodiments, when control of stereochemistry is desired, proper control of reaction conditions and selection of substituents for the reagents can at least partially dictate or preserve the formation of the various stereoisomers.

In some embodiments, the various substituents of Formula I-1 or I-2 are as defined herein. However, derivatization thereof prior to reacting in any step, and/or further derivatization of the resulting reaction product, provides various compounds of Formula I. Appropriate starting materials and reagents can be purchased or prepared by methods known to one of skill in the art. Upon each reaction completion, each of the intermediate or final compounds can be recovered, and optionally purified, by conventional techniques such as neutralization, extraction, precipitation, chromatography, filtration, and the like. Other modifications to arrive at compounds of this disclosure are within the skill of the art.

In some embodiments, provided is a process for preparing a compound of Formula I, or a pharmaceutically acceptable salt, isotopically enriched analog, stereoisomer, mixture of stereoisomers, or prodrug thereof, comprising contacting a compound of Formula I-1:

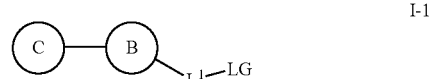

with a compound of Formula 1-2:

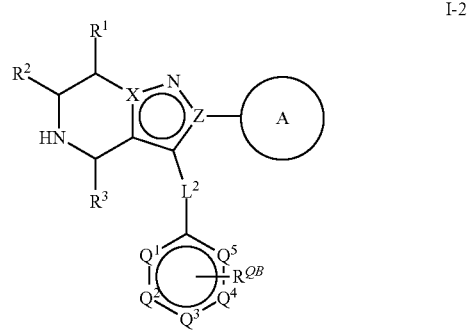

wherein ring A, ring B, ring C, X, Z, $Q^1$, $Q^2$, $Q^3$, $Q^4$, $Q^5$, $L^1$, $L^2$, $R^1$, $R^2$, $R^3$, and $R^{QB}$ are as defined herein, and LG is a leaving group, under conditions sufficient to provide the compound of Formula I, or a pharmaceutically acceptable salt, isotopically enriched analog, stereoisomer, mixture of stereoisomers, or prodrug thereof.

In some embodiments, the process further comprises a hydrolysis or transesterification step prior to or after the contacting. In some embodiments, the process comprises a base. In some embodiments, the process comprises elevated temperature.

EXAMPLES

This disclosure is further understood by reference to the following examples, which are intended to be purely exemplary of the disclosure. The present disclosure is not limited in scope by the exemplified embodiments, which are intended as illustrations of single aspects of the disclosure only.

Any methods that are functionally equivalent are within the scope of the disclosure. Various modifications of the disclosure in addition to those described herein will become apparent to those skilled in the art from the foregoing description and accompanying figures. Such modifications fall within the scope of the appended claims.

Abbreviations (as Used Herein):

| | |
|---|---|
| $CCl_4$ | carbon tetrachloride |
| $CH_2Cl_2$ | dichloromethane |
| $CH_3CN$ | acetonitrile |
| CuI | cuprous iodide |
| DCM or $CH_2Cl_2$ | dichloromethane |
| DIPEA | N,N-Diisopropylethylamine |
| DMF | N,N-dimethyl-formamide |
| EtOAc | ethyl acetate |
| EtOH | ethanol |
| h | hour |
| HATU | 2-(7-Azabenzotriazol-1-yl)-N,N,N',N'-tetramethyluronium hexafluorophosphate |
| HCl | hydrochloric acid |
| $H_2NCO_2NH_4$ | ammonium carbamate |
| $H_2O$ | water |
| $K_2CO_3$ | potassium carbonate |
| LiHMDS | lithium bis(trimethylsilyl)amide |
| MeOH | methanol |
| MeSNa | sodium methanethiolate |
| MeI | iodomethane |
| $NaBH_4$ | sodium borohydride |
| NaH | sodium hydride |
| $Na_2SO_4$ | sodium sulfate |
| NMP | N-Methyl-2-pyrrolidone |
| $PhI(OAc)_2$ | (diacetoxyiodo)benzene |
| PE | Petrol ether |
| prep. HPLC | Preparative High Performance Liquid Chromatography |
| rt | room temperature |
| SFC | Supercritical Fluid Chromatography |
| THF | tetrahydrofuran |
| TEA or $Et_3N$ | triethylamine |
| TFA | trifluoroacetic acid |

General information: All evaporations or concentrations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (100-200 mesh). Solvent systems were reported as mixtures by volume. NMR spectra were recorded on a Bruker 400 or Varian (400 MHz) spectrometer. $^1H$ chemical shifts are reported in δ values in ppm with the deuterated solvent as the internal standard. Data are reported as follows: chemical shift, multiplicity (s=singlet, d=doublet, t=triplet, q=quartet, br=broad, mn=multiplet), coupling constant (Hz), integration. LCMS spectra were obtained on SHIMADZU LC20-MS2020 or Agilent 1260 series 6125B mass spectrometer or Agilent 1200 series, 6110 or 6120 mass spectrometer with electrospray ionization and excepted as otherwise indicated.

Example A1

3-[(1S,2S)-1-(2-{[(4S)-3-[3-(1-azanylidene-1-oxo-2,3-dihydro-1λ$^6$-benzo[b]thiophen-5-yl)-2-oxoimidazol-1-yl]-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 101)

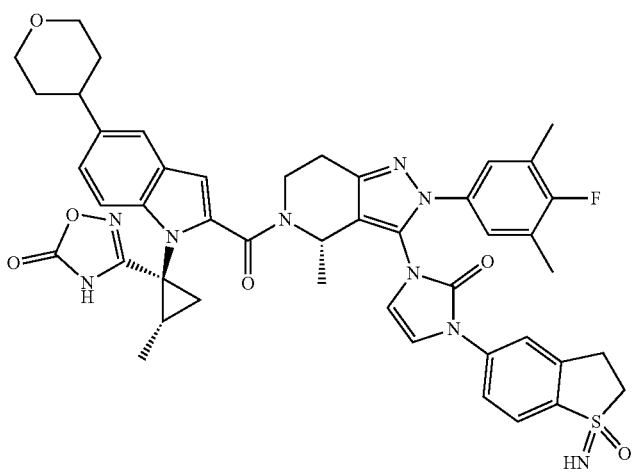

Compound 101

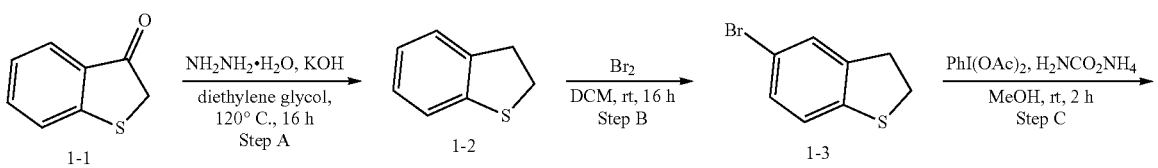

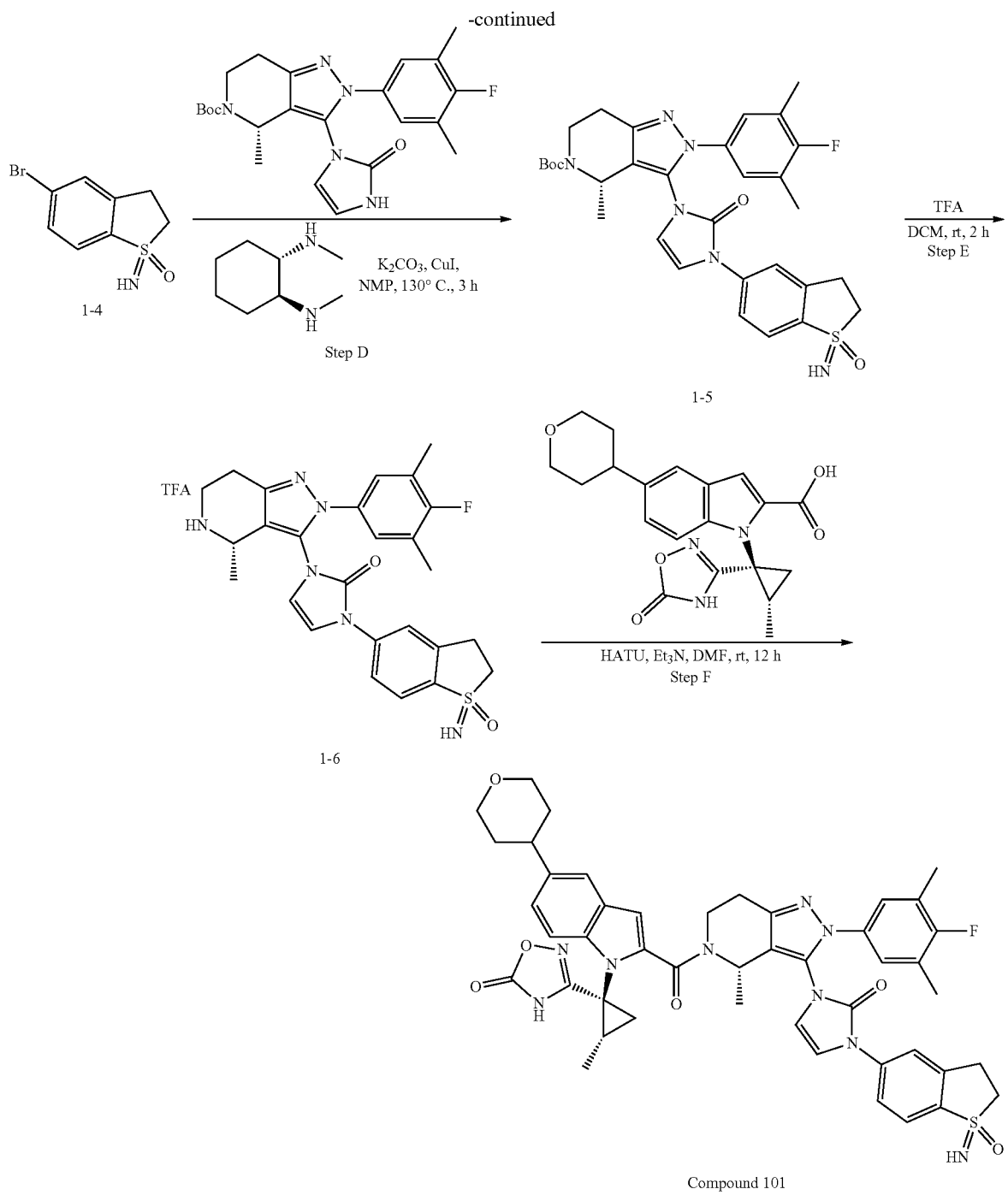

Compound 101

Step A 2,3-dihydrobenzo[b]thiophene

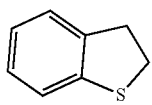

To a solution of 2,3-dihydrobenzo[b]thiophen-3-one (500 mg, 3.329 mmol) in EtOH (8 mL) was added N₂H4 hydrate (2.6 mL). The mixture was heated to reflux and stir for 45 min. The mixture was allowed to cool to rt and then concentrated. The residue was dissolved in diethylene glycol (20 mL) and KOH (560 mg, 9.987 mmol) was added. The resulting mixture was stirred at 120° C. for 16 h. The mixture was cooled to rt, diluted with EtOAc (50 mL) and the pH was adjusted with 1 M aq. HCl to pH<4. The organic layer was separated, washed with brine, dried over Na₂SO₄ and concentrated. The residue was purified by flash silica gel chromatography (Silica Flash Column, Eluent of 0~10% EtOAc/PE gradient) to obtain 2,3-dihydrobenzo[b]thiophene (347 mg, 76.5% yield). ¹H NMR (400 MHz, DMSO-d6) δ 7.26-7.17 (m, 2H), 7.11 (t, J=7.6 Hz, 1H), 7.00 (t, J=7.2 Hz, 1H), 3.38-3.33 (m, 2H), 3.30-3.25 (m, 2H).

Step B 5-bromo-2,3-dihydrobenzothiophene

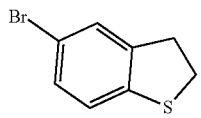

To a solution of 2,3-dihydrobenzothiophene (1350 mg, 9.911 mmol) in DCM (20 mL) was added Br$_2$ (0.463 mL, 8.424 mmol) at 0° C. The mixture was stirred at rt for 16 h. The mixture was diluted with H$_2$O and extracted with DCM (50 mL×2). The combined organic layers were washed with brine, dried over Na$_2$SO$_4$ and concentrated. The residue was purified by flash silica gel chromatography (Silica Flash Column, Eluent of 0~10% EtOAc/PE gradient) to obtain 5-bromo-2,3-dihydrobenzothiophene (650 mg, 30.5% yield). $^1$H NMR (400 MHz, DMSO-d6) δ 7.30 (d, J$_1$=2.0 Hz, 1H), 7.23 (dd, J$_1$=8.4 Hz, J$_2$=2.0 Hz, 1H), 7.08 (d, J=8.0 Hz, 1H), 3.38-3.33 (m, 2H), 3.30-3.25 (m, 2H).

Step C 1-azanylidene-5-bromo-2,3-dihydro-1λ$^6$-benzo[b]thiophen-1-one

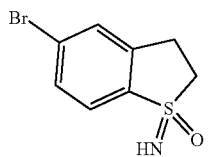 [SMILES: N=S1(=O)CCc2cc(Br)ccc21]

To a solution of 5-bromo-2,3-dihydrobenzo[b]thiophene (650 mg, 3.022 mmol) in MeOH (5 mL) was added PhI(OAc)$_2$ (1.96 g, 6.043 mmol) and H$_2$NCO$_2$NH$_4$ (472 mg, 6.043 mmol). The mixture was stirred at rt for 2 h under N$_2$. Then the reaction mixture was poured into water (100 mL), extracted with DCM (100 mL×2). The combined organic layers were washed with brine, dried over Na$_2$SO$_4$, filtered and concentrated. The residue was purified by flash silica gel chromatography (Silica Flash Column, Eluent of 0~5% MeOH/DCM gradient) to obtain 1-azanylidene-5-bromo-2,3-dihydro-1λ$^6$-benzo[b]thiophen-1-one (450 mg, 60.5% yield). LC-MS: m/z: 246.1 (M+H)$^+$.

Step D tert-butyl(4S)-3-[3-(1-azanylidene-1-oxo-2,3-dihydro-1λ$^6$-benzo[b]thiophen-5-yl)-2-oxoimidazol-1-yl]-2-(4-fluoro-3,5-dimethylphenyl)-4-methyl-4,5,6,7-tetrahydropyrazolo[4,3-c]pyridine-5-carboxylate

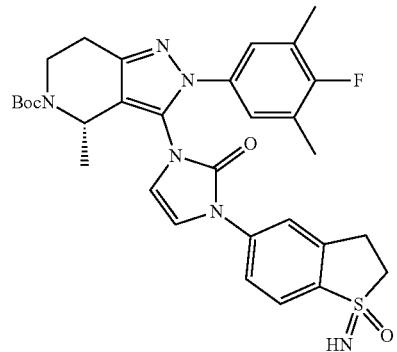 [SMILES: Cc1cc(-n2nc3c(c2-n2ccn(-c4ccc5c(c4)CCS5(=N)=O)c2=O)[C@H](C)N(C(=O)OC(C)(C)C)CC3)cc(C)c1F]

To a solution of 1-azanylidene-5-bromo-2,3-dihydro-1λ$^6$-benzo[b]thiophen-1-one (290 mg, 1.178 mmol) in NMP (5 mL) was added methyl[(1R,2R)-2-(methylamino)cyclohexyl]amine (67 mg, 0.471 mmol), K$_2$CO$_3$ (488 mg, 3.535 mmol), CuI (45 mg, 0.236 mmol) and tert-butyl(4S)-2-(4-fluoro-3,5-dimethylphenyl)-4-methyl-3-(2-oxo-3H-imidazol-1-yl)-4,5,6,7-tetrahydropyrazolo[4,3-c]pyridine-5-carboxylate (520 mg, 1.178 mmol). The reaction mixture was stirred at 130° C. for 5 h under N$_2$. After cooling, the reaction mixture was diluted with EtOAc (50 mL) and water (25 mL). The organic layer was separated, washed with brine, dried with Na$_2$SO$_4$ and concentrated. The residue was purified by flash silica gel chromatography (Silica Flash Column, Eluent of 0~5% MeOH/DCM gradient) to obtain tert-butyl(4S)-3-[3-(1-azanylidene-1-oxo-2,3-dihydro-1λ$^6$-benzo[b]thiophen-5-yl)-2-oxoimidazol-1-yl]-2-(4-fluoro-3,5-dimethylphenyl)-4-methyl-4,5,6,7-tetrahydropyrazolo[4,3-c]pyridine-5-carboxylate (462 mg, 64.6% yield). LC-MS: m/z 607.4 (M+H)$^+$.

Step E 3-(1-azanylidene-1-oxo-2,3-dihydro-1'6-benzo[b]thiophen-5-yl)-1-[(4S)-2-(4-fluoro-3,5-dimethylphenyl)-4-methyl-4,5,6,7-tetrahydropyrazolo[4,3-c]pyridin-3-yl]-2,3-dihydro-1H-imidazol-2-one TFA salt

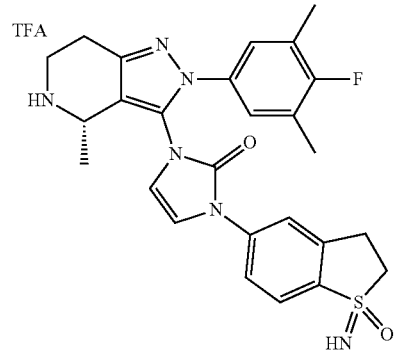 [SMILES: Cc1cc(-n2nc3c(c2-n2ccn(-c4ccc5c(c4)CCS5(=N)=O)c2=O)[C@H](C)NCC3)cc(C)c1F]

To a solution of tert-butyl(4S)-3-[3-(1-azanylidene-1-oxo-2,3-dihydro-1λ⁶-benzo[b]thiophen-5-yl)-2-oxoimidazol-1-yl]-2-(4-fluoro-3,5-dimethylphenyl)-4-methyl-4,5,6,7-tetrahydropyrazolo[4,3-c]pyridine-5-carboxylate (528 mg, 0.870 mmol) in DCM (5 mL) was added TFA (3.3 mL). The reaction mixture was stirred at rt for 2 h under N₂. The reaction mixture was concentrated to obtain 3-(1-azanylidene-1-oxo-2,3-dihydro-1λ⁶-benzo[b]thiophen-5-yl)-1-[(4S)-2-(4-fluoro-3,5-dimethylphenyl)-4-methyl-4,5,6,7-tetrahydropyrazolo[4,3-c]pyridin-3-yl]-2,3-dihydro-1H-imidazol-2-one TFA salt (265 mg, 49.0% yield). LC-MS: m/z 507.3 (M+H)⁺.

Step F 3-[(1S,2S)-1-(2-{[(4S)-3-[3-(1-azanylidene-1-oxo-2,3-dihydro-1λ⁶-benzo[b]thiophen-5-yl)-2-oxoimidazol-1-yl]-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 101)

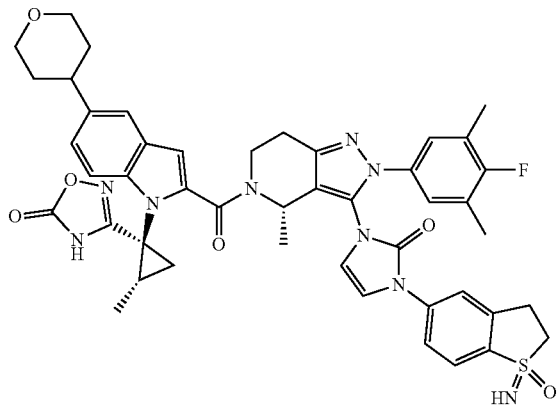 [SMILES: Cc1cc(-n2nc3c(c2-n2ccn(-c4ccc5c(c4)CCS5(=N)=O)c2=O)[C@H](C)N(C(=O)c2cc4cc(C5CCOCC5)ccc4n2[C@@]2(c4noc(=O)[nH]4)C[C@@H]2C)CC3)cc(C)c1F]

To a solution of 3-(1-azanylidene-1-oxo-2,3-dihydro-1λ⁶-benzo[b]thiophen-5-yl)-1-[(4S)-2-(4-fluoro-3,5-dimethylphenyl)-4-methyl-4,5,6,7-tetrahydropyrazolo[4,3-c]pyridin-3-yl]-2,3-dihydro-1H-imidazol-2-one TFA salt (100 mg, 0.197 mmol) in DMF (5 mL) was added 1-[(1S,2S)-2-methyl-1-(5-oxo-4H-1,2,4-oxadiazol-3-yl)cyclopropyl]-5-(3,4,5,6-tetrahydro-2H-pyran-4-yl)indole-2-carboxylic acid (75.7 mg, 0.197 mmol), TEA (0.082 mL, 0.592 mmol) and HATU (112.6 mg, 0.296 mmol). The reaction mixture was stirred at rt for 12 h under N₂. The mixture was filtered and the residue was purified by prep. HPLC (Column: Sunfire C1819*250 mm*10 μm; Mobile Phase A: Water (0.1% formic acid), B: CH₃CN; Flow rate: 20 mL/min; Gradient: 58% B to 68% B; Retention Time: 8.7 min) to obtain 3-[(1S,2S)-1-(2-{[(4S)-3-[3-(1-azanylidene-1-oxo-2,3-dihydro-1λ⁶-benzo [b]thiophen-5-yl)-2-oxoimidazol-1-yl]-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (4.89 mg, 2.84% yield). LC-MS: m/z 872.4 (M+H)⁺. ¹H NMR (400 MHz, DMSO-d6) δ 7.74-7.65 (m, 3H), 7.52 (s, 1H), 7.50-7.42 (m, 1H), 7.28-7.25 (m, 2H), 7.14 (d, J=6.0 Hz, 2H), 6.91-6.81 (m, 2H), 5.69-5.44 (m, 1H), 4.55-4.27 (m, 1H), 3.99-3.94 (m, 2H), 3.50-3.47 (m, 4H), 3.32-3.28 (m, 2H), 2.92-2.86 (m, 5H), 2.22 (s, 6H), 1.76-1.70 (m, 7H), 1.43 (s, 3H), 1.18 (s, 3H).

Example A2

3-[(1S,2S)-1-(2-{[(4S)-3-(3-{6-[azanylidene(methyl)(oxo)-λ⁶-sulfanyl]pyridin-3-yl}-2-oxoimidazol-1-yl)-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 102)

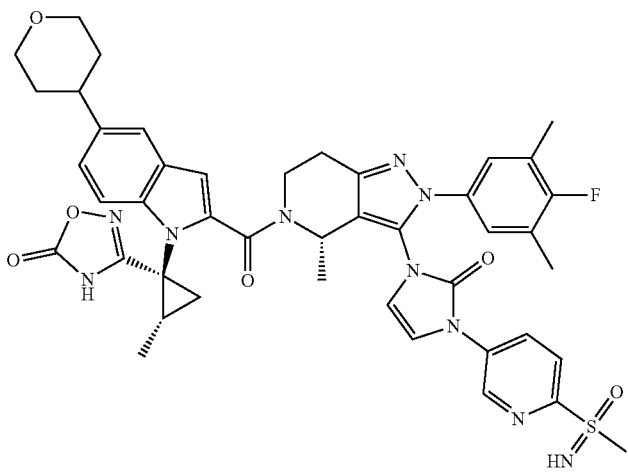

Compound 102

-continued
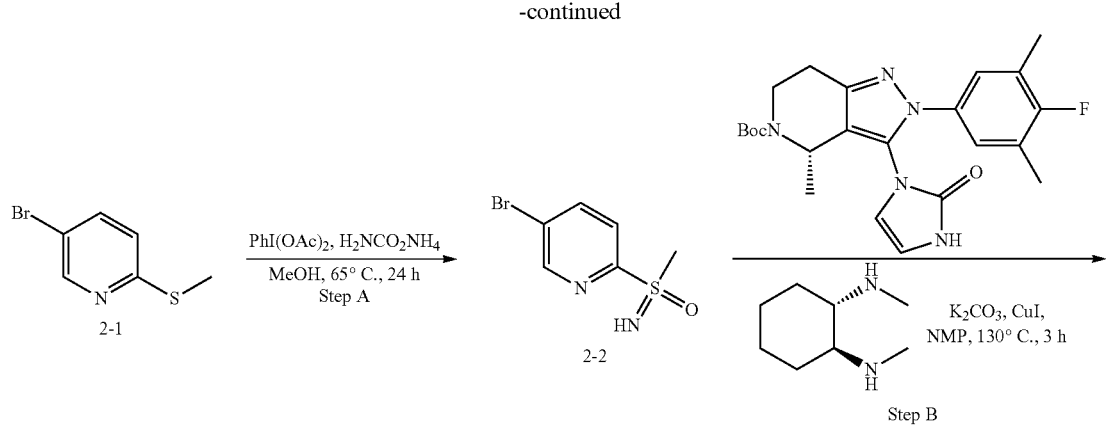
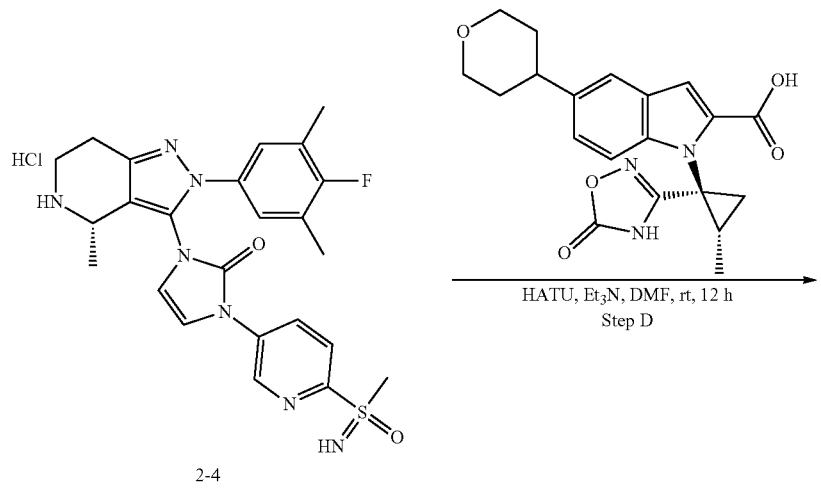

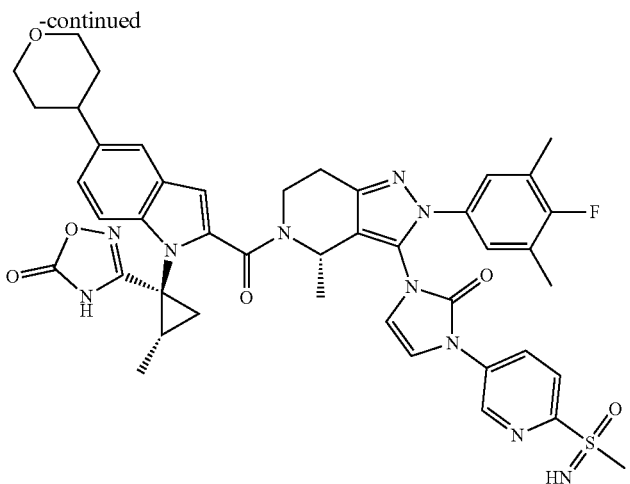

Compound 102

Step A (5-bromopyridin-2-yl)(imino)(methyl)-sulfanone

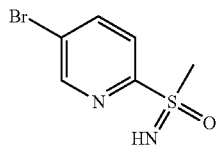

To a solution of 5-bromo-2-(methylthio)pyridine (1000 mg, 4.900 mmol) in MeOH (20 mL) was added PhI(OAc)₂ (3.96 g, 12.249 mmol) and H₂NCO₂NH₄ (765 mg, 9.800 mmol). The reaction mixture was stirred at 65° C. for 24 h. After cooling, the reaction mixture was concentrated. The residue was purified by flash silica gel chromatography (Silica Flash Column, Eluent of 0~50% EtOAc/PE gradient) to give (5-bromopyridin-2-yl)(imino)(methyl)-sulfanone (723 mg, 62.8% yield). LC-MS: m/z 235.0 (M+H)⁺.

Step B tert-butyl(4S)-2-(4-fluoro-3,5-dimethylphenyl)-4-methyl-3-(3-(6-(S-methylsulfonimidoyl)pyridin-3-yl)-2-oxo-2,3-dihydro-1H-imidazol-1-yl)-2,4,6,7-tetrahydro-5H-pyrazolo[4,3-c]pyridine-5-carboxylate

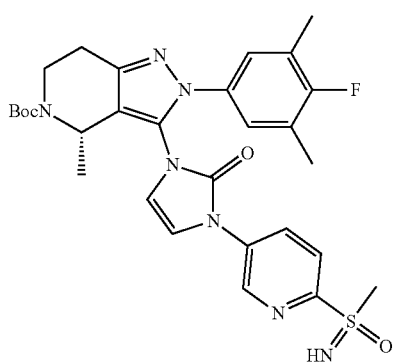 [SMILES: Cc1cc(-n2nc3c(c2-n2ccn(-c4ccc(S(C)(=N)=O)nc4)c2=O)[C@H](C)N(C(=O)OC(C)(C)C)CC3)cc(C)c1F]

To a solution of (5-bromopyridin-2-yl)(imino)(methyl)-sulfanone (80 mg, 0.340 mmol) in NMP (5 mL) was added tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (150 mg, 0.340 mmol), (1S,2S)-N1,N2-dimethylcyclohexane-1,2-diamine (19 mg, 0.136 mmol), and K₂CO₃ (141 mg, 1.021 mmol), CuI (13 mg, 0.068 mmol). The reaction mixture was stirred at 130° C. for 3 h. After cooling and concentration, the residue was purified by flash silica gel chromatography (Silica Flash Column, Eluent of 0~25% EtOAc/PE gradient) to give tert-butyl(4S)-2-(4-fluoro-3,5-dimethylphenyl)-4-methyl-3-(3-(6-(S-methylsulfonimidoyl)pyridin-3-yl)-2-oxo-2,3-dihydro-1H-imidazol-1-yl)-2,4,6,7-tetrahydro-5H-pyrazolo[4,3-c]pyridine-5-carboxylate (150 mg, 74.0% yield). LC-MS: m/z 596.3 (M+H)⁺.

Step C 1-((S)-2-(4-fluoro-3,5-dimethylphenyl)-4-methyl-4,5,6,7-tetrahydro-2H-pyrazolo[4,3-c]pyridin-3-yl)-3-(6-(S-methylsulfonimidoyl)pyridin-3-yl)-1,3-dihydro-2H-imidazol-2-one HCl salt

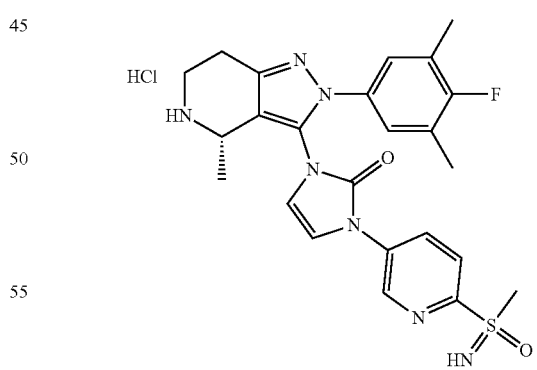

To a solution of tert-butyl(4S)-2-(4-fluoro-3,5-dimethylphenyl)-4-methyl-3-(3-(6-(S-methylsulfonimidoyl)pyridin-3-yl)-2-oxo-2,3-dihydro-1H-imidazol-1-yl)-2,4,6,7-tetrahydro-5H-pyrazolo[4,3-c]pyridine-5-carboxylate (55 mg, 0.092 mmol) in DCM (10 mL) was added 4 M HCl (gas) in 1,4-dioxane (0.23 mL) at 0° C. The reaction mixture was stirred at room temperature for 2 h. Then the reaction mixture was concentrated to give the crude 1-((S)-2-(4- fluoro-3,5-dimethylphenyl)-4-methyl-4,5,6,7-tetrahydro-2H-pyrazolo[4,3-c]pyridin-3-yl)-3-(6-(S-methylsulfonimidoyl)pyridin-3-yl)-1,3-dihydro-2H-imidazol-2-one HCl salt (45 mg, 98.4% yield). LC-MS: m/z 496.3 (M+H)$^+$.

Step D 3-[(1S,2S)-1-(2-{[(4S)-3-(3-{6-[azanylidene(methyl)(oxo)-$\lambda^6$-sulfanyl]pyridin-3-yl}-2-oxoimidazol-1-yl)-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 102)

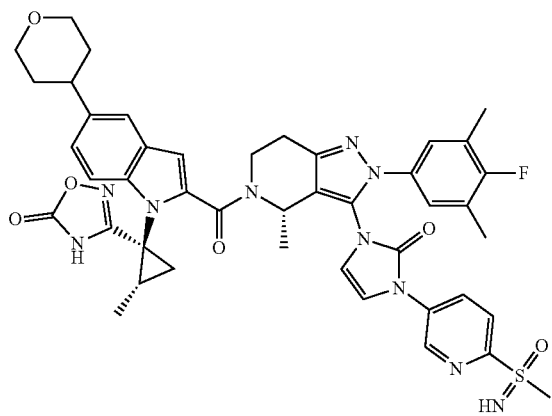 [SMILES: Cc1cc(-n2nc3c(c2-n2ccn(-c4ccc(S(C)(=N)=O)nc4)c2=O)[C@H](C)N(C(=O)c2cc4cc(C5CCOCC5)ccc4n2[C@@]2(c4noc(=O)[nH]4)C[C@@H]2C)CC3)cc(C)c1F]

To a solution of 1-((S)-2-(4-fluoro-3,5-dimethylphenyl)-4-methyl-4,5,6,7-tetrahydro-2H-pyrazolo[4,3-c]pyridin-3-yl)-3-(6-(S-methylsulfonimidoyl)pyridin-3-yl)-1,3-dihydro-2H-imidazol-2-one HCl salt (45 mg, 0.091 mmol) in DMF (2 mL) was added Et$_3$N (0.025 mL, 0.182 mmol), 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (34.8 mg, 0.091 mmol), HATU (51.8 mg, 0.136 mmol). The reaction mixture was stirred at room temperature for 12 h. The mixture was filtered and the residue was purified by prep. HPLC (Column: XBridge C18 19*250 mm*10 μm; Mobile Phase A: Water (10 mM NH$_4$ICO$_3$), B: CH$_3$CN; Flow rate: 20 mL/min; Gradient: 32% B to 42% B; Retention Time: 8.25-9.2 min) to obtain 3-[(1S,2S)-1-(2-{[(4S)-3-(3-{6-[azanylidene(methyl)(oxo)-$\lambda^6$-sulfanyl]pyridin-3-yl}-2-oxoimidazol-1-yl)-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (12.6 mg, 16.1% yield). LC-MS: m/z 861.5 (M+H)$^+$. $^1$H NMR (400 MHz, DMSO-d6) δ 11.70 (s, 1H), 9.08 (s, 1H), 8.45 (d, J=8.4 Hz, 1H), 8.19 (d, J=8.8 Hz, 1H), 7.54 (d, J=8.4 Hz, 2H), 7.40 (d, J=9.2 Hz, 1H), 7.26-7.23 (m, 1H), 7.17-7.13 (m, 3H), 6.94 (s, 1H), 5.60 (s, 1H), 4.46-4.34 (m, 2H), 3.98-3.95 (m, 2H), 3.51-3.44 (m, 2H), 3.24 (s, 3H), 2.94-2.81 (m, 3H), 2.21 (s, 6H), 1.72-1-60 (m, 7H), 1.40-1.38 (m, 2H), 1.32-1.24 (m, 2H), 1.14-1.13 (m, 2H).

Example A3

3-[(1S,2S)-1-(2-{[(4S)-3-(3-{4-[azanylidene(methyl)(oxo)-$\lambda^6$-sulfanyl]phenyl}-2-oxotetrahydro-1H-imidazol-1-yl)-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 103)

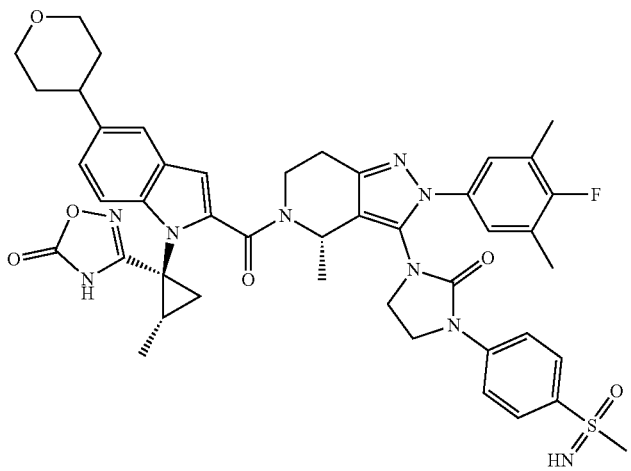

Compound 103

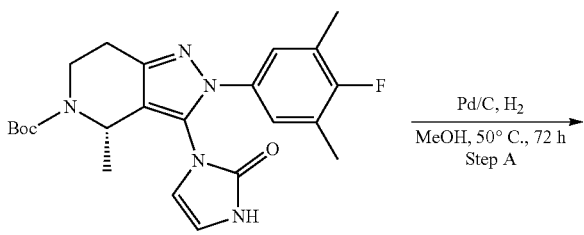

3-1

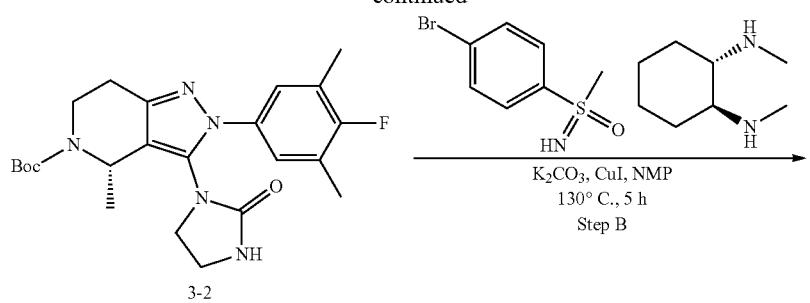

Step A tert-butyl(4S)-2-(4-fluoro-3,5-dimethylphenyl)-4-methyl-3-(2-oxotetrahydro-1H-imidazol-1-yl)-4,5,6,7-tetrahydropyrazolo[4,3-c]pyridine-5-carboxylate

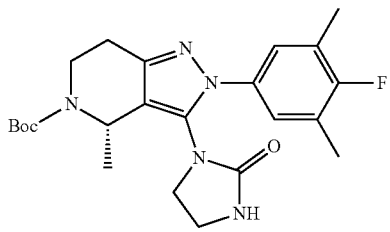 [SMILES: Cc1cc(-n2nc3c(c2N2CCNC2=O)[C@H](C)N(C(=O)OC(C)(C)C)CC3)cc(C)c1F]

The mixture of tert-butyl(S)-2-(4-fluoro-3,5-dimethylphenyl)-4-methyl-3-(2-oxo-2,3-dihydro-1H imidazol-1-yl)-2,4,6,7-tetrahydro-5H-pyrazolo[4,3-c]pyridine-5-carboxylate (100 mg, 0.226 mmol) and 10% Pd/C (24.1 mg) in MeOH (10 mL) was stirred at 50° C. under $H_2$ balloon for 72 h. After cooling and filtration, the filtrate was concentrated. The residue was purified by reverse ISCO (water (0.1% formic acid)/$CH_3CN$) to obtain tert-butyl(4S)-2-(4-fluoro-3,5-dimethylphenyl)-4-methyl-3-(2-oxotetrahydro-1H-imidazol-1-yl)-4,5,6,7-tetrahydropyrazolo[4,3-c]pyridine-5-carboxylate (20 mg, 19.9% yield). LC-MS: m/z 444.8 $(M+H)^+$.

Step B tert-butyl(4S)-3-(3-{4-[azanylidene(methyl)(oxo)-$\lambda^6$-sulfanyl]phenyl}-2-oxotetrahydro-1H-imidazol-1-yl)-2-(4-fluoro-3,5-dimethylphenyl)-4-methyl-4,5,6,7-tetrahydropyrazolo[4,3-c]pyridine-5-carboxylate

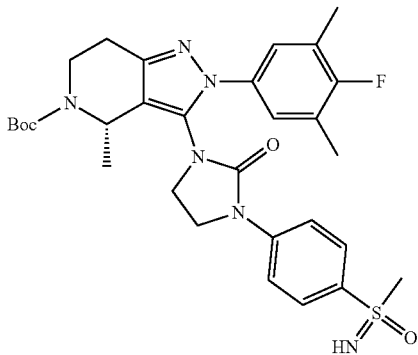

The mixture of 1-bromo-4-(S-methylsulfonimidoyl)benzene (105 mg, 0.449 mmol), tert-butyl(4S)-2-(4-fluoro-3,5-dimethylphenyl)-4-methyl-3-(2-oxotetrahydro-1H-imidazol-1-yl)-4,5,6,7-tetrahydropyrazolo[4,3-c]pyridine-5-carboxylate (199 mg, 0.449 mmol), CuI (17.1 mg, 0.090 mmol), (1S,2S)-N1,N2-dimethylcyclohexane-1,2-diamine (25.5 mg, 0.179 mmol) and $K_2CO_3$ (186 mg, 1.346 mmol) in NMP (5 mL) was stirred at 130° C. for 5 h under Biotage microwave. After cooling and filtration, the filtrate was purified by reverse ISCO (water (0.1% formic acid)/CH3CN) to obtain tert-butyl(4S)-3-(3-{4-[azanylidene(methyl)(oxo)-$\lambda^6$-sulfanyl]phenyl}-2-oxotetrahydro-1H-imidazol-1-yl)-2-(4-fluoro-3,5-dimethylphenyl)-4-methyl-4,5,6,7-tetrahydropyrazolo[4,3-c]pyridine-5-carboxylate (50 mg, 18.7% yield). LC-MS: m/z 597.4 $(M+H)^+$.

Step C (4-{1-[(4S)-2-(4-fluoro-3,5-dimethylphenyl)-4-methyl-4,5,6,7-tetrahydropyrazolo[4,3-c]pyridin-3-yl]-2-oxotetrahydro-1H-imidazol-3-yl}phenyl)(methyl)(oxo)-$\lambda^6$-sulfanimine HCl salt

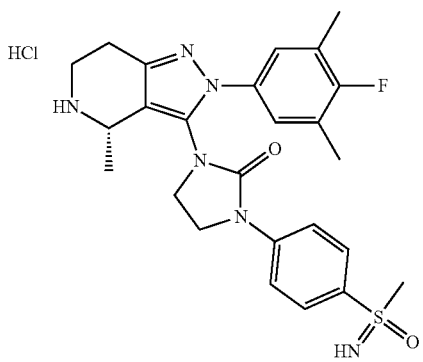 [SMILES: Cl ; Cc1cc(-n2nc3c(c2N2CCN(c4ccc(S(C)(=N)=O)cc4)C2=O)[C@H](C)NCC3)cc(C)c1F]

The mixture of tert-butyl(4S)-3-(3-{4-[azanylidene(methyl)(oxo)-$\lambda^6$-sulfanyl]phenyl}-2-oxotetrahydro-1H-imidazol-1-yl)-2-(4-fluoro-3,5-dimethylphenyl)-4-methyl-4,5,6,7-tetrahydropyrazolo[4,3-c]pyridine-5-carboxylate (50 mg, 0.084 mmol) and 4 M HCl (gas) in 1,4-dioxane (0.5 mL) in DCM (2 mL) was stirred at rt for 16 h. The reaction mixture was concentrated to obtain (4-{1-[(4S)-2-(4-fluoro-3,5-dimethylphenyl)-4-methyl-4,5,6,7-tetrahydropyrazolo[4,3-c]pyridin-3-yl]-2-oxotetrahydro-1H-imidazol-3-yl}phenyl)(methyl)(oxo)-$\lambda^6$-sulfanimine hydrochloric acid salt (44 mg, 98.3% yield). LC-MS: m/z 497.1 $(M+H)^+$.

Step D 3-[(1S,2S)-1-(2-{[(4S)-3-(3-{4-[azanylidene(methyl)(oxo)-$\lambda^6$-sulfanyl]phenyl}-2-oxotetrahydro-1H-imidazol-1-yl)-2-(4-fluoro-3,5-dimethylphenyl)-4-methyl-4,5,6,7-tetrahydropyrazolo1[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 103)

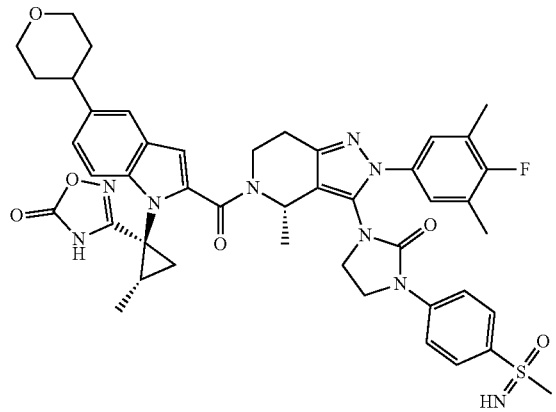 [SMILES: Cc1cc(-n2nc3c(c2N2CCN(c4ccc(S(C)(=N)=O)cc4)C2=O)[C@H](C)N(C(=O)c2cc4cc(C5CCOCC5)ccc4n2[C@@]2(c4noc(=O)[nH]4)C[C@@H]2C)CC3)cc(C)c1F]

The mixture of (4-{1-[(4S)-2-(4-fluoro-3,5-dimethylphenyl)-4-methyl-4,5,6,7-tetrahydropyrazolo1[4,3-c]pyridin-3-yl]-2-oxotetrahydro-1H-imidazol-3-yl}phenyl)(methyl)

(oxo)-$\lambda^6$-sulfanimine hydrochloric acid salt (44 mg, 0.083 mmol), 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (31.7 mg, 0.083 mmol), HATU (62.8 mg, 0.165 mmol) and DIPEA (31.9 mg, 0.248 mmol) in DMF (2 mL) was stirred at rt for 16 h. The mixture was filtrated and purified by prep. HPLC (Column: XBridge C18, 19*250 mm*10 μm; Mobile Phase A: Water (10 mM NH$_4$HCO$_3$), B: CH$_3$CN; Flow rate: 20 mL/min; Gradient: 40% B to 45% B; Retention Time: 7.7 min) to obtain 3-[(1S,2S)-1-(2-{[(4S)-3-(3-{4-[azanylidene(methyl)(oxo)-$\lambda^6$-sulfanyl]phenyl}-2-oxotetrahydro-1H-imidazol-1-yl)-2-(4-fluoro-3,5-dimethylphenyl)-4-methyl-4,5,6,7-tetrahydro-pyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (31.6 mg, 44.4% yield). LC-MS: m/z 862.4 (M+H). $^1$H NMR (400 MHz, DMSO-d6) δ 8.00-7.64 (m, 4H), 7.51 (s, 1H), 7.46-7.43 (m, 1H), 7.32-7.18 (m, 4H), 6.81 (brs, 1H), 5.79-5.44 (m, 1H), 4.40 (brs, 1H), 4.03-3.92 (m, 4H), 3.72-3.56 (m, 2H), 3.55-3.45 (m, 3H), 2.95-2.75 (m, 4H), 2.26 (s, 6H), 2.05 (d, J=4.0 Hz, 3H), 1.81-1.59 (m, 7H), 1.50 (s, 3H), 1.17 (brs, 3H).

Example compound 166 and 167, 168 and 169, 173, 174 and 175, 176 and 177, 178, 179, 181, 183, 184, 189 and 190 were synthesized using a similar procedure described in the Example A3 above using the appropriate materials.

Example A4

6-{3-[(4S)-2-(4-fluoro-3,5-dimethylphenyl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-4-methyl-4,5,6,7-tetrahydropyrazolo[4,3-c]pyridin-3-yl]-2-oxoimidazol-1-yl}-1-methyl-3,4-dihydro-1$\lambda^6$-benzo[2,1-e][1,2]thiazin-1-one (Compound 108)

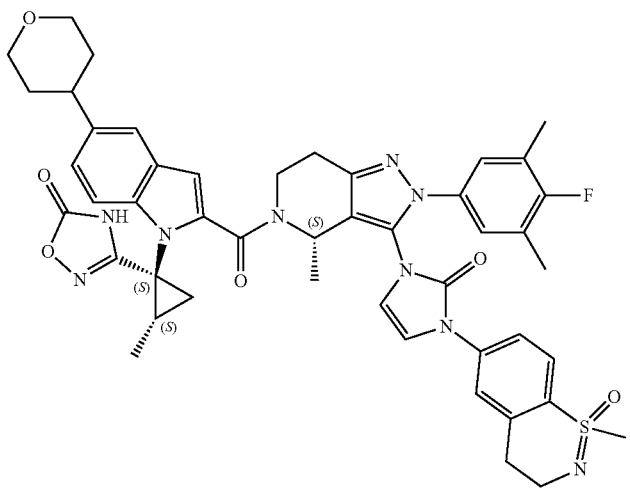

Compound 108

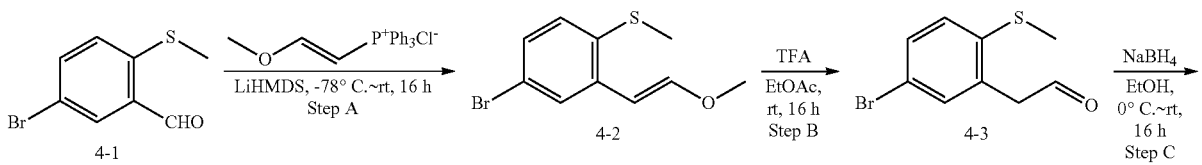

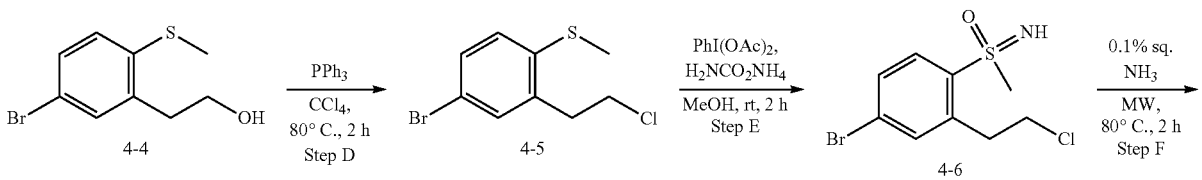

-continued
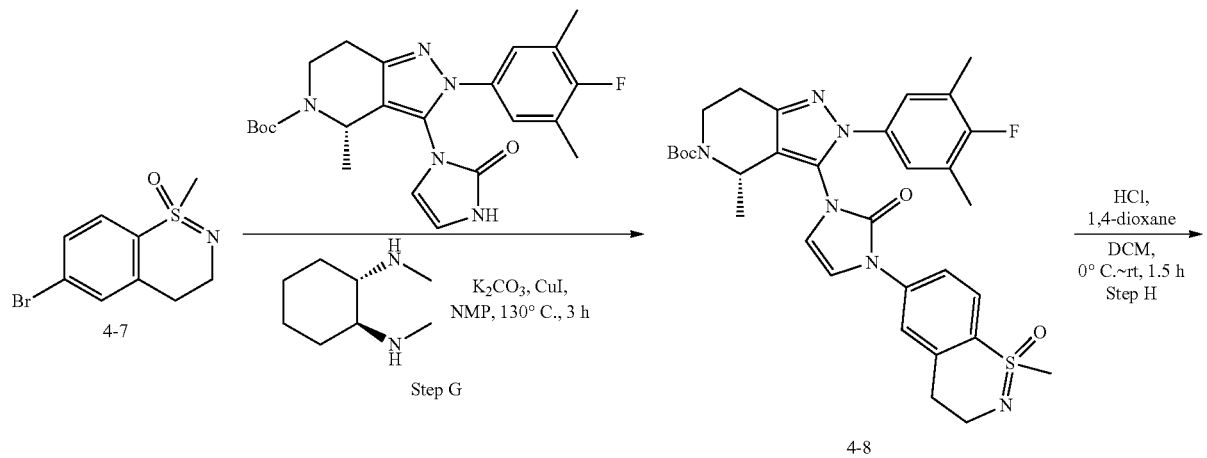
4-7 → 4-8
Step G: K₂CO₃, CuI, NMP, 130° C., 3 h
Step H: HCl, 1,4-dioxane, DCM, 0° C.~rt, 1.5 h
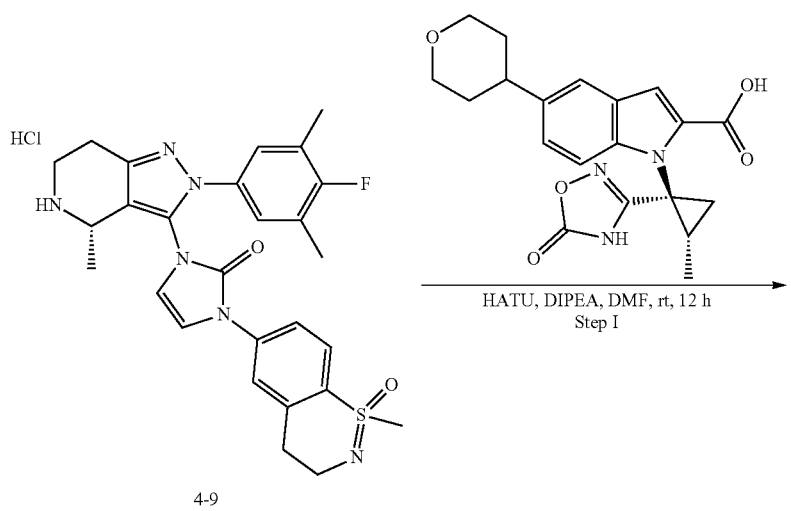
4-9
Step I: HATU, DIPEA, DMF, rt, 12 h
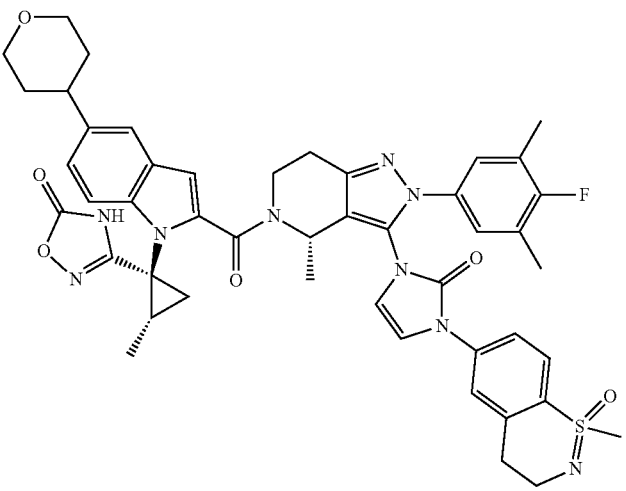
Compound 108

Step A (E)-(4-bromo-2-(2-methoxyvinyl)phenyl)(methyl)sulfane

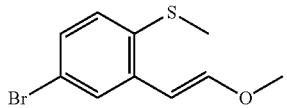

To a solution of (methoxymethyl)triphenylphosphanium chloride (12.52 g, 36.519 mmol) in THF (100 mL) was added 1 M LiHMDS in THF (45.7 mL, 45.7 mmol). After being stirred at −78° C. for 10 min and rt for 2 h, the mixture was cooled to −78° C. again. Then 5-bromo-2-(methylsulfanyl)benzene-1-carbaldehyde (4.22 g, 18.260 mmol) was added. The reaction mixture was warmed to rt and stirred for 16 h. The mixture was quenched with water (50 mL), extracted with EtOAc (200 mL×3). The combined organic layer was washed with brine, dried with $Na_2SO_4$ and concentrated. The residue was purified by flash silica gel chromatography (Silica Flash Column, Eluent of 100% PE) to afford (E)-(4-bromo-2-(2-methoxyvinyl)phenyl)(methyl)sulfane (3.13 g, 47.3% yield). LC-MS: m/z 259.0 $(M+H)^+$.

Step B 2-(5-bromo-2-(methylthio)phenyl)acetaldehyde

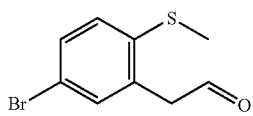

To a solution of (E)-(4-bromo-2-(2-methoxyvinyl)phenyl)(methyl)sulfane (3.13 g, 12.13 mmol) in EtOAc (30 mL) was added TFA (6.26 mL, 81.750 mmol) at 0° C. The reaction mixture was warmed to rt and stirred for 16 h. The mixture was diluted with EtOAc (100 mL) and water (100 mL). The organic layer was separated, washed with brine, and concentrated. The residue was purified by flash silica gel chromatography (Silica Flash Column, Eluent of 100% PE) to afford 2-(5-bromo-2-(methylthio)phenyl)acetaldehyde (2.96 g, 99% yield). LC-MS: m/z 245.0 $(M+H)^+$.

Step C 2-(5-bromo-2-(methylthio)phenyl)ethan-1-ol

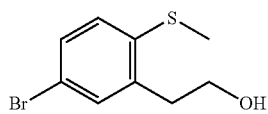

To a solution of 2-(5-bromo-2-(methylthio)phenyl)acetaldehyde (1.30 g, 5.303 mmol) in EtOH (15 mL) was added $NaBH_4$ (401.25 mg, 10.607 mmol) at 0° C. The reaction mixture was warmed to rt and stirred for 16 h. The mixture was diluted with EtOAc (100 mL) and water (100 mL). The organic layer was separated, washed with brine, and concentrated. The residue was purified by flash silica gel chromatography (Silica Flash Column, Eluent of 0-20% EtOAc/PE gradient) to afford 2-(5-bromo-2-(methylthio)phenyl)ethan-1-ol (289 mg, 22.0% yield). $^1$H NMR (400 MHz, $CD_3OD$-d4) δ 7.35-7.34 (m, 2H), 7.07 (d, J=8.8 Hz, 1H), 3.87 (t, J=6.4 Hz, 2H), 2.96 (t, J=6.4 Hz, 2H), 2.45 (s, 3H).

Step D (4-bromo-2-(2-chloroethyl)phenyl)(methyl)sulfane

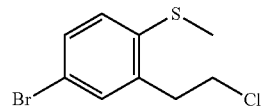

To a solution of 2-(5-bromo-2-(methylthio)phenyl)ethan-1-ol (370 mg, 1.497 mmol) in $CCl_4$ (3.7 mL) was added $PPh_3$ (510 mg, 1.946 mmol). The mixture was stirred at 80° C. for 2 h under $N_2$. The mixture was poured into water (100 mL) and extracted with EtOAc (100 mL×2). The combined organic layer was washed with brine, dried over sodium sulfate, filtered and concentrated. The residue was purified by flash silica gel chromatography (Silica Flash Column, Eluent of 0~10% EtOAc/PE gradient) to obtain (4-bromo-2-(2-chloroethyl)phenyl)(methyl)sulfane (80 mg, 20.1% yield). $^1$H NMR (400 MHz, DMSO-d6) δ 7.51-7.44 (m, 2H), 7.24-7.19 (m, 1H), 3.84 (t, J=7.2 Hz, 2H), 3.11 (t, J=7.2 Hz, 2 H), 2.51 (s, 3H).

Step E [4-bromo-2-(2-chloroethyl)phenyl](methyl)(oxo)-λ$^6$-sulfanimine

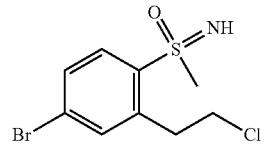

To a solution of (4-bromo-2-(2-chloroethyl)phenyl)(methyl)sulfane (80 mg, 0.301 mmol) in MeOH (5 mL) was added $PhI(OAc)_2$ (244 mg, 0.753 mmol) and $H_2NCO_2NH_4$ (59 mg, 0.753 mmol). The mixture was stirred at rt for 2 h under $N_2$. The mixture was poured into water (100 mL) and extracted with DCM (100 mL×2). The combined organic layer was washed with brine, dried over sodium sulfate, filtered and concentrated. The residue was purified by flash silica gel chromatography (Silica Flash Column, Eluent of 0-5% MeOH/DCM gradient) to obtain [4-bromo-2-(2-chloroethyl)phenyl](methyl)(oxo)-λ$^6$-sulfanimine (50 mg, 54.1% yield). LC-MS: m/z 295.9 $(M+H)^+$.

Step F 6-bromo-1-methyl-3,4-dihydro-1λ$^4$-benzo[e][1,2]thiazine 1-oxide

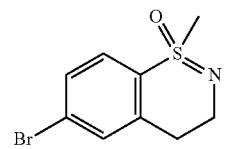

To a solution of [4-bromo-2-(2-chloroethyl)phenyl](methyl)(oxo)-λ$^6$-sulfanimine (50 mg, 0.169 mmol) in dioxane (2 mL) was added 0.1% aq. NH₃·H₂O (1 mL). The mixture was stirred at 80° C. for 2 h under N₂ in a sealed tube. After cooling, the mixture was poured into water (100 mL) and extracted with DCM (100 mL×2). The combined organic layer was washed with brine, dried over sodium sulfate, filtered and concentrated to obtain 6-bromo-1-methyl-3,4-dihydro-1λ⁴-benzo[e][1,2]thiazine 1-oxide (40 mg, 79.4% yield). LC-MS: m/z 260.0 (M+H)⁺.

Step G tert-butyl(4S)-2-(4-fluoro-3,5-dimethylphenyl)-4-methyl-3-[1-(1-methyl-1-oxo-3,4-dihydro-1λ⁶-benzo[2,1-e][1,2]thiazin-6-yl)-2-oxoimidazol-3-yl]-4,5,6,7-tetrahydropyrazolo[4,3-c]pyridine-5-carboxylate

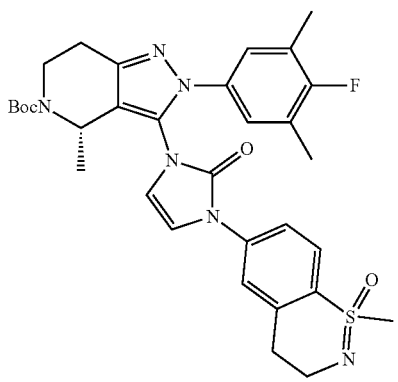 [SMILES: Cc1cc(-n2nc3c(c2-n2ccn(-c4ccc5c(c4)CCN=S5(C)=O)c2=O)[C@H](C)N(C(=O)OC(C)(C)C)CC3)cc(C)c1F]

To a solution of 6-bromo-1-methyl-3,4-dihydro-1λ⁴-benzo[e][1,2]thiazine 1-oxide (40 mg, 0.154 mmol) and tert-butyl(4S)-2-(4-fluoro-3,5-dimethylphenyl)-4-methyl-3-(2-oxo-3H-imidazol-1-yl)-4,5,6,7-tetrahydropyrazolo[4,3-c]pyridine-5-carboxylate (27 mg, 0.062 mmol) in NMP (5 mL) was added methyl[(1S,2S)-2-(methylamino)cyclohexyl]amine (22 mg, 0.154 mmol), K₂CO₃ (64 mg, 0.461 mmol), CuI (6 mg, 0.031 mmol). The mixture was stirred at 130° C. for 5 h under N₂. After cooling, the mixture was poured into water (50 mL) and extracted with DCM (50 mL×2). The combined organic layer was washed with brine, dried over sodium sulfate, filtered and concentrated. The residue was purified by flash silica gel chromatography (Silica Flash Column, Eluent of 0-5% MeOH/DCM gradient) to obtain tert-butyl(4S)-2-(4-fluoro-3,5-dimethylphenyl)-4-methyl-3-[1-(1-methyl-1-oxo-3,4-dihydro-1λ⁶-benzo[2,1-e][1,2]thiazin-6-yl)-2-oxoimidazol-3-yl]-4,5,6,7-tetrahydropyrazolo[4,3-c]pyridine-5-carboxylate (100 mg, 72.0% yield). LC-MS: m/z 621.4 (M+H)⁺.

Step H 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-1-methyl-3,4-dihydro-1λ⁶-benzo[2,1-e][1,2]thiazin-1-one hydrochloride salt

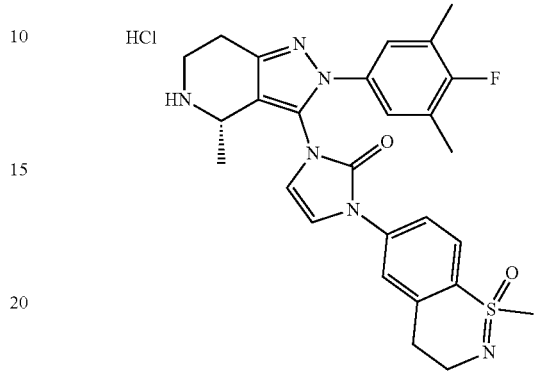

To a solution of tert-butyl(4S)-2-(4-fluoro-3,5-dimethylphenyl)-4-methyl-3-[1-(1-methyl-1-oxo-3,4-dihydro-1λ⁶-benzo[2,1-e][1,2]thiazin-6-yl)-2-oxoimidazol-3-yl]-4,5,6,7-tetrahydropyrazolo[4,3-c]pyridine-5-carboxylate (100 mg, 0.111 mmol) in DCM (10 mL) was added 4 M HCl (gas)/dioxane (0.4 mL) at 0° C. The mixture was stirred at rt for 1.5 h under N₂. The mixture was concentrated to afford 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-1-methyl-3,4-dihydro-1λ⁶-benzo[2,1-e][1,2]thiazin-1-one hydrochloride salt (100 mg, crude). LC-MS: m/z 521.3 (M+H)⁺.

Step I 6-{3-[(4S)-2-(4-fluoro-3,5-dimethylphenyl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-4-methyl-4,5,6,7-tetrahydropyrazolo[4,3-c]pyridin-3-yl]-2-oxoimidazol-1-yl}-1-methyl-3,4-dihydro-1λ⁶-benzo[2,1-e][1,2]thiazin-1-one (Compound 108)

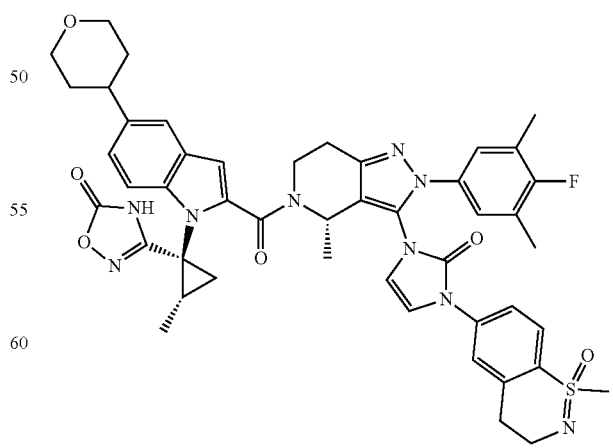

To a solution of 6-{3-[(4S)-2-(4-fluoro-3,5-dimethylphenyl)-4-methyl-4,5,6,7-tetrahydropyrazolo[4,3-c]pyridin-3- yl]-2-oxoimidazol-1-yl}-1-methyl-3,4-dihydro-1λ⁶-benzo[2,1-e][1,2]thiazin-1-one hydrochloride salt (100 mg, 0.180 mmol) in DMF (2 mL) was added 1-[(1S,2S)-2-methyl-1-(5-oxo-4H-1,2,4-oxadiazol-3-yl)cyclopropyl]-5-(3,4,5,6-tetrahydro-2H-pyran-4-yl)indole-2-carboxylic acid (69 mg, 0.180 mmol), HATU (102 mg, 0.269 mmol), DIPEA (116 mg, 0.898 mmol). The mixture was stirred at rt for 3 h under $N_2$. The mixture was filtrated and purified by prep. HPLC (Column: Sunfire C18 19*250 mm*10 μm; Mobile Phase A: Water (0.1% formic acid), B: $CH_3CN$; Flow rate: 20 mL/min; Gradient: 57% B to 67% B; Retention Time: 9.0 min) to obtain 6-{3-[(4S)-2-(4-fluoro-3,5-dimethylphenyl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-4-methyl-4,5,6,7-tetrahydropyrazolo [4,3-c]pyridin-3-yl]-2-oxoimidazol-1-yl}-1-methyl-3,4-dihydro-1λ⁶-benzo[2,1-e][1,2]thiazin-1-one (15.4 mg, 9.5% yield). LC-MS: m/z 886.4 (M+H)⁺. ¹H NMR (400 MHz, DMSO-d6) δ 8.05-7.95 (m, 1H), 7.88-7.78 (m, 1H), 7.73-7.64 (m, 1H), 7.56 (s, 1H), 7.47 (d, J=8.8 Hz, 1H), 7.37-7.28 (m, 2H), 7.18 (d, J=6.0 Hz, 2 H), 7.01-6.85 (m, 2H), 6.97-6.85 (m, 2H), 5.70-5.50 (m, 1H), 4.57-4.38 (m, 1H), 4.01 (d, J=10.8 Hz, 2H), 3.68-3.43 (m, 5H), 3.25 (s, 1H), 2.97-2.84 (m, 4H), 2.80-2.69 (m, 1H), 2.25 (s, 6H), 1.82-1-66 (m, 7H), 1.51-1.42 (m, 3H), 1.25-1.12 (m, 3H).

Example compound 185 and 186, 187 and 188, 197 and 198, 199 and 200, 212 and 213 were synthesized using a similar procedure described in the Example A4 above using the appropriate materials.

Example A5

3-[(1S,2S)-1-(2-{[(4S)-3-[3-(4-{[azanylidene(methyl)(oxo)-λ⁶-sulfanyl]methyl}phenyl)-2-oxo-imidazol-1-yl]-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 111)

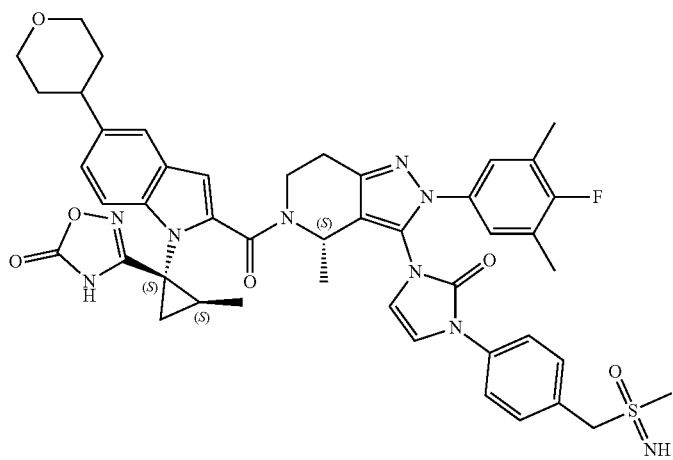

Compound 111

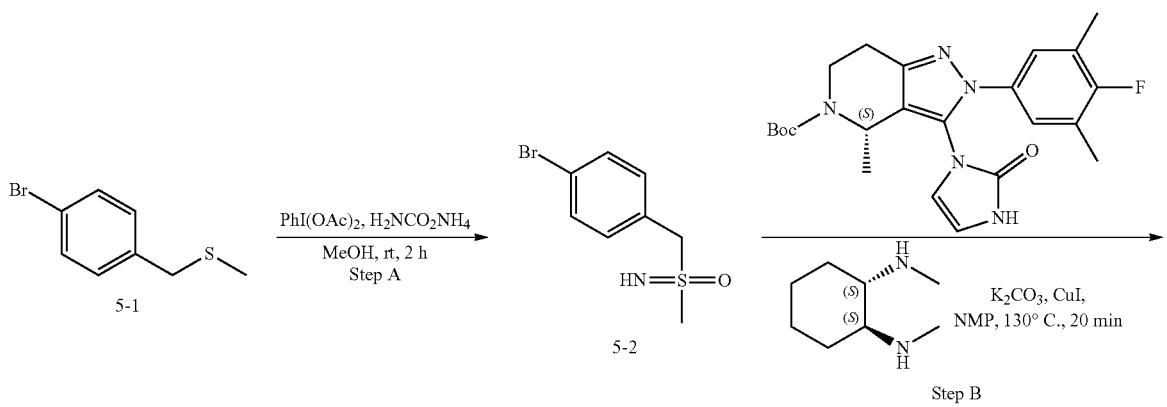

Step B

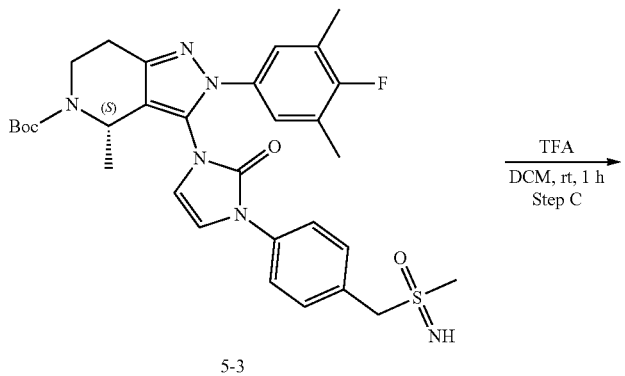

5-3

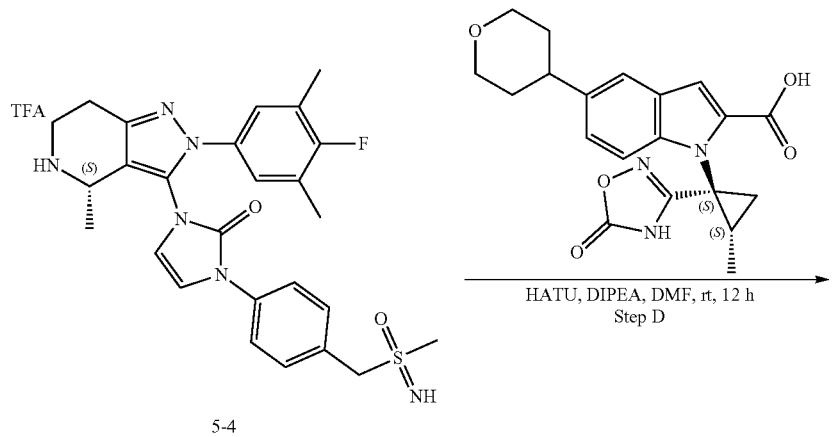

5-4

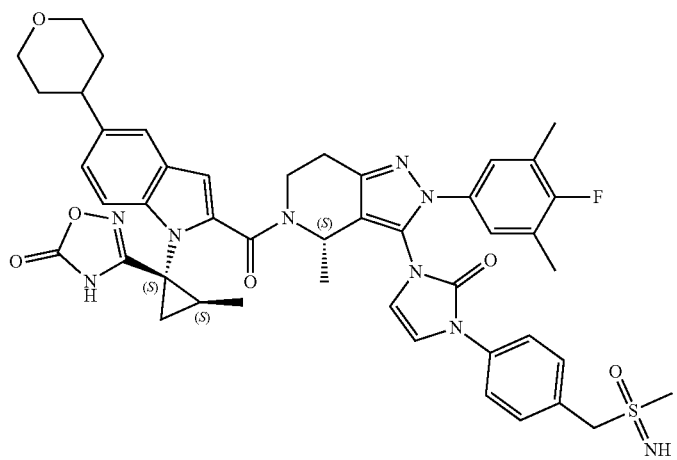

Compound 111

Step A (4-bromobenzyl)(imino)(methyl)-λ⁶-sulfanone

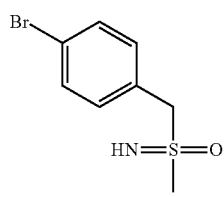

To a solution of [(4-bromophenyl)methyl](methyl)sulfane (500 mg, 2.303 mmol) in EtOH (50 mL) was added PhI(OAc)$_2$ (2239 mg, 6.909 mmol) and H$_2$NCO$_2$NH$_4$ (719 mg, 9.211 mmol). The reaction mixture was stirred at rt for 2 h under N$_2$. The reaction mixture was concentrated, the residue was purified by reverse ISCO (water (0.1% formic acid)/CH$_3$CN system) to afford the (4-bromobenzyl)(imino)(methyl)-λ⁶-sulfanone (134 mg, 23.5% yield). LC-MS: m/z 248.1 (M+H)⁺.

Step B tert-butyl(4S)-2-(4-fluoro-3,5-dimethylphenyl)-4-methyl-3-(3-(4-((S-methylsulfonimidoyl)methyl)phenyl)-2-oxo-2,3-dihydro-1H-imidazol-1-yl)-2,4,6,7-tetrahydro-5H-pyrazolo[4,3-c]pyridine-5-carboxylate

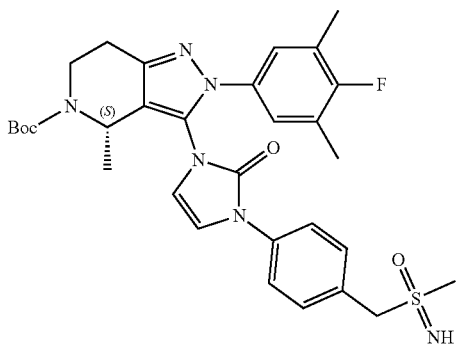

To a solution of [(4-bromophenyl)methyl](methyl)(oxo)-λ⁶-sulfanimine (90 mg, 0.363 mmol) in NMP (3 mL) was added tert-butyl(4S)-2-(4-fluoro-3,5-dimethylphenyl)-4-methyl-3-(2-oxo-3H-imidazol-1-yl)-4,5,6,7-tetrahydropyrazolo[4,3-c]pyridine-5-carboxylate (144 mg, 0.326 mmol), methyl[(1S,2S)-2-(methylamino)cyclohexyl]amine (20.6 mg, 0.145 mmol), K$_2$CO$_3$ (150 mg, 1.088 mmol), CuI (13.8 mg, 0.073 mmol). The reaction mixture was stirred at 130° C. for 20 min under N$_2$.

After cooling and filtration, the solution was purified by reverse ISCO (water (0.1% formic acid)/CH$_3$CN system) to afford tert-butyl(4S)-2-(4-fluoro-3,5-dimethylphenyl)-4-methyl-3-(3-(4-((S-methylsulfonimidoyl)methyl)phenyl)-2-oxo-2,3-dihydro-1H-imidazol-1-yl)-2,4,6,7-tetrahydro-5H-pyrazolo[4,3-c]pyridine-5-carboxylate (53 mg, 9.5% yield). LC-MS: m/z 609.6 (M+H)⁺.

Step C 1-((S)-2-(4-fluoro-3,5-dimethylphenyl)-4-methyl-4,5,6,7-tetrahydro-2H-pyrazolo[4,3-c]pyridin-3-yl)-3-(4-((S-methylsulfonimidoyl)methyl)phenyl)-1,3-dihydro-2H-imidazol-2-one TFA salt

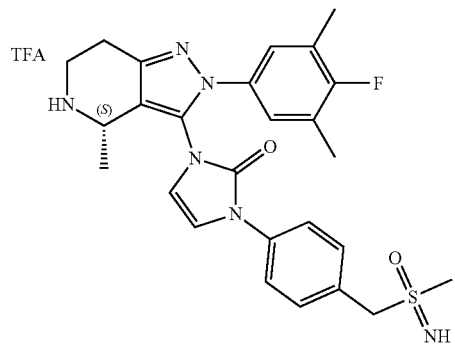

To a solution of tert-butyl(4S)-3-[3-(4-{[azanylidene(methyl)(oxo)-⁶-sulfanyl]methyl}phenyl)-2-oxoimidazol-1-yl]-2-(4-fluoro-3,5-dimethylphenyl)-4-methyl-4,5,6,7-tetrahydropyrazolo[4,3-c]pyridine-5-carboxylate (40 mg, 0.066 mmol) in DCM (3 mL) was added TFA (0.38 mL, 4.897 mmol).

The reaction mixture was stirred at rt for 1 h under N$_2$. The solvent was removed to afford 1-((S)-2-(4-fluoro-3,5-dimethylphenyl)-4-methyl-4,5,6,7-tetrahydro-2H-pyrazolo[4,3-c]pyridin-3-yl)-3-(4-((S-methylsulfonimidoyl)methyl)phenyl)-1,3-dihydro-2H-imidazol-2-one TFA salt (40 mg, 96.9% yield). LC-MS: m/z 509.6 (M+H)⁺.

Step D 3-[(1S,2S)-1-(2-{[(4S)-3-[3-(4-{[azanylidene(methyl)(oxo)-λ⁶-sulfanyl]methyl}phenyl)-2-oxo-imidazol-1-yl]-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 111)

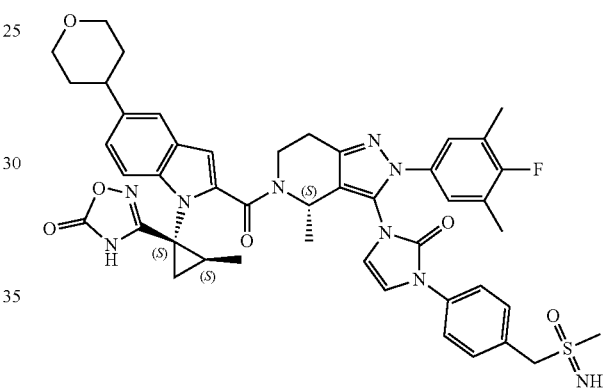

To a solution of 1-((S)-2-(4-fluoro-3,5-dimethylphenyl)-4-methyl-4,5,6,7-tetrahydro-2H-pyrazolo[4,3-c]pyridin-3-yl)-3-(4-((S-methylsulfonimidoyl)methyl)phenyl)-1,3-dihydro-2H-imidazol-2-one TFA salt (40 mg, 0.066 mmol) in DMF (1 mL) was added DIPEA (11.5 mg, 0.089 mmol), 1-[(1S,2S)-2-methyl-1-(5-oxo-4H-1,2,4-oxadiazol-3-yl)cyclopropyl]-5-(3,4,5,6-tetrahydro-2H-pyran-4-yl)indole-2-carboxylic acid (11.4 mg, 0.030 mmol), HATU (17 mg, 0.045 mmol). The reaction mixture was stirred at rt for 12 h under N$_2$. After filtration, the solution was purified using prep. HPLC (Column: Sunfire C18 19*250 mm*10 μm; Mobile Phase A: Water (0.05% TFA), B: CH$_3$CN; Flow rate: 20 mL/min; Gradient: 57% B to 67% B; Retention Time: 9.0 min) to afford 3-[(1S,2S)-1-(2-{[(4S)-3-[3-(4-{[azanylidene(methyl)(oxo)-λ⁶-sulfanyl]methyl}phenyl)-2-oxoimidazol-1-yl]-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (13.9 mg, 52.6% yield). LC-MS: m/z 874.5 (M+H)⁺. ¹H NMR (400 MHz, DMSO-d6) δ 7.78-7.64 (m, 2H), 7.59-7.50 (m, 3H), 7.43 (d, J=8.4 Hz, 1H), 7.30-7.21 (m, 2H), 7.15 (d, J=6.0 Hz, 2H), 6.97-6.83 (m, 2H), 5.72-5.42 (m, 1H), 4.66 (s, 2H), 4.45 (brs, 1H), 3.98 (d, J=10.8 Hz, 2H), 3.53-3.46 (m, 2H), 3.06 (s, 2H), 2.95-2.81 (m, 3H), 2.22 (s, 6H), 2.05 (s, 3H), 1.81-1-60 (m, 7H), 1.44 (d, J=3.6 Hz, 3H), 1.18 (d, J=6.0 Hz, 3H).

Example A6
3-[(1S,2S)-1-(2-{[(S)-2-(4-fluoro-3,5-xylyl)-3-{3-[4-(iminomethyloxothio)-3-methoxyphenyl]-2-oxo-1,3-dihydro-1-imidazolyl}-4-methyl-4,5,6,7-tetrahydro-2H-1,2,5-triazainden-5-yl]carbonyl}-5-(tetrahydro-2H-pyran-4-yl)-1-indolyl)-2-methylcyclopropyl]-1,2,4-oxadiazol-5(4H)-one (Compound 123)
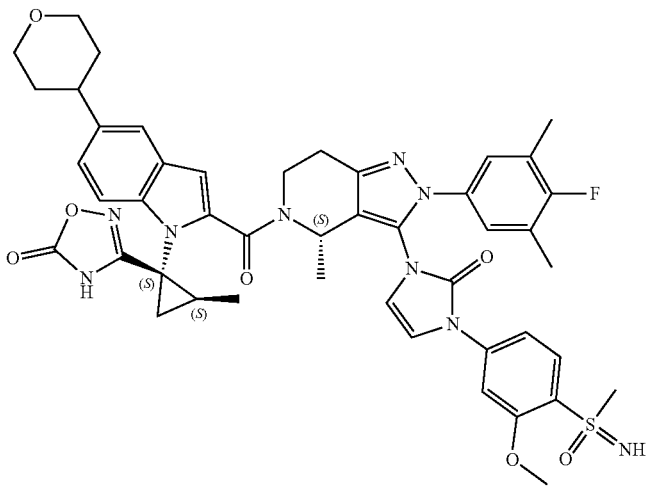
Compound 123
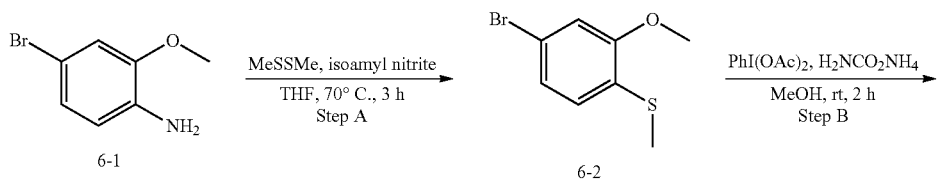
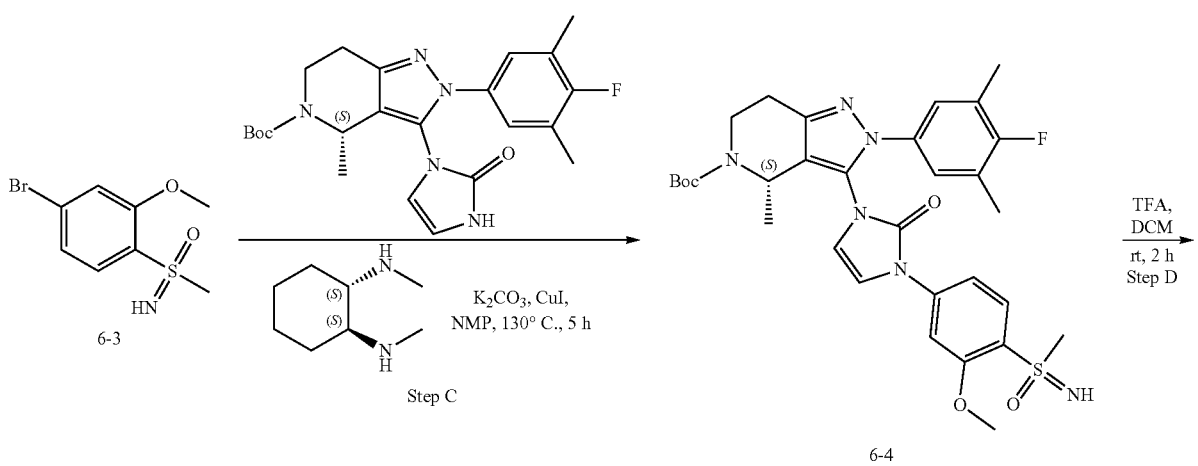

-continued

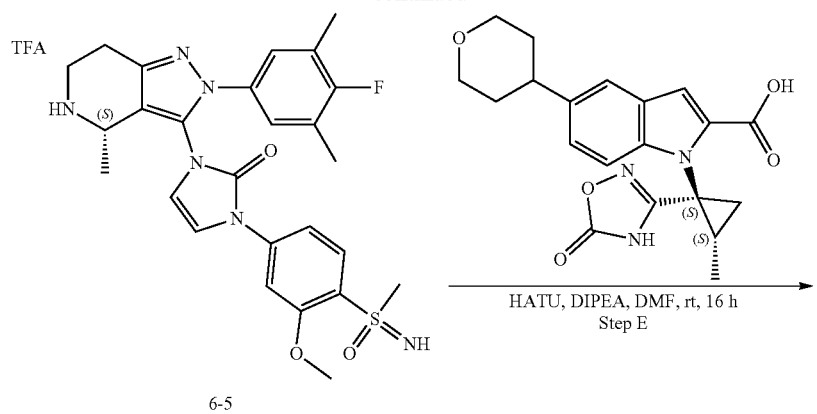

6-5

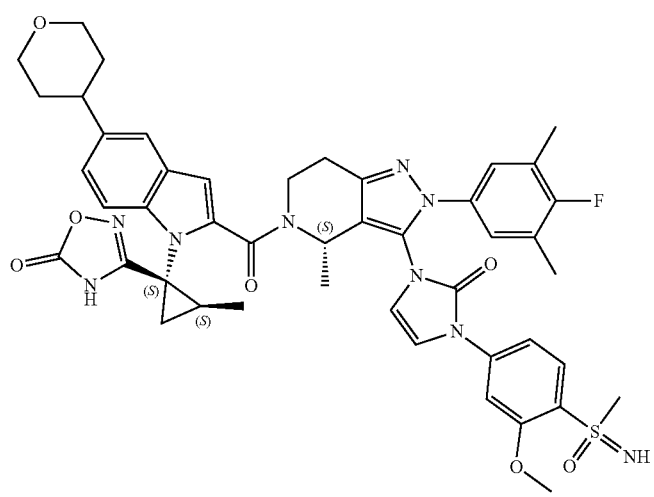

Compound 123

Step A (4-bromo-2-methoxyphenyl)(methyl)sulfane

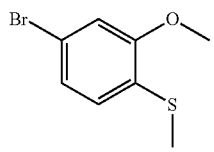

To a solution of dimethylsulfane (0.11 mL, 1.485 mmol) and isoamyl nitrite (0.30 mL, 1.980 mmol) in THF (5 mL) was added 4-bromo-2-methoxyaniline (200 mg, 0.990 mmol). The reaction mixture was stirred at 70° C. for 3 h. After cooling and concentration, the residue was purified by flash silica gel chromatography (Silica Flash Column, Eluent of 0~10% EtOAc/PE gradient) to obtain (4-bromo-2-methoxyphenyl)(methyl)sulfane (210 mg, 91.0% yield). LC-MS: m/z 234.1 (M+H)$^+$.

Step B
(4-bromo-2-methoxyphenyl)(imino)(methyl)-sulfanone

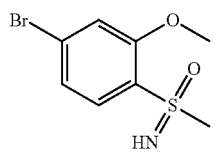

To a solution of (4-bromo-2-methoxyphenyl)(methyl) sulfane (210 mg, 0.901 mmol) in MeOH (10 mL) was added PhI(OAc)$_2$ (1022 mg, 3.153 mmol) and H$_2$NCO$_2$NH$_4$ (246 mg, 3.153 mmol). The reaction mixture was stirred at room temperature 2 h under N$_2$. The reaction mixture was diluted with EtOAc (50 mL) and water (50 mL). The organic layer was separated, washed with brine, dried with Na$_2$SO$_4$ and concentrated. The residue was purified by flash silica gel chromatography (Silica Flash Column, Eluent of 0~50% EtOAc/PE gradient) to obtain (4-bromo-2-methoxyphenyl)(imino)(methyl)-sulfanone (200 mg, 84.0% yield). LC-MS: m/z 264.0 (M+H)⁺.

Step C tert-butyl(4S)-2-(4-fluoro-3,5-dimethylphenyl)-3-(3-(3-methoxy-4-(S-methylsulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate

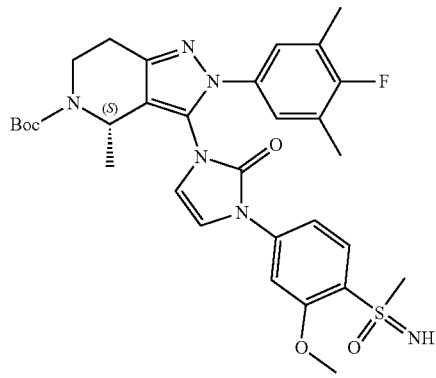

To a solution of (4-bromo-2-methoxyphenyl)(imino)(methyl)-sulfanone (200 mg, 0.757 mmol) in NMP (3 mL) was added methyl[(1R,2R)-2-(methylamino)cyclohexyl]amine (43 mg, 0.303 mmol), tert-butyl(4S)-2-(4-fluoro-3,5-dimethylphenyl)-4-methyl-3-(2-oxo-3H-imidazol-1-yl)-4,5,6,7-tetrahydropyrazolo[4,3-c]pyridine-5-carboxylate (368 mg, 0.833 mmol), K₂CO₃ (314 mg, 2.272 mmol), CuI (28.8 mg, 0.151 mmol). The reaction mixture was stirred at 130° C. for 5 h under N₂. After cooling, the reaction mixture was diluted with EtOAc (50 mL) and water (50 mL). The organic layer was separated, washed with brine, dried with Na₂SO₄ and concentrated. The residue was purified by flash silica gel chromatography (Silica Flash Column, Eluent of 0~5% MeOH/DCM gradient) to obtain tert-butyl(4S)-2-(4-fluoro-3,5-dimethylphenyl)-3-(3-(3-methoxy-4-(S-methylsulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (400 mg, 84.6% yield). LC-MS: m/z 625.4 (M+H)⁺.

Step D 1-((S)-2-(4-fluoro-3,5-dimethylphenyl)-4-methyl-4,5,6,7-tetrahydro-2H-pyrazolo[4,3-c]pyridin-3-yl)-3-(3-methoxy-4-(S-methylsulfonimidoyl)phenyl)-1,3-dihydro-2H-imidazol-2-one TFA salt

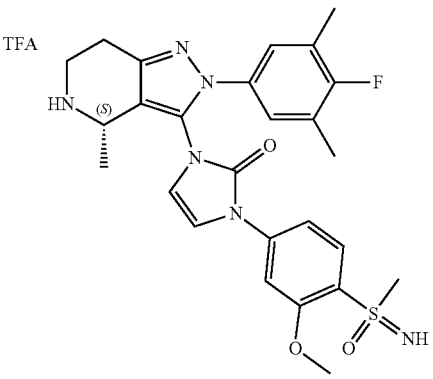

To a solution of tert-butyl(4S)-2-(4-fluoro-3,5-dimethylphenyl)-3-(3-(3-methoxy-4-(S-methylsulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (120 mg, 0.192 mmol) in DCM (5 mL) was added TFA (0.5 mL) at 0° C. The resulting mixture was stirred at rt for 2 h under N₂. The reaction mixture was concentrated to obtain 1-((S)-2-(4-fluoro-3,5-dimethylphenyl)-4-methyl-4,5,6,7-tetrahydro-2H-pyrazolo[4,3-c]pyridin-3-yl)-3-(3-methoxy-4-(S-methylsulfonimidoyl)phenyl)-1,3-dihydro-2H-imidazol-2-one TFA salt (120 mg, 95.3% yield). LC-MS: m/z 525.3 (M+H)⁺.

Step E 3-[(1S,2S)-1-(2-{[(4S)-3-(3-{4-[azanylidene(methyl)(oxo)-λ⁶-sulfanyl]-3-methoxyphenyl}-2-oxoimidazol-1-yl)-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 123)

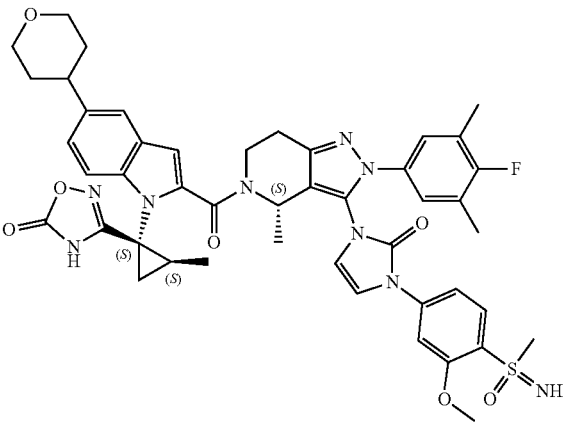

To a solution of 1-((S)-2-(4-fluoro-3,5-dimethylphenyl)-4-methyl-4,5,6,7-tetrahydro-2H-pyrazolo[4,3-c]pyridin-3-yl)-3-(3-methoxy-4-(S-methylsulfonimidoyl)phenyl)-1,3-dihydro-2H-imidazol-2-one TFA salt (120 mg, 0.183 mmol)

in DMF (2 mL) was added 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (88 mg, 0.229 mmol), DIPEA (88 mg, 0.686 mmol) and HATU (131 mg, 0.343 mmol). The reaction mixture was stirred at rt for 2 h under $N_2$. The mixture was filtered and the residue was purified by prep.

HPLC (Column: Sunfire C18 19*250 mm*10 μm; Mobile Phase A: Water (0.05% TFA), B: $CH_3CN$; Flow rate: 20 mL/min; Gradient: 50% B to 60% B; Retention Time: 8.0 min) to obtain 3-[(1S,2S)-1-(2-{[(4S)-3-(3-{4-[azanylidene(methyl)(oxo)-$\lambda^6$-sulfanyl]-3-methoxyphenyl}-2-oxoimidazol-1-yl)-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (10.8 mg, 5.3% yield). LC-MS: m/z 890.4 (M+H)$^+$. $^1$H NMR (400 MHz, DMSO-d6) δ 11.59 (s, 1H), 7.91 (d, J=8.0 Hz, 1H), 7.70-7.40 (m, 5H), 7.27 (d, J=9.2 Hz, 1H), 7.16-7.14 (m, 2H), 7.01-6.84 (m, 2H), 5.69-5.44 (m, 1H), 4.58-4.39 (m, 1H), 4.04-3.87 (m, 5H), 3.64-3.43 (m, 4H), 3.32 (s, 3H), 2.95-2.84 (m, 3H), 2.23 (s, 6H), 1.81-1.61 (m, 7H), 1.44 (s, 3H), 1.17 (s, 3H).

Example compound 124 was synthesized using a similar procedure described in the Example A6 above using the appropriate materials.
N

Example A7

3-[(1S,2S)-1-(2-{[(4S)-2-(4-fluoro-3,5-dimethylphenyl)-3-(1-{4-[(S)-azanylidene(methyl)(oxo)-$\lambda^6$-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one and 3-[(1S,2S)-1-(2-{[(4S)-2-(4-fluoro-3,5-dimethylphenyl)-3-(1-{4-[(R)-azanylidene(methyl)(oxo)-$\lambda^6$-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compounds 114 and 115)

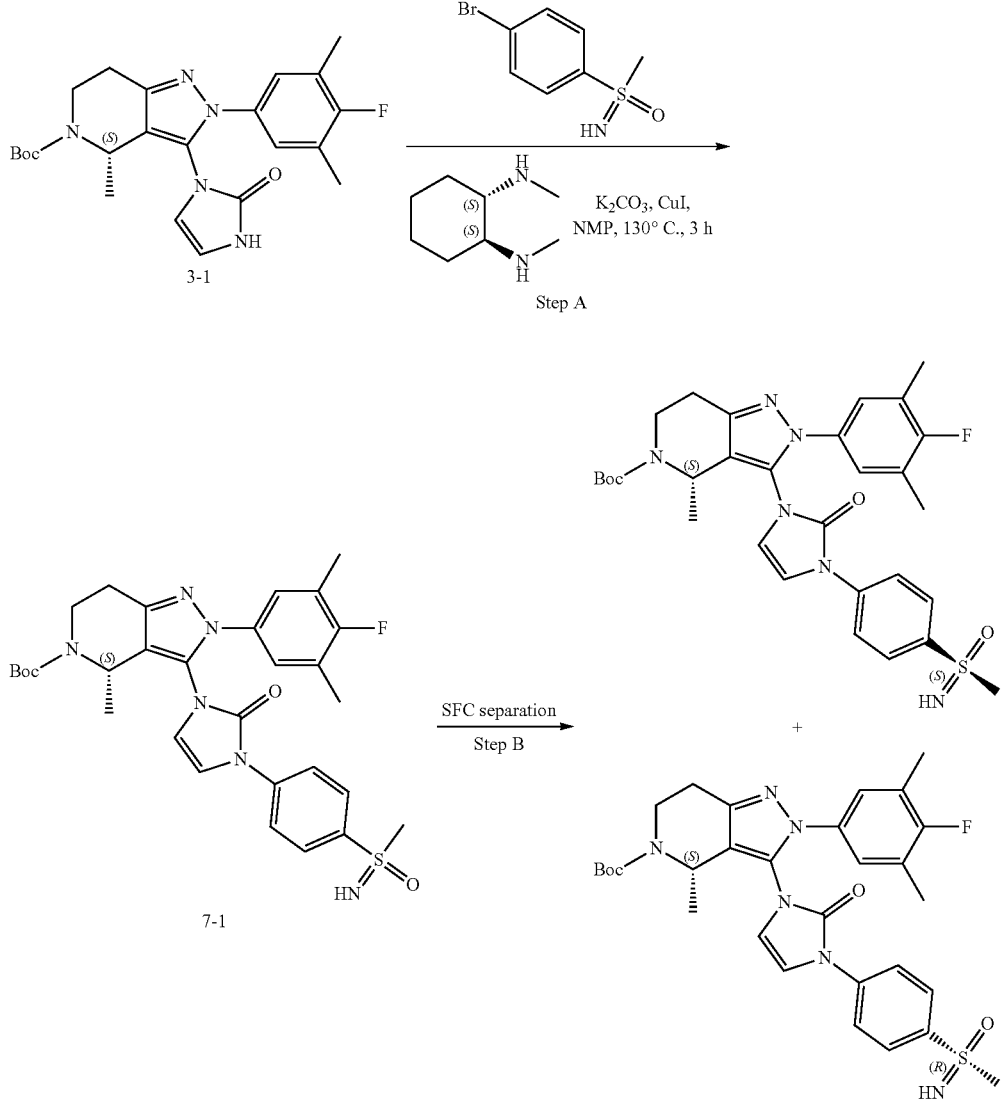

-continued
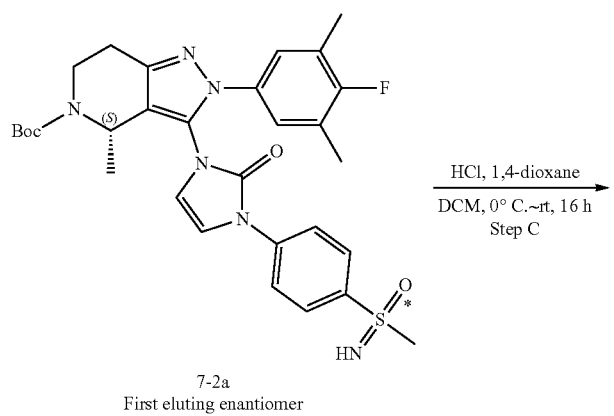
7-2a
First eluting enantiomer
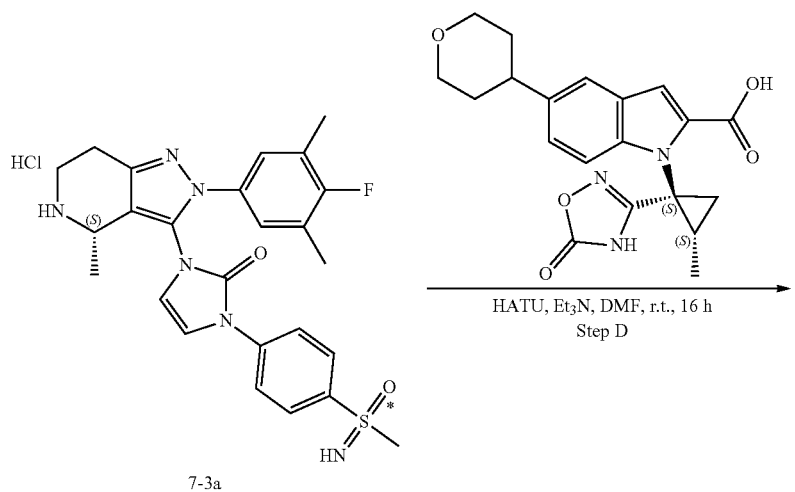
7-3a
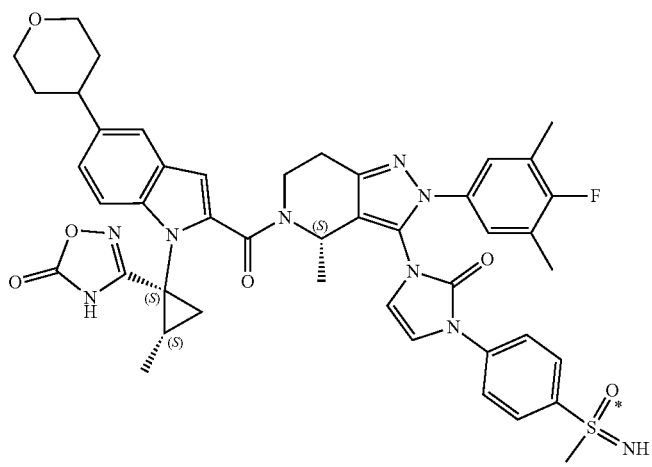
Compound 114

-continued
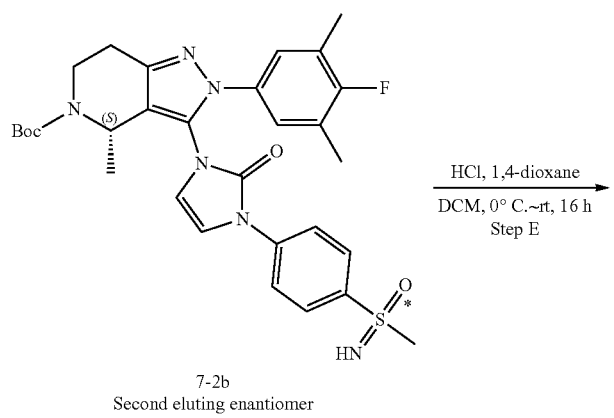
7-2b
Second eluting enantiomer
HCl, 1,4-dioxane
DCM, 0° C.~rt, 16 h
Step E
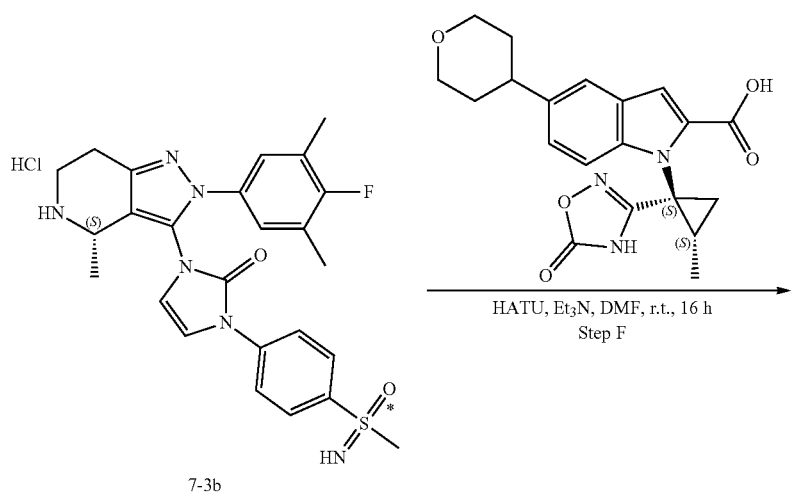
7-3b
HATU, Et₃N, DMF, r.t., 16 h
Step F
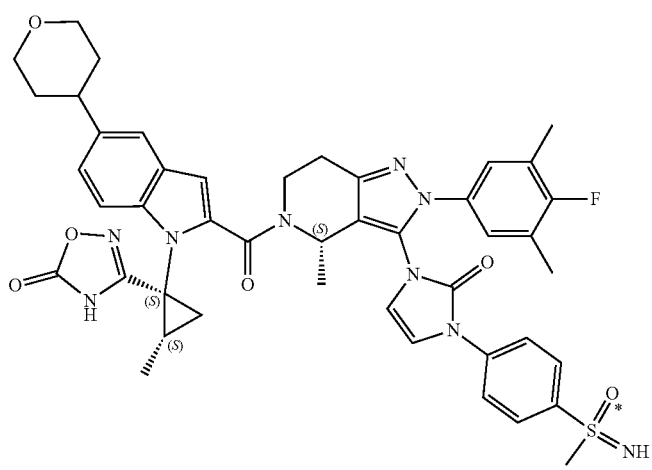
Compound 115

Step A tert-butyl(4S)-3-(3-{4-[azanylidene(methyl)(oxo)-λ⁶-sulfanyl]phenyl}-2-oxoimidazol-1-yl)-2-(4-fluoro-3,5-dimethylphenyl)-4-methyl-4,5,6,7-tetrahydropyrazolo[4,3-c]pyridine-5-carboxylate

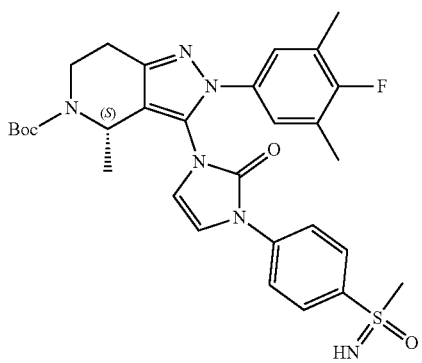

To a solution of 1-bromo-4-(S-methylsulfonimidoyl)benzene (400 mg, 1.709 mmol) in NMP (30 mL) was added tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (754 mg, 1.709 mmol), (1S,2S)-N1,N2-dimethylcyclohexane-1,2-diamine (97 mg, 0.683 mmol) and K₂CO₃ (708 mg, 5.126 mmol), CuI (65 mg, 0.342 mmol). The reaction mixture was stirred at 130° C. for 3 h. After cooling and concentration, the residue was purified by flash silica gel chromatography (Silica Flash Column, Eluent of 0~50% EtOAc/PE gradient) to give tert-butyl(4S)-3-(3-{4-[azanylidene(methyl)(oxo)-λ⁶-sulfanyl]phenyl}-2-oxoimidazol-1-yl)-2-(4-fluoro-3,5-dimethylphenyl)-4-methyl-4,5,6,7-tetrahydropyrazolo[4,3-c]pyridine-5-carboxylate (1000 mg, 98.4% yield). LC-MS: m/z 595.3 (M+H)⁺.

Step B tert-butyl(4S)-2-(4-fluoro-3,5-dimethylphenyl)-3-(3-{4-[azanylidene(methyl)(oxo)-λ⁶-sulfanyl]phenyl}-2-oxoimidazol-1-yl)-4-methyl-4,5,6,7-tetrahydropyrazolo[4,3-c]pyridine-5-carboxylate 7-2a (first eluting enantiomer) and tert-butyl(4S)-2-(4-fluoro-3,5-dimethylphenyl)-3-(3-{4-[azanylidene(methyl)(oxo)-λ⁶-sulfanyl]phenyl}-2-oxoimidazol-1-yl)-4-methyl-4,5,6,7-tetrahydropyrazolo[4,3-c]pyridine-5-carboxylate 7-2b (second eluting enantiomer)

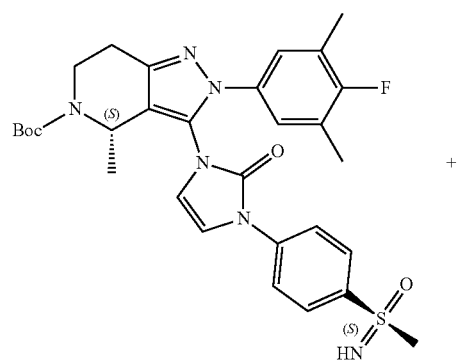

+

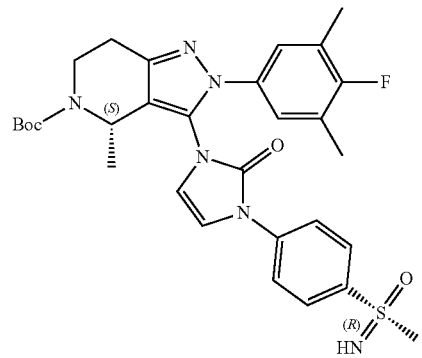

The compound mixture tert-butyl(4S)-3-(3-{4-[azanylidene(methyl)(oxo)-λ⁶-sulfanyl]phenyl}-2-oxoimidazol-1-yl)-2-(4-fluoro-3,5-dimethylphenyl)-4-methyl-4,5,6,7-tetrahydropyrazolo[4,3-c]pyridine-5-carboxylate (1.20 g, 2.02 mmol) was separated by SFC (Column: DAICELCHIRAL-CEL® IC 250*25 mm 10 m, Mobile phase A (Supercritical CO2), Mobile phase B (MeOH (0.1% 7.0 M ammonia in MeOH)), Gradient: A/B=45/55, Flow rate: 70 mL/min) to afford tert-butyl(4S)-2-(4-fluoro-3,5-dimethylphenyl)-3-(3-{4-[(S)-azanylidene(methyl)(oxo)-λ⁶-sulfanyl]phenyl}-2-oxoimidazol-1-yl)-4-methyl-4,5,6,7-tetrahydropyrazolo[4,3-c]pyridine-5-carboxylate 7-2a (307 mg, 25.6% yield) as the fast eluent (Rt=6.03 min), LC-MS: m/z 595.3 (M+H)⁺. And tert-butyl(4S)-2-(4-fluoro-3,5-dimethylphenyl)-3-(3-{4-[(R)-azanylidene(methyl)(oxo)-λ⁶-sulfanyl]phenyl}-2-oxoimidazol-1-yl)-4-methyl-4,5,6,7-tetrahydropyrazolo[4,3-c]pyridine-5-carboxylate 7-2b (260 mg, 6.8% yield) as the slow eluent (Rt=7.85 min), LC-MS: m/z 595.3 (M+H)⁺.

Step C 1-[(4S)-2-(4-fluoro-3,5-dimethylphenyl)-4-methyl-4,5,6,7-tetrahydropyrazolo[4,3-c]pyridin-3-yl]-3-{4-[azanylidene(methyl)(oxo)-λ⁶-sulfanyl]phenyl}-2,3-dihydro-1H-imidazol-2-one hydrochloride salt 7-3a To a solution of tert-butyl(4S)-2-(4-fluoro-3,5-dimethylphenyl)-3-(3-{4-azanylidene(methyl)(oxo)-λ⁶-sulfanyl]phenyl}-2-oxoimidazol-1-yl)-4-methyl-4,5,6,7-tetrahydropyrazolo[4,3-c]pyridine-5-carboxylate 7-2a (60 mg, 0.101 mmol) in DCM (10 mL) was added 4.0 M HCl (gas) in 1,4-dioxane HCl (0.25 mL) at 0° C. The reaction mixture was stirred at room temperature for 16 h. Then it was concentrated to afford 1-[(4S)-2-(4-fluoro-3,5-dimethylphenyl)-4-methyl-4,5,6,7-tetrahydropyrazolo[4,3-c]pyridin-3-yl]-3-{4-[azanylidene(methyl)(oxo)-λ⁶-sulfanyl]phenyl}-2,3-dihydro-1H-imidazol-2-one hydrochloride salt 7-3a (50 mg, 99% yield). LC-MS: m/z 495.3 (M+H)⁺.

Step D 3-[(1S,2S)-1-(2-{[(4S)-2-(4-fluoro-3,5-dimethylphenyl)-3-(1-{4-[azanylidene(methyl)(oxo)-λ⁶-sulfanyl]phenyl}-2-oxoimidazol-3-yl)-4-methyl-4,5,6,7-tetrahydropyrazolo [4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 114)

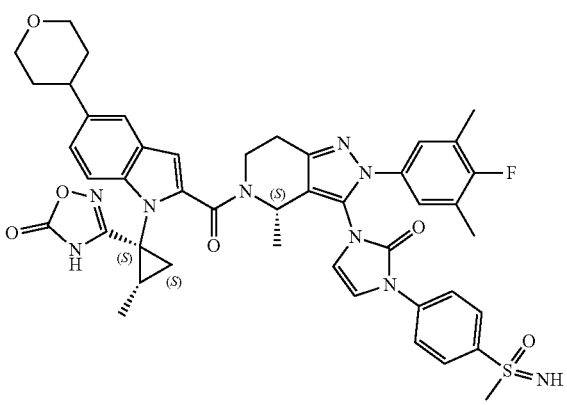

Enantiomer 1

To a solution of 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (38.8 mg, 0.101 mmol) and 1-[(4S)-2-(4-fluoro-3,5-dimethylphenyl)-4-methyl-4,5,6,7-tetrahydropyrazolo[4,3-c]pyridin-3-yl]-3-{4-[azanylidene(methyl)(oxo)-λ⁶-sulfanyl]phenyl}-2,3-dihydro-1H-imidazol-2-one hydrochloride salt 7-3a (50 mg, 0.101 mmol) in DMF (2 mL), was added Et₃N (0.028 mL, 0.202 mmol) and HATU (58 mg, 0.152 mmol). The reaction mixture was stirred at room temperature for 16 h. After filtration, the solution was purified by prep. HPLC (Column: Sunfire C18 19*250 mm*10 μm; Mobile Phase A: Water (0.1% formic acid), B: CH₃CN; Flow rate: 20 mL/min; Gradient: 58% B to 68% B; Retention Time: 8.7 min) to obtain 3-[(1S,2S)-1-(2-{[(4S)-2-(4-fluoro-3,5-dimethylphenyl)-3-(1-{4-[azanylidene(methyl)(oxo)-λ⁶-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (enantiomer 1) (33.3 mg, 38.3% yield). LC-MS: m/z 860.4 (M+H)⁺. ¹H NMR (400 MHz, DMSO-d6) δ 8.00-7.87 (m, 4H), 7.53 (s, 1H), 7.44 (d, J=8.4 Hz, 1H), 7.34-7.27 (m, 3H), 7.15 (d, J=6.0 Hz, 2H), 6.93-6.87 (m, 2H), 5.62-5.45 (m, 1H), 4.63-4.51 (m, 1H), 3.99-3.97 (m, 2H), 3.63-3.60 (m, 4H), 3.11 (s, 3H), 2.91-2.86 (m, 3H), 2.21 (s, 6H), 1.78-1-62 (m, 7H), 1.44 (brs, 3H), 1.18 (brs, 3H).

Step E 1-[(4S)-2-(4-fluoro-3,5-dimethylphenyl)-4-methyl-4,5,6,7-tetrahydropyrazolo[4,3-c]pyridin-3-yl]-3-{4-[-azanylidene(methyl)(oxo)-λ⁶-sulfanyl]phenyl}-2,3-dihydro-1H-imidazol-2-one hydrochloride salt 7-3b To a solution of tert-butyl(4S)-2-(4-fluoro-3,5-dimethylphenyl)-3-(3-{4-[azanylidene(methyl)(oxo)-λ⁶-sulfanyl]phenyl}-2-oxoimidazol-1-yl)-4-methyl-4,5,6,7-tetrahydropyrazolo[4,3-c]pyridine-5-carboxylate 7-3a (60 mg, 0.101 mmol) in DCM (10 mL) was added 4.0 M HCl (gas) in 1,4-dioxane HCl (0.25 mL) at 0° C. The reaction mixture was stirred at room temperature for 16 h. Then it was concentrated to afford 1-[(4S)-2-(4-fluoro-3,5-dimethylphenyl)-4-methyl-4,5,6,7-tetrahydropyrazolo[4,3-c]pyridin-3-yl]-3-{4-[azanylidene(methyl)(oxo)-λ⁶-sulfanyl]phenyl}-2,3-dihydro-1H-imidazol-2-one hydrochloride salt 7-3b (55 mg, 100% yield). LC-MS: m/z 495.3 (M+H)⁺.

Step F 3-[(1S,2S)-1-(2-{[(4S)-2-(4-fluoro-3,5-dimethylphenyl)-3-(1-{4-[azanylidene(methyl)(oxo)-λ⁶-sulfanyl]phenyl}-2-oxoimidazol-3-yl)-4-methyl-4,5,6,7-tetrahydropyrazolo [4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 115)

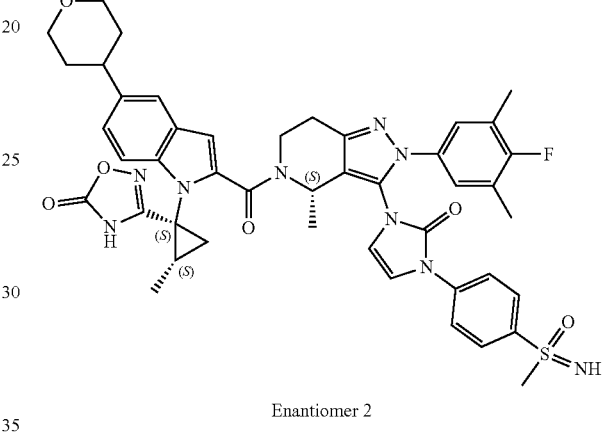

Enantiomer 2

To a solution of 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (42.64 mg, 0.111 mmol) and 1-[(4S)-2-(4-fluoro-3,5-dimethylphenyl)-4-methyl-4,5,6,7-tetrahydropyrazolo[4,3-c]pyridin-3-yl]-3-{4-[azanylidene(methyl)(oxo)-λ⁶-sulfanyl]phenyl}-2,3-dihydro-1H-imidazol-2-one hydrochloride salt 7-3b (55 mg, 0.111 mmol) in DMF (2 mL), were added HATU (63 mg, 0.167 mmol) and Et₃N (0.03 mL, 0.222 mmol). The reaction mixture was stirred at room temperature for 16 h. After filtration, the solution was purified by prep. HPLC (Column: Sunfire C18 19*250 mm*10 μm; Mobile Phase A: Water (0.1% formic acid), B: CH₃CN; Flow rate: 20 mL/min; Gradient: 62% B to 62% B; Retention Time: 8.1 min) to obtain 3-[(1S,2S)-1-(2-{[(4S)-2-(4-fluoro-3,5-dimethylphenyl)-3-(1-{4-[azanylidene(methyl)(oxo)-λ⁶-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (enantiomer 2) (15.3 mg, 16.0% yield). LC-MS: m/z 860.4 (M+H)⁺. ¹H NMR (400 MHz, DMSO-d6) δ 11.73 (brs, 1H), 8.00-7.80 (m, 4H), 7.53 (s, 1H), 7.44 (d, J=8.4 Hz, 1H), 7.33-7.27 (m, 3H), 7.15 (d, J=6.4 Hz, 2H), 6.92-6.88 (m, 2H), 5.62-5.45 (m, 1H), 4.63-4.51 (m, 1H), 3.99-3.97 (m, 2H), 3.63-3.60 (m, 4H), 3.11 (s, 3H), 2.91-2.86 (m, 3H), 2.21 (s, 6H), 1.78-1-62 (m, 7H), 1.44 (brs, 3H), 1.18 (brs, 3H).

Example compounds 116 and 117, 132 and 133, 134 and 135, 136 and 137, 138 and 139, 140 and 141 were synthesized using a similar procedure described in the Example A7 above using the appropriate materials.

Example A8

3-[(1S,2S)-1-(2-{[(4S)-2-(4-fluoro-3,5-dimethylphenyl)-3-(1-{4-[(S)-methyl(methylazanylidene)(oxo)-$\lambda^6$-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one and 3-[(1S,2S)-1-(2-{[(4S)-2-(4-fluoro-3,5-dimethylphenyl)-3-(1-{4-[(R)-methyl(methylazanylidene)(oxo)-$\lambda^6$-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compounds 112 and 121)

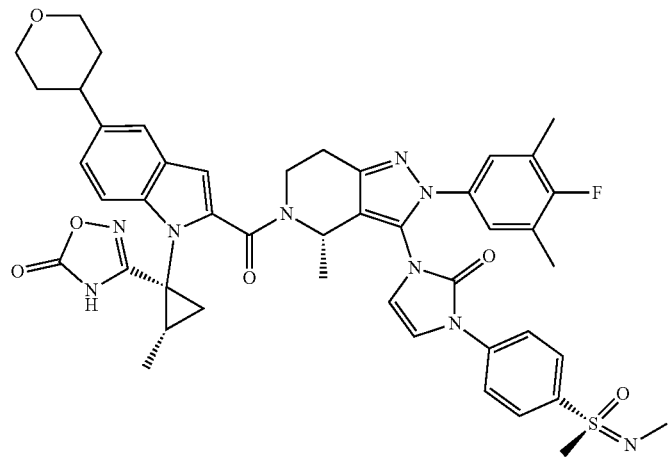

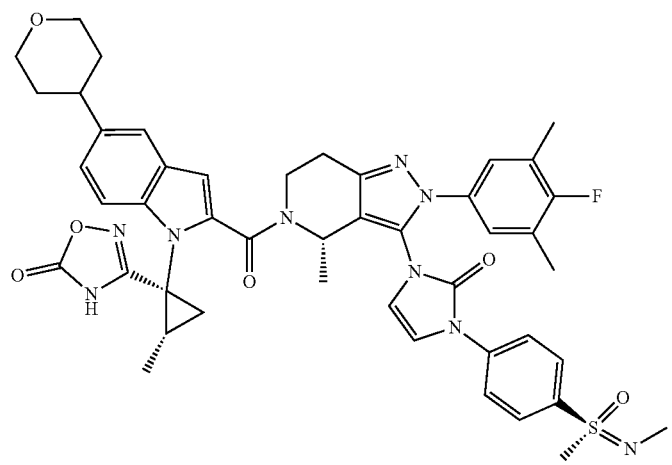

-continued
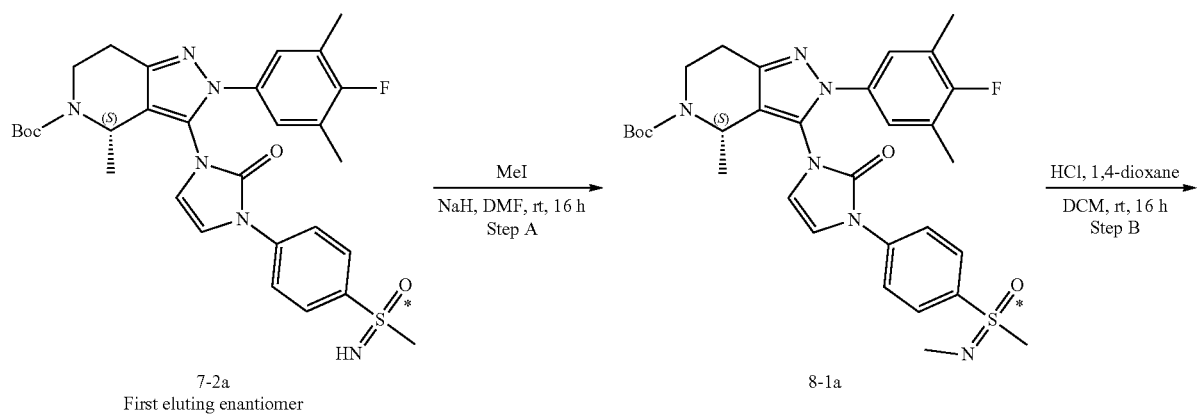
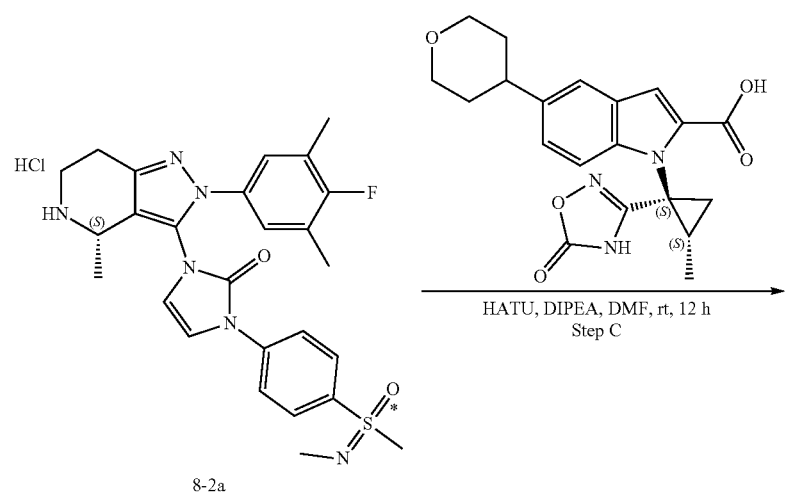
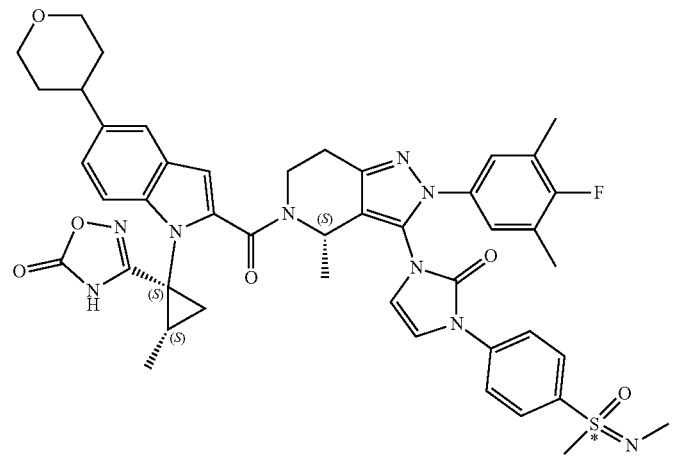

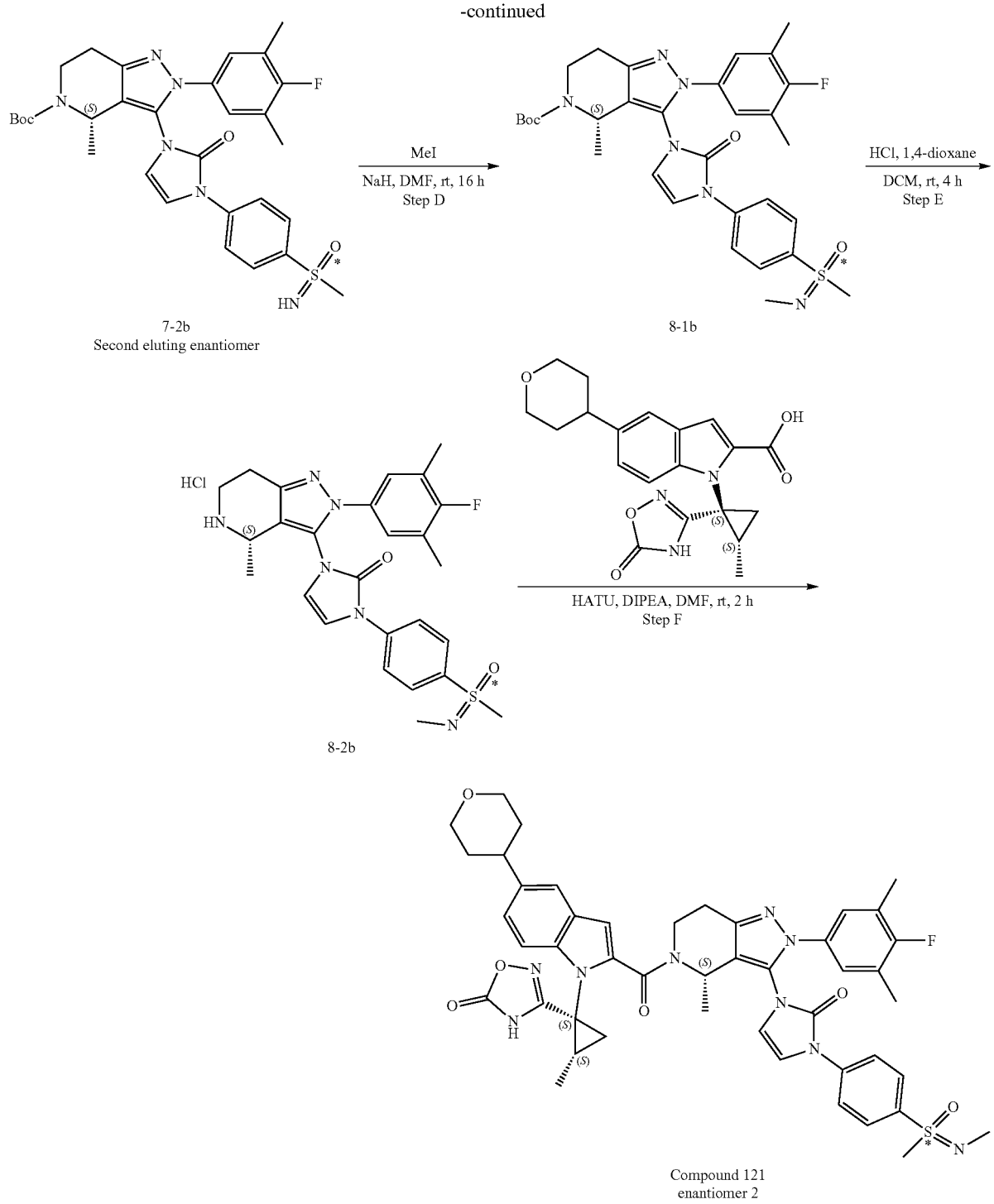

-continued 7-2b
Second eluting enantiomer 8-1b 8-2b

Compound 121
enantiomer 2

Step A tert-butyl(4S)-2-(4-fluoro-3,5-dimethylphenyl)-3-(3-{4-[methyl(methylazanylidene)(oxo)-λ⁶-sulfanyl]phenyl}-2-oxoimidazol-1-yl)-4-methyl-4,5,6,7-tetrahydropyrazolo[4,3-c]pyridine-5-carboxylate 8-1a To a solution of tert-butyl(4S)-2-(4-fluoro-3,5-dimethylphenyl)-3-(3-{4-[azanylidene(methyl)(oxo)-λ⁶-sulfanyl]phenyl}-2-oxoimidazol-1-yl)-4-methyl-4,5,6,7-tetrahydropyrazolo[4,3-c]pyridine-5-carboxylate 7-2a (80 mg, 0.135 mmol) in DMF (5 mL) was added NaH (10.8 mg, 0.269 mmol, 60% in oil) at rt. After being stirred at rt for 0.5 h, then iodomethane (0.025 mL, 0.404 mmol) was added. The resulting mixture was stirred at rt for another 16 h. The mixture was poured into water (50 mL), extracted with EtOAc (50 mL×2). The combined organic layer was washed with brine, dried over Na₂SO₄, filtered and the residue was concentrated to obtain tert-butyl(4S)-2-(4-fluoro-3,5-dimethylphenyl)-3-(3-{4-[methyl(methylazanylidene)(oxo)-λ⁶-sulfanyl]phenyl}-2-oxoimidazol-1-yl)-4-methyl-4,5,6,7-tetrahydropyrazolo[4,3-c]pyridine-5-carboxylate 8-la (80 mg, 97.7% yield). LC-MS: m/z 609.3 (M+H)+.

Step B 1-[(4S)-2-(4-fluoro-3,5-dimethylphenyl)-4-methyl-4,5,6,7-tetrahydropyrazolo[4,3-c]pyridin-3-yl]-3-{4-[methyl(methylazanylidene)(oxo)-λ⁶-sulfanyl]phenyl}-2,3-dihydro-1H-imidazol-2-one hydrochloride salt 8-2a The mixture of tert-butyl(4S)-2-(4-fluoro-3,5-dimethylphenyl)-3-(3-{4-[methyl(methylazanylidene)(oxo)-λ⁶-sulfanyl]phenyl}-2-oxoimidazol-1-yl)-4-methyl-4,5,6,7-tetrahydropyrazolo[4,3-c]pyridine-5-carboxylate 8-la (40 mg, 0.066 mmol) and 4 M HCl (gas) in 1,4-dioxane solution (0.2 mL) in DCM (1 mL) was stirred at rt for 16 h. The mixture was concentrated to obtain 1-(4-(N, dimethylsulfonimidoyl)phenyl)-3-((S)-2-(4-fluoro-3,5-dimethylphenyl)-4-methyl-4,5,6,7-tetrahydro-2H-pyrazolo[4,3-c]pyridin-3-yl)-1,3-dihydro-2H-imidazol-2-one hydrochloride salt 8-2a (35 mg, 97.7% yield). LC-MS: m/z 509.2 (M+H)+.

Step C 3-[(1S,2S)-1-(2-{[(4S)-2-(4-fluoro-3,5-dimethylphenyl)-3-(1-{4-[methyl(methylazanylidene)(oxo)-λ⁶-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (enantiomer 1) (Compound 112)

The mixture of 1-(4-(N, dimethylsulfonimidoyl)phenyl)-3-((S)-2-(4-fluoro-3,5-dimethylphenyl)-4-methyl-4,5,6,7-tetrahydro-2H-pyrazolo[4,3-c]pyridin-3-yl)-1,3-dihydro-2H-imidazol-2-one hydrochloride salt 8-2a (70 mg, 0.128 mmol), 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (49.2 mg, 0.128 mmol), HATU (97.6 mg, 0.257 mmol) and DIPEA (49.7 mg, 0.385 mmol) in DMF (2 mL) was stirred at rt for 12 h. The mixture was purified by prep. HPLC (Column: XBridge C18 19*250 mm*10 μm; Mobile Phase A: Water (0.05% NH₃·H₂O), B: CH₃CN; Flow rate: 20 mL/min; Gradient: 27% B to 34% B; Retention Time: 8.85-10.03 min) to obtain 3-[(1S,2S)-1-(2-{[(4S)-2-(4-fluoro-3,5-dimethylphenyl)-3-(1-{4-[-methyl(methylazanylidene)(oxo)-λ⁶-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (enantiomer 1) (51.5 mg, 45.9% yield). LC-MS: m/z 874.4 (M+H)+. ¹H NMR (400 MHz, DMSO-d6) δ 8.02-7.92 (m, 3H), 7.85 (s, 1H), 7.56-7.35 (m, 3H), 7.28-7.06 (m, 4H), 6.98-6.79 (m, 1H), 6.59-6.50 (m, 1H), 5.71-5.56 (m, 1H), 4.44-4.32 (m, 1H), 4.02-3.92 (m, 2H), 3.65-3.50 (m, 1H), 3.47-3.39 (m, 3H), 3.14 (s, 3H), 3.10-3.08 (m, 1H), 2.91-2.79 (m, 2H), 2.48 (s, 3H), 2.19 (s, 6H), 1.83-1.70 (m, 4H), 1-65-1.56 (m, 1H), 1.40-1.32 (m, 1H), 1.25-1.05 (m, 7H).

Step D tert-butyl(4S)-2-(4-fluoro-3,5-dimethylphenyl)-3-(3-{4-[methyl(methylazanylidene)(oxo)-λ⁶-sulfanyl]phenyl}-2-oxoimidazol-1-yl)-4-methyl-4,5,6,7-tetrahydropyrazolo [4,3-c]pyridine-5-carboxylate The mixture of tert-butyl(4S)-2-(4-fluoro-3,5-dimethylphenyl)-3-(3-{4-[-azanylidene(methyl)(oxo)-λ⁶-sulfanyl]phenyl}-2-oxoimidazol-1-yl)-4-methyl-4,5,6,7-tetrahydropyrazolo[4,3-c]pyridine-5-carboxylate 7-2b (50 mg, 0.084 mmol) in DMF (4 mL) was added NaH (4.0 mg, 0.101 mmol, 60% in oil) and MeI (11.93 mg, 0.084 mmol). The reaction mixture was stirred at rt for 16 h under N₂. Then reaction was quenched with water (50 ml), extracted with EtOAc (50 ml). The organic layer was washed with brine, dried over Na₂SO₄ and concentrated to afford tert-butyl(4S)-2-(4-fluoro-3,5-dimethylphenyl)-3-(3-{4-[methyl(methylazanylidene)(oxo)-λ⁶-sulfanyl]phenyl}-2-oxoimidazol-1-yl)-4-methyl-4,5,6,7-tetrahydropyrazolo[4,3-c]pyridine-5-carboxylate 8-lb (67 mg, crude). LC-MS: m/z 609.0 (M+H)+.

Step E 1-[(4S)-2-(4-fluoro-3,5-dimethylphenyl)-4-methyl-4,5,6,7-tetrahydropyrazolo[4,3-c]pyridin-3-yl]-3-{4-[methyl(methylazanylidene)(oxo)-λ⁶-sulfanyl]phenyl}-2,3-dihydro-1H-imidazol-2-one hydrochloride salt 8-2b The mixture of tert-butyl(4S)-2-(4-fluoro-3,5-dimethylphenyl)-3-(3-{4-[methyl(methylazanylidene)(oxo)-λ⁶-sulfanyl]phenyl}-2-oxoimidazol-1-yl)-4-methyl-4,5,6,7-tetrahydropyrazolo[4,3-c]pyridine-5-carboxylate 8-1b (67 mg, 0.110 mmol) in DCM (4 mL) was added 4 M HCl (gas) in dioxane (0.27 mL). The reaction mixture was stirred rt for 4 h under N₂. The reaction mixture was concentrated to afford 1-[(4S)-2-(4-fluoro-3,5-dimethylphenyl)-4-methyl-4,5,6,7-tetrahydropyrazolo[4,3-c]pyridin-3-yl]-3-{4-[methyl(methylazanylidene)(oxo)-λ⁶-sulfanyl]phenyl}-2,3-dihydro-1H-imidazol-2-one hydrochloride salt 8-2b (67 mg, crude). LC-MS: m/z 509.0 (M+H)+.

Step F 3-[(1S,2S)-1-(2-{[(4S)-2-(4-fluoro-3,5-dimethylphenyl)-3-(1-{4-[methyl(methylazanylidene)(oxo)-λ⁶-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (enantiomer 2) (Compound 121)

To a solution of 1-[(4S)-2-(4-fluoro-3,5-dimethylphenyl)-4-methyl-4,5,6,7-tetrahydropyrazolo[4,3-c]pyridin-3-yl]-3-{4-[methyl(methylazanylidene)(oxo)-λ⁶-sulfanyl]phenyl}-2,3-dihydro-1H-imidazol-2-one hydrochloride salt 8-2b (67 mg, 0.132 mmol) in DMF (2 mL) was added 1-[(1S,2S)-2-methyl-1-(5-oxo-4H-1,2,4-oxadiazol-3-yl)cyclopropyl]-5-(3,4,5,6-tetrahydro-2H-pyran-4-yl)indole-2-carboxylic acid (76 mg, 0.198 mmol), DIPEA (85 mg, 0.659 mmol), HATU (75 mg, 0.198 mmol). The reaction mixture was stirred at rt for 2 h under N₂. The reaction mixture was purified using prep. HPLC (Column: Sunfire C18 19*250 mm*10 lm; Mobile Phase A: Water (0.1% formic acid), B: CH₃CN; Flow rate: 20 mL/min; Gradient: 31% B to 41% B; Retention Time: 8.0-9.5 min) to afford 3-[(1S,2S)-1-(2-{[(4S)-2-(4-fluoro-3,5-dimethylphenyl)-3-(1-{4-[(R)-methyl(methylazanylidene)(oxo)-λ⁶-sulfanyl]phenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (enantiomer 2) (11.3 mg, 9.8% yield). LC-MS: m/z 874.5 (M+H)+. ¹H NMR (400 MHz, DMSO-d6) δ 8.01-7.91 (m, 3H), 7.85-7.76 (m, 1H), 7.51-7.40 (m, 2H), 7.41 (d, J=8.0 Hz, 1H), 7.29-7.23 (m, 1H), 7.17-7.09 (m, 3H), 6.98-6.82 (m, 1H), 5.63-5.56 (m, 1H), 4.46-4.32 (m, 1H), 3.97 (d, J=8.0 Hz, 2H), 3.71-3.53 (m, 1H), 3.50-3.36 (m, 3H), 3.13-3.09 (m, 3H), 2.94-2.84 (m, 2H), 2.12 (s, 6H), 1.80-1-65 (m, 7H), 1-65-1.56 (m, 1H), 1.41-1.37 (m, 2H), 1.31-1.27 (m, 1H), 1.17-1.01 (m, 3H).

Example compounds 113 and 122, 144, 148, 149 and 150, 151 and 152 were synthesized using a similar procedure described in the Example A8 above using the appropriate materials, e.g., in step D.

Example A9

3-[(1S,2S)-1-(2-{[(S)-2-(4-fluoro-3,5-xylyl)-3-{3-[4-(iminomethyloxothio)-3-(methylamino)phenyl]-2-oxo-1,3-dihydro-1-imidazolyl}-4-methyl-4,5,6,7-tetrahydro-2H-1,2,5-triazainden-5-yl]carbonyl}-5-(tetrahydro-2H-pyran-4-yl)-1-indolyl)-2-methylcyclopropyl]-1,2,4-oxadiazol-5(4H)-one (Compound 105)

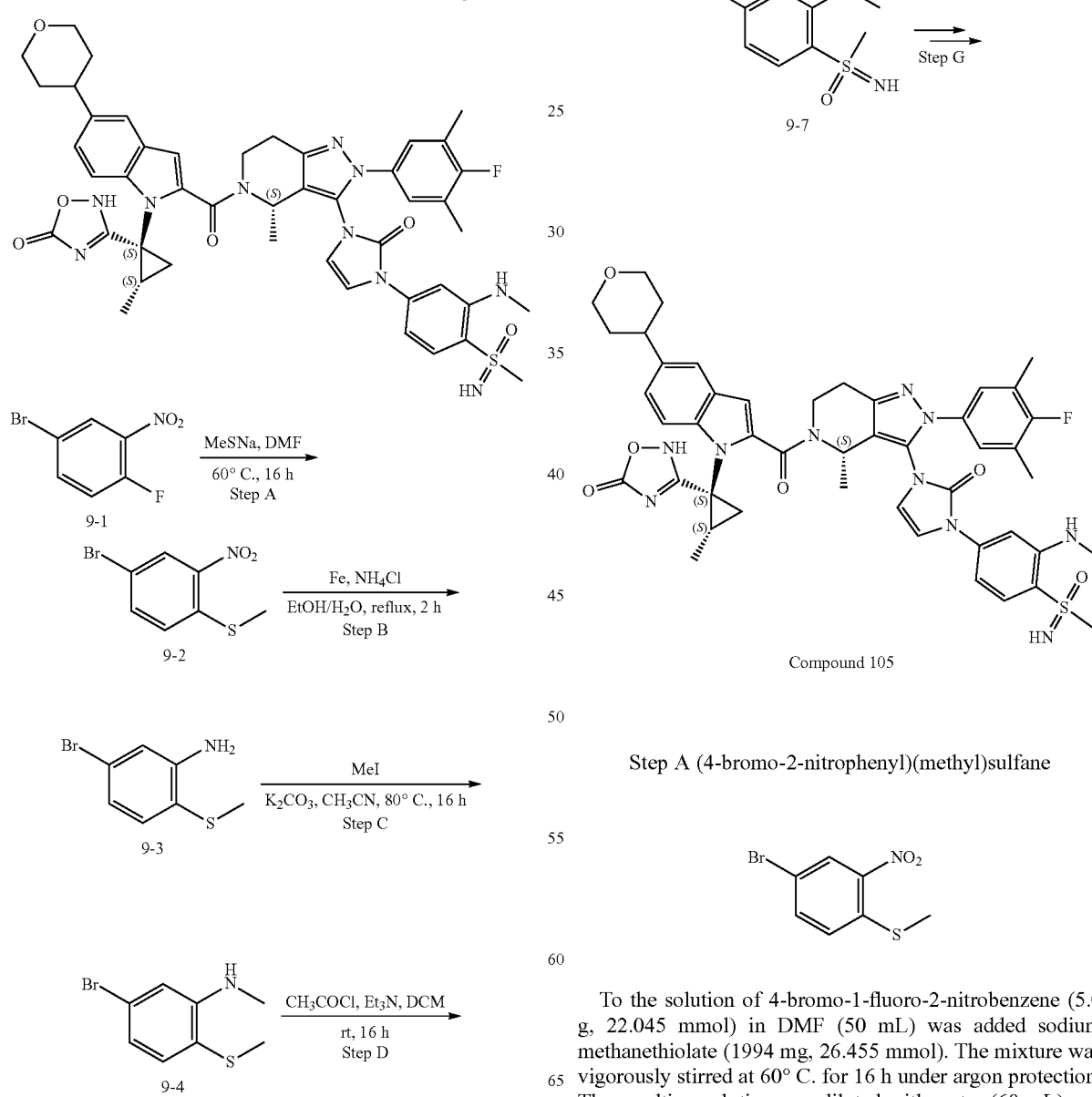

Step A (4-bromo-2-nitrophenyl)(methyl)sulfane

To the solution of 4-bromo-1-fluoro-2-nitrobenzene (5.0 g, 22.045 mmol) in DMF (50 mL) was added sodium methanethiolate (1994 mg, 26.455 mmol). The mixture was vigorously stirred at 60° C. for 16 h under argon protection. The resulting solution was diluted with water (60 mL) and extracted by dichloromethane (60 mL×3). The combined organic layer was washed with brine, dried over Na₂SO₄, filtered and concentrated. The residue was purified by flash silica gel chromatography (Silica Flash Column, Eluent of 100% PE) to (4-bromo-2-nitrophenyl)(methyl)sulfane (2.7 g, 49.6% yield). ¹H NMR (400 MHz, DMSO-d6) δ 8.37 (d, J=2.0 Hz, 1H), 7.93 (dd, J₁=8.8 Hz, J₂=2.4 Hz, 1H), 7.54 (d, J=8.4 Hz, 1H), 2.82 (s, 3H).

Step B 5-bromo-2-(methylthio)aniline

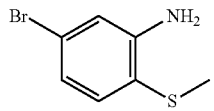

To a solution of (4-bromo-2-nitrophenyl)(methyl)sulfane (2.33 g, 9.392 mmol) in EtOH/H₂O (50 mL/7 mL) was added Fe powder (2.62 g, 55.84 mmol) and NH₄Cl (5.02 g, 93.92 mmol). The mixture was stirred at 75° C. for 2 h. After cooling, the mixture was diluted with EtOAc (100 mL) and water (50 mL). The organic layer was separated, washed with brine, dried over Na₂SO₄ and concentrated to afford 5-bromo-2-(methylthio)aniline (2.16 g, crude). LC-MS: m/z 218.0 (M+H)⁺.

Step C 5-bromo-N-methyl-2-(methylthio)aniline

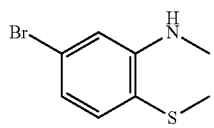

To a solution of 5-bromo-2-(methylthio)aniline (380 mg, 1.742 mmol) in CH₃CN (15 mL) was added iodomethane (0.21 mL, 2.613 mmol) and K₂CO₃ (482 mg, 3.484 mmol). The reaction mixture was stirred at 80° C. for 16 h. After cooling, the mixture was diluted with EtOAc (100 mL) and water (50 mL). The organic layer was separated, washed with brine, dried with Na₂SO₄ and concentrated. The residue was purified by flash silica gel chromatography (Silica Flash Column, Eluent of 0-15% EtOAc/PE gradient) to afford the title compound 5-bromo-N-methyl-2-(methylthio)aniline (230 mg, 56.9% yield). LC-MS: m/z 232.0 (M+H)⁺.

Step D N-(5-bromo-2-(methylthio)phenyl)-N-methylacetamide

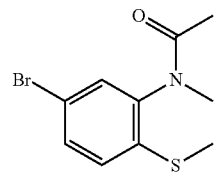

To the mixture of 5-bromo-2-(methylsulfanyl)phenyl](methyl)amine (1.20 g, 5.062 mmol) and TEA (2.11 mL, 15.185 mmol) in DCM (10.0 mL) at 0° C., was added CH₃COCl (0.72 mL, 10.12 mmol). After addition, the reaction mixture was warmed to room temperature and stirred for 16 h. The reaction was quenched with water (50 mL), extracted with EtOAc (50 mL×2). The organic layer was washed with brine, dried over Na₂SO₄ and concentrated. The residue was purified by flash silica gel chromatography (Silica Flash Column, Eluent of 0~10% EtOAc/PE gradient) to afford N-(5-bromo-2-(methylthio)phenyl)-N-methylacetamide (1.0 g, 72.3% yield). LC-MS: m/z 274.0 (M+H)⁺.

Step E N-(5-bromo-2-(S-methylsulfonimidoyl)phenyl)-N-methylacetamide

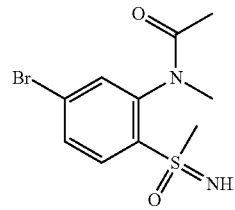 [SMILES: CC(=O)N(C)c1cc(Br)ccc1S(C)(=N)=O]

To a solution of N-(5-bromo-2-(methylthio)phenyl)-N-methylacetamide (1.0 g, 3.66 mmol) in MeOH (10 mL) was added PhI(OAc)₂ (2.36 g, 7.29 mmol) and H₂NCO₂NH₄ (570 mg, 7.29 mmol). The reaction mixture was stirred at rt for 2 h under N₂. The mixture was poured into water (100 mL), extracted with DCM (100 mL×2). The combined organic layer was washed with brine, dried over Na₂SO₄, filtered and concentrated. The residue was purified by flash silica gel chromatography (Silica Flash Column, Eluent of 0-5% MeOH/DCM gradient) to afford N-(5-bromo-2-(S-methylsulfonimidoyl)phenyl)-N-methylacetamide (300 mg, 26.9% yield). LC-MS: m/z 305.1 (M+H)⁺.

Step F N-(5-bromo-2-(S-methylsulfonimidoyl)phenyl)-N-methylacetamide

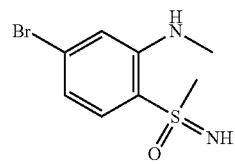

411

To a solution of N-(5-bromo-2-(S-methylsulfonimidoyl)phenyl)-N-methylacetamide (220 mg, 0.721 mmol) in MeOH (5 mL) was added K$_2$CO$_3$ (399 mg, 2.883 mmol). The mixture was stirred at 70° C. for 16 h under N$_2$ in a sealed tube. After cooling, the mixture was poured into water (100 mL), extracted with DCM (100 mL×2). The combined organic layer was washed with brine, dried over sodium sulfate, filtered and concentrated to obtain N-(5-bromo-2-(S-methylsulfonimidoyl)phenyl)-N-methylacetamide (134 mg, 70.6% yield). LC-MS: m/z 263.0 (M+H)$^+$.

Step G 3-[(1S,2S)-1-(2-{[(S)-2-(4-fluoro-3,5-xylyl)-3-{3-[4-(iminomethyloxothio)-3-(methylamino)phenyl]-2-oxo-1,3-dihydro-1-imidazolyl}-4-methyl-4,5,6,7-tetrahydro-2H-1,2,5-triazainden-5-yl]carbonyl}-5-(tetrahydro-2H-pyran-4-yl)-1-indolyl)-2-methylcyclopropyl]-1,2,4-oxadiazol-5(4H)-one (Compound 105)

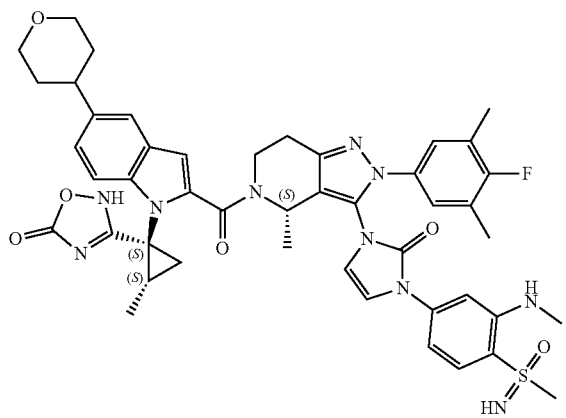

3-[(1S,2S)-1-(2-{[(S)-2-(4-fluoro-3,5-xylyl)-3-{3-[4-(iminomethyloxothio)-3-(methylamino)phenyl]-2-oxo-1,3-dihydro-1-imidazolyl}-4-methyl-4,5,6,7-tetrahydro-2H-1,2,5-triazainden-5-yl]carbonyl}-5-(tetrahydro-2H-pyran-4-yl)-1-indolyl)-2-methylcyclopropyl]-1,2,4-oxadiazol-5(4H)-one (Compound 105) was synthesized according to the procedures described for the preparation of Example A2 (step B to D) by using N-(5-bromo-2-(S-methylsulfonimidoyl)phenyl)-N-methylacetamide in step B. LC-MS: m/z 889.4 (M+H)$^+$. (400 MHz, DMSO-d6) δ 7.74 (s, 1H), 7.52 (s, 1H), 7.44 (d, J=8.4 Hz, 1H), 7.28-7.26 (m, 2H), 7.15 (d, J=6.0 Hz, 2H), 7.06 (s, 1H), 6.87 (s, 1H), 5.67-5.39 (m, 1H), 4.50 (brs, 1H), 3.52-3.43 (m, 4H), 3.01 (s, 3H), 2.91-2.75 (m, 3H), 2.22 (s, 6H), 1.78-1-68 (m, 7H), 1.43 (s, 3H), 1.17 (brs, 3H).

412

Example A10

(4S)-2-(4-fluoro-3,5-dimethylphenyl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-3-(3-{4-[(1S)-1-oxo-1λ$^6$-4H,3H,5H-1,2-thiazol-1-yl]phenyl}-2-oxoimidazol-1-yl)-4-methyl-4,5,6,7-tetrahydropyrazolo[4,3-c]pyridine and (4S)-2-(4-fluoro-3,5-dimethylphenyl)-3-(3-{4-[(1R)-1-oxo-1λ$^6$-4H,3H,5H-1,2-thiazol-1-yl]phenyl}-2-oxoimidazol-1-yl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-4-methyl-4,5,6,7-tetrahydropyrazolo[4,3-c]pyridine (Compounds 142 and 143)

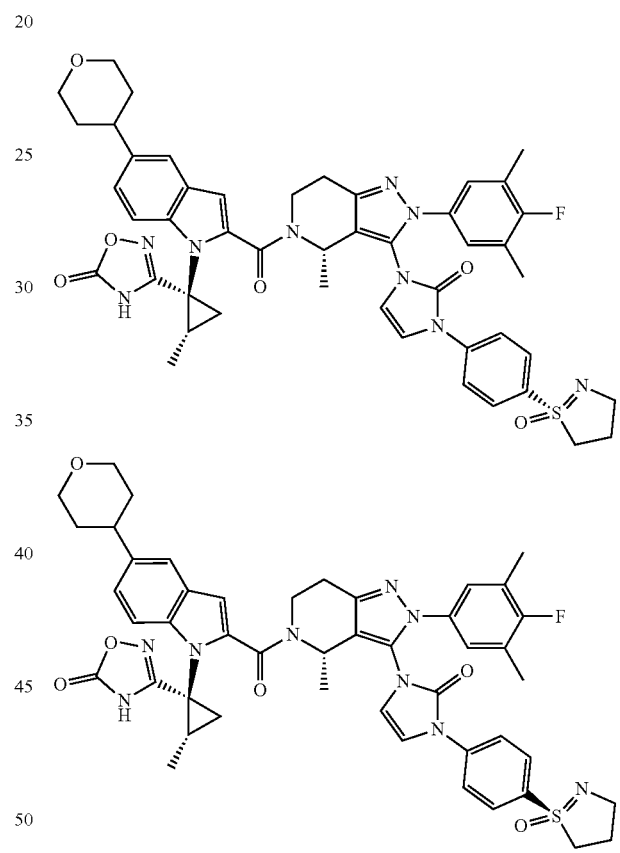

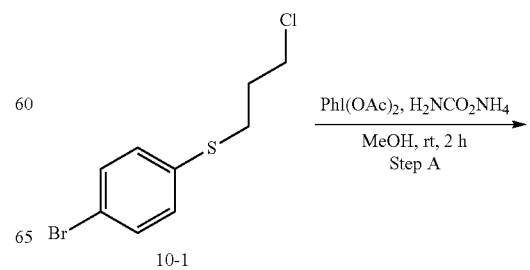

413
-continued
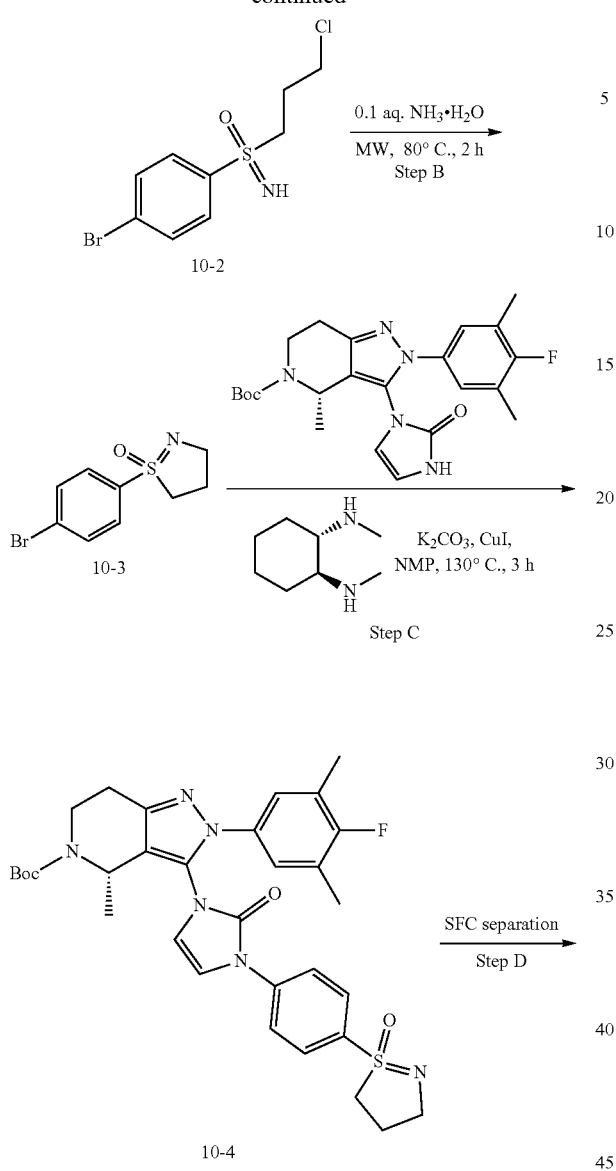
414
-continued
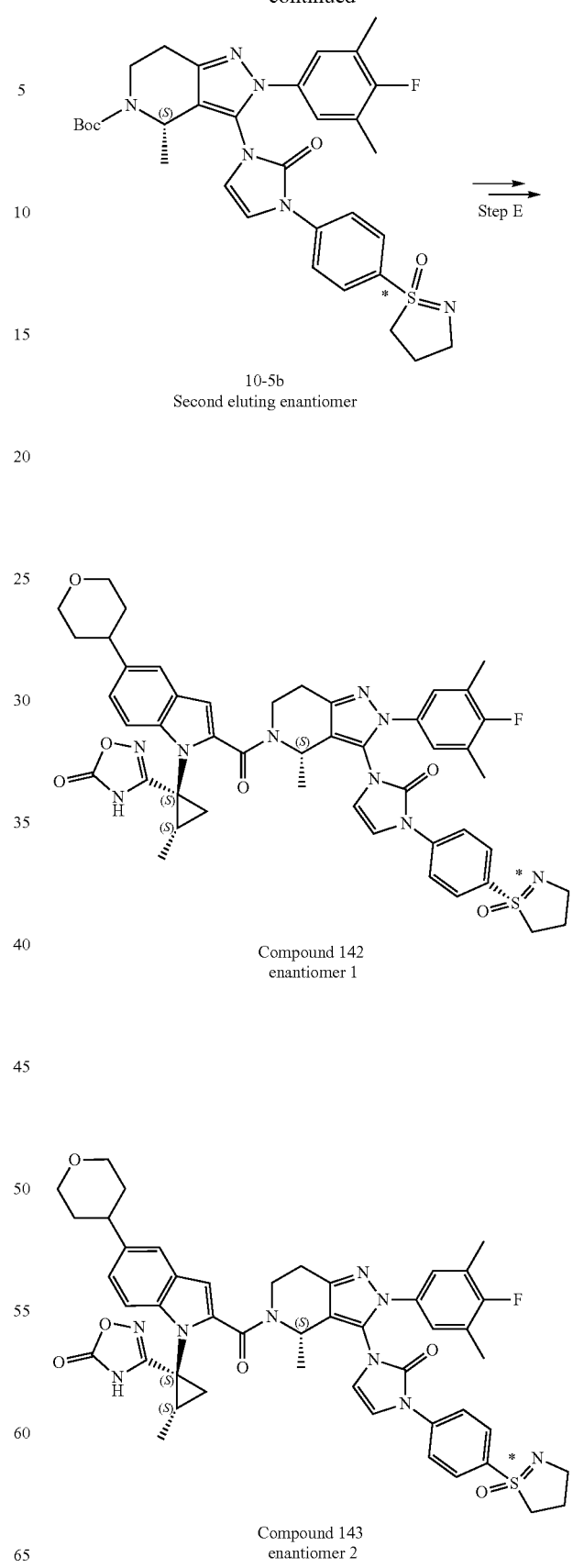

Step A (4-bromophenyl)(3-chloropropyl)(oxo)-λ⁶-sulfanimine

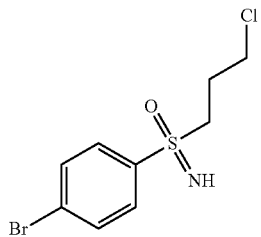 [SMILES: N=S(=O)(CCCCl)c1ccc(Br)cc1]

To a solution of (4-bromophenyl)(3-chloropropyl)sulfane (3.78 g, 14.214 mmol) in MeOH (45 mL) was added PhI(OAc)$_2$ (13.73 g, 42.641 mmol) and H$_2$NCO$_2$NH$_4$ (4.43 g, 56.855 mmol). The reaction mixture was stirred at 25° C. for 2 h under N$_2$. The reaction mixture was poured into sat. aq. sodium bicarbonate solution (20 mL), extracted with EtOAc (20 mL×3). The residue was purified by flash silica gel chromatography (Silica Flash Column, Eluent of 0-50% EtOAc/PE gradient) to afford (4-bromophenyl)(3-chloropropyl)(oxo)-λ⁶-sulfanimine (3.50 g, 83.1% yield). LC-MS: m/z 296.0 (M+H)⁺.

Step B 1-(4-bromophenyl)-1λ⁶-5H,4H,3H-1,2-thiazol-1-one

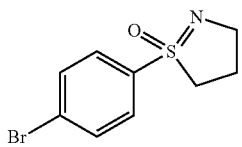 [SMILES: O=S1(c2ccc(Br)cc2)=NCCC1]

A mixture of (4-bromophenyl)(3-chloropropyl)(oxo)-λ⁶-sulfanimine (3.503 g, 11.877 mmol) in 0.1% aq. NH$_3$·H$_2$O (72 mL) was stirred at 80° C. for 2 h under N$_2$ in a sealed tube. After cooling, the mixture was poured into water (100 mL) and extracted with DCM (100 mL×2). The combined organic layer was washed with brine, dried over sodium sulfate, filtered and concentrated. The residue was purified by flash silica gel chromatography (Silica Flash Column, Eluent of 0-50% EtOAc/PE gradient) to afford 1-(4-bromophenyl)-1λ⁶-5H,4H,3H-1,2-thiazol-1-one (1.43 g, 46.2% yield). LC-MS: m/z 260.1 (M+H)⁺.

Step C tert-butyl(4S)-2-(4-fluoro-3,5-dimethylphenyl)-4-methyl-3-{2-oxo-3-[4-(1-oxo-1λ⁶-4H,5H,3H-1,2-thiazol-1-yl)phenyl]imidazol-1-yl}-4,5,6,7-tetrahydropyrazolo[4,3-c]pyridine-5-carboxylate

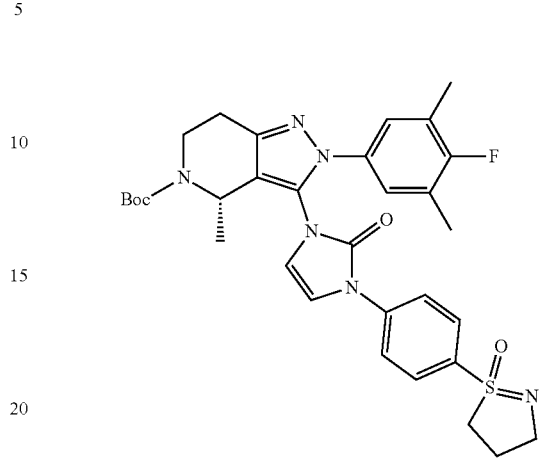

To a solution of 1-(4-bromophenyl)-1λ⁶-5H,4H,3H-1,2-thiazol-1-one (1.43 g, 5.485 mmol) and tert-butyl(4S)-2-(4-fluoro-3,5-dimethylphenyl)-4-methyl-3-(2-oxo-3H-imidazol-1-yl)-4,5,6,7-tetrahydropyrazolo[4,3-c]pyridine-5-carboxylate (2.20 g, 4.987 mmol) in NMP (30 mL) was added methyl[(1S,2S)-2-(methylamino)cyclohexyl]amine (1.06 g, 7.480 mmol), potassium carbonate (1.38 g, 9.973 mmol), and CuI (1.14 g, 5.984 mmol). The reaction mixture was stirred at 120° C. for 4 h under N$_2$. After cooling, the mixture was poured into water (20 mL), extracted with EtOAc (20 mL×3). The combined organic layers were washed with brine (20 mL×3), dried over anhydrous sodium sulfate, filtered and concentrated. The resulting residue was purified by flash silica gel chromatography (Silica Flash Column, Eluent of 0-50% EtOAc/PE gradient) to afford the tert-butyl(4S)-2-(4-fluoro-3,5-dimethylphenyl)-4-methyl-3-{2-oxo-3-[4-(1-oxo-1λ⁶-4H,5H,3H-1,2-thiazol-1-yl)phenyl]imidazol-1-yl}-4,5,6,7-tetrahydropyrazolo[4,3-c]pyridine-5-carboxylate (3.12 g, 91.7% yield). LC-MS: m/z 621.4 (M+H)⁺.

Step D tert-butyl(4S)-2-(4-fluoro-3,5-dimethylphenyl)-3-(3-{4-[1-oxo-1λ⁶-4H,5H,3H-1,2-thiazol-1-yl]phenyl}-2-oxoimidazol-1-yl)-4-methyl-4,5,6,7-tetrahydropyrazolo[4,3-c]pyridine-5-carboxylate 10-5a (first eluting enantiomer) and tert-butyl(4S)-2-(4-fluoro-3,5-dimethylphenyl)-3-(3-{4-[1-oxo-1λ⁶-4H,5H,3H-1,2-thiazol-1-yl]phenyl}-2-oxoimidazol-1-yl)-4-methyl-4,5,6,7-tetrahydropyrazolo[4,3-c]pyridine-5-carboxylate 10-5b (second eluting enantiomer)

The compound mixture tert-butyl(4S)-2-(4-fluoro-3,5-dimethylphenyl)-4-methyl-3-{2-oxo-3-[4-(1-oxo-1λ⁶-4H,5H,3H-1,2-thiazol-1-yl)phenyl]imidazol-1-yl}-4,5,6,7-tetrahydropyrazolo[4,3-c]pyridine-5-carboxylate (4.20 g, 6.774 mmol) was separated by SFC (Column: REGIS (S,S) WHELK-01 250*25 mm 10 m, Mobile phase A (Supercritical CO$_2$), Mobile phase B (MeOH (0.1% 7.0 M ammonia in MeOH)), Gradient: A/B=65/35, Flow rate: 70 mL/min) to afford tert-butyl(4S)-2-(4-fluoro-3,5-dimethylphenyl)-3-(3-{4-[-1-oxo-1λ⁶-4H,5H,3H-1,2-thiazol-1-yl]phenyl}-2-oxoimidazol-1-yl)-4-methyl-4,5,6,7-tetrahydropyrazolo[4,3-c]pyridine-5-carboxylate 10-5a (first eluting enantiomer)

(2.00 g, 47.6% yield) as the fast eluent (Rt=1.95 min), LC-MS: m/z 621.4 (M+H)+. And tert-butyl(4S)-2-(4-fluoro-3,5-dimethylphenyl)-3-(3-{4-[-1-oxo-1λ⁶-4H,5H,3H-1,2-thiazol-1-yl]phenyl}-2-oxoimidazol-1-yl)-4-methyl-4,5,6,7-tetrahydropyrazolo[4,3-c]pyridine-5-carboxylate 10-5b (second eluting enantiomer) (2.20 g, 52.4% yield) as the slow eluent (Rt=2.74 min), LC-MS: m/z 621.4 (M+H)+.

Step E (4S)-2-(4-fluoro-3,5-dimethylphenyl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-3-(3-{4-[1-oxo-1λ⁶-4H,3H,5H-1,2-thiazol-1-yl]phenyl}-2-oxoimidazol-1-yl)-4-methyl-4,5,6,7-tetrahydropyrazolo[4,3-c]pyridine and (4S)-2-(4-fluoro-3,5-dimethylphenyl)-3-(3-{4-[1-oxo-1λ⁶-4H,3H,5H-1,2-thiazol-1-yl]phenyl}-2-oxoimidazol-1-yl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-4-methyl-4,5,6,7-tetrahydropyrazolo[4,3-c]pyridine
(Compounds 142 and 143)

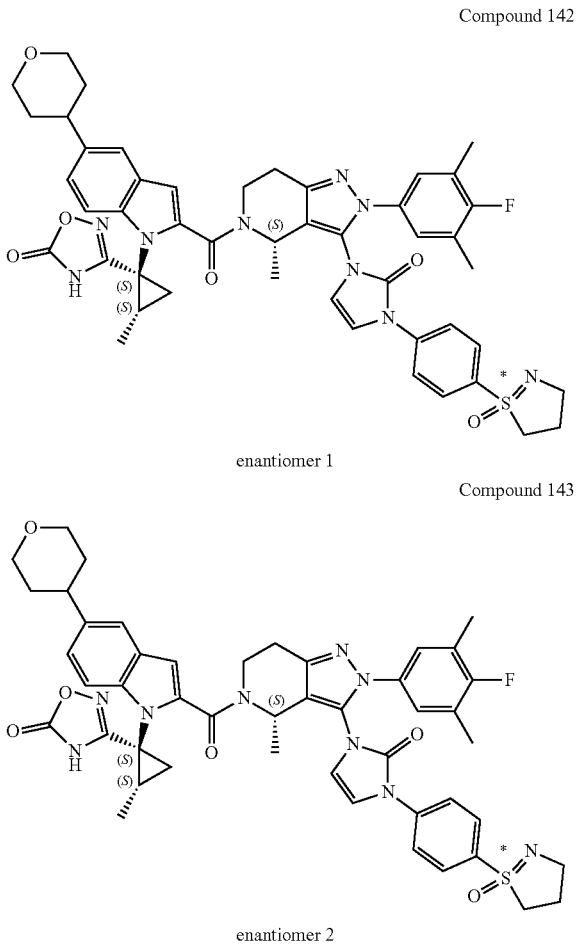

Compound 142
enantiomer 1

Compound 143
enantiomer 2

(4S)-2-(4-fluoro-3,5-dimethylphenyl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-3-(3-{4-[1-oxo-1λ⁶-4H,3H,5H-1,2-thiazol-1-yl]phenyl}-2-oxoimidazol-1-yl)-4-methyl-4,5,6,7-tetrahydropyrazolo[4,3-c]pyridine (Compound 142) (enantiomer 1) and (4S)-2-(4-fluoro-3,5-dimethylphenyl)-3-(3-{4-[1-oxo-1λ⁶-4H,3H, 5H-1,2-thiazol-1-yl]phenyl}-2-oxoimidazol-1-yl)-5-({1-[(1S,2S)-2-methyl-1-(5-oxo-4H-1,2,4-oxadiazol-3-yl)cyclopropyl]-5-(3,4,5,6-tetrahydro-2H-pyran-4-yl)indol-2-yl}carbonyl)-4-methyl-4,5,6,7-tetrahydropyrazolo[4,3-c] pyridine (Compound 143) (enantiomer 2) were synthesized according to the procedures described for the preparation of Example A7 (step C to F) by using tert-butyl(4S)-2-(4-fluoro-3,5-dimethylphenyl)-3-(3-{4-[1-oxo-1λ⁶-4H,5H,3H-1,2-thiazol-1-yl]phenyl}-2-oxoimidazol-1-yl)-4-methyl-4,5,6,7-tetrahydropyrazolo[4,3-c]pyridine-5-carboxylate 10-5a (first eluting enantiomer) in step C and tert-butyl(4S)-2-(4-fluoro-3,5-dimethylphenyl)-3-(3-{4-[1-oxo-1λ⁶-4H,5H,3H-1,2-thiazol-1-yl]phenyl}-2-oxoimidazol-1-yl)-4-methyl-4,5,6,7-tetrahydropyrazolo[4,3-c]pyridine-5-carboxylate 10-5b (second eluting enantiomer) in step E.

Compound 142: LC-MS: m/z 886.4 (M+H)+. ¹H NMR (400 MHz, DMSO-d6) δ 7.95-7.88 (m, 4H), 7.49 (s, 1H), 7.43 (d, J=8.4 Hz, 1H), 7.32 (m, 1H), 7.23 (d, J=8.4 Hz, 1H), 7.17-7.15 (m, 2H), 6.98 (m, 1H), 6.77 (m, 1H), 5.55 (m, 1H), 4.39 (m, 1H), 4.00-3.97 (m, 2H), 3.86-3.81 (m, 1H), 3.72-3.69 (m, 1H), 3.52-3.46 (m, 2H), 3.40-3.32 (m, 2H), 2.90-2.83 (m, 3H), 2.33-2.26 (m, 3H), 2.22 (s, 6H), 1.76-1-69 (m, 5H), 1-65 (m, 2H), 1.39 (s, 3H), 1.20 (s, 3H).

Compound 143: LC-MS: m/z 886.4 (M+H)+. ¹H NMR (400 MHz, DMSO-d6) δ 11.59 (brs, 1H), 7.95-7.91 (m, 4H), 7.53 (s, 1H), 7.44 (d, J=8.4 Hz, 1H), 7.37 (m, 1H), 7.28 (d, J=8.4 Hz, 1H), 7.16-7.14 (m, 2H), 6.96 (m, 1H), 6.88 (m, 1H), 5.57 (m, 1H), 4.50 (m, 1H), 4.00-3.97 (m, 2H), 3.89-3.84 (m, 1H), 3.77-3.72 (m, 1H), 3.53-3.46 (m, 4H), 2.92-2.86 (m, 2H), 2.36-2.28 (m, 3H), 2.22 (s, 6H), 2.05-2.02 (m, 1H), 1.78-1.73 (m, 6H), 1-66 (m, 1H), 1.43 (s, 3H), 1.17 (s, 3H).

Example compound 130 and 131 was synthesized using a similar procedure described in the Example A10 above using the appropriate materials in step D.

Example A11

1-((S)-2-(4-fluoro-3,5-dimethylphenyl)-4-methyl-5-(1-(1-(5-methyl-1,3,4-oxadiazol-2-yl) cyclopropyl)-5-(tetrahydro-2H-pyran-4-yl)-1H-indole-2-carbonyl)-4,5,6,7-tetrahydro-2H-pyrazolo[4,3-c]pyridin-3-yl)-3-(4-(1-oxido-4,5-dihydro-3H-1λ⁶-isothiazol-1-yl) phenyl)-1,3-dihydro-2H-imidazol-2-one (Compound 156) and 1-((S)-2-(4-fluoro-3,5-dimethylphenyl)-4-methyl-5-(1-(1-(5-methyl-1,3,4-oxadiazol-2-yl) cyclopropyl)-5-(tetrahydro-2H-pyran-4-yl)-1H-indole-2-carbonyl)-4,5,6,7-tetrahydro-2H-pyrazolo[4,3-c]pyridin-3-yl)-3-(4-(1-oxido-4,5-dihydro-3H-1λ⁶-isothiazol-1-yl) phenyl)-1,3-dihydro-2H-imidazol-2-one (Compound 155)

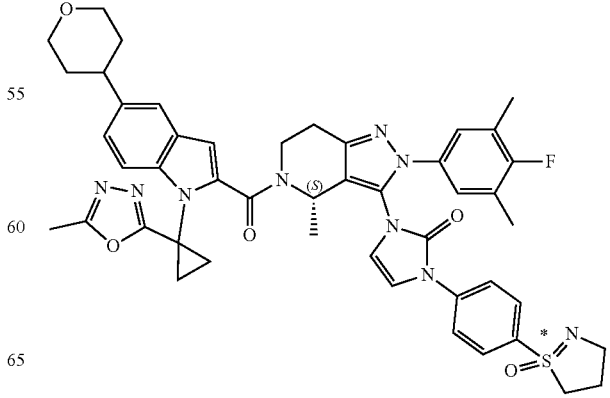

Compound 156

-continued
Compound 155
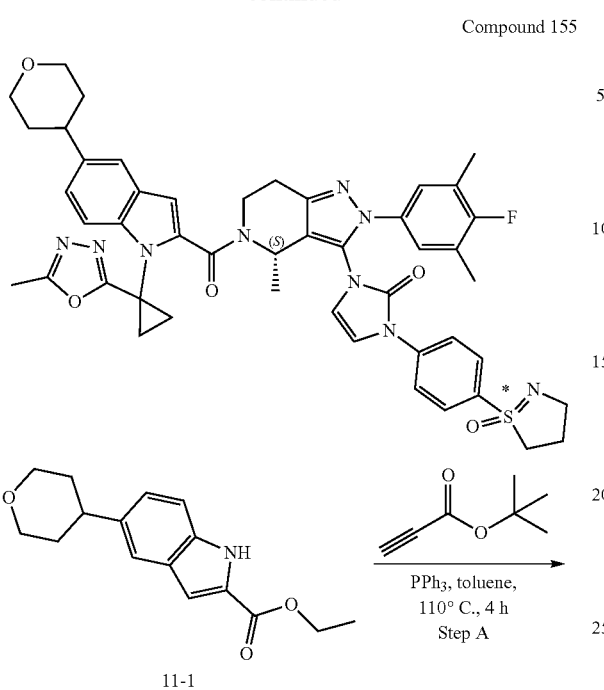
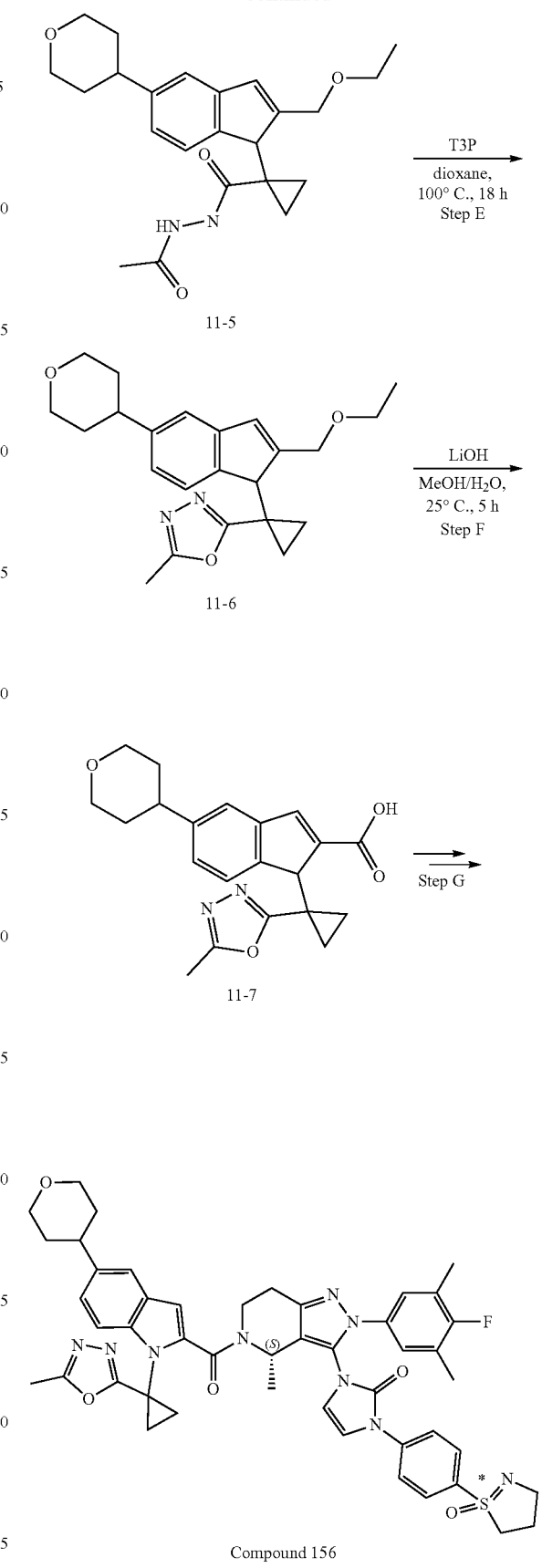
Compound 156

421
-continued

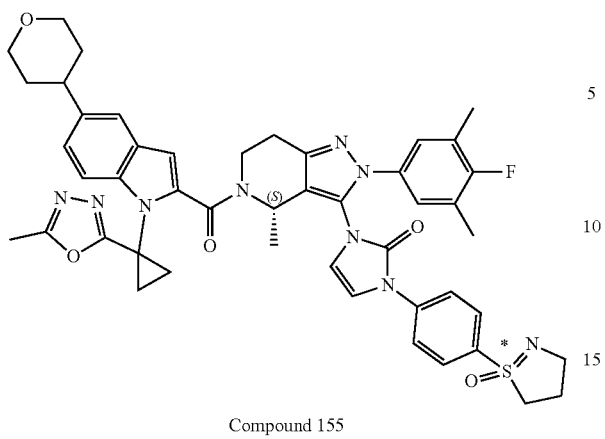

Compound 155

Step A ethyl 1-(3-(tert-butoxy)-3-oxoprop-1-en-2-yl)-5-(tetrahydro-2H-pyran-4-yl)-1H-indole-2-carboxylate

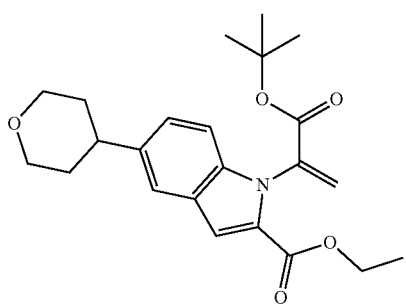 [SMILES: C=C(C(=O)OC(C)(C)C)n1c(C(=O)OCC)cc2cc(C3CCOCC3)ccc21]

To a solution of ethyl 5-(tetrahydro-2H-pyran-4-yl)-1H-indole-2-carboxylate (4.00 g, 14.63 mmol) in toluene (40 mL) were added triphenylphosphane (2.69 g, 10.24 mmol) and tert-butyl propiolate (2.77 g, 21.95 mmol). After addition, the reaction mixture was stirred at 110° C. for 4 h under N2 atmosphere. After cooling, the reaction mixture was diluted with H$_2$O (40 mL), extracted with ethyl acetate (40 mL×3). The combined organic layers were washed with brine, dried over Na$_2$SO$_4$, filtered and concentrated. The residue was purified by silica gel column chromatography eluting with 0-50% EtOAc/PE to give ethyl 1-(3-(tert-butoxy)-3-oxoprop-1-en-2-yl)-5-(tetrahydro-2H-pyran-4-yl)-1H-indole-2-carboxylate (3.00 g, 51.3% yield). LC-MS: m/z 400.4 (M+H)$^+$.

422

Step B ethyl 1-(1-(tert-butoxycarbonyl) cyclopropyl)-5-(tetrahydro-2H-pyran-4-yl)-1H-indole-2-carboxylate

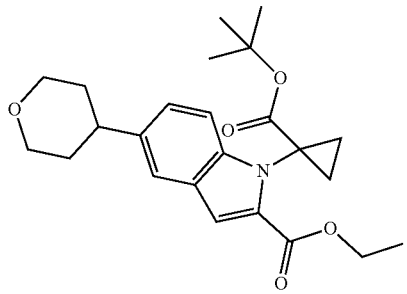 [SMILES: CCOC(=O)c1cc2cc(C3CCOCC3)ccc2n1C1(C(=O)OC(C)(C)C)CC1]

To a solution of NaH (0.27 g, 11.26 mmol, 60% purity) in DMSO (40 mL) was added trimethylsulfoxonium iodide (2.48 g, 11.26 mmol) in portions for 30 min, followed by ethyl 1-(3-(tert-butoxy)-3-oxoprop-1-en-2-yl)-5-(tetrahydro-2H-pyran-4-yl)-1H-indole-2-carboxylate (3.00 g, 7.51 mmol) at 0° C. After addition, the reaction mixture was stirred at 25° C. for 2 h under N2 atmosphere.

The resulting mixture was diluted with H$_2$O (50 mL) and extracted with ethyl acetate (50 mL×3). The combined organic layers were washed with brine, dried over Na$_2$SO$_4$, filtered and concentrated. The residue was purified by silica gel column chromatography eluting with 0-50% EtOAc/PE to give ethyl 1-(1-(tert-butoxycarbonyl) cyclopropyl)-5-(tetrahydro-2H-pyran-4-yl)-1H-indole-2-carboxylate (2.00 g, 64.5% yield). LC-MS: m/z 414.4 (M+H)$^+$.

Step C 1-(2-(ethoxycarbonyl)-5-(tetrahydro-2H-pyran-4-yl)-1H-indol-1-yl) cyclopropane-1-carboxylic acid

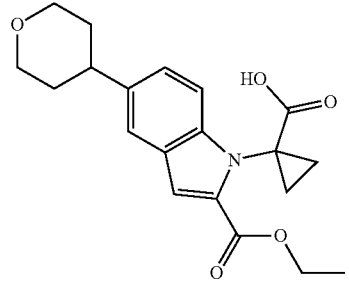 [SMILES: CCOC(=O)c1cc2cc(C3CCOCC3)ccc2n1C1(C(=O)O)CC1]

To a solution of ethyl 1-(1-(tert-butoxycarbonyl) cyclopropyl)-5-(tetrahydro-2H-pyran-4-yl)-1H-indole-2-carboxylate (0.70 g, 1-693 mmol) in DCM (10 mL) was added TFA (10 mL, 152 mmol). After addition, the reaction mixture was stirred at 25° C. for 3 h. The resulting mixture was concentrated to give 1-(2-(ethoxycarbonyl)-5-(tetrahydro-2H-pyran-4-yl)-1H-indol-1-yl) cyclopropane-1-carboxylic acid (0.60 g, crude), which was used for the next step directly without further purification. LC-MS: m/z 358.3 (M+H)$^+$.

Step D ethyl 1-(1-(2-acetylhydrazine-1-carbonyl) cyclopropyl)-5-(tetrahydro-2H-pyran-4-yl)-1H-indole-2-carboxylate

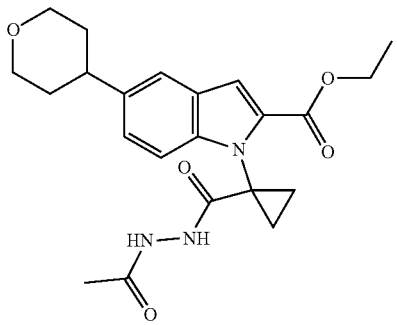 [SMILES: CCOC(=O)c1cc2cc(C3CCOCC3)ccc2n1C1(C(=O)NNC(C)=O)CC1]

To a solution of 1-(2-(ethoxycarbonyl)-5-(tetrahydro-2H-pyran-4-yl)-1H-indol-1-yl) cyclopropane-1-carboxylic acid (600.0 mg, 3.02 mmol) in DMF (10 mL) were added acetohydrazide (185.0 mg, 2.52 mmol), HATU (957.0 mg, 2.52 mmol) and DIEA (1.17 mL, 6.72 mmol). After addition, the mixture was stirred at 25° C. for 2 h. The resulting mixture was diluted with H$_2$O (20 mL) and extracted with ethyl acetate (20 mL×3). The combined organic layers were washed with brine, dried over Na$_2$SO$_4$, filtered and concentrated. The residue was purified by silica gel column chromatography eluting with 5-10% MeOH/DCM to afford ethyl 1-(1-(2-acetylhydrazine-1-carbonyl) cyclopropyl)-5-(tetrahydro-2H-pyran-4-yl)-1H-indole-2-carboxylate (0.40 g, 57.6% yield). LC-MS: m/z 414.2 (M+H)$^+$.

Step E ethyl 1-(1-(5-methyl-1,3,4-oxadiazol-2-yl) cyclopropyl)-5-(tetrahydro-2H-pyran-4-yl)-1H-indole-2-carboxylate

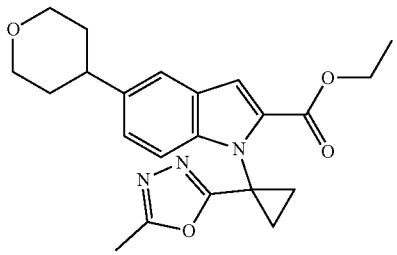 [SMILES: CCOC(=O)c1cc2cc(C3CCOCC3)ccc2n1C1(c2nnc(C)o2)CC1]

To a solution of ethyl 1-(1-(2-acetylhydrazine-1-carbonyl) cyclopropyl)-5-(tetrahydro-2H-pyran-4-yl)-1H-indole-2-carboxylate (700.0 mg, 1.81 mmol) in 1,4-dioxane (10 mL) was added T3P (1.54 g, 4.84 mmol, 50% purity). After addition, the mixture was degassed and purged with N2 for 3 times and stirred at 100° C. for 18 h under N2 atmosphere. The reaction mixture was diluted with H$_2$O (20 mL) and extracted with ethyl acetate (20 mL×3). The combined organic layers were washed with brine, dried over Na$_2$SO$_4$, filtered and concentrated. The residue was purified by silica gel column chromatography 10-30% EtOAc/PE to afford ethyl 1-(1-(5-methyl-1,3,4-oxadiazol-2-yl) cyclopropyl)-5-(tetrahydro-2H-pyran-4-yl)-1H-indole-2-carboxylate (200.0 mg, 52.3% yield). LC-MS: m/z 396.2 (M+H)$^+$.

Step F 1-(1-(5-methyl-1,3,4-oxadiazol-2-yl) cyclopropyl)-5-(tetrahydro-2H-pyran-4-yl)-1H-indole-2-carboxylic acid

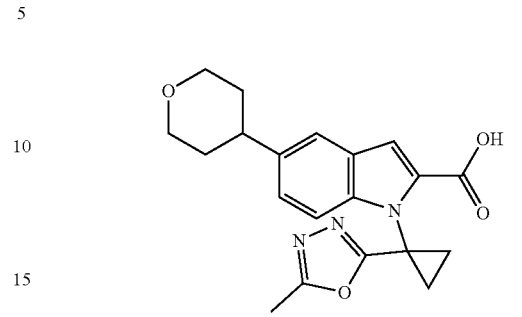

To a solution of ethyl 1-(1-(5-methyl-1,3,4-oxadiazol-2-yl) cyclopropyl)-5-(tetrahydro-2H-pyran-4-yl)-1H-indole-2-carboxylate (200.0 mg, 0.51 mmol) in THF (0.95 mL), MeOH (0.95 mL) and H$_2$O (0.95 mL) was added lithium hydroxide (24.23 mg, 1.01 mmol). The mixture was stirred at 25° C. for 5 h. The resulting mixture was concentrated under reduced pressure to remove solvent. The residue was diluted with water (5 mL) and adjusted pH to ~4 with 1 M HCl, extracted with EtOAc (20 mL×3).

The combined organic layers were dried over Na$_2$SO$_4$, filtered and concentrated to give 1-(1-(5-methyl-1,3,4-oxadiazol-2-yl) cyclopropyl)-5-(tetrahydro-2H-pyran-4-yl)-1H-indole-2-carboxylic acid (150.0 mg, 80.6% yield). LC-MS: m/z 368.2 (M+H)$^+$.

1-((S)-2-(4-fluoro-3,5-dimethylphenyl)-4-methyl-5-(1-(1-(5-methyl-1,3,4-oxadiazol-2-yl) cyclopropyl)-5-(tetrahydro-2H-pyran-4-yl)-1H-indole-2-carbonyl)-4,5,6,7-tetrahydro-2H-pyrazolo [4,3-c]pyridin-3-yl)-3-(4-(1-oxido-4,5-dihydro-3H-1λ$^6$-isothiazol-1-yl) phenyl)-1,3-dihydro-2H-imidazol-2-one (Compound 156) and 1-((S)-2-(4-fluoro-3,5-dimethylphenyl)-4-methyl-5-(1-(1-(5-methyl-1,3,4-oxadiazol-2-yl) cyclopropyl)-5-(tetrahydro-2H-pyran-4-yl)-1H-indole-2-carbonyl)-4,5,6,7-tetrahydro-2H-pyrazolo[4,3-c]pyridin-3-yl)-3-(4-(1-oxido-4,5-dihydro-3H-1λ$^6$-isothiazol-1-yl) phenyl)-1,3-dihydro-2H-imidazol-2-one (Compound 155).

Compound 156

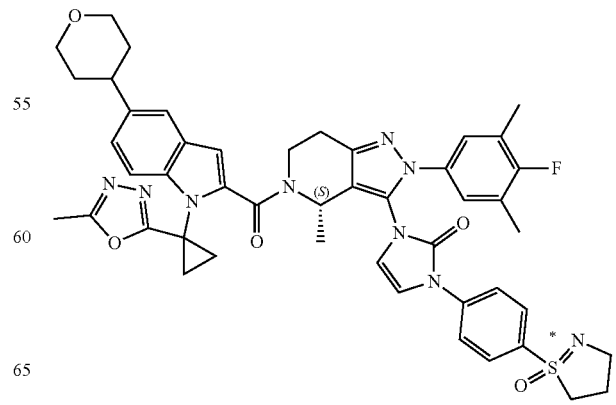

Compound 155

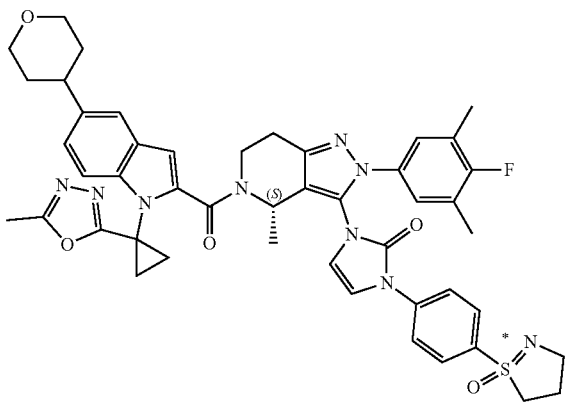

1-((S)-2-(4-fluoro-3,5-dimethylphenyl)-4-methyl-5-(1-(1-(5-methyl-1,3,4-oxadiazol-2-yl) cyclopropyl)-5-(tetrahydro-2H-pyran-4-yl)-1H-indole-2-carbonyl)-4,5,6,7-tetrahydro-2H-pyrazolo[4,3-c]pyridin-3-yl)-3-(4-(1-oxido-4,5-dihydro-3H-1λ⁶-isothiazol-1-yl) phenyl)-1,3-dihydro-2H-imidazol-2-one (Compound 156) (enantiomer 1) and 1-((S)-2-(4-fluoro-3,5-dimethylphenyl)-4-methyl-5-(1-(1-(5-methyl-1,3,4-oxadiazol-2-yl) cyclopropyl)-5-(tetrahydro-2H-pyran-4-yl)-1H-indole-2-carbonyl)-4,5,6,7-tetrahydro-2H-pyrazolo[4,3-c]pyridin-3-yl)-3-(4-(1-oxido-4,5-dihydro-3H-1λ⁶-isothiazol-1-yl) phenyl)-1,3-dihydro-2H-imidazol-2-one (Compound 155) (enantiomer 2) were synthesized according to the procedures described for the preparation of Example A10 (step E).

Compound 156: LC-MS: m/z 870.2 (M+H)⁺. ¹H NMR (400 MHz, DMSO-d6) δ 7.95 (m, 4H), 7.55-7.52 (m, 2H), 7.40-7.38 (m, 1H), 7.26 (d, J=8.0 Hz, 1H), 7.17 (d, J=4.0 Hz, 2H), 7.04-7.02 (m, 1H), 6.80 (s, 1H), 5.55-5.53 (m, 1H), 4.03-4.00 (m, 2H), 3.89-3.83 (m, 1H), 3.75-3.70 (m, 1H), 3.55-3.49 (m, 2H), 3.47-3.36 (m, 3H), 2.86 (s, 3H), 2.39-2.36 (m, 3H), 2.35-2.29 (m, 2H), 2.25-2.23 (s, 6H), 1.89-1.76 (m, 8H), 1.37-1.34 (m, 4H).

Compound 155: LC-MS: m/z 870.2 (M+H)⁺. ¹H NMR (400 MHz, DMSO-d6) δ 7.94 (m, 4H), 7.55-7.52 (m, 2H), 7.40-7.38 (m, 1H), 7.26 (d, J=8.0 Hz, 1H), 7.16 (d, J=4.0 Hz, 2H), 7.04-7.02 (m, 1H), 6.80 (s, 1H), 5.55-5.50 (m, 1H), 4.03-4.01 (m, 2H), 3.87-3.83 (m, 1H), 3.76-3.71 (m, 1H), 3.56-3.49 (m, 2H), 3.47-3.37 (m, 3H), 2.95-2.82 (m, 3H), 2.40 (s, 3H), 2.34-2.27 (m, 2H), 2.24-2.23 (s, 6H), 1.90-1.73 (m, 8H), 1.37-1.30 (m, 4H).

Example compounds 153, 157 and 158, 159 to 163, 165, 170 and 171 were synthesized using a similar procedure described in the Example A11 above using the appropriate materials.

Example A12

3-[(1S,2S)-1-{5-[(4S)-2,2-dimethyl-3,4,5,6-tetrahydro-2H-pyran-4-yl]-2-{[(4S)-2-(4-fluoro-3,5-dimethylphenyl)-3-(1-{4-[cyclopropyl(methylazanylidene)(oxo)-λ⁶-sulfanyl]-2-fluoro-3-methylphenyl}-2-oxoimidazol-3-yl)-4-methyl-4,5,6,7-tetrahydropyrazolo[4,3-c]pyridin-5-yl]carbonyl}indol-1-yl}-2-methylcyclopropyl]-4H,5H-1,2,4-oxadiazol-5-one (Compound 195) (enantiomer 1) and 3-[(1S,2S)-1-{5-[(4S)-2,2-dimethyl-3,4,5,6-tetrahydro-2H-pyran-4-yl]-2-{[(4S)-2-(4-fluoro-3,5-dimethylphenyl)-3-(1-{4-[cyclopropyl(methylazanylidene)(oxo)-λ⁶-sulfanyl]-2-fluoro-3-methylphenyl}-2-oxoimidazol-3-yl)-4-methyl-4,5,6,7-tetrahydropyrazolo[4,3-c]pyridin-5-yl]carbonyl}indol-1-yl}-2-methylcyclopropyl]-4H,5H-1,2,4-oxadiazol-5-one (Compound 196)

Compound 195

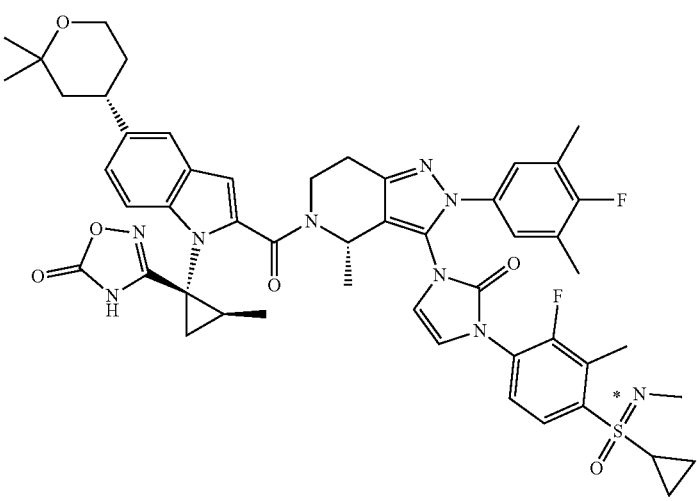

-continued
Compound 196
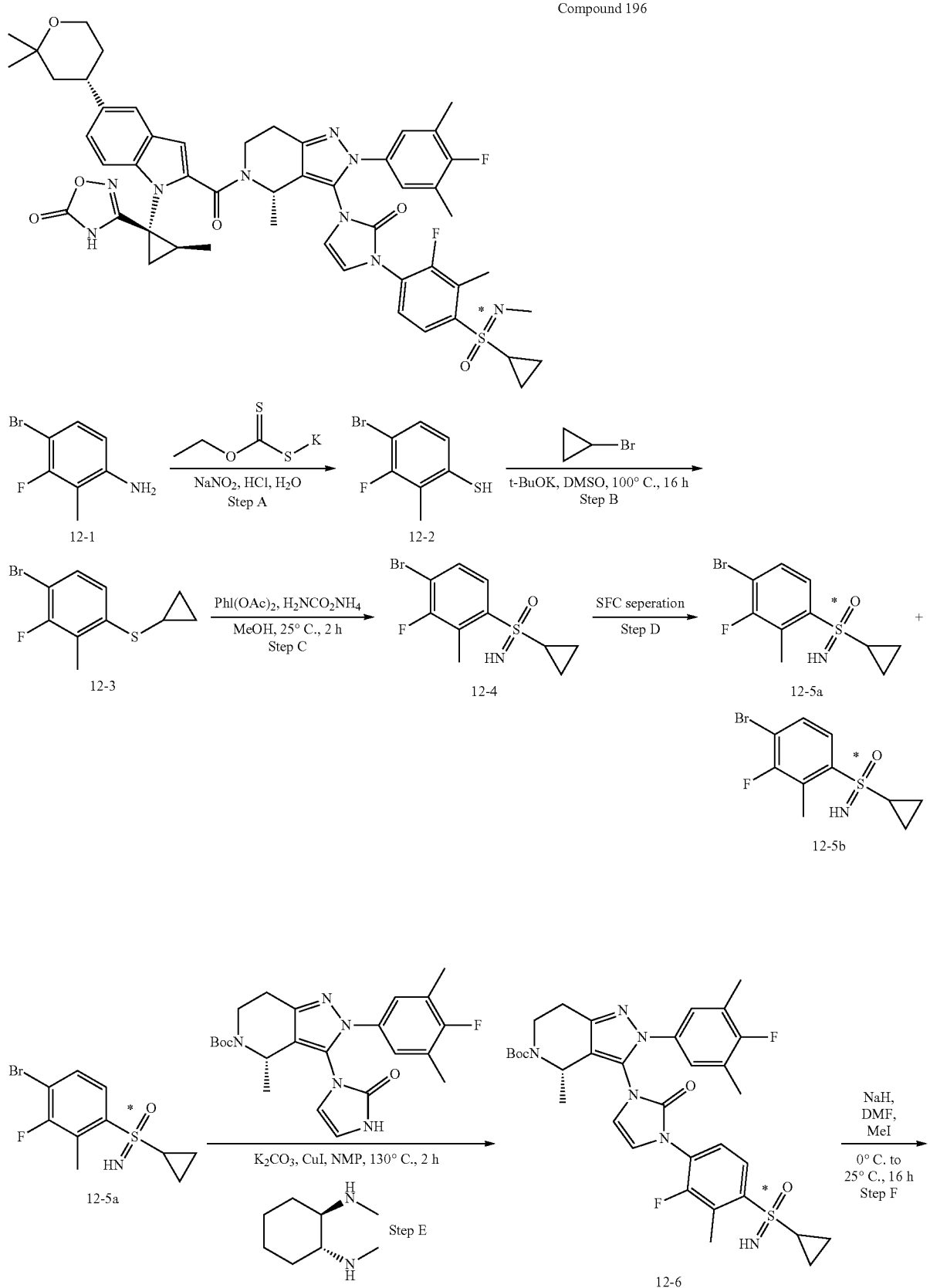

-continued
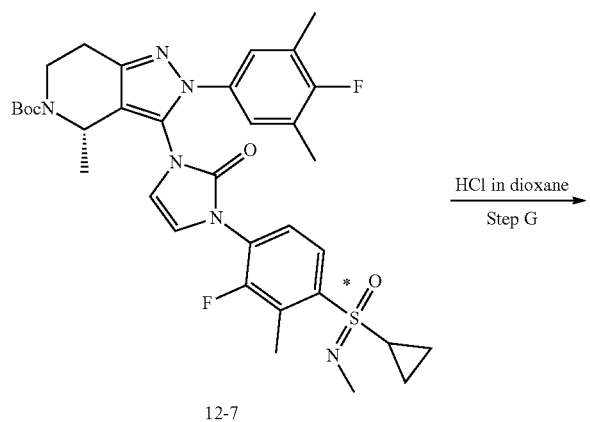
12-7
HCl in dioxane
Step G
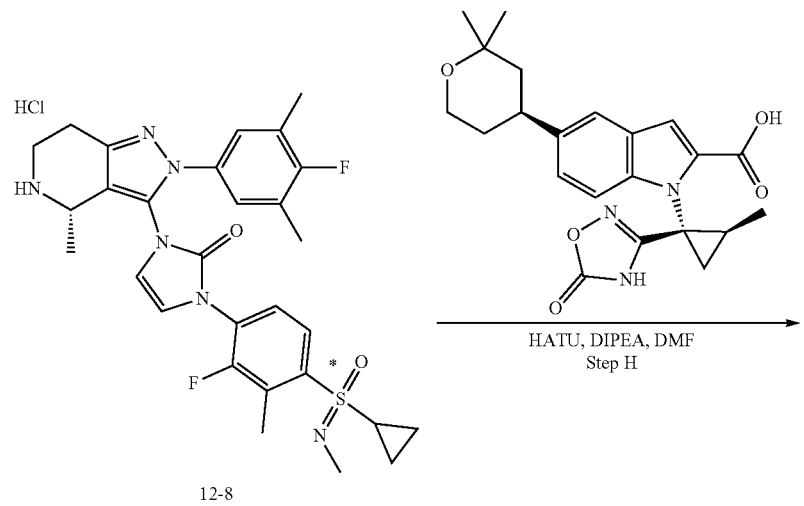
12-8
HATU, DIPEA, DMF
Step H
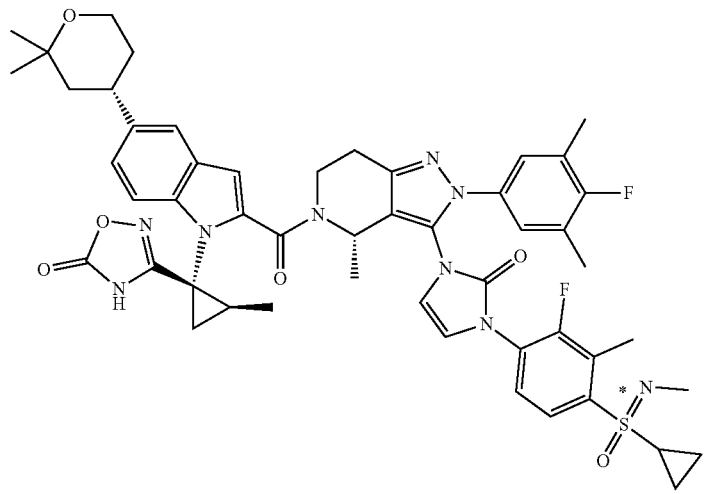
Compound 195

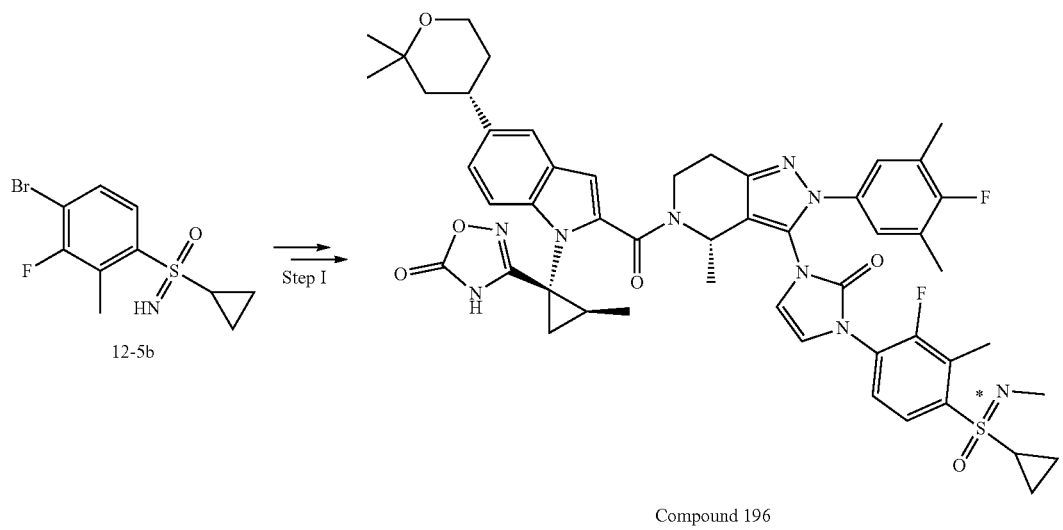 [SMILES: Cc1c(S(=N)(=O)C2CC2)ccc(Br)c1F ; CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1C)C1CC1]

Compound 196

Step A 4-bromo-3-fluoro-2-methylbenzene-1-thiol

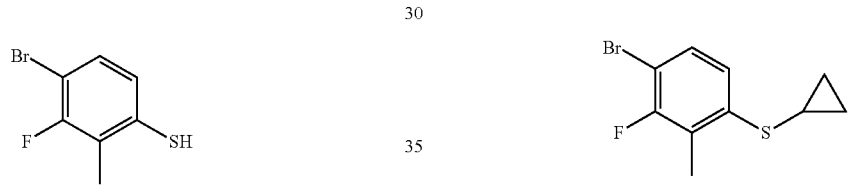

To a mixture of 4-bromo-3-fluoro-2-methylaniline (2.7 g, 13.233 mmol) in H$_2$O (10 mL) was added conc. HCl (2.205 mL, 26.465 mmol). The reaction mixture was cooled in an ice/NaCl bath (approximately −5 to −10° C.), a solution of sodium nitrite (958.6 mg, 13.894 mmol) in H$_2$O (10 mL) was added slowly over 10 minutes. The mixture was stirred for an additional 30 minutes with cooling. Separately, a solution of [(ethoxythioxomethyl)sulfanyl]potassium (2545.3 mg, 15.879 mmol) in H20 (30 mL) was prepared and heated to 65° C. The cold solution of diazonium salt was then added slowly over 20 minutes to the warmed solution of potassium ethyl xanthogenate. The reaction mixture was stirred for an additional 30 minutes at 65° C. and then cooled to ambient temperature. A solution of NaOH (2646.6 mg, 66.165 mmol) in H$_2$O (10 mL) was added, the reaction was stirred at 70° C. for 18 h.

After the reaction was completed, monitored by TLC, the mixture was cooled to rt, the mixture was poured into ice (200 g), acidified with concentrated HCl to pH=1, the mixture was extracted with EtOAc (50 mL×3). The combined organic extracts were dried over anhydrous Na$_2$SO$_4$, filtered and concentrated to afford 4-bromo-3-fluoro-2-methylbenzene-1-thiol (3.7 g, crude), used for the next step without purification.

Step B (4-bromo-3-fluoro-2-methylphenyl)(cyclopropyl)sulfane

To a solution of 4-bromo-3-fluoro-2-methylbenzene-1-thiol (3.7 g, 16.735 mmol) in DMSO (60 mL) were added potassium tert-butoxide (3.76 g, 33.471 mmol) and bromocyclopropane (10.12 g, 83.676 mmol), the reaction was stirred at 100° C. for 18 h under N$_2$. TLC showed the reaction was completed. The mixture was poured into water (100 mL), extracted with EtOAc (200 mL×2). The combined organic layers were washed with brine, dried over Na$_2$SO$_4$, filtered and concentrated. The resulting residue was purified by silica gel chromatography (eluting PE 100%) to afford (4-bromo-3-fluoro-2-methylphenyl)(cyclopropyl)sulfane (2.23 g, 50.3% yield).

Step C (4-bromo-3-fluoro-2-methylphenyl)(cyclopropyl)(oxo)-λ$^6$-sulfanimine

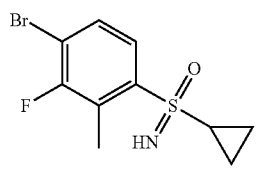

To a solution of (4-bromo-2-fluorophenyl)(cyclopropyl)sulfane (2.2 g, 8.524 mmol) in MeOH (30 mL) was added (diacetoxyiodo)benzene (8.29 g, 25.572 mmol) and ammonium carbaminate (2.66 g, 34.095 mmol). The reaction was stirred at room temperature for 1 h. After the reaction was completed, water (50 mL) was added. The mixture was extracted with EtOAc (30 mL×3). The combined organic layers were washed with brine, dried over sodium sulfate, filtered and concentrated. The resulting residue was purified by silica gel chromatography (eluting 0-50% EtOAc/PE) to afford (4-bromo-3-fluoro-2-methylphenyl)(cyclopropyl)(oxo)-$\lambda^6$-sulfanimine (1.17 g, 47.5% yield). LC-MS: m/z 294.0 (M+H)$^+$.

Step D (4-bromo-3-fluoro-2-methylphenyl)(cyclopropyl)(oxo)-$\lambda^6$-sulfanimine (enantiomer 1) 12-5a

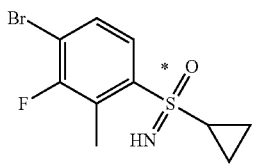

The compound mixture(4-bromo-3-fluoro-2-methylphenyl)(cyclopropyl)(oxo)-$\lambda^6$-sulfanimine (1.17 g, 4.00 mmol) was separated by SFC (Column: DAICELCHIRALCEL® AS 250 mm*25 mm, 10 m, Mobile phase A (Supercritical CO$_2$), Mobile phase B (MeOH (0.1% 7.0 M Ammonia in MeOH)), Gradient: B=20%, Flow rate: 100 mL/min, Column temp: 25° C.) to afford (4-bromo-3-fluoro-2-methylphenyl)(cyclopropyl)(oxo)-$\lambda^6$-sulfanimine (enantiomer 1) (517 mg, 44.2% yield) as the fast eluent, LC-MS: m/z 294.0 (M+H)$^+$. And (4-bromo-3-fluoro-2-methylphenyl)(cyclopropyl)(oxo)-$\lambda^6$-sulfanimine (enantiomer 2) (460 mg, 39.3% yield) as the slow eluent, LC-MS: m/z 294.0 (M+H)$^+$.

Step E 2-methylpropan-2-yl(4S)-2-(4-fluoro-3,5-dimethylphenyl)-3-(3-{4-[azanylidene(cyclopropyl)(oxo)-$\lambda^6$-sulfanyl]-2-fluoro-3-methylphenyl}-2-oxoimidazol-1-yl)-4-methyl-4,5,6,7-tetrahydropyrazolo[4,3-c]pyridine-5-carboxylate

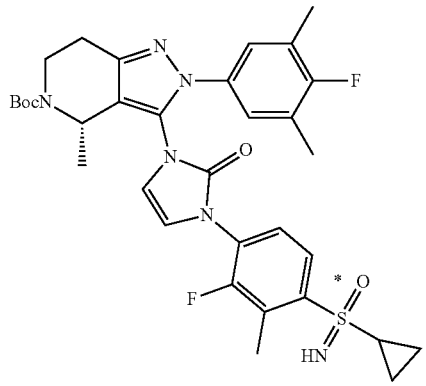 [SMILES: Cc1cc(-n2nc3c(c2-n2ccn(-c4ccc(S(=N)(=O)C5CC5)c(C)c4F)c2=O)[C@H](C)N(C(=O)OC(C)(C)C)CC3)cc(C)c1F]

To a solution of 2-methylpropan-2-yl(4S)-2-(4-fluoro-3,5-dimethylphenyl)-4-methyl-3-(2-oxo-3H-imidazol-1-yl)-4,5,6,7-tetrahydropyrazolo[4,3-c]pyridine-5-carboxylate (2.35 g, 5.320 mmol) in NMP (10 mL) were added (4-bromo-3-fluoro-2-methylphenyl)(cyclopropyl)(oxo)-$\lambda^6$-sulfanimine (520 mg, 1.780 mmol), methyl[(1R,2R)-2-(methylamino)cyclohexyl]amine (379.8 mg, 2.670 mmol), CuI (406.8 mg, 2.136 mmol) and K$_2$CO$_3$ (491.9 mg, 3.560 mmol). The reaction mixture was stirred at 130° C. for 2 h under N2. After cooling, the mixture was poured into water (30 mL), extracted with EtOAc (30 mL×2). The combined organic layers were washed with brine, dried over Na$_2$SO$_4$, filtered and concentrated under vacuum. The resulting residue was purified by silica gel chromatography (eluting DCM/MeOH=30/1) to afford 2-methylpropan-2-yl(4S)-2-(4-fluoro-3,5-dimethylphenyl)-3-(3-{4-[azanylidene(cyclopropyl)(oxo)-$\lambda^6$-sulfanyl]-2-fluoro-3-methylphenyl}-2-oxoimidazol-1-yl)-4-methyl-4,5,6,7-tetrahydropyrazolo[4,3-c]pyridine-5-carboxylate (1.10 g, 90% yield). LC-MS: m/z 653.7 (M+H)$^+$.

Step F 2-methylpropan-2-yl(4S)-3-(1-{4-[cyclopropyl(methylazanylidene)(oxo)-$\lambda^6$-sulfanyl]-2-fluoro-3-methylphenyl}-2-oxoimidazol-3-yl)-2-(4-fluoro-3,5-dimethylphenyl)-4-methyl-4,5,6,7-tetrahydropyrazolo[4,3-c]pyridine-5-carboxylate

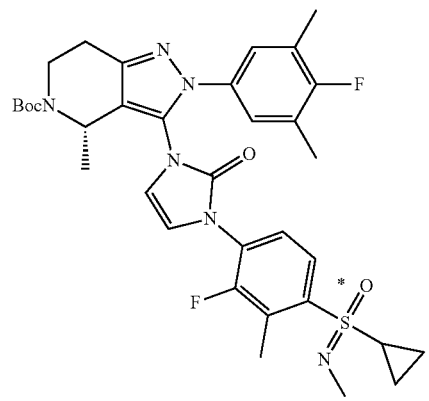 [SMILES: CN=S(=O)(c1ccc(-n2ccn(-c3c4c(nn3-c3cc(C)c(F)c(C)c3)CCN(C(=O)OC(C)(C)C)[C@H]4C)c2=O)c(F)c1C)C1CC1]

To a solution of 2-methylpropan-2-yl(4S)-2-(4-fluoro-3,5-dimethylphenyl)-3-(3-{4-[azanylidene(cyclopropyl)(oxo)-$\lambda^6$-sulfanyl]-2-fluoro-3-methylphenyl}-2-oxoimidazol-1-yl)-4-methyl-4,5,6,7-tetrahydropyrazolo[4,3-c]pyridine-5-carboxylate (1.1 g, 1-685 mmol) in DMF (10 mL) were added NaH (0.17 g, 4.213 mmol) at 0° C. under N2. The mixture was stirred at 0° C. for 10 min, then iodomethane (0.164 mL, 2.022 mmol) was added, the reaction was stirred at 25° C. for 18 h under N2. The reaction mixture was poured into water (20 mL), extracted with EA (20 mL×2). The combined organic layers were washed with brine, dried over Na$_2$SO$_4$, filtered and concentrated. The resulting residue was purified by silica gel chromatography (eluting DCM/MeOH=50/1) to afford 2-methylpropan-2-yl (4S)-3-(1-{4-[cyclopropyl(methylazanylidene)(oxo)-$\lambda^6$-sulfanyl]-2-fluoro-3-methylphenyl}-2-oxoimidazol-3-yl)-2-(4-fluoro-3,5-dimethylphenyl)-4-methyl-4,5,6,7-tetrahydropyrazolo[4,3-c]pyridine-5-carboxylate (830 mg, 73.9% yield). LC-MS: m/z 667.5 (M+H)$^+$.

Step G 1-[(4S)-2-(4-fluoro-3,5-dimethylphenyl)-4-methyl-4,5,6,7-tetrahydropyrazolo[4,3-c]pyridin-3-yl]-3-{4-[cyclopropyl(methylazanylidene)(oxo)-λ⁶-sulfanyl]-2-fluoro-3-methylphenyl}-2,3-dihydro-1H-imidazol-2-one HCl salt

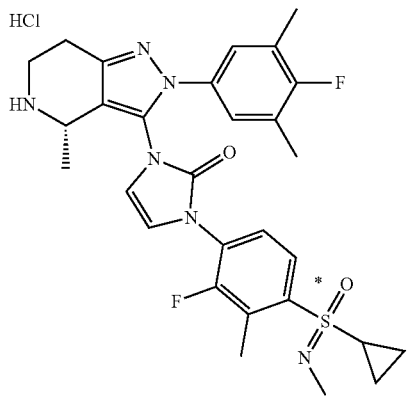 [SMILES: Cl ; CN=S(=O)(c1ccc(-n2ccn(-c3c4c(nn3-c3cc(C)c(F)c(C)c3)CCN[C@H]4C)c2=O)c(F)c1C)C1CC1]

To a solution of 2-methylpropan-2-yl(4S)-3-(1-{4-[cyclopropyl(methylazanylidene)(oxo)-λ⁶-sulfanyl]-2-fluoro-3-methylphenyl}-2-oxoimidazol-3-yl)-2-(4-fluoro-3,5-dimethylphenyl)-4-methyl-4,5,6,7-tetrahydropyrazolo[4,3-c]pyridine-5-carboxylate (50 mg, 0.075 mmol) in dioxane (2 mL) was added HCl-dioxane (4M, 2 mL). The reaction was stirred at 25° C. for 1 h. LCMS showed the reaction was completed. The reaction was concentrated to give 1-[(4S)-2-(4-fluoro-3,5-dimethylphenyl)-4-methyl-4,5,6,7-tetrahydropyrazolo[4,3-c]pyridin-3-yl]-3—{4-[cyclopropyl(methylazanylidene)(oxo)-λ⁶-sulfanyl]-2-fluoro-3-methylphenyl}-2,3-dihydro-1H-imidazol-2-one HCl salt (45 mg, 84.7% yield). LC-MS: m/z 567.5 (M+H)⁺.

Step H 3-[(1S,2S)-1-{5-[(4S)-2,2-dimethyl-3,4,5,6-tetrahydro-2H-pyran-4-yl]-2-{[(4S)-2-(4-fluoro-3,5-dimethylphenyl)-3-(1-{4-[cyclopropyl(methylazanylidene)(oxo)-λ⁶-sulfanyl]-2-fluoro-3-methylphenyl}-2-oxoimidazol-3-yl)-4-methyl-4,5,6,7-tetrahydropyrazolo[4,3-c]pyridin-5-yl]carbonyl}indol-1-yl}-2-methylcyclopropyl]-4H,5H-1,2,4-oxadiazol-5-one (Compound 195) (enantiomer 1)

To a solution of 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (30.5 mg, 0.074 mmol) and HATU (28.2 mg, 0.074 mmol) in DMF (5 mL) was added 1-[(4S)-2-(4-fluoro-3,5-dimethylphenyl)-4-methyl-4,5,6,7-tetrahydropyrazolo[4,3-c]pyridin-3-yl]-3-{4-[cyclopropyl(methylazanylidene)(oxo)-λ⁶-sulfanyl]-2-fluoro-3-methylphenyl}-2,3-dihydro-1H-imidazol-2-one HCl salt (42 mg, 0.074 mmol) and DIEA (9.56 mg, 0.074 mmol) in DMF (5 mL), the reaction was stirred at rt for 18 h. After the reaction was completed, water (20 mL) was added into the reaction mixture. The mixture was extracted with EtOAc (20 mL×3). The combined organic layers were washed with brine, dried over Na₂SO₄, filtered and concentrated. The resulting residue was purified by prep. TLC (DCM/CH₃OH=10/1) and further by prep. HPLC (Waters 3767/Qda Column: SunFire Sunfire C18, 19*250 mm*10 um; Mobile Phase A: 0.1% FA/H₂O, B: CH₃CN; Flow rate: 20 ml/min; Gradient: 64%-74%; Retention Time: 7.6-8.7 min of 17 min) to afford 3-[(1S,2S)-1-{5-[(4S)-2,2-dimethyl-3,4,5,6-tetrahydro-2H-pyran-4-yl]-2-{[(4S)-2-(4-fluoro-3,5-dimethylphenyl)-3-(1-{4-[cyclopropyl(methylazanylidene)(oxo)-λ⁶-sulfanyl]-2-fluoro-3-methylphenyl}-2-oxoimidazol-3-yl)-4-methyl-4,5,6,7-tetrahydropyrazolo[4,3-c]pyridin-5-yl]carbonyl}indol-1-yl}-2-methylcyclopropyl]-4H,5H-1,2,4-oxadiazol-5-one (19.8 mg, 27.4% yield). LC-MS: m/z 960.8 (M+H)⁺. ¹H NMR (400 MHz, DMSO-d6) δ 11.58 (brs, 1H), 7.77-7.74 (m, 1H), 7.65-7.52 (m, 2H), 7.42 (d, J=8.8 Hz, 1H), 7.27-7.24 (dd, J₁=8.8 Hz, J₂=1.6 Hz, 1H), 7.16 (d, J=6.0 Hz, 2H), 7.02 (m, 1H), 6.87 (m, 2H), 5.62-5.54 (m, 1H), 4.44 (m, 1H), 3.74 (d, J=9.2 Hz, 2H), 3.57 (m, 1H), 3.03 (m, 2H), 2.90-2.86 (m, 2H), 2.63 (s, 3H), 2.56 (s, 3H), 2.25 (s, 6H), 1.72-1.54 (m, 7 H), 1.51-1.45 (m, 3H), 1.29 (m, 4H), 1.20-1.12 (m, 7H), 0.94-0.83 (m, 2H).

Step I 3-[(1S,2S)-1-{5-[(4S)-2,2-dimethyl-3,4,5,6-tetrahydro-2H-pyran-4-yl]-2-{[(4S)-2-(4-fluoro-3,5-dimethylphenyl)-3-(1-{4-[cyclopropyl(methylazanylidene)(oxo)-λ⁶-sulfanyl]-2-fluoro-3-methylphenyl}-2-oxoimidazol-3-yl)-4-methyl-4,5,6,7-tetrahydropyrazolo[4,3-c]pyridin-5-yl]carbonyl}indol-1-yl}-2-methylcyclopropyl]-4H,5H-1,2,4-oxadiazol-5-one (Compound 196) (enantiomer 2)

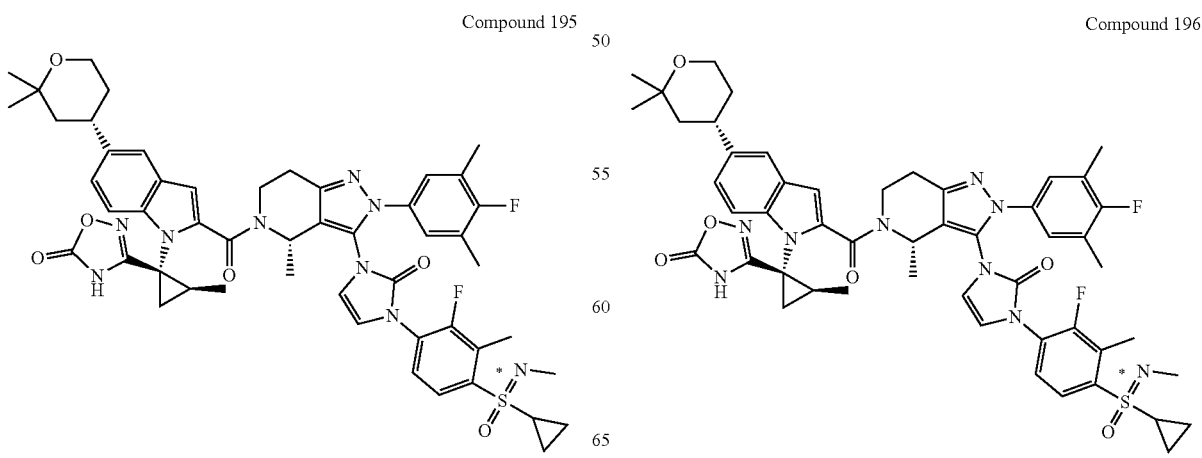

Compound 195

Compound 196

3-[(1S,2S)-1-{5-[(4S)-2,2-dimethyl-3,4,5,6-tetrahydro-2H-pyran-4-yl]-2-{[(4S)-2-(4-fluoro-3,5-dimethylphenyl)-3-(1-{4-[cyclopropyl(methylazanylidene)(oxo)-$\lambda^6$-sulfanyl]-2-fluoro-3-methylphenyl}-2-oxoimidazol-3-yl)-4-methyl-4,5,6,7-tetrahydropyrazolo[4,3-c]pyridin-5-yl]carbonyl}indol-1-yl]-2-methylcyclopropyl]-4H,5H-1,2,4-oxadiazol-5-one (Compound 196) (enantiomer 2) were synthesized according to the procedures described for the preparation of Compound 195) (enantiomer 1) (step E to step H). LC-MS: m/z 960.8 (M+H)$^+$. $^1$H NMR (400 MHz, DMSO-d6) δ 11.58 (brs, 1H), 7.75 (m, 1H), 7.64-7.53 (m, 2H), 7.41 (d, J=8.4 Hz, 1H), 7.26 (d, J=8.8 Hz, 1H), 7.16 (d, J=6.0 Hz, 2H), 7.01 (m, 1H), 6.87 (m, 2H), 5.57 (m, 1H), 4.43 (m, 1H), 3.74 (d, J=8.8 Hz, 2H), 3.58 (m, 1H), 3.04-3.01 (m, 2H), 2.90-2.86 (m, 2H), 2.63 (s, 3H), 2.56 (s, 3H), 2.24 (s, 6H), 1.72-1-63 (m, 4H), 1-62-1.46 (m, 6 H), 1.29 (m, 4H), 1.20-1.12 (m, 7H), 0.94-0.81 (m, 2H).

Example compounds 193 and 194, 214 and 215, 216, 217, 219 and 220 were synthesized using a similar procedure described in the Example A12 above using the appropriate materials.

Example A12-a 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (Compound 195) and 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 2) (Compound 196)

Compound 195

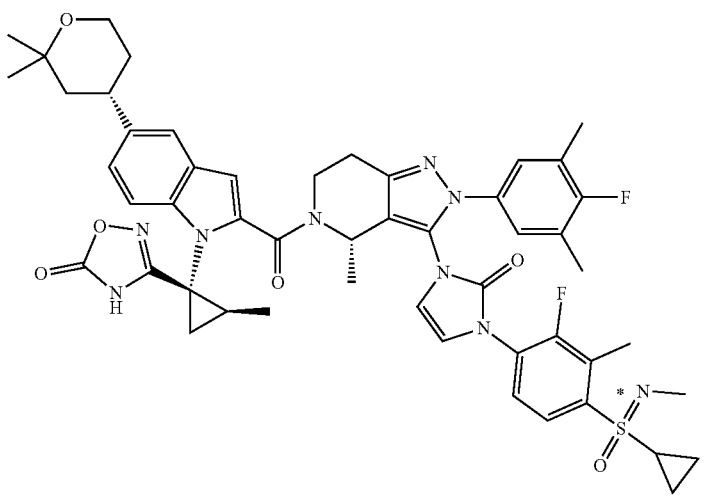

Compound 196

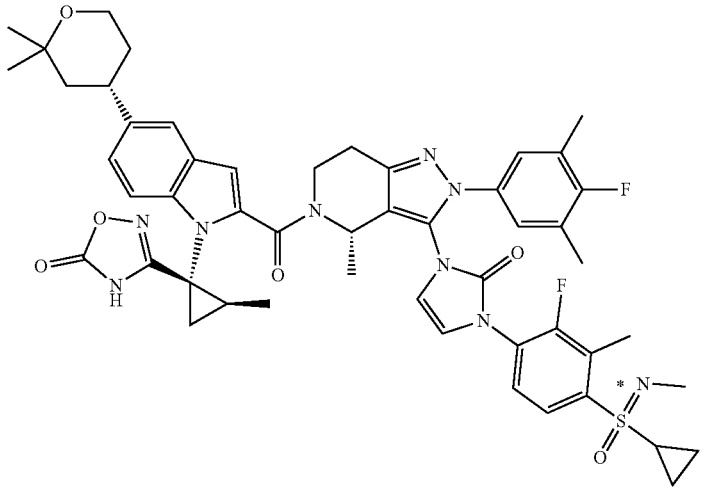

-continued
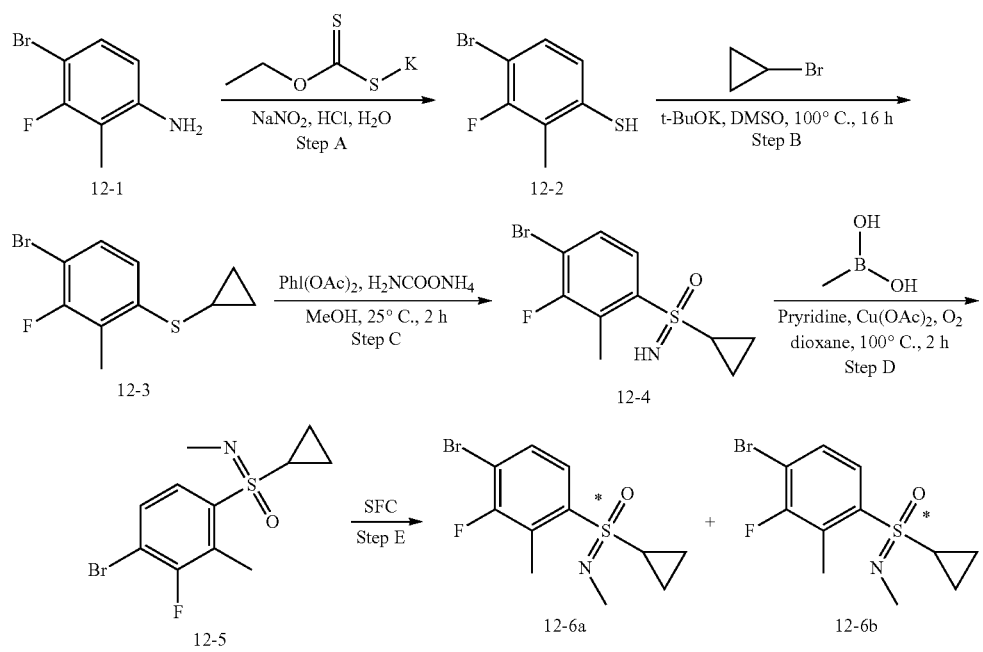
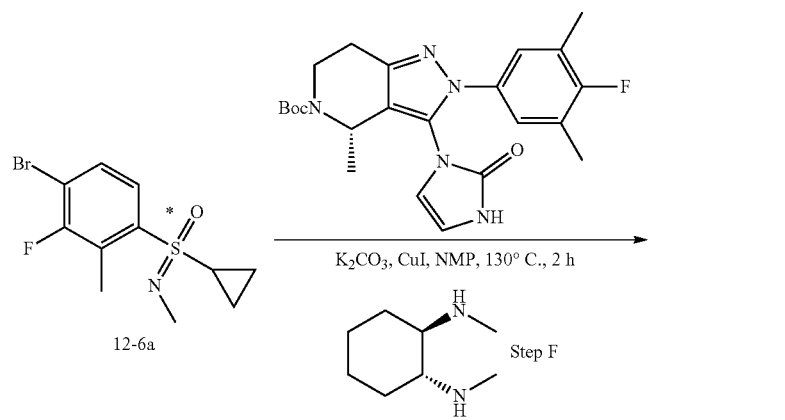
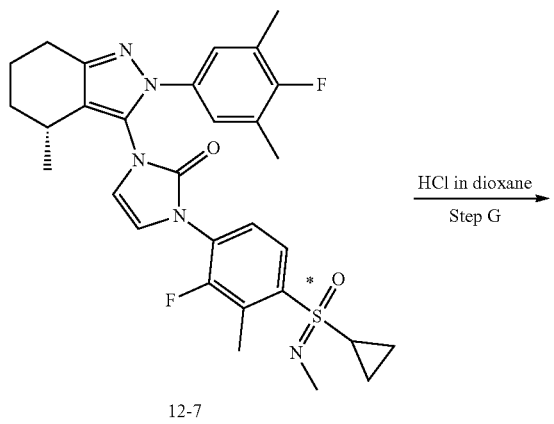

-continued
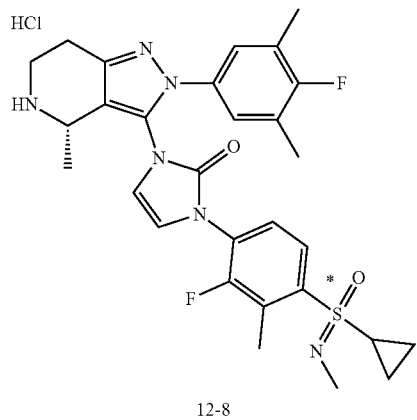
12-8
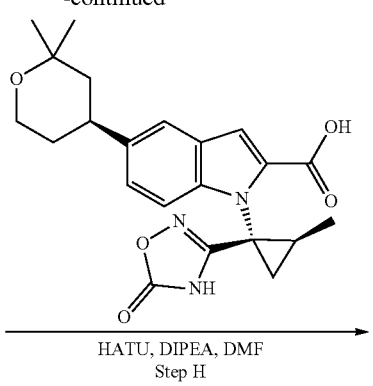
HATU, DIPEA, DMF
Step H
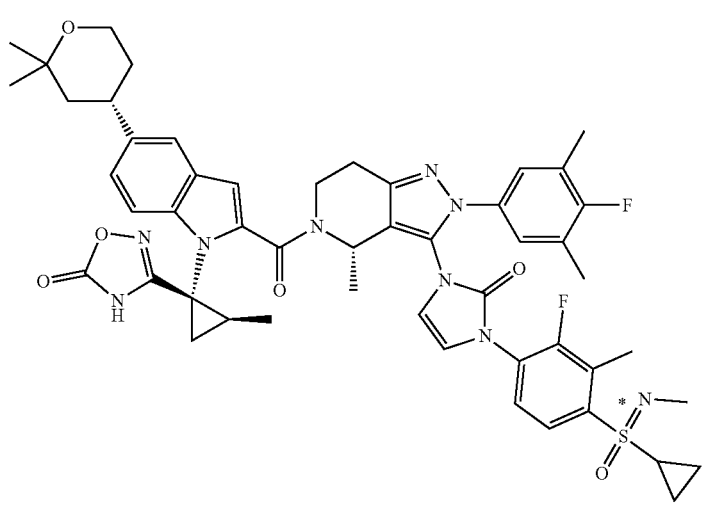
Compound 195
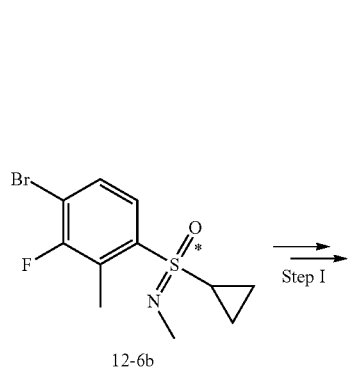
12-6b
Step I
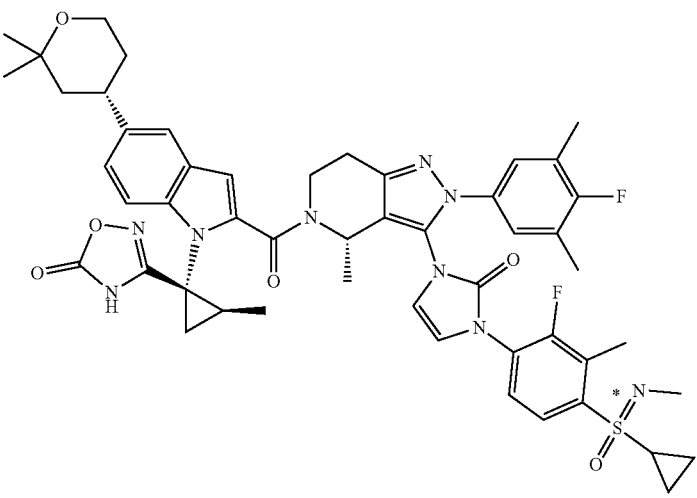
Compound 196

Step A 4-bromo-3-fluoro-2-methylbenzene-1-thiol

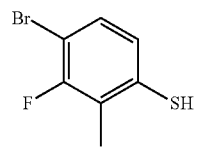

To a mixture of 4-bromo-3-fluoro-2-methylaniline (2.7 g, 13.233 mmol) in H$_2$O (10 mL) was added conc. HCl (2.205 mL, 26.465 mmol). The reaction mixture was cooled in an ice/NaCl bath (approximately −5 to −10° C.), a solution of sodium nitrite (958.6 mg, 13.894 mmol) in H$_2$O (10 mL) was added slowly over 10 minutes. The mixture was stirred for an additional 30 minutes with cooling. Separately, a solution of [(ethoxythioxomethyl)sulfanyl]potassium (2545.3 mg, 15.879 mmol) in H$_2$O (30 mL) was prepared and heated to 65° C. The cold solution of diazonium salt was then added slowly over 20 minutes to the warmed solution of potassium ethyl xanthogenate. The reaction mixture was stirred for an additional 30 minutes at 65° C. and then cooled to ambient temperature. A solution of NaOH (2646.6 mg, 66.165 mmol) in H$_2$O (10 mL) was added, the reaction was stirred at 70° C. for 18 h. After the reaction was completed, monitored by TLC, the mixture was cooled to rt, the mixture was poured into ice (200 g), acidified with concentrated HCl to pH=1, the mixture was extracted with EtOAc (50 mL×3). The combined organic extracts were dried over anhydrous Na$_2$SO$_4$, filtered and concentrated to afford 4-bromo-3-fluoro-2-methylbenzene-1-thiol (3.7 g, crude), used for the next step without purification.

Step B (4-bromo-3-fluoro-2-methylphenyl)(cyclopropyl)sulfane

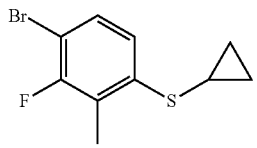

To a solution of 4-bromo-3-fluoro-2-methylbenzene-1-thiol (3.7 g, 16.735 mmol) in DMSO (60 mL) were added potassium tert-butoxide (3.76 g, 33.471 mmol) and bromocyclopropane (10.12 g, 83.676 mmol), the reaction was stirred at 100° C. for 18 h under N$_2$. TLC showed the reaction was completed. The mixture was poured into water (100 mL), extracted with EtOAc (200 mL×2). The combined organic layers were washed with brine, dried over Na$_2$SO$_4$, filtered and concentrated. The resulting residue was purified by silica gel chromatography (eluting PE 100%) to afford (4-bromo-3-fluoro-2-methylphenyl)(cyclopropyl)sulfane (2.23 g, 50.3% yield) as a colorless oil. $^1$H NMR (400 MHz, CDCl$_3$) δ 7.24-7.28 (m, 1H), 7.10-7.12 (m, 1H), 2.13 (s, 3H), 2.01-2.05 (m, 1H), 1.02-1.07 (m, 2H), 0.60-0.64 (m, 2H).

Step C (4-bromo-3-fluoro-2-methylphenyl)(cyclopropyl)(oxo)-λ$^6$-sulfanimine

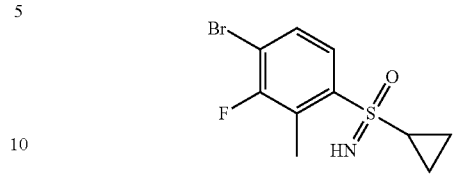

To a solution of (4-bromo-2-fluorophenyl)(cyclopropyl)sulfane (2.2 g, 8.524 mmol) in MeOH (30 mL) was added (diacetoxyiodo)benzene (8.29 g, 25.572 mmol) and ammonium carbaminate (2.66 g, 34.095 mmol). The reaction was stirred at room temperature for 1 h. After the reaction was completed, water (50 mL) was added. The mixture was extracted with EtOAc (30 mL×3). The combined organic layers were washed with brine, dried over sodium sulfate, filtered and concentrated. The resulting residue was purified by silica gel chromatography (eluting 0-50% EtOAc/PE) to afford (4-bromo-3-fluoro-2-methylphenyl)(cyclopropyl)(oxo)-λ$^6$-sulfanimine (1.17 g, 69.2% yield). LC-MS: m/z 292.0 (M+H)$^+$.

Step D 1-(4-bromo-3-fluoro-2-methylphenyl)-1-cyclopropyl-N-methyl-1-oxo-λ$^6$-sulfanimine

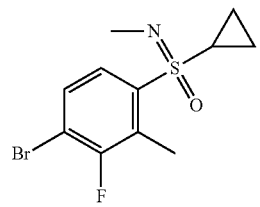 [SMILES: CN=S(=O)(c1ccc(Br)c(F)c1C)C1CC1]

To a solution of (4-bromo-3-fluoro-2-methylphenyl)(cyclopropyl)(oxo)-λ$^6$-sulfanimine (3200 mg, 10.953 mmol) in dioxane (50 mL) were added cupric bis(acetate) (5967.92 mg, 32.858 mmol), Pyridine (3.543 mL, 43.810 mmol) and methylboranediol (2622.47 mg, 43.810 mmol). The reaction was stirred at 100° C. for 2 h under 02. The mixture was concentrated under vacuum. The resulting residue was purified by silica gel chromatography (eluting PE/EA=10/1) to afford 1-(4-bromo-3-fluoro-2-methylphenyl)-1-cyclopropyl-N-methyl-1-oxo-λ$^6$-sulfanimine (2616 mg, 78.01%) as a yellow oil. LC-MS: m/z 306.2 (M+H)$^+$.

Step E 1-(4-bromo-3-fluoro-2-methylphenyl)-1-cyclopropyl-N-methyl-1-oxo-λ$^6$-sulfanimine (enantiomer 1) and 1-(4-bromo-3-fluoro-2-methylphenyl)-1-cyclopropyl-N-methyl-1-oxo-λ$^6$-sulfanimine (enantiomer 2)

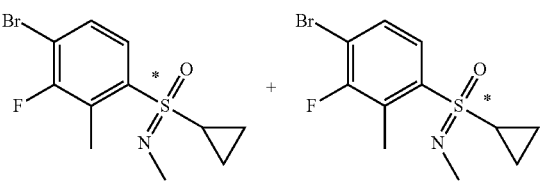 [SMILES: CN=S(=O)(c1ccc(Br)c(F)c1C)C1CC1 ; CN=S(=O)(c1ccc(Br)c(F)c1C)C1CC1]

The compound mixture 1-(4-bromo-3-fluoro-2-methylphenyl)-1-cyclopropyl-N-methyl-1-oxo-λ⁶-sulfanimine (2616 mg, 8.544 mmol) was separated by SFC (system: Waters SFC 150; Column name: DAICELCHIRALPAK® IG; Column size: 250*25 mm 10 μm; Mobile Phase A: Supercritical CO$_2$; Mobile Phase B: IPA (+0.1% 7.0 mol/L Ammonia in MeOH); Gradient: A/B=80/20; Flow rate: 100 mL/min) to afford 1-(4-bromo-3-fluoro-2-methylphenyl)-1-cyclopropyl-N-methyl-1-oxo-λ⁶-sulfanimine (enantiomer 1) (1.25 g, 37.42%) as the fast eluent, R.T=1.28 min, LC-MS: m/z 306.2 (M+H)⁺. And 1-(4-bromo-3-fluoro-2-methylphenyl)-1-cyclopropyl-N-methyl-1-oxo-λ⁶-sulfanimine (enantiomer 2) (1.16 g, 34.72%) as the slow eluent, R.T=1.97 min. LC-MS: m/z 306.2 (M+H)⁺.

Step F tert-butyl(4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1)

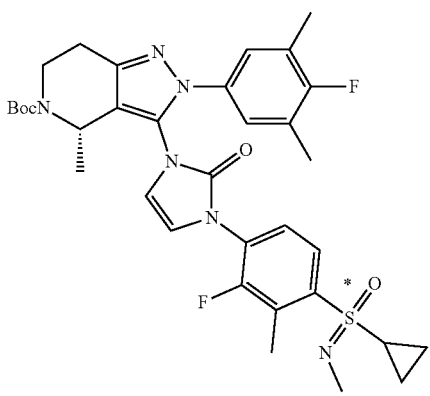 [SMILES: CN=S(=O)(c1ccc(-n2ccn(-c3c4c(nn3-c3cc(C)c(F)c(C)c3)CCN(C(=O)OC(C)(C)C)[C@H]4C)c2=O)c(F)c1C)C1CC1]

To a solution of 1-(4-bromo-3-fluoro-2-methylphenyl)-1-cyclopropyl-N-methyl-1-oxo-λ⁶-sulfanimine (enantiomer 1) (775 mg, 2.531 mmol) in NMP (15 mL) were added 2-methylpropan-2-yl(4S)-2-(4-fluoro-3,5-dimethylphenyl)-4-methyl-3-(2-oxo-3H-imidazol-1-yl)-4,5,6,7-tetrahydropyrazolo[4,3-c]pyridine-5-carboxylate (1117.51 mg, 2.531 mmol), CuI (578.46 mg, 3.037 mmol), K$_2$CO$_3$ (699.60 mg, 5.062 mmol) and methyl[(1R,2R)-2-(methylamino)cyclohexyl]amine (540.08 mg, 3.797 mmol), the reaction was stirred at 130° C. for 3 h under N$_2$. The mixture was added to water (50 mL), extracted with EA (30 mL×2), the combined organic layers were washed with brine (30 mL×3), dried over sodium sodium sulfate, filtered and concentrated under vacuum. The resulting residue was purified by flash column chromatography (eluting PE/EA=½), then purified by C18 column chromatography (eluting 50% of ACN in water, 0.1% FA) to afford tert-butyl(4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1) (1100 mg, 65.18%) as a yellow solid. LC-MS: m/z 667.7 (M+H)⁺.

Step G 1-((S)-2-(4-fluoro-3,5-dimethylphenyl)-4-methyl-4,5,6,7-tetrahydro-2H-pyrazolo[4,3-c]pyridin-3-yl)-3-(2-fluoro-3-methyl-4-(N-methylcyclopropanesulfonimidoyl)phenyl)-1,3-dihydro-2H-imidazol-2-one, HCl salt (enantiomer 1)

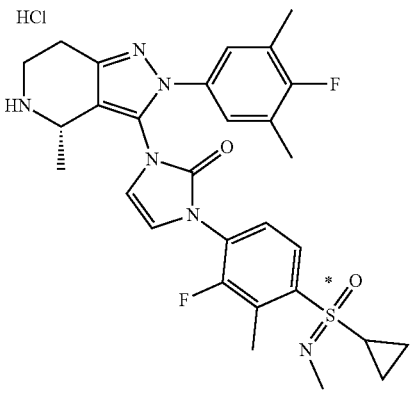 [SMILES: Cl ; CN=S(=O)(c1ccc(-n2ccn(-c3c4c(nn3-c3cc(C)c(F)c(C)c3)CCN[C@H]4C)c2=O)c(F)c1C)C1CC1]

To a solution of tert-butyl(4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1) (1050 mg, 1.575 mmol) in DCM (10 mL) were added HCl (3.937 mL, 15.747 mmol), the mixture was stirred at rt for 16 h under N$_2$ protection. The mixture was concentrated under vacuum to afford 1-((S)-2-(4-fluoro-3,5-dimethylphenyl)-4-methyl-4,5,6,7-tetrahydro-2H-pyrazolo[4,3-c]pyridin-3-yl)-3-(2-fluoro-3-methyl-4-(N-methylcyclopropanesulfonimidoyl)phenyl)-1,3-dihydro-2H-imidazol-2-one, HCl salt (enantiomer 1) (893 mg, 100.0%), used for the next step with no purification. LC-MS: m/z 567.1 (M+H-HCl)+.

Step H 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (Compound 195)

Compound 195

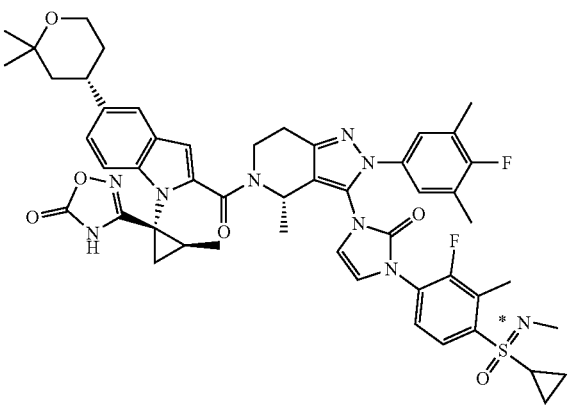

To a solution of 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (778.15 mg, 1.891 mmol) and HATU (898.25 mg, 2.364 mmol) in DMF (20 mL) was added a solution of 1-((S)-2-(4-fluoro-3,5-dimethylphenyl)-4-methyl-4,5,6,7-tetrahydro-2H-pyrazolo[4,3-c]pyridin-3-yl)-3-(2-fluoro-3-methyl-4-(N-methylcyclopropanesulfonimidoyl)phenyl)-1,3-dihydro-2H-imidazol-2-one, HCl salt (enantiomer 1) (893 mg, 1.576 mmol) and DIPEA (1.370 mL, 7.879 mmol) in DMF (5 mL), the mixture was stirred at rt for 18 h under Ar. After the reaction was completed, water (50 mL) was added. The mixture was extracted with EA (50 mL×3). The combined organic layers were washed with brine (50 mL×3), dried over sodium sodium sulfate, filtered and concentrated under vacuum. The resulting residue was purified by silica gel chromatography (DCM/MeOH=50/1), then purified by C18 column chromatography (48% of MeCN in water, 0.1% FA) and C18 column chromatography (50% of MeCN in water, 0.1% NH$_4$HCO$_3$) to afford 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (791 mg, 51.38%). LC-MS: m/z 960.9 (M+H)$^+$. $^1$H NMR (400 MHz, DMSO-d6) δ 11.60 (brs, 1H), 7.76-7.74 (m, 1H), 7.59-7.53 (m, 2H), 7.42 (d, J=8.4 Hz, 1H), 7.27-7.24 (dd, J$_1$=8.4 Hz, J$_2$=1.6 Hz, 1H), 7.16 (d, J=6.4 Hz, 2 H), 7.01 (m, 1H), 6.86 (m, 2H), 5.56-5.54 (m, 1H), 4.48-4.42 (m, 1H), 3.75-3.72 (m, 2H), 3.61-3.51 (m, 1H), 2.90-2.86 (m, 2H), 2.63 (s, 3H), 2.57 (s, 3H), 2.25 (s, 6H), 1.78-1.45 (m, 11H), 1.31-1.26 (m, 5H), 1.20-1.12 (m, 7H), 0.96-0.91 (m, 1H), 0.87-0.82 (m, 1H).

Step I 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 2) (Compound 196)

Compound 196

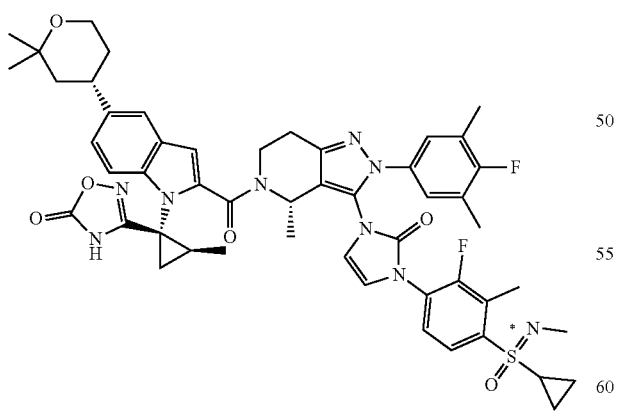

3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-methyl-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 2) (Compound 196) were synthesized according to the procedures described for the preparation of Compound 195) (enantiomer 1) (step F to step H). LC-MS: m/z 960.8 (M+H)$^+$. $^1$H NMR (400 MHz, DMSO-d6) δ 11.58 (brs, 1H), 7.75 (m, 1H), 7.64-7.53 (m, 2H), 7.41 (d, J=8.4 Hz, 1H), 7.26 (d, J=8.8 Hz, 1H), 7.16 (d, J=6.0 Hz, 2H), 7.01 (m, 1H), 6.87 (m, 2H), 5.57 (m, 1H), 4.43 (m, 1H), 3.74 (d, J=8.8 Hz, 2H), 3.58 (m, 1H), 3.04-3.01 (m, 2H), 2.90-2.86 (m, 2H), 2.63 (s, 3H), 2.56 (s, 3H), 2.24 (s, 6H), 1.72-1-63 (m, 4H), $_{1-62}$-1.46 (m, 6H), 1.29 (m, 4H), 1.20-1.12 (m, 7H), 0.94-0.81 (m, 2H).

Example A13

3-[(1S,2S)-1-(2-{[(4S)-2-(4-fluoro-3,5-dimethylphenyl)-3-(1-{4-[cyclopropyl(methylazanylidene)(oxo)-)$^6$-sulfanyl]-2-fluorophenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one (Compound 221) (enantiomer 1) and 3-[(1S,2S)-1-(2-{[(4S)-2-(4-fluoro-3,5-dimethylphenyl)-3-(1-{4-[cyclopropyl(methylazanylidene)(oxo)-λ$^6$-sulfanyl]-2-fluorophenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one (Compound 222) (enantiomer 2)

Compound 221

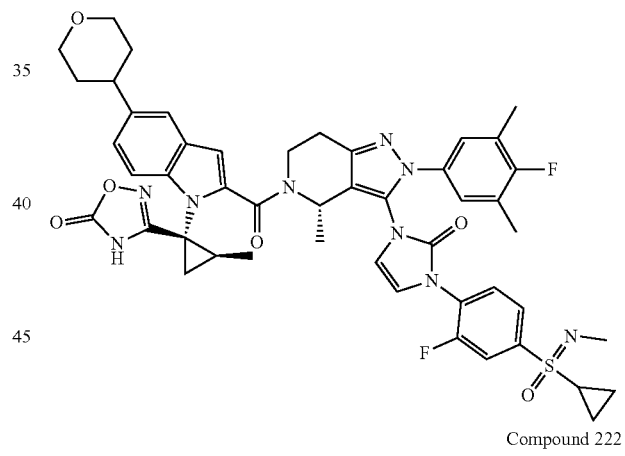

Compound 222

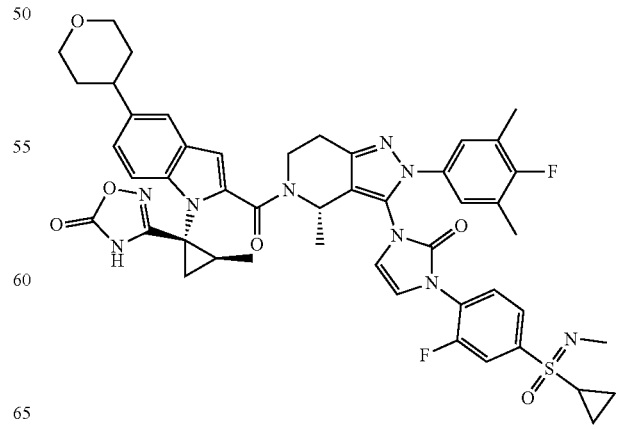

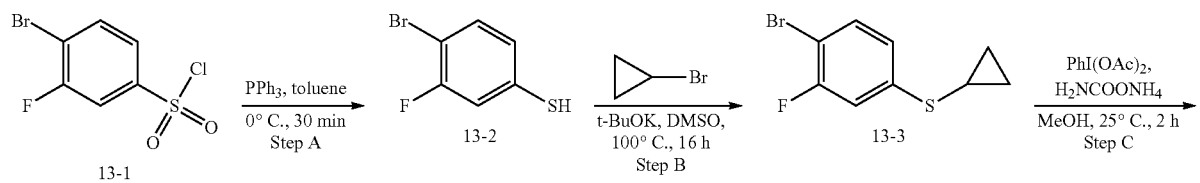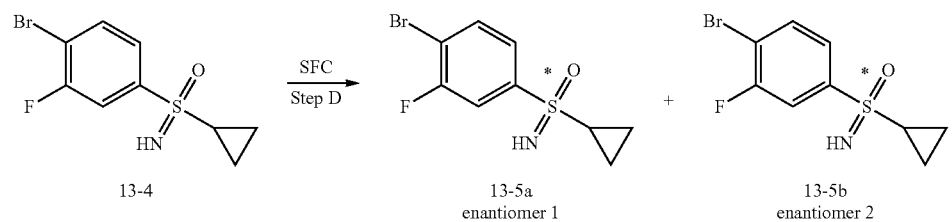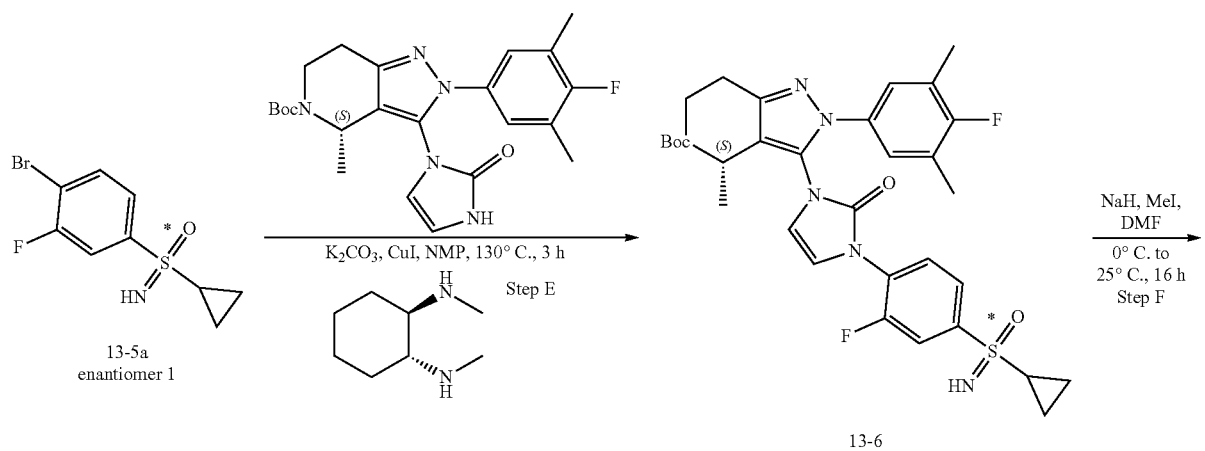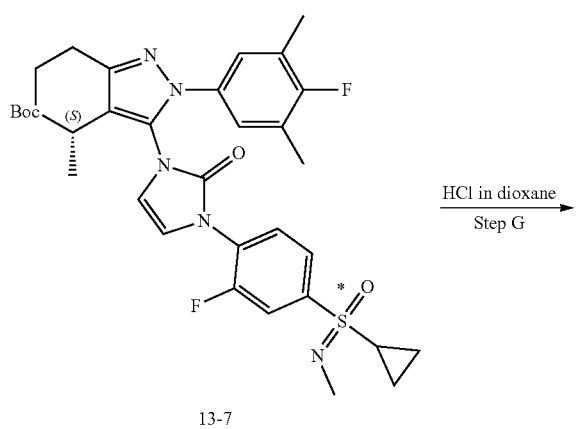

-continued
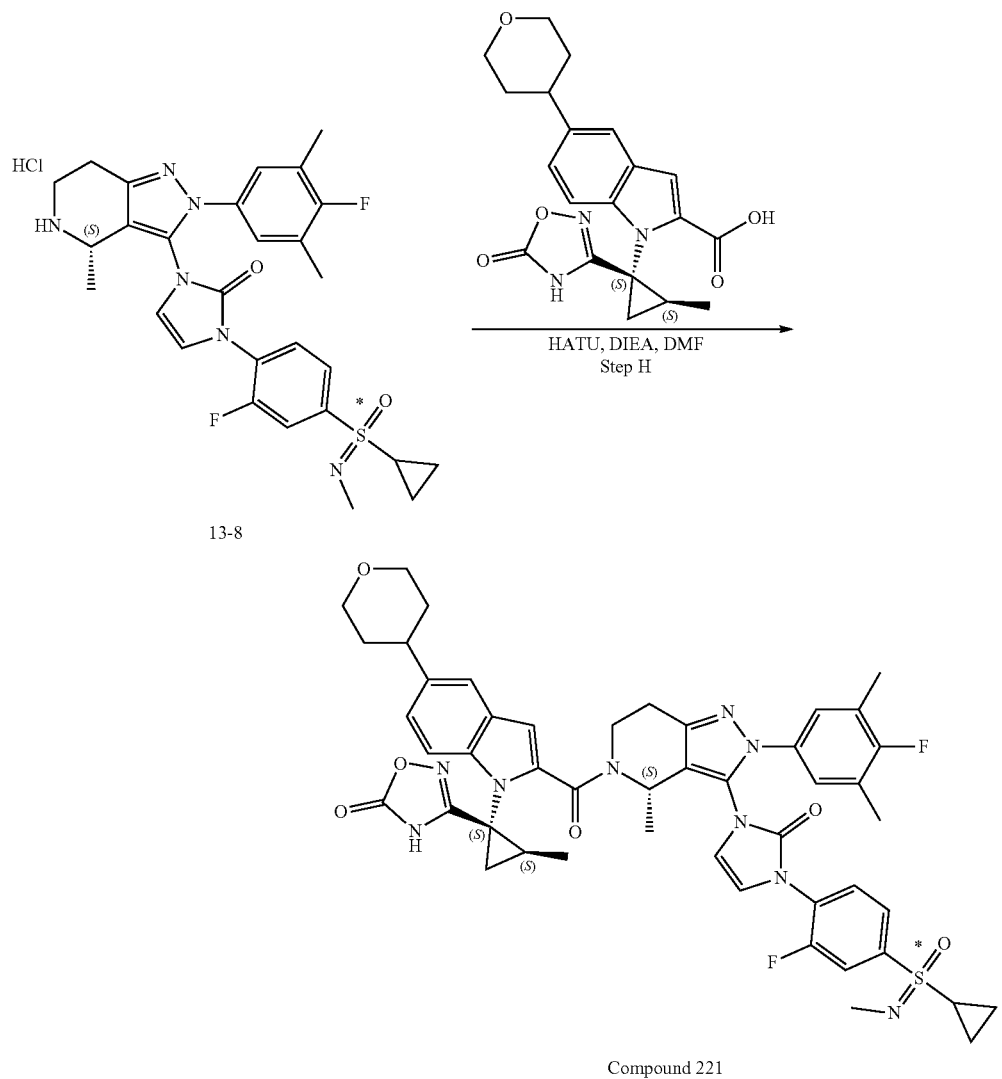
Compound 221
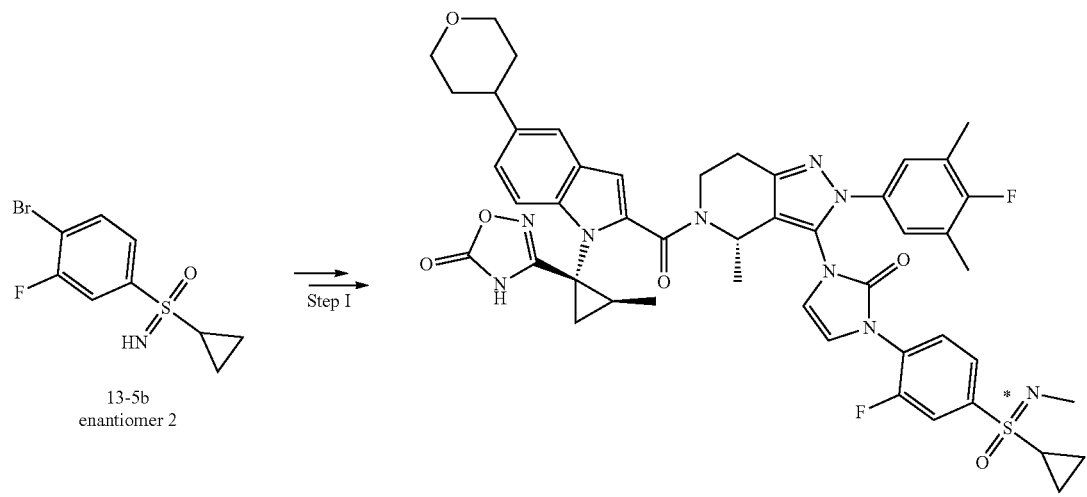
Compound 222

Step A 4-bromo-3-fluorobenzene-1-thiol

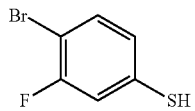

To a stirred solution 4-bromo-3-fluorobenzenesulfonyl chloride (3 g, 10.969 mmol) in toluene (30 mL) was added triphenylphosphane (11.51 g, 43.876 mmol). The reaction mixture was stirred at room temperature for 40 minutes. TLC indicated completion of reaction. The reaction was diluted with water (15 mL) and stirred for 10 minutes. The two phases were separated, and the organic phase was washed with 10% sodium hydroxide solution (25 mL×2). The combined sodium hydroxide solution phase was washed with toluene (50 mL), acidified with dilute HCl to pH 4~5, and extracted with $CH_2Cl_2$ (40 mL×2). The organic phases were dried over anhydrous sodium sulfate and filtered. The filtrate was concentrated under vacuum, and the residue was purified by flash column chromatography on silica gel (eluting with ethyl acetate in petroleum ether from 0 to 3%) to afford 4-bromo-3-fluorobenzene-1-thiol (1.8 g, 79.3% yield).

Step B (4-bromo-3-fluorophenyl)(cyclopropyl)sulfane

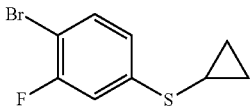

To a solution of 4-bromo-3-fluoro-2-methylbenzene-1-thiol (1.0 g, 4.830 mmol) in DMSO (10 mL) were added potassium 2-methylpropan-2-olate (1-62 g, 14.489 mmol) and bromocyclopropane (3.095 mL, 38.636 mmol), the reaction was stirred at 100° C. for 18 h under N2. TLC showed the reaction was completed. The mixture was added to water (100 mL), extracted with EA (100 mL×2). The combined organic layers were washed with brine (100 mL×3), dried over sodium sulfate, filtered and concentrated under vacuum. The resulting residue was purified by silica gel chromatography (eluting 100% PE) to afford (4-bromo-3-fluorophenyl)(cyclopropyl)sulfane (1.4 g, 52.9% yield).

Step C (4-bromo-3-fluorophenyl)(cyclopropyl)(oxo)-$\lambda^6$-sulfanimine

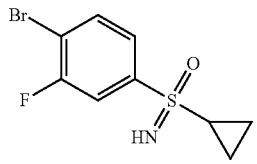

To a solution of (4-bromo-3-fluorophenyl)(cyclopropyl)sulfane (6.4 g, 25.897 mmol) in MeOH (60 mL) was added (diacetoxyiodo)benzene (25.18 g, 77.692 mmol) and ammonium carbamate (8.09 g, 103.589 mmol). The reaction was stirred at room temperature for 1 h. After the reaction was completed, water (100 mL) was added. The mixture was extracted with EA (50 mL×3). The combined organic layers were washed with brine, dried over sodium sulfate, filtered and concentrated under vacuum. The resulting residue was purified by silica gel chromatography (PE/EA=4/1) to afford (4-bromo-3-fluorophenyl)(cyclopropyl)(oxo)-$\lambda^6$-sulfanimine (3.0 g, 41.6% yield). LC-MS: m/z 280.0 $(M+H)^+$.

Step D (4-bromo-3-fluorophenyl)(cyclopropyl)(oxo)-$\lambda^6$-sulfanimine (enantiomer 1) 13-5a

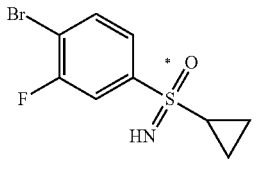 [SMILES: N=S(=O)(c1ccc(Br)c(F)c1)C1CC1]

enantiomer 1

The compound mixture (4-bromo-3-fluorophenyl)(cyclopropyl)(oxo)-$\lambda^6$-sulfanimine (3.0 g, 4.00 mmol) was separated by SFC (Column: DAICELCHIRALCEL® AS 250 mm*25 mm, 10 m, Mobile phase A (Supercritical $CO_2$), Mobile phase B (MeOH (0.1% 7.0 M Ammonia in MeOH)), Gradient: B=20%, Flow rate: 100 mL/min, Column temp: 25° C.) to afford (4-bromo-3-fluorophenyl)(cyclopropyl)(oxo)-$\lambda^6$-sulfanimine (enantiomer 1) (1.34 g, 44.6% yield) as the fast eluent, LC-MS: m/z 280.0 (M+H)+ and (4-bromo-3-fluorophenyl)(cyclopropyl)(oxo)-$\lambda^6$-sulfanmine (enantiomer 2) (1.36 g, 45.3% yield) as the slow eluent, LC-MS: m/z 280.0 $(M+H)^+$.

Step E 2-methylpropan-2-yl(4S)-2-(4-fluoro-3,5-dimethylphenyl)-3-(1-{4-[azanylidene(cyclopropyl)(oxo)-$\lambda^6$-sulfanyl]-2-fluorophenyl}-2-oxoimidazol-3-yl)-4-methyl-4,5,6,7-tetrahydropyrazolo[4,3-c]pyridine-5-carboxylate

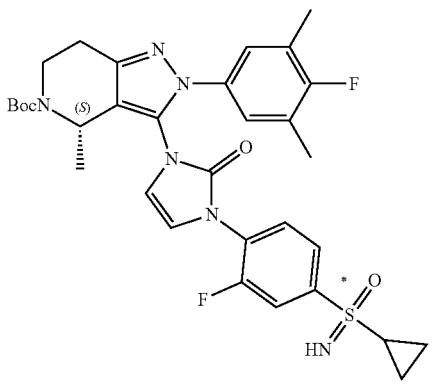

To a solution of 2-methylpropan-2-yl(4S)-2-(4-fluoro-3,5-dimethylphenyl)-4-methyl-3-(2-oxo-1H-imidazol-3-yl)-4,5,6,7-tetrahydropyrazolo[4,3-c]pyridine-5-carboxylate (67 mg, 0.152 mmol) in NMP (10 mL) was added (4-bromo-3-fluorophenyl)(cyclopropyl)(oxo)-$\lambda^6$-sulfanimine (50.65 mg, 0.182 mmol), (1R,2R)-N1,N2-dimethylcyclohexane-1,2-diamine (32.32 mg, 0.228 mmol), CuI (57.80 mg, 0.304 mmol) and K$_2$CO$_3$ (41.94 mg, 0.304 mmol), the mixture was stirred at 130° C. for 3 h. After the reaction was completed, water (20 mL) was added. The mixture was extracted with EA (20 mL×3). The combined organic layers were washed with brine (15 mL), dried over anhydrous sodium sulfate, filtered and concentrated under vacuum. The resulting residue was purified by prep-TLC (PE/EA=1/1) to afford 2-methylpropan-2-yl(4S)-2-(4-fluoro-3,5-dimethylphenyl)-3-(1-{4-[azanylidene(cyclopropyl)(oxo)-$\lambda^6$-sulfanyl]-2-fluorophenyl}-2-oxoimidazol-3-yl)-4-methyl-4,5,6,7-tetrahydropyrazolo[4,3-c]pyridine-5-carboxylate (100 mg, 0.119 mmol, 78.4%) (1.10 g, 90% yield). LC-MS: m/z 639.5 (M+H)$^+$.

Step F 2-methylpropan-2-yl(4S)-3-(1-{4-[cyclopropyl(methylazanylidene)(oxo)-$\lambda^6$-sulfanyl]-2-fluoro-3-methylphenyl}-2-oxoimidazol-3-yl)-2-(4-fluoro-3,5-dimethylphenyl)-4-methyl-4,5,6,7-tetrahydropyrazolo[4,3-c]pyridine-5-carboxylate

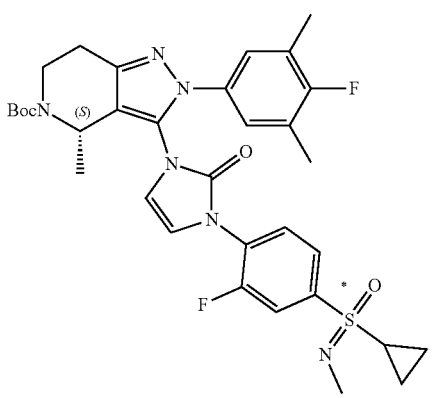

To a solution of 2-methylpropan-2-yl(4S)-2-(4-fluoro-3,5-dimethylphenyl)-3-(1-{4-[azanylidene(cyclopropyl)(oxo)-$\lambda^6$-sulfanyl]-2-fluorophenyl}-2-oxoimidazol-3-yl)-4-methyl-4,5,6,7-tetrahydropyrazolo[4,3-c]pyridine-5-carboxylate (50 mg, 0.078 mmol) in DMF (6 mL) was added NaH (3.76 mg, 0.157 mmol) at 0° C., and the reaction was stirred at 0° C. for 1 h. CH$_3$I (0.019 mL, 0.235 mmol) was added, the reaction was stirred at rt for 18 h. After the reaction was completed, water (10 mL) was added. The mixture was extracted with EtOAc (10 mL×3). The combined organic layers were washed with brine (15 mL), dried over anhydrous sodium sulfate, filtered and concentrated under vacuum. The resulting residue was purified by prep. TLC (MeOH/DCM=1/20) to afford 2-methylpropan-2-yl(4S)-3-(1-{4-[cyclopropyl(methylazanylidene)(oxo)-$\lambda^6$-sulfanyl]-2-fluoro-3-methylphenyl}-2-oxoimidazol-3-yl)-2-(4-fluoro-3,5-dimethylphenyl)-4-methyl-4,5,6,7-tetrahydropyrazolo[4,3-c]pyridine-5-carboxylate (35 mg, 68.5% yield). LC-MS: m/z 653.4 (M+H)$^+$.

Step G 1-[(4S)-2-(4-fluoro-3,5-dimethylphenyl)-4-methyl-4,5,6,7-tetrahydropyrazolo[4,3-c]pyridin-3-yl]-3-{4-[cyclopropyl(methylazanylidene)(oxo)-$\lambda^6$-sulfanyl]-2-fluorophenyl}-2,3-dihydro-1H-imidazol-2-one HCl salt

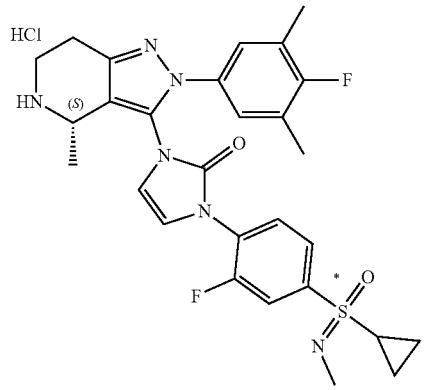

To a solution of 2-methylpropan-2-yl(4S)-3-(1-{4-[cyclopropyl(methylazanylidene)(oxo)-$\lambda^6$-sulfanyl]-2-fluoro-3-methylphenyl}-2-oxoimidazol-3-yl)-2-(4-fluoro-3,5-dimethylphenyl)-4-methyl-4,5,6,7-tetrahydropyrazolo[4,3-c]pyridine-5-carboxylate (50 mg, 0.077 mmol) in dioxane (2 mL) was added HCl in dioxane (4 mL). The reaction was stirred at 25° C. for 18 h. LCMS showed the reaction was completed. The reaction was concentrated under vacuum to give 1-[(4S)-2-(4-fluoro-3,5-dimethylphenyl)-4-methyl-4,5,6,7-tetrahydropyrazolo[4,3-c]pyridin-3-yl]-3-{4-[cyclopropyl(methylazanylidene)(oxo)-$\lambda^6$-sulfanyl]-2-fluorophenyl}-2,3-dihydro-1H-imidazol-2-one HCl salt (50 mg, 88.9%) as a yellow solid. LC-MS: m/z 553.2 (M+H)$^+$.

Step H 3-[(1S,2S)-1-(2-{[(4S)-2-(4-fluoro-3,5-dimethylphenyl)-3-(1-{4-[cyclopropyl(methylazanylidene)(oxo)-λ⁶-sulfanyl]-2-fluorophenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one (Compound 221) (enantiomer 1)

Step I 3-[(1S,2S)-1-(2-{[(4S)-2-(4-fluoro-3,5-dimethylphenyl)-3-(1-{4-[cyclopropyl(methylazanylidene)(oxo)-λ⁶-sulfanyl]-2-fluorophenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one (Compound 222) (enantiomer 2)

Compound 221

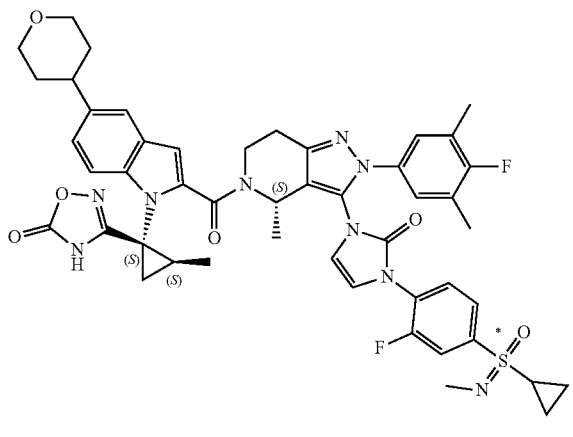

Compound 222

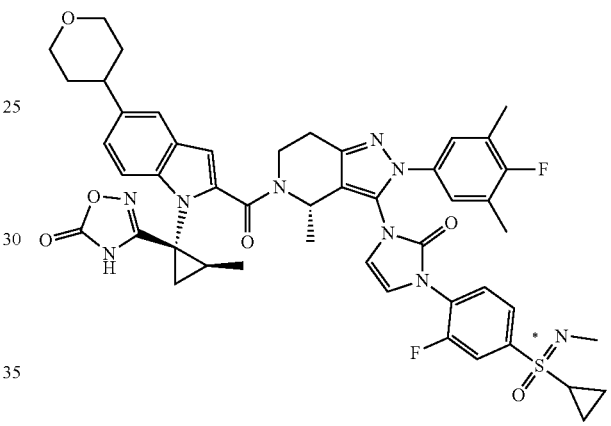

To a solution of 1-[(4S)-2-(4-fluoro-3,5-dimethylphenyl)-4-methyl-4,5,6,7-tetrahydropyrazolo[4,3-c]pyridin-3-yl]-3-{4-[cyclopropyl(methylazanylidene)(oxo)-λ⁶-sulfanyl]-2-fluorophenyl}-2,3-dihydro-1H-imidazol-2-one HCl salt (42 mg, 0.076 mmol) and HATU (57.76 mg, 0.152 mmol) in N,N-dimethylmethanamide (8 mL) was added 1-[(1S,2S)-2-methyl-1-(5-oxo-4H-1,2,4-oxadiazol-3-yl)cyclopropyl]-5-(3,4,5,6-tetrahydro-2H-pyran-4-yl)indole-2-carboxylic acid (29.14 mg, 0.076 mmol) and DIEA (49.02 mg, 0.380 mmol), the reaction was stirred at rt for 2 h. After the reaction was completed, water (20 mL) was added. The mixture was extracted with EA (20 mL×3). The combined organic layers were washed with brine (15 mL), dried over sulfate, filtered and concentrated under vacuum. The resulting residue was purified by prep. HPLC(Waters 2767/Qda, Column: SunFire Sunfire C18, 19*250 mm, 10 μm; Mobile Phase A: 0.1% FA/H₂O, B: CH₃CN; flow rate: 20 mL/min; gradient: 72%~77%; Retention Time: 7.1-7.9 min of 17 min) to afford 3-[(1S,2S)-1-(2-{[(4S)-2-(4-fluoro-3,5-dimethylphenyl)-3-(1-{4-[cyclopropyl(methylazanylidene)(oxo)-λ⁶-sulfanyl]-2-fluorophenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one (11.4 mg, 16.2% yield). LC-MS: m/z 918.3 (M+H)⁺. ¹H NMR (400 MHz, DMSO-d6) δ 11.60 (brs, 1H), 7.77-7.71 (m, 3H), 7.53 (s, 1H), 7.44 (d, J=8.4 Hz, 1H), 7.28 (d, J=9.2 Hz, 1H), 7.16 (d, J=6.0 Hz, 2H), 7.05 (s, 1H), 6.88 (s, 2H), 5.58 (m, 1H), 4.46 (m, 1H), 4.00-3.97 (d, J=10.8 Hz, 2H), 3.58-3.46 (m, 3H), 2.91-2.87 (m, 3H), 2.80-2.77 (m, 1H), 2.59 (s, 3H), 2.25 (s, 6H), 1.76-1-62 (m, 7H), 1.46 (m, 3H), 1.27-1.12 (m, 4H), 1.10-1.08 (m, 1H), 1.01-0.91 (m, 2H).

3-[(1S,2S)-1-(2-{[(4S)-2-(4-fluoro-3,5-dimethylphenyl)-3-(1-{4-[cyclopropyl(methylazanylidene)(oxo)-λ⁶-sulfanyl]-2-fluorophenyl}-2-oxoimidazol-3-yl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one (Compound 222) (enantiomer 2) were synthesized according to the procedures described for the preparation of Compound 221) (enantiomer 1) (step E to step H). LC-MS: m/z 918.3 (M+H)⁺. ¹H NMR (400 MHz, DMSO-d6) δ 11.59 (brs, 1H), 7.78-7.75 (m, 3H), 7.53 (s, 1H), 7.44 (d, J=8.4 Hz, 1H), 7.28 (d, J=8.8 Hz, 1H), 7.16 (d, J=6.4 Hz, 2H), 7.05 (s, 1 H), 6.88 (s, 2H), 5.58 (m, 1H), 4.48 (m, 1H), 4.00-3.97 (m, 2H), 3.59-3.46 (m, 3H), 2.91-2.87 (m, 2H), 2.80-2.77 (m, 1H), 2.60 (s, 3H), 2.25 (s, 6H), 1.76-1.72 (m, 6H), 1-64 (m, 1H), 1.46 (m, 3H), 1.27-1.08 (m, 6H), 1.01-0.91 (m, 2H).

Example compounds 164, 203, 204 and 205, 208 and 209 were synthesized using a similar procedure described in the Example A13 above using the appropriate materials.

Example A14
3-[(1S,2S)-1-{5-[(4S)-2,2-dimethyl-3,4,5,6-tetra-hydro-2H-pyran-4-yl]-2-{[(4S)-2-(4-fluoro-3,5-dimethylphenyl)-3-(1-{4-[cyclopropyl(methylazanylidene)(oxo)-$\lambda^6$-sulfanyl]-2-fluorophenyl}-2-oxoimidazol-3-yl)-4-methyl-4,5,6,7-tetrahydropyrazolo[4,3-c]pyridin-5-yl]carbonyl}indol-1-yl}-2-methylcyclopropyl]-4H,5H-1,2,4-oxadiazol-5-one (Compound 180)
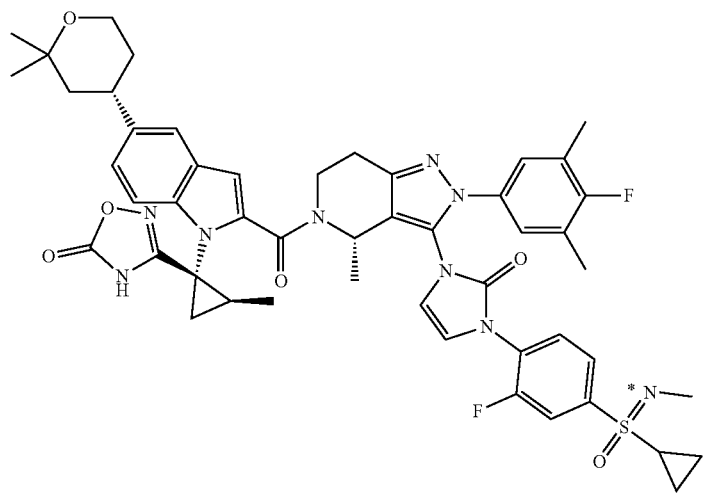
Compound 180
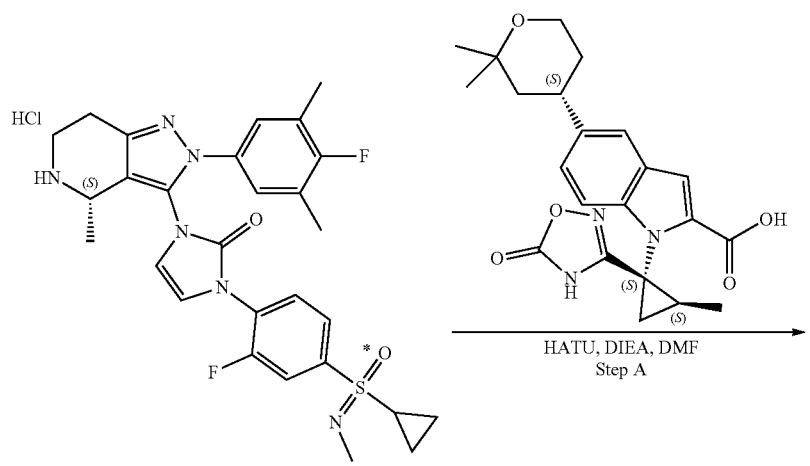
13-8
HATU, DIEA, DMF
Step A -continued

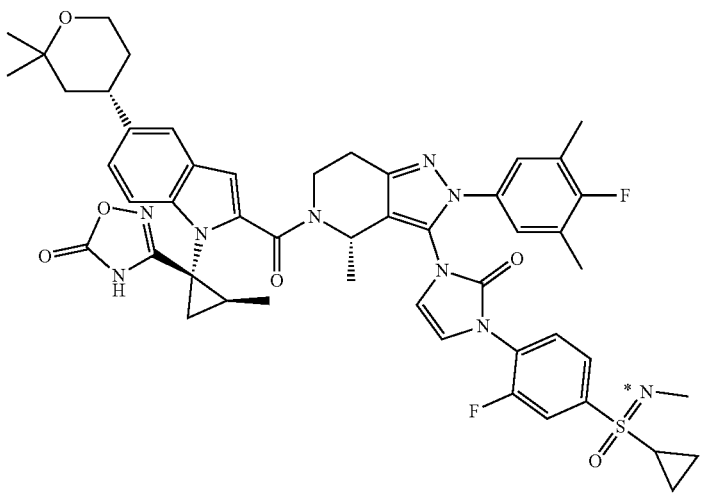

Compound 180

Step A 3-[(1S,2S)-1-{5-[(4S)-2,2-dimethyl-3,4,5,6-tetrahydro-2H-pyran-4-yl]-2-{[(4S)-2-(4-fluoro-3,5-dimethylphenyl)-3-(1-{4-[cyclopropyl(methylazanylidene)(oxo)-λ⁶-sulfanyl]-2-fluorophenyl}-2-oxoimidazol-3-yl)-4-methyl-4,5,6,7-tetrahydropyrazolo [4,3-c]pyridin-5-yl]carbonyl}indol-1-yl]-2-methylcyclopropyl]-4H,5H-1,2,4-oxadiazol-5-one (Compound 180)

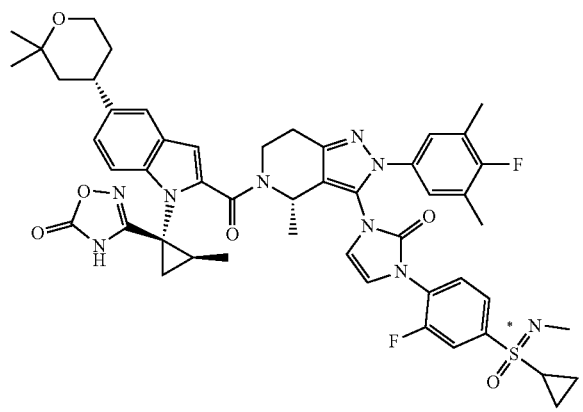 [SMILES: CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1)C1CC1]

To a solution of 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (37.23 mg, 0.090 mmol) and HATU (68.76 mg, 0.181 mmol) in N,N-dimethylmethanamide (8 mL) was added 3-[(4S)-2-(4-fluoro-3,5-dimethylphenyl)-4-methyl-4,5,6,7-tetrahydropyrazolo[4,3-c]pyridin-3-yl]-1-{4-[cyclopropyl(methylazanylidene)(oxo)-λ⁶-sulfanyl]-2-fluorophenyl}-2,3-dihydro-1H-imidazol-2-one (50 mg, 0.090 mmol) and DIEA (58.36 mg, 0.452 mmol). The mixture was stirred at rt for 2 h. After the reaction was completed, water (20 mL) was added into the mixture. The solution was extracted with EtOAc (20 mL×3). The combined organic layers were washed with brine, dried over sulfate, filtered and concentrated under vacuum. The resulting residue was purified by prep. HPLC (Waters 2767/Qda, Column: SunFire Sunfire C18, 19*250 mm, 10 μm; Mobile Phase A: 0.1% FA/H2O, B: CH$_3$CN; flow rate: 20 mL/min; gradient: 76%-81%; Retention Time: 7.9-8.7 min of 17 min) to afford 3-[(1S,2S)-1-{5-[(4S)-2,2-dimethyl-3,4,5,6-tetrahydro-2H-pyran-4-yl]-2-{[(4S)-2-(4-fluoro-3,5-dimethylphenyl)-3-(1-{4-[cyclopropyl(methylazanylidene)(oxo)-λ⁶-sulfanyl]-2-fluorophenyl}-2-oxoimidazol-3-yl)-4-methyl-4,5,6,7-tetrahydropyrazolo[4,3-c]pyridin-5-yl]carbonyl}indol-1-yl]-2-methylcyclopropyl]-4H,5H-1,2,4-oxadiazol-5-one (39.9 mg, 46.7% yield). LC-MS: m/z 946.7 (M+H)⁺. ¹H NMR (400 MHz, DMSO-d6) δ 11.55 (brs, 1H), 7.78-7.75 (m, 3H), 7.51 (s, 1H), 7.42 (d, J=8.4 Hz, 1H), 7.24 (d, J=8.0 Hz, 1H), 7.16 (d, J=6.4 Hz, 2H), 7.04 (s, 1H), 6.89-6.76 (m, 2H), 5.54 (m, 1H), 4.40 (m, 1H), 3.74 (d, J=9.2 Hz, 2H), 3.51 (m, 1H), 2.83 (m, 1H), 2.79 (m, 1H), 2.59 (s, 3H), 2.24 (s, 6H), 1.73-1.55 (m, 8H), 1.44 (s, 3H), 1.30-1.21 (m, 11H), 1.10 (m, 1H), 0.98-0.90 (m, 2H).

Example A15
3-[(1S,2S)-1-(2-{[(4S)-3-{1-[4-(1-azanylidene-1-oxo-1λ⁶-thian-4-yl)phenyl]-2-oxoimidazol-3-yl}-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one
(Compound 182)
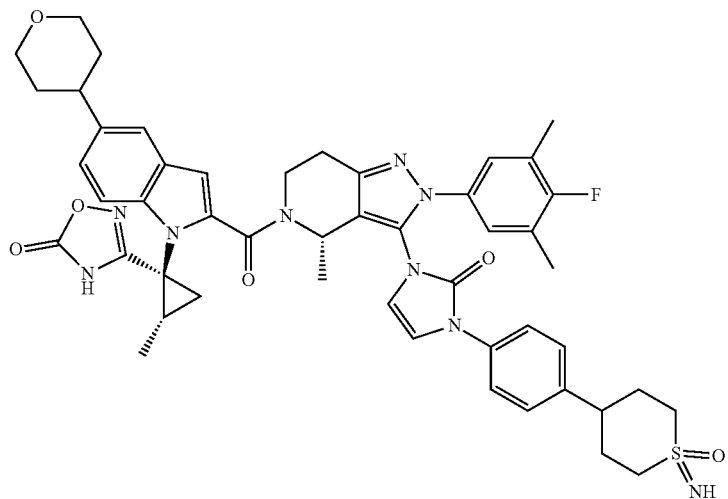
Compound 182
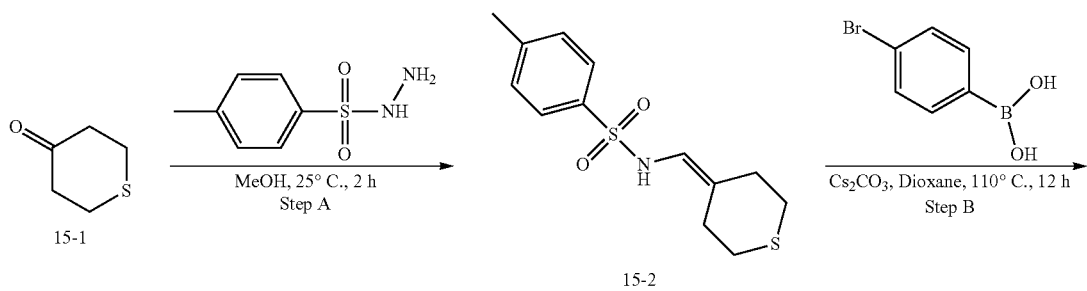
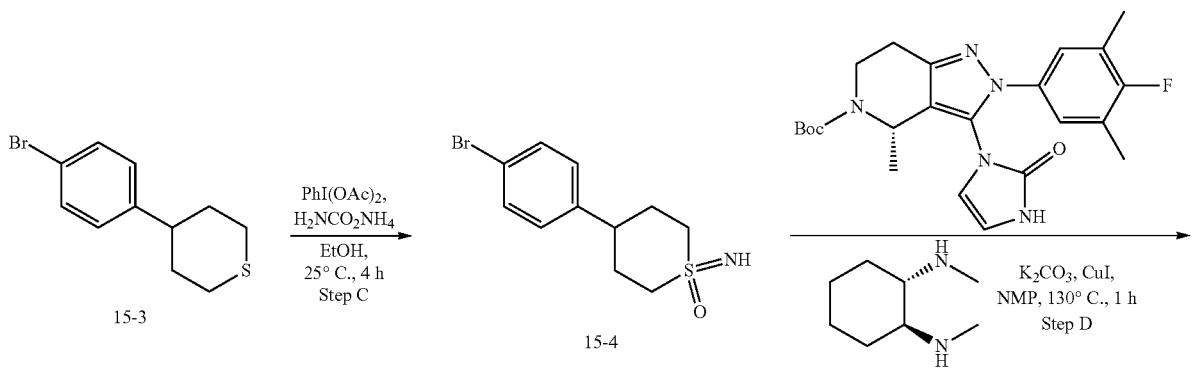

-continued
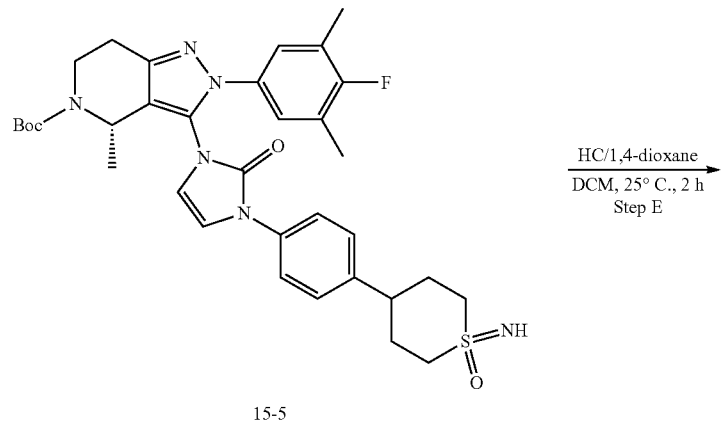
15-5
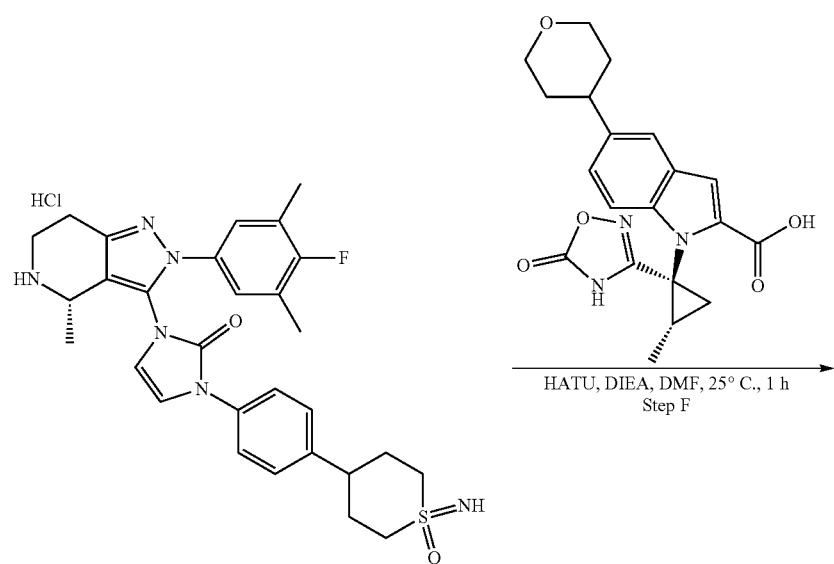
15-6

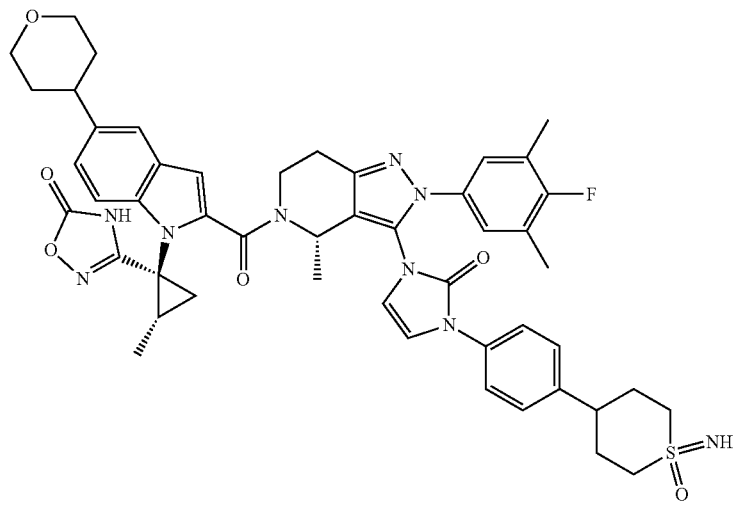

Compound 182

Step A 4-methyl-N'-(tetrahydro-4H-thiopyran-4-ylidene) benzenesulfonohydrazide

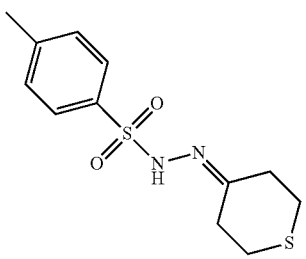 [SMILES: Cc1ccc(S(=O)(=O)NN=C2CCSCC2)cc1]

To a solution of tetrahydro-4H-thiopyran-4-one (5.00 g, 43.00 mmol) in MeOH (50 mL) was added 4-methylbenzenesulfonohydrazide (8.01 g, 43.00 mmol). The mixture was stirred at 25° C. for 2 h.

The reaction mixture was filtered and the cake was washed with cold ethanol (3 mL). The filter cake was dried under reduced pressure to afford 4-methyl-N'-(tetrahydro-4H-thiopyran-4-ylidene) benzenesulfonohydrazide (11.20 g, 91.6% yield). LC-MS: m/z: 285.3 (M+H)$^+$.

Step B 4-(4-bromophenyl) tetrahydro-2H-thiopyran

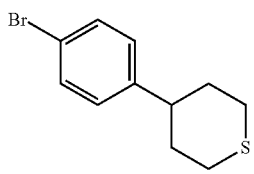 [SMILES: Brc1ccc(C2CCSCC2)cc1]

To a solution of (4-bromophenyl) boronic acid (1.00 g, 4.98 mmol) in dioxane (10 mL) were added 4-methyl-N'-(tetrahydro-4H-thiopyran-4-ylidene) benzenesulfonohydrazide (1.70 g, 5.98 mmol) and cesium carbonate (2.43 g, 7.47 mmol). The mixture was degassed and purged with N2 for 3 times and was stirred at 110° C. for 12 h under N2 atmosphere. After cooling, the resulting mixture was diluted with H$_2$O (20 mL) and extracted with EtOAc (20 mL×3). The combined organic layers were washed with brine, dried over Na$_2$SO$_4$, filtered and concentrated. The residue was purified by silica gel column chromatography eluting with 0-3% EtOAc/PE to afford 4-(4-bromophenyl) tetrahydro-2H-thiopyran (0.39 g, 30.1% yield). $^1$H NMR (400 MHz, DMSO-d6) δ 7.46 (d, J=8.0 Hz, 2H), 7.19 (d, J=8.0 Hz, 2H), 2.80-2.62 (m, 2H), 2.59-2.58 (m, 2H), 2.55-2.56 (m, 1H), 2.03-1.99 (m, 2H), 1.98-1-63 (m, 2H).

Step C 4-(4-bromophenyl)-1-iminohexahydro-1λ$^6$-thiopyran 1-oxide

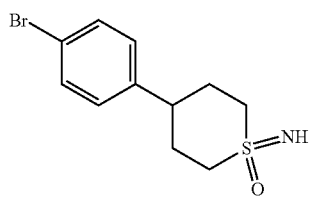 [SMILES: N=S1(=O)CCC(c2ccc(Br)cc2)CC1]

To a solution of 4-(4-bromophenyl)tetrahydro-2H-thiopyran (386.0 mg, 1.50 mmol) in EtOH (4.0 mL) were added iodobenzene diacetate (1450.0 mg, 4.50 mmol) and ammonium acetate (463.0 mg, 6.00 mmol). The mixture was stirred at 25° C. for 4 h. The resulting mixture was diluted with H$_2$O (2 mL) and extracted with EtOAc (2 mL×3). The combined organic layers were dried over Na$_2$SO$_4$, filtered and concentrated. The residue was purified by prep. TLC (SiO$_2$, DCM: MeOH=20: 1) to afford 4-(4-bromophenyl)-1-iminohexahydro-1λ$^6$-thiopyran 1-oxide (227.0 mg, 52.5% yield). LC-MS: m/z: 287.8 (M+H)$^+$.

Step D tert-butyl(S)-2-(4-fluoro-3,5-dimethylphenyl)-3-(3-(4-(1-imino-1-oxidohexahydro-1λ⁶-thiopyran-4-yl)phenyl)-2-oxo-2,3-dihydro-1H-imidazol-1-yl)-4-methyl-2,4,6,7-tetrahydro-5H-pyrazolo[4,3-c]pyridine-5-carboxylate

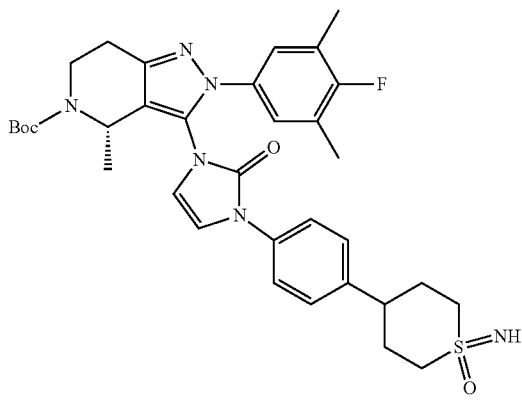 [SMILES: Cc1cc(-n2nc3c(c2-n2ccn(-c4ccc(C5CCS(=N)(=O)CC5)cc4)c2=O)[C@H](C)N(C(=O)OC(C)(C)C)CC3)cc(C)c1F]

To a solution of 4-(4-bromophenyl)-1-iminohexahydro-1λ⁶-thiopyran 1-oxide (100.0 mg, 0.35 mmol) in NMP (1 mL) were added tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (230.0 mg, 0.52 mmol), (1S,2S)-N1,N2-dimethylcyclohexane-1,2-diamine (24.7 mg, 0.17 mmol), copper(I) iodide (132.0 mg, 0.69 mmol) and K₂CO₃ (96.0 mg, 0.69 mmol). The mixture was degassed and purged with N2 for 3 times and stirred at 130° C. for 1 h under N2 atmosphere. After cooling, the resulting mixture was diluted with H₂O (5 mL) and extracted with EtOAc (5 mL×3). The combined organic layers were washed with brine, dried over Na₂SO₄, filtered and concentrated. The residue was purified by prep. TLC (SiO2, DCM: MeOH=15: 1) to afford tert-butyl(S)-2-(4-fluoro-3,5-dimethylphenyl)-3-(3-(4-(1-imino-1-oxidohexahydro-1λ⁶-thiopyran-4-yl)phenyl)-2-oxo-2,3-dihydro-1H-imidazol-1-yl)-4-methyl-2,4,6,7-tetrahydro-5H-pyrazolo[4,3-c]pyridine-5-carboxylate (85.0 mg, 37.8% yield). LC-MS: m/z 649.9 (M+H)⁺.

Step E (S)-1-(2-(4-fluoro-3,5-dimethylphenyl)-4-methyl-4,5,6,7-tetrahydro-2H-pyrazolo[4,3-c]pyridin-3-yl)-3-(4-(1-imino-1-oxidohexahydro-1λ⁶-thiopyran-4-yl)phenyl)-1,3-dihydro-2H-imidazol-2-one HCl salt

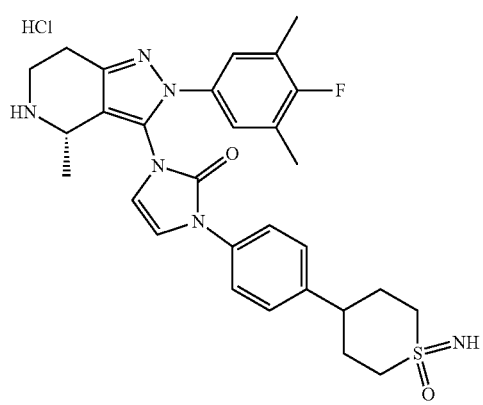 [SMILES: Cl ; Cc1cc(-n2nc3c(c2-n2ccn(-c4ccc(C5CCS(=N)(=O)CC5)cc4)c2=O)[C@H](C)NCC3)cc(C)c1F]

To a solution of tert-butyl(S)-2-(4-fluoro-3,5-dimethylphenyl)-3-(3-(4-(1-imino-1-oxidohexahydro-1λ⁶-thiopyran-4-yl)phenyl)-2-oxo-2,3-dihydro-1H-imidazol-1-yl)-4-methyl-2,4,6,7-tetrahydro-5H-pyrazolo[4,3-c]pyridine-5-carboxylate (85.0 mg, 0.13 mmol) in DCM (2 mL) was added HCl (0.85 mL, 4 mol/L in dioxane). After addition, the mixture was stirred at 25° C. for 2 h. The resulting mixture was concentrated to give (S)-1-(2-(4-fluoro-3,5-dimethylphenyl)-4-methyl-4,5,6,7-tetrahydro-2H-pyrazolo[4,3-c]pyridin-3-yl)-3-(4-(1-imino-1-oxidohexahydro-1λ⁶-thiopyran-4-yl)phenyl)-1,3-dihydro-2H-imidazol-2-one HCl salt (86.0 mg, crude), which was used in next step directly without further purification. LC-MS: m/z 549.4 (M+H)⁺.

Step F 3-[(1S,2S)-1-(2-{[(4S)-3-{1-[4-(1-aza-nylidene-1-oxo-1λ⁶-thian-4-yl)phenyl]-2-oxoimida-zol-3-yl}-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one (Compound 182)

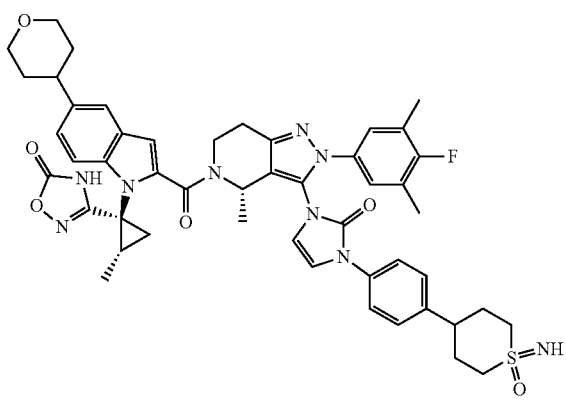 [SMILES: Cc1cc(-n2nc3c(c2-n2ccn(-c4ccc(C5CCS(=N)(=O)CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]

To a solution of (S)-1-(2-(4-fluoro-3,5-dimethylphenyl)-4-methyl-4,5,6,7-tetrahydro-2H-pyrazolo[4,3-c]pyridin-3-yl)-3-(4-(1-imino-1-oxidohexahydro-1λ⁶-thiopyran-4-yl)phenyl)-1,3-dihydro-2H-imidazol-2-one HCl salt (30.0 mg, 0.050 mmol) in DMF (0.9 mL) were added 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (19.7 mg, 0.050 mmol), HATU (21.4 mg, 0.060 mmol) and DIEA (0.036 mL, 0.21 mmol). After addition, the mixture was stirred at 25° C. for 1 h. The resulting mixture was diluted with H$_2$O (5 mL) and extracted with ethyl acetate (5 mL×3). The combined organic layers were dried over dried over Na$_2$SO$_4$, filtered and concentrated. The residue was purified by prep. TLC (SiO$_2$, DCM: MeOH=20:1), then further purified by prep. HPLC (SHIMADZU LC-20AP, Column: YMC Triart C18, 20*250 mm, 5 μm; Mobile Phase A: 0.1% FA, B: CH$_3$CN; gradient: 70-90% B, flow rate: 15 mL/min; Retention Time: 17-20 min of 30 min) to give 3-[(1S,2S)-1-(2-{[(4S)-3-{1-[4-(1-azanylidene-1-oxo-1λ⁶-thian-4-yl)phenyl]-2-oxoimidazol-3-yl}-2-(4-fluoro-3,5-dimethylphenyl)-4-methyl-4,5,6,7-tetrahydropyrazolo [4,3-c]pyridin-5-yl]carbonyl}-5-(3,4,5,6-tetrahydro-2H-pyran-4-yl)indol-1-yl)-2-methylcyclopropyl]-5H,4H-1,2,4-oxadiazol-5-one (8.2 mg, 17.9% yield). LC-MS: m/z 914.8 (M+H)⁺. 1H NMR (400 MHz, DMSO-d6) δ 7.60-7.45 (m, 3H), 7.43-7.30 (m, 3H), 7.26-7.20 (m, 2H), 7.13 (d, J=8.0 Hz, 2H), 6.92-6.80 (m, 2H), 5.62-5.55 (m, 1H), 4.50-4.35 (m, 1H), 4.00-3.93 (m, 2H), 3.55-3.40 (m, 4H), 3.05-2.99 (m, 3H), 2.95-2.80 (m, 3H), 2.21-2.19 (m, 6H), 2.18-2.00 (m, 5H), 1.85-1.55 (m, 7H), 1.45-1.30 (m, 4H), 1.20-1.05 (m, 3H).

Example A16

4-fluoro-5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1-methyl-3H-1λ⁶-benzo[2,1-d][1,2]thiazol-1-one (Compound 187) and 4-fluoro-5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1-methyl-3H-1λ⁶-benzo[2,1-d][1,2]thiazol-1-one (Compound 188)

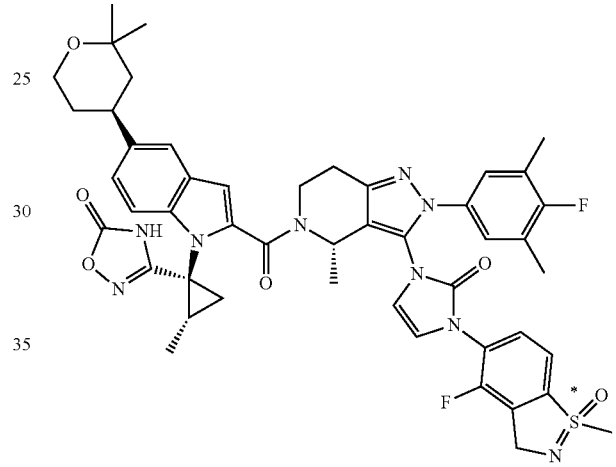

Compound 187

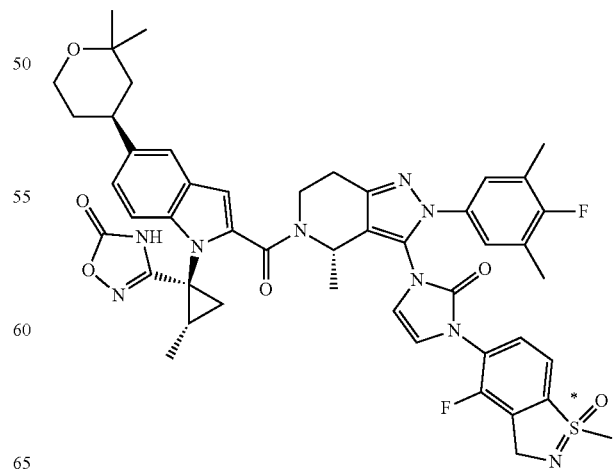

Compound 188

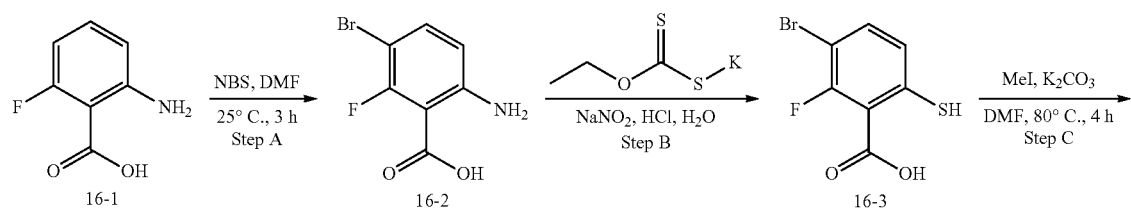
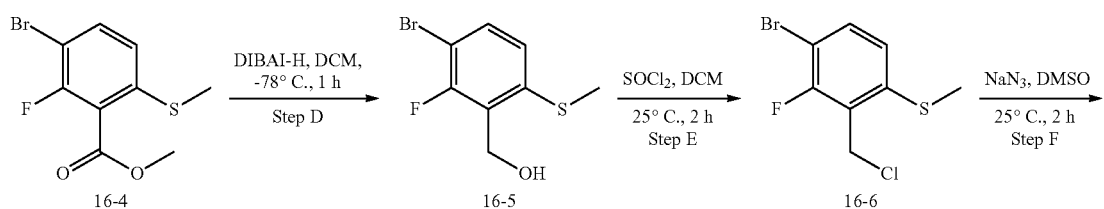
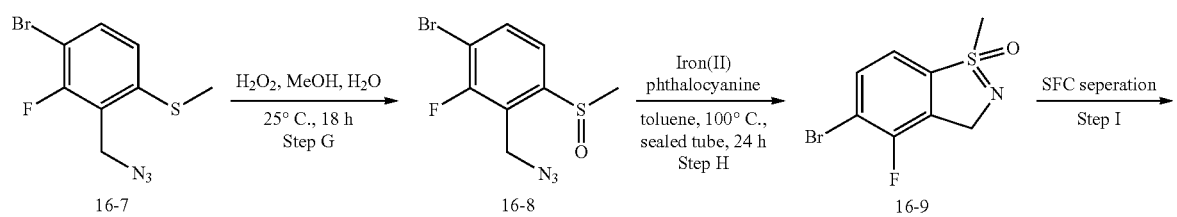
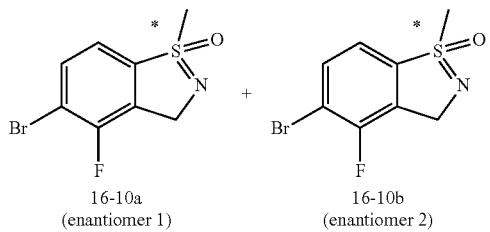
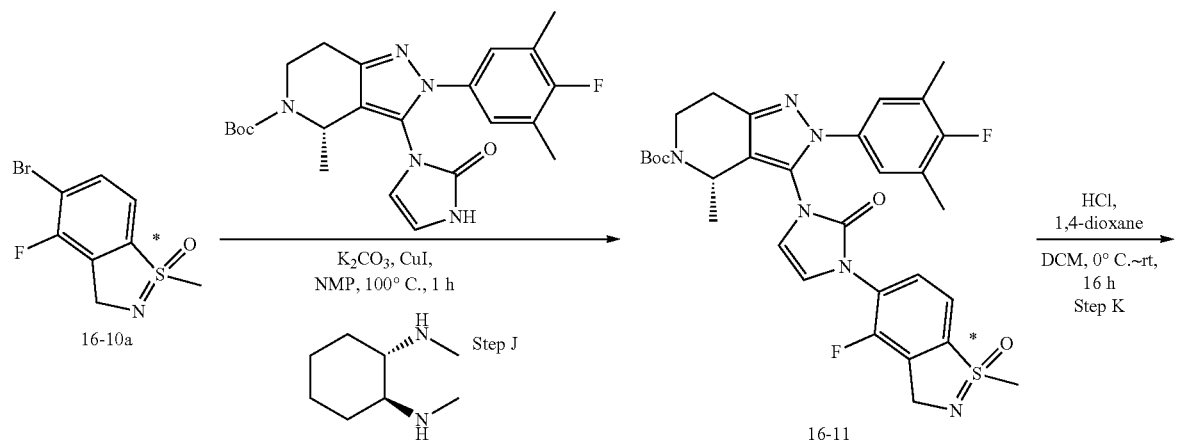

-continued
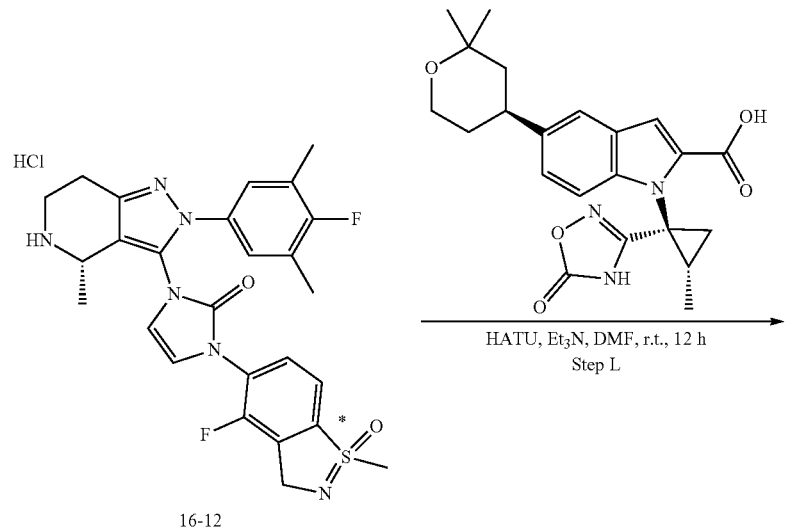
16-12
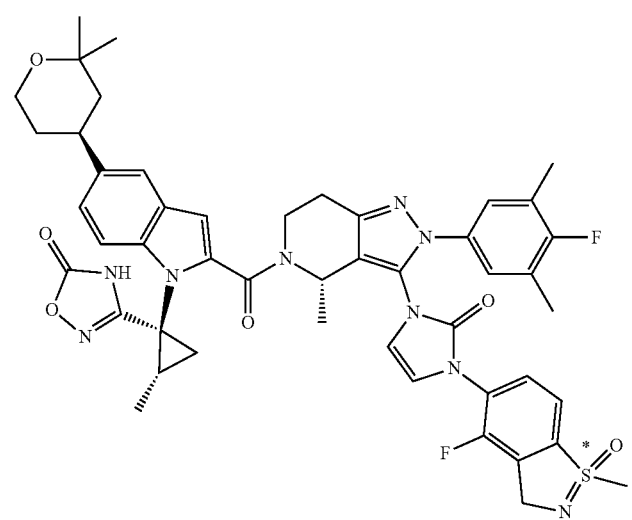
Compound 187
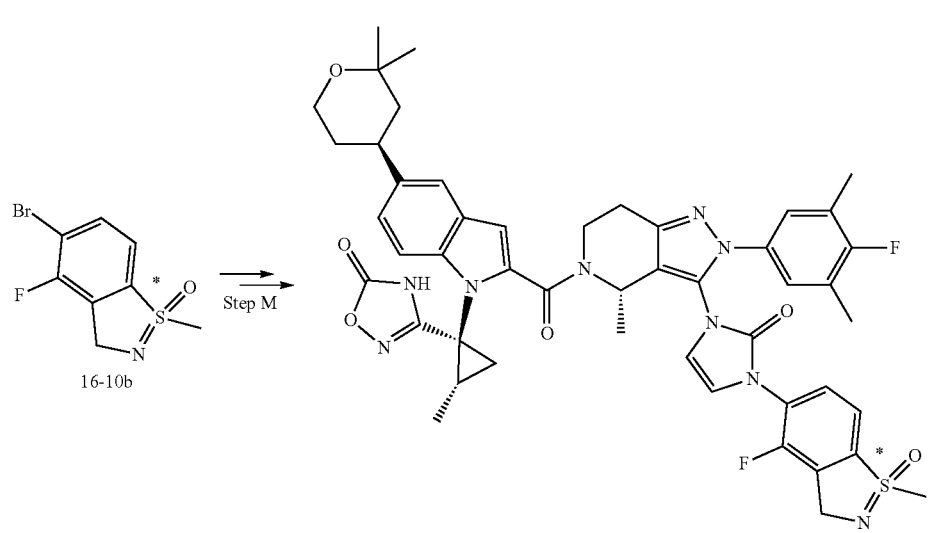
Compound 188

Step A 2-amino-5-bromo-4-fluorobenzoic acid

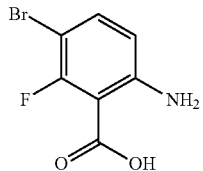 [SMILES: Nc1ccc(Br)c(F)c1C(=O)O]

To a mixture of 2-amino-4-fluorobenzoic acid (10 g, 64.462 mmol) in DMF (100 ml) was added NBS (11.24 g, 63.173 mmol) in DMF (50 ml) at −10° C. The reaction mixture was stirred for 2 h at −10° C. The reaction mixture was poured into ice (500 mL), quenched with aq. $Na_2S_2O_3$ (100 mL). After being stirred for 30 min. The mixture was filtered, and the cake was washed with water, dried under vacuum to afford 2-amino-5-bromo-4-fluorobenzoic acid (12.7 g, 84.2% yield). LC-MS: m/z 234.0 $(M+H)^+$.

Step B 3-bromo-2-fluoro-6-sulfanylbenzoic acid

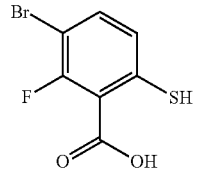

A mixture of concentrated HCl (0.7 mL) and chilled water (1 mL) was added dropwise to a stirred solution of 6-amino-3-bromo-2-fluorobenzoic acid (4.5 g, 19.229 mmol), NaOH (0.77 g, 19.229 mmol) and sodium nitrite (1.33 g, 19.229 mmol) in water (10 mL) by maintaining the internal temperature 3-6° C. The reaction mixture was stirred at 0° C. for 30 min, and then neutralized with KOAc (6.23 g, 63.456 mmol). This solution was added to a solution of potassium ethoxymethanedithioate (9.25 g, 57.687 mmol) in water (6 mL) which had preheated to 90° C. The mixture was stirred at the same temperature for 30 min, cooled to 0° C., and acidified with conc. HCl (2.5 mL). The reaction mixture was basified with 10% aq. NaOH, and then stirred at 85° C. for 2 h. The mixture was filtered, cooled to 0° C., and acidified with conc. HCl until pH=1. The precipitate was collected by filtration and washed with $H_2O$ to obtain 3-bromo-2-fluoro-6-sulfanylbenzoic acid (4.4 g, 91.1% yield). H NMR (400 MHz, DMSO-d6) δ 7.86 (t, J=8.4 Hz, 1H), 7.86 (d, J=8.8 Hz, 1H).

Step C methyl 3-bromo-2-fluoro-6-(methylsulfanyl)benzoate

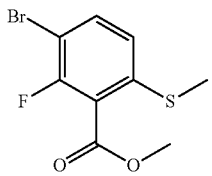

To a solution of 3-bromo-2-fluoro-6-sulfanylbenzoic acid (4.4 g, 17.525 mmol) in DMF (10 mL) were added iodomethane (7.111 mL, 87.625 mmol), and $K_2CO_3$ (12.11 g, 87.625 mmol). The reaction mixture was stirred at 80° C. for 3 h. After cooling, the reaction mixture was poured into $H_2O$ (10 mL) and extracted with EA (10 mL×3). The combined organics was washed brine and dried over $Na_2SO_4$, filtered and concentrated. The resulting residue was purified by silica gel column chromatography eluting with 10% EtOAc/PE to afford methyl 3-bromo-2-fluoro-6-(methylsulfanyl)benzoate (2.5 g, 51.1% yield). $^1$H NMR (400 MHz, DMSO-d6) δ 7.54 (t, J=8.4 Hz, 1H), 6.97 (d, J=8.4 Hz, 1H), 3.96 (s, 3H), 2.46 (s, 3H).

Step D [3-bromo-2-fluoro-6-(methylsulfanyl)phenyl]methanol

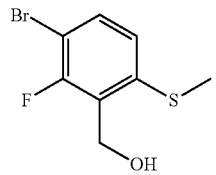

To a solution of methyl 3-bromo-2-fluoro-6-(methylsulfanyl)benzoate (2.5 g, 8.957 mmol) in DCM (25 mL) was added bis(2-methylpropyl)aluminum hydride (17.914 mL, 26.871 mmol). The reaction mixture was stirred at −78° C. for 3 h under Ar. TLC showed the reaction was completed. The reaction mixture was poured into water (50 mL) and extracted with DCM (50 mL×2). The combined organic layer was washed with brine, dried over $Na_2SO_4$, filtered and concentrated. The residue was purified by silica gel column chromatography eluting with 30% EtOAc/PE to obtain [3-bromo-2-fluoro-6-(methylsulfanyl)phenyl]methanol (2 g, 88.9% yield). $^1$H NMR (400 MHz, CDCl$_3$) δ 7.45 (t, J=7.2 Hz, 1H), 6.96 (d, J=8.4 Hz, 1H), 4.86 (d, J=2.0 Hz, 1H), 2.50 (s, 3H).

Step E [4-bromo-2-(chloromethyl)-3-fluorophenyl](methyl)sulfane

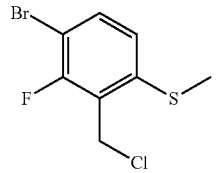

To a solution of [3-bromo-2-fluoro-6-(methylsulfanyl)phenyl]methanol (500 mg, 1.991 mmol) in DCM (10 mL) were added thionyl chloride (1421.2 mg, 11.947 mmol). The reaction mixture was stirred at room temperature for 2 h. TLC showed the reaction was completed. The reaction mixture was concentrated to give [4-bromo-2-(chloromethyl)-3-fluorophenyl](methyl)sulfane (500 mg, crude).

Step F [2-(azidomethyl)-4-bromo-3-fluorophenyl](methyl)sulfane

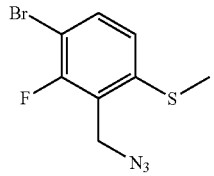

To a solution of [4-bromo-2-(chloromethyl)-3-fluorophenyl](methyl)sulfane (0.51 g, 1.892 mmol) in DMSO (5 mL) was added NaN₃ (0.14 g, 2.081 mmol). The reaction mixture was stirred at room temperature for 2 h. TLC showed the reaction was completed. The reaction mixture was quenched with water (20 mL), extracted with EA (20 mL×3). The combined organic layers were washed with brine, dried over sodium sulfate, filtered and concentrated. The resulting residue was purified by prep. TLC (SiO₂, PE 100%) to afford [2-(azidomethyl)-4-bromo-3-fluorophenyl](methyl)sulfane (490 mg, 93.8% yield).

Step G [2-(azidomethyl)-4-bromo-3-fluorophenyl](methyl)(oxo)-$\lambda^4$-sulfane

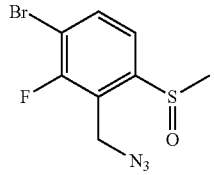

To a solution of [2-(azidomethyl)-4-bromo-3-fluorophenyl](methyl)sulfane (950 mg, 3.440 mmol) in MeOH (5 mL) and H₂O (1 mL), was added H₂O₂ (1.147 mL, 34.404 mmol). The reaction mixture was stirred at room temperature for 18 h. After the reaction was completed, water (5 mL) was added. The mixture was extracted with EtOAc (10 mL×3). The combined organic layers were washed with brine, dried over sodium sulfate, filtered and concentrated under vacuum. The residue was purified by prep. TLC (SiO₂, PE/EA=1/1) to afford [2-(azidomethyl)-4-bromo-3-fluorophenyl](methyl)(oxo)-$\lambda^4$-sulfane (730 mg, 72.6% yield). LC-MS: m/z 292.1 (M+H)⁺.

Step H 5-bromo-4-fluoro-1-methyl-1-oxo-3H-1$\lambda^6$-benzo[2,1-d][1,2]thiazole

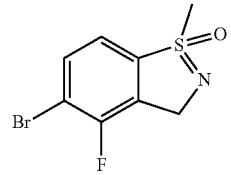

To a solution of [2-(azidomethyl)-4-bromo-3-fluorophenyl](methyl)(oxo)-$\lambda^4$-sulfane (430 mg, 1.472 mmol) in toluene (5 mL) was added iron(II) phthalocyanine (84.00 mg, 0.148 mmol). The reaction was stirred at 100° C. for 18 h in a sealed tube. After cooling, the mixture poured into water, extracted with EtOAc (10 mL×3). The combined organic layers were washed with brine, dried over sodium sulfate, filtered and concentrated. The resulting residue was purified by prep. TLC (SiO₂, EA/PE=5/1) to afford 5-bromo-4-fluoro-1-methyl-1-oxo-3H-1$\lambda^6$-benzo[2,1-d][1,2]thiazole (388 mg, 99.7% yield). LC-MS: m/z 264.1 (M+H)⁺.

Step I 5-bromo-4-fluoro-1-methyl-1-oxo-3H-1$\lambda^6$-benzo[2,1-d][1,2]thiazole 16-10a (enantiomer 1) and 5-bromo-4-fluoro-1-methyl-1-oxo-3H-1$\lambda^6$-benzo[2,1-d][1,2]thiazole 16-10b (enantiomer 2)

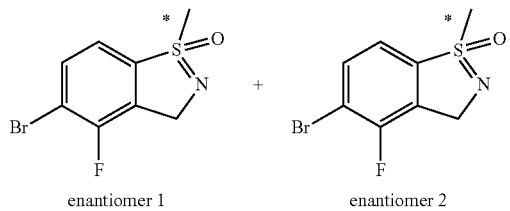

enantiomer 1    enantiomer 2

5-bromo-4-fluoro-1-methyl-1-oxo-3H-1$\lambda^6$-benzo[2,1-d][1,2]thiazole (388 mg, 1.14 mmol) was separated by SFC (Column: DAICELCHIRALPAK® IG; Column size: 250 mm*25 mm, 10 μm; Mobile Phase A: Supercritical CO₂; Mobile Phase B: MeOH (0.1% 7.0 M Ammonia in MeOH); Gradient: B=20%). Flow rate: 70 mL/min, Column temp: 25° C.) to afford 5-bromo-4-fluoro-1-methyl-1-oxo-3H-1$\lambda^6$-benzo[2,1-d][1,2]thiazole 16-10a (enantiomer 1) (103 mg, 26.5% yield) Rt=1.392 min, LC-MS: m/z 264.1 (M+H) and 5-bromo-4-fluoro-1-methyl-1-oxo-3H-1$\lambda^6$-benzo[2,1-d][1,2]thiazole 16-1Ob (enantiomer 2) (80 mg, 20.6% yield). Rt=2.273 min, LC-MS: m/z 264.1 (M+H)⁺.

Step J tert-butyl(4S)-2-(4-fluoro-3,5-dimethylphenyl)-3-[1-(4-fluoro-1-methyl-1-oxo-3H-1$\lambda^6$-benzo[2,1-d][1,2]thiazol-5-yl)-2-oxoimidazol-3-yl]-4-methyl-4,5,6,7-tetrahydropyrazolo[4,3-c]pyridine-5-carboxylate

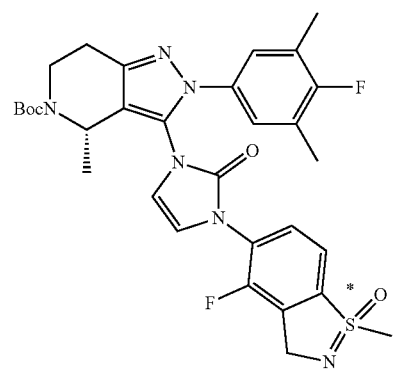 [SMILES: Cc1cc(-n2nc3c(c2-n2ccn(-c4ccc5c(c4F)CN=S5(C)=O)c2=O)[C@H](C)N(C(=O)OC(C)(C)C)CC3)cc(C)c1F]

To a solution of 5-bromo-4-fluoro-1-methyl-1-oxo-3H-1$\lambda^6$-benzo[2,1-d][1,2]thiazole 16-10a (enantiomer 1) (50 mg, 0.189 mmol) and tert-butyl(4S)-2-(4-fluoro-3,5-dimethylphenyl)-4-methyl-3-(2-oxo-1H-imidazol-3-yl)-4,5,6,7-tetrahydropyrazolo[4,3-c]pyridine-5-carboxylate (83.58 mg, 0.189 mmol) in NMP (8 mL) was added methyl[(1R,2R)-2-(methylamino)cyclohexyl]amine (40.40 mg, 0.284 mmol), copper iodide (43.27 mg, 0.227 mmol) and potassium carbonate (52.33 mg, 0.379 mmol). The reaction was stirred at 100° C. for 1 h. After the reaction was completed, water (20 mL) was added. The mixture was extracted with EtOAc (20 mL×3). The combined organic layers were washed with brine, dried over sodium sulfate, filtered and concentrated. The resulting residue was purified by prep. TLC (SiO$_2$, MeOH/DCM=1/10) to afford tert-butyl(4S)-2-(4-fluoro-3,5-dimethylphenyl)-3-[1-(4-fluoro-1-methyl-1-oxo-3H-1λ$^6$-benzo[2,1-d][1,2]thiazol-5-yl)-2-oxoimidazol-3-yl]-4-methyl-4,5,6,7-tetrahydropyrazolo[4,3-c]pyridine-5-carboxylate (100 mg, 84.6% yield). LC-MS: m/z 625.5 (M+H)$^+$.

Step K 4-fluoro-5-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-1-methyl-3H-1λ$^6$-benzo[2,1-d][1,2]thiazol-1-one HCl salt

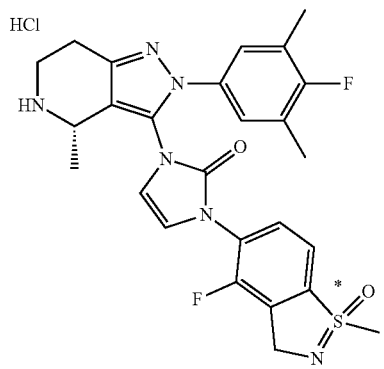 [SMILES: Cl ; Cc1cc(-n2nc3c(c2-n2ccn(-c4ccc5c(c4F)CN=S5(C)=O)c2=O)[C@H](C)NCC3)cc(C)c1F]

To a solution of tert-butyl(4S)-2-(4-fluoro-3,5-dimethylphenyl)-3-[1-(4-fluoro-i-methyl-1-oxo-3H-1λ$^6$-benzo[2,1-d][1,2]thiazol-5-yl)-2-oxoimidazol-3-yl]-4-methyl-4,5,6,7-tetrahydropyrazolo[4,3-c]pyridine-5-carboxylate (80 mg, 0.128 mmol) in dioxane (2 mL) was added HCl in dioxane (2 mL). The reaction was stirred at 25° C. for 1 h. LCMS showed the reaction was completed. The reaction was concentrated under vacuum to give 4-fluoro-5-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-1-methyl-3H-1λ$^6$-benzo[2,1-d][1,2]thiazol-1-one HCl salt (70 mg, 88.6% yield). LC-MS: m/z 525.4 (M+H)$^+$.

Step L 4-fluoro-5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1-methyl-3H-1λ$^6$-benzo[2,1-d][1,2]thiazol-1-one (Compound 187)

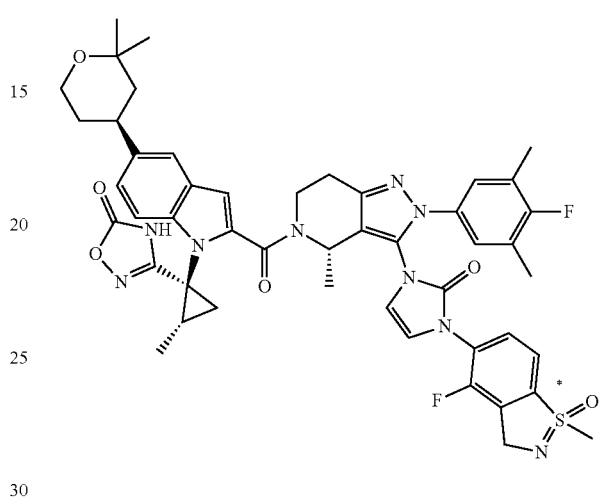

To a solution of 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (35.30 mg, 0.086 mmol) and HATU (35.95 mg, 0.095 mmol) in DMF (8 mL) was added 4-fluoro-5-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-1-methyl-3H-1λ$^6$-benzo[2,1-d][1,2]thiazol-1-one HCl salt (45 mg, 0.086 mmol) and DIEA (55.47 mg, 0.430 mmol), the mixture was stirred at rt for 18 h. After the reaction was completed, water (20 mL) was added.

The mixture was extracted with EtOAc (20 mL×3). The combined organic layers were washed with brine, dried over sodium sulfate, filtered and concentrated under vacuum. The resulting residue was purified by prep. HPLC (Waters 3767/Qda Column: SunFire Sunfire C18, 19*250 mm*10 μm; Mobile Phase A: 0.1% FA/H$_2$O, B: CH$_3$CN; Flow rate: 20 mL/min; Gradient: 54-59% B; Retention Time: 8.5 of 16 min) to afford 4-fluoro-5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1-methyl-3H-1λ$^6$-benzo[2,1-d][1,2]thiazol-1-one (17.8 mg, 22.2% yield). LC-MS: m/z 918.8 (M+H)$^+$. $^1$HNMR (400 MHz, DMSO-d6) δ 11.60 (brs, 1H), 7.97 (m, 1H), 7.79-7.70 (m, 1H), 7.51 (s, 1H), 7.41 (d, J=8.0 Hz, 1H), 7.25 (d, J=8.4 Hz, 1H), 7.15 (d, J=6.4 Hz, 2H), 7.02 (m, 1H), 6.90-6.79 (m, 2H), 5.69-5.55 (m, 1H), 4.82 (d, J=17.2 Hz, 1H), 4.68 (d, J=18.0 Hz, 1H), 4.48-4.33 (m, 1H), 3.74 (d, J=8.8 Hz, 2H), 3.46 (s, 3H), 2.89-2.84 (m, 1H), 2.24 (s, 6H), 1.78-1-69 (m, 4H), 1-61-1.54 (m, 4H), 1.40 (m, 3H), 1.29 (m, 4H), 1.20 (m, 7H).

Step M 4-fluoro-5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1-methyl-3H-1λ⁶-benzo[2,1-d][1,2]thiazol-1-one (Compound 188)

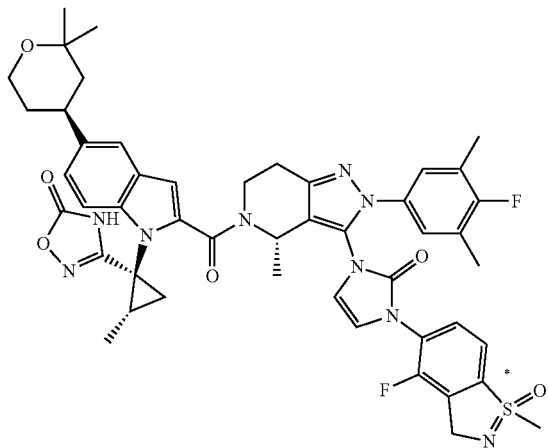 [SMILES: Cc1cc(-n2nc3c(c2-n2ccn(-c4ccc5c(c4F)CN=S5(C)=O)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

4-fluoro-5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo [4,3-c]pyridin-3-yl]-2-oxoimidazol-1-yl}-1-methyl-3H-1λ6-benzo[2,1-d][1,2]thiazol-1-one (Compound 188) was synthesized according to the procedures described for the preparation of Compound 187) (enantiomer 1) (step J to step L). LC-MS: m/z 918.8 (M+H)⁺. ¹H NMR (400 MHz, DMSO-d6) δ 11.57 (brs, 1H), 7.99 (m, 1H), 7.77 (m, 1H), 7.51 (s, 1H), 7.41 (d, J=8.8 Hz, 1H), 7.25 (d, J=8.4 Hz, 1H), 7.16 (d, J=6.4 Hz, 2H), 7.02 (m, 1H), 6.89-6.84 (m, 2H), 5.68 (m, 1H), 4.82 (d, J=17.6 Hz, 1H), 4.68 (d, J=17.6 Hz, 1H), 4.43-4.39 (m, 1H), 3.74 (d, J=9.2 Hz, 2H), 3.46 (s, 3H), 2.88-2.85 (m, 1H), 2.24 (s, 6H), 1.72-1.70 (m, 4H), 1-61-1.54 (m, 4H), 1.44 (m, 3H), 1.29 (m, 4H), 1.20 (m, 7H).

Example compounds 191 and 192, 201 and 202 were synthesized using a similar procedure described in the Example A16 above using the appropriate materials.

Example A17

6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1,3-dimethyl-1λ⁶-benzo[2,1-e][1,2]thiazin-1-one (Compound 206) and 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1,3-dimethyl-1λ⁶-benzo[2,1-e][1,2]thiazin-1-one (Compound 207)

Compound 206

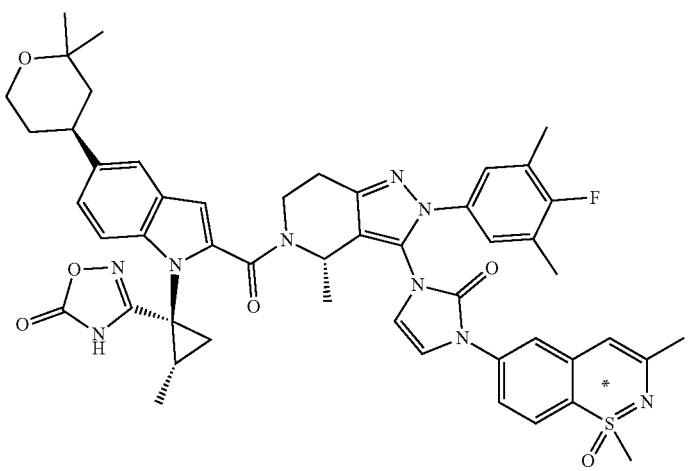

Compound 207
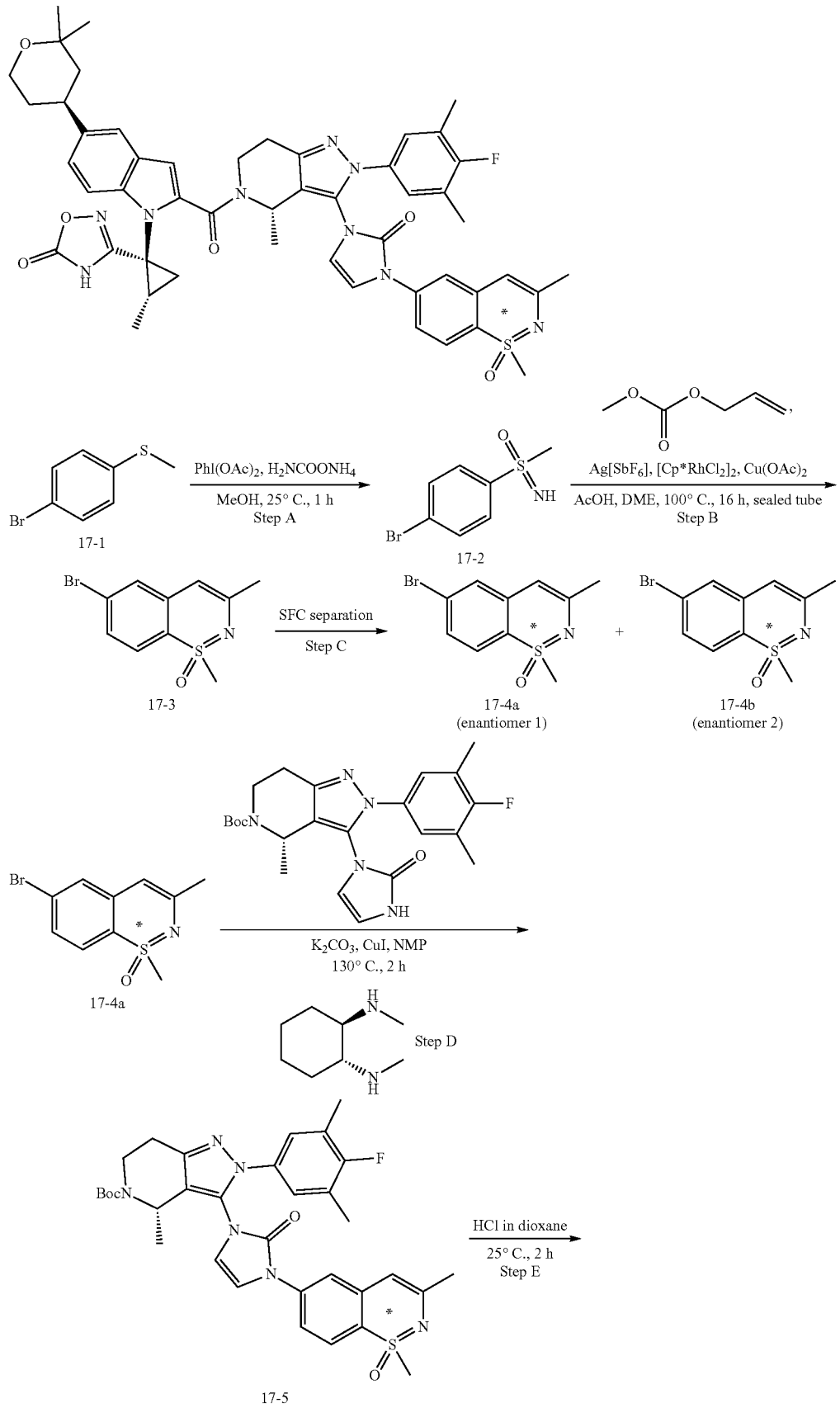

-continued
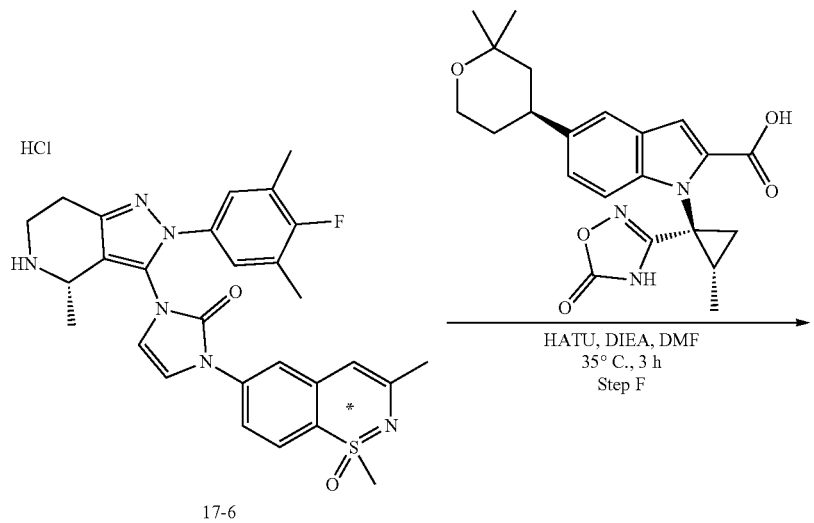
Step F
HATU, DIEA, DMF
35° C., 3 h
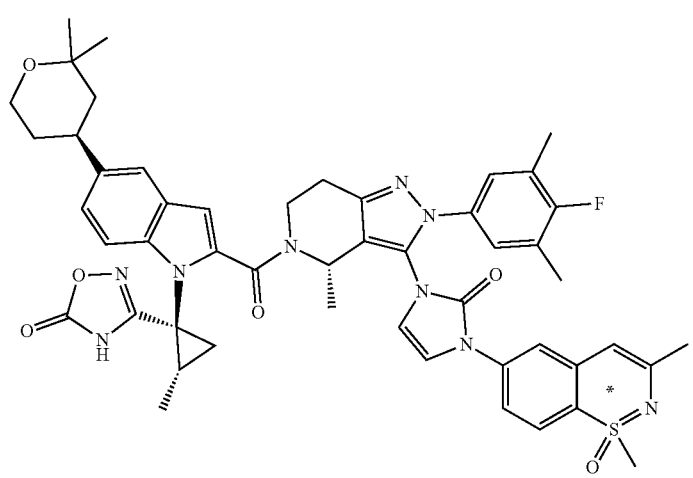
Compound 206
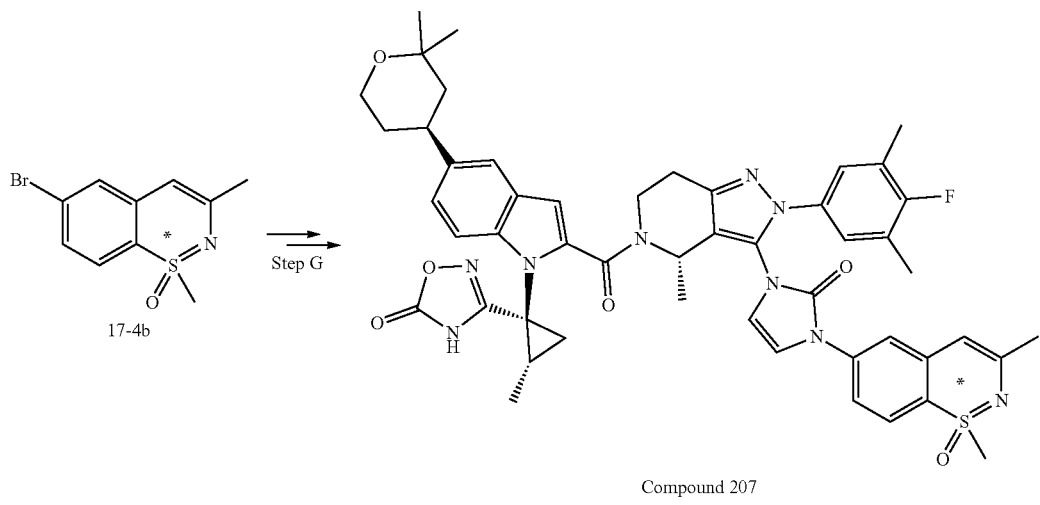 [SMILES: CC1=Cc2cc(Br)ccc2S(C)(=O)=N1 ; CC1=Cc2cc(-n3ccn(-c4c5c(nn4-c4cc(C)c(F)c(C)c4)CCN(C(=O)c4cc6cc([C@H]7CCOC(C)(C)C7)ccc6n4[C@@]4(c6noc(=O)[nH]6)C[C@@H]4C)[C@H]5C)c3=O)ccc2S(C)(=O)=N1]
Step G
Compound 207

Step A (4-bromophenyl)(methyl)(oxo)-λ⁶-sulfanimine

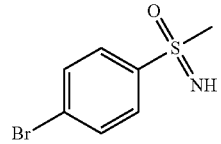

To a solution of (4-bromophenyl)(methyl)sulfane (2.0 g, 9.847 mmol) in MeOH (60 mL) were added PhI(OAc)₂ (11.10 g, 34.466 mmol) and H₂NCOONH₄ (2.69 g, 34.466 mmol). The reaction was stirred at rt for 1 h. After the reaction was completed, the mixture was poured into water (50 mL), extracted with EtOAc (50 mL×3), the combined organic layers were washed with brine (20 mL×3), dried over anhydrous sodium sulfate, filtered and concentrated under vacuum. The resulting residue was purified by silica gel chromatography eluting with 10% MeOH/DCM to afford (4-bromophenyl)(methyl)(oxo)-λ⁶-sulfanimine (2.1 g, 91.1% yield). LC-MS: m/z 236.1 (M+H)⁺.

Step B 6-bromo-1,3-dimethyl-1λ⁶-benzo[2,1-e][1,2]thiazin-1-one

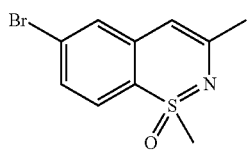

To a solution of (4-bromophenyl)(methyl)(oxo)-λ⁶-sulfanimine (400 mg, 1.709 mmol) in DME (10 mL) were added methyl(prop-2-enyloxy)methanoate (595.21 mg, 5.126 mmol) and silver hexafluoroantimonate (93.94 mg, 0.273 mmol), bis(1,2,3,4,5-pentamethylcyclopentane) bis[dichlororhodium(II)](42.93 mg, 0.068 mmol) and copper (II) acetate monohydrate (716.36 mg, 3.588 mmol). The reaction was stirred at 100° C. for 18 h under Ar in a sealed tube. LC-MS showed the reaction was completed. The mixture was cooled, poured into water (30 mL), extracted with EtOAc (50 mL×3).

The combined organic layers were washed with brine, dried over anhydrous sodium sulfate, filtered and concentrated. The resulting residue was purified by prep. TLC (SiO₂, PE/EtOAc=1/1) to afford 6-bromo-1,3-dimethyl-1λ⁶-benzo[2,1-e][1,2]thiazin-1-one (95 mg, 20.2% yield). LC-MS: m/z 274.1 (M+H)⁺.

Step C 6-bromo-1,3-dimethyl-1λ⁶-benzo[2,1-e][1,2]thiazin-1-one (enantiomer 1) and 6-bromo-1,3-dimethyl-1λ⁶-benzo[2,1-e][1,2]thiazin-1-one (enantiomer 2)

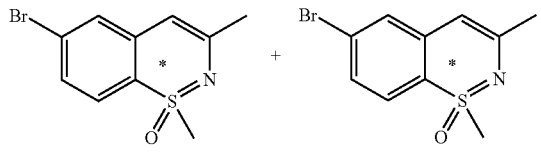

enantiomer 1      enantiomer 2

6-bromo-1,3-dimethyl-1λ⁶-benzo[2,1-e][1,2]thiazin-1-one (95 mg, 0.349 mmol) was separated by SFC (Column: DAICELCHIRALPAK® AD; Column size: 250 mm*25 mm, 10 μm; Mobile Phase A: Supercritical CO₂; Mobile Phase B: MeOH(0.1% 7.0 M Ammonia in MeOH); Gradient: B=30%). Flow rate: 120 mL/min, Column temp: 25° C.) to afford 6-bromo-1,3-dimethyl-1λ⁶-benzo[2,1-e][1,2]thiazin-1-one 17-4a (enantiomer 1) (30 mg, 31.6% yield) Rt=1.142 min, LC-MS: m/z 274.1 (M+H)+ and 6-bromo-1,3-dimethyl-1λ⁶-benzo[2,1-e][1,2]thiazin-1-one 17-4b (enantiomer 2) (55 mg, 57.9% yield). Rt=2.208 min, LC-MS: m/z 274.1 (M+H)⁺.

Step D tert-butyl(4S)-3-[1-(1,3-dimethyl-1-oxo-1λ⁶-benzo[2,1-e][1,2]thiazin-6-yl)-2-oxoimidazol-3-yl]-2-(4-fluoro-3,5-dimethylphenyl)-4-methyl-4,5,6,7-tetrahydropyrazolo[4,3-c]pyridine-5-carboxylate

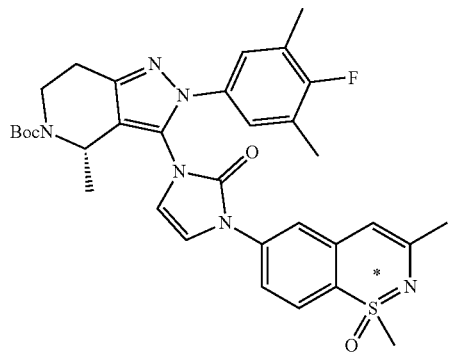 [SMILES: CC1=Cc2cc(-n3ccn(-c4c5c(nn4-c4cc(C)c(F)c(C)c4)CCN(C(=O)OC(C)(C)C)[C@H]5C)c3=O)ccc2S(C)(=O)=N1]

To a solution of 6-bromo-1,3-dimethyl-1λ⁶-benzo[2,1-e][1,2]thiazin-1-one 17-4a (enantiomer 1) (30 mg, 0.110 mmol) in NMP (5 mL) were added tert-butyl(4S)-2-(4-fluoro-3,5-dimethylphenyl)-4-methyl-3-(2-oxo-1H-imidazol-3-yl)-4,5,6,7-tetrahydropyrazolo[4,3-c]pyridine-5-carboxylate (48.7 mg, 0.110 mmol), methyl[(1R,2R)-2-(methylamino)cyclohexyl]amine (23.5 mg, 0.165 mmol), CuI (25.2 mg, 0.132 mmol) and K₂CO₃ (30.5 mg, 0.220 mmol). The reaction was stirred at 130° C. for 3 h under Ar. After cooling, the mixture was poured into water (10 mL), extracted with EtOAc (10 mL×3). The combined organic layers were washed with brine, dried over anhydrous sodium sulfate, filtered and concentrated. The resulting residue was purified by prep. TLC (SiO₂, PE/EtOAc=1/1) to afford tert-butyl(4S)-3-[1-(1,3-dimethyl-1-oxo-1λ⁶-benzo[2,1-e][1,2]thiazin-6-yl)-2-oxoimidazol-3-yl]-2-(4-fluoro-3,5-dimethylphenyl)-4-methyl-4,5,6,7-tetrahydropyrazolo[4,3-c]pyridine-5-carboxylate (45 mg, 64.5% yield). LC-MS: m/z 633.4 (M+H)⁺.

Step E 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-1,3-dimethyl-1λ⁶-benzo[2,1-e][1,2]thiazin-1-one HCl salt

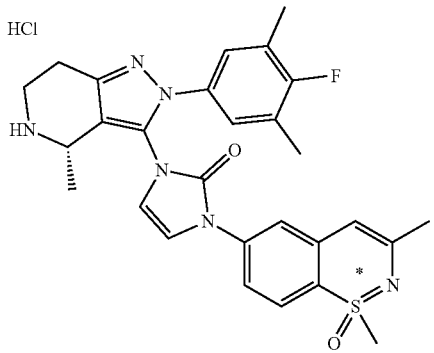 [SMILES: Cl ; CC1=Cc2cc(-n3ccn(-c4c5c(nn4-c4cc(C)c(F)c(C)c4)CCN[C@H]5C)c3=O)ccc2S(C)(=O)=N1]

To a solution of tert-butyl(4S)-3-[1-(1,3-dimethyl-1-oxo-1λ⁶-benzo[2,1-e][1,2]thiazin-6-yl)-2-oxoimidazol-3-yl]-2-(4-fluoro-3,5-dimethylphenyl)-4-methyl-4,5,6,7-tetrahydropyrazolo[4,3-c]pyridine-5-carboxylate (45 mg, 0.071 mmol) in dioxane (2 mL) was added 4 M HCl (gas) in dioxane (5 mL). The mixture was stirred at 25° C. for 1 h. The reaction mixture was concentrated under vacuum to afford 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-1,3-dimethyl-1λ⁶-benzo[2,1-e][1,2]thiazin-1-one HCl salt (30 mg, 79.2% yield), which used for the next step without purification. LC-MS: m/z 533.1 (M+H)⁺.

Step F 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1,3-dimethyl-1λ⁶-benzo[2,1-e][1,2]thiazin-1-one (Compound 206)

To a solution of 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (30.90 mg, 0.075 mmol) and HATU (31.41 mg, 0.083 mmol) in DMF (5 mL) was added a solution of 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-1,3-dimethyl-1λ⁶-benzo[2,1-e][1,2]thiazin-1-one HCl salt (40 mg, 0.075 mmol) and DIEA (48.53 mg, 0.375 mmol) in DMF (2 mL). The reaction was stirred at rt for 18 h. After the reaction was completed, the mixture was poured into water (10 mL), extracted with EtOAc (10 mL×3). The combined organic layers were washed with brine, dried over anhydrous sodium sulfate, filtered and concentrated. The resulting residue was purified by prep. TLC (SiO2, PE/EA=1/1) and then further purified by prep. HPLC (Waters 3767/Qda Column: XBridge XBridge C18, 19*250 mm*10 μm; Mobile Phase A: 10 mmol/L NaHCO₃/H₂O, B: CH₃CN; Flow rate: 20 mL/min; Gradient: 25%-30% B; Retention Time: 8.02-9.75 min of 17 min) to afford 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1,3-dimethyl-1λ⁶-benzo[2,1-e][1,2]thiazin-1-one (Compound 206) (27 mg, 38.9% yield). LC-MS: m/z 926.2 (M+H)⁺. ¹H NMR (400 MHz, DMSO-d6) δ 11.62 (brs, 1H), 8.09-8.06 (m, 1H), 7.69-7.58 (m, 2H), 7.51 (s, 1 H), 7.42 (d, J=8.8 Hz, 1H), 7.31-7.25 (m, 2H), 7.15 (d, J=6.0 Hz, 2H), 6.91-6.85 (m, 2H), 6.00 (m, 1H), 5.56 (m, 1H), 4.45 (m, 1H), 3.73 (d, J=7.6 Hz, 2H), 3.66 (s, 3H), 2.90-2.86 (m, 1H), 2.21 (s, 6 H), 2.13 (s, 3H), 1.78-1.58 (m, 7H), 1.53-1.42 (m, 5H), 1.28 (s, 3H), 1.19-1.15 (m, 7H).

Step G 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1,3-dimethyl-1λ⁶-benzo[2,1-e][1,2]thiazin-1-one (Compound 207)

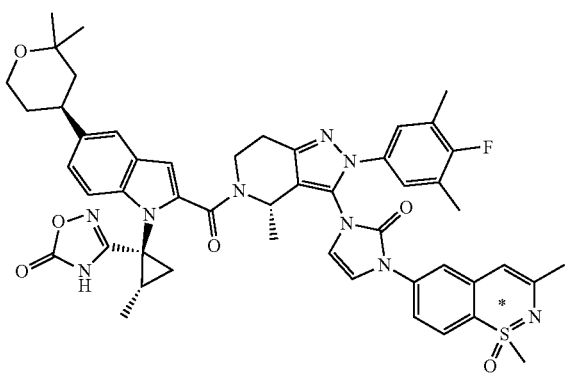 [SMILES: CC1=Cc2cc(-n3ccn(-c4c5c(nn4-c4cc(C)c(F)c(C)c4)CCN(C(=O)c4cc6cc([C@H]7CCOC(C)(C)C7)ccc6n4[C@@]4(c6noc(=O)[nH]6)C[C@@H]4C)[C@H]5C)c3=O)ccc2S(C)(=O)=N1]

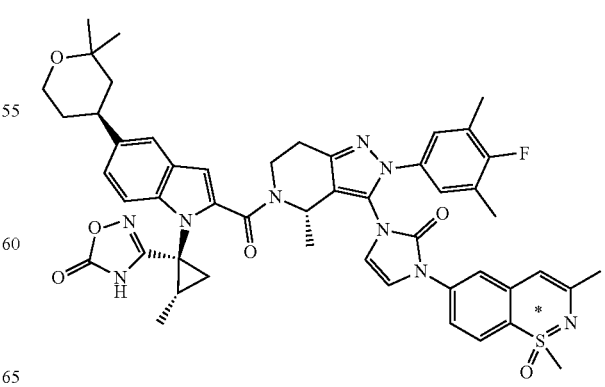

6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-1,3-dimethyl-1$\lambda^6$-benzo[2,1-e][1,2]thiazin-1-one (Compound 207) was synthesized according to the procedures described for the preparation of Compound 206 (enantiomer 1) (step D to step F). LC-MS: m/z 926.2 (M+H)$^+$. $^1$H NMR (400 MHz, DMSO-d6) δ 11.47 (brs, 1H), 8.06 (m, 1H), 7.67-7.57 (m, 2H), 7.51 (s, 1H), 7.42 (d, J=8.4 Hz, 1H), 7.31-7.24 (m, 2H), 7.15 (d, J=6.4 Hz, 2H), 6.92-6.85 (m, 2H), 6.01 (m, 1H), 5.58 (m, 1H), 4.42 (m, 1H), 3.73 (d, J=7.6 Hz, 2H), 3.66 (s, 3H), 2.90-2.84 (m, 1H), 2.21 (s, 6H), 2.12 (s, 3 H), 1.78-1.57 (m, 7H), 1.53-1.43 (m, 5H), 1.29 (s, 3H), 1.22-1.19 (m, 7H).

Example A18

1-cyclopropyl-5-fluoro-6-{3-[(4S)-2-(4-fluoro-3,5-dimethylphenyl)-5-({5-[(4S)-2,2-dimethyl-3,4,5,6-tetrahydro-2H-pyran-4-yl]-1-(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-3-methyl-1$\lambda^6$-benzo[2,1-e][1,2]thiazin-1-one (Compound 210) and 1-cyclopropyl-5-fluoro-6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-3-methyl-1$\lambda^6$-benzo[2,1-e][1,2]thiazin-1-one (Compound 211)

Compound 210

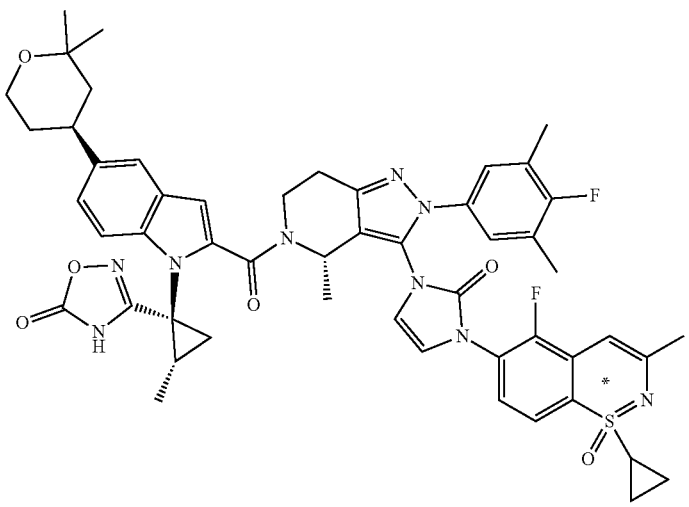

Compound 211

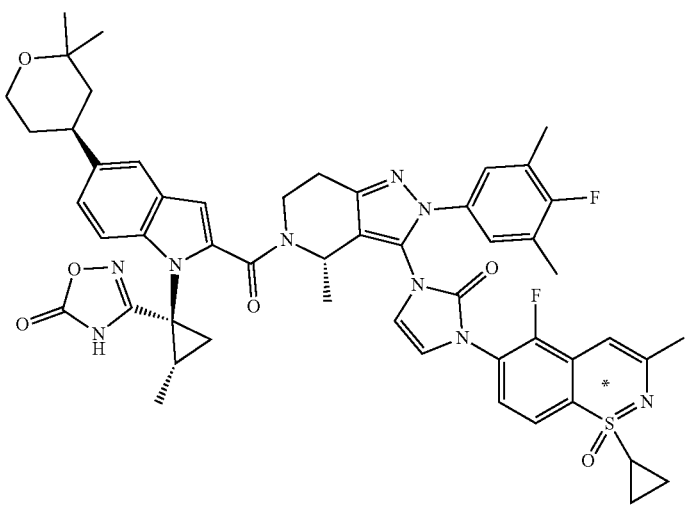

-continued
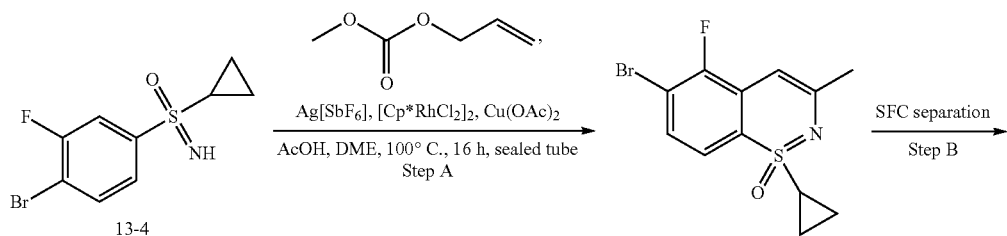
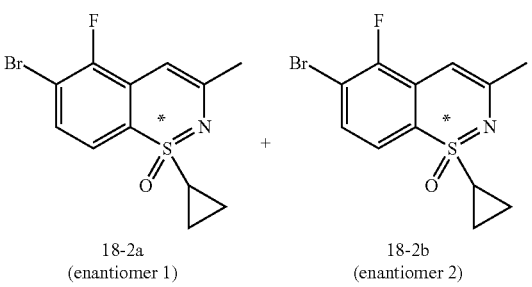
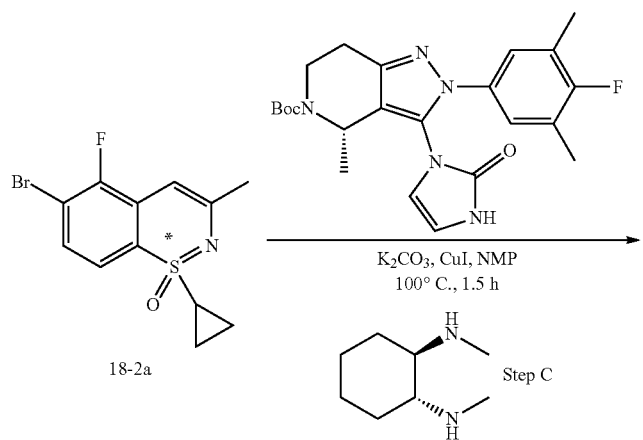
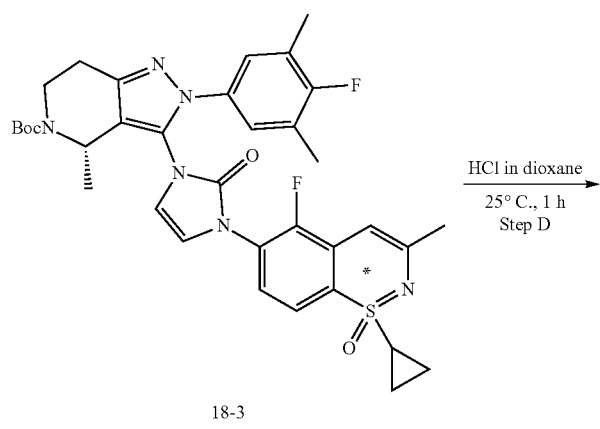

-continued
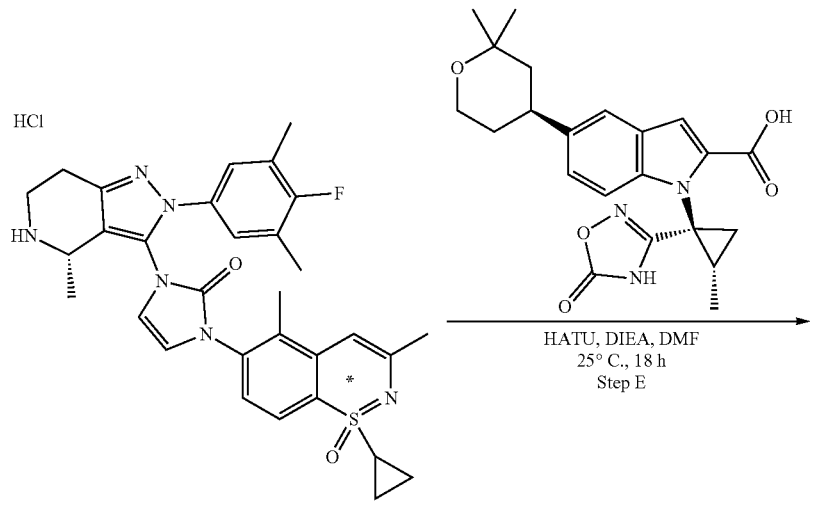
18-4
HATU, DIEA, DMF
25° C., 18 h
Step E
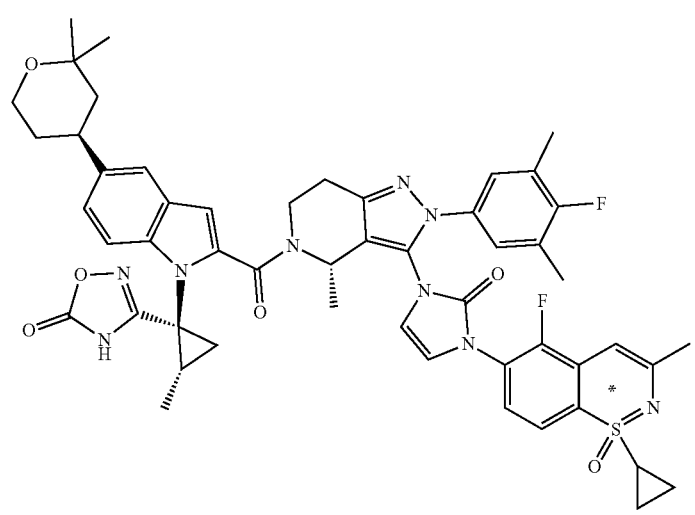
Compound 210
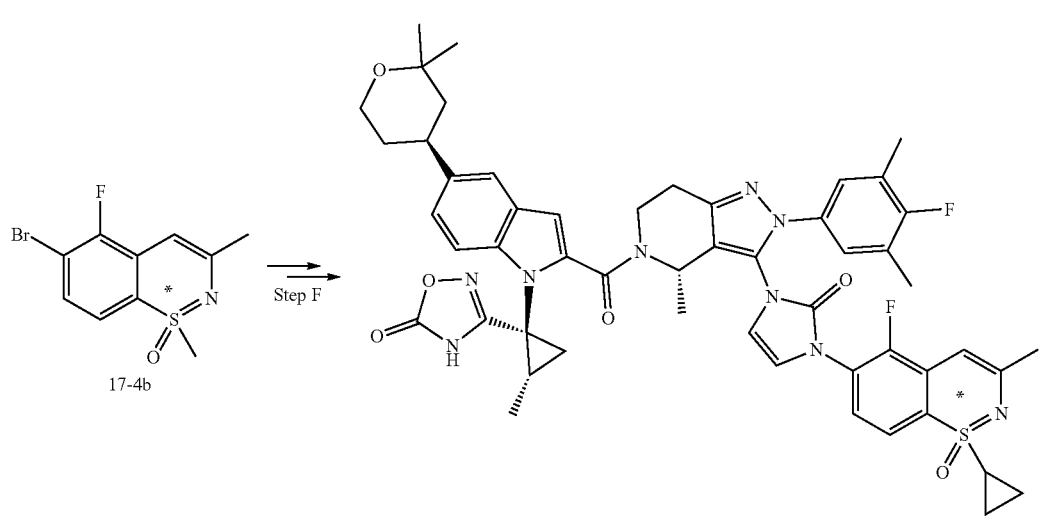
17-4b
Step F
Compound 211

Step A 6-bromo-1-cyclopropyl-5-fluoro-3-methyl-1λ⁶-benzo[2,1-e][1,2]thiazin-1-one

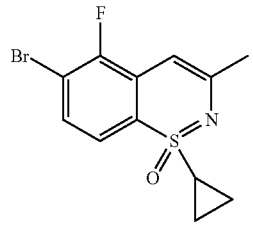 [SMILES: CC1=Cc2c(ccc(Br)c2F)S(=O)(C2CC2)=N1]

To a solution of (4-bromo-3-fluorophenyl)(methyl)(oxo)-λ⁶-sulfanimine (400 mg, 1.587 mmol) in DME (15 mL) were added methyl(prop-2-enyloxy)methanoate (500.9 mg, 4.314 mmol), silver hexafluoroantimonate (78.7 mg, 0.230 mmol), bis(1,2,3,4,5-pentamethylcyclopentane) bis[dichlororhodium(II)](40 mg, 0.064 mmol) and Copper(II) acetate monohydrate (600.9 mg, 3.020 mmol), AcOH (86.34 mg, 1.438 mmol). The reaction mixture was stirred at 120° C. for 34 h under N2 in a sealed tube. The mixture was cooled, poured into water (30 mL), extracted with EtOAc (50 mL×3). The combined organic layers were washed with brine, dried over anhydrous sodium sulfate, filtered and concentrated. The resulting residue was purified by prep. TLC (SiO₂, PE/EtOAc=1/1) to afford 6-bromo-1,3-dimethyl-1λ⁶-benzo[2,1-e][1,2]thiazin-1-one (150 mg, 30% yield). LC-MS: m/z 318.1 (M+H)⁺.

Step B 6-bromo-1-cyclopropyl-5-fluoro-3-methyl-1λ⁶-benzo[2,1-e][1,2]thiazin-1-one (enantiomer 1) and 6-bromo-1-cyclopropyl-5-fluoro-3-methyl-1λ⁶-benzo[2,1-e][1,2]thiazin-1-one (enantiomer 2)

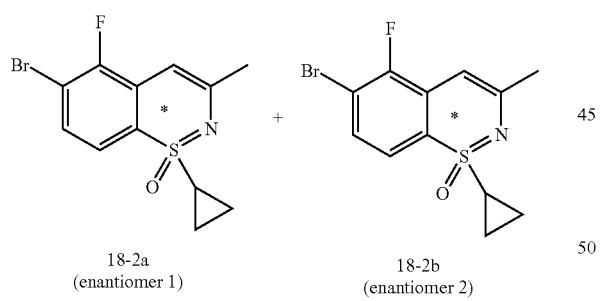

18-2a (enantiomer 1)   18-2b (enantiomer 2)

6-bromo-1-cyclopropyl-5-fluoro-3-methyl-λ⁶-benzo[2,1-e][1,2]thiazin-1-one (150 mg, 0.475 mmol) was separated by SFC (Column: DAICELCHIRALCEL® AD; Column size: 250 mm*25 mm, 10 m; Mobile Phase A: Supercritical CO₂; Mobile Phase B: MeOH(0.1% 7.0 M Ammonia in MeOH); Gradient: B=16%). Flow rate: 120 mL/min, Column temp.: 25° C.) to afford 6-bromo-1-cyclopropyl-5-fluoro-3-methyl-1λ⁶-benzo[2,1-e][1,2]thiazin-1-one 18-2a (enantiomer 1) (55 mg, 36.7% yield), Rt=1.292 min, LC-MS: m/z 318.1 (M+H)+ and 6-bromo-1-cyclopropyl-5-fluoro-3-methyl-1λ⁶-benzo[2,1-e][1,2]thiazin-1-one 18-2b (enantiomer 2) (50 mg, 33.3% yield), Rt=2.358 min, LC-MS: m/z 318.1 (M+H)⁺.

Step C tert-butyl(4S)-3-[1-(1-cyclopropyl-5-fluoro-3-methyl-1-oxo-1λ⁶-benzo[2,1-e][1,2]thiazin-6-yl)-2-oxoimidazol-3-yl]-2-(4-fluoro-3,5-dimethylphenyl)-4-methyl-4,5,6,7-iterahydropyrazolo4,3-c]pyridine-5 carhoxylate

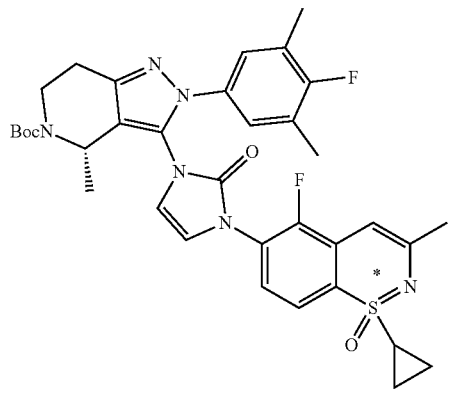 [SMILES: CC1=Cc2c(ccc(-n3ccn(-c4c5c(nn4-c4cc(C)c(F)c(C)c4)CCN(C(=O)OC(C)(C)C)[C@H]5C)c3=O)c2F)S(=O)(C2CC2)=N1]

To a solution of 6-bromo-1-cyclopropyl-5-fluoro-3-methyl-λ⁶-benzo[2,1-e][1,2]thiazin-1-one 18-2a (enantiomer 1) (55 mg, 0.174 mmol) and tert-butyl(4S)-2-(4-fluoro-3,5-dimethylphenyl)-4-methyl-3-(2-oxo-1H-imidazol-3-yl)-4,5,6,7-tetrahydropyrazolo[4,3-c]pyridine-5-carboxylate (76.8 mg, 0.174 mmol) in NMP (5 mL), was added methyl[(1R,2R)-2-(methylamino)cyclohexyl]amine (37.1 mg, 0.261 mmol), copper iodide (39.8 mg, 0.209 mmol) and potassium carbonate (48.08 mg, 0.348 mmol). The mixture was stirred at 100° C. for 1.5 h. After cooling, the mixture was poured into water (20 mL). The mixture was extracted with EtOAc (20 mL×3). The combined organic layers were washed with brine, dried over sulfate, filtered and concentrated. The resulting residue was purified by prep. TLC (SiO₂, MeOH/DCM=¹/₁₀) to afford tert-butyl(4S)-2-(4-fluoro-3,5-dimethylphenyl)-3-{1-[(1R)-1-cyclopropyl-5-fluoro-3-methyl-1-oxo-1λ⁶-benzo[2,1-e][1,2]thiazin-6-yl]-2-oxoimidazol-3-yl}-4-methyl-4,5,6,7-tetrahydropyrazolo[4,3-c]pyridine-5-carboxylate (77 mg, 65.4% yield). LC-MS: m/z 677.7 (M+H)⁺.

Step D 1-cyclopropyl-5-fluoro-6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-3-methyl-λ⁶-benzo[2,1-e][1,2]thiazin-1-one HCl salt

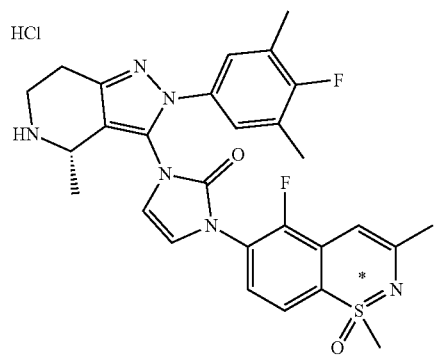 [SMILES: Cl ; CC1=Cc2c(ccc(-n3ccn(-c4c5c(nn4-c4cc(C)c(F)c(C)c4)CCN[C@H]5C)c3=O)c2F)S(C)(=O)=N1]

To a solution of tert-butyl(4S)-2-(4-fluoro-3,5-dimethylphenyl)-3-{1-[(1R)-1-cyclopropyl-5-fluoro-3-methyl-1-oxo-1λ⁶-benzo[2,1-e][1,2]thiazin-6-yl]-2-oxoimidazol-3-yl}-4-methyl-4,5,6,7-tetrahydropyrazolo[4,3-c]pyridine-5-carboxylate (77 mg, 0.114 mmol) in dioxane (2 mL) was added 4 M HCl (gas) in dioxane (2 mL). The reaction was stirred at 25° C. for 1 h. LCMS showed the reaction was completed. The reaction was concentrated under vacuum to give 1-cyclopropyl-5-fluoro-6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-3-methyl-1λ⁶-benzo[2,1-e][1,2]thiazin-1-one HCl salt (65 mg, crude). LC-MS: m/z 577.6 (M+H)⁺.

Step E 1-cyclopropyl-5-fluoro-6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-3-methyl-1λ⁶-benzo[2,1-e][1,2]thiazin-i-one (Compound 210)

To a solution of 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (46.4 mg, 0.113 mmol) and HATU (47.15 mg, 0.124 mmol) in N,N-dimethylmethanamide (5 mL) was added 1-cyclopropyl-5-fluoro-6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-3-methyl-1λ⁶-benzo[2,1-e][1,2]thiazin-1-one HCl salt (65 mg, 0.113 mmol) and DIEA (72.84 mg, 0.564 mmol). The mixture was stirred at rt for 18 h. The reaction mixture was poured into water (20 mL), extracted with EtOAc (20 mL×3). The combined organic layers were washed with brine, dried over sulfate, filtered and concentrated. The resulting residue was purified by prep. HPLC (Waters 3767/Qda Column: XBridge XBridge C18, 19*250 mm*10 µm; Mobile Phase A: 10 mmol/L NaHCO₃/H₂O, B: CH₃CN; Flow rate: 20 mL/min; Gradient: 35%-40% B; Retention Time: 9.12-10.50 min of 17 min) to afford 1-cyclopropyl-5-fluoro-6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-3-methyl-1λ⁶-benzo[2,1-e][1,2]thiazin-1-one (Compound 210) (37.5 mg, 34.3% yield). LC-MS: m/z 970.3 (M+H)⁺. 1H NMR (400 MHz, DMSO-d6) δ 11.64 (brs, 1H), 7.92 (d, J=8.4 Hz, 1H), 7.52-7.48 (m, 2H), 7.43 (d, J=8.0 Hz, 1H), 7.27 (d, J=8.0 Hz, 1H), 7.16 (d, J=6.0 Hz, 2 H), 7.03 (s, 1H), 6.88 (m, 2H), 6.14 (s, 1H), 5.72-5.60 (m, 1H), 4.45-4.30 (m, 1H), 3.74 (d, J=7.6 Hz, 2H), 3.60-3.56 (m, 1H), 3.32-3.29 (m, 1H), 2.90-2.87 (m, 1H), 2.25 (s, 6H), 2.20 (s, 3H), 1.85-1.80 (m, 4H), 1.74-1.70 (m, 3H), 1-63-1-62 (m, 2H), 1.51-1.35 (m, 4H), 1.29 (m, 4H), 1.25-1.10 (m, 7H), 1.03-1.00 (m, 1H).

Step F 1-cyclopropyl-5-fluoro-6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-3-methyl-1λ⁶-benzo[2,1-e][1,2]thiazin-1-one (Compound 211)

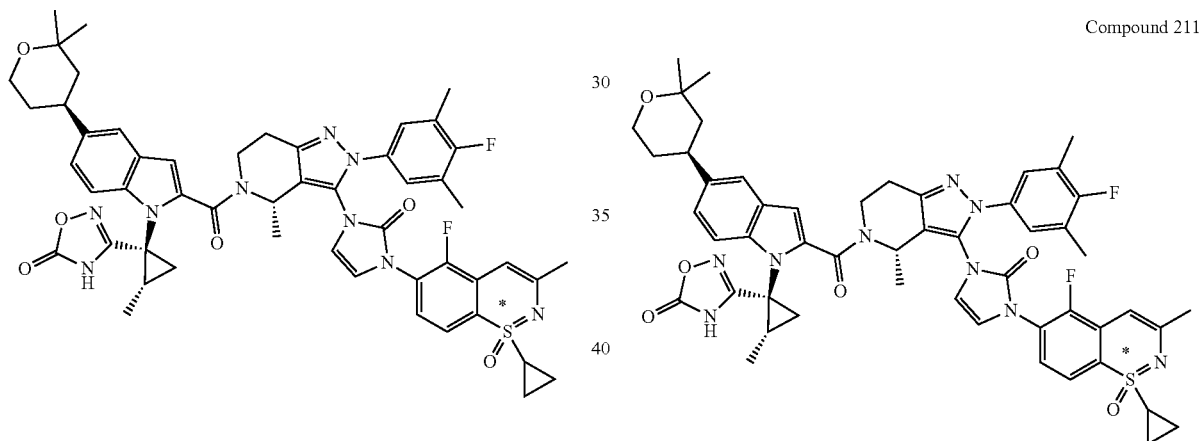

Compound 210

Compound 211

1-cyclopropyl-5-fluoro-6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo [4,3-c]pyridin-3-yl]-2-oxoimidazol-1-yl}-3-methyl-1λ⁶-benzo[2,1-e][1,2]thiazin-1-one (Compound 211) was synthesized according to the procedures described for the preparation of Compound 210 (enantiomer 1) (step C to step E). LC-MS: m/z 970.3 (M+H)⁺. ¹H NMR (400 MHz, DMSO-d6) δ 11.63 (brs, 1H), 7.90 (m, 1H), 7.52-7.48 (m, 2H), 7.43 (d, J=8.4 Hz, 1H), 7.27 (d, J=8.0 Hz, 1H), 7.16 (d, J=6.0 Hz, 2H), 7.04 (s, 1H), 6.88 (m, 2H), 6.14 (s, 1H), 5.72-5.60 (m, 1H), 4.45-4.30 (m, 1H), 3.74 (d, J=7.6 Hz, 2H), 3.60-3.56 (m, 1H), 3.32-3.29 (m, 1H), 2.90-2.87 (m, 1H), 2.25 (s, 6H), 2.20 (s, 3H), 1.85-1.80 (m, 4H), 1.75-1.72 (m, 4H), 1-63-1-62 (m, 3H), 1.51-1.35 (m, 4H), 1.29 (m, 4H), 1.25-1.10 (m, 7 H), 1.04-1.01 (m, 1H).

Example A19
3-((1S,2S)-1-(2-((S)-2-(4-fluoro-3,5-dimethylphenyl)-3-(3-(4-((1-imino-1-oxidohexahydro-1λ⁶-thiopyran-4-yl)oxy)phenyl)-2-oxo-2,3-dihydro-1H-imidazol-1-yl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5(4H)-one (Compound 226)
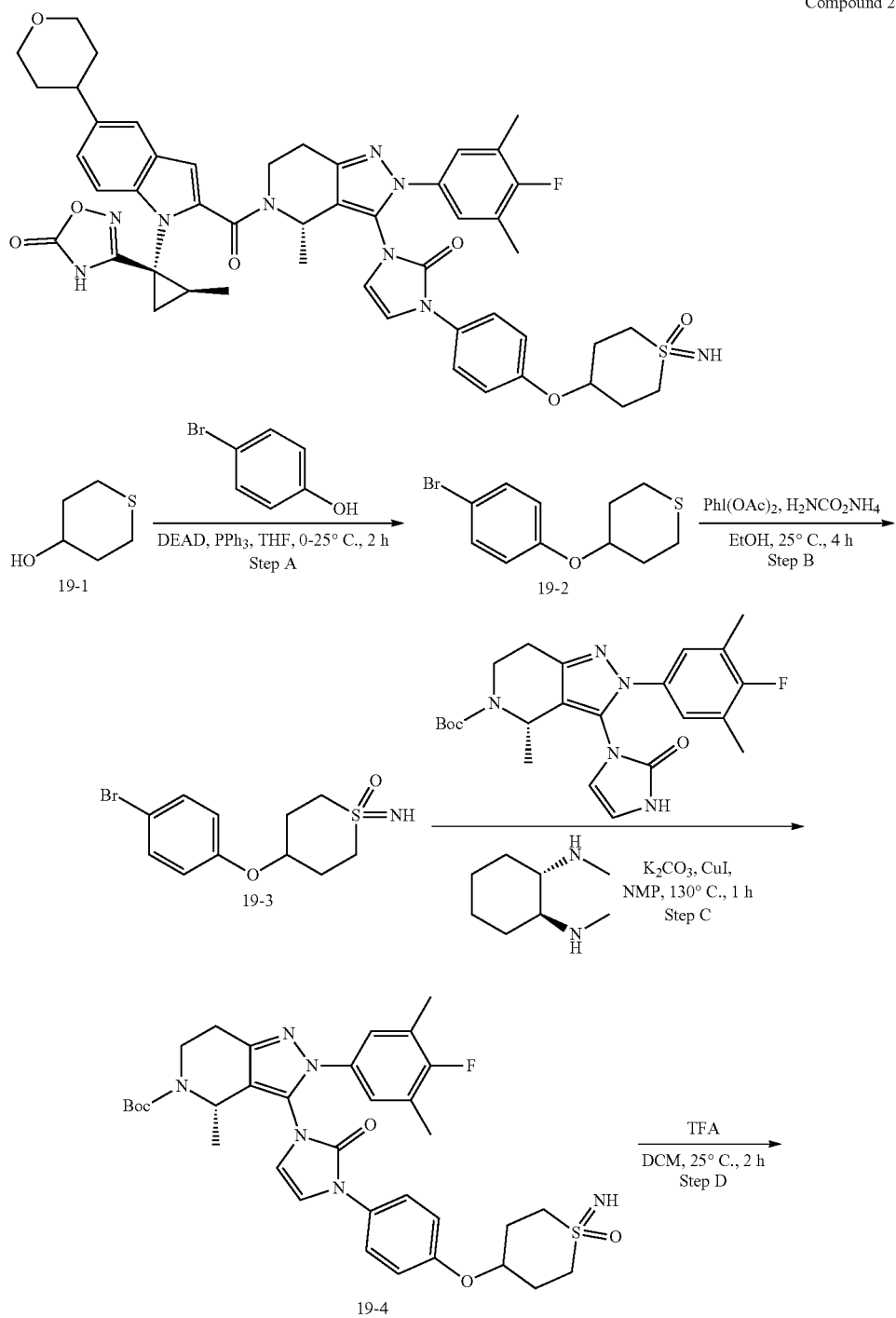

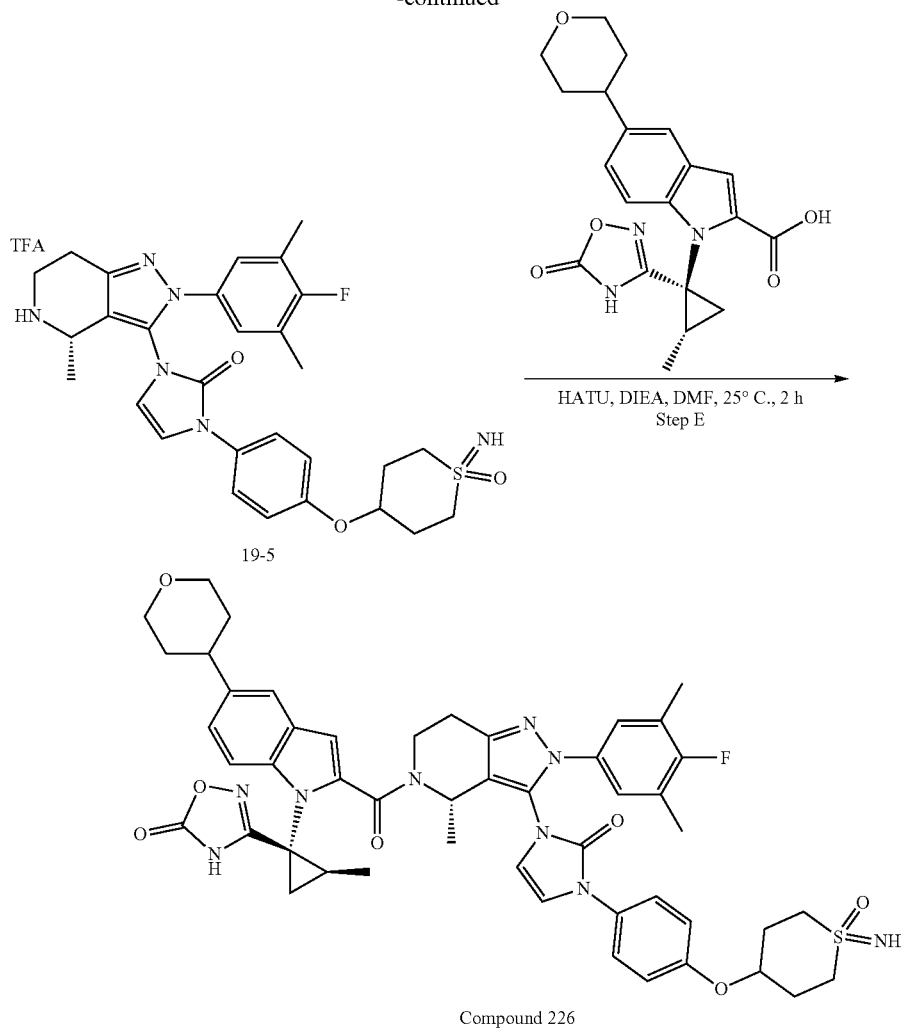

Compound 226

Step A 4-(4-bromophenoxy) tetrahydro-2H-thiopyran

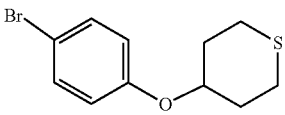

To a solution of tetrahydro-2H-thiopyran-4-ol (1.00 g, 8.46 mmol) in THF (10 mL) were added 4-bromophenol (1.24 g, 7.19 mmol) and triphenylphosphine (2.66 g, 10.15 mmol). After addition, the reaction mixture was stirred at 25° C. for 0.5 h under N2 atmosphere. Then, to the mixture was added diethyl azodicarboxylate (1.77 g, 10.15 mmol) at 0° C. After addition, the reaction mixture was stirred at 25° C. for 1.5 h under N2 atmosphere. The mixture was poured into ice water (20 mL) and extracted with EtOAc (20 mL×3). The combined organic layers were washed with brine, dried over Na$_2$SO$_4$, filtered and concentrated. The residue was purified by silica gel column chromatography (3%-10% EtOAc/PE) to afford 4-(4-bromophenoxy) tetrahydro-2H-thiopyran (0.60 g, 26.0% yield).

Step B 4-(4-bromophenoxy)-1-iminohexahydro-1λ$^6$-thiopyran 1-oxide

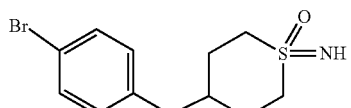

To a solution of 4-(4-bromophenoxy)tetrahydro-2H-thiopyran (0.25 g, 0.92 mmol) in EtOH (0.3 mL) were added ammonium acetate (0.28 g, 3.66 mmol) and iodobenzene diacetate (0.88 g, 2.75 mmol).

The mixture was stirred at 25° C. for 4 h. The resulting mixture was diluted with H$_2$O (10 mL) and extracted with EtOAc (10 mL×3). The combined organic layers were washed with brine, dried over Na$_2$SO$_4$, filtered and concentrated. The residue was purified by prep. TLC (SiO$_2$, DCM: MeOH=20: 1) to give 4-(4-bromophenoxy)-1-iminohexahydro-1λ$^6$-thiopyran 1-oxide (0.15 g, 53.9% yield). LC-MS: m/z: 303.8 (M+H)$^+$.

507

Step C tert-butyl(S)-2-(4-fluoro-3,5-dimethylphenyl)-3-(3-(4-((1-imino-1-oxidohexahydro-1λ⁶-thiopyran-4-yl)oxy)phenyl)-2-oxo-2,3-dihydro-1H-imidazol-1-yl)-4-methyl-2,4,6,7-tetrahydro-5H-pyrazolo[4,3-c]pyridine-5-carboxylate

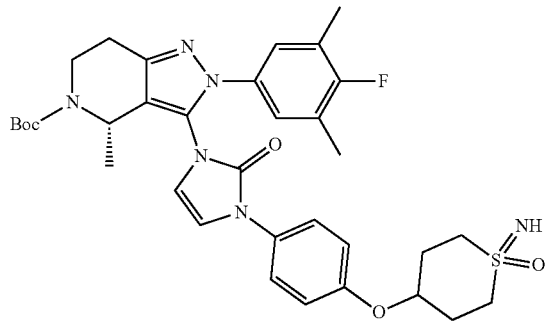 [SMILES: Cc1cc(-n2nc3c(c2-n2ccn(-c4ccc(OC5CCS(=N)(=O)CC5)cc4)c2=O)[C@H](C)N(C(=O)OC(C)(C)C)CC3)cc(C)c1F]

A mixture of tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (50.0 mg, 0.11 mmol), (1S,2S)-N1,N2-dimethylcyclohexane-1,2-diamine (8.05 mg, 0.057 mmol), 4-(4-bromophenoxy)-1-iminohexahydro-1λ⁶-thiopyran 1-oxide (51.7 mg, 0.17 mmol), copper(I) iodide (43.1 mg, 0.23 mmol) and K₂CO₃ (31.3 mg, 0.23 mmol) in NMP (0.5 mL) was degassed and purged with N2 for 3 times. The mixture was stirred at 130° C. for 1 h under N2 atmosphere. The resulting mixture was diluted with H₂O (20 mL) and extracted with EtOAc (20 mL×3). The combined organic layers were washed with brine, dried over Na₂SO₄, filtered and concentrated. The residue was purified by prep. TLC (SiO₂, DCM:MeOH=20: 1) to give tert-butyl(S)-2-(4-fluoro-3,5-dimethylphenyl)-3-(3-(4-((1-imino-1-oxidohexahydro-1λ⁶-thiopyran-4-yl)oxy)phenyl)-2-oxo-2,3-dihydro-1H-imidazol-1-yl)-4-methyl-2,4,6,7-tetrahydro-5H-pyrazolo[4,3-c]pyridine-5-carboxylate (70.0 mg, 93.2% yield). LC-MS: m/z: 665.5 (M+H)⁺.

508

Step D (S)-1-(2-(4-fluoro-3,5-dimethylphenyl)-4-methyl-4,5,6,7-tetrahydro-2H-pyrazolo[4,3-c]pyridin-3-yl)-3-(4-((1-imino-1-oxidohexahydro-1λ⁶-thiopyran-4-yl)oxy)phenyl)-1,3-dihydro-2H-imidazol-2-one TFA salt

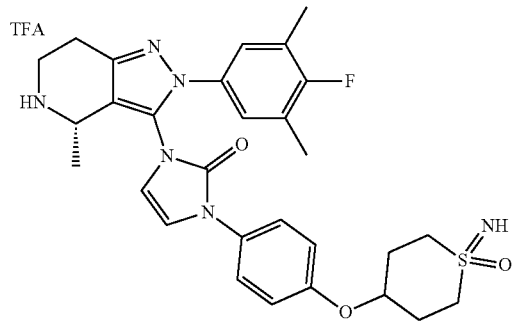 [SMILES: Cc1cc(-n2nc3c(c2-n2ccn(-c4ccc(OC5CCS(=N)(=O)CC5)cc4)c2=O)[C@H](C)NCC3)cc(C)c1F]

To a solution of tert-butyl(S)-2-(4-fluoro-3,5-dimethylphenyl)-3-(3-(4-((1-imino-1-oxidohexahydro-1λ⁶-thiopyran-4-yl)oxy)phenyl)-2-oxo-2,3-dihydro-1H-imidazol-1-yl)-4-methyl-2,4,6,7-tetrahydro-5H-pyrazolo[4,3-c]pyridine-5-carboxylate (50.0 mg, 0.075 mmol) in DCM (1 mL) was added TFA (0.4 mL, 5.19 mmol). The mixture was stirred at 25° C. for 2 h. The resulting mixture was concentrated to give (S)-1-(2-(4-fluoro-3,5-dimethylphenyl)-4-methyl-4,5,6,7-tetrahydro-2H-pyrazolo[4,3-c]pyridin-3-yl)-3-(4-((1-imino-1-oxidohexahydro-1λ⁶-thiopyran-4-yl)oxy)phenyl)-1,3-dihydro-2H-imidazol-2-one TFA salt (40.0 mg, crude), which was used for the next step directly without further purification. LC-MS: m/z 565.1 (M+H)⁺.

Step E 3-((1S,2S)-1-(2-((S)-2-(4-fluoro-3,5-dimethylphenyl)-3-(3-(4-((1-imino-1-oxidohexahydro-1λ⁶-thiopyran-4-yl)oxy)phenyl)-2-oxo-2,3-dihydro-1H-imidazol-1-yl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5(4H)-one (Compound 226)

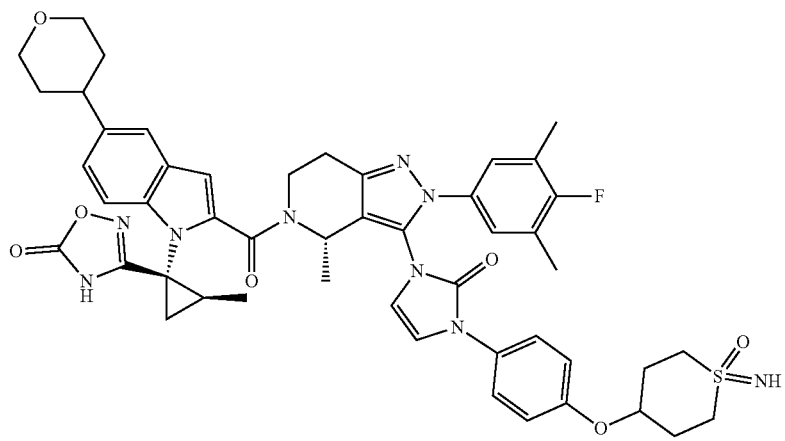 [SMILES: Cc1cc(-n2nc3c(c2-n2ccn(-c4ccc(OC5CCS(=N)(=O)CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]

To a solution of (S)-1-(2-(4-fluoro-3,5-dimethylphenyl)-4-methyl-4,5,6,7-tetrahydro-2H-pyrazolo[4,3-c]pyridin-3-yl)-3-(4-((1-imino-1-oxidohexahydro-1λ⁶-thiopyran-4-yl)oxy)phenyl)-1,3-dihydro-2H-imidazol-2-one TFA salt (26.0 mg, 0.046 mmol) in DMF (0.5 ml) were added DIEA (0.032 ml, 0.18 mmol), 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (17.7 mg, 0.046 mmol) and HATU (21.01 mg, 0.055 mmol). The mixture was stirred at 25° C. for 2 h. The residue was diluted with H₂O (10 mL) and extracted with EtOAc (10 mL×3). The combined organic layers were dried over dried over Na₂SO₄, filtered and concentrated. The residue was purified by prep. TLC (SiO₂, DCM: MeOH=20: 1) and then purified by prep. HPLC (SHIMADZU LC-20AP, Column: YMC Triart C18, 20*250 mm, 5 µm; Mobile Phase A: 0.1% FA, B: CH₃CN; flow rate: 15 mL/min; gradient: 70-90% B; Retention Time: 17-20 min of 30 min) to give 3-((1S,2S)-1-(2-((S)-2-(4-fluoro-3,5-dimethylphenyl)-3-(3-(4-((1-imino-1-oxidohexahydro-1λ⁶-thiopyran-4-yl)oxy)phenyl)-2-oxo-2,3-dihydro-1H-imidazol-1-yl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5(4H)-one (6.4 mg, 15.0% yield). LC-MS: m/z 930.2 (M+H)⁺. ¹H NMR (400 MHz, DMSO-d6) δ 7.60-7.40 (m, 4H), 7.28 (d, J=8.0 Hz, 1H), 7.20-7.10 (m, 5H), 6.95-6.80 (m, 2H), 5.62-5.55 (m, 1H), 4.70 (s, 1H), 4.40-4.35 (m, 1H), 4.00-3.96 (m, 2H), 3.75-3.73 (m, 1H), 3.67-3.60 (m, 1H), 3.52-3.45 (m, 2H), 3.11-3.08 (m, 3H), 2.91-2.85 (m, 2H), 2.24-2.17 (m, 9H), 1.78-1-64 (m, 6H), 1.45-1.40 (m, 2H), 1.32-1.24 (m, 6H), 1.22-1.15 (m, 2H).

Example A20

3-[(1S,2S)-1-(2-{[(4S)-2-(4-fluoro-3,5-dimethylphenyl)-3-[1-(2-fluoro-3-methyl-4-{[1-(methylazanylidene)-1-oxo-1λ⁶-thian-4-yl]oxy}phenyl)-2-oxoimidazol-3-yl]-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 232) and 3-[(1S,2S)-1-(2-{[(4S)-2-(4-fluoro-3,5-dimethylphenyl)-3-[1-(2-fluoro-3-methyl-4-{[1-(methylazanylidene)-1-oxo-1λ⁶-thian-4-yl]oxy}phenyl)-2-oxoimidazol-3-yl]-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 233)

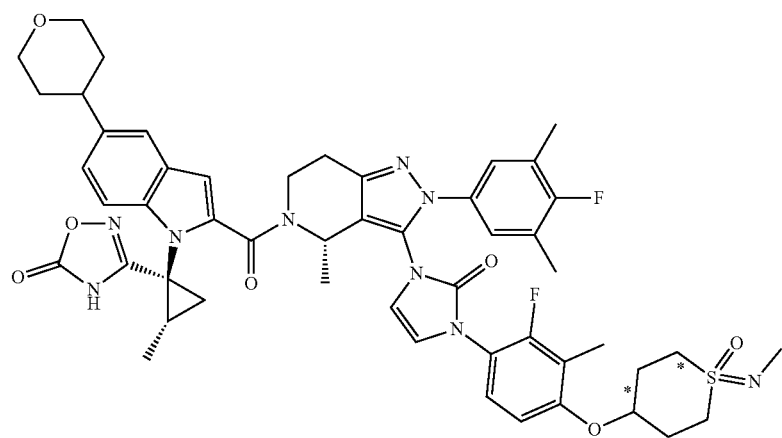

Compound 232

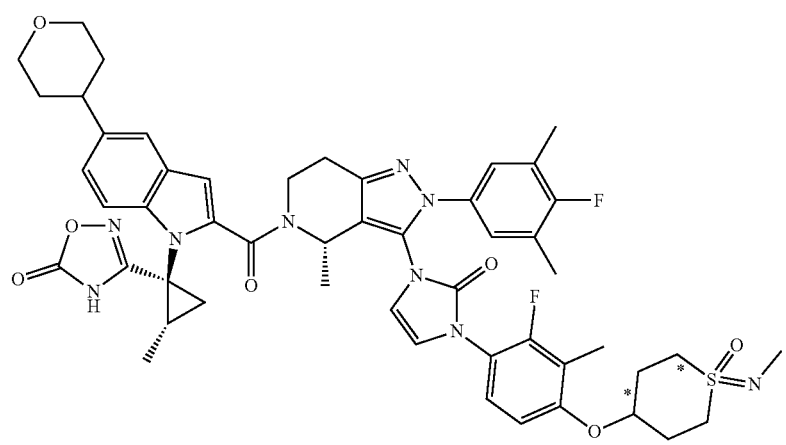

Compound 233

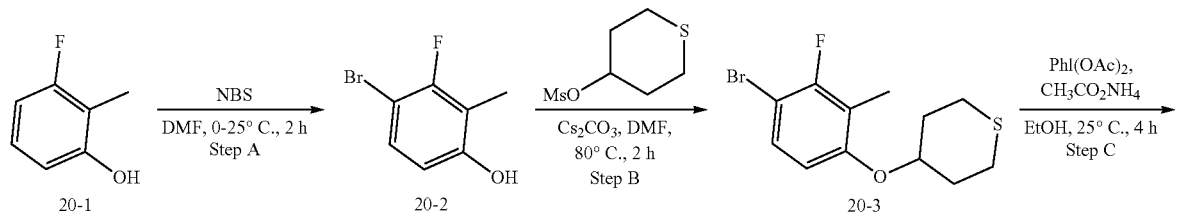
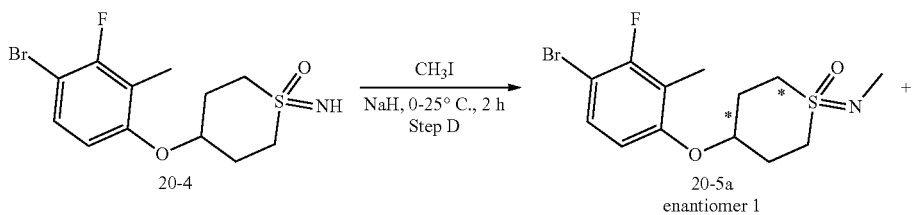
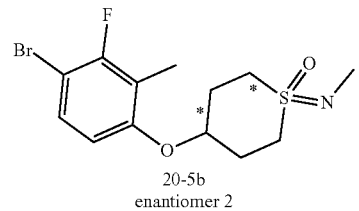
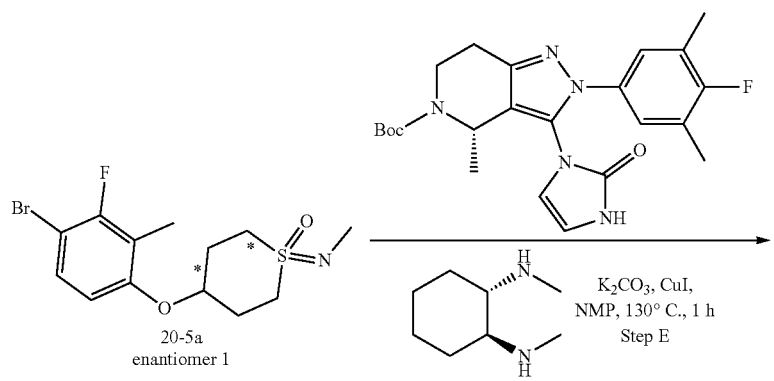
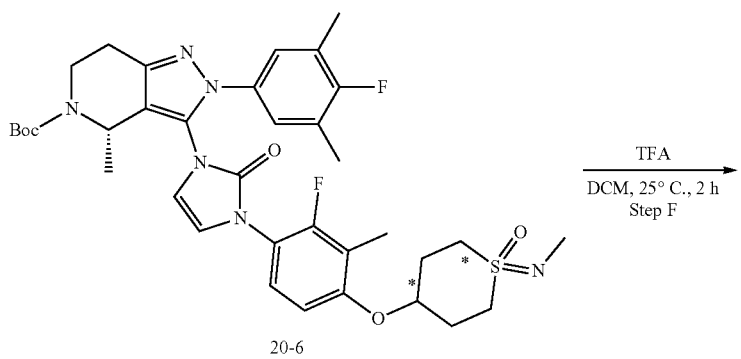

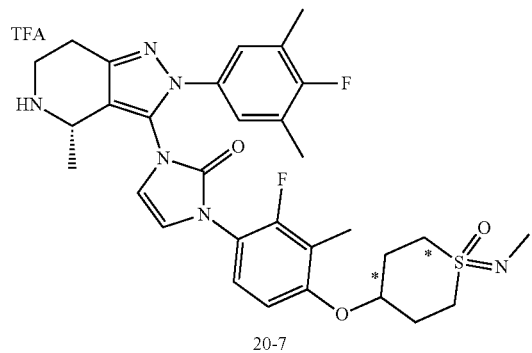
20-7
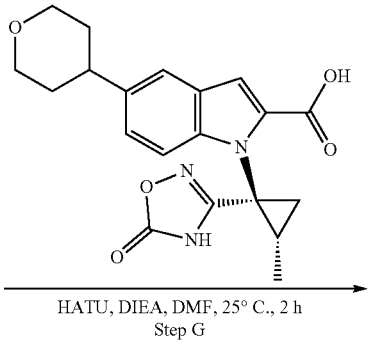
-continued
HATU, DIEA, DMF, 25° C., 2 h
Step G
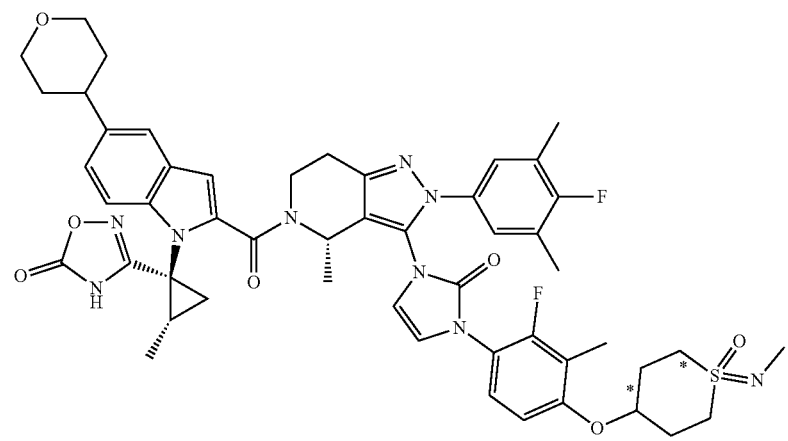
Compound 232
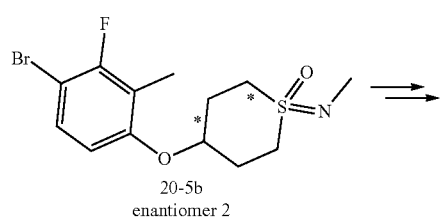
20-5b
enantiomer 2
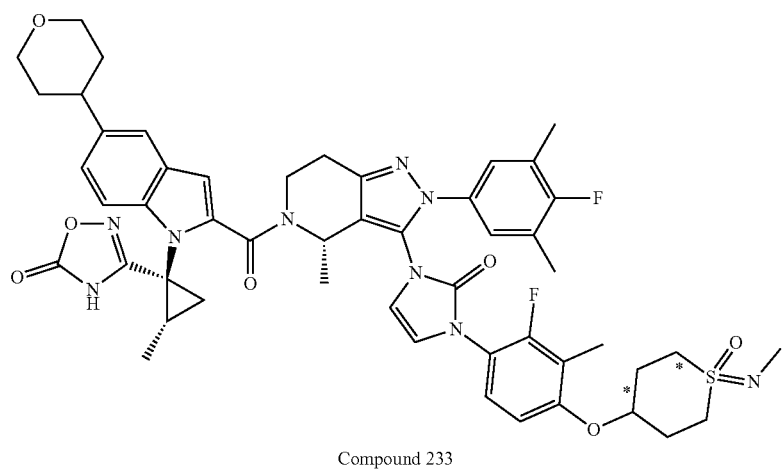
Compound 233

Step A 4-bromo-3-fluoro-2-methylphenol

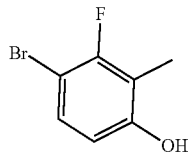

To a solution of 3-fluoro-2-methylphenol (1.00 g, 7.93 mmol) in DMF (10 mL) was added NBS (1.40 g, 7.93 mmol) at 0° C. After addition, the reaction mixture was stirred at 25° C. for 2 h. The mixture was diluted with water (10 mL) and extracted with EtOAc (10 mL×3). The combined organic layers were washed with brine, dried over $Na_2SO_4$, filtered and concentrated. The residue was purified by silica gel column chromatography eluting with 10%-20% EtOAc/PE to give 4-bromo-3-fluoro-2-methylphenol (0.90 g, 55.4% yield). $^1$H NMR (400 MHz, $CDCl_3$) δ 7.19 (t, J=8.0 Hz, 1H), 6.51 (dd, $J_1$=8.0 Hz, $J_2$=0.4 Hz, 1H), 5.61 (s, 1H), 2.19 (s, 3H).

Step B 1-(4-(azetidin-3-yl)-1-(4-fluoro-3,5-dimethylphenyl)-1H-pyrazol-5-yl)-3-(1-methyl-1H-indazol-5-yl)-1,3-dihydro-2H-imidazol-2-one TFA salt

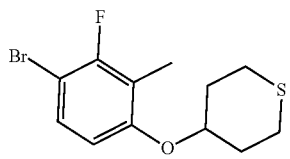 [SMILES: Cc1c(OC2CCSCC2)ccc(Br)c1F]

To a solution of 4-bromo-3-fluoro-2-methylphenol (400.0 mg, 1.95 mmol) in DMF (4 mL) was added tetrahydro-2H-thiopyran-4-yl methanesulfonate (383.0 mg, 1.95 mmol). After addition, the reaction mixture was stirred at 80° C. for 2 h. The mixture was diluted with water (10 mL) and extracted with EtOAc (10 mL×3). The combined organic layers were washed with brine, dried over $Na_2SO_4$, filtered and concentrated. The residue was purified by silica gel column chromatography eluting with 0% to 10% EtOAc/PE to give 1-(4-(azetidin-3-yl)-1-(4-fluoro-3,5-dimethylphenyl)-1H-pyrazol-5-yl)-3-(1-methyl-1H-indazol-5-yl)-1,3-dihydro-2H-imidazol-2-one TFA salt (380.0 mg, 63.8% yield). $^1$H NMR (400 MHz, $CDCl_3$) δ 7.26 (t, J=8.0 Hz, 1H), 6.52 (dd, $J_1$=8.0 Hz, $J_2$=0.4 Hz, 1H), 4.43-4.34 (m, 1H), 2.97-2.88 (m, 2H), 2.58-2.51 (m, 2H), 2.20 (s, 3H), 2.17-2.12 (m, 2H), 2.09-2.01 (m, 2H).

Step C 4-(4-bromo-3-fluoro-2-methylphenoxy)-1-iminohexahydro-1λ$^6$-thiopyran 1-oxide

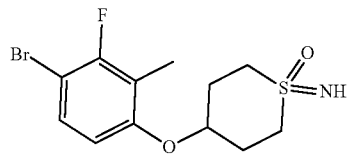 [SMILES: Cc1c(OC2CCS(=N)(=O)CC2)ccc(Br)c1F]

To a solution of 4-(4-bromo-3-fluoro-2-methylphenoxy) tetrahydro-2H-thiopyran (380.0 mg, 1.25 mmol) in EtOH (4 mL) was added (diacetoxyiodo)benzene (1.20 g, 3.72 mmol) and ammonium acetate (384.0 mg, 5.0 mmol) in one portion at 25° C. After addition, the reaction mixture was stirred at 25° C. for 4 h. The reaction mixture was concentrated, the residue was diluted with water (10 mL), extracted with EtOAc (15 mL×3). The combined organic layers were washed with brine, dried over $Na_2SO_4$, filtered and concentrated. The residue was purified by silica gel column chromatography eluting with 30% to 50% EtOAc/PE to give 4-(4-bromo-3-fluoro-2-methylphenoxy)-1-iminohexahydro-1λ$^6$-thiopyran 1-oxide (300.0 mg, 71.6% yield). LC-MS: m/z 335.9 (M+H)$^+$.

Step D 4-[(4-bromo-3-fluoro-2-methylphenyl)oxy]-1-(methylazanylidene)-1λ$^6$-thian-1-one 20-5a (enantiomer 1) and 4-[(4-bromo-3-fluoro-2-methylphenyl)oxy]-1-(methylazanylidene)-1λ$^6$-thian-1-one 20-5b (enantiomer 2)

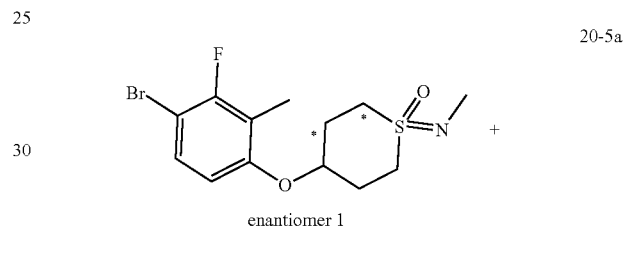

enantiomer 1

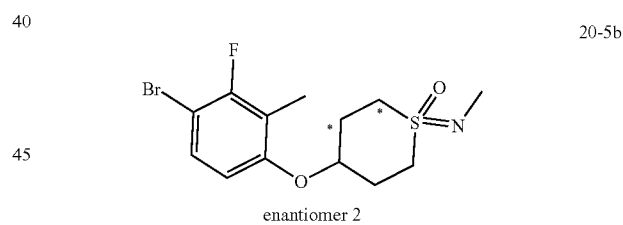

enantiomer 2

To a solution of 4-(4-bromo-3-fluoro-2-methylphenoxy)-1-iminohexahydro-1λ$^6$-thiopyran 1-oxide (300.0 mg, 0.90 mmol) in DMF (3.0 mL) was added 60% NaH (43.0 mg, 1.2 mmol) at 0° C. and stirred at 0° C. for 0.5 h under N2 atmosphere. Then, to the mixture was added iodomethane (190.0 mg, 1.34 mmol). After addition, the reaction mixture was stirred at 25° C. for 1.5 h under N2 atmosphere. The mixture was poured into ice water (10 mL) and extracted with EtOAc (10 mL×3). The combined organic layers were washed with brine, dried over $Na_2SO_4$, filtered and concentrated. The residue was purified by prep. TLC ($SiO_2$, DCM: MeOH=20: 1) to give 4-[(4-bromo-3-fluoro-2-methylphenyl)oxy]-1-(methylazanylidene)-1λ$^6$-thian-1-one 20-5a (enantiomer 1) (50.0 mg, 16.0% yield), LC-MS: m/z 349.9 (M+H)$^+$. And 4-[(4-bromo-3-fluoro-2-methylphenyl)oxy]-1-(methylazanylidene)-1λ$^6$-thian-1-one 20-5b (enantiomer 2) (50.0 mg, 16.0% yield), LC-MS: m/z 349.9 (M+H)$^+$.

517

Step E tert-butyl(4S)-2-(4-fluoro-3,5-dimethylphenyl)-3-[3-(2-fluoro-3-methyl-4-{[1-(methylazanylidene)-1-oxo-1λ⁶-thian-4-yl]oxy}phenyl)-2-oxoimidazol-1-yl]-4-methyl-4,5,6,7-tetrahydropyrazolo[4,3-c]pyridine-5-carboxylate

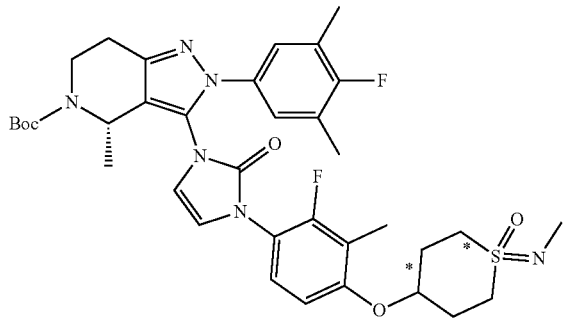 [SMILES: CN=S1(=O)CCC(Oc2ccc(-n3ccn(-c4c5c(nn4-c4cc(C)c(F)c(C)c4)CCN(C(=O)OC(C)(C)C)[C@H]5C)c3=O)c(F)c2C)CC1]

To a solution of 4-[(4-bromo-3-fluoro-2-methylphenyl)oxy]-1-(methylazanylidene)-1λ⁶-thian-1-one 20-5a (enantiomer 1) (50.0 mg, 0.14 mmol) in NMP (0.5 mL) were added tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (40.0 mg, 0.14 mmol), K$_2$CO$_3$ (31.0 mg, 0.28 mmol), copper(I) iodide (43.0 mg, 0.28 mmol) and (1S,2S)-N1,N2-dimethylcyclohexane-1,2-diamine (8.1 mg, 0.07 mmol) at 25° C. After addition, the mixture was purged with N2 for 3 times and stirred at 130° C. for 1 h under N2 atmosphere. After cooling to room temperature, the resulting mixture was added water (5 mL) and extracted with ethyl acetate (5 mL×3). The combined organic layers were washed with brine. dried over Na$_2$SO$_4$, filtered and concentrated. The residue was purified by silica gel column chromatography eluting with 50% to 100% EtOAc/PE to give tert-butyl(4S)-2-(4-fluoro-3,5-dimethylphenyl)-3-[3-(2-fluoro-3-methyl-4-{[1-(methylazanylidene)-1-oxo-1λ⁶-thian-4-yl]oxy}phenyl)-2-oxoimidazol-1-yl]-4-methyl-4,5,6,7-tetrahydropyrazolo[4,3-c]pyridine-5-carboxylate (50.0 mg, 50.2% yield). LC-MS: m/z 711.2 (M+H)⁺.

518

Step F 1-[(4S)-2-(4-fluoro-3,5-dimethylphenyl)-4-methyl-4,5,6,7-tetrahydropyrazolo[4,3-c]pyridin-3-yl]-3-(2-fluoro-3-methyl-4-{[1-(methylazanylidene)-1-oxo-1λ⁶-thian-4-yl]oxy}phenyl)-2,3-dihydro-1H-imidazol-2-one TFA salt

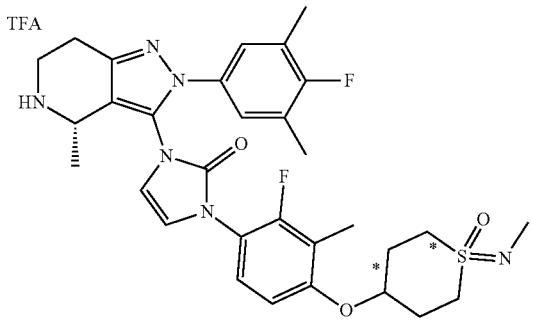 [SMILES: CN=S1(=O)CCC(Oc2ccc(-n3ccn(-c4c5c(nn4-c4cc(C)c(F)c(C)c4)CCN[C@H]5C)c3=O)c(F)c2C)CC1]

To a solution of tert-butyl(4S)-2-(4-fluoro-3,5-dimethylphenyl)-3-[3-(2-fluoro-3-methyl-4-{[1-(methylazanylidene)-1-oxo-1λ⁶-thian-4-yl]oxy}phenyl)-2-oxoimidazol-1-yl]-4-methyl-4,5,6,7-tetrahydropyrazolo[4,3-c]pyridine-5-carboxylate (40.0 mg, 0.06 mmol) in DCM (1 mL) was added TFA (0.5 mL, 6.5 mmol) at 25° C. After addition, the reaction mixture was stirred at 25° C. for 1 h. The resulting mixture was concentrated to give 1-[(4S)-2-(4-fluoro-3,5-dimethylphenyl)-4-methyl-4,5,6,7-tetrahydropyrazolo[4,3-c]pyridin-3-yl]-3-(2-fluoro-3-methyl-4-{[1-(methylazanylidene)-1-oxo-1λ⁶-thian-4-yl]oxy}phenyl)-2,3-dihydro-1H-imidazol-2-one TFA salt (40.0 mg, crude), which was used for the next step directly without further purification. LC-MS: m/z 611.2 (M+H)⁺.

Step G 3-[(1S,2S)-1-(2-{[(4S)-2-(4-fluoro-3,5-dimethylphenyl)-3-[1-(2-fluoro-3-methyl-4-{[1-(methylazanylidene)-1-oxo-1λ⁶-thian-4-yl]oxy}phenyl)-2-oxoimidazol-3-yl]-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 232)

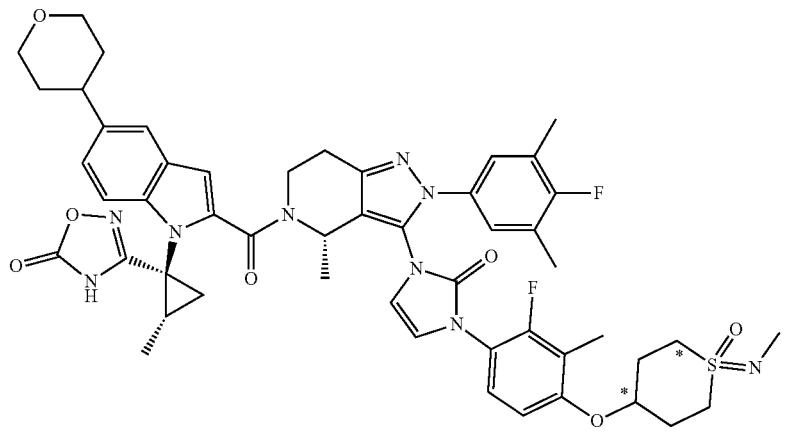 [SMILES: CN=S1(=O)CCC(Oc2ccc(-n3ccn(-c4c5c(nn4-c4cc(C)c(F)c(C)c4)CCN(C(=O)c4cc6cc(C7CCOCC7)ccc6n4[C@@]4(c6noc(=O)[nH]6)C[C@@H]4C)[C@H]5C)c3=O)c(F)c2C)CC1]

To a solution of 1-[(4S)-2-(4-fluoro-3,5-dimethylphenyl)-4-methyl-4,5,6,7-tetrahydropyrazolo[4,3-c]pyridin-3-yl]-3-(2-fluoro-3-methyl-4-{[1-(methylazanylidene)-1-oxo-1$\lambda^6$-thian-4-yl]oxy}phenyl)-2,3-dihydro-1H-imidazol-2-one TFA salt (40.0 mg, 0.07 mmol) and 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (25.0 mg, 0.07 mmol) in DMF (0.5 mL) were added HATU (30.0 mg, 0.08 mmol) and DIEA (0.043 mL, 0.28 mmol) at 25° C. After addition, the reaction mixture was stirred at 25° C. for 2 h. The reaction mixture was diluted with H$_2$O (5 mL) and extracted with EtOAc (5 mL×3). The combined organic layers were washed with brine, dried over Na$_2$SO$_4$, filtered and concentrated. The residue was purified by prep. TLC (SiO$_2$, DCM: MeOH=20: 1) and then purified by prep. HPLC (SHIMADZU LC-20AP, Column: YMC Triart C18, 20*250 mm, 5 m, Mobile Phase A: 0.1% FA, B: CH$_3$CN, flow rate: 15 mL/min; gradient: 55-75% B, Retention time: 12 min of 20 min) to give 3-[(1S,2S)-1-(2-{[(4S)-2-(4-fluoro-3,5-dimethylphenyl)-3-[1-(2-fluoro-3-methyl-4-{[1-(methylazanylidene)-1-oxo-1$\lambda^6$-thian-4-yl]oxy}phenyl)-2-oxoimidazol-3-yl]-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 232) (5.0 mg, 7.3% yield). LC-MS: m/z 976.4 (M+H)$^+$. $^1$H NMR (400 MHz, DMSO-d6) δ 7.49 (s, 1H), 7.42-7.38 (m, 1H), 7.33-7.19 (m, 2H), 7.14 (d, J=8.0 Hz, 2H), 7.02-6.95 (m, 1H), 6.89-6.75 (m, 3H), 5.65-5.55 (m, 1H), 4.85-4.74 (m, 1H), 4.01-3.97 (m, 2H), 3.55-3.40 (m, 3H), 2.97-2.80 (m, 3H), 2.66 (s, 3H), 2.24-2.10 (m, 14H), 1.85-1.55 (m, 8H), 1.48-1.32 (m, 4H), 1.26-1.05 (m, 5H).

Step H 3-[(1S,2S)-1-(2-{[(4S)-2-(4-fluoro-3,5-dimethylphenyl)-3-[1-(2-fluoro-3-methyl-4-{[1-(methylazanylidene)-1-oxo-1$\lambda^6$-thian-4-yl]oxy}phenyl)-2-oxoimidazol-3-yl]-4-methyl-4,5,6,7-tetrahydropyrazolo1[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 233)

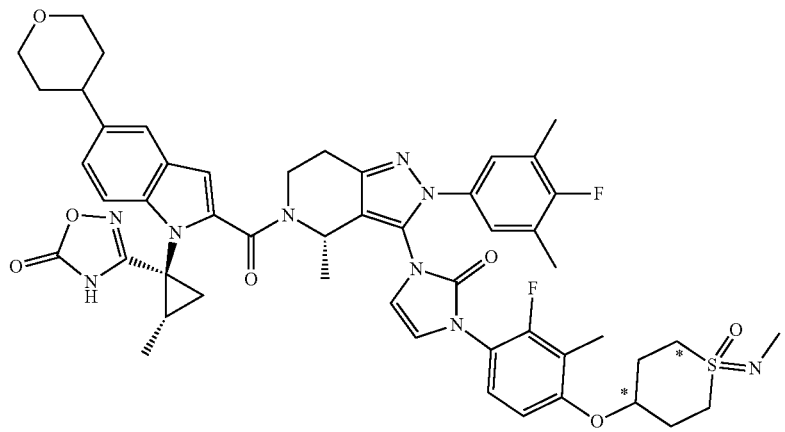 [SMILES: CN=S1(=O)CCC(Oc2ccc(-n3ccn(-c4c5c(nn4-c4cc(C)c(F)c(C)c4)CCN(C(=O)c4cc6cc(C7CCOCC7)ccc6n4[C@@]4(c6noc(=O)[nH]6)C[C@@H]4C)[C@H]5C)c3=O)c(F)c2C)CC1]

3-[(1S,2S)-1-(2-{[(4S)-2-(4-fluoro-3,5-dimethylphenyl)-3-[1-(2-fluoro-3-methyl-4-{[1-(methylazanylidene)-1-oxo-1$\lambda^6$-thian-4-yl]oxy}phenyl)-2-oxoimidazol-3-yl]-4-methyl-4,5,6,7-tetrahydropyrazolo1[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 233) (enantiomer 2) was synthesized according to the procedures described for the preparation of Compound 232 (enantiomer 1) (step E to step G). LC-MS: m/z 976.4 (M+H)$^+$. 1H NMR (400 MHz, DMSO-d6) δ 7.49 (s, 1H), 7.42-7.35 (m, 1H), 7.33-7.19 (m, 2H), 7.14 (d, J=8.0 Hz, 2H), 7.02-6.95 (m, 1H), 6.89-6.75 (m, 3H), 5.65-5.55 (m, 1H), 4.85-4.74 (m, 1H), 4.01-3.90 (m, 2H), 3.65-3.40 (m, 3H), 2.97-2.80 (m, 3H), 2.64 (s, 3H), 2.24-2.10 (m, 14H), 1.85-1.55 (m, 8H), 1.48-1.32 (m, 4H), 1.26-1.05 (m, 5H).

Example A21

3-[(1S,2S)-1-(2-{[(4S)-3-{1-[3-(difluoromethyl)-4-{[1-(methylazanylidene)-1-oxo-1λ⁶-thian-4-yl]oxy}phenyl]-2-oxoimidazol-3-yl}-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 234) and 3-[(1S,2S)-1-(2-{[(4S)-3-{1-[3-(difluoromethyl)-4-{[1-(methylazanylidene)-1-oxo-1λ⁶-thian-4-yl]oxy}phenyl]-2-oxoimidazol-3-yl}-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 235)

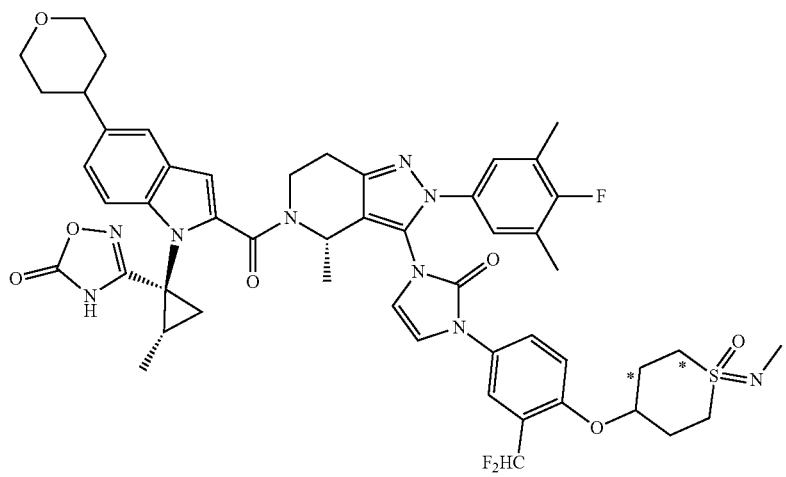

Compound 234

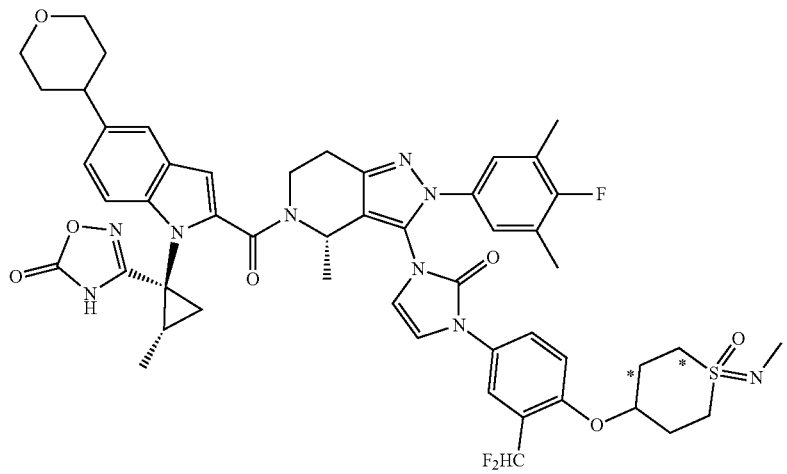

Compound 235

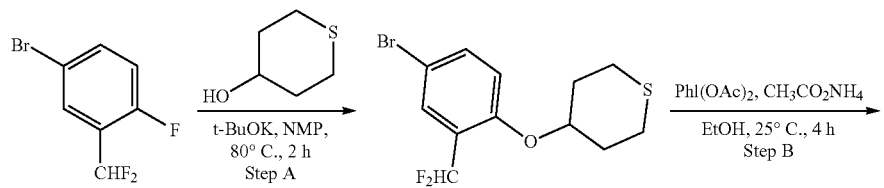

-continued
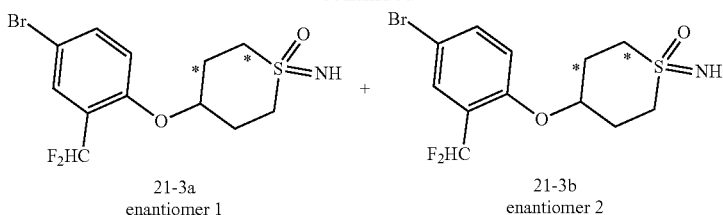
21-3a
enantiomer 1
21-3b
enantiomer 2
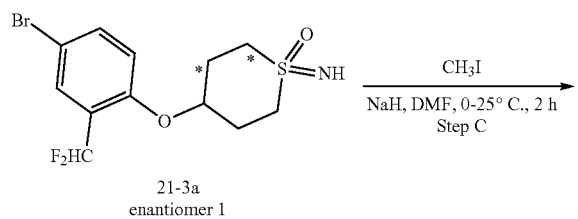
21-3a
enantiomer 1
CH₃I
———————————→
NaH, DMF, 0-25° C., 2 h
Step C
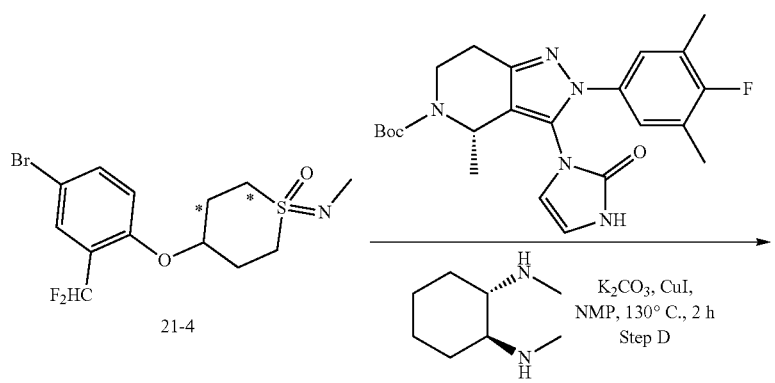
21-4
K₂CO₃, CuI,
NMP, 130° C., 2 h
Step D
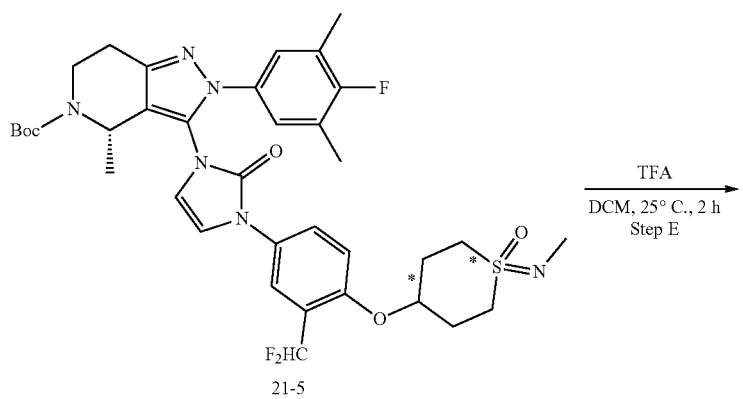
21-5
TFA
———————————→
DCM, 25° C., 2 h
Step E -continued
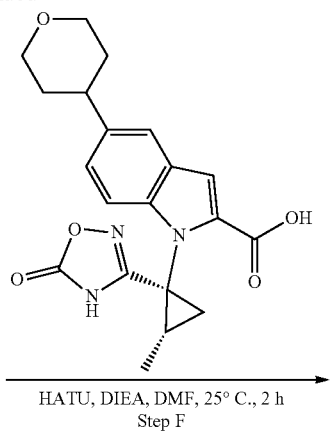
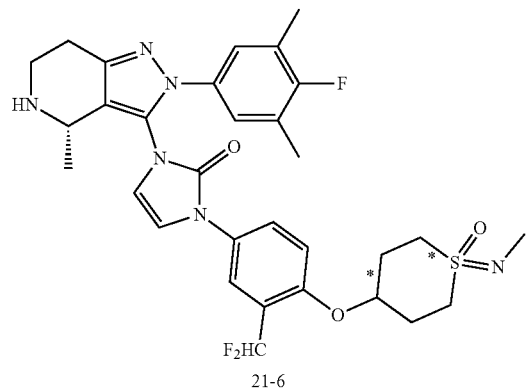
21-6
HATU, DIEA, DMF, 25° C., 2 h
Step F
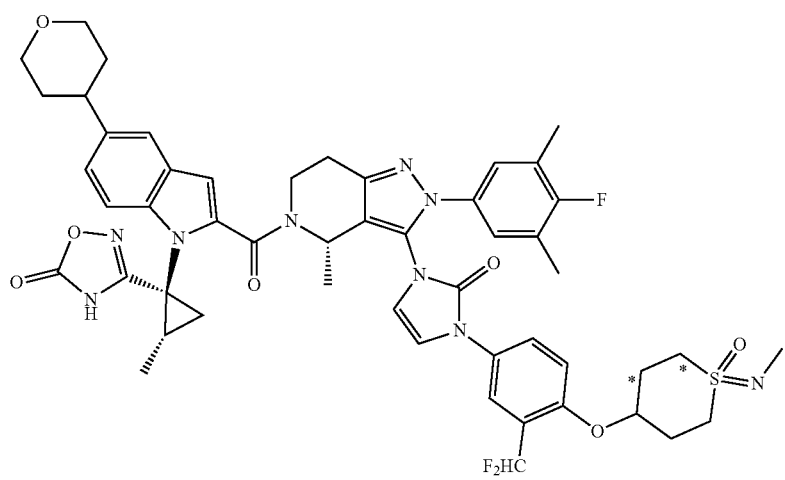
Compound 234
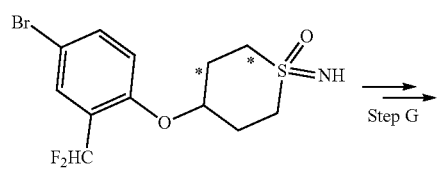
21-3b
enantiomer 2
Step G

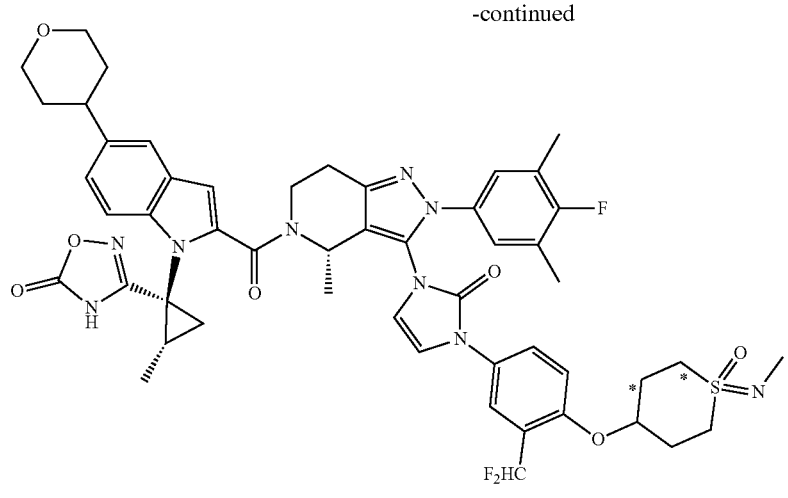

Compound 235

Step A 4-(4-bromo-3-(difluoromethyl)phenoxy)tetrahydro-2H-thiopyran

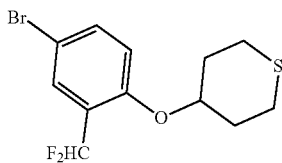 [SMILES: FC(F)c1cc(Br)ccc1OC1CCSCC1]

To a solution of 4-bromo-2-(difluoromethyl)-1-fluorobenzene (1.00 g, 4.44 mmol) in NMP (10 mL) were added tetrahydro-2H-thiopyran-4-ol (0.53 g, 4.44 mmol) and potassium tert-butoxide (1.00 g, 8.91 mmol). The reaction mixture was stirred at 80° C. for 2 h. After cooling, the mixture was diluted with H₂O (10 mL), extracted with EtOAc (10 mL×3). The combined organic layers were washed with brine (10 mL×3), dried over Na₂SO₄, filtered and concentrated. The residue was purified by silica gel column chromatography eluting with 10%-30% EtOAc/PE to afford 4-(4-bromo-3-(difluoromethyl)phenoxy)tetrahydro-2H-thiopyran (0.75 g, 2.32 mmol, 52.3% yield).

Step B 1-azanylidene-4-{[4-bromo-2-(difluoromethyl)phenyl]oxy}-1λ⁶-thian-1-one 21-3a (enantiomer 1) and 1-azanylidene-4-{[4-bromo-2-(difluoromethyl)phenyl]oxy}-1λ⁶-thian-1-one 21-3b (enantiomer 2)

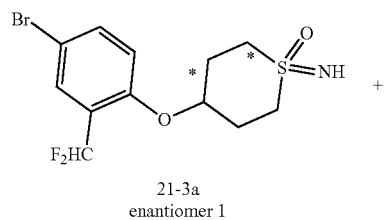

21-3a
enantiomer 1

+

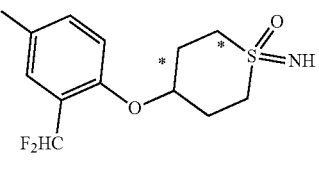

21-3b
enantiomer 2

To a solution of 4-(4-bromo-3-(difluoromethyl)phenoxy) tetrahydro-2H-thiopyran (0.75 g, 2.32 mmol) in EtOH (7.5 ml) were added ammonium acetate (0.72 g, 9.29 mmol) and iodobenzene diacetate (2.24 g, 6.95 mmol). The mixture was stirred at 25° C. for 4 h. The resulting mixture was diluted with H₂O (10 mL) and extracted with ethyl acetate (10 mL×3). The combined organic layers were washed with brine, dried over Na₂SO₄, filtered and concentrated. The residue was purified by prep. TLC (SiO₂, DCM: MeOH=20: 1) to give 1-azanylidene-4-{[4-bromo-2-(difluoromethyl)phenyl]oxy}-1'-thian-1-one 21-3a (enantiomer 1) (0.25 g, 30.6% yield), LC-MS: m/z 355.9 (M+H)⁺. And 1-azanylidene-4-{[4-bromo-2-(difluoromethyl)phenyl]oxy}-1λ⁶-thian-1-one 21-3b (enantiomer 2) (0.24 g, 0.68 mmol, 29.3% yield), LC-MS: m/z 355.9 (M+H)⁺.

Step C 4-{[4-bromo-2-(difluoromethyl)phenyl]oxy}-1-(methylazanylidene)-1λ⁶-thian-1-one

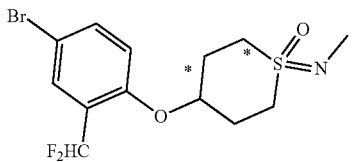 [SMILES: CN=S1(=O)CCC(Oc2ccc(Br)cc2C(F)F)CC1]

To a solution of 1-azanylidene-4-{[4-bromo-2-(difluoromethyl)phenyl]oxy}-1λ⁶-thian-1-one 21-3a (enantiomer 1) (200 mg, 0.56 mmol) in DMF (2 ml) was added 60% NaH (20.3 mg, 0.85 mmol).

After addition, the mixture was stirred at 0° C. for 30 min. Then, to the reaction mixture was added iodomethane (42 µL, 0.68 mmol). The resulting mixture was stirred at 25° C. for 1.5 h. The mixture was diluted with H₂O (1 mL) and extracted with ethyl acetate (1 mL×3). The combined organic layers were washed with brine, dried over Na₂SO₄, filtered and concentrated. The residue was purified by prep. TLC (SiO₂, DCM: MeOH=20: 1) to give 4-{[4-bromo-2-(difluoromethyl)phenyl]oxy}-1-(methylazanylidene)-1λ⁶-thian-1-one (40.0 mg, 19.4% yield). LC-MS: m/z 369.9 (M+H)⁺.

Step D tert-butyl(4S)-3-{1-[3-(difluoromethyl)-4-{[1-(methylazanylidene)-1-oxo-1λ⁶-thian-4-yl]oxy}phenyl]-2-oxoimidazol-3-yl}-2-(4-fluoro-3,5-dimethylphenyl)-4-methyl-4,5,6,7-tetrahydropyrazolo1[4,3-c]pyridine-5-carboxylate A mixture of tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (50.0 mg, 0.11 mmol), 4-{[4-bromo-2-(difluoromethyl)phenyl]oxy}-1-(methylazanylidene)-1λ⁶-thian-1-one (40.0 mg, 0.10 mmol), copper(I) iodide (12.3 mg, 0.05 mmol), K₂CO₃ (30.1 mg, 0.22 mmol) and (1S,2S)-N1,N2-dimethylcyclohexane-1,2-diamine (8 mg, 0.05 mmol) in NMP (1 ml) was degassed and purged with N2 for 3 times. The mixture was stirred at 130° C. for 2 h under N2 atmosphere. The resulting mixture was diluted with H₂O (20 mL) and extracted with EtOAc (20 mL×3). The combined organic layers were washed with brine, dried over Na₂SO₄, filtered and concentrated. The residue was purified by prep. TLC (SiO₂, DCM: MeOH=20: 1) to give tert-butyl(4S)-3-{1-[3-(difluoromethyl)-4-{[1-(methylazanylidene)-1-oxo-1λ⁶-thian-4-yl]oxy}phenyl]-2-oxoimidazol-3-yl}-2-(4-fluoro-3,5-dimethylphenyl)-4-methyl-4,5,6,7-tetrahydropyrazolo[4,3-c]pyridine-5-carboxylate (70.0 mg, 96.0% yield). LC-MS: m/z 729.2 (M+H)⁺.

Step E 1-[3-(difluoromethyl)-4-{[1-(methylazanylidene)-1-oxo-1λ⁶-thian-4-yl]oxy}phenyl]-3-[(4S)-2-(4-fluoro-3,5-dimethylphenyl)-4-methyl-4,5,6,7-tetrahydropyrazolo[4,3-c]pyridin-3-yl]-2,3-dihydro-1H-imidazol-2-one TFA salt

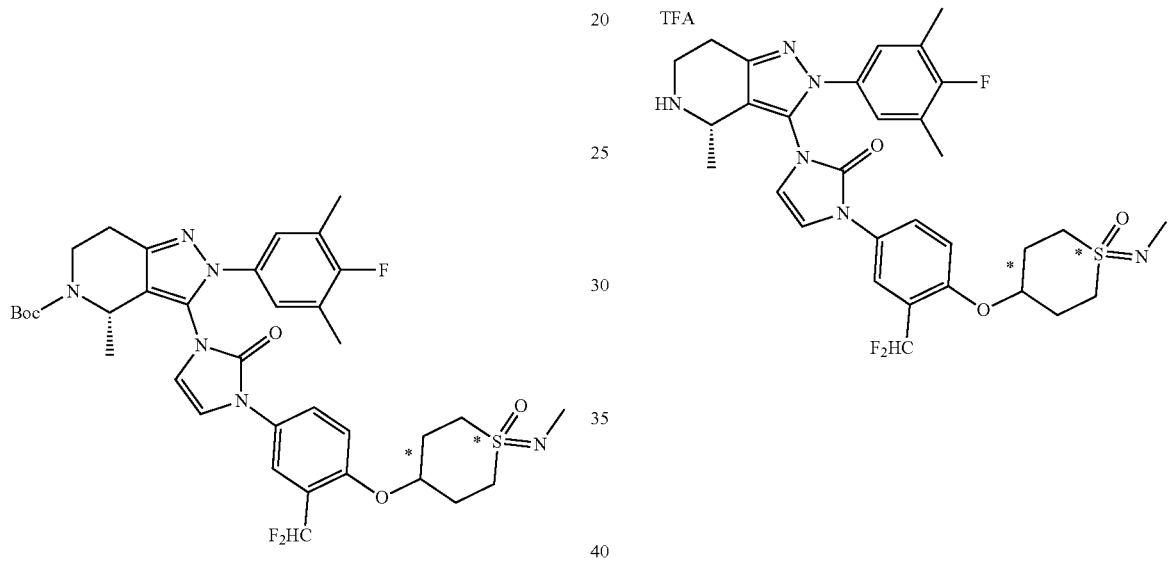

To a solution of tert-butyl(4S)-3-{1-[3-(difluoromethyl)-4-{[1-(methylazanylidene)-1-oxo-1λ⁶-thian-4-yl]oxy}phenyl]-2-oxoimidazol-3-yl}-2-(4-fluoro-3,5-dimethylphenyl)-4-methyl-4,5,6,7-tetrahydropyrazolo[4,3-c]pyridine-5-carboxylate (70.0 mg, 0.096 mmol) in DCM (1 mL) was added TFA (500 µL, 6.49 mmol). The mixture was stirred at 25° C. for 2 h. The resulting mixture was concentrated to give 1-[3-(difluoromethyl)-4-{[1-(methylazanylidene)-1-oxo-1λ⁶-thian-4-yl]oxy}phenyl]-3-[(4S)-2-(4-fluoro-3,5-dimethylphenyl)-4-methyl-4,5,6,7-tetrahydropyrazolo[4,3-c]pyridin-3-yl]-2,3-dihydro-1H-imidazol-2-one TFA salt (60.0 mg, crude), which was used for the next step directly without further purification. LC-MS: m/z 629.1 (M+H)⁺.

Step F 3-[(1S,2S)-1-(2-{[(4S)-3-{1-[3-(difluoromethyl)-4-{[1-(methylazanylidene)-1-oxo-1λ⁶-thian-4-yl]oxy}phenyl]-2-oxoimidazol-3-yl}-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 234)

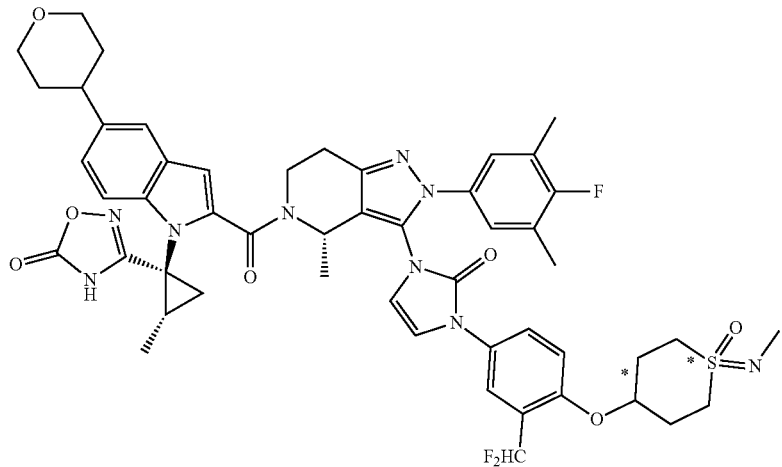 [SMILES: CN=S1(=O)CCC(Oc2ccc(-n3ccn(-c4c5c(nn4-c4cc(C)c(F)c(C)c4)CCN(C(=O)c4cc6cc(C7CCOCC7)ccc6n4[C@@]4(c6noc(=O)[nH]6)C[C@@H]4C)[C@H]5C)c3=O)cc2C(F)F)CC1]

To a solution of 1-[3-(difluoromethyl)-4-{[1-(methylazanylidene)-1-oxo-1λ⁶-thian-4-yl]oxy}phenyl]-3-[(4S)-2-(4-fluoro-3,5-dimethylphenyl)-4-methyl-4,5,6,7-tetrahydropyrazolo[4,3-c]pyridin-3-yl]-2,3-dihydro-1H-imidazol-2-one TFA salt (50.0 mg, 0.08 mmol) in DMF (1 ml) were added DIEA (0.056 ml, 0.32 mmol), 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (36.6 mg, 0.95 mmol) and HATU (36.3 mg, 0.10 mmol). The mixture was stirred at 25° C. for 2 h. The resulting mixture was diluted with $H_2O$ (10 mL) and extracted with EtOAc (10 mL×3). The combined organic layers were dried over dried over $Na_2SO_4$, filtered and concentrated. The residue was purified by prep. TLC ($SiO_2$, DCM: MeOH=20: 1) and then purified by prep. HPLC (SHIMADZU LC-20AP, Column: YMC Triart C18, 20*250 mm, 5 μm; Mobile Phase A: 0.1% FA, B: $CH_3CN$; flow rate: 15 mL/min; gradient: 50-70% B; Retention Time: 15 min of 20 min) to give 3-[(1S,2S)-1-(2-{[(4S)-3-{1-[3-(difluoromethyl)-4-{[1-(methylazanylidene)-1-oxo-1λ⁶-thian-4-yl]oxy}phenyl]-2-oxoimidazol-3-yl}-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 234) (10.8 mg, 13.6% yield). LC-MS: m/z 994.2 (M+H)⁺. ¹H NMR (400 MHz, DMSO-d6) δ 11.68 (s, 1H), 7.80-7.65 (m, 2H), 7.49 (s, 1H), 7.42-7.38 (m, 1H), 7.37-7.19 (m, 3H), 7.15-7.10 (m, 3H), 7.02-6.80 (m, 2H), 5.65-5.55 (m, 1H), 4.90-4.80 (m, 1H), 4.50-4.20 (m, 1H), 4.01-3.90 (m, 2H), 3.65-3.40 (m, 3H), 2.92-2.80 (m, 3H), 2.66 (s, 3H), 2.24-2.10 (m, 11H), 1.90-1.55 (m, 8H), 1.50-1.10 (m, 8H).

Step G 3-[(1S,2S)-1-(2-{[(4S)-3-{1-[3-(difluoromethyl)-4-{[1-(methylazanylidene)-1-oxo-1λ⁶-thian-4-yl]oxy}phenyl]-2-oxoimidazol-3-yl}-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 235)

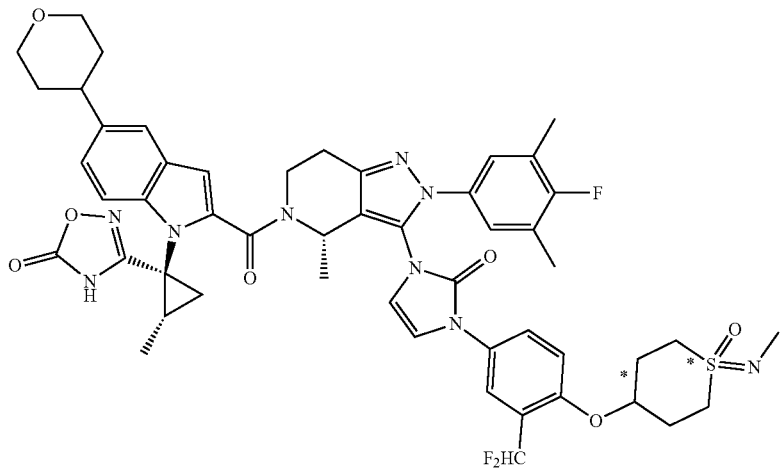 [SMILES: CN=S1(=O)CCC(Oc2ccc(-n3ccn(-c4c5c(nn4-c4cc(C)c(F)c(C)c4)CCN(C(=O)c4cc6cc(C7CCOCC7)ccc6n4[C@@]4(c6noc(=O)[nH]6)C[C@@H]4C)[C@H]5C)c3=O)cc2C(F)F)CC1]

533

3-[(1S,2S)-1-(2-{[(4S)-3-{1-[3-(difluoromethyl)-4-{[1-(methylazanylidene)-1-oxo-1$\lambda^6$-thian-4-yl]oxy}phenyl]-2-oxoimidazol-3-yl}-2-(4-fluoro-3,5-dimethylphenyl)-4-methyl-4,5,6,7-tetrahydropyrazolo[4,3-c]pyridin-5-yl]carbonyl}-5-(3,4,5,6-tetrahydro-2H-pyran-4-yl)indol-1-yl)-2-methylcyclopropyl]-4H,5H-1,2,4-oxadiazol-5-one (Compound 235) (enantiomer 2) was synthesized according to the procedures described for the preparation of Compound 234 (enantiomer 1) (step C to step F). LC-MS: m/z 994.2 (M+H)$^+$. $^1$H NMR (400 MHz, DMSO-d6) δ 11.68 (s, 1H), 7.80-7.60 (m, 2H), 7.49 (s, 1H), 7.45-7.30 (m, 3H), 7.26-7.19 (m, 2H), 7.13 (d, J=8.0 Hz, 2H), 6.95-6.75 (m, 2H), 5.70-5.55 (m, 1H), 4.90-4.85 (m, 1H), 4.50-4.25 (m, 1H), 4.00-3.90 (m, 2H), 3.65-3.40 (m, 3H), 2.95-2.80 (m, 3H), 2.64 (s, 3H), 2.30-2.10 (m, 11H), 1.90-1.55 (m, 8H), 1.50-1.00 (m, 8H).

Example compounds 236 and 237 were synthesized using a similar procedure described in the Example A21 above using the appropriate materials.

534

Example A22

5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-3H-2$\lambda^6$-benzo[c][1,2]thiazol-2-one (Compound 227)

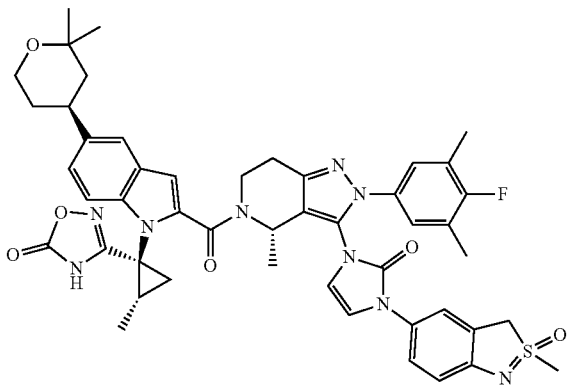

Compound 227

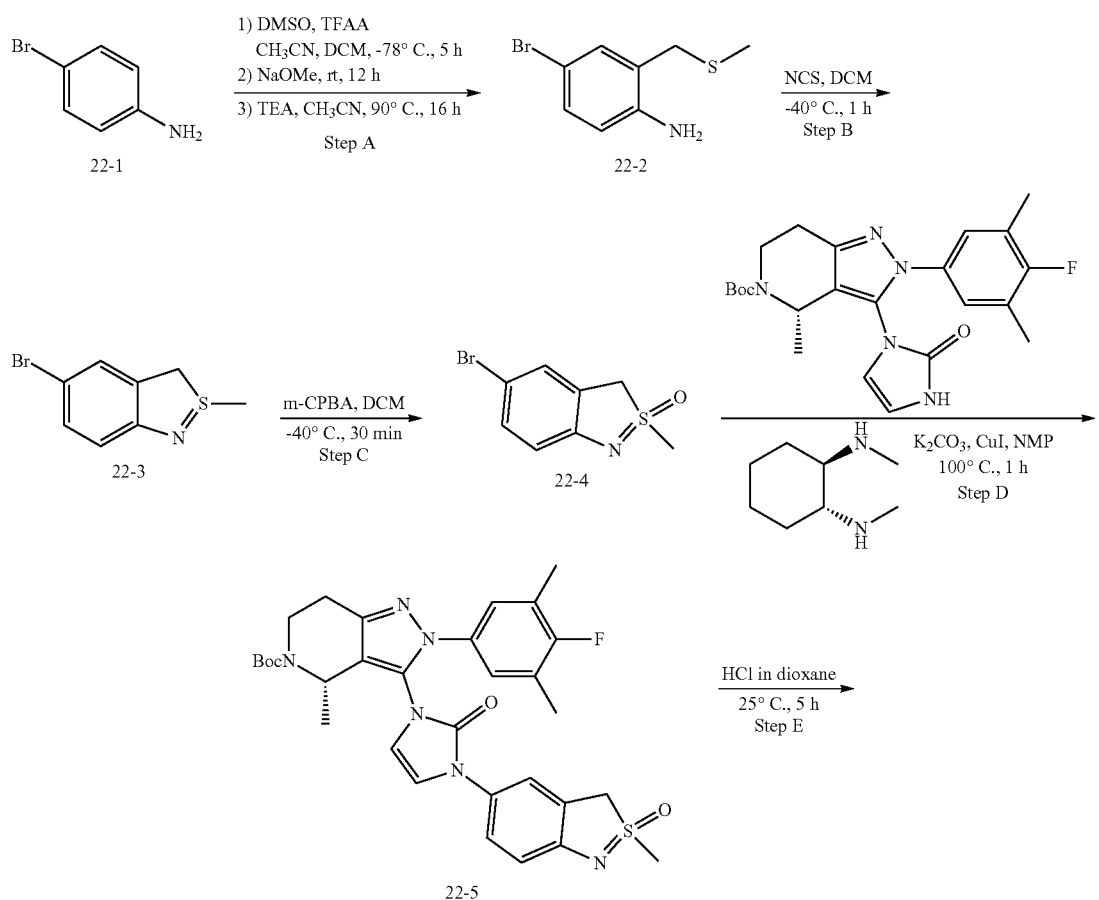

-continued

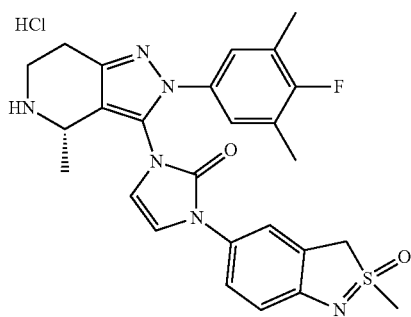

22-6

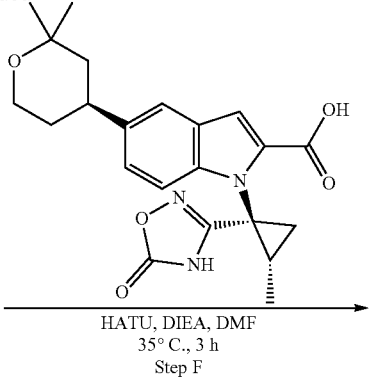

HATU, DIEA, DMF
35° C., 3 h
Step F

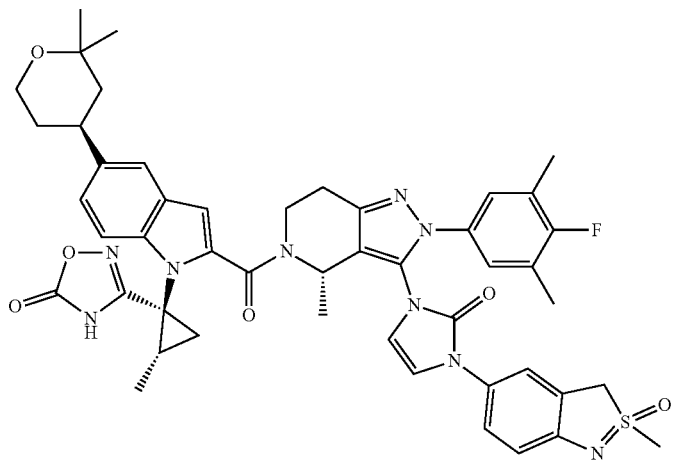

Compound 227

Step A 4-bromo-2-[(methylsulfanyl)methyl]aniline

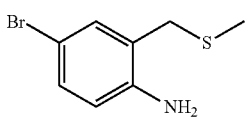

To a solution of DMSO (3.849 mL, 53.991 mmol) in CH$_3$CN (10 mL) and DCM (10 mL) were added TFAA (6.30 g, 29.995 mmol) at −78° C. under Ar. Then 4-bromoaniline (5.16 g, 29.995 mmol) in CH$_3$CN (10 mL) was added. After being stirred at −78° C. for 5 h, a solution of MeONa (2.07 g, 89.984 mmol) in MeOH (16.6 mL) were added. The reaction was stirred at 25° C. for 18 h. The mixture was quenched with 2.8 M aq. NaOH (60 mL), extracted with DCM (50 mL×3). The combined organic layers were washed with brine, dried over anhydrous sodium sulfate, filtered and concentrated. The residue was dissolved in the mixture of TEA (10 mL) and CH$_3$CN (100 mL). After being stirred at 90° C. for 18 h under Ar. The mixture was concentrated, the residue was purified by silica gel column chromatography eluting with 10% EtOAc/PE to give 4-bromo-2-[(methylsulfanyl)methyl]aniline (4.2 g, 63.6% yield). LC-MS: m/z 232.1 (M+H)$^+$.

Step B 5-bromo-2-methyl-3H-2R$^4$-benzo[c][1,2]thiazole

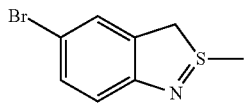

To a solution of 4-bromo-2-[(methylsulfanyl)methyl]aniline (3.4 g, 14.646 mmol) in DCM (50 mL) was added NCS (1.96 g, 14.646 mmol) in DCM (50 mL) dropwise at −40° C. under Ar. The mixture was stirred at −40° C. for 1 h under Ar. LCMS showed the reaction was completed. The mixture was quenched by 10% aq. NaOH (10 mL) and allowed to warm to 25° C. The mixture was poured into water (100 mL), extracted with DCM (100 mL). The organic layer was dried over Na$_2$SO$_4$, filtrated and then used in the next step directly. LC-MS: m/z 230.1 (M+H)$^+$.

Step C 5-bromo-2-methyl-3H-2λ⁶-benzo[c][1,2]thiazol-2-one

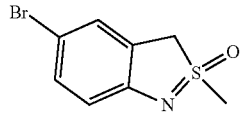

The above solution was cooled to −40° C., a solution of m-CPBA (3.046 g, 15.004 mmol) in DCM (15 mL) was added. The resulting mixture was stirred at −40° C. for 0.5 h and warmed to 25° C. LCMS showed the reaction was completed. The mixture was washed with aq. NaHSO₃ (100 mL×2) and then aq. NaHCO₃ (100 mL×2). The organic layers was dried over sodium sulfate, filtered and concentrated.

The resulting residue was purified by silica gel column chromatography eluting with 2% MeOH/DCM to give 5-bromo-2-methyl-3H-2λ⁶-benzo[c][1,2]thiazol-2-one (2.28 g, 63.3% yield). LC-MS: m/z 248.1 (M+H)⁺.

Step D tert-butyl(4S)-2-(4-fluoro-3,5-dimethylphenyl)-4-methyl-3-[1-(2-methyl-2-oxo-3H-2λ⁶-benzo[c][1,2]thiazol-5-yl)-2-oxoimidazol-3-yl]-4,5,6,7-tetrahydropyrazolo[4,3-c]pyridine-5-carboxylate

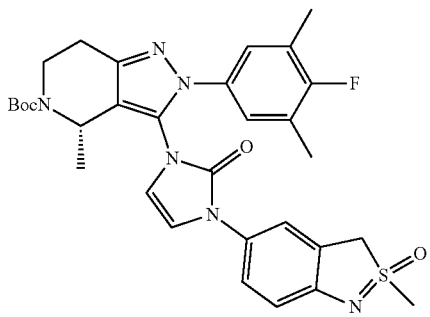 [SMILES: Cc1cc(-n2nc3c(c2-n2ccn(-c4ccc5c(c4)CS(C)(=O)=N5)c2=O)[C@H](C)N(C(=O)OC(C)(C)C)CC3)cc(C)c1F]

To a solution of tert-butyl(4S)-2-(4-fluoro-3,5-dimethylphenyl)-4-methyl-3-(2-oxo-1H-imidazol-3-yl)-4,5,6,7-tetrahydropyrazolo[4,3-c]pyridine-5-carboxylate (164 mg, 0.371 mmol) in NMP (5 mL) were added copper(1+) iodide (84.89 mg, 0.446 mmol), potassium carbonate (154.0 mg, 1.114 mmol), 5-bromo-2-methyl-3H-2λ⁶-benzo[c][1,2]thiazol-2-one (100.6 mg, 0.409 mmol) and methyl[(1S,2S)-2-(methylamino)cyclohexyl]amine (79.3 mg, 0.557 mmol). The reaction mixture was stirred at 100° C. for 1 h. After cooling, the mixture was diluted with water (15 mL), extracted with EtOAc (20 mL×3). The combined organic layers were washed with brine, dried over sodium sulfate and concentrated. The residue was purified by prep. TLC (SiO₂, DCM/MeOH=10/1) to afford tert-butyl(4S)-2-(4-fluoro-3,5-dimethylphenyl)-4-methyl-3-[1-(2-methyl-2-oxo-3H-2λ⁶-benzo[c][1,2]thiazol-5-yl)-2-oxoimidazol-3-yl]-4,5,6,7-tetrahydropyrazolo[4,3-c]pyridine-5-carboxylate (243 mg, 98.1% yield). LC-MS: m/z 607.5 (M+H)⁺.

Step E 5-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-2-methyl-3H-2λ⁶-benzo[c][1,2]thiazol-2-one HCl salt

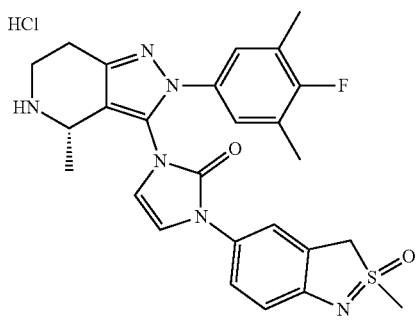 [SMILES: Cl ; Cc1cc(-n2nc3c(c2-n2ccn(-c4ccc5c(c4)CS(C)(=O)=N5)c2=O)[C@H](C)NCC3)cc(C)c1F]

The mixture of tert-butyl(4S)-2-(4-fluoro-3,5-dimethylphenyl)-4-methyl-3-[1-(2-methyl-2-oxo-3H-2λ⁶-benzo[c][1,2]thiazol-5-yl)-2-oxoimidazol-3-yl]-4,5,6,7-tetrahydropyrazolo[4,3-c]pyridine-5-carboxylate (223 mg, 0.368 mmol) in 4 M HCl (gas)/dioxane (5 mL) was stirred at 25° C. for 1 h. The reaction mixture was concentrated under vacuum to give 5-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-2-methyl-3H-2λ⁶-benzo[c][1,2]thiazol-2-one HCl salt (183 mg, 98.3% yield). LC-MS: m/z 507.3 (M+H)⁺.

Step F 5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-3H-2R⁶-benzo[c][1,2]thiazol-2-one (Compound 227)

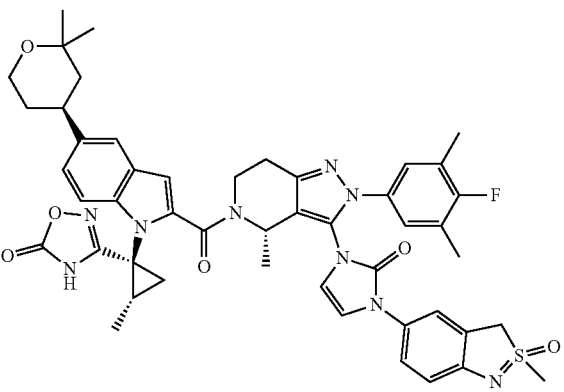 [SMILES: Cc1cc(-n2nc3c(c2-n2ccn(-c4ccc5c(c4)CS(C)(=O)=N5)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

To a solution of 5-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-2-methyl-3H-2λ⁶-benzo[c][1,2]thiazol-2-one HCl salt (91 mg, 0.180 mmol) and 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (74.1 mg, 0.180 mmol) in DMF (5 mL) was added HATU (75.1 mg, 0.198 mmol) and DIEA (116.1 mg, 0.898 mmol) under Ar.

The reaction was stirred at 25° C. for 18 h. the reaction mixture was diluted with water (20 mL), extracted with EtOAc (20 mL×3). The combined organic layers were washed with brine, dried over anhydrous sodium sulfate, filtered and concentrated. The residue was purified by purified by prep. TLC (SiO₂, DCM/CH₃OH=10/1) and then by prep. HPLC (Waters 3767/Qda Column: SunFire Sunfire C18, 19*250 mm, 10 μm; Mobile Phase A: 10 M NH₄HCO₃/H₂O, B: CH₃CN; Flow rate: 20 mL/min; Gradient: 37%-47% B; Retention Time: 9.3-9.95 min of 16 min) to afford 5-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-3H-2λ⁶-benzo[c][1,2]thiazol-2-one (5.91 mg, 3.5% yield). LC-MS: m/z 900.6 (M+H)⁺. ¹H NMR (400 MHz, DMSO-d6) δ 11.72 (brs, 1H), 7.52 (s, 1H), 7.43-7.40 (m, 2H), 7.27-7.25 (m, 2H), 7.14 (d, J=6.4 Hz, 2H), 6.98 (m, 1H), 6.86 (m, 1H), 6.81-6.74 (m, 2H), 5.63 (m, 1H), 4.98 (d, J=17.6 Hz, 1H), 4.52 (d, J=17.6 Hz, 1H), 4.41 (m, 1H), 3.74-3.72 (m, 2H), 3.47 (s, 3H), 2.89-2.83 (m, 1H), 2.23 (s, 6H), 1.77-1.70 (m, 4H), 1-65-1.50 (m, 4H), 1.43 (m, 3H), 1.29 (m, 4H), 1.20-1.14 (m, 7H).

Example compounds 225 were synthesized using a similar procedure described in the Example A22 above using the appropriate materials.

Example A23

6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-3,4-dihydro-2W⁶-benzo[c][1,2]thiazin-2-one (Compound 228) and 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-3,4-dihydro-2W⁶-benzo[c][1,2]thiazin-2-one (Compound 229)

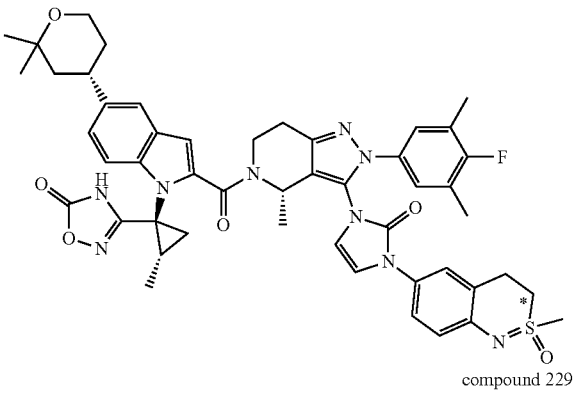

compound 228

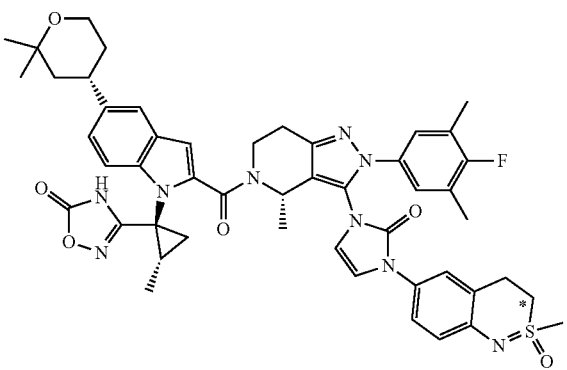

compound 229

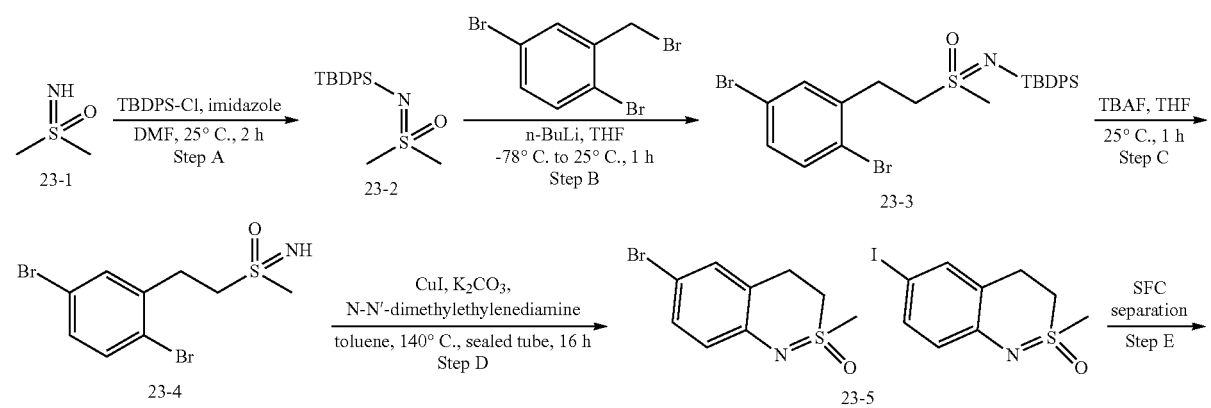

-continued
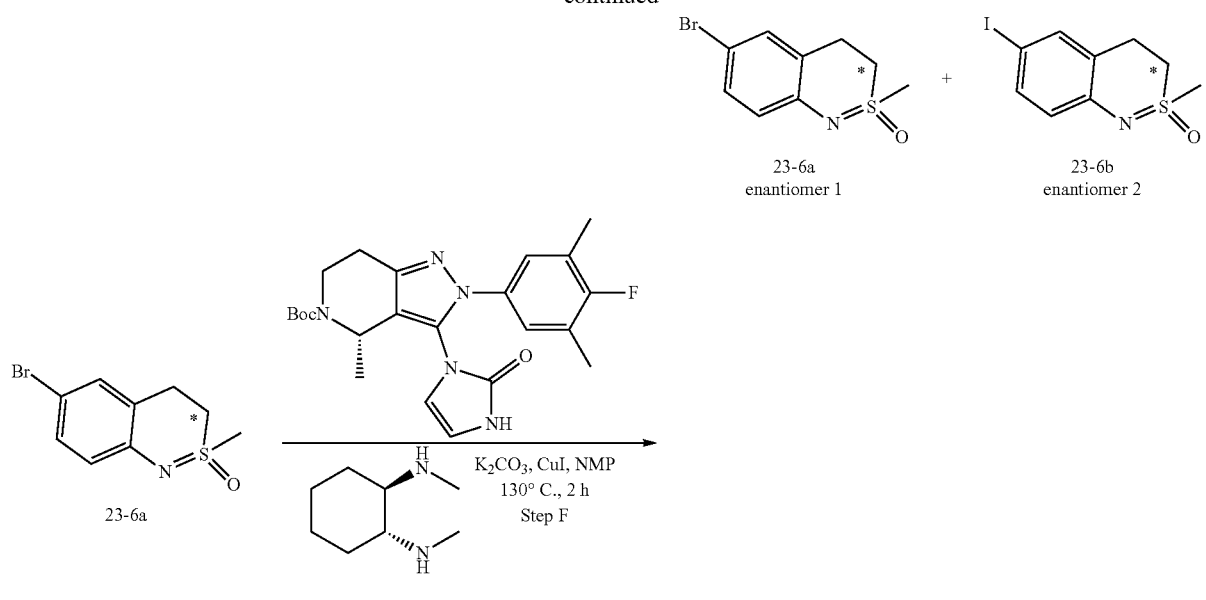
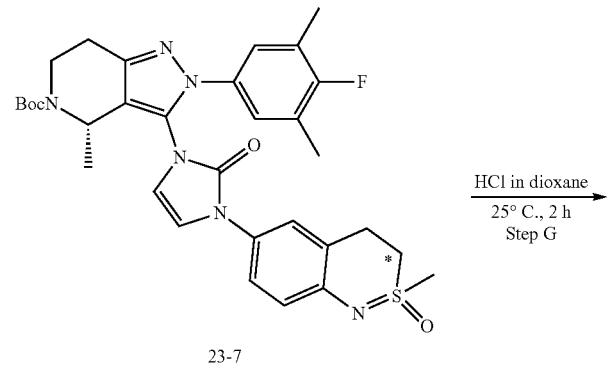
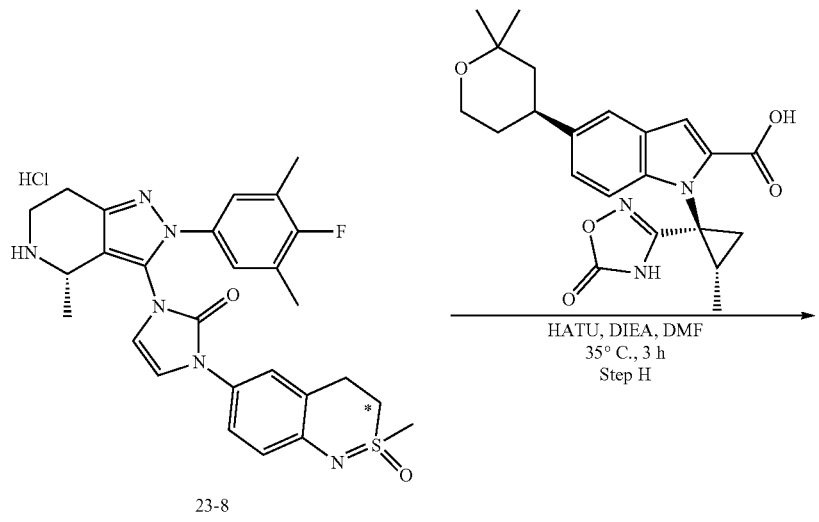

-continued

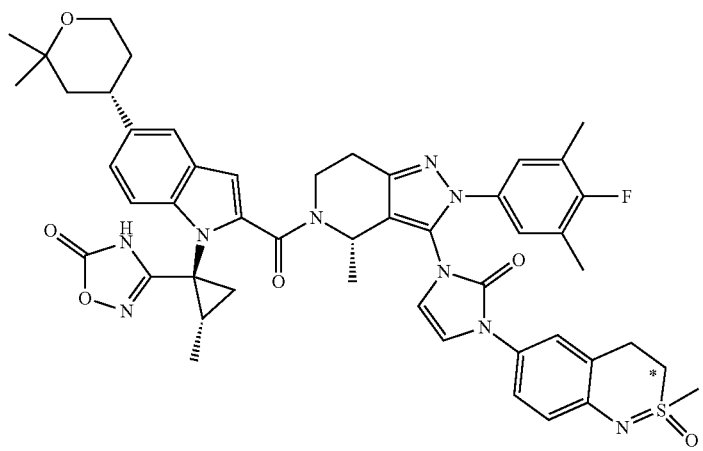

compound 228

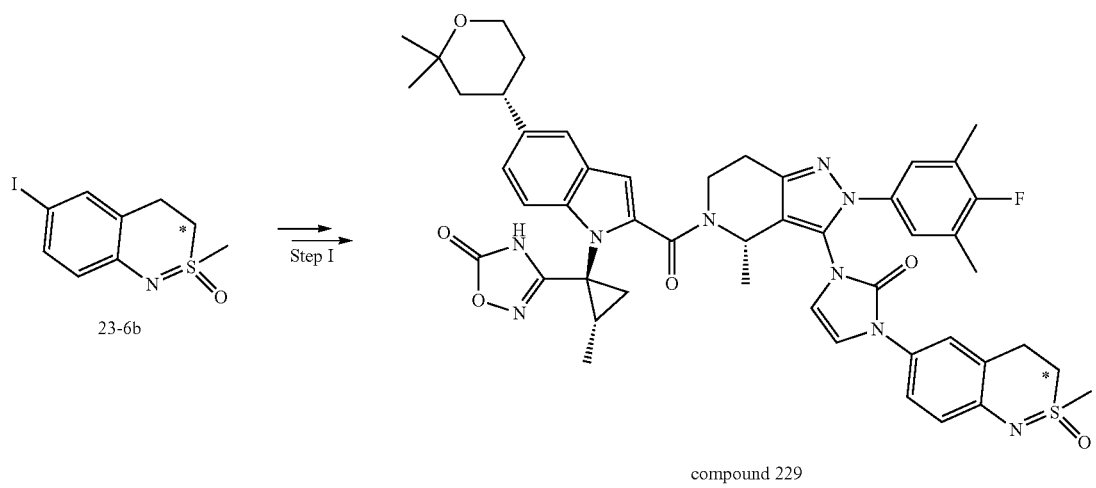

compound 229

Step A 1,1-dimethyl-N-[(2-methylprop-2-yl)diphenylsilyl]-1-oxo-λ⁶-sulfanimine

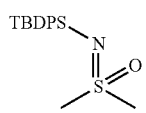

To a solution of dimethyl(oxo)-λ⁶-sulfanimine (500 mg, 5.368 mmol) in DMF (10 mL) was added imidazole (1.09 g, 16.105 mmol) and TBDPS-Cl (1.77 g, 6.442 mmol). The reaction mixture was stirred at 25° C. for 2 h under N2. The reaction mixture was poured into water (100 mL) and extracted with EtOAc (100 mL×2). The combined organic layer was washed with brine, dried over sodium sulfate and concentrated. The residue was purified by silica gel chromatography eluting with 0-20% EtOAc/PE to obtain 1,1-dimethyl-N-[(2-methylprop-2-yl)diphenylsilyl]-1-oxo-λ⁶-sulfanimine (1.25 g, 70.2% yield). LC-MS: m/z 332.3 (M+H)⁺.

Step B 1-[2-(2,5-dibromophenyl)ethyl]-1-methyl-N-[(2-methylprop-2-yl)diphenylsilyl]-1-oxo-λ⁶-sulfanimine

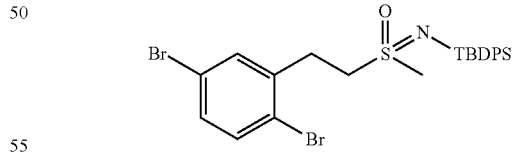

To a solution of 1,1-dimethyl-N-[(2-methylprop-2-yl)diphenylsilyl]-1-oxo-λ⁶-sulfanimine (1.25 g, 3.468 mmol) in THF (100 mL) was added n-BuLi (1-6 mol/L, 2.4 mL, 3.82 mmol) at −78° C. dropwise. The solution was stirred at −78° C. for 0.5 h, then a solution of 1,4-dibromo-2-(bromomethyl)benzene (1.37 g, 4.17 mmol) in THF (10 mL) was added slowly. After addition, the reaction mixture was warmed to rt and stirred for 16 h under Ar. The reaction mixture was poured into water (100 mL) and extracted with EtOAc (100 mL×2). The combined organic layer was washed with brine, dried over sodium sulfate, filtered and concentrated. The residue was purified by silica gel chromatography eluting with 0-25% EtOAc/PE to obtain 1-[2-(2,5-dibromophenyl)ethyl]-1-methyl-N-[(2-methylprop-2-yl)diphenylsilyl]-1-oxo-$\lambda^6$-sulfanimine (570 mg, 28.4% yield). LC-MS: m/z 580.4 (M+H)$^+$.

Step C [2-(2,5-dibromophenyl)ethyl](methyl)(oxo)-$\lambda^6$-sulfanimine

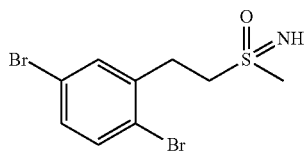

To a solution of 1-[2-2,5-dibromophenyl)ethyl]-1-methyl-N-[(2-methylprop-2-yl)diphenylsilyl]-1-oxo-$\lambda^6$-sulfanimine (570 mg, 0.984 mmol) in THF (20 mL) was added TBAF (1M in THF, 3.604 mL, 3.604 mmol) at rt. After being stirred at rt for 2 h, H$_2$O (20 ml) was added to the mixture. It was extracted with EtOAc (20 mL×2). The combined organic layers were dried over sodium sulfate, filtered and concentrated. The residue was purified by silica gel chromatography eluting with 100% EtOAc to afford [2-(2,5-dibromophenyl)ethyl](methyl)(oxo)-$\lambda^6$-sulfanimine (330 mg, 98.3% yield). LC-MS: m/z 340.1 (M+H)$^+$.

Step D 6-bromo-2-methyl-3,4-dihydro-2$\lambda^6$-benzo[c][1,2]thiazin-2-one and 2$\lambda^6$-iodo-2-methyl-3,4-dihydro-2$\lambda^6$-benzo[c][1,2]thiazin-2-one

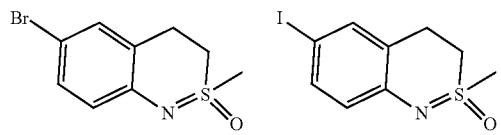

To a solution of [2-(2,5-dibromophenyl)ethyl](methyl)(oxo)-$\lambda^6$-sulfanimine (330 mg, 0.967 mmol) in toluene (50 mL) was added K$_2$CO$_3$ (533.8 mg, 3.87 mmol), CuI (18.5 mg, 0.097 mmol) and N,N'-dimethylethylenediamine (16.7 mg, 0.19 mmol). The reaction mixture was stirred at 140° C. for 18 h under N2 in a sealed tube. The reaction mixture was poured into water (50 mL) and extracted with EtOAc (50 mL×2). The combined organic layers were washed with brine, dried over sodium sulfate, filtered and concentrated. The residue was purified by silica gel chromatography eluting with 100% EtOAc 100% to afford a mixture of 6-bromo-2-methyl-3,4-dihydro-2$\lambda^6$-benzo[c][1,2]thiazin-2-one and 6-iodo-2-methyl-3,4-dihydro-2$\lambda^6$-benzo[c][1,2]thiazin-2-one (120 mg).

Step E 6-bromo-2-methyl-3,4-dihydro-2$\lambda^6$-benzo[c][1,2]thiazin-2-one and 2$\lambda^6$-iodo-2-methyl-3,4-dihydro-2$\lambda^6$-benzo[c][1,2]thiazin-2-one

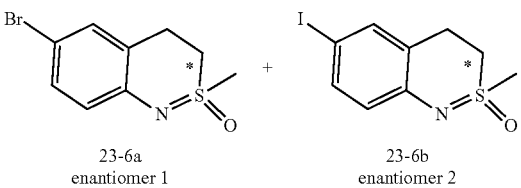

23-6a
enantiomer 1

23-6b
enantiomer 2

The mixture of 6-bromo-2-methyl-3,4-dihydro-2$\lambda^6$-benzo[c][1,2]thiazin-2-one and 2$\lambda^6$-iodo-2-methyl-3,4-dihydro-2$\lambda^6$-benzo[c][1,2]thiazin-2-one (120 mg) was purified by SFC (system: Waters SFC 150; Column name: DAICELCHIRALCEL® AD; Column size: 250*25 mm, 10 µm; Mobile Phase A: Supercritical CO$_2$; Mobile Phase B: MeOH (+0.1% 7.0 M ammonia in MeOH); Gradient: A/B=75/25; Flow rate: 100 mL/min, Column temp: RT) to give 6-bromo-2-methyl-3,4-dihydro-2$\lambda^6$-benzo[c][1,2]thiazin-2-one (18 mg) (the 1$^{st}$ eluting fraction, enantiomer 1), LC-MS: m/z 260.1 (M+H)$^+$.

And 2$\lambda^6$-iodo-2-methyl-3,4-dihydro-2$\lambda^6$-benzo[c][1,2]thiazin-2-one (20 mg) (the 4$^{th}$ eluting fraction, enantiomer 2), LC-MS: m/z 308.0 (M+H)$^+$.

Step F tert-butyl(4S)-2-(4-fluoro-3,5-dimethylphenyl)-4-methyl-3-[1-(2-methyl-2-oxo-3,4-dihydro-2$\lambda^6$-benzo[c][1,2]thiazin-6-yl)-2-oxoimidazol-3-yl]-4,5,6,7-tetrahydropyrazolo[4,3-c]pyridine-5-carboxylate

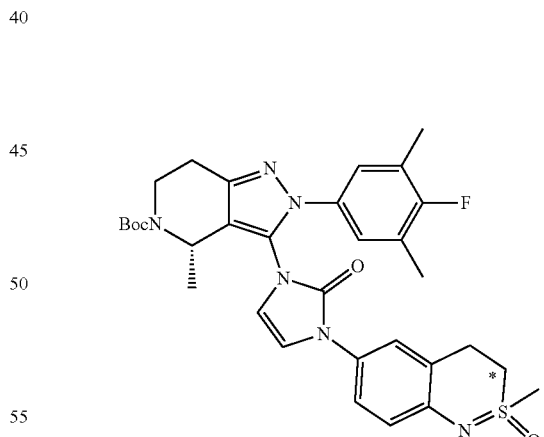

To a solution of 6-bromo-2-methyl-3,4-dihydro-2$\lambda^6$-benzo[c][1,2]thiazin-2-one (18.21 mg, 0.070 mmol) in NMP (5 mL) were added tert-butyl(4S)-2-(4-fluoro-3,5-dimethylphenyl)-4-methyl-3-(2-oxo-1H-imidazol-3-yl)-4,5,6,7-tetrahydropyrazolo[4,3-c]pyridine-5-carboxylate (31 mg, 0.070 mmol), methyl[(1R,2R)-2-(methylamino)cyclohexyl]amine (14.98 mg, 0.105 mmol), CuI (16.01 mg, 0.084 mmol) and K$_2$CO$_3$ (19.41 mg, 0.140 mmol). The reaction was stirred at 130° C. for 3 h under N2. After cooling, the mixture was diluted with water (30 mL), extracted with EtOAc (30 mL×2). The combined organic layers were washed with brine, dried over sodium sulfate, filtered and concentrated. The residue was purified by silica gel chromatography eluting with 0-3% MeOH, DCM to afford tert-butyl(4S)-2-(4-fluoro-3,5-dimethylphenyl)-4-methyl-3-[1-(2-methyl-2-oxo-3,4-dihydro-2λ$^6$-benzo[c][1,2]thiazin-6-yl]-2-oxoimidazol-3-yl]-4,5,6,7-tetrahydropyrazolo[4,3-c]pyridine-5-carboxylate (20 mg, 46.0% yield). LC-MS: m/z 621.1 (M+H)$^+$.

Step G 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-2-methyl-3,4-dihydro-2λ$^6$-benzo[c][1,2]thiazin-2-one HCl salt

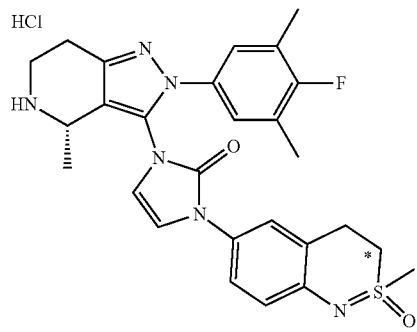 [SMILES: Cl ; Cc1cc(-n2nc3c(c2-n2ccn(-c4ccc5c(c4)CCS(C)(=O)=N5)c2=O)[C@H](C)NCC3)cc(C)c1F]

To a solution of tert-butyl-2-(4-fluoro-3,5-dimethylphenyl)-4-methyl-3-(3-((R)-2-methyl-2-oxido-3,4-dihydro-214-benzo[c][1,2]thiazin-6-yl)-2-oxo-2,3-dihydro-1H-imidazol-1-yl)-2,4,6,7-tetrahydro-5H-pyrazolo[4,3-c]pyridine-5-carboxylate (20 mg, 0.032 mmol) in dioxane (3 mL) were added 4 M HCl (gas) in dioxane (0.5 mL). The mixture was stirred at rt for 1 h under N2. The reaction mixture was concentrated under reduced pressure to afford 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-2-methyl-3,4-dihydro-2λ$^6$-benzo[c][1,2]thiazin-2-one HCl salt (17 mg crude). LC-MS: m/z 521.1 (M+H)$^+$.

Step H 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo [4,3-c]pyridin-3-yl]-2-oxoimidazol-1-yl}-2-methyl-3,4-dihydro-2λ$^6$-benzo[c][1,2]thiazin-2-one (Compound 228)

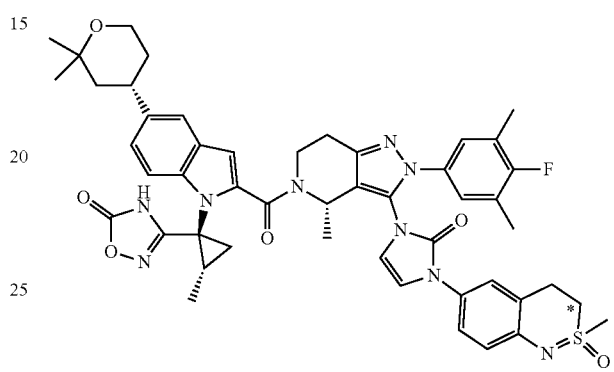

To a solution of 6-{3-[(4S)-2-(4-fluoro-3,5-dimethylphenyl)-4-methyl-4,5,6,7-tetrahydropyrazolo [4,3-c]pyridin-3-yl]-2-oxoimidazol-1-yl}-2-methyl-3,4-dihydro-2λ$^6$-benzo[c][1,2]thiazin-2-one HCl salt (17 mg, 0.033 mmol) in DMF (5 mL), was added 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (13.44 mg, 0.033 mmol), HATU (13.66 mg, 0.036 mmol) and DIEA (21.10 mg, 0.163 mmol). The reaction mixture was stirred at 35° C. for 18 h under N2. After the reaction was completed, water (20 mL) was added, the mixture was extracted with EtOAc (20 mL×3).

The combined organic layers were washed with brine, dried over anhydrous sodium sulfate, filtered and concentrated. The resulting residue was purified by purified by prep. TLC (SiO$_2$, DCM/CH$_3$OH=15/1) and then prep. HPLC (Waters 3767/Qda Column: XBridge XBridge C18, 19*250 mm, 10 μm; Mobile Phase A: 0.05% NH$_3$H2O/H$_2$O, B: CH$_3$CN; Flow rate: 20 mL/min; Gradient: 29%-39% B; Retention Time: 9-10 min of 17 min) to afford 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-3,4-dihydro-2λ$^6$-benzo[c][1,2]thiazin-2-one (Compound 228) (enantiomer 1) (1.0 mg, 3.4% yield). LC-MS: m/z 914.5 (M+H)$^+$. $^1$H NMR (400 MHz, DMSO-d6) δ 7.41 (m, 2H), 7.25-7.14 (m, 5H), 6.92-6.72 (m, 3H), 6.51 (m, 1H), 5.35 (m, 1H), 3.75-3.73 (m, 2H), 3.41-3.38 (m, 3H), 3.25 (m, 5H), 2.67 (m, 3H), 2.21 (s, 6H), 1.76-1.72 (m, 4H), 1-65-1.47 (m, 6H), 1.33-1.16 (m, 11H).

Step I 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-3,4-dihydro-2λ⁶-benzo[c][1,2]thiazin-2-one (Compound 229)

Example A24

6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-2λ⁶-benzo[c][1,2]thiazin-2-one (Compound 230) and 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-2λ⁶-benzo[c][1,2]thiazin-2-one (Compound 231)

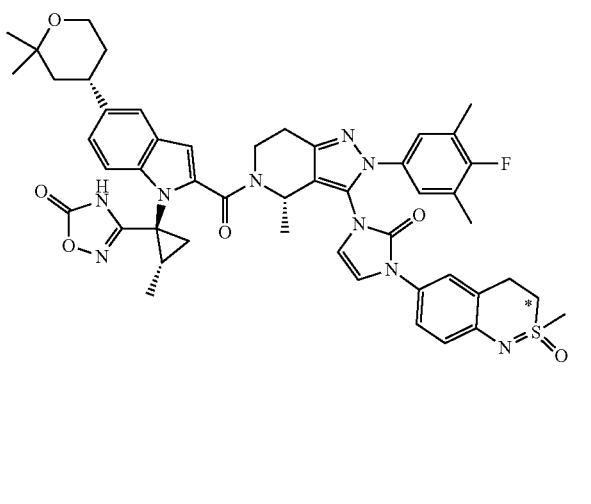

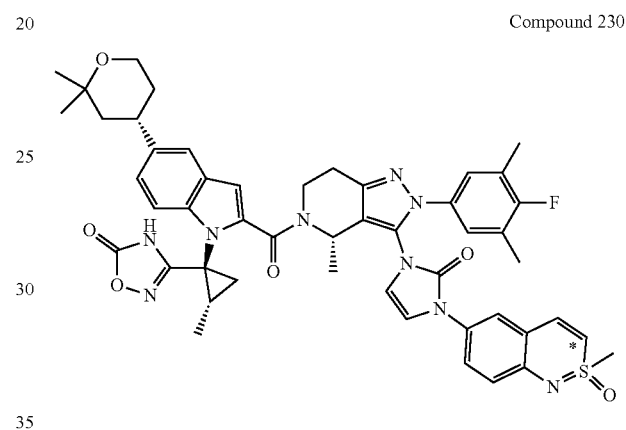

Compound 230

6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-3,4-dihydro-2λ⁶-benzo[c][1,2]thiazin-2-one (Compound 229) (enantiomer 2) was synthesized according to the procedures described for the preparation of Compound 228 (enantiomer 1) (step F to step H). LC-MS: m/z 914.5 (M+H)⁺. $^1$H NMR (400 MHz, DMSO-d6) δ 7.50 (s, 1H), 7.42 (d, J=8.4 Hz, 1H), 7.25-7.23 (m, 3H), 7.14 (d, J=6.4 Hz, 2H), 6.99 (m, 1H), 6.67 (m, 3 H), 5.55 (m, 1H), 4.44 (m, 1H), 3.75-3.73 (m, 2H), 3.39 (m, 1H), 3.38 (m, 2H), 3.25 (m, 4H), 3.01 (m, 1H), 2.90-2.80 (m, 2H), 2.22 (d, J=1.2 Hz, 6H), 1.77-1.70 (m, 4H), 1-64-1.41 (m, 6H), 1.29 (m, 4H), 1.20 (m, 7H).

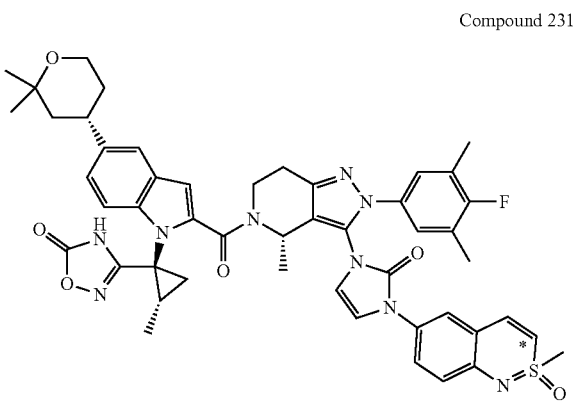

Compound 231

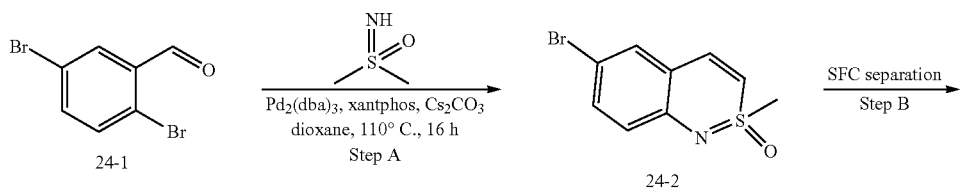

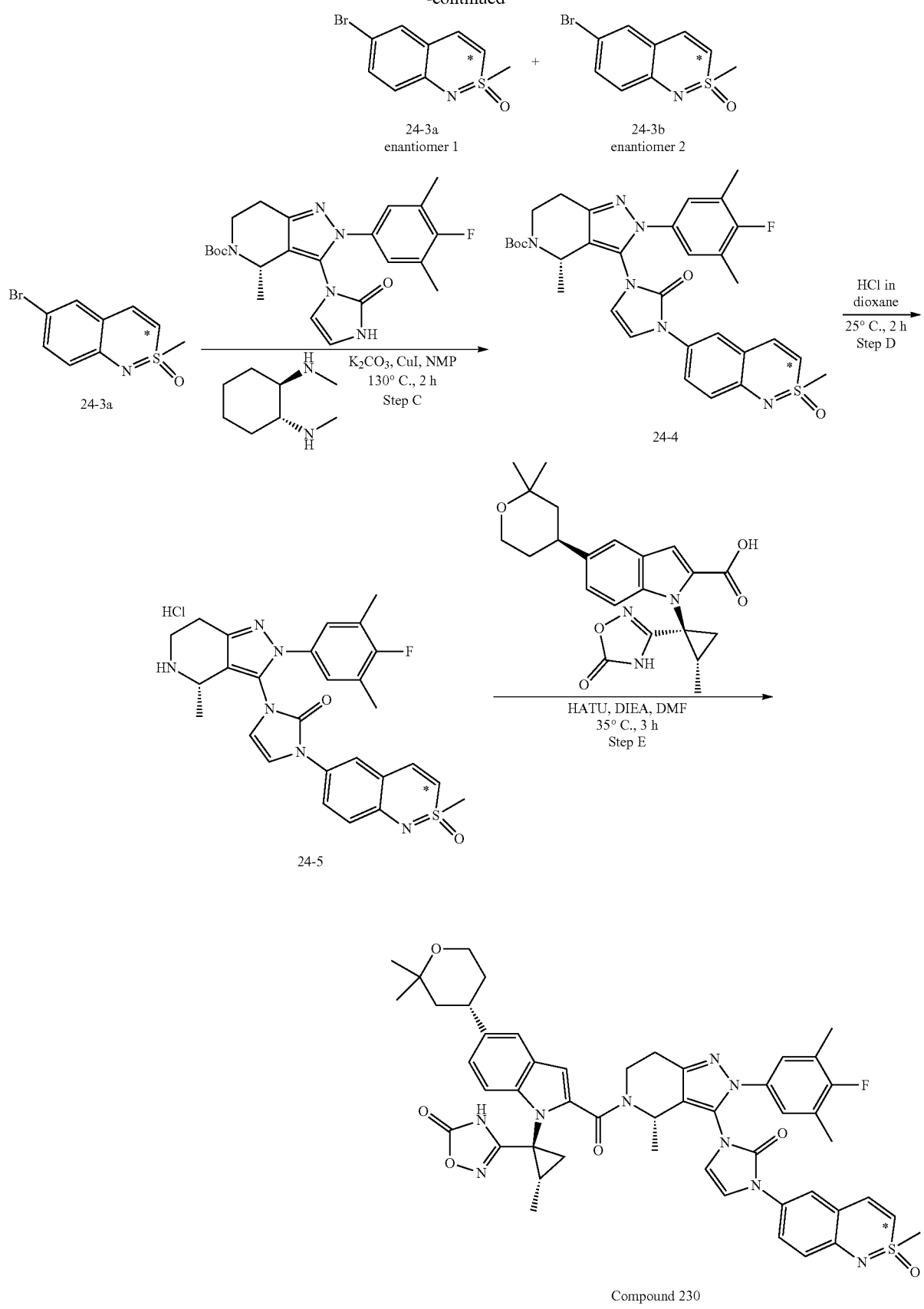
Compound 230

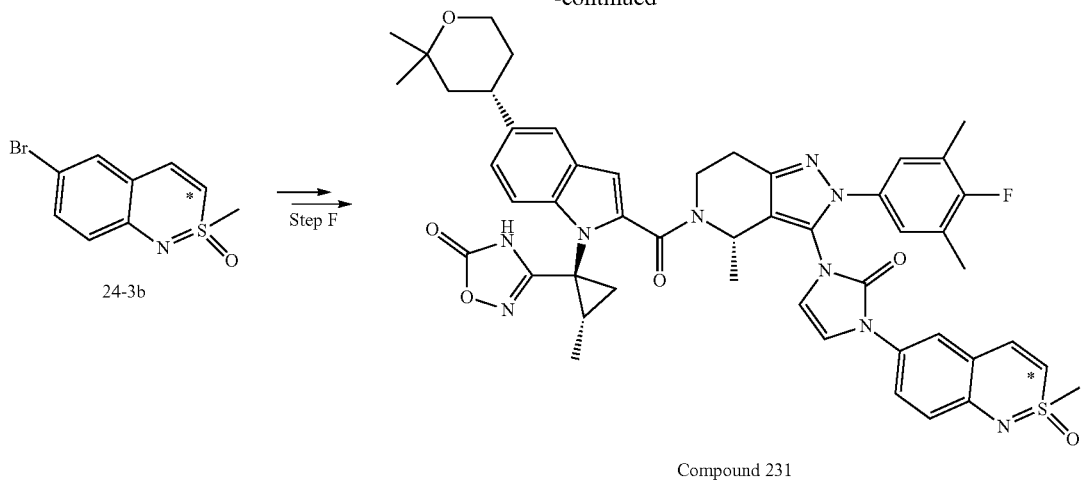

Compound 231

Step A 6-bromo-2-methyl-$\lambda^6$-benzo[c][1,2]thiazin-2-one

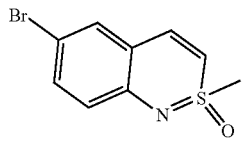

Pd$_2$(dba)$_3$ (173 mg, 0.189 mmol) and Cs$_2$CO$_3$ (1.851 g, 5.684 mmol) were added to 2,5-dibromobenzene-1-carbaldehyde (1.0 g, 3.789 mmol) and dimethylsulfoximine (352 mg, 3.789 mmol) in 1,4-dioxane (20 mL) at rt, and the reaction mixture was heated at reflux for 3 h. The mixture was allowed to cool to rt, filtered, and the filtrate was evaporated. The residue was purified by silica gel chromatography eluting with 15%-50% EtOAc/PE to afford 6-bromo-2-methyl-2$\lambda^6$-benzo[c][1,2]thiazin-2-one (435 mg, 44.5%). LC-MS: m/z 260.0 (M+H)$^+$.

Step B 6-bromo-2-methyl-2$\lambda^6$-benzo[c][1,2]thiazin-2-one 24-3a (enantiomer 1) and 6-bromo-2-methyl-2$\lambda^6$-benzo[c][1,2]thiazin-2-one 24-3b (enantiomer 2)

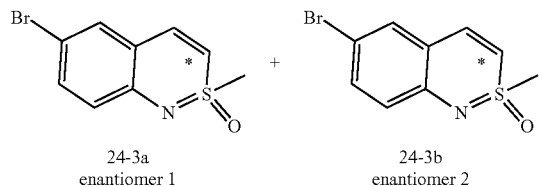

The 6-bromo-2-methyl-2$\lambda^6$-benzo[c][1,2]thiazin-2-one (435 mg) was purified by SFC (system: Waters SFC 150; Column name: DAICELCHIRALCEL® AD; Column size: 250*25 mm, 10 μm; Mobile Phase A: Supercritical CO$_2$; Mobile Phase B: MeOH (+0.1% 7.0 M ammonia in MeOH); Gradient: A/B =70/30; Flow rate: 100 mL/min, Column temp: RT) to give 6-bromo-2-methyl-2$\lambda^6$-benzo[c][1,2]thi- azin-2-one 24-3a (enantiomer 1) (210 mg, 48.3% yield), LC-MS: m/z 260.0 (M+H)$^+$. And 6-bromo-2-methyl-2$\lambda^6$-benzo[c][1,2]thiazin-2-one 24-3b (enantiomer 2) (200 mg, 45.9 yield), LC-MS: m/z 260.0 (M+H)$^+$.

Step C tert-butyl(4S)-2-(4-fluoro-3,5-dimethylphenyl)-4-methyl-3-[1-(2-methyl-2-oxo-2$\lambda^6$-benzo[c][1,2]thiazin-6-yl)-2-oxoimidazol-3-yl]-4,5,6,7-tetrahydropyrazolo[4,3-c]pyridine-5-carboxylate To a solution of tert-butyl(4S)-2-(4-fluoro-3,5-dimethylphenyl)-4-methyl-3-(2-oxo-1H-imidazol-3-yl)-4,5,6,7-tetrahydropyrazolo[4,3-c]pyridine-5-carboxylate (72 mg, 0.163 mmol) in NMP (5 mL) were added 6-bromo-2-methyl-2$\lambda^6$-benzo[c][1,2]thiazin-2-one 24-3a (enantiomer 1) (50.5 mg, 0.196 mmol), methyl[(1R,2R)-2-(methylamino)cyclohexyl]amine (34.8 mg, 0.245 mmol), CuI (37.27 mg, 0.196 mmol) and K$_2$CO$_3$ (45.1 mg, 0.326 mmol). The reaction mixture was stirred at 100° C. for 2 h under Ar. After the reaction was completed, the mixture was poured into to water (30 mL), extracted with EtOAc (30 mL×2). The combined organic layers were washed with brine, dried over sodium sulfate, filtered and concentrated. The residue was purified by silica gel chromatography eluting 0-3% MeOH/DCM to afford tert-butyl(4S)-2-(4-fluoro-3,5-dimethylphenyl)-4-methyl-3-[1-(2-methyl-2-oxo-2$\lambda^6$-benzo[c][1,2]thiazin-6-yl)-2-oxoimidazol-3-yl]-4,5,6,7-tetrahydropyrazolo[4,3-c]pyridine-5-carboxylate (170 mg, crude). LC-MS: m/z 619.4 (M+H)$^+$.

Step D 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-2-methyl-2λ⁶-benzo[c][1,2]thiazin-2-one HCl salt

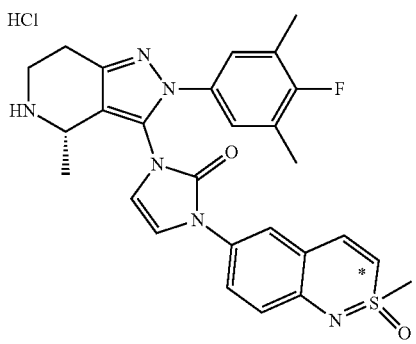 [SMILES: Cl ; Cc1cc(-n2nc3c(c2-n2ccn(-c4ccc5c(c4)C=CS(C)(=O)=N5)c2=O)[C@H](C)NCC3)cc(C)c1F]

To a solution of tert-butyl(4S)-2-(4-fluoro-3,5-dimethylphenyl)-4-methyl-3-[1-(2-methyl-2-oxo-2λ⁶-benzo[c][1,2]thiazin-6-yl)-2-oxoimidazol-3-yl]-4,5,6,7-tetrahydropyrazolo[4,3-c]pyridine-5-carboxylate (170 mg, 0.275 mmol) in dioxane (4 mL) were added 4M HCl (gas) in dioxane (2 mL). The mixture was stirred at rt for 1 h under Ar. The reaction mixture was concentrated to get 6-{3-[(4S)-2-(4-fluoro-3,5-dimethylphenyl)-4-methyl-4,5,6,7-tetrahydropyrazolo[4,3-c]pyridin-3-yl]-2-oxoimidazol-1-yl}-2-methyl-2λ⁶-benzo[c][1,2]thiazin-2-one HCl salt (112 mg, 78.3% yield). LC-MS: m/z 519.3 (M+H)⁺.

Step E 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-2R⁶-benzo[c][1,2]thiazin-2-one (Compound 230)

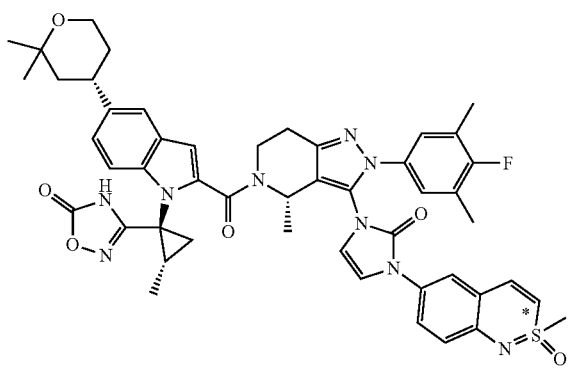

To a solution of 6-{3-[(4S)-2-(4-fluoro-3,5-dimethylphenyl)-4-methyl-4,5,6,7-tetrahydropyrazolo [4,3-c]pyridin-3-yl]-2-oxoimidazol-1-yl}-2-methyl-2λ⁶-benzo[c][1,2]thiazin-2-one HCl salt (112 mg, 0.216 mmol) in DMF (5 mL) was added 5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indole-2-carboxylic acid (88.9 mg, 0.216 mmol), HATU (90.3 mg, 0.238 mmol) and DIEA (139.6 mg, 1.080 mmol). The reaction was stirred at 30° C. for 18 h under N2. The reaction mixture was poured into water (30 mL), extracted with EtOAc (30 mL×3). The combined organic layers were washed with brine, dried over sodium sulfate, filtered and concentrated under vacuum. The resulting residue was purified by prep. TLC (SiO₂, DCM/MeOH=15/1) to afford a crude product (80 mg), and then further purified by prep. HPLC (Waters 3767/Qda Column: SunFire Sunfire C18, 19*250 mm, 10 μm; Mobile Phase A: 0.05% NH₃H2O/H₂O, B: CH₃CN; Flow rate: 20 mL/min; Gradient: 26%-36% B; Retention Time: 11-12 min of 18 min) to afford 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-2λ⁶-benzo[c][1,2]thiazin-2-one (Compound 230) (12.9 mg, 10.1% yield). LC-MS: m/z 912.6 (M+H)⁺.
¹H NMR (400 MHz, DMSO-d6) δ 7.80-7.51 (m, 4H), 7.42 (d, J=8.4 Hz, 1H), 7.25 (d, J=8.4 Hz, 1H), 7.15-7.07 (m, 5 H), 6.83-6.80 (m, 2H), 5.55 (m, 1H), 4.45 (m, 1H), 3.74-3.72 (m, 2H), 3.57 (m, 1H), 3.49 (s, 3H), 3.01-2.84 (m, 2H), 2.22 (d, J=2.0 Hz, 6H), 1.72-1.69 (m, 4H), 1-63-1.54 (m, 3H), 1.51-1.44 (m, 3 H), 1.29 (m, 4H), 1.20-1.13 (m, 6H).

Step F 6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-2λ⁶-benzo[c][1,2]thiazin-2-one (Compound 231)

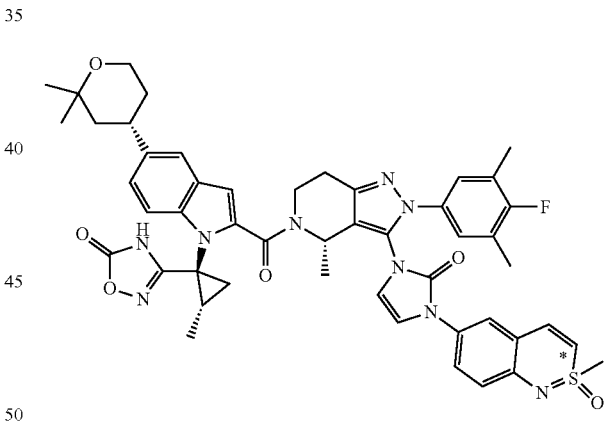

6-{3-[(4S)-2-(4-fluoro-3,5-dimethylphenyl)-5-({5-[(4S)-2,2-dimethyl-3,4,5,6-tetrahydro-2H-pyran-4-yl]-1-[(1S,2S)-2-methyl-1-(5-oxo-4H-1,2,4-oxadiazol-3-yl)cyclopropyl]indol-2-yl}carbonyl)-4-methyl-4,5,6,7-tetrahydropyrazolo[4,3-c]pyridin-3-yl]-2-oxoimidazol-1-yl}-2-methyl-2λ⁶-benzo[c][1,2]thiazin-2-one (Compound 231) (enantiomer 2) was synthesized according to the procedures described for the preparation of Compound 230 (enantiomer 1) (step C to step E). LC-MS: m/z 912.6 (M+H)⁺. ¹H NMR (400 MHz, DMSO-d6) δ 7.80-7.51 (m, 4H), 7.42 (d, J=8.4 Hz, 1H), 7.25 (d, J=8.4 Hz, 1H), 7.15-7.07 (m, 5H), 6.83-6.80 (m, 2H), 5.55 (m, 1H), 4.45 (m, 1H), 3.74-3.72 (m, 2H), 3.57 (m, 1H), 3.49 (s, 3H), 3.01-2.84 (m, 2H), 2.22 (d, J=2.0 Hz, 6H), 1.72-1-69 (m, 4H), 1-63-1.54 (m, 3H), 1.51-1.44 (m, 3H), 1.29 (m, 4H), 1.20-1.13 (m, 6H).

Example A25
3-((1S,2S)-1-(5-(((S)-2,2-dimethyltetrahydro-2H-pyran-4-yl)-2-((4S)-2-(4-fluoro-3,5-dimethylphenyl)-3-(2-fluoro-4-(N-methylethylsulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (Compound 164)
Compound 164
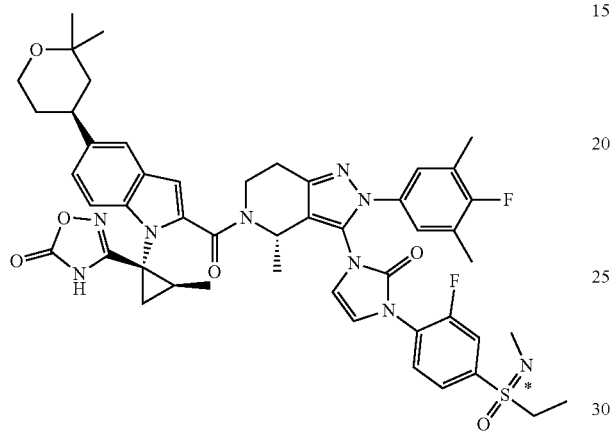
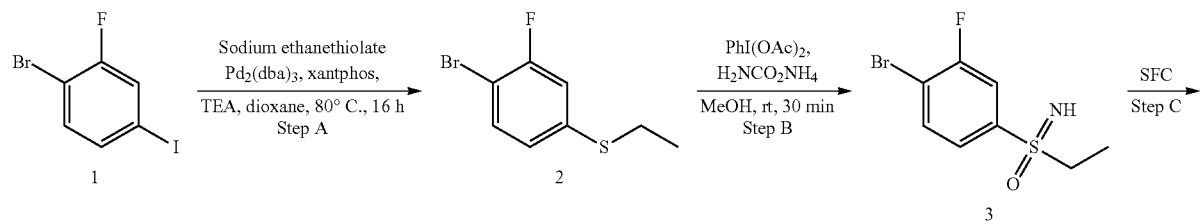
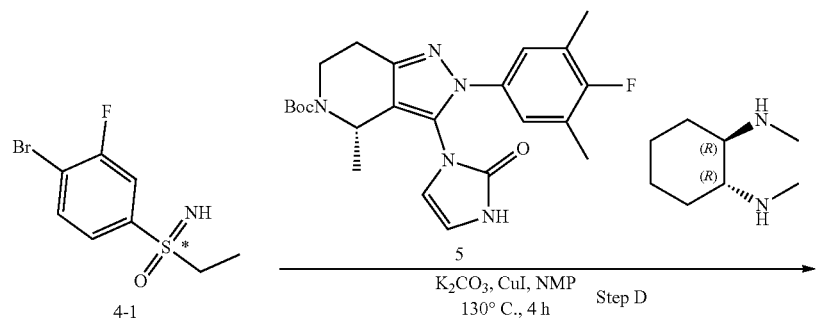
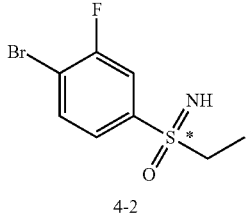

-continued
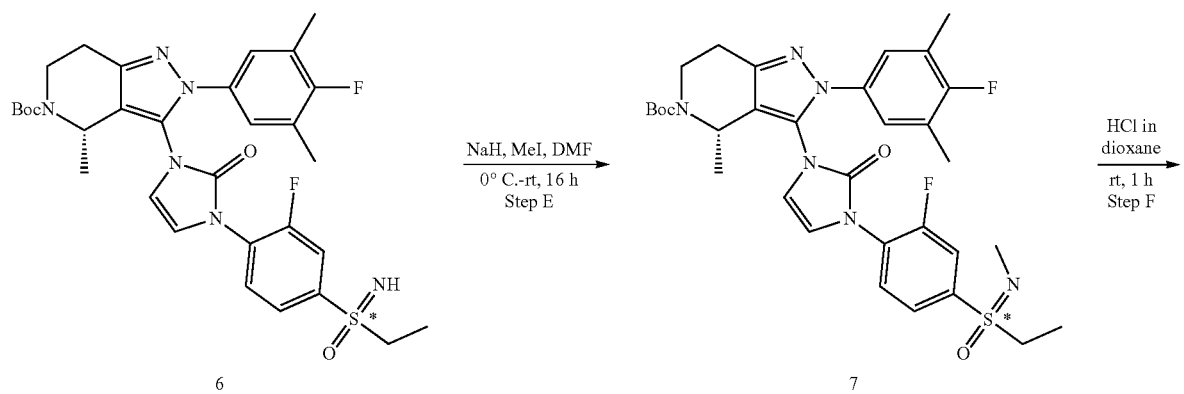
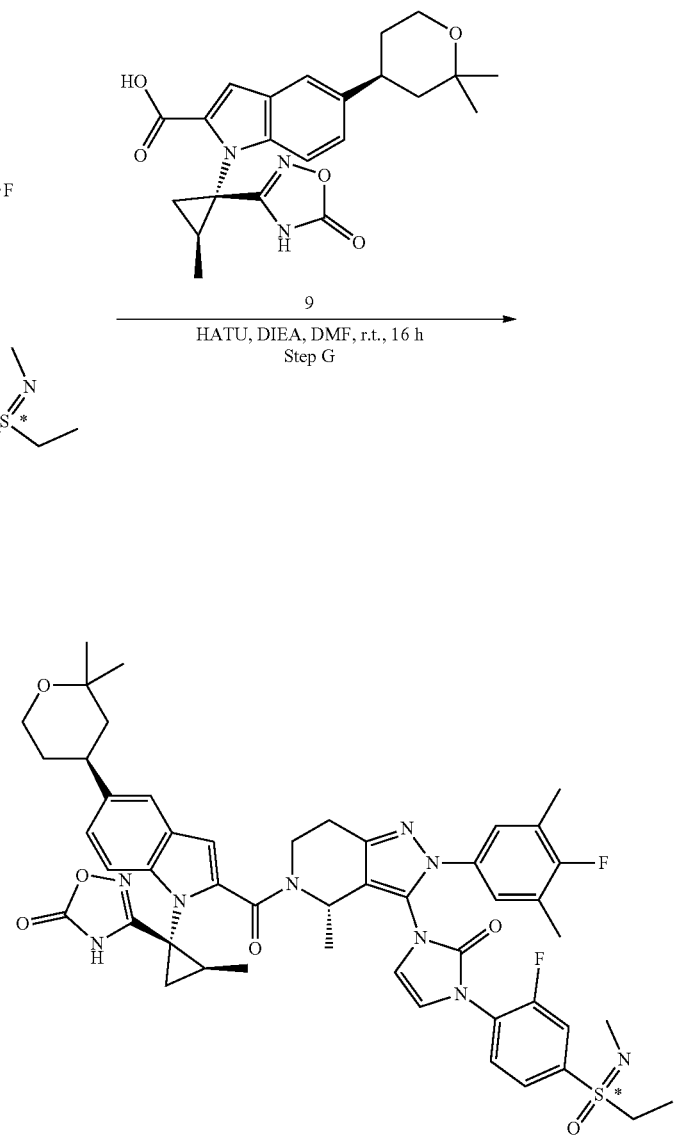
Compound 164

Step A (4-bromo-3-fluorophenyl)(ethyl)sulfane

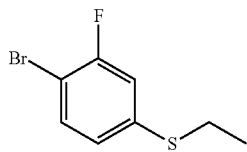

A mixture of 1-bromo-2-fluoro-4-iodobenzene (10 g, 33.234 mmol), (ethylsulfanyl)sodium (3.35 g, 39.880 mmol), $Pd_2(dba)_3$ (1.52 g, 1-662 mmol) and xantphos (1.92 g, 3.323 mmol) in dry dioxane (200 mL) was stirred at 80° C. for 16 hrs. The reaction mixture was poured into water (500 mL), extracted with EA (3×200 mL). The organic layers were dried over $Na_2SO_4$, and concentrated in vacuum. The residue was purified by silica gel column chromatography eluting with PE (100%) to afford (4-bromo-3-fluorophenyl)(ethyl)sulfane (6.3 g, 80.63%) as a colorless oil. $^1H$ NMR (400 MHz, $CDCl_3$) δ 7.44-7.40 (m, 1H), 7.05 (dd, J=9.2, 2.0 Hz, 1H), 6.95 (dd, J=8.4, 2.0 Hz, 1H), 2.94 (q, J=7.2 Hz, 2H), 1.33 (t, J=7.2 Hz, 3H).

Step B (4-bromo-3-fluorophenyl)(ethyl)(imino)-$λ^6$-sulfanone

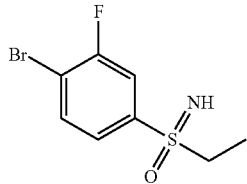

To a solution of (4-bromo-3-fluorophenyl)(ethyl)sulfane (4.00 g, 17.013 mmol) in MeOH (100 mL) were added (diacetoxyiodo)benzene (16.54 g, 51.039 mmol), ammonium aminomethanoate (5.31 g, 68.052 mmol), and the reaction mixture was stirred at room temperature for 30 min. The reaction mixture was poured into water (500 mL), extracted with EA (3×200 mL). The organic layers were washed with saturated NaCl solution, dried over $Na_2SO_4$, and concentrated in vacuum. The residue was purified by using silica gel column chromatography eluting with EA in PE (1/1) to afford both isomers.

Step C (4-bromo-3-fluorophenyl)(ethyl)(imino)-$λ^6$-sulfanone (enantiomer 1) and (4-bromo-3-fluorophenyl)(ethyl)(imino)-$λ^6$-sulfanone (enantiomer 2)

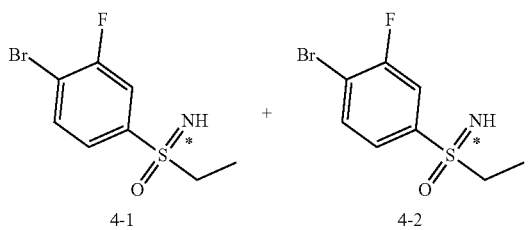

(4-bromo-3-fluorophenyl)(ethyl)(imino)-$λ^6$-sulfanone obtained above was separated by SFC (Column: DAICELCHIRALPAK® AS; Column size: 250 mm*40 mm, 10 μm; Mobile Phase A: Supercritical $CO_2$; Mobile Phase B: MeOH (0.1% 7.0 M Ammonia in MeOH); Gradient: B=10%). Flow rate: 140 mL/min, Column temp.: 25° C.) to afford (4-bromo-3-fluorophenyl)(ethyl)(imino)-$λ^6$-sulfanone (enantiomer 1) (1500 mg, 33.13%) as a colorless oil as the fast eluent, R.T=1.16 min. LC-MS: m/z 266.0 $(M+H)^+$. And (4-bromo-3-fluorophenyl)(ethyl)(imino)-$λ^6$-sulfanone (enantiomer 2) (1500 mg, 33.13%) as the slow eluent, R.T=1.47 min. LC-MS: m/z 266.0 $(M+H)^+$.

Step D tert-butyl(4S)-3-(3-(4-(ethylsulfonimidoyl)-2-fluorophenyl)-2-oxo-2,3-dihydro-1H-imidazol-1-yl)-2-(4-fluoro-3,5-dimethylphenyl)-4-methyl-2,4,6,7-tetrahydro-5H-pyrazolo [4,3-c]pyridine-5-carboxylate (enantiomer 1)

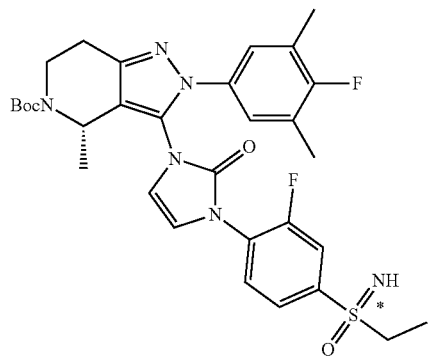 [SMILES: CCS(=N)(=O)c1ccc(-n2ccn(-c3c4c(nn3-c3cc(C)c(F)c(C)c3)CCN(C(=O)OC(C)(C)C)[C@H]4C)c2=O)c(F)c1]

To a solution of tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (2 g, 4.530 mmol) in NMP (24 mL) were added copper "iodide (1.04 g, 5.436 mmol), potassium carbonate (1.25 g, 9.060 mmol), (4-bromo-3-fluorophenyl)(ethyl)(imino)-$λ^6$-sulfanone (enantiomer 1) (1.57 g, 5.889 mmol) and (1R, 2R)-N',$N^2$-dimethylcyclohexane-1,2-diamine (0.64 g, 4.530 mmol), and the reaction mixture was stirred at 130° C. for 4 hrs under $N_2$. The mixture was poured into water (50 mL), extracted with EA ((3×30 mL), washed with brine ((3×20 mL). The organic layer was dried and concentrated in vacuum. The residue was purified by silica gel column chromatography eluting with (eluting PE/EA=1/1) to afford tert-butyl(4S)-3-(3-(4-(ethylsulfonimidoyl)-2-fluorophenyl)-2-oxo-2,3-dihydro-1H-imidazol-1-yl)-2-(4-fluoro-3,5-dimethylphenyl)-4-methyl-2,4,6,7-tetrahydro-5H-pyrazolo [4,3-c]pyridine-5-carboxylate (enantiomer 1) (1.75 g, 61.64%). LC-MS: m/z 627.8 $(M+H)^+$.

Step E tert-butyl(4S)-2-(4-fluoro-3,5-dimethylphenyl)-3-(3-(2-fluoro-4-(N-methylethylsulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1)

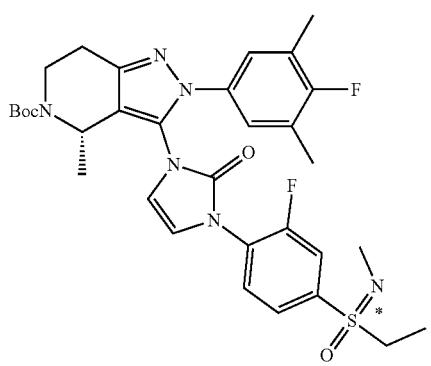 [SMILES: CCS(=O)(=NC)c1ccc(-n2ccn(-c3c4c(nn3-c3cc(C)c(F)c(C)c3)CCN(C(=O)OC(C)(C)C)[C@H]4C)c2=O)c(F)c1]

To a solution of tert-butyl(4S)-3-(3-(4-(ethylsulfonimidoyl)-2-fluorophenyl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxylate (enantiomer 1) (500 mg, 0.798 mmol) in DMF (10 mL) was added sodium hydride (19.15 mg, 0.798 mmol) at 0° C. under N₂. The reaction mixture was stirred at 0° C. for 1 hr and iodomethane (0.078 mL, 0.957 mmol) was added. The reaction mixture was stirred at room temperature for another 16 hrs. The mixture was poured into water (50 mL), extracted with EA (20 mL×3). The combined organic layers were washed with brine (50 mL), dried over Na₂SO₄, filtered and concentrated under vacuum. The residue was purified by silica gel column chromatography eluting with (eluting PE/EA=1/1) to give tert-butyl(4S)-2-(4-fluoro-3,5-dimethylphenyl)-3-(3-(2-fluoro-4-(N-methylethylsulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1) (200 mg, 97.81%). LC-MS: m/z 641.4 (M+H)⁺.

Step F 1-((S)-2-(4-fluoro-3,5-dimethylphenyl)-4-methyl-4,5,6,7-tetrahydro-2H-pyrazolo[4,3-c]pyridin-3-yl)-3-(2-fluoro-4-(N-methylethylsulfonimidoyl)phenyl)-1,3-dihydro-2H-imidazol-2-one, hydrochloride salt (enantiomer 1)

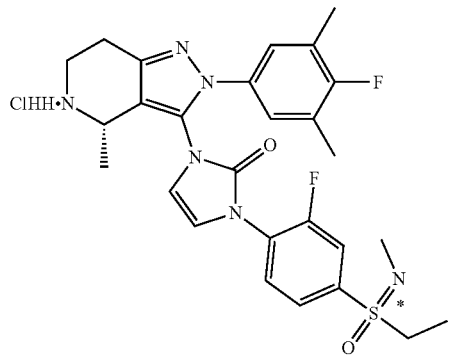

A solution of tert-butyl(4S)-2-(4-fluoro-3,5-dimethylphenyl)-3-(3-(2-fluoro-4-(N-methylethylsulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1) (215 mg, 0.312 mmol) in HCl/dioxane (3 mL) was stirred at room temperature for 1 hr. The reaction mixture was concentrated in vacuum to afford 1-((S)-2-(4-fluoro-3,5-dimethylphenyl)-4-methyl-4,5,6,7-tetrahydro-2H-pyrazolo[4,3-c]pyridin-3-yl)-3-(2-fluoro-4-(N-methylethylsulfonimidoyl)phenyl)-1,3-dihydro-2H-imidazol-2-one, hydrochloride salt (enantiomer 1) (168 mg, 99.77%) which was used in the next step without further purification. LC-MS: m/z 541.2 (M+H-HCl)+.

Step G 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-4-(N-methylethylsulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (Compound 164)

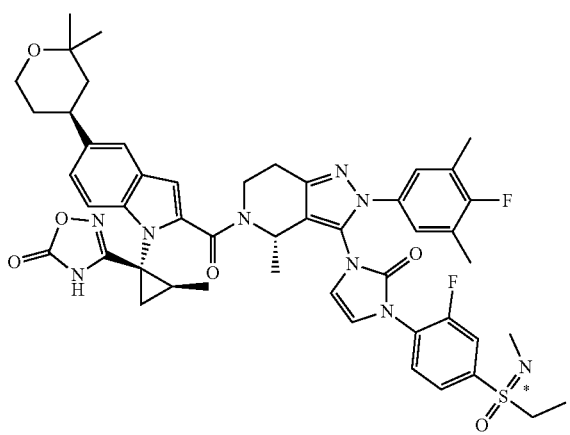 [SMILES: CCS(=O)(=NC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1]

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (114.16 mg, 0.277 mmol) in DMF (3 mL) were added HATU (158.25 mg, 0.416 mmol), DIPEA (143.44 mg, 1.110 mmol), and 1-((S)-2-(4-fluoro-3,5-dimethylphenyl)-4-methyl-4,5,6,7-tetrahydro-2H-pyrazolo[4,3-c]pyridin-3-yl)-3-(2-fluoro-4-(N-methylethylsulfonimidoyl)phenyl)-1,3-dihydro-2H-imidazol-2-one, hydrochloride salt (enantiomer 1) (150 mg, 0.277 mmol), and the reaction mixture was stirred at room temperature for 16 hrs. The mixture was poured into water (50 mL), extracted with EA (20 mL×3). The combined organic layers were washed with brine (50 mL), dried over Na$_2$SO$_4$, filtered and concentrated under vacuum. The residue was purified by silica gel column chromatography eluting with 3% MeOH in DCM and then prep-HPLC (NH$_4$HCO$_3$) to afford 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-4-(N-methylethylsulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (63.60 mg, 24.24%).

LC-MS: m/z 934.2 (M+H)$^+$. $^1$H NMR (400 MHz, DMSO-d$_6$) δ 11.50 (s, 1H), 7.75-7.73 (m, 3H), 7.53 (s, 1H), 7.42 (d, J=8.4 Hz, 1H), 7.30-7.21 (m, 1H), 7.16 (d, J=6.4 Hz, 2H), 7.04 (s, 1H), 6.90-6.88 (m, 2H), 5.60 (s, 1H), 4.47 (s, 1H), 3.75-3.72 (m, 2H), 3.60 (s, 1H), 3.31-3.25 (m, 2H), 2.90-2.86 (m, 1H), 2.57 (s, 3H), 2.25 (d, J=$_{1-6}$ Hz, 6H), 1.76-1.71 (m, 4H), 1-66-1-63 (m, 2H), 1-62-1.58 (m, 2H), 1.45 (s, 3H), 1.30-1.29 (m, 4H), 1.20-1.13 (m, 9H). $^{19}$F NMR (376 MHz, DMSO-d$_6$) δ-118.55, -122.06.

Example A26

3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-(methylamino)-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (Compound 238)

Compound 238

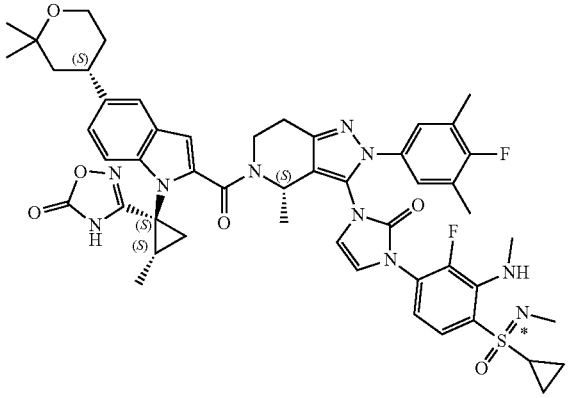

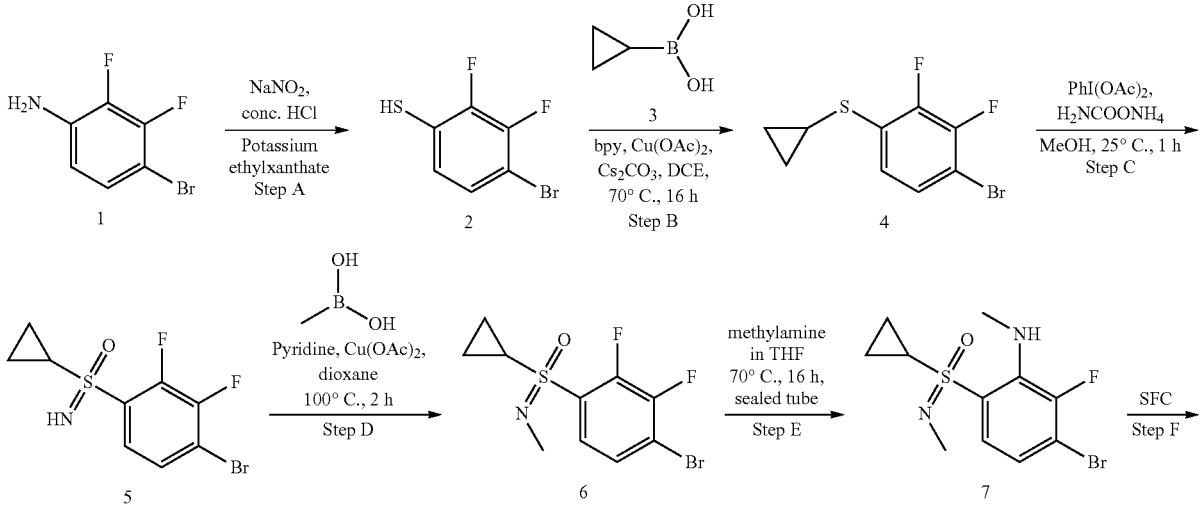

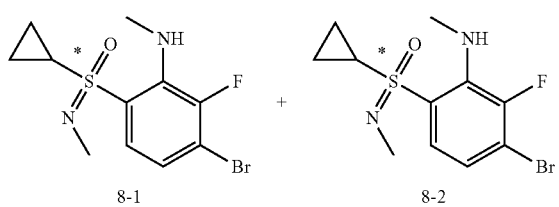

-continued
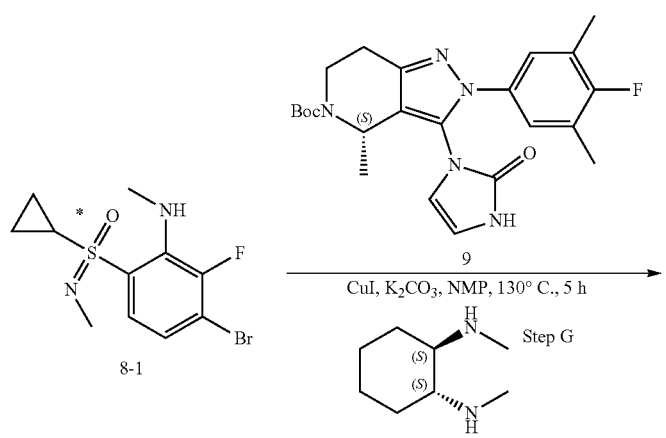
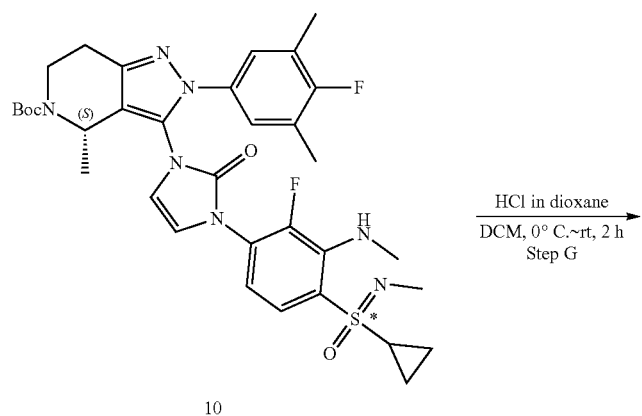
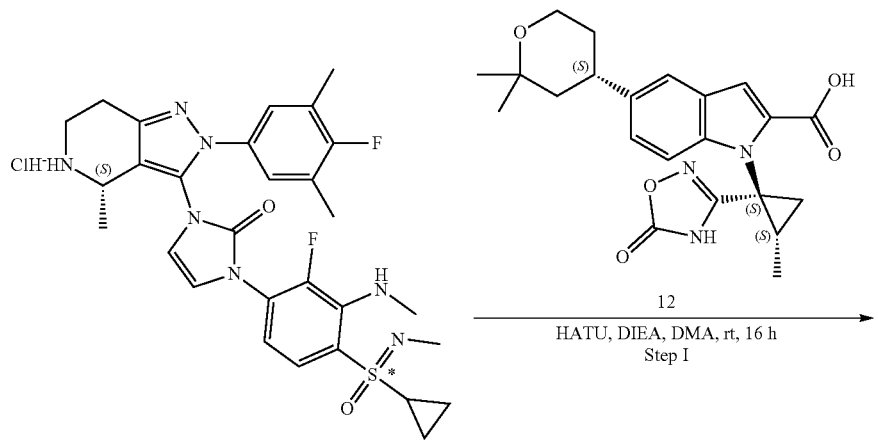

-continued

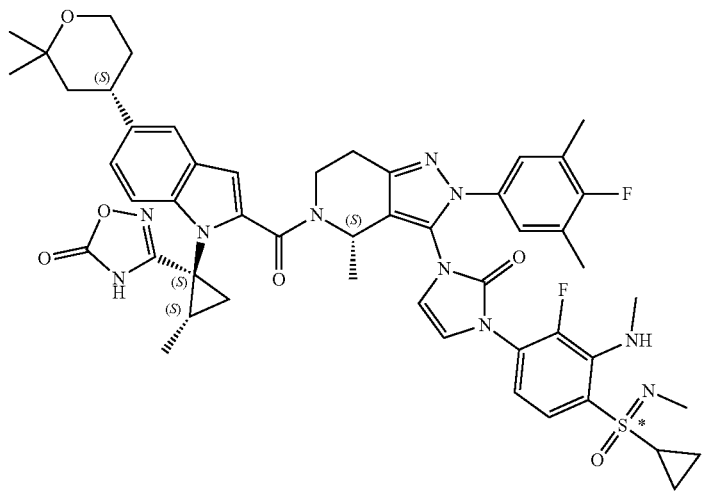

Step A 4-bromo-2,3-difluorobenzenethiol

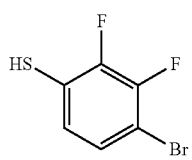

To a solution of 4-bromo-2,3-difluoroaniline (1000 mg, 4.807 mmol) in con. HCl (25 mL) was added sodium nitrite (398. mg, 5.769 mmol) at 0° C. The mixture was stirred at room temperature for 5 min. To the mixture was added potassium ethylxanthate (1926.47 mg, 12.019 mmol) at 0° C. The mixture was stirred for 20 min at 0° C. The mixture was diluted with water (30 mL), extracted with EA (3×30 mL). The combined EA layers were washed with brine (3×10 mL), dried over Na$_2$SO$_4$, filtered and concentrated. The residue was purified by flash column chromatography, eluting with PE/EA (100:1) to afford the intermediate. The intermediate was dissolved with EtOH (10 mL). To the solution was added KOH (1348.73 mg, 24.037 mmol). The mixture was stirred for another 10 min at 75° C. The mixture was concentrated. The residue was diluted with water (20 mL), extracted with DCM (3×10 mL). The aqueous layer was adjusted to pH 1-2 with HCl (aq.), extracted with EA (3×20 mL). The combined organic layers were washed with brine (3×10 mL), dried over Na$_2$SO$_4$, filtered and concentrated. The residue was purified by flash column chromatography, eluting with DCM/MeOH (20/1) to afford 4-bromo-2,3-difluorobenzenethiol (500 mg, 46.21%). $^1$H NMR (400 MHz, CDCl$_3$) δ 7.22-7.18 (m, 1H), 6.97-6.93 (m, 1H), 3.68 (s, 1H).

Step B
(4-bromo-2,3-difluorophenyl)(cyclopropyl)sulfane

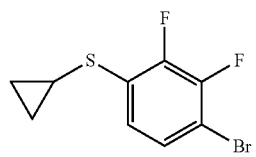 [SMILES: Fc1c(Br)ccc(SC2CC2)c1F]

To a solution of 4-bromo-2,3-difluorobenzenethiol (500 mg, 2.222 mmol) and cyclopropylboranediol (286.27 mg, 3.333 mmol) in DCE (10 mL) were added 2-(pyridin-2-yl)pyridine (347.01 mg, 2.222 mmol), cupric bis(acetate) (403.53 mg, 2.222 mmol) and Cs$_2$CO$_3$ (723.88 mg, 2.222 mmol). The reaction mixture was sealed up and stirred at 70° C. for 16 hrs under O2. The reaction mixture was filtered and the filtrate was concentrated. The residue was purified by flash column chromatography, eluting with PE/EA (100/1) to afford (4-bromo-2,3-difluorophenyl)(cyclopropyl)sulfane (150 mg, 25.47%). $^1$H NMR (400 MHz, CDCl$_3$) δ 7.31-7.24 (m, 1H), 7.17-7.13 (m, 1H), 2.20-2.15 (m, 1H), 1.11-1.06 (m, 2H), 0.73-0.69 (m, 2H).

Step C (4-bromo-2,3-difluorophenyl)(cyclopropyl)(imino)-λ$^6$-sulfanone

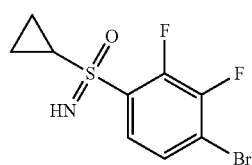 [SMILES: N=S(=O)(c1ccc(Br)c(F)c1F)C1CC1]

To a solution of (4-bromo-2,3-difluorophenyl)(cyclopropyl)sulfane (400 mg, 1.509 mmol) in methanol (500 mL) were added ammonium aminomethanoate (235.58 mg, 3.018 mmol) and 1-[(acetoxyphenyl-,3-iodanyl)oxy]ethan-1-one (1222.50 mg, 3.772 mmol). The reaction mixture was stirred for 1 hr at room temperature. The mixture was concentrated and the residue was purified by flash column chromatography, eluting with PE/EA (2/1) to afford (4-bromo-2,3-difluorophenyl)(cyclopropyl)(imino)-$\lambda^6$-sulfanone (300 mg, 67.15%). LC-MS: m/z 296.0 (M+H)$^+$.

Step D (4-bromo-2,3-difluorophenyl)(cyclopropyl)(methylimino)-$\lambda^6$-sulfanone

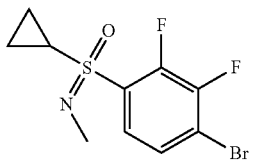 [SMILES: CN=S(=O)(c1ccc(Br)c(F)c1F)C1CC1]

To a solution of (4-bromo-2,3-difluorophenyl)(cyclopropyl)(imino)-$\lambda^6$-sulfanone (280 mg, 0.946 mmol) in dry dioxane (3 mL) were added cupric bis(acetate) (515.21 mg, 2.837 mmol), pyridine (0.306 mL, 3.782 mmol) and methylboronic acid (808.56 mg, 13.508 mmol). The reaction mixture was sealed up and stirred at 100° C. for 2 hrs under O$_2$. The mixture was filtered and the filtrate was concentrated in vacuum. The resulting residue was purified by silica gel chromatography (eluting PE/EA=1/1) to afford (4-bromo-2,3-difluorophenyl)(cyclopropyl)(methylimino)-$\lambda^6$-sulfanone (200 mg, 68.20%). LC-MS: m/z 309.9 (M+H)$^+$.

Step E (4-bromo-3-fluoro-2-(methylamino)phenyl)(cyclopropyl)(methylimino)-$\lambda^6$-sulfanone

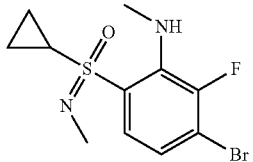

To a solution of (4-bromo-2,3-difluorophenyl)(cyclopropyl)(methylimino)-$\lambda^6$-sulfanone (200 mg, 0.645 mmol) in THF (3 mL) was added methylamine in THF (2 mol/L, 5 mL). The reaction mixture was sealed up and stirred at 70° C. for 16 hrs under N$_2$. To the mixture was added water (30 mL), extracted with EA (30 mL×3). The combined organic layers were washed with brine (30 mL×3), dried over Na$_2$SO$_4$, filtered and concentrated under vacuum. The resulting residue was purified by silica gel chromatography, eluting with PE/EA (3/1) to afford (4-bromo-3-fluoro-2-(methylamino)phenyl)(cyclopropyl)(methylimino)-$\lambda^6$-sulfanone (200 mg, 96.56%). LC-MS: m/z 320.7 (M+H)$^+$.

Step F (4-bromo-3-fluoro-2-(methylamino)phenyl)(cyclopropyl)(methylimino)-$\lambda^6$-sulfanone (enantiomer 1) and (4-bromo-3-fluoro-2-(methylamino)phenyl)(cyclopropyl)(methylimino)-$\lambda^6$-sulfanone (enantiomer 2)

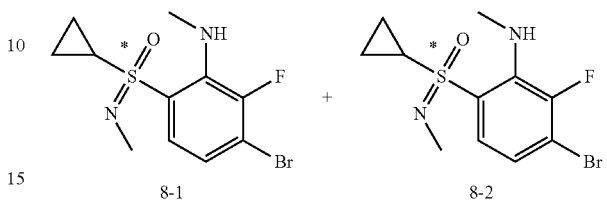

(4-bromo-3-fluoro-2-(methylamino)phenyl)(cyclopropyl)(methylimino)-$\lambda^6$-sulfanone (200 mg) was separated by SFC (Column: DAICELCHIRALPAKRAY; Column size: 250 mm*40 mm, 10 μm; Mobile Phase A: Supercritical CO$_2$; Mobile Phase B: EtOH (0.1% 7.0 M Ammonia in MeOH); Gradient: B=15%). Flow rate: 140 mL/min, Column temp.: 25° C.) to afford (4-bromo-3-fluoro-2-(methylamino)phenyl)(cyclopropyl)(methylimino)-$\lambda^6$-sulfanone (enantiomer 1) (100 mg, 99% ee, 50%) as a colorless oil as the fast eluent, R.T=2.19 min. LC-MS: m/z 320.7 (M+H)$^+$. And (4-bromo-3-fluoro-2-(methylamino)phenyl)(cyclopropyl)(methylimino)-$\lambda^6$-sulfanone (enantiomer 2) (90 mg, 45%) as the slow eluent, R.T=3.23 min. LC-MS: m/z 320.7 (M+H)$^+$.

Step G tert-butyl(4S)-2-(4-fluoro-3,5-dimethylphenyl)-3-(3-(2-fluoro-3-(methylamino)-4-(N-methylcyclopropanesulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1)

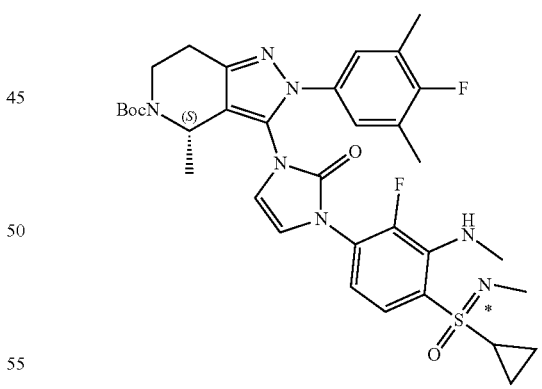

To a solution of tert-butyl(S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (106 mg, 0.240 mmol) in NMP (2.4 mL) were added copper$^{(1+)}$iodide (54.87 mg, 0.288 mmol), potassium carbonate (66.36 mg, 0.480 mmol), (4-bromo-3-fluoro-2-(methylamino)phenyl)(cyclopropyl)(methylimino)-$\lambda^6$-sulfanone (enantiomer 1) (100 mg, 0.310 mmol) and methyl [(1R,2R)-2-(methylamino)cyclohexyl]amine (34.15 mg, 0.240 mmol), and the reaction mixture was stirred at 130° C.

for 4 hrs under N₂. The mixture was poured into water (15 mL), extracted with EA (20 mL×3), washed with brine (20 mL×3). The organic layer was dried and concentrated in vacuum. The residue was purified by silica gel column chromatography, eluting with PE/EA (1/1) to afford tert-butyl(4S)-2-(4-fluoro-3,5-dimethylphenyl)-3-(3-(2-fluoro-3-(methylamino)-4-(N-methylcyclopropanesulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1) (155 mg, 85.2%). LC-MS: m/z 682.4 (M+H)⁺.

Step H 1-((S)-2-(4-fluoro-3,5-dimethylphenyl)-4-methyl-4,5,6,7-tetrahydro-2H-pyrazolo[4,3-c]pyridin-3-yl)-3-(2-fluoro-3-(methylamino)-4-(N-methylcyclopropanesulfonimidoyl)phenyl)-1,3-dihydro-2H-imidazol-2-one, hydrochloride salt (enantiomer 1)

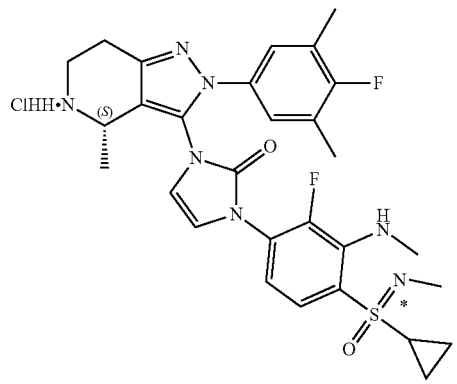

A solution of tert-butyl(4S)-2-(4-fluoro-3,5-dimethylphenyl)-3-(3-(2-fluoro-3-(methylamino)-4-(N-methylcyclopropanesulfonimidoyl)phenyl)-2-oxo-2,3-dihydro-1H-imidazol-1-yl)-4-methyl-2,4,6,7-tetrahydro-5H-pyrazolo[4,3-c]pyridine-5-carboxylate (enantiomer 1) (155 mg, 0.227 mmol) in HCl/dioxane (4 mol/L, 10 mL) was stirred at rt for 2 hrs. The residue was concentrated in vacuum to afford 1-((S)-2-(4-fluoro-3,5-dimethylphenyl)-4-methyl-4,5,6,7-tetrahydro-2H-pyrazolo[4,3-c]pyridin-3-yl)-3-(2-fluoro-3-(methylamino)-4-(N-methylcyclopropanesulfonimidoyl)phenyl)-1,3-dihydro-2H-imidazol-2-one, hydrochloride salt (enantiomer 1) (130 mg, 88.48%) which was used in the next step without further purification. LC-MS: m/z 582.4 (M+H-HCl)+.

Step I 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-(methylamino)-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (Compound 238)

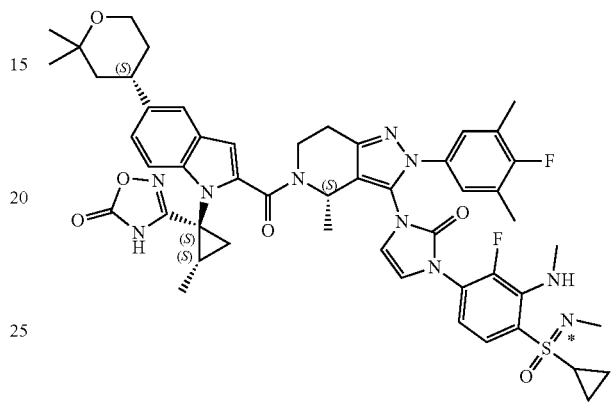

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (30 mg, 0.073 mmol) in DMA (2 mL) were added DIPEA (56.54 mg, 0.437 mmol), HATU (33.27 mg, 0.087 mmol) and the mixture was stirred at room temperature for 30 min. 1-((S)-2-(4-fluoro-3,5-dimethylphenyl)-4-methyl-4,5,6,7-tetrahydro-2H-pyrazolo[4,3-c]pyridin-3-yl)-3-(2-fluoro-3-(methylamino)-4-(N-methylcyclopropanesulfonimidoyl)phenyl)-1,3-dihydro-2H-imidazol-2-one, hydrochloride salt (enantiomer 1) (42.41 mg, 0.073 mmol) was added and the reaction mixture was further stirred at room temperature for 16 hrs. The reaction mixture was diluted with EA (50 mL) and washed with saturated NaCl solution (20 mL×3). The organic layer was concentrated in vacuum and the crude was purified by prep-HPLC (FA) to afford 3-((1S,2S)-1-(5-((S)-2,2-dimethyltetrahydro-2H-pyran-4-yl)-2-((4S)-2-(4-fluoro-3,5-dimethylphenyl)-3-(3-(2-fluoro-3-(methylamino)-4-(N-methylcyclopropanesulfonimidoyl)phenyl)-2-oxo-2,3-dihydro-1H-imidazol-1-yl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5(4H)-one (enantiomer 1) (40 mg, 56.26%).

LC-MS: m/z 488.4 (½M+H)⁺. ¹H NMR (400 MHz, DMSO-d₆) δ 11.58 (s, 1H), 7.52 (s, 1H), 7.48-7.37 (m, 2H), 7.25 (d, J=7.2 Hz, 1H), 7.29-7.21 (m, 2H), 7.03-6.66 (m, 5H), 5.54 (s, 1H), 4.44 (s, 1H), 3.79-3.68 (d, J=7.2 Hz, 2H), 3.56 (s, 1H), 3.18-3.05 (m, 5H), 2.93-2.77 (m, 2H), 2.64 (s, 3H), 2.30-2.20 (d, J=1-6 Hz, 6H), 1.90-1.38 (m, 10H), 1.33-1.05 (m, 11H), 0.98-0.81 (m, 2H). ¹⁹F NMR (376 MHz, DMSO-d₆) δ-122.13, -136.34.

The following molecules were synthesized using a similar procedure described in the Examples above using the appropriate starting material. SFC Separation conditions for certain intermediates is as follows.

For compounds 116 and 117, 132 and 133, the sulfoximine intermediate were separated as follows: SFC separation (Column: DAICELCHIRALCEL® AS (250 mm*25 mm, 10 m); mobile phase: A for CO₂, B for [0.1% 7.0 M Ammonia in MeOH]; B %: 15%). Flow rate: 90 mL/min, Column temp.: 25° C.

For compounds 134 and 135, the sulfoximine intermediate were separated as follows: SFC separation (Column: ChiralCel OX (250 mm*30 mm, 10 m); mobile phase: A for CO₂, B for [0.1% 7.0 M Ammonia in MeOH]; B %: 30%). Flow rate: 150 mL/min, Column temp.: 38° C.

For compounds 136 and 137, the sulfoximine intermediate were separated as follows: SFC separation (Column: ChiralPak IC (250 mm*30 mm, 10 m); mobile phase: A for CO₂, B for [0.1% 7.0 M Ammonia in MeOH]; B %: 30%). Flow rate: 150 mL/min, Column temp.: 38° C.

For compounds 138 and 139, the sulfoximine intermediate were separated as follows: SFC separation (Column: ChiralPak IC (250 mm*30 mm, 10 m); mobile phase: A for CO₂, B for [0.1% 7.0 M Ammonia in MeOH]; B %: 30%). Flow rate: 80 mL/min, Column temp.: 38° C.

For compounds 140 and 141, the sulfoximine intermediate were separated as follows: SFC separation (Column: DAICELCHIRALCEL® AS (250 mm*25 mm, 10 m); mobile phase: A for CO₂, B for [0.1% 7.0 M Ammonia in MeOH]; B %: 10%). Flow rate: 100 mL/min, Column temp.: 25° C.

For compounds 174 and 175, the sulfoximine intermediate were separated as follows: SFC separation (Column: DAICELCHIRALPAK® AY; Column size: 250 mm*25 mm, 10 μm; Mobile Phase A: Supercritical CO₂; Mobile Phase B: MeOH (0.1% 7.0 M Ammonia in MeOH); Gradient: B=10%). Flow rate: 100 mL/min, Column temp.: 25° C.

For compounds 176 and 177, the sulfoximine intermediate were separated as follows: SFC separation (Column: REGIS (S,S)WHELK-01 250 mm*25 mm, 10 m, Mobile phase A (Supercritical CO₂), Mobile phase B (MeOH (0.1% 7.0 M Ammonia in MeOH)), Gradient: B=35%). Flow rate: 70 mL/min, Column temp.: 25° C.

For compounds 187 and 188, the sulfoximine intermediate were separated as follows: SFC separation (Column: DAICELCHIRALPAK® IG; Column size: 250 mm*25 mm, 10 μm; Mobile Phase A: Supercritical CO₂; Mobile Phase B: MeOH (0.1% 7.0 M Ammonia in MeOH); Gradient: B=20%). Flow rate: 70 mL/min, Column temp.: 25° C.

For compounds 189 and 190, the sulfoximine intermediate were separated as follows: SFC separation (Column: DAICELCHIRALPAK® IG; Column size: 250 mm*25 mm, 10 μm; Mobile Phase A: Supercritical CO₂; Mobile Phase B: MeOH(0.1% 7.0 M Ammonia in MeOH); Gradient: B=35%). Flow rate: 70 mL/min, Column temp.: 25° C.

For compounds 191 and 192, the sulfoximine intermediate were separated as follows: SFC separation (Column: DAICELCHIRALCEL® AS; Column size: 250 mm*25 mm, 10 μm; Mobile Phase A: Supercritical CO₂; Mobile Phase B: MeOH(0.1% 7.0 M Ammonia in MeOH); Gradient: B=35%). Flow rate: 70 mL/min, Column temp.: 25° C.

For compounds 197 and 198, the sulfoximine intermediate were separated as follows: SFC separation (Column: DAICELCHIRALCEL® AS; Column size: 250 mm*25 mm, 10 μm; Mobile Phase A: Supercritical CO₂; Mobile Phase B: MeOH(0.1% 7.0 M Ammonia in MeOH); Gradient: B=12%). Flow rate: 120 mL/min, Column temp.: 25° C.

For compounds 199 and 200, the sulfoximine intermediate were separated as follows: SFC separation (Column: DAICELCHIRALPAK® IC; Column size: 250*25 mm, 10 μm; Mobile Phase A: Supercritical CO₂; Mobile Phase B: MeOH(0.1% 7.0 M Ammonia in MeOH); Gradient: B=50%). Flow rate: 70 mL/min, Column temp.: 25° C.

For compounds 201 and 202, the sulfoximine intermediate were separated as follows: SFC separation (Column: DAICELCHIRALPAK® AS; Column size: 250*25 mm, 10 μm; Mobile Phase A: Supercritical CO₂; Mobile Phase B: MeOH(0.1% 7.0 M Ammonia in MeOH); Gradient: B=17%). Flow rate: 120 mL/min, Column temp.: 25° C.

For compounds 206 and 207, the sulfoximine intermediate were separated as follows: SFC separation (Column: DAICELCHIRALPAK® AD; Column size: 250 mm*25 mm, 10 μm; Mobile Phase A: Supercritical CO₂; Mobile Phase B: MeOH(0.1% 7.0 M Ammonia in MeOH); Gradient: B=30%). Flow rate: 120 mL/min, Column temp.: 25° C.

For compounds 210 and 211, the sulfoximine intermediate were separated as follows: SFC separation (Column: DAICELCHIRALCEL® AD; Column size: 250 mm*25 mm, 10 μm; Mobile Phase A: Supercritical CO₂; Mobile Phase B: MeOH(0.1% 7.0 M Ammonia in MeOH); Gradient: B=16%). Flow rate: 120 mL/min, Column temp.: 25° C.

For compounds 212 and 213, the sulfoximine intermediate were separated as follows: SFC separation (DAICELCHIRALPAK® AD; Column size: 250*25 mm, 10 μm; Mobile Phase A: Supercritical CO₂; Mobile Phase B: MeOH(0.1% 7.0 M Ammonia in MeOH); Gradient: B=30%). Flow rate: 120 mL/min, Column temp.: 25° C.

For compounds 204 and 205, the sulfoximine intermediate were separated as follows: SFC separation (Column: ChiralPak AD 150 mm*4.6 mm, 10 m, Mobile phase A (Supercritical CO₂), Mobile phase B (EtOH (0.05% DEA in EtOH)), Gradient: B=30%). Flow rate: 50 mL/min, Column temp.: 25° C.

For compounds 214 and 215, the sulfoximine intermediate were separated as follows: SFC separation (Column: Chiral Whelk—01 (S,S) 250 mm*30 mm, 5 μm, Mobile phase A (Supercritical CO₂), Mobile phase B (EtOH (0.1% NH₃H₂O in EtOH)), Gradient: B=40%). Flow rate: 50 mL/min, Column temp.: 25° C.

For compounds 219 and 220, the sulfoximine intermediate were separated as follows: SFC separation (Column: Chiral Pak IG-H 250 mm*30 mm, 5 μm, Mobile phase A (Supercritical CO₂), Mobile phase B (EtOH)), Gradient: B=10%). Flow rate: 50 mL/min, Column temp.: 25° C.

| Compound No. | LC-MS: m/z | ¹H NMR |
| --- | --- | --- |
| 101 | 872.4 (M + H)⁺ | (400 MHZ, DMSO-d6) δ 7.74-7.65 (m, 3H), 7.52 (s, 1H), 7.50-7.42 (m, 1H), 7.28-7.25 (m, 2H), 7.14 (d, J = 6.0 Hz, 2H), 6.91-6.81 (m, 2H), 5.69-5.44 (m, 1H), 4.55-4.27 (m, 1H), 3.99-3.94 (m, 2H), 3.50-3.47 (m, 4H), 3.32-3.28 (m, 2H), 2.92-2.86 (m, 5H), 2.22 (s, 6H), 1.76-1.70 (m, 7H), 1.43 (s, 3H), 1.18 (s, 3H). |
| 102 | 861.5 (M + H)⁺ | (400 MHz, DMSO-d6) δ 11.70 (brs, 1H), 9.08 (s, 1H), 8.45 (d, J = 8.4 Hz, 1H), 8.19 (d, J = 8.8 Hz, 1H), 7.54 (d, J = 8.4 Hz, 2H), 7.40 (d, J = 9.2 Hz, 1H), 7.26-7.23 (m, 1H), 7.17-7.13 (m, 3H), 6.94 (s, 1H), 5.60 (s, 1H), 4.46-4.34 (m, 2H), 3.98-3.95 (m, 2H), 3.51-3.44 (m, 2H), 3.24 (s, 3H), 2.94-2.81 (m, 3H), 2.21 (s, 6H), 1.72-1.60 (m, 7H), 1.40-1.38 (m, 2H), 1.32-1.24 (m, 2H), 1.14-1.13 (m, 2H). |

-continued

| Compound No. | LC-MS: m/z | ¹H NMR |
|---|---|---|
| 103 | 862.4 (M + H)⁺ | (400 MHz, DMSO-d6) δ 8.00-7.64 (m, 4H), 7.51 (s, 1H), 7.46-7.43 (m, 1H), 7.32-7.18 (m, 4H), 6.81 (brs, 1H), 5.79-5.44 (m, 1H), 4.40 (brs, 1H), 4.03-3.92 (m, 4H), 3.72-3.56 (m, 2H), 3.55-3.45 (m, 3H), 2.95-2.75 (m, 4H), 2.26 (s, 6H), 2.05 (d, J = 4.0 Hz, 3H), 1.81-1.59 (m, 7H), 1.50 (s, 3H), 1.17 (brs, 3H). |
| 105 | 889.5 (M + H)⁺ | (400 MHZ, DMSO-d6) δ 7.74 (s, 1H), 7.52 (s, 1H), 7.44 (d, J = 8.4 Hz, 1H), 7.28-7.26 (m, 2H), 7.15 (d, J = 6.0 Hz, 2H), 7.06 (s, 1H), 6.87 (s, 1H), 5.67-5.39 (m, 1H), 4.50 (brs, 1H), 3.52-3.43 (m, 4H), 3.01 (s, 3H), 2.91-2.75 (m, 3H), 2.22 (s, 6H), 1.78-1.68 (m, 7H), 1.43 (s, 3H), 1.17 (brs, 3H). |
| 106 | 847.3 (M + H)⁺ | (400 MHZ, DMSO-d6) δ 7.99-7.94 (m, 2H), 7.86-7.81 (m, 2H), 7.40 (d, J = 8.4 Hz, 1H), 7.25-7.23 (m, 1H), 7.08-7.03 (m, 4H), 6.85 (s, 1H), 6.65 (s, 1H), 5.65-5.40 (m, 1H), 4.41 (brs, 1H), 3.73-3.71 (m, 4H), 3.34-3.32 (m, 2H), 3.12 (s, 3H), 3.04-3.02 (m, 4H), 2.90-2.80 (m, 2H), 2.13 (s, 6H), 1.76-1.58 (m, 3H), 1.76-1.58 (m, 3H), 1.48 1.47 (m, 1H), 1.30 (d, J = 6.8 Hz, 3H). |
| 107 | 846.4 (M + H)⁺ | (400 MHZ, DMSO-d6) δ 8.34-8.32 (m, 2H), 8.03-7.96 (m, 4H), 7.89-7.87 (m, 1H), 7.19 (s, 1H), 7.13-7.12 (m, 3H), 7.03 (s, 1H), 6.59 (d, J = 7.2 Hz, 1H), 6.24 (s, 1H), 5.73-5.48 (m, 1H), 4.01-3.92 (m, 4H), 3.51-3.43 (m, 4H), 2.76-2.70 (m, 1H), 2.18 (s, 6H), 1.81-1.61 (m, 7H), 1.46-1.41 (m, 2H), 1.29-1.23 (m, 3H). |
| 108 | 886.5 (M + H)⁺ | (400 MHZ, DMSO-d6) δ 8.07-8.01 (m, 1H), 7.85-7.73 (m, 2H), 7.57-7.53 (m, 2H), 7.43-7.41 (m, 2H), 7.34-7.32 (m, 1H), 7.27-7.25 (m, 2H), 7.14-7.13 (m, 3H), 6.93 (s, 1H), 6.86 (s, 1H), 6.24 (s, 1H), 5.59-5.48 (m, 1H), 4.50-4.45 (m, 1H), 4.01-3.92 (m, 4H), 3.52-3.38 (m, 5H), 2.91-2.82 (m, 5H), 2.21 (s, 6H), 1.76-1.71 (m, 7H), 1.46-1.41 (m, 4H), 1.29-1.23 (m, 2H). |
| 109 | 846.3 (M + H)⁺ | (400 MHZ, DMSO-d6) δ 8.58-8.39 (m, 3H), 8.12-8.09 (m, 1H), 8.02-7.96 (m, 1H), 7.51 (s, 1H), 7.41-7.39 (m, 1H), 7.23-7.21 (m, 2H), 6.81-677 (m, 1H), 6.72 (s, 1H), 5.73-5.61 (m, 1H), 5.43-5.40 (m, 1H), 4.37-4.31 (m, 3H), 3.17 (s, 3H), 2.76-2.70 (m, 1H), 2.22 (s, 6H), 2.17-2.01 (m, 4H), 1.79-1.75 (m, 2H), 1.53-1.47 (m, 5H). |
| 110 | 860.4 (M + H)⁺ | (400 MHz, DMSO-d6) δ 11.71 (brs, 1H), 8.03-7.95 (m, 3H), 7.54-7.40 (m, 3H), 7.28 (d, J = 8.8 Hz, 1H), 7.16-7.08 (m, 3H), 6.96-6.86 (m, 1H), 5.60-5.58 (m, 1H), 4.40-4.38 (m, 1H), 4.60-4.25 (m, 1H), 3.97-3.96 (m, 2H), 3.64-3.62 (m, 1H), 3.46-3.44 (m, 2H), 3.27-3.20 (m, 1H), 3.18 (s, 3H), 2.91-2.82 (m, 2H), 2.22 (s, 6H), 1.73 (s, 5H), 1.64-1.59 (m, 1H), 1.54-1.52 (m, 2H), 1.43-1.38 (m, 2H), 1.32-1.24 (m, 2H), 1.19-1.04 (m, 1H). |
| 111 | 874.5 (M + H)⁺ | (400 MHz, DMSO-d6) δ 7.78-7.64 (m, 2H), 7.59-7.50 (m, 3H), 7.43 (d, J = 8.4 Hz, 1H), 7.30-7.21 (m, 2H), 7.15 (d, J = 6.0 Hz, 2H), 6.97-6.83 (m, 2H), 5.72-5.42 (m, 1H), 4.66 (s, 2H), 4.45 (brs, 1H), 3.98 (d, J = 10.8 Hz, 2H), 3.53-3.46 (m, 2H), 3.06 (s, 2H), 2.95-2.81 (m, 3H), 2.22 (s, 6H), 2.05 (s, 3H), 1.81-1.60 (m, 7H), 1.44 (d, J = 3.6 Hz, 3H), 1.18 (d, J = 6.0 Hz, 3H). |
| 112 | 874.4 (M + H)⁺ | (400 MHz, DMSO-d6) δ 8.02-7.92 (m, 3H), 7.85 (s, 1H), 7.56-7.35 (m, 3H), 7.28-7.06 (m, 4H), 6.98-6.79 (m, 1H), 6.59-6.50 (m, 1H), 5.71-5.56 (m, 1H), 4.44-4.32 (m, 1H), 4.02-3.92 (m, 2H), 3.65-3.50 (m, 1H), 3.47-3.39 (m, 3H), 3.14 (s, 3H), 3.10-3.08 (m, 1H), 2.91-2.79 (m, 2H), 2.48 (s, 3H), 2.19 (s, 6H), 1.83-1.70 (m, 4H), 1.65-1.56 (m, 1H), 1.40-1.32 (m, 1H), 1.25-1.05 (m, 7H). |
| 113 | 885.4 (M + H)⁺ | (400 MHZ, DMSO-d6) δ 8.17-8.15 (m, 3H), 8.11-7.78 (m, 1H), 7.60-7.47 (m, 2H), 7.41 (d, J = 8.8 Hz, 1H), 7.28 (d, J = 8.8 Hz, 1H), 7.20-7.07 (m, 3H), 6.97 (s, 1H), 5.76-5.50 (m, 1H), 4.44-4.32 (m, 1H), 3.97 (d, J = 10.4 Hz, 2H), 3.73-3.71 (m, 3H), 3.67-3.58 (m, 1H), 3.50-3.44 (m, 2H), 3.27-3.19 (m, 1H), 2.92-2.84 (m, 2H), 2.22 (s, 6H), 1.82-1.62 (m, 7H), 1.40 (brs, 3H), (brs, 3H). |
| 114 | 860.4 (M + H)⁺ | (400 MHZ, DMSO-d6) δ 8.00-7.87 (m, 4H), 7.53 (s, 1H), 7.44 (d, J = 8.4 Hz, 1H), 7.34-7.27 (m, 3H), 7.15 (d, J = 6.0 Hz, 2H), 6.93-6.87 (m, 2H), 5.62-5.45 (m, 1H), 4.63-4.51 (m, 1H), 3.99-3.97 (m, 2H), 3.63-3.60 (m, 4H), 3.11 (s, 3H), 2.91-2.86 (m, 3H), 2.21 (s, 6H), 1.78-1.62 (m, 7H), 1.44 (brs, 3H), 1.18 (brs, 3H). |
| 115 | 860.4 (M + H)⁺ | (400 MHZ, DMSO-d6) δ 11.73 (brs, 1H), 8.00-7.80 (m, 4H), 7.53 (s, 1H), 7.44 (d, J = 8.4 Hz, 1H), 7.33-7.27 (m, 3H), 7.15 (d, J = 6.4 Hz, 2H), 6.92-6.88 (m, 2H), 5.62-5.45 (m, 1H), 4.63-4.51 (m, 1H), 3.99-3.97 (m, 2H), 3.63-3.60 (m, 4H), 3.11 (s, 3H), 2.91-2.86 (m, 3H), 2.21 (s, 6H), 1.78-1.62 (m, 7H), 1.44 (brs, 3H), 1.18 (brs, 3H). |
| 116 | 874.4 (M + H)⁺ | (400 MHZ, DMSO-d6) δ 11.72 (brs, 1H), 7.95-7.78 (m, 4H), 7.53 (s, 1H), 7.40 (d, J = 8.8 Hz, 1H), 7.34 (s, 1H), 7.27 (d, J = 8.0 Hz, 1H), 7.18-7.12 (m, 2H), 6.88-6.83 (m, 2H), 5.70-5.48 (m, 1H), 4.59-4.43 (m, 1H), 3.98-3.95 (m, 2H), 3.49-3.43 (m, 3H), 3.18-3.09 (m, 3H), 2.94-2.84 (m, 2H), 2.21 (s, 6H), 1.76-1.63 (m, 7H), 1.64-1.61 (m, 3H), 1.18-1.13 (m, 6H). |

-continued

| Compound No. | LC-MS: m/z | ¹H NMR |
|---|---|---|
| 117 | 874.4 (M + H)⁺ | (400 MHz, DMSO-d6) δ 11.72 (brs, 1H), 7.97-7.93 (m, 3H), 7.93-7.73 (m, 1H), 7.53-7.48 (m, 2H), 7.40 (d, J = 8.0 Hz, 1H), 7.27 (d, J = 8.0 Hz, 1H), 7.17-7.15 (m, 2H), 7.11-7.06 (s, 1H), 6.96-6.86 (m, 1H), 5.64-5.55 (m, 1H), 4.43-4.33 (m, 1H), 3.98-3.95 (m, 2H), 3.67-3.58 (m, 1H), 3.51-3.40 (m, 3H), 3.20-3.14 (m, 3H), 2.94-2.84 (m, 2H), 2.21 (s, 6H), 1.72-1.62 (s, 7H), 1.66-1.55 (m, 1H), 1.39-1.37 (m, 2H), 1.14 (d, J = 8.0 Hz, 2H), 1.09-1.02 (m, 4H). |
| 118 | 872.5 (M + H)⁺ | (400 MHz, DMSO-d6) δ 11.59 (brs, 1H), 8.03-7.90 (m, 4H), 7.53 (s, 1H), 7.47-7.38 (m, 2H), 7.29-7.22 (m, 3H), 7.06-6.80 (m, 3H), 5.71-5.44 (m, 1H), 4.65-4.31 (m, 1H), 3.98 (d, J = 10.4 Hz, 2H), 3.70-3.37 (m, 4H), 2.97-2.84 (m, 3H), 2.45-2.37 (m, 1H), 2.05 (s, 3H), 1.85-1.66 (m, 7H), 1.44 (s, 3H), 1.18 (s, 3H), 0.96 (d, J = 8.4 Hz, 2H), 0.68-0.44 (m, 2H). |
| 119 | 955.4 (M + H)⁺ | (400 MHz, DMSO-d6) δ 8.50 (d, J = 4.8 Hz, 2H), 8.03-8.00 (m, 4H), 7.93-7.87 (m, 2H), 7.74-7.70 (m, 1H), 7.63-7.57 (m, 2H), 7.33-7.32 (m, 1H), 7.24-7.16 (m, 4H), 7.05-7.03 (m, 1H), 6.95-6.85 (m, 2H), 5.40-5.35 (m, 1H), 4.25-4.21 (m, 1H), 4.01-3.98 (m, 1H), 3.56-3.45 (m, 4H), 2.93-2.89 (m, 1H), 2.87 (s, 3H), 2.74 2.64 (m, 2H), 2.20 (s, 6H), 1.82-1.70 (m, 4H), 1.14-1.08 (m, 3H). |
| 121 | 874.5 (M + H)⁺ | (400 MHZ, DMSO-d6) δ 8.01-7.91 (m, 3H), 7.85-7.76 (m, 1H), 7.51-7.40 (m, 2H), 7.41 (d, J = 8.0 Hz, 1H), 7.29-7.23 (m, 1H), 7.17-7.09 (m, 3H), 6.98-6.82 (m, 1H), 5.63-5.56 (m, 1H), 4.46-4.32 (m, 1H), 3.97 (d, J = 8.0 Hz, 2H), 3.71-3.53 (m, 1H), 3.50-3.36 (m, 3H), 3.13-3.09 (m, 3H), 2.94-2.84 (m, 2H), 2.12 (s, 6H), 1.80-1.65 (m, 7H), 1.65-1.56 (m, 1H), 1.41-1.37 (m, 2H), 1.31-1.27 (m, 1H), 1.17-1.01 (m, 3H). |
| 122 | 885.4 (M + H)⁺ | (400 MHz, DMSO-d6) δ 8.17-8.07 (m, 3H), 8.04-7.86 (m, 1H), 7.63-7.49 (m, 2H), 7.41 (d, J = 7.6 Hz, 1H), 7.28 (d, J = 6.8 Hz, 1H), 7.21-7.08 (m, 3H), 6.97 (s, 1H), 5.78-5.57 (m, 1H), 4.44-4.35 (m, 1H), 4.01-3.92 (m, 3H), 3.79-3.66 (m, 5H), 2.96-2.81 (m, 3H), 2.22 (s, 6H), 1.73-1.56 (m, 7H), 1.39-1.14 (m, 3H), 1.11-0.96 (m, 3H). |
| 123 | 890.4 (M + H)⁺ | (400 MHZ, DMSO-d6) δ 11.59 (brs, 1H), 7.91 (d, J = 8.0 Hz, 1H), 7.70-7.40 (m, 5H), 7.27 (d, J = 9.2 Hz, 1H), 7.16-7.14 (m, 2H), 7.01-6.84 (m, 2H), 5.69-5.44 (m, 1H), 4.58-4.39 (m, 1H), 4.04-3.87 (m, 5H), 3.64-3.43 (m, 4H), 3.32 (s, 3H), 2.95-2.84 (m, 3H), 2.23 (s, 6H), 1.81-1.61 (m, 7H), 1.44 (s, 3H), 1.17 (s, 3H). |
| 124 | 874.4 (M + H)⁺ | (400 MHz, DMSO-d6) δ 8.08-7.97 (m, 1H), 7.81-7.58 (m, 2H), 7.53 (s, 1H), 7.35-7.26 (m, 2H), 6.95-6.78 (m, 2H), 5.71-5.31 (m, 1H), 4.61-4.30 (m, 1H), 3.97 (d, J = 12.0 Hz, 2H), 3.51-3.44 (m, 3H), 2.94 (s, 3H), 2.71 (s, 3H), 2.21 (s, 6H), 1.75-1.72 (m, 5H), 1.66-1.58 (m, 2H), 1.45 (s, 2H), 1.32-1.23 (m, 3H). |
| 125 | 924.3 (M + H)⁺ | (400 MHZ, DMSO-d6) δ 8.50-8.41 (m, 3H), 8.06-8.00 (m, 2H), 7.96-7.92 (m, 2H), 7.37 (d, J = 3.2 Hz, 1H), 7.17-7.11 (m, 3H), 7.04-7.00 (m, 1H), 6.72 (d, J = 6.8 Hz, 1H), 5.72-5.70 (m, 1H), 4.00-3.94 (m, 3H), 3.51-3.43 (m, 3H), 3.05-3.00 (m, 3H), 2.20 (s, 6H), 1.87-1.70 (m, 4H), 1.50-1.47 (m, 1H), 1.37-1.18 (m, 5H), 0.86-0.83 (m, 3H). |
| 130 | 888.3 (M + H)⁺ | (400 MHz, DMSO-d6) δ 12.62 (brs, 1H), 8.00-7.93 (m, 4H), 7.50-7.44 (m, 3H), 7.23 (d, J = 8.4 Hz, 1H), 7.16-7.14 (m, 2H), 7.07 (s, 1H), 6.84 (s, 1H), 5.62-5.60 (m, 1H), 4.34-4.24 (m, 1H), 3.83-3.78 (m, 1H), 3.69-3.67 (m, 1H), 3.50-3.43 (m, 3H), 3.40-3.35 (m, 2H), 2.86-2.83 (m, 2H), 2.29-2.26 (m, 3H), 2.20 (s, 6H), 1.90-1.85 (m, 1H), 1.80-1.65 (m, 5H), 1.57-1.48 (m, 2H), 1.30-1.24 (m, 4H). |
| 131 | 888.4 (M + H)⁺ | (400 MHz, DMSO-d6) δ 12.60 (brs, 1H), 8.00-7.93 (m, 4H), 7.48-7.42 (m, 3H), 7.20 (s, 1H), 7.15-7.13 (m, 2H), 7.10 (s, 1H), 6.74 (s, 1H), 5.62-5.60 (m, 1H), 4.34-4.24 (m, 1H), 3.98-3.96 (m, 2H), 3.83-3.77 (m, 1H), 3.71-3.65 (m, 1H), 3.48-3.41 (m, 3H), 3.38-3.35 (m, 2H), 2.86-2.83 (m, 2H), 2.33-2.24 (m, 3H), 2.20 (s, 6H), 1.90-1.85 (m, 1H), 1.80-1.65 (m, 5H), 1.57-1.48 (m, 2H), 1.32-1.24 (m, 4H). |
| 132 | 877.2 (M + H)⁺ | (400 MHZ, DMSO-d6) δ 8.26 (s, 1H), 8.14-8.09 (m, 2H), 7.88 (s, 1H), 7.80-7.78 (d, J = 8.0 Hz, 1H), 7.57-7.54 (m, 2H), 7.39 (d, J = 6.8 Hz, 1H), 7.14-7.09 (m, 2H), 7.01 (s, 1H), 5.65 (q, J = 4.8 Hz, 1H), 4.12-4.09 (m, 1H), 3.99 (d, J = 10.4 Hz, 2H), 3.87-3.84 (m, 1H), 3.50-3.42 (m, 3H), 2.93-2.89 (m, 1H), 2.67-2.64 (m, 2H), 2.33-2.16 (m, 7H), 1.75 (m, 4H), 1.51-1.47 (m, 3H), 1.23-1.20 (m, 7H). |
| 134 | 886.2 (M + H)⁺ | (400 MHZ, DMSO-d6) δ 11.60 (brs, 1H), 8.04-7.78 (m, 4H), 7.51 (s, 1H), 7.42-7.37 (m, 2H), 7.26 (d, J = 8.4 Hz, 1H), 6.98-6.97 (m, 2H), 7.00-6.89 (m, 2H), 5.62-5.60 (m, 1H), 4.47-4.40 (m, 1H), 4.05-3.94 (m, 3H), 3.68-3.44 (m, 4H), 2.90-2.83 (m, 2H), 2.66-2.64 (m, 1H), 2.20 (s, 6H), 1.85-1.69 (m, 7H), 1.53-1.38 (m, 3H), 1.20-1.11 (m, 4H), 1.01-0.88 (m, 3H). |
| 135 | 886.3 (M + H)⁺ | (400 MHz, DMSO-d6) δ 11.65 (brs, 1H), 8.04-7.78 (m, 4H), 7.51 (s, 1H), 7.42-7.37 (m, 2H), 7.26 (d, J = 8.4 Hz, 1H), 6.98-6.97 (m, 2H), 7.00-6.89 (m, 2H), 5.62-5.60 (m, 1H), 4.40-4.35 (m, 1H), 4.05-3.94 (m, 3H), 3.68-3.44 (m, 4H), 2.90-2.83 (m, 2H), 2.66-2.64 (m, 1H), 2.20 (s, 6H), 1.85-1.69 (m, 7H), 1.53-1.38 (m, 3H), 1.20-1.11 (m, 4H), 1.01-0.88 (m, 3H). |

| Compound No. | LC-MS: m/z | ¹H NMR |
|---|---|---|
| 136 | 908.2 (M + H)⁺ | (400 MHZ, DMSO-d6) δ 11.69 (brs, 1H), 8.06-7.96 (m, 2H), 7.74 (s, 1H), 7.52 (s, 1H), 7.43 (d, J = 8.0 Hz, 1H), 7.27 (d, J = 8.0 Hz, 1H), 7.18-7.17 (m, 2H), 7.05-6.89 (m, 3H), 5.72-5.63 (m, 1H), 4.40-4.35 (m, 2H), 4.01-3.96 (m, 2H), 3.60-3.47 (m, 3H), 3.27-3.21 (m, 2H), 2.92-2.85 (m, 2H), 2.25 (s, 6H), 1.85-1.69 (m, 7H), 1.52-1.35 (m, 3H), 1.26-1.12 (m, 6H). |
| 137 | 908.2 (M + H)⁺ | (400 MHZ, DMSO-d6) δ 11.65 (brs, 1H), 8.07-7.96 (m, 2H), 7.74 (s, 1H), 7.52 (s, 1H), 7.43 (d, J = 8.0 Hz, 1H), 7.27 (d, J = 8.0 Hz, 1H), 7.18-7.17 (m, 2H), 7.05-6.86 (m, 3H), 5.72-5.60 (m, 1H), 4.40-4.35 (m, 2H), 4.00-3.96 (m, 2H), 3.60-3.46 (m, 3H), 3.27-3.21 (m, 2H), 2.92-2.85 (m, 2H), 2.25 (s, 6H), 1.80-1.69 (m, 7H), 1.52-1.35 (m, 3H), 1.26-1.12 (m, 6H). |
| 138 | 892.0 (M + H)⁺ | (400 MHZ, DMSO-d6) δ 11.66 (brs, 1H), 7.96-7.75 (m, 3H), 7.53 (s, 1H), 7.43 (d, J = 8.0 Hz, 1H), 7.29 (d, J = 8.0 Hz, 1H), 7.16-7.08 (m, 3H), 7.00-6.90 (m, 2H), 5.65-5.61 (m, 1H), 4.40-4.35 (m, 2H), 4.00-3.96 (m, 2H), 3.60-3.45 (m, 3H), 3.25-3.19 (m, 2H), 2.92-2.84 (m, 2H), 2.24 (s, 6H), 1.78-1.71 (m, 7H), 1.52-1.34 (m, 3H), 1.21-1.12 (m, 6H). |
| 139 | 892.3 (M + H)⁺ | (400 MHz, DMSO-d6) δ 11.54 (brs, 1H), 7.78-7.71 (m, 3H), 7.45 (s, 1H), 7.35 (d, J = 8.0 Hz, 1H), 7.20 (d, J = 8.0 Hz, 1H), 7.11-6.99 (m, 3H), 6.93-6.83 (m, 2H), 5.65-5.61 (m, 1H), 4.37-4.31 (m, 1H), 3.92-3.88 (m, 2H), 3.52-3.35 (m, 4H), 3.25-3.19 (m, 2H), 2.85-2.76 (m, 2H), 2.16 (s, 6H), 1.70-1.61 (m, 7H), 1.50-1.30 (m, 3H), 1.11-1.10 (m, 6H). |
| 140 | 875.6 (M + H)⁺ | (400 MHZ, DMSO-d6) δ 11.59 (brs, 1H), 9.03 (s, 1H), 8.36 (s, 1H), 8.12 (s, 1H), 7.51 (s, 1H), 7.43-7.41 (m, 2H), 7.27 (d, J = 8.8 Hz, 1H), 7.15-7.13 (m, 2H), 6.97-6.86 (m, 2H), 5.62-5.57 (m, 1H), 4.50-4.40 (m, 1H), 3.99-3.96 (m, 2H), 3.57-3.45 (m, 3H), 3.25-3.29 (m, 2H), 2.91-2.84 (m, 2H), 2.21 (s, 6H), 1.75-1.72 (m, 6H), 1.68-1.67 (m, 2H), 1.43-1.40 (m, 3H), 1.17-1.30 (m, 6H). |
| 141 | 875.6 (M + H)⁺ | (400 MHZ, DMSO-d6) δ 11.64 (brs, 1H), 9.02 (s, 1H), 8.36 (s, 1H), 8.13 (s, 1H), 7.48 (s, 1H), 7.43-7.41 (m, 2H), 7.23 (d, J = 8.0 Hz, 1H), 7.15-7.13 (m, 2H), 6.81-6.71 (m, 2H), 5.60-5.54 (m, 1H), 4.12-4.04 (m, 1H), 3.98-3.96 (m, 2H), 3.51-3.45 (m, 3H), 3.35-3.29 (m, 2H), 2.87-2.82 (m, 2H), 2.20 (s, 6H), 1.77-1.71 (m, 6H), 1.67-1.64 (m, 2H), 1.43-1.40 (m, 3H), 1.17-1.30 (m, 6H). |
| 142 | 886.4 (M + H)⁺ | (400 MHZ, DMSO-d6) δ 7.95-7.88 (m, 4H), 7.49 (s, 1H), 7.43 (d, J = 8.4 Hz, 1H), 7.32 (m, 1H), 7.23 (d, J = 8.4 Hz, 1H), 7.17-7.15 (m, 2H), 6.98 (m, 1H), 6.77 (m, 1H), 5.55 (m, 1H), 4.39 (m, 1H), 4.00-3.97 (m, 2H), 3.86-3.81 (m, 1H), 3.72-3.69 (m, 1H), 3.52-3.46 (m, 2H), 3.40-3.32 (m, 2H), 2.90-2.83 (m, 3H), 2.33-2.26 (m, 3H), 2.22 (s, 6H), 1.76-1.69 (m, 5H), 1.65 (m, 2H), 1.39 (s, 3H), 1.20 (s, 3H). |
| 143 | 886.2 (M + H)⁺ | (400 MHZ, DMSO-d6) δ 11.59 (brs, 1H), 7.95-7.91 (m, 4H), 7.53 (s, 1H), 7.44 (d, J = 8.4 Hz, 1H), 7.37 (m, 1H), 7.28 (d, J =8.4 Hz, 1H), 7.16-7.14 (m, 2H), 6.96 (m, 1H), 6.88 (m, 1H), 5.57 (m, 1H), 4.50 (m, 1H), 4.00-3.97 (m, 2H), 3.89-3.84 (m, 1H), 3.77-3.72 (m, 1H), 3.53-3.46 (m, 4H), 2.92-2.86 (m, 2H), 2.36-2.28 (m, 3H), 2.22 (s, 6H), 2.05-2.02 (m, 1H), 1.78-1.73 (m, 6H), 1.66 (m, 1H), 1.43 (s, 3H), 1.17 (s, 3H). |
| 144 | 888.3 (M + H)⁺ | (400 MHZ, DMSO-d6) δ 11.62 (brs, 1H), 7.95-7.88 (m, 4H), 7.56 (s, 1H), 7.48 (d, J = 8.4 Hz, 1H), 7.37 (s, 1H), 7.31 (d, J = 8.8 Hz, 1H), 7.20-7.18 (m, 2H), 6.97 (s, 1H), 6.90 (s, 1H), 5.63-5.58 (m, 1H), 4.53-4.48 (m, 1H), 4.03-4.00 (m, 2H), 3.56-3.50 (m, 3H), 3.27-3.22 (m, 2H), 2.94-2.91 (m, 2H), 2.58 (s, 3H), 2.25 (s, 6H), 1.81-1.65 (m, 7H), 1.46 (s, 3H), 1.31-1.30 (m, 1H). 1.18-1.16 (m, 2H), 1.15-1.13 (m, 4H). |
| 147 | 890.4 (M + H)⁺ | (400 MHZ, DMSO-d6) δ 12.49 (brs, 1H), 7.98 (m, 2H), 7.30 (d, J = 7.6 Hz, 2H), 7.55 (s, 1H), 7.52 (d, J = 8.4 Hz, 1H), 7.39 (s, 1H), 7.29 (d, J = 8.8 Hz, 1H), 7.19 (d, J = 6.0 Hz, 1H), 7.00-6.99 (m, 1H), 6.85 (s, 1H), 5.66-5.63 (m, 1H), 4.52 (m, 1H), 3.99-3.92 (m, 5H), 3.56-3.50 (m, 3H), 3.35 (q, J = 7.2 Hz, 2H), 2.92-2.88 (m, 2H), 2.61 (s, 3H), 2.26 (d, J = 1.6 Hz, 6H), 1.96-1.95 (m, 1H), 1.82-1.77 (m, 4H), 1.57-1.56 (m, 1H), 1.43-1.41 (m, 2H), 1.17 (t, J = 8.8 Hz, 3H). |
| 148 | 904.3 (M + H)⁺ | (400 MHZ, DMSO-d6) δ 12.91 (brs, 1H), 8.02 (d, J = 8.8 Hz, 2H), 7.30 (d, J = 8.8 Hz, 2H), 7.59-7.50 (m, 2H), 7.46 (d, J = 8.4 Hz, 1H), 7.31 (d, J = 8.0 Hz, 1H), 7.16-7.14 (m, 2H), 6.91 (s, 1H), 6.89 (s, 1H), 5.67 (q, J = 6.8 Hz, 1H), 4.37-4.34 (m, 1H), 3.98-3.95 (m, 2H), 3.70-3.64 (m, 1H), 3.49-3.43 (m, 2H), 3.24-3.17 (m, 3H), 2.92-2.82 (m, 2H), 2.22 (s, 6H), 1.89-1.86 (m, 1H), 1.76-1.65 (m, 6H), 1.53-1.50 (m, 1H), 1.42-1.40 (m, 2H), 1.06 (t, J = 6.0 Hz, 3H), 0.92 (d, J = 5.2 Hz, 3H). |
| 149 | 906.1 (M + H)⁺ | (400 MHZ, DMSO-d6) δ 11.68 (s, 1H), 7.98-7.65 (m, 3H), 7.53 (s, 1H), 7.43 (d, J = 8.0 Hz, 1H), 7.28 (d, J = 8.0 Hz, 1H), 7.17-7.09 (m, 3H), 6.95-6.90 (m, 2H), 5.65-5.61 (m, 1H), 4.00-3.97 (m, 2H), 3.59-3.47 (m, 3H), 3.32-3.25 (m, 3H), 2.91-2.85 (m, 2H), 2.56 (s, 3H), 2.24 (s, 6H), 1.78-1.64 (m, 7H), 1.65-1.63 (m, 3H), 1.16-1.08 (m, 6H). |

| Compound No. | LC-MS: m/z | ¹H NMR |
|---|---|---|
| 150 | 906.3 (M + H)⁺ | (400 MHz, DMSO-d6) δ 11.64 (brs, 1H), 7.98-7.65 (m, 3H), 7.53 (s, 1H), 7.43 (d, J = 8.0 Hz, 1H), 7.28 (d, J = 8.0 Hz, 1H), 7.17-7.09 (m, 3H), 6.95-6.90 (m, 2H), 5.70-5.62 (m, 1H), 4.40-4.35 (m, 1H), 4.00-3.96 (m, 2H), 3.62-3.48 (m, 3H), 3.32-3.25 (m, 3H), 2.91-2.85 (m, 2H), 2.56 (s, 3H), 2.24 (s, 6H), 1.78-1.64 (m, 7H), 1.65-1.63 (m, 3H), 1.16-1.08 (m, 6H). |
| 151 | 922.2 (M + H)⁺ | (400 MHZ, DMSO-d6) δ 11.67 (brs, 1H), 7.98-7.78 (m, 3H), 7.53 (s, 1H), 7.43 (d, J = 8.0 Hz, 1H), 7.28 (d, J = 8.0 Hz, 1H), 7.18-7.16 (m, 2H), 7.03-6.92 (m, 3H), 5.71-5.62 (m, 1H), 4.40-4.35 (m, 1H), 4.01-3.96 (m, 2H), 3.60-3.46 (m, 3H), 3.32-3.25 (m, 2H), 2.91-2.84 (m, 2H), 2.56 (s, 3H), 2.25 (s, 6H), 1.77-1.63 (m, 7H), 1.46 (s, 3H), 1.16-1.08 (m, 6H). |
| 152 | 922.1 (M + H)⁺ | (400 MHz, DMSO-d6) δ 11.68 (brs, 1H), 7.97-7.78 (m, 3H), 7.54 (s, 1H), 7.43 (d, J = 8.0 Hz, 1H), 7.28 (d, J = 8.0 Hz, 1H), 7.18-7.16 (m, 2H), 7.02-6.92 (m, 3H), 5.71-5.62 (m, 1H), 4.40-4.35 (m, 1H), 4.01-3.96 (m, 2H), 3.60-3.46 (m, 3H), 3.32-3.25 (m, 2H), 2.92-2.84 (m, 2H), 2.56 (s, 3H), 2.23 (s, 6H), 1.78-1.63 (m, 7H), 1.46 (s, 3H), 1.17-1.08 (m, 6H). |
| 153 | 830.5 (M + H)⁺ | (400 MHz, DMSO-d6) δ 8.00-7.98 (d, J = 8.8 Hz, 2H), 7.95-7.93 (d, J = 8.8 Hz, 2H), 7.59-7.57 (d, J = 8.8 Hz, 1H), 7.55 (s, 1H), 7.35-7.34 (d, J = 3.2 Hz, 1H), 7.25-7.23 (d, J = 8.4 Hz, 1H), 7.17-7.16 (d, J = 6.4 Hz, 2H), 7.14 (s, 1H), 6.91 (s, 1H), 6.85 (s, 1H), 5.82 (s, 1H), 5.62 (s, 2H), 5.46-5.43 (m, 1H), 4.43-4.41 (m, 1H), 4.04-3.97 (m, 2H), 3.71 (s, 3H), 3.56-3.49 (m, 2H), 3.40-3.33 (m, 1H), 3.21-3.15 (m, 2H), 2.94-2.87 (m, 1H), 2.84-2.78 (m, 2H), 2.24 (s, 6H), 1.81-1.76 (m, 4H), 1.31-1.30 (d, J = 6.4 Hz, 3H), 1.15 (t, J = 7.4 Hz, 3H). |
| 155 | 870.2 (M + H)⁺ | (400 MHz, DMSO-d6) δ 7.94 (m, 4H), 7.55-7.52 (m, 2H), 7.40-7.38 (m, 1H), 7.26 (d, J = 8.0 Hz, 1H), 7.16 (d, J = 4.0 Hz, 2H), 7.04-7.02 (m, 1H), 6.80 (s, 1H), 5.55-5.50 (m, 1H), 4.03-4.01 (m, 2H), 3.87-3.83 (m, 1H), 3.76-3.71 (m, 1H), 3.56-3.49 (m, 2H), 3.47-3.37 (m, 3H), 2.95-2.82 (m, 3H), 2.40 (s, 3H), 2.34-2.27 (m, 2H), 2.24-2.23 (s, 6H), 1.90-1.73 (m, 8H), 1.37-1.30 (m, 4H) |
| 156 | 870.3 (M + H)⁺ | (400 MHz, DMSO-d6) δ 7.95 (m, 4H), 7.55-7.52 (m, 2H), 7.40-7.38 (m, 1H), 7.26 (d, J = 8.0 Hz, 1H), 7.17 (d, J = 4.0 Hz, 2H), 7.04-7.02 (m, 1H), 6.80 (s, 1H), 5.55-5.53 (m, 1H), 4.03-4.00 (m, 2H), 3.89-3.83 (m, 1H), 3.75-3.70 (m, 1H), 3.55-3.49 (m, 2H), 3.47-3.36 (m, 3H), 2.86 (s, 3H), 2.39-2.36 (m, 3H), 2.35-2.29 (m, 2H), 2.25-2.23 (s, 6H), 1.89-1.76 (m, 8H), 1.37-1.34 (m, 4H). |
| 157 | 844.2 (M + H)⁺ | (400 MHZ, DMSO-d6) δ 7.96 (m, 4H), 7.61 (d, J = 8.0 Hz, 1H), 7.55 (s, 1H), 7.43-7.36 (m, 1H), 7.27 (d, J = 8.0 Hz, 1H), 7.16 (d, J = 4.0 Hz, 2H), 7.05-7.00 (m, 1H), 6.91 (s, 1H), 5.86-5.75 (m, 2H), 5.60-5.55 (m, 1H), 4.03-4.00 (m, 2H), 3.87-3.83 (m, 1H), 3.76-3.70 (m, 1H), 3.55-3.49 (m, 2H), 3.44-3.35 (m, 3H), 2.93-2.83 (m, 3H), 2.40 (s, 3H), 2.34-2.27 (m, 2H), 2.24-2.23 (s, 6H), 1.81-1.74 (m, 4H), 1.39-1.30 (m, 3H). |
| 158 | 844.0 (M + H)⁺ | (400 MHz, DMSO-d6) δ 7.96 (m, 4H), 7.61 (d, J = 8.0 Hz, 1H), 7.55 (s, 1H), 7.41-7.39 (m, 1H), 7.27 (d, J = 8.0 Hz, 1H), 7.17 (d, J = 4.0 Hz, 2H), 7.02-7.00 (m, 1H), 6.91 (s, 1H), 5.86-5.75 (m, 2H), 5.60-5.55 (m, 1H), 4.55-4.40 (m, 1H), 4.03-4.00 (m, 2H), 3.89-3.83 (m, 1H), 3.75-3.70 (m, 1H), 3.55-3.34 (m, 5H), 2.92-2.84 (m, 3H), 2.40 (s, 3H), 2.33-2.26 (m, 2H), 2.25-2.24 (s, 6H), 1.81-1.75 (m, 4H), 1.40-1.36 (m, 3H). |
| 159 | 845.2 (M + H)⁺ | (400 MHz, DMSO-d6) δ 8.97 (s, 1H), 7.92 (m, 4H), 7.48 (s, 1H), 7.37 (s, 1H), 7.14-7.12 (d, J = 6.0 Hz, 2H), 6.94 (s, 1H), 6.89 (s, 1H), 5.92-5.88 (m, 1H), 5.82-5.77 (m, 1H), 5.51-5.49 (m, 1H), 4.38 (m, 1H), 4.00-3.98 (m, 2H), 3.85-3.81 (m, 1H), 3.73-3.69 (m, 1H), 3.54-3.47 (m, 2H), 3.43-3.33 (m, 3H), 3.02-3.00 (m, 2H), 2.91-2.83 (m, 2H), 2.39 (s, 3H), 2.25-2.24 (m, 1H), 2.21 (m, 6H), 1.86-1.82 (m, 4H), 1.34 (d, J = 6.8 Hz, 3H). |
| 160 | 871.5 (M + H)⁺ | (400 MHz, DMSO-d6) δ 8.90 (s, 1H), 8.45 (s, 1H), 7.91 (m, 3H), 7.49 (s, 1H), 7.33 (s, 1H), 7.14-7.12 (d, J = 6.4 Hz, 2H), 6.96 (s, 1H), 6.80 (s, 1H), 5.56-5.54 (m, 1H), 4.01-3.98 (m, 2H), 3.84-3.83 (m, 1H), 3.73-3.68 (m, 1H), 3.51-3.49 (m, 2H), 3.38-3.02 (m, 3H), 3.05-3.36 (m, 1H), 2.85-2.80 (m, 2H), 2.36-2.27 (m, 5H), 2.21 (m, 7H), 1.99-1.95 (m, 1H), 1.89-1.86 (m, 7H), 1.34-1.33 (d, J = 6.8 Hz, 3H). |
| 161 | 842.4 (M + H)⁺ | (400 MHZ, DMSO-d6) δ 8.03 (s, 1H), 7.5 (t, J = 8.8 Hz, 2H), 7.39 (d, J = 2.8 Hz, 1H), 7.25-7.23 (d, J = 8.8 Hz, 1H), 7.17-7.15 (d, J = 6.0 Hz, 2H), 6.95 (s, 1H), 6.85 (s, 1H), 5.82 (d, J = 1.2 Hz, 1H), 5.61 (s, 2H), 5.44 (s, 1H), 4.42 (s, 1H), 4.04-4.00 (m, 2H), 3.95-3.90 (m, 1H), 3.82-3.76 (m, 1H), 3.71 (s, 3H), 3.67-3.61 (m, 2H), 3.55-3.49 (m, 2H), 2.94 (s, 1H), 2.90-2.87 (m, 1H), 2.82-2.78 (m, 2H), 2.48-2.35 (m, 2H), 2.24 (d, J = 1.2 Hz, 6H), 1.81-1.76 (m, 4H), 1.31-1.29 (d, J = 6.4 Hz, 3H). |
| 162 | 820.5 (M + H)⁺ | (400 MHz, DMSO-d6) δ 8.34 (s, 1H), 7.96-7.93 (d, J = 8.4 Hz, 2H), 7.87-7.85 (d, J = 8.8 Hz, 2H), 7.53-7.51 (d, J = 8.4 Hz, 1H), 7.47 (s, 1H), 7.33 (s, 1H), 7.18-7.16 (d, J = 8.4 Hz, 1H), 7.14-7.13 (d, J = 6.0 Hz, 2H), 6.86 (m, 1H), 6.72 (s, 1H), 5.50 (m, 1H), 4.87-4.81 (m, 1H), 4.70-4.64 (m, 1H), 4.47-4.43 (m, 2H), 4.35-4.20 (m, 2H), 4.00-3.97 (m, 2H), 3.53-3.41 (m, 3H), 3.24-3.19 (m, 3H), 2.94-2.81 (m, 2H), |

-continued

| Compound No. | LC-MS: m/z | ¹H NMR |
|---|---|---|
| 163 | 834.2 (M + H)⁺ | 2.67-2.62 (m, 1H), 2.55 (s, 3H), 2.33-2.29 (m, 1H), 2.21 (s, 6H), 1.79-1.77 (m, 4H), 1.39-1.38 (d, J = 6.8 Hz, 3H), 1.12 (t, J = 7.4 Hz, 3H). (400 MHZ, DMSO-d6) δ 7.99-7.95 (m, 2H), 7.89-7.87 (d, J = 8.8 Hz, 2H), 7.51-7.47 (m, 2H), 7.37-7.35 (m, 1H), 7.18-7.14 (m, 3H), 6.94-6.92 (m, 1H), 6.72-6.71 (d, J = 3.2 Hz, 1H), 5.61-5.48 (m, 1H), 4.49-4.31 (m, 3H), 4.00-3.97 (m, 3H), 3.53-3.46 (m, 4H), 3.31-3.25 (m, 3H), 2.86 (m, 3H), 2.57 (s, 3H), 2.21 (s, 6H), 1.92 (m, 1H), 1.79-1.73 (m, 6H), 1.55 (m, 1H), 1.41-1.37 (m, 3H), 1.13 (t, J = 7.2 Hz, 3H). |
| 164 | 934.3 (M + H)⁺ | (400 MHz, DMSO-d6) δ 11.71 (brs, 1H), 7.79-7.73 (m, 3H), 7.54 (s, 1H), 7.46-7.44 (d, J = 8.4 Hz, 1H), 7.28-7.26 (d, J = 8.4 Hz, 1H), 7.20-7.19 (d, J = 6.0 Hz, 2H), 7.06 (m, 1H), 6.95 (m, 1H), 6.84 (m, 1H), 5.62 (m, 1H), 4.49 (m, 1H), 3.78-3.77 (d, J = 7.6 Hz, 2H), 3.56 (m, 1H), 3.35-3.29 (m, 2H), 2.89 (m, 1H), 2.60 (s, 3H), 2.28 (s, 6H), 1.77-1.55 (m, 8H), 1.47 (m, 3H), 1.33-1.28 (m, 4H), 1.24-1.16 (m, 9H). |
| 165 | 820.5 (M + H)⁺ | (400 MHZ, DMSO-d6) δ 7.97 (d, J = 8.8 Hz, 2H), 7.87 (d, J = 8.8 Hz, 2H), 7.54 (d, J = 8.8 Hz, 1H), 7.50 (s, 1H), 7.35 (d, J = 3.2 Hz, 1H), 7.19 (d, J = 8.4 Hz, 1H), 7.16 (d, J = 6.4 Hz, 2H), 6.93 (s, 1H), 6.77 (s, 1H), 5.59-5.57 (m, 1H), 4.96-4.94 (m, 1H), 4.64-4.59 (m, 1H), 4.55-4.48 (m, 2H), 4.38-4.37 (m, 1H), 4.15-4.10 (m, 1H), 4.00-3.98 (m, 2H), 3.53-3.44 (m, 3H), 3.24-3.18 (m, 3H), 2.98-2.75 (m, 4H), 2.56 (s, 3H), 2.22 (s, 6H), 1.80-1.74 (m, 4H), 1.38-1.36 (d, J = 6.4 Hz, 3H), 1.13 (t, J = 7.2 Hz, 3H). |
| 166 | 904.1 (M + H)⁺ | (400 MHZ, DMSO-d6) δ 7.75-7.70 (m, 3H), 7.51 (s, 1H), 7.43 (d, J = 9.6 Hz, 1H), 7.26-7.24 (m, 3H), 7.06-6.99 (m, 2H), 6.93-6.83 (m, 2H), 5.56 (s, 1H), 4.44 (s, 1H), 3.99 (d, J = 10.8 Hz, 2H), 3.58-3.42 (m, 2H), 3.31-3.26 (m, 2H), 2.89-2.84 (m, 2H), 2.57 (s, 3H), 2.08-2.05 (m, 1H), 1.76-1.64 (m, 7H), 1.43 (s, 3H), 1.20-1.13 (m, 6H), 1.00 (d, J = 7.6 Hz, 2H), 0.67-0.64 (m, 2H). |
| 167 | 904.3 (M + H)⁺ | (400 MHZ, DMSO-d6) δ 7.82-7.66 (m, 3H), 7.45-7.40 (m, 2H), 7.29-7.17 (m, 3H), 7.01-6.98 (m, 3H), 6.61 (m, 1H), 4.19 (m, 1H), 3.99-3.97 (m, 2H), 3.52-3.46 (m, 2H), 3.24-3.18 (m, 3H), 2.90-2.83 (m, 3H), 2.74-2.72 (m, 1H), 2.05 (m, 1H), 1.77-1.73 (m, 5H), 1.61 (m, 2H), 1.35 (m, 3H), 1.27-1.23 (m, 3H), 1.14 (t, J = 7.2 Hz, 3H), 0.98-0.96 (d, J = 8.8 Hz, 2H), 0.68-0.65 (m, 2H). |
| 168 | 918.4 (M + H)⁺ | (400 MHZ, DMSO-d6) δ 11.61 (brs, 1H), 7.81-7.78 (m, 2H), 7.52 (s, 1H), 7.44 (d, J = 8.8 Hz, 1H), 7.27 (d, J = 8.0 Hz, 1H), 7.16 (d, J = 6.4 Hz, 2H), 7.02 (s, 1H), 6.88 (s, 2H), 5.57 (m, 1H), 4.44 (m, 1H), 4.16 (m, 1H), 4.04-3.97 (m, 3H), 3.52-3.46 (m, 3H), 2.90-2.86 (m, 2H), 2.41-2.36 (m, 2H), 2.24 (s, 6H), 2.19-2.04 (m, 2H), 1.94-1.84 (m, 2H), 1.78-1.70 (m, 7H), 1.63 (m, 1H), 1.45 (s, 3H), 1.19 (s, 3H). |
| 169 | 918.4 (M + H)⁺ | (400 MHz, DMSO-d6) δ 11.61 (brs, 1H), 7.78 (m, 3H), 7.52 (s, 1H), 7.44 (d, J = 8.4 Hz, 1H), 7.27 (d, J = 8.4 Hz, 1H), 7.16 (d, J = 6.0 Hz, 2H), 7.02 (s, 1H), 6.89 (m, 2H), 5.55 (m, 1H), 4.43 (m, 1H), 4.17 (m, 1H), 4.01-3.97 (m, 3H), 3.52-3.46 (m, 3H), 2.89-2.87 (m, 2H), 2.41-2.36 (m, 2H), 2.24 (s, 6H), 2.17-2.06 (m, 2H), 1.91-1.85 (m, 2H), 1.76-1.72 (m, 6H), 1.64 (m, 1H), 1.44 (s, 3H), 1.19 (s, 3H). |
| 170 | 874.2 (M + H)⁺ | (400 MHz, DMSO-d6) δ 8.40-8.25 (m, 2H), 7.85-7.68 (m, 3H), 7.63-7.55 (m, 1H), 7.50 (s, 1H), 7.19-7.14 (m, 3H), 7.10-7.05 (m, 1H), 6.90-6.86 (m, 1H), 6.82 (s, 1H), 5.66-5.56 (m, 2H), 5.54-5.40 (m, 1H), 4.50-4.35 (m, 1H), 4.25-4.24 (m, 1H), 3.99-3.96 (m, 1H), 3.88-3.85 (m, 1H), 3.51-3.45 (m, 2H), 3.32-3.26 (m, 3H), 2.86-2.76 (m, 3H), 2.55 (s, 3H), 2.36-2.34 (m, 3H), 2.25-2.24 (m, 6H), 1.77-1.71 (m, 3H), 1.31-1.26 (m, 3H), 1.13 (t, J = 8.0 Hz, 3H). |
| 171 | 873.0 (M + H)⁺ | (400 MHz, DMSO-d6) δ 8.42 (s, 1H), 7.83-7.69 (m, 4H), 7.57-7.55 (m, 2H), 7.41-7.39 (m, 1H), 7.23 (d, J = 8.0 Hz, 1H), 7.17 (d, J = 8.0 Hz, 2H), 7.11-7.09 (m, 1H), 6.90 (s, 2H), 5.64-5.53 (m, 2H), 5.45-5.40 (m, 1H), 4.44-4.40 (m, 1H), 4.04-4.39 (m, 2H), 3.55-3.48 (m, 3H), 3.40-3.33 (m, 3H), 2.94-2.87 (m, 1H), 2.80-2.76 (m, 1H), 2.59 (s, 3H), 2.50-2.48 (m, 3H), 2.29-2.27 (m, 6H), 1.81-1.75 (m, 4H), 1.36-1.34 (m, 3H), 1.18 (t, J = 4.0 Hz, 3H). |
| 172 | 856.2 (M + H)⁺ | (400 MHz, DMSO-d6) δ 7.90 (m, 4H), 7.52 (s, 1H), 7.39-7.35 (m, 2H), 7.20 (d, J = 8.0 Hz, 1H), 7.13 (d, J = 8.0 Hz, 2H), 7.01-7.00 (m, 1H), 6.80 (s, 1H), 5.56-5.45 (m, 1H), 4.45-4.40 (m, 1H), 4.03-4.00 (m, 2H), 3.89-3.83 (m, 1H), 3.75-3.70 (m, 1H), 3.50-3.44 (m, 3H), 3.31-3.29 (m, 3H), 2.90-2.78 (m, 3H), 2.31-2.28 (m, 2H), 2.26 (s, 6H), 1.86-1.60 (m, 8H), 1.40-1.36 (m, 3H). |
| 173 | 906.1 (M + H)⁺ | (400 MHZ, DMSO-d6) δ 11.61 (brs, 1H), 7.85-7.80 (m, 3H), 7.52 (s, 1H), 7.47-7.38 (m, 1H), 7.28-7.24 (m, 1H), 7.20-7.05 (m, 3H), 6.99-6.80 (m, 2H), 5.65-5.60 (m, 1H), 4.40-4.35 (m, 1H), 4.02-3.89 (m, 2H), 3.69-3.40 (m, 4H), 3.17-3.10 (m, 2H), 2.95-2.80 (m, 3H), 2.24-2.21 (m, 6H), 1.82-1.64 (m, 7H), 1.61-1.35 (m, 4H), 1.20-0.88 (m, 7H). |
| 174 | 892.5 (M + H)⁺ | (400 MHZ, DMSO-d6) δ 11.54 (brs, 1H), 7.53 (m, 2H), 7.49-7.46 (m, 1H), 7.43 (d, J = 8.4 Hz, 1H), 7.39-7.37 (m, 1H), 7.27 (d, J = 8.0 Hz, 1H), 7.16 (d, J = 6.4 Hz, 2H), 6.93 (s, 1H), 6.88 (s, 1H), 6.82 (s, 1H), 5.57 (m, 1H), 4.49-4.42 (m, 3H), 4.00-3.97 (m, 2H), 3.58-3.46 (m, |

| Compound No. | LC-MS: m/z | ¹H NMR |
|---|---|---|
| | | 3H), 3.00-2.88 (m, 2H), 2.86 (s, 3H), 2.25 (d, J = 0.8 Hz, 6H), 1.78-1.65 (m, 8H), 1.46 (s, 3H), 1.19 (s, 3H). |
| 175 | 892.5 (M + H)⁺ | (400 MHZ, DMSO-d6) δ 11.56 (brs, 1H), 7.53-7.46 (m, 3H), 7.43 (d, J = 8.4 Hz, 1H), 7.39-7.37 (m, 1H), 7.27 (d, J = 8.4 Hz, 1H), 7.16 (d, J = 6.4 Hz, 2H), 6.94 (s, 1H), 6.87-6.82 (m, 2H), 5.57 (m, 1H), 4.48-4.41 (m, 3H), 4.00-3.97 (m, 2H), 3.59-3.46 (m, 3H), 2.91-2.88 (m, 2H), 2.85 (s, 3H), 2.25 (s, 6H), 1.77-1.63 (m, 8H), 1.46 (m, 3H), 1.20 (s, 3H). |
| 176 | (M + H)⁺ | (400 MHZ, DMSO-d6) δ 7.63 (m, 4H), 7.51 (s, 1H), 7.43 (d, J = 8.4 Hz, 1H), 7.26 (d, J = 8.4 Hz, 1H), 7.23-7.20 (m, 1H), 7.15 (d, J = 6.0 Hz, 2H), 6.88-6.81 (m, 2H), 5.56 (m, 1H), 4.44 (m, 1H), 4.00-3.97 (m, 2H), 3.52-3.46 (m, 3H), 2.91-2.84 (m, 2H), 2.74 (s, 3H), 2.22 (s, 6H), 1.78-1.64 (m, 8H), 1.58-1.53 (m, 1H), 1.41-1.37 (m, 3H), 1.27-1.16 (m, 6H). |
| 177 | 450.9 (M + H)⁺ | (400 MHZ, DMSO-d6) δ 7.64 (m, 4H), 7.48 (s, 1H), 7.42 (d, J = 8.4 Hz, 1H), 7.23-7.14 (m, 4H), 6.89 (m, 1H), 6.75 (m, 1H), 5.56 (m, 1H), 4.42 (m, 1H), 4.00-3.97 (m, 2H), 3.52-3.46 (m, 2H), 3.37 (m, 1H), 2.88-2.84 (m, 2H), 2.74 (s, 3H), 2.21 (s, 6H), 1.76-1.70 (m, 6H), 1.65 (m, 2H), 1.57-1.53 (m, 1H), 1.37 (m, 3H), 1.27-1.14 (m, 6H). |
| 178 | 918.4 (M + H)⁺ | (400 MHz, DMSO-d6) δ 11.60 (brs, 1H), 7.84-7.71 (m, 3H), 7.52 (s, 1H), 7.44-7.41 (d, J = 8.4 Hz, 1H), 7.27-7.25 (d, J = 8.4 Hz, 1H), 7.16-7.15 (d, J = 6.4 Hz, 2H), 7.02 (s, 1H), 6.88-6.84 (m, 2H), 5.56 (m, 1H), 4.44 (m, 1H), 4.17 (m, 1H), 3.99-3.97 (m, 2H), 3.52-3.46 (m, 3H), 3.19-3.17 (m, 2H), 2.92-2.84 (m, 2H), 2.24 (s, 6H), 1.76-1.72 (m, 7H), 1.64-1.63 (m, 1H), 1.45 (s, 3H), 1.19 (s, 3H), 0.96-0.93 (m, 1H), 0.48-0.46 (m, 2H), 0.15 (m, 2H). |
| 179 | 923.3 (M + H)⁺ | (400 MHZ, DMSO-d6) δ 13.5 (brs, 1H), 7.95-7.85 (m, 4H), 7.54 (s, 1H), 7.42-7.36 (m, 2H), 7.23-7.20 (m, 1H), 7.14 (d, J = 4.0 Hz, 2H), 7.00-6.95 (m, 1H), 6.82 (s, 1H), 5.56-5.54 (m, 1H), 4.47-4.45 (m, 1H), 4.06 (s, 1H), 4.00-3.97 (m, 2H), 3.53-3.46 (m, 3H), 2.92-2.79 (m, 3H), 2.69-2.62 (m, 1H), 2.23-2.21 (m, 6H), 1.86-1.55 (m, 8H), 1.35-1.26 (m, 3H), 1.14-1.09 (m, 1H), 1.03-0.86 (m, 3H). |
| 180 | 946.7 (M + H)⁺ | (400 MHZ, DMSO-d6) δ 11.55 (brs, 1H), 7.78-7.75 (m, 3H), 7.51 (s, 1H), 7.42 (d, J = 8.4 Hz, 1H), 7.24 (d, J = 8.0 Hz, 1H), 7.16 (d, J = 6.4 Hz, 2H), 7.04 (s, 1H), 6.89-6.76 (m, 2H), 5.54 (m, 1H), 4.40 (m, 1H), 3.74 (d, J = 9.2 Hz, 2H), 3.51 (m, 1H), 2.83 (m, 1H), 2.79 (m, 1H), 2.59 (s, 3H), 2.24 (s, 6H), 1.73-1.55 (m, 8H), 1.44 (s, 3H), 1.30-1.21 (m, 11H), 1.10 (m, 1H), 0.98-0.90 (m, 2H). |
| 181 | 932.6 (M + H)⁺ | (400 MHZ, DMSO-d6) δ 11.61 (brs, 1H), 7.84-7.72 (m, 3H), 7.54 (s, 1H), 7.42 (d, J = 8.4 Hz, 1H), 7.26 (d, J = 8.4 Hz, 1H), 7.16 (d, J = 6.4 Hz, 2H), 7.04 (s, 1H), 6.87 (m, 2H), 5.59 (m, 1H), 4.42 (m, 1H), 4.22 (m, 1H), 3.74 (d, J = 8.8 Hz, 2H), 3.55 (m, 1H), 2.90-2.86 (m, 1H), 2.76 (m, 1H), 2.25 (s, 6H), 1.73-1.45 (m, 11H), 1.30-1.21 (m, 4H), 1.19-1.17 (m, 7H), 1.06-0.97 (m, 3H). |
| 182 | 914.8 (M + H)⁺ | (400 MHZ, DMSO-d6) δ 7.60-7.45 (m, 3H), 7.43-7.30 (m, 3H), 7.26-7.20 (m, 2H), 7.13 (d, J = 8.0 Hz, 2H), 6.92-6.80 (m, 2H), 5.62-5.55 (m, 1H), 4.50-4.35 (m, 1H), 4.00-3.93 (m, 2H), 3.55-3.40 (m, 4H), 3.05-2.99 (m, 3H), 2.95-2.80 (m, 3H), 2.21-2.19 (m, 6H), 2.18-2.00 (m, 5H), 1.85-1.55 (m, 7H), 1.45-1.30 (m, 4H), 1.20-1.05 (m, 3H). |
| 183 | 946.1 (M + H)⁺ | (400 MHZ, DMSO-d6) δ 11.61 (brs, 1H), 7.81-7.68 (m, 3H), 7.53 (s, 1H), 7.42 (d, J = 8.4 Hz, 1H), 7.26 (d, J = 8.4 Hz, 1H), 7.15 (d, J = 6.4 Hz, 2H), 7.03 (s, 1H), 6.87 (m, 2H), 5.57 (m, 1H), 4.45 (m, 1H), 4.16 (m, 1H), 4.06-3.97 (m, 1H), 3.75-3.73 (m, 2H), 3.58-3.55 (m, 1H), 3.02-2.87 (m, 2H), 2.41-2.34 (m, 2H), 2.24 (s, 6H), 2.19-2.03 (m, 2H), 1.91-1.71 (m, 6H), 1.64-1.51 (m, 3H), 1.45 (m, 3H), 1.30 (s, 3H), 1.21-1.18 (m, 6H). |
| 184 | 946.6 (M + H)⁺ | (400 MHZ, DMSO-d6) δ 7.87-7.75 (m, 3H), 7.49 (s, 1H), 7.41 (d, J = 8.4 Hz, 1H), 7.22 (d, J = 8.4 Hz, 1H), 7.16 (d, J = 6.4 Hz, 2H), 7.01-6.78 (m, 3H), 5.69 (s, 1H), 4.41 (m, 1H), 4.17 (s, 1H), 3.75-3.73 (m, 2H), 3.52-3.48 (m, 1H), 3.18 (d, J = 7.2 Hz, 2H), 2.89-2.80 (m, 1H), 2.24 (s, 6H), 1.76-1.58 (m, 6H), 1.55-1.52 (m, 1H), 1.44-1.42 (m, 3H), 1.30-1.27 (m, 4H), 1.21 (s, 6H), 0.98-0.90 (m, 1H), 0.49-0.46 (m, 2H), 0.16-0.15 (m, 2H). |
| 185 | 932.8 (M + H)⁺ | (400 MHZ, DMSO-d6) δ 11.64 (brs, 1H), 7.89 (m, 1H), 7.61 (m, 1H), 7.51 (s, 1H), 7.42 (d, J = 8.8 Hz, 1H), 7.25 (d, J = 8.8 Hz, 1H), 7.16 (d, J = 6.4 Hz, 2H), 6.99 (s, 1H), 6.88-6.74 (m, 2H), 5.56 (m, 1H), 4.41 (m, 1H), 3.74 (d, J = 9.2 Hz, 2H), 3.48-3.45 (m, 2H), 3.25 (s, 3H), 2.88-2.79 (m, 2H), 2.69-2.60 (m, 1H), 2.24 (s, 6H), 1.73-1.55 (m, 8H), 1.45-1.39 (m, 3H), 1.30 (s, 4H), 1.21-1.15 (m, 7H). |
| 186 | 932.8 (M + H)⁺ | (400 MHZ, DMSO-d6) δ 11.62 (brs, 1H), 7.88 (m, 1H), 7.60 (m, 1H), 7.50 (s, 1H), 7.42 (d, J = 8.8 Hz, 1H), 7.23 (d, J = 8.4 Hz, 1H), 7.16 (d, J = 6.4 Hz, 2H), 6.97 (s, 1H), 6.89-6.71 (m, 2H), 5.56 (m, 1H), 4.40 (m, 1H), 3.74 (d, J = 8.0 Hz, 2H), 3.48-3.45 (m, 2H), 3.25 (s, 3H), 2.85-2.77 (m, 2H), 2.68-2.60 (m, 1H), 2.24 (s, 6H), 1.73-1.55 (m, 8H), 1.43 (m, 3H), 1.30 (s, 4H), 1.21 (m, 7H). |

| Compound No. | LC-MS: m/z | ¹H NMR |
|---|---|---|
| 187 | 918.8 (M + H)⁺ | (400 MHZ, DMSO-d6) δ 11.60 (brs, 1H), 7.97 (m, 1H), 7.79-7.70 (m, 1H), 7.51 (s, 1H), 7.41 (d, J = 8.0 Hz, 1H), 7.25 (d, J = 8.4 Hz, 1H), 7.15 (d, J = 6.4 Hz, 2H), 7.02 (m, 1H), 6.90-6.79 (m, 2H), 5.69-5.55 (m, 1H), 4.82 (d, J = 17.2 Hz, 1H), 4.68 (d, J = 18.0 Hz, 1H), 4.48-4.33 (m, 1H), 3.74 (d, J = 8.8 Hz, 2H), 3.46 (s, 3H), 2.89-2.84 (m, 1H), 2.24 (s, 6H), 1.78-1.69 (m, 4H), 1.61-1.54 (m, 4H), 1.40 (m, 3H), 1.29 (m, 4H), 1.20 (m, 7H). |
| 188 | 918.8 (M + H)⁺ | (400 MHZ, DMSO-d6) δ 11.57 (brs, 1H), 7.99 (m, 1H), 7.77 (m, 1H), 7.51 (s, 1H), 7.41 (d, J = 8.8 Hz, 1H), 7.25 (d, J = 8.4 Hz, 1H), 7.16 (d, J = 6.4 Hz, 2H), 7.02 (m, 1H), 6.89-6.84 (m, 2H), 5.68 (m, 1H), 4.82 (d, J = 17.6 Hz, 1H), 4.68 (d, J = 17.6 Hz, 1H), 4.43-4.39 (m, 1H), 3.74 (d, J = 9.2 Hz, 2H), 3.46 (s, 3H), 2.88-2.85 (m, 1H), 2.24 (s, 6H), 1.72-1.70 (m, 4H), 1.61-1.54 (m, 4H), 1.44 (m, 3H), 1.29 (m, 4H), 1.20 (m, 7H). |
| 189 | 946.7 (M + H)⁺ | (400 MHZ, DMSO-d6) δ 11.60 (brs, 1H), 7.83 (d, J = 9.6 Hz, 1H), 7.57-7.53 (m, 2H), 7.42 (d, J = 8.8 Hz, 1H), 7.27 (dd, J₁ = 8.4 Hz, J₂ = 1.2 Hz, 1H), 7.15 (d, J = 6.4 Hz, 2H), 7.00 (s, 1H), 6.86 (s, 2H), 5.57 (m, 1H), 4.45 (m, 1H), 3.75-3.73 (m, 2H), 3.56 (m, 1H), 2.91-2.86 (m, 3H), 2.72 (s, 3H), 2.25 (s, 6H), 1.75-1.70 (m, 4H), 1.62-1.58 (m, 2H), 1.54-1.51 (m, 2H), 1.47-1.38 (m, 3H), 1.29-1.25 (m, 4H), 1.21 (m, 6H), 1.09-1.01 (m, 4H). |
| 190 | 946.7 (M + H)⁺ | (400 MHz, DMSO-d6) δ 11.63 (brs, 1H), 7.83 (d, J = 9.6 Hz, 1H), 7.57-7.52 (m, 2H), 7.41 (d, J = 8.4 Hz, 1H), 7.26 (dd, J₁ = 8.4 Hz, J₂ = 0.8 Hz, 1H), 7.15 (d, J = 6.0 Hz, 2H), 7.00 (s, 1H), 6.86 (s, 2H), 5.58 (m, 1H), 4.43 (m, 1H), 3.74-3.72 (m, 2H), 3.55 (m, 1H), 2.91-2.85 (m, 3H), 2.71 (s, 3H), 2.24 (s, 6H), 1.84-1.71 (m, 4H), 1.63-1.54 (m, 4H), 1.45 (m, 3H), 1.29 (m, 4H), 1.18 (m, 6H), 1.10-1.02 (m, 4H). |
| 191 | 944.6 (M + H)⁺ | (400 MHz, DMSO-d6) δ 11.60 (brs, 1H), 7.90 (m, 1H), 7.75 (m, 1H), 7.52 (s, 1H), 7.41 (d, J = 8.4 Hz, 1H), 7.26 (d, J = 8.0 Hz, 1H), 7.16 (d, J = 6.4 Hz, 2H), 7.03 (m, 1H), 6.85 (m, 2H), 5.57 (m, 1H), 4.79 (d, J = 18.4 Hz, 1H), 4.63 (d, J = 18.0 Hz, 1H), 4.44 (m, 1H), 3.74-3.72 (m, 2H), 3.58 (m, 1H), 3.01-2.85 (m, 3H), 2.24 (s, 6H), 1.72-1.70 (m, 4H), 1.64-1.45 (m, 8H), 1.29 (s, 3H), 1.20-1.16 (m, 7H), 1.01 (m, 1H), 0.71 (m, 1H). |
| 192 | 944.6 (M + H)⁺ | (400 MHz, DMSO-d6) δ 11.61 (brs, 1H), 7.90 (m, 1H), 7.77 (m, 1H), 7.52 (s, 1H), 7.41 (d, J = 8.8 Hz, 1H), 7.26 (d, J = 8.8 Hz, 1H), 7.16 (d, J = 6.4 Hz, 2H), 7.03 (m, 1H), 6.86 (m, 2H), 5.57 (m, 1H), 4.80 (d, J = 18.0 Hz, 1H), 4.63 (d, J = 17.6 Hz, 1H), 4.47 (m, 1H), 3.74-3.72 (m, 2H), 3.56 (m, 1H), 2.98-2.85 (m, 3H), 2.24 (s, 6H), 1.72-1.70 (m, 4H), 1.64-1.45 (m, 8H), 1.29 (s, 3H), 1.20-1.16 (m, 7H), 1.00 (m, 1H), 0.71 (m, 1H). |
| 193 | 960.3 (M + H)⁺ | (400 MHz, DMSO-d6) δ 11.61 (brs, 1H), 7.73 (m, 1H), 7.61 (s, 1H), 7.53 (s, 1H), 7.43 (d, J = 8.4 Hz, 1H), 7.27 (d, J = 8.4 Hz, 1H), 7.16 (d, J = 6.0 Hz, 2H), 7.03 (s, 2H), 6.87 (m, 2H), 5.56 (m, 1H), 4.45 (m, 2H), 3.75 (d, J = 9.2 Hz, 2H), 3.56 (s, 1H), 2.91-2.86 (m, 2H), 2.67 (s, 3H), 2.56 (s, 3H), 2.25 (s, 6H), 1.74-1.70 (m, 4H), 1.64-1.54 (m, 4H), 1.47-1.46 (m, 3H), 1.30 (s, 4H), 1.21 (s, 4H), 1.15-1.13 (m, 2H), 0.94-0.84 (m, 3H). |
| 194 | 960.7 (M + H)⁺ | (400 MHz, DMSO-d6) δ 11.60 (brs, 1H), 7.73-7.70 (m, 1H), 7.60 (m, 1H), 7.52 (s, 1H), 7.41 (d, J = 8.8 Hz, 1H), 7.25 (d, J = 8.4 Hz, 1H), 7.15 (d, J = 6.4 Hz, 2H), 7.02 (s, 1H), 6.87 (s, 2H), 5.57 (m, 1H), 4.45 (m, H2), 3.74-3.72 (m, 2H), 3.57 (m, 1H), 2.90-2.87 (m, 2H), 2.65 (s, 3H), 2.55 (s, 3H), 2.24 (s, 6H), 1.73-1.69 (m, 4H), 1.63-1.46 (m, 6H), 1.29-1.26 (m, 6H), 1.20-1.10 (m, 7H), 0.95-0.82 (m, 2H). |
| 195 | 960.8 (M + H)⁺ | (400 MHz, DMSO-d6) δ 11.58 (brs, 1H), 7.77-7.74 (m, 1H), 7.65-7.52 (m, 2H), 7.42 (d, J = 8.8 Hz, 1H), 7.27-7.24 (dd, J₁ = 8.8 Hz, J₂ = 1.6 Hz, 1H), 7.16 (d, J = 6.0 Hz, 2H), 7.02 (m, 1H), 6.87 (m, 2H), 5.62 5.54 (m, 1H), 4.44 (m, 1H), 3.74 (d, J = 9.2 Hz, 2H), 3.57 (m, 1H), 3.03 (m, 2H), 2.90-2.86 (m, 2H), 2.63 (s, 3H), 2.56 (s, 3H), 2.25 (s, 6H), 1.72-1.54 (m, 7H), 1.51-1.45 (m, 3H), 1.29 (m, 4H), 1.20-1.12 (m, 7H), 0.94-0.83 (m, 2H). |
| 196 | 960.8 (M + H)⁺ | (400 MHz, DMSO-d6) δ 11.58 (brs, 1H), 7.75 (m, 1H), 7.64-7.53 (m, 2H), 7.41 (d, J = 8.4 Hz, 1H), 7.26 (d, J = 8.8 Hz, 1H), 7.16 (d, J = 6.0 Hz, 2H), 7.01 (m, 1H), 6.87 (m, 2H), 5.57 (m, 1H), 4.43 (m, 1H), 3.74 (d, J = 8.8 Hz, 2H), 3.58 (m, 1H), 3.04-3.01 (m, 2H), 2.90-2.86 (m, 2H), 2.63 (s, 3H), 2.56 (s, 3H), 2.24 (s, 6H), 1.72-1.63 (m, 4H), 1.62-1.46 (m, 6H), 1.29 (m, 4H), 1.20-1.12 (m, 7H), 0.94-0.81 (m, 2H). |
| 197 | 958.8 (M + H)⁺ | (400 MHz, DMSO-d6) δ 11.73 (brs, 1H), 7.95 (d, J = 8.0 Hz, 1H), 7.69 (t, J = 7.6 Hz, 1H), 7.53 (s, 1H), 7.41 (d, J = 8.4 Hz, 1H), 7.27 (d, J = 8.8 Hz, 1H), 7.16-7.14 (m, 3H), 7.01 (m, 1H), 6.94 (m, 1H), 5.57 (m, 1H), 4.39-4.37 (m, 1H), 3.72-3.70 (m, 3H), 3.44-3.42 (m, 2H), 3.06-3.03 (m, 1H), 2.90-2.85 (m, 2H), 2.67-2.65 (m, 1H), 2.24 (s, 6H), 1.72-1.52 (m, 8H), 1.42-1.40 (m, 4H), 1.32-1.27 (m, 4H), 1.23-1.10 (m, 7H), 0.94-0.82 (m, 2H). |

-continued

| Compound No. | LC-MS: m/z | ¹H NMR |
|---|---|---|
| 198 | 958.8 (M + H)⁺ | (400 MHZ, DMSO-d6) δ 11.74 (brs, 1H), 7.95 (d, J = 8.0 Hz, 1H), 7.69 (t, J = 7.6 Hz, 1H), 7.53 (s, 1H), 7.41 (d, J = 8.4 Hz, 1H), 7.27 (d, J = 8.8 Hz, 1H), 7.16-7.14 (m, 3H), 7.00 (m, 1H), 6.94 (m, 1H), 5.57 (m, 1H), 4.39-4.37 (m, 1H), 3.72-3.70 (m, 3H), 3.44-3.42 (m, 2H), 3.06-3.03 (m, 1H), 2.90-2.85 (m, 3H), 2.67-2.65 (m, 1H), 2.24 (s, 6H), 1.72-1.52 (m, 8H), 1.42-1.40 (m, 4H), 1.32-1.27 (m, 4H), 1.23-1.09 (m, 7H), 0.90-0.81 (m, 2H). |
| 199 | 918.6 (M + H)⁺ | (400 MHZ, DMSO-d6) δ 11.63 (brs, 1H), 8.19 (m, 1H), 7.79 (m, 1H), 7.52 (s, 1H), 7.41 (d, J = 8.4 Hz, 1H), 7.26 (d, J = 8.8 Hz, 1H), 7.16 (d, J = 6.4 Hz, 2H), 7.02 (s, 1H), 6.87 (m, 2H), 5.58 (m, 1H), 4.73 (d, J = 17.2 Hz, 1H), 4.58 (d, J = 19.2 Hz, 1H), 4.42 (m, 1H), 3.74-3.72 (m, 2H), 3.57 (m, 1H), 3.44 (s, 3H), 2.91-2.84 (m, 1H), 2.25 (s, 6H), 1.73-1.69 (m, 4H), 1.63-1.54 (m, 4H), 1.46 (m, 3H), 1.29 (m, 4H), 1.20 (m, 6H). |
| 200 | 918.6 (M + H)⁺ | (400 MHZ, DMSO-d6) δ 11.62 (brs, 1H), 8.19 (m, 1H), 7.80 (m, 1H), 7.52 (s, 1H), 7.41 (d, J = 8.4 Hz, 1H), 7.26 (d, J = 8.8 Hz, 1H), 7.15 (d, J = 6.4 Hz, 2H), 7.02 (s, 1H), 6.87 (m, 2H), 5.56 (m, 1H), 4.73 (d, J = 16.8 Hz, 1H), 4.58 (d, J = 16.0 Hz, 1H), 4.45 (m, 1H), 3.74 (d, J = 8.8 Hz, 2H), 3.58 (m, 1H), 3.44 (s, 3H), 2.89-2.85 (m, 1H), 2.25 (s, 6H), 1.75-1.69 (m, 4H), 1.63-1.51 (m, 4H), 1.46 (m, 3H), 1.29 (m, 4H), 1.20 (m, 6H). |
| 201 | 934.6 (M + H)⁺ | (400 MHZ, DMSO-d6) δ 8.11 (m, 1H), 7.71 (m, 1H), 7.50 (s, 1H), 7.41 (d, J = 8.0 Hz, 1H), 7.24 (d, J = 8.8 Hz, 1H), 7.17 (d, J = 6.4 Hz, 2H), 6.90 (m, 2H), 6.81 (m, 1H), 5.57 (m, 1H), 4.69-4.55 (m, 2H), 4.41 (m, 1H), 3.73 (d, J = 8.8 Hz, 2H), 3.47 (m, 3H), 2.85 (m, 1H), 2.25 (s, 6H), 1.73-1.55 (m, 8H), 1.45 (m, 3H), 1.38-1.34 (m, 1H), 1.29 (m, 3H), 1.20 (m, 6H), 0.92-0.88 (m, 1H). |
| 202 | 934.6 (M + H)⁺ | (400 MHZ, DMSO-d6) δ 8.15-8.13 (m, 1H), 7.72 (m, 1H), 7.51 (s, 1H), 7.41 (d, J = 8.8 Hz, 1H), 7.24 (d, J = 8.0 Hz, 1H), 7.18 (d, J = 6.4 Hz, 2H), 6.95-6.90 (m, 2H), 6.81 (m, 1H), 5.62-5.48 (m, 1H), 4.69-4.57 (m, 2H), 4.41 (m, 1H), 3.73 (d, J = 8.8 Hz, 2H), 3.47 (m, 3H), 2.88-2.82 (m, 1H), 2.25 (s, 6H), 1.73-1.52 (m, 8H), 1.45 (m, 3H), 1.38-1.34 (m, 1H), 1.29 (m, 3H), 1.20 (m, 6H), 0.92-0.87 (m, 1H). |
| 203 | 962.2 (M + H)⁺ | (400 MHz, DMSO-d6) δ 11.68 (brs, 1H), 7.90-7.70 (m, 3H), 7.53 (s, 1H), 7.41 (d, J = 8.0 Hz, 1H), 7.30-7.24 (m, 3H), 7.15-7.10 (m, 3H), 7.00-6.85 (m, 2H), 5.65-5.60 (m, 1H), 4.45-4.35 (m, 1H), 3.75 (d, J = 8.8 Hz, 2H), 3.65-3.55 (m, 1H), 3.05-3.02 (m, 1H), 3.00-2.75 (m, 2H), 2.58 (s, 3H), 2.40-2.36 (m, 6H), 1.80-1.69 (m, 4H), 1.66-1.40 (m, 7H), 1.29 (s, 3H), 1.28-1.22 (m, 3H), 1.20 (s, 3H), 1.15-1.04 (m, 2H), 1.00-0.85 (m, 2H). |
| 204 | 962.0 (M + H)⁺ | (400 MHz, DMSO-d6) δ 11.62 (brs, 1H), 8.00-7.70 (m, 3H), 7.52 (s, 1H), 7.41-7.37 (m, 1H), 7.28-7.20 (m, 1H), 7.15 (d, J = 4.0 Hz, 2H), 7.05-6.80 (m, 3H), 5.65-5.58 (m, 1H), 4.45-4.30 (m, 1H), 3.73 (d, J = 8.8 Hz, 2H), 3.64-3.50 (m, 1H), 3.06-2.99 (m, 1H), 2.90-2.80 (m, 2H), 2.56 (s, 3H), 2.25-2.23 (m, 6H), 1.75-1.68 (m, 4H), 1.65-1.37 (m, 7H), 1.28 (s, 3H), 1.26-1.21 (m, 2H), 1.19 (s, 3H), 1.18-1.15 (m, 1H), 1.14-1.05 (m, 2H), 0.98-0.84 (m, 2H). |
| 205 | 961.9 (M + H)⁺ | (400 MHz, DMSO-d6) δ 11.65 (brs, 1H), 8.05-7.70 (m, 3H), 7.51 (s, 1H), 7.41-7.37 (m, 1H), 7.24 (d, J = 8.0 Hz, 1H), 7.15 (d, J = 4.0 Hz, 2H), 7.05-6.80 (m, 3H), 5.65-5.58 (m, 1H), 4.45-4.30 (m, 1H), 3.73 (d, J = 8.8 Hz, 2H), 3.64-3.50 (m, 1H), 3.06-2.99 (m, 1H), 2.90-2.80 (m, 2H), 2.57 (s, 3H), 2.25-2.23 (m, 6H), 1.75-1.68 (m, 4H), 1.65-1.37 (m, 7H), 1.28 (s, 3H), 1.26-1.21 (m, 2H), 1.19 (s, 3H), 1.16-1.14 (m, 1H), 1.13-1.05 (m, 2H), 0.99-0.84 (m, 2H). |
| 206 | 926.2 (M + H)⁺ | (400 MHz, DMSO-d6) δ 11.62 (brs, 1H), 8.09-8.06 (m, 1H), 7.69-7.58 (m, 2H), 7.51 (s, 1H), 7.42 (d, J = 8.8 Hz, 1H), 7.31-7.25 (m, 2H), 7.15 (d, J = 6.0 Hz, 2H), 6.91-6.85 (m, 2H), 6.00 (m, 1H), 5.56 (m, 1H), 4.45 (m, 1H), 3.73 (d, J = 7.6 Hz, 2H), 3.66 (s, 3H), 2.90-2.86 (m, 1H), 2.21 (s, 6H), 2.13 (s, 3H), 1.78-1.58 (m, 7H), 1.53-1.42 (m, 5H), 1.28 (s, 3H), 1.19-1.15 (m, 7H). |
| 207 | 926.2 (M + H)⁺ | (400 MHz, DMSO-d6) δ 11.47 (brs, 1H), 8.06 (m, 1H), 7.67-7.57 (m, 2H), 7.51 (s, 1H), 7.42 (d, J = 8.4 Hz, 1H), 7.31-7.24 (m, 2H), 7.15 (d, J = 6.4 Hz, 2H), 6.92-6.85 (m, 2H), 6.01 (m, 1H), 5.58 (m, 1H), 4.42 (m, 1H), 3.73 (d, J = 7.6 Hz, 2H), 3.66 (s, 3H), 2.90-2.84 (m, 1H), 2.21 (s, 6H), 2.12 (s, 3H), 1.78-1.57 (m, 7H), 1.53-1.43 (m, 5H), 1.29 (s, 3H), 1.22-1.19 (m, 7H). |
| 208 | 960.0 (M + H)⁺ | (400 MHz, DMSO-d6) δ 11.60 (brs, 1H), 7.90-7.72 (m, 3H), 7.51 (s, 1H), 7.41 (d, J = 8.0 Hz, 1H), 7.24 (d, J = 8.0 Hz, 1H), 7.20-7.08 (m, 3H), 7.00-6.85 (m, 2H), 5.75-5.60 (m, 1H), 4.50-4.47 (m, 1H), 3.80-3.70 (m, 3H), 3.08-2.81 (m, 6H), 2.24-2.20 (m, 6H), 1.90-1.51 (m, 8H), 1.47-1.38 (m, 2H), 1.30-1.20 (m, 10H), 1.12-1.05 (m, 4H), 0.95-0.85 (m, 2H). |
| 209 | 972.5 (M + H)⁺ | (400 MHz, DMSO-d6) δ 11.68 (brs, 1H), 7.88-7.78 (m, 3H), 7.53 (s, 1H), 7.41 (d, J = 8.0 Hz, 1H), 7.26 (d, J = 8.0 Hz, 1H), 7.20-7.10 (m, 3H), 7.00-6.85 (m, 2H), 5.75-5.60 (m, 1H), 4.45-4.30 (m, 1H), 3.82-3.46 (m, 3H), 3.08-2.99 (m, 2H), 2.90-2.80 (m, 2H), 2.42-2.33 (m, |

| Compound No. | LC-MS: m/z | ¹H NMR |
|---|---|---|
| | | 1H), 2.25-2.23 (m, 6H), 1.85-1.38 (m, 10H), 1.31-1.20 (m, 10H), 1.14-1.08 (m, 1H), 0.95-0.85 (m, 2H), 0.48-0.35 (m, 3H), 0.30-0.25 (m, 1H). |
| 210 | 970.3 (M + H)⁺ | (400 MHZ, DMSO-d6) δ 11.64 (brs, 1H), 7.92 (d, J = 8.4 Hz, 1H), 7.52-7.48 (m, 2H), 7.43 (d, J = 8.0 Hz, 1H), 7.27 (d, J = 8.0 Hz, 1H), 7.16 (d, J = 6.0 Hz, 2H), 7.03 (s, 1H), 6.88 (m, 2H), 6.14 (s, 1H), 5.72-5.60 (m, 1H), 4.45-4.30 (m, 1H), 3.74 (d, J = 7.6 Hz, 2H), 3.60-3.56 (m, 1H), 3.32-3.29 (m, 1H), 2.90-2.87 (m, 1H), 2.25 (s, 6H), 2.20 (s, 3H), 1.85-1.80 (m, 4H), 1.74-1.70 (m, 3H), 1.63-1.62 (m, 2H), 1.51-1.35 (m, 4H), 1.29 (m, 4H), 1.25-1.10 (m, 7H), 1.03-1.00 (m, 1H). |
| 211 | 970.3 (M + H)⁺ | (400 MHz, DMSO-d6) δ 11.63 (brs, 1H), 7.90 (m, 1H), 7.52-7.48 (m, 2H), 7.43 (d, J = 8.4 Hz, 1H), 7.27 (d, J = 8.0 Hz, 1H), 7.16 (d, J = 6.0 Hz, 2H), 7.04 (s, 1H), 6.88 (m, 2H), 6.14 (s, 1H), 5.72-5.60 (m, 1H), 4.45-4.30 (m, 1H), 3.74 (d, J = 7.6 Hz, 2H), 3.60-3.56 (m, 1H), 3.32-3.29 (m, 1H), 2.90-2.87 (m, 1H), 2.25 (s, 6H), 2.20 (s, 3H), 1.85-1.80 (m, 4H), 1.75-1.72 (m, 4H), 1.63-1.62 (m, 3H), 1.51-1.35 (m, 4H), 1.29 (m, 4H), 1.25-1.10 (m, 7H), 1.04-1.01 (m, 1H). |
| 212 | 954.9 (M + H)⁺ | (400 MHZ, DMSO-d6) δ 11.59 (brs, 1H), 7.78 (m, 2H), 7.68 (m, 1H), 7.52 (s, 1H), 7.43 (d, J = 8.4 Hz, 1H), 7.32 (s, 1H), 7.26 (d, J = 7.2 Hz, 1H), 7.16 (d, J = 6.0 Hz, 2H), 6.92 (m, 1H), 6.86 (m, 2H), 5.72-5.60 (m, 1H), 4.45-4.30 (m, 1H), 3.75 (d, J = 7.6 Hz, 2H), 3.60-3.54 (m, 1H), 3.26-3.19 (m, 2H), 2.91-2.76 (m, 3H), 2.22 (s, 6H), 2.04 (m, 1H), 1.75-1.67 (m, 5H), 1.66-1.62 (m, 2H), 1.57-1.51 (m, 2H), 1.42 (m, 3H), 1.29-1.27 (m, 4H), 1.20-1.15 (m, 8H), 1.04-1.01 (m, 2H), 0.94-0.90 (m, 1H). |
| 213 | 954.9 (M + H)⁺ | (400 MHZ, DMSO-d6) δ 11.61 (brs, 1H), 7.79 (m, 2H), 7.68 (m, 1H), 7.52 (s, 1H), 7.43 (d, J = 8.4 Hz, 1H), 7.32 (s, 1H), 7.26 (d, J = 7.2 Hz, 1H), 7.16 (d, J = 6.0 Hz, 2H), 6.91 (m, 1H), 6.86 (m, 2H), 5.72-5.60 (m, 1H), 4.45-4.30 (m, 1H), 3.74 (d, J = 7.6 Hz, 2H), 3.60-3.54 (m, 1H), 3.26-3.17 (m, 2H), 2.89-2.79 (m, 3H), 2.22 (s, 6H), 2.04 (m, 1H), 1.75-1.67 (m, 5H), 1.65-1.61 (m, 2H), 1.57-1.51 (m, 2H), 1.42 (m, 3H), 1.29-1.27 (m, 4H), 1.20-1.15 (m, 8H), 1.05-1.03 (m, 2H), 0.93-0.90 (m, 1H). |
| 214 | 980.3 (M + H)⁺ | (400 MHZ, DMSO-d6) δ 11.64 (brs, 1H), 7.89-7.81 (m, 2H), 7.53 (s, 1H), 7.42 (d, J = 8.0 Hz, 1H), 7.27 (d, J = 8.0 Hz, 1H), 7.16-7.15 (m, 3H), 6.97-6.92 (m, 2H), 5.70-5.60 (m, 1H), 4.40-4.30 (m, 1H), 3.73 (d, J = 7.6 Hz, 2H), 3.60-3.54 (m, 1H), 3.26-3.10 (m, 3H), 2.89-2.81 (m, 1H), 2.54 (s, 3H), 2.25 (s, 6H), 1.75-1.65 (m, 4H), 1.65-1.47 (m, 6H), 1.37-1.33 (m, 2H), 1.30 (m, 3H), 1.29-1.27 (m, 6H), 1.00-0.96 (m, 1H), 0.86-0.84 (m, 1H). |
| 215 | 980.3 (M + H)⁺ | (400 MHZ, DMSO-d6) δ 11.63 (brs, 1H), 7.87-7.79 (m, 2H), 7.51 (s, 1H), 7.41 (d, J = 8.0 Hz, 1H), 7.25 (d, J = 8.0 Hz, 1H), 7.14-7.13 (m, H3), 6.96-6.89 (m, 2H), 5.70-5.60 (m, 1H), 4.40-4.30 (m, 1H), 3.73 (d, J = 7.6 Hz, 2H), 3.60-3.54 (m, 1H), 3.26-3.10 (m, 3H), 2.89-2.81 (m, 1H), 2.54 (s, 3H), 2.25 (s, 6H), 1.73-1.63 (m, 4H), 1.61-1.45 (m, 6H), 1.37-1.33 (m, 2H), 1.31 (m, 3H), 1.29-1.27 (m, 6H), 1.00-0.95 (m, 1H), 0.86-0.84 (m, 1H). |
| 216 | 948.3 (M + H)⁺ | (400 MHz, DMSO-d6) δ 11.64 (brs, 1H), 7.81-7.77 (m, 1H), 7.60-7.52 (m, 1H), 7.42 (d, J = 8.4 Hz, 1H), 7.26 (d, J = 8.8 Hz, 1H), 7.17 (d, J = 6.0 Hz, 2H), 7.00 (m, 1H), 6.86-6.80 (m, 2H), 5.70-5.60 (m, 1H), 4.40-4.30 (m, 1H), 3.73 (d, J = 7.6 Hz, 2H), 3.60-3.54 (m, 1H), 3.31-3.25 (m, 2H), 3.10-3.05 (m, 1H), 2.89-2.81 (m, 1H), 2.85 (m, 1H), 2.58 (s, 3H), 2.56 (s, 3H), 2.25 (d, J = 1.6 Hz, 6H), 1.75-1.70 (m, 4H), 1.64-1.61 (m, 3H), 1.45 (m, 3H), 1.30 (s, 3H), 1.20-1.13 (m, 9H). |
| 217 | 972.3 (M + H)⁺ | (400 MHZ, DMSO-d6) δ 7.76 (m, 2H), 7.55-7.50 (m, 1H), 7.42 (d, J = 8.0 Hz, 1H), 7.28-7.22 (m, 3H), 7.01-7.00 (m, 2H), 6.92 (m, 1H), 6.79 (m, 1H), 5.70-5.60 (m, 1H), 4.40-4.30 (m, 1H), 3.73 (d, J = 7.6 Hz, 2H), 3.54-3.44 (m, 1H), 2.85-2.83 (m, 2H), 2.63 (s, 3H), 2.57 (s, 3H), 1.74-1.69 (m, 4H), 1.64-1.55 (m, 4H), 1.40 (m, 3H), 1.31-1.30 (m, 5H), 1.27-1.15 (m, 7H), 1.00-0.98 (m, 2H), 0.92-0.90 (m, 1H), 0.85-0.80 (m, 1H), 0.68-0.65 (m, 2H). |
| 218 | 957.6 (M + H)⁺ | (400 MHZ, DMSO-d6) δ 11.57 (brs, 1H), 7.57-7.47 (m, 2H), 7.42 (d, J = 8.4 Hz, 1H), 7.28 (s, 1H), 7.25 (d, J = 8.8 Hz, 1H), 7.16 (d, J = 6.0 Hz, 2H), 7.06-7.02 (m, 2H), 6.90 (m, 1H) 6.82 (m, 1H), 5.70-5.60 (m, 1 H), 4.40-4.30 (m, 1H), 3.75 (d, J = 8.0 Hz, 2H), 2.89-2.76 (m, 5H), 2.61 (s, 3H), 2.22 (s, 6H), 1.72-1.51 (m, 8H), 1.41 (m, 3H), 1.30-1.27 (m, 6H), 1.22-1.17 (m, 7H), 1.06-1.01 (m, 1H), 0.82-0.80 (m, 1H). |
| 219 | 988.3 (M + H)⁺ | (400 MHZ, DMSO-d6) δ 11.61 (brs, 1H), 7.79 (m, 1H), 7.61 (m, 1H), 7.52 (s, 1H), 7.40 (d, J = 8.0 Hz, 1H), 7.25 (d, J = 8.0 Hz, 1H), 7.14 (s, 2H), 7.06 (m, 1H), 6.92-6.88 (m, 2H), 5.70-5.60 (m, 1H), 4.38-4.28 (m, 2H), 3.72 (d, J = 7.6 Hz, 2H), 3.58-3.54 (m, 1H), 3.05-3.00 (m, 1H), 2.89-2.80 (m, 2H), 2.58 (s, 3H), 2.24 (d, J = 1.6 Hz, 6H), 1.72-1.67 (m, 4H), 1.63-1.50 (m, 6H), 1.45-1.20 (m, 11H), 1.27-1.18 (m, 7H), 0.98-0. 96 (m, 1H), 0.85-0.79 (m, 1H). |

| Compound No. | LC-MS: m/z | ¹H NMR |
|---|---|---|
| 220 | 988.3 (M + H)⁺ | (400 MHZ, DMSO-d6) δ 11.62 (brs, 1H), 7.79 (m, 1H), 7.61 (m, 1H), 7.51 (s, 1H), 7.40 (d, J = 8.0 Hz, 1H), 7.25 (d, J = 8.0 Hz, 1H), 7.14 (s, 2H), 7.07 (m, 1H), 6.92-6.88 (m, 2H), 5.70-5.60 (m, 1H), 4.38-4.28 (m, 2H), 3.72 (d, J = 7.6 Hz, 2H), 3.58-3.54 (m, 1H), 3.05-3.00 (m, 1H), 2.89-2.80 (m, 2H), 2.58 (s, 3H), 2.24 (d, J = 1.6 Hz, 6H), 1.72-1.67 (m, 4H), 1.63-1.50 (m, 6H), 1.45-1.20 (m, 11H), 1.27-1.18 (m, 7H), 0.98-0.96 (m, 1H), 0.85-0.79 (m, 1H). |
| 221 | 918.3 (M + H)⁺ | (400 MHZ, DMSO-d6) δ 11.60 (brs, 1H), 7.77-7.71 (m, 3H), 7.53 (s, H1), 7.44 (d, J = 8.4 Hz, 1H), 7.28 (d, J =9.2 Hz, 1H), 7.16 (d, J = 6.0 Hz, 2H), 7.05 (s, 1H), 6.88 (s, 2H), 5.58 (m, 1H), 4.46 (m, 1H), 4.00-3.97 (d, J = 10.8 Hz, 2H), 3.58-3.46 (m, 3H), 2.91-2.87 (m, 3H), 2.80-2.77 (m, 1H), 2.59 (s, 3H), 2.25 (s, 6H), 1.76-1.62 (m, 7H), 1.46 (m, 3H), 1.27-1.12 (m, 4H), 1.10-1.08 (m, 1H), 1.01-0.91 (m, 2H). |
| 222 | 918.3 (M + H)⁺ | (400 MHZ, DMSO-d6) δ 11.59 (brs, 1H), 7.78-7.75 (m, 3H), 7.53 (s, 1H), 7.44 (d, J = 8.4 Hz, 1H), 7.28 (d, J = 8.8 Hz, 1H), 7.16 (d, J = 6.4 Hz, 2H), 7.05 (s, 1H), 6.88 (s, 2H), 5.58 (m, 1H), 4.48 (m, 1H), 4.00-3.97 (m, 2H), 3.59-3.46 (m, 3H), 2.91-2.87 (m, 2H), 2.80-2.77 (m, 1H), 2.60 (s, 3H), 2.25 (s, 6H), 1.76-1.72 (m, 6H), 1.64 (m, 1H), 1.46 (m, 3H), 1.27-1.08 (m, 6H), 1.01-0.91 (m, 2H). |
| 225 | 872.5 (M + H)⁺ | (400 MHz, DMSO-d6) δ 11.77 (brs, 1H), 7.52 (s, 1H), 7.43-7.41 (m, 2H), 7.28-7.25 (m, 2H), 7.14 (d, J = 6.0 Hz, 2H), 6.98 (m, 1H), 6.87 (m, 1H), 6.80-6.74 (m, 2H), 5.64 (m, 1H), 4.98 (d, J = 17.6 Hz, 1H), 4.52 (d, J = 17.2 Hz, 1H), 4.48-4.36 (m, 1H), 3.99-3.96 (m, 2H), 3.55-3.45 (m, 6H), 2.89-2.86 (m, 2H), 2.23 (s, 6H), 1.77-1.61 (m, 8H), 1.43 (m, 3H), 1.17 (m, 3H). |
| 226 | 930.2 (M + H)⁺ | (400 MHz, DMSO-d6) δ 7.60-7.40 (m, 4H), 7.28 (d, J = 8.0 Hz, 1H), 7.20-7.10 (m, 5H), 6.95-6.80 (m, 2H), 5.62-5.55 (m, 1H), 4.70 (s, 1H), 4.40-4.35 (m, 1H), 4.00-3.96 (m, 2H), 3.75-3.73 (m, 1H), 3.67-3.60 (m, 1H), 3.52-3.45 (m, 2H), 3.11-3.08 (m, 3H), 2.91-2.85 (m, 2H), 2.24-2.17 (m, 9H), 1.78-1.64 (m, 6H), 1.45-1.40 (m, 2H), 1.32-1.24 (m, 6H), 1.22-1.15 (m, 2H). |
| 227 | 900.6 (M + H)⁺ | (400 MHz, DMSO-d6) δ 11.72 (brs, 1H), 7.52 (s, 1H), 7.43-7.40 (m, 2H), 7.27-7.25 (m, 2H), 7.14 (d, J = 6.4 Hz, 2H), 6.98 (m, 1H), 6.86 (m, 1H), 6.81-6.74 (m, 2H), 5.63 (m, 1H), 4.98 (d, J = 17.6 Hz, 1H), 4.52 (d, J = 17.6 Hz, 1H), 4.41 (m, 1H), 3.74-3.72 (m, 2H), 3.47 (s, 3H), 2.89-2.83 (m, 1H), 2.23 (s, 6H), 1.77-1.70 (m, 4H), 1.65-1.50 (m, 4H), 1.43 (m, 3H), 1.29 (m, 4H), 1.20-1.14 (m, 7H). |
| 228 | 914.5 (M + H)⁺ | (400 MHz, DMSO-d6) δ 7.41 (m, 2H), 7.25-7.14 (m, 5H), 6.92-6.72 (m, 3H), 6.51 (m, 1H), 5.35 (m, 1H), 3.75-3.73 (m, 2H), 3.41-3.38 (m, 3H), 3.25 (m, 5H), 2.67 (m, 3H), 2.21 (s, 6H), 1.76-1.72 (m, 4H), 1.65-1.47 (m, 6H), 1.33-1.16 (m, 11H). |
| 229 | 914.5 (M + H)⁺ | (400 MHz, DMSO-d6) δ 7.50 (s, 1H), 7.42 (d, J = 8.4 Hz, 1H), 7.25-7.23 (m, 3H), 7.14 (d, J = 6.4 Hz, 2H), 6.99 (m, 1H), 6.67 (m, 3H), 5.55 (m, 1H), 4.44 (m, 1H), 3.75-3.73 (m, 2H), 3.39 (m, 1H), 3.38 (m, 2H), 3.25 (m, 4H), 3.01 (m, 1H), 2.90-2.80 (m, 2H), 2.22 (d, J = 1.2 Hz, 6H), 1.77-1.70 (m, 4H), 1.64-1.41 (m, 6H), 1.29 (m, 4H), 1.20 (m, 7H) |
| 230 | 912.6 (M + H)⁺ | (400 MHz, DMSO-d6) δ 7.80-7.51 (m, 4H), 7.42 (d, J = 8.4 Hz, 1H), 7.25 (d, J = 8.4 Hz, 1H), 7.15-7.07 (m, 5H), 6.83-6.80 (m, 2H), 5.55 (m, 1H), 4.45 (m, 1H), 3.74-3.72 (m, 2H), 3.57 (m, 1H), 3.49 (s, 3H), 3.01-2.84 (m, 2H), 2.22 (d, J = 2.0 Hz, 6H), 1.72-1.69 (m, 4H), 1.63-1.54 (m, 3H), 1.51-1.44 (m, 3H), 1.29 (m, 4H), 1.20-1.13 (m, 6H). |
| 231 | 912.6 (M + H)⁺ | (400 MHz, DMSO-d6) δ 7.80-7.51 (m, 4H), 7.42 (d, J = 8.4 Hz, 1H), 7.25 (d, J = 8.4 Hz, 1H), 7.15-7.07 (m, 5H), 6.83-6.80 (m, 2H), 5.55 (m, 1H), 4.45 (m, 1H), 3.74-3.72 (m, 2H), 3.57 (m, 1H), 3.49 (s, 3H), 3.01-2.84 (m, 2H), 2.22 (d, J = 2.0 Hz, 6H), 1.72-1.69 (m, 4H), 1.63-1.54 (m, 3H), 1.51-1.44 (m, 3H), 1.29 (m, 4H), 1.20-1.13 (m, 6H). |
| 232 | 976.4 (M + H)⁺ | (400 MHz, DMSO-d6) δ 7.49 (s, 1H), 7.42-7.38 (m, 1H), 7.33-7.19 (m, 2H), 7.14 (d, J = 8.0 Hz, 2H), 7.02-6.95 (m, 1H), 6.89-6.75 (m, 3H), 5.65-5.55 (m, 1H), 4.85-4.74 (m, 1H), 4.01-3.97 (m, 2H), 3.55-3.40 (m, 3H), 2.97-2.80 (m, 3H), 2.66 (s, 3H), 2.24-2.10 (m, 14H), 1.85-1.55 (m, 8H), 1.48-1.32 (m, 4H), 1.26-1.05 (m, 5H) |

-continued

| Compound No. | LC-MS: m/z | $^1$H NMR |
|---|---|---|
| 233 | 976.4 (M + H)$^+$ | (400 MHZ, DMSO-d6) δ 7.49 (s, 1H), 7.42-7.35 (m, 1H), 7.33-7.19 (m, 2H), 7.14 (d, J = 8.0 Hz, 2H), 7.02-6.95 (m, 1H), 6.89-6.75 (m, 3H), 5.65-5.55 (m, 1H), 4.85-4.74 (m, 1H), 4.01-3.90 (m, 2H), 3.65-3.40 (m, 3H), 2.97-2.80 (m, 3H), 2.64 (s, 3H), 2.24-2.10 (m, 14H), 1.85-1.55 (m, 8H), 1.48-1.32 (m, 4H), 1.26-1.05 (m, 5H). |
| 234 | 994.2 (M + H)$^+$ | (400 MHz, DMSO-d6) δ 11.68 (s, 1H), 7.80-7.65 (m, 2H), 7.49 (s, 1H), 7.42-7.38 (m, 1H), 7.37-7.19 (m, 3H), 7.15-7.10 (m, 3H), 7.02-6.80 (m, 2H), 5.65-5.55 (m, 1H), 4.90-4.80 (m, 1H), 4.50-4.20 (m, 1H), 4.01-3.90 (m, 2H), 3.65-3.40 (m, 3H), 2.92-2.80 (m, 3H), 2.66 (s, 3H), 2.24-2.10 (m, 11H), 1.90-1.55 (m, 8H), 1.50-1.10 (m, 8H). |
| 235 | 994.2 (M + H)$^+$ | (400 MHZ, DMSO-d6) δ 11.68 (s, 1H), 7.80-7.60 (m, 2H), 7.49 (s, 1H), 7.45-7.30 (m, 3H), 7.26-7.19 (m, 2H), 7.13 (d, J = 8.0 Hz, 2H), 6.95-6.75 (m, 2H), 5.70-5.55 (m, 1H), 4.90-4.85 (m, 1H), 4.50-4.25 (m, 1H), 4.00-3.90 (m, 2H), 3.65-3.40 (m, 3H), 2.95-2.80 (m, 3H), 2.64 (s, 3H), 2.30-2.10 (m, 11H), 1.90-1.55 (m, 8H), 1.50-1.00 (m, 8H). |
| 236 | 1012.4 (M + H)$^+$ | (400 MHZ, DMSO-d6) δ 11.61 (s, 1H), 7.51 (s, 1H), 7.45-7.30 (m, 2H), 7.25 (d, J = 8.0 Hz, 1H), 7.20-7.07 (m, 4H), 7.05-6.75 (m, 3H), 5.65-5.50 (m, 1H), 4.80-4.65 (m, 1H), 4.45-4.30 (m, 1H), 3.75-3.70 (m, 2H), 3.65-3.45 (m, 1H), 3.30-3.20 (m, 3H), 3.05-2.99 (m, 1H), 2.96-2.83 (m, 1H), 2.66 (s, 3H), 2.30-2.10 (m, 12H), 1.85-1.65 (m, 4H), 1.64-1.50 (m, 3H), 1.45-1.33 (m, 3H), 1.30-1.25 (m, 4H), 1.20-1.10 (m, 6H), 0.98-0.90 (m, 2H), 0.70-0.55 (m, 2H). |
| 237 | 1012.4 (M + H)$^+$ | (400 MHZ, DMSO-d6) δ 11.63 (s, 1H), 7.51 (s, 1H), 7.45-7.30 (m, 2H), 7.25 (dd, J$_1$ = 8.0, J$_2$ = 2.0 Hz, 1H), 7.20-7.00 (m, 5H), 6.95-6.75 (m, 2H), 5.65-5.50 (m, 1H), 4.80-4.70 (m, 1H), 4.45-4.30 (m, 1H), 3.75-3.70 (m, 2H), 3.65-3.45 (m, 1H), 3.30-3.20 (m, 3H), 3.05-2.99 (m, 1H), 2.96-2.83 (m, 1H), 2.64 (s, 3H), 2.30-2.10 (m, 12H), 1.85-1.65 (m, 4H), 1.64-1.50 (m, 3H), 1.45-1.33 (m, 3H), 1.30-1.25 (m, 4H), 1.20-1.10 (m, 6H), 0.98-0.90 (m, 2H), 0.70-0.55 (m, 2H). |
| 238 | 488.4 (1/2M + H)$^+$ | $^1$H NMR (400 MHZ, DMSO-d$_6$) δ 11.58 (s, 1H), 7.52 (s, 1H), 7.48-7.37 (m, 2H), 7.25 (d, J = 7.2 Hz, 1H), 7.29-7.21 (m, 2H), 7.03-6.66 (m, 5H), 5.54 (s, 1H), 4.44 (s, 1H), 3.79-3.68 (d, J = 7.2 Hz, 2H), 3.56 (s, 1H), 3.18-3.05 (m, 5H), 2.93-2.77 (m, 2H), 2.64 (s, 3H), 2.30-2.20 (d, J = 1.6 Hz, 6H), 1.90-1.38 (m, 10H), 1.33-1.05 (m, 11H), 0.98-0.81 (m, 2H). |

Biological Examples cAMP Assays

Activation of GLP-1 receptor is known to stimulate cyclic AMP (cAMP) production in cells which indicates primary coupling to the G as subunit of the G protein heterotrimeric complex. Evidence suggests signaling through G as induced cAMP stimulation elicits the desired pharmacological response regarding insulin release from pancreatic β-cells.

To optimize functional activity directed toward G as coupling, a HEK293/CRE-Luc cell line developed by HDB stably expressing the GLP-1 Receptor was used. 200× concentration of compound working solutions were prepared (Agilent Technologies Bravo) with ½ log serial dilution in 384-well Echo LDV plate (Labcyte, CatOLP-0200). 50 nL/well 200× concentration of compound working solutions were moved to 384-well white low volume plate (Greiner, Cat4784075) using Labcyte ECH0550.1×10 5 cells/mL HEK293/GLP1R/CRE-LUC (HD Biosciences) cell suspensions prepared with assay buffer (DPBS containing 0.5 mM IBMX (Sigma, Cat15879) and 0.10 BSA (GENVIEW, Cat4FA016-100g)), 10 uL cell suspensions were added to each well of previous generated assay plate which already contains 50 n$^l$ compound at 200 xconcentration using ThermioFisher Multidrop Combi (1000 cells/well). Seal the plate and incubate at 37 with 500 $CO_2$ for 30 m.

After incubation the cAMP assay signal was generated using cAMP dynamic 2 Kit (Cisbio). 5 μL cAMP-d2 working solution was added to each well, followed with 5 L Anti-cAMP antibody-cryptate working solution added to each well using ThermoFisher Multidrop Combi. Incubate at room temperature for 1 hour protected from light. Read the fluorescence at 665 and 615 nm with Reader PerkinElmer EnVision.

% oActivity=100%×(mean RLU of test sample–mean RLU of vehicle control)/(mean RLU of MAX control–mean RLU of vehicle control)

Table 3 shows the biological activity of compounds in GLP-1R agonist cAMP stimulation assay ($EC_{50}$, nM).

TABLE 3

| Compound No. | $EC_{50}$ (nM) |
|---|---|
| 101 | 0.067 |
| 102 | 0.17 |
| 103 | 0.14 |
| 105 | 0.009 |
| 106 | 0.67 |
| 107 | 0.46 |
| 108 | 0.013 |
| 109 | 0.27 |
| 110 | 0.028 |
| 111 | 0.014 |
| 112 | 0.057 |
| 113 | 0.035 |
| 114 | 0.017 |
| 115 | 0.049 |
| 116 | 0.049 |
| 117 | 0.011 |
| 118 | 0.04 |
| 119 | 1 |
| 121 | 0.019 |
| 122 | 0.046 |
| 123 | 0.071 |
| 124 | 0.01 |

TABLE 3-continued

| Compound No. | EC$_{50}$ (nM) |
|---|---|
| 130 | 0.23 |
| 131 | 0.05 |
| 132 | 0.98 |
| 134 | 0.0051 |
| 135 | 0.001 |
| 136 | 0.047 |
| 137 | 0.15 |
| 138 | 0.001 |
| 139 | 0.062 |
| 140 | 0.099 |
| 141 | 0.022 |
| 142 | 0.045 |
| 143 | 0.019 |
| 144 | 0.017 |
| 147 | 0.12 |
| 148 | 0.12 |
| 149 | 0.023 |
| 150 | 0.11 |
| 151 | 0.072 |
| 152 | 0.6 |
| 155 | 0.99 |
| 156 | 1.5 |
| 157 | 1.5 |
| 158 | 2.5 |
| 159 | 5.9 |
| 160 | 2.8 |
| 161 | 5.5 |
| 162 | 3.2 |
| 163 | 20 |
| 164 | 0.024 |
| 165 | 9.9 |
| 166 | 0.019 |
| 167 | 0.12 |
| 168 | 0.011 |
| 169 | 0.07 |
| 170 | 1.8 |
| 171 | 8.8 |
| 172 | 0.037 |
| 173 | 0.012 |
| 174 | 0.067 |
| 175 | 0.025 |
| 176 | 0.024 |
| 177 | 0.026 |
| 178 | 0.094 |
| 179 | 0.21 |
| 180 | 0.034 |
| 181 | 0.018 |
| 182 | 0.077 |
| 183 | 0.001 |
| 184 | 0.01 |
| 185 | 0.016 |
| 186 | 0.0047 |
| 187 | 0.01 |
| 188 | 0.017 |
| 189 | 0.047 |
| 190 | 0.026 |
| 191 | 0.0096 |
| 192 | 0.02 |
| 193 | 0.1 |
| 194 | 0.046 |
| 195 | 0.018 |
| 196 | 0.039 |
| 197 | 0.018 |
| 198 | 0.023 |
| 199 | 0.01 |
| 200 | 0.01 |
| 201 | 0.011 |
| 202 | 0.018 |
| 203 | 0.032 |
| 204 | 0.039 |
| 205 | 0.072 |
| 206 | 0.02 |
| 207 | 0.02 |
| 208 | 0.11 |
| 209 | 0.22 |
| 210 | 0.067 |
| 211 | 0.041 |
| 212 | 0.038 |
| 213 | 0.12 |
| 214 | 0.033 |
| 215 | 0.074 |
| 216 | 0.065 |
| 217 | 0.2 |
| 218 | 0.083 |
| 219 | 0.193 |
| 220 | 0.134 |
| 221 | 0.030 |
| 222 | 0.084 |
| 225 | 0.028 |
| 226 | 0.025 |
| 227 | 0.015 |
| 228 | 0.34 |
| 229 | 0.042 |
| 230 | 0.048 |
| 231 | 0.014 |
| 232 | 0.037 |
| 233 | 0.028 |
| 234 | 0.058 |
| 235 | 0.057 |
| 236 | 0.053 |
| 237 | 0.07 |
| 238 | 0.11 |

Certain compounds were tested in the assays as described below. As shown by the data presented below, certain compounds of the present disclsoure exhibit one or more improved properties, such as increased half-life (t1/2), enhanced potency, improved permeability/reduced efflux ratio, increased exposure, and/or improved solubility (Tables 4,5A and SB3). Compounds C-1, C-2, C-3, C-4, C-5, and C-6 were synthesized according to literature procedures (see, e.g., WO2022/048665, WO2022/017388, and WO2018/056453).

Caco-2 Study Protocol:

Incubations with Caco-2 cell monolayers were performed in duplicate in a 96-well Transwell plate. Transport buffer solution (HBSS, 10 mM HEPES, pH 7.4, with 0.5% BSA) containing test article (10 µM), and either the control compounds metoprolol (10 µM), cimetidine (10 µM) and erythromycin (10 µM), was added to appropriate donor wells of the apical or basolateral plate. The transport buffer with DMSO was added to appropriate wells of receiver wells. Following incubation at 37° C. for 2 hours, the cell plates were removed and 50 µL samples from both apical and basolateral sides were transferred into new 96-well plates. Subsequently, 200 µL of acetonitrile containing internal standard was added to all samples to precipitate protein prior to analysis by UPLC-MS/MS. Lucifer yellow was used as a marker to confirm the integrity of the cell monolayers after 2 hours incubation.

FaSSIF Solubility Protocol:

Stock solution of test article and control compound (chlorpromazine, astemizole, and phenytoin) were prepared in DMSO at 10 mM. 50 µL each of stock solutions were dried down, followed by reconstitution to 1 mM with FaSSIF buffer in the well. The incubation plate was shaked at 25° C., 1,100 rpm for 4 hours. And then, the samples were filtered by using the vacuum manifold. 10 µL aliquots from each well was transferred to a new 96-well plate and adjust the volume to 80 µL with blank buffer. Using a mixture of H$_2$O and acetonitrile containing internal standard (1:1) to dilute the sample 100-fold, 500-fold and 2,500-fold. The samples are evaluated by LC/MS/MS analysis. All compounds were tested in singlet.

Data for select compounds are shown in Table 4.
TABLE 4
| Compound No. | Structure | Data |
|---|---|---|
| 121 | 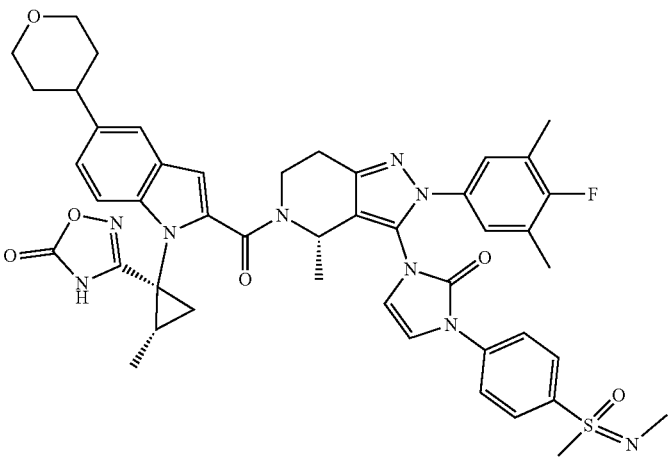<br>Enatiomer 2 | EC$_{50}$: 15 pM<br>Caco-2 Perm (nm/s): 1.0<br>Efflux: 90.8<br>Solubility (FaSSIF, μM): 7.3 |
| 142 | 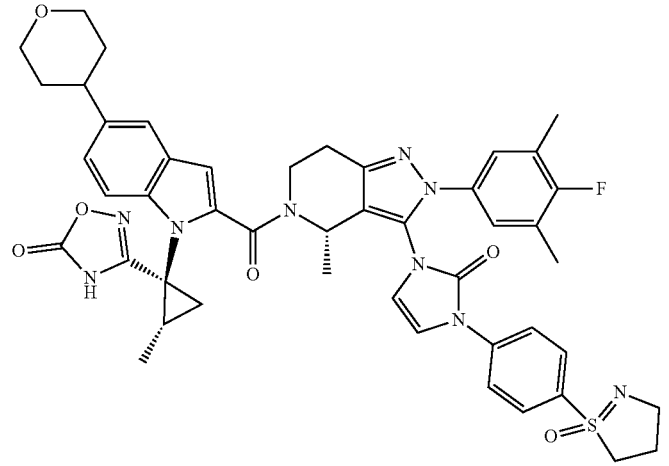 [SMILES: Cc1cc(-n2nc3c(c2-n2ccn(-c4ccc(S5(=O)=NCCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]<br>Enatiomer 1 | EC$_{50}$: 63 pM<br>Caco-2 Perm (nm/s): <0.5<br>Efflux: >156.2<br>Solubility (FaSSIF, μM): 8.07 |
| 143 | 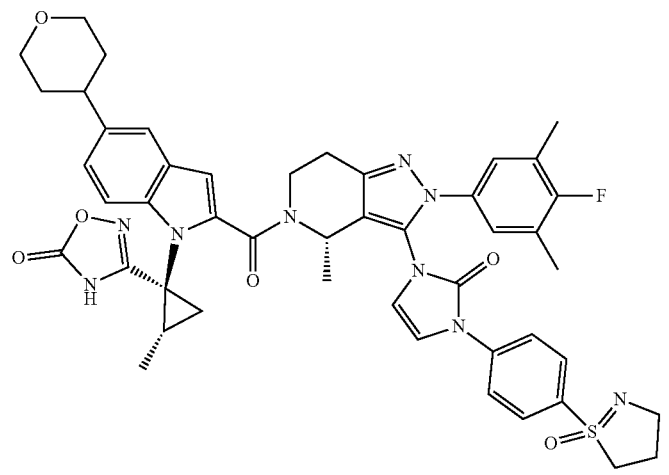 [SMILES: Cc1cc(-n2nc3c(c2-n2ccn(-c4ccc(S5(=O)=NCCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]<br>Enatiomer 2 | EC$_{50}$: 19 pM<br>Caco-2 Perm (nm/s): 1.2<br>Efflux: 99.3<br>Solubility (FaSSIF, μM): 4.98 |

TABLE 4-continued
| Compound No. | Structure | Data |
|---|---|---|
| 144 | 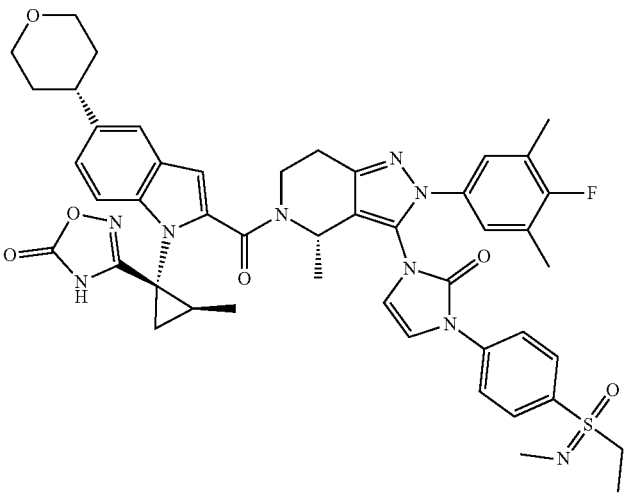  Single unknown enatiomer | EC$_{50}$: 17 pM<br>Caco-2 Perm (nm/s): 3.6<br>Efflux: 24.1<br>Solubility (FaSSIF, μM): 2.56 |
| 149 | 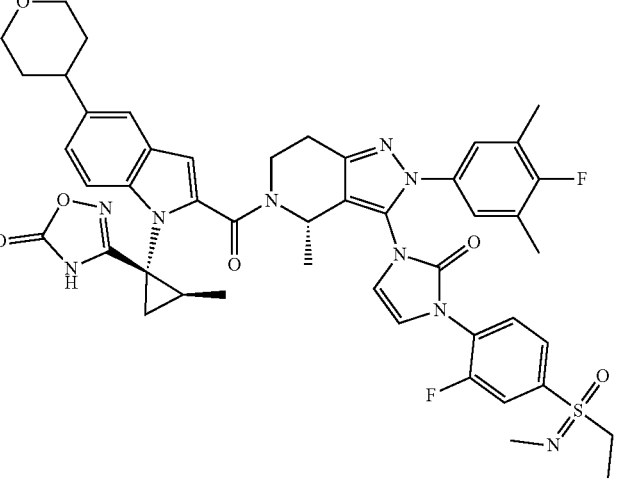  Enatiomer 1 | EC$_{50}$: 23 pM<br>Caco-2 Perm (nm/s): 3.3<br>Efflux: 26<br>Solubility (FaSSIF, μM): 2.04 |
| 151 | 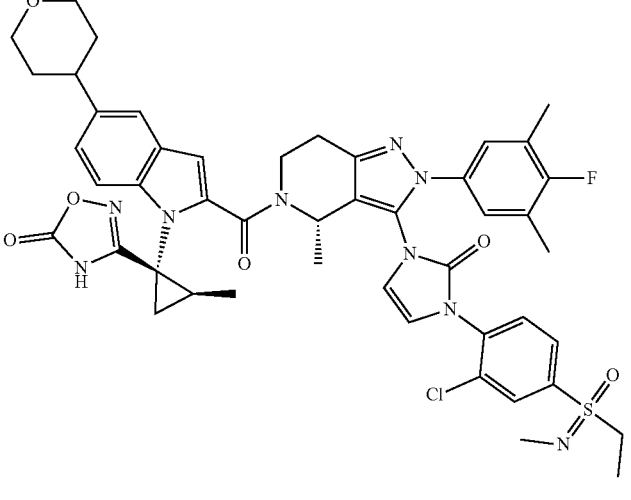  Enatiomer 1 | EC$_{50}$: 72 pM<br>Caco-2 Perm (nm/s): 3.0<br>Efflux: 36.8 |

TABLE 4-continued

| Compound No. | Structure | Data |
|---|---|---|
| 164 | 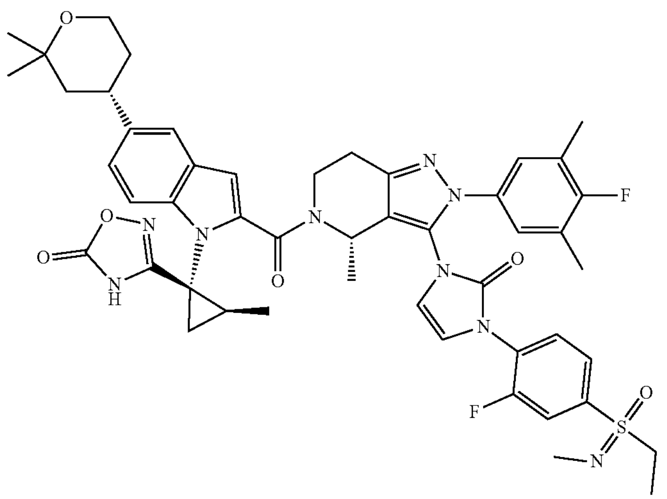 | EC$_{50}$: 24 pM<br>Caco-2 Perm (nm/s): 6.2<br>Efflux: 5.5<br>Solubility (FaSSIF, μM): 8.9 |
| | Single unknown enatiomer | |
| 168 | 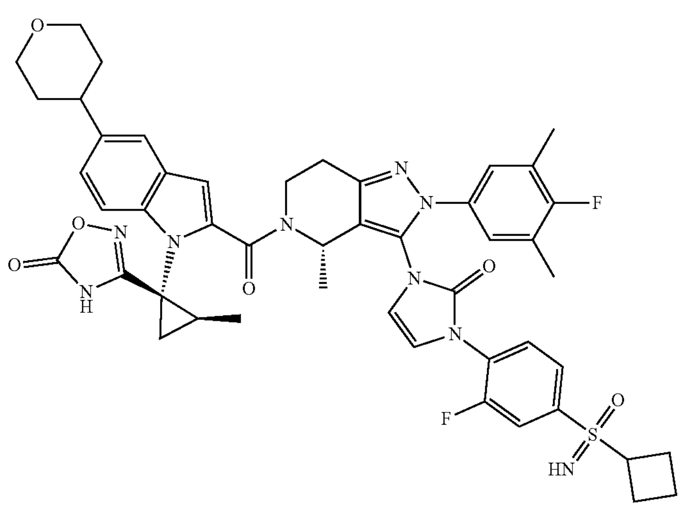 | EC$_{50}$: 11 pM<br>Caco-2 Perm (nm/s): 2.1<br>Efflux: 50 |
| | Enatiomer 1 | |

TABLE 4-continued

| Compound No. | Structure | Data |
|---|---|---|
| 180 | Single unknown enatiomer | EC$_{50}$: 30 pM<br>Caco-2 Perm (nm/s): 6.1<br>Efflux: 5.4<br>Solubility (FaSSIF, μM): 30 |
| 181 | Single unknown enatiomer | EC$_{50}$: 14 pM<br>Caco-2 Perm (nm/s): 2.4<br>Efflux: 38 |
| 183 | Single unknown enatiomer | EC$_{50}$: 11 pM<br>Caco-2 Perm (nm/s): 1.9<br>Efflux: 45 |

TABLE 4-continued
| Compound No. | Structure | Data |
|---|---|---|
| 195 | 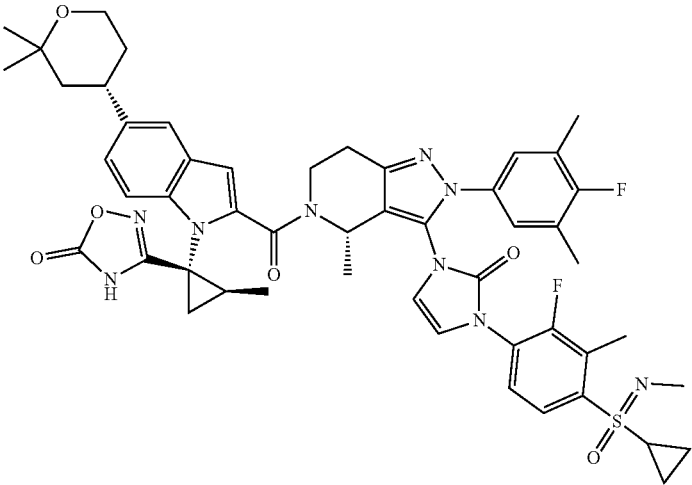 [SMILES: CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1C)C1CC1]<br>Enatiomer 1 | EC$_{50}$: 18 pM<br>Caco-2 Perm (nm/s): 2.2<br>Efflux: 12<br>Solubility (FaSSIF, μM): 7.2 |
| 214 | 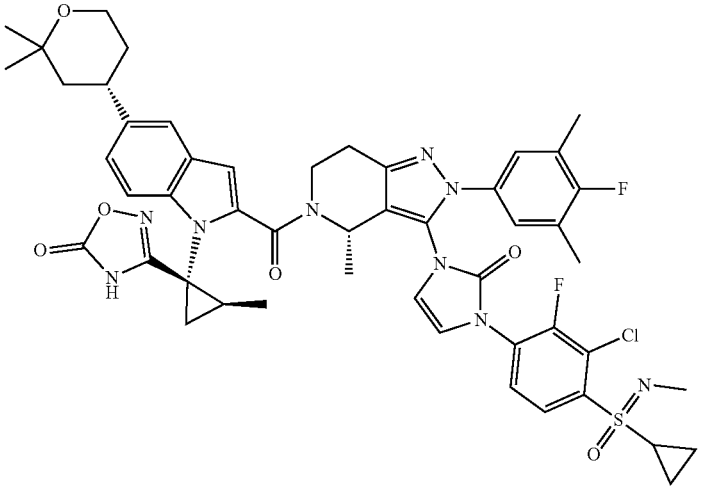<br>Enatiomer 1 | EC$_{50}$: 33 pM<br>Caco-2 Perm (nm/s): 3.4<br>Efflux: 11.4<br>Solubility (FaSSIF, μM): 9.9 |

TABLE 4-continued

| Compound No. | Structure | Data |
| --- | --- | --- |
| 216 | 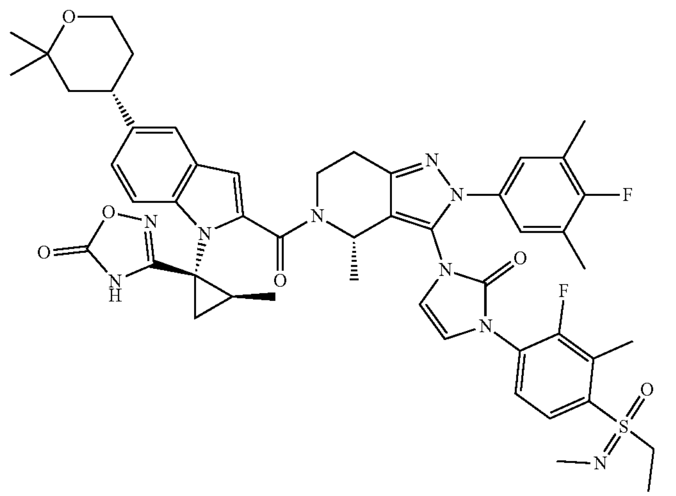 [SMILES: CCS(=O)(=NC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1C] | EC$_{50}$: 68 pM<br>Caco-2 Perm (nm/s): 3.2<br>Efflux: 15.7<br>Solubility (FaSSIF, μM): 7.9 |
| | Single unknown enantiomer | |
| 218 | 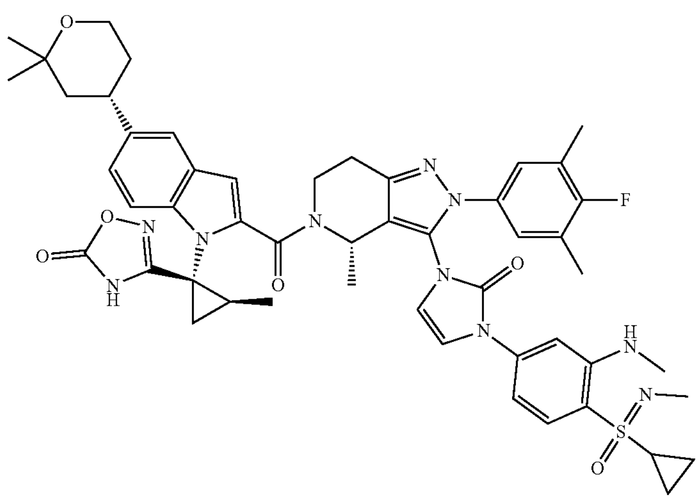 [SMILES: CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)cc1NC)C1CC1] | EC$_{50}$: 59 pM<br>Caco-2 Perm (nm/s): 0.9<br>Efflux: 20.7 |
| | Single unknown enantiomer | |
| 221 | 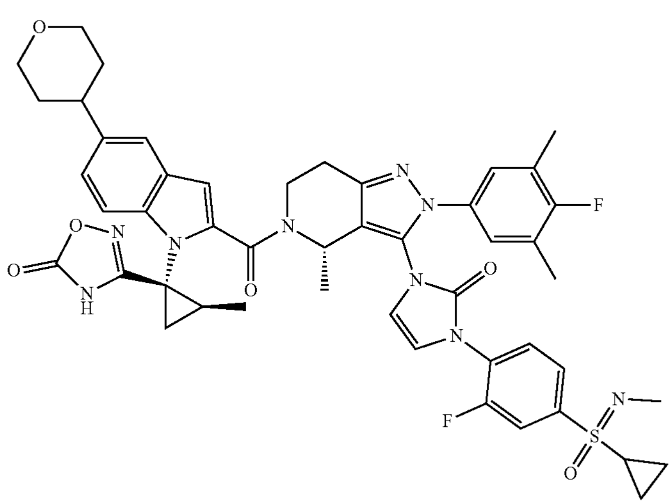 [SMILES: CN=S(=O)(c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(F)c1)C1CC1] | EC$_{50}$: 31 pM<br>Caco-2 Perm (nm/s): 3.4<br>Efflux: 38.5<br>Solubility (FaSSIF, μM): 4.05 |
| | Enantiomer 1 | |

TABLE 4-continued
| Compound No. | Structure | Data |
|---|---|---|
| 238 | 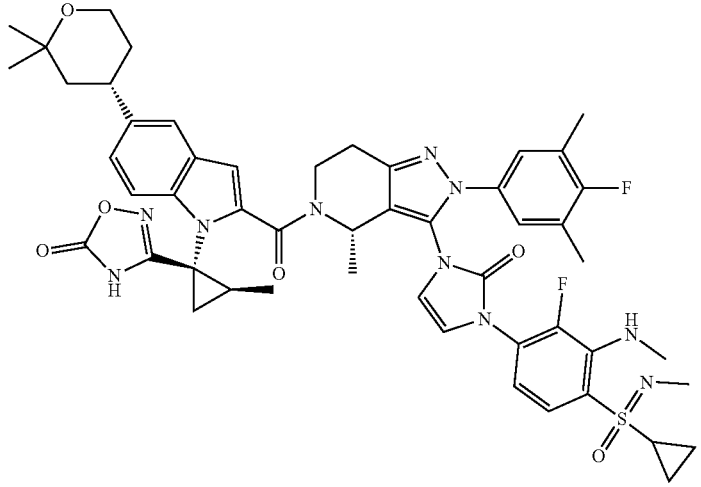 [SMILES: CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1NC)C1CC1] Single unknown enantiomer | EC$_{50}$ 110 pM<br>Caco-2 Perm (nm/s): 1.9<br>Efflux: 9.8<br>Solubility (FaSSIF, μM): 26 |
| C-1 | 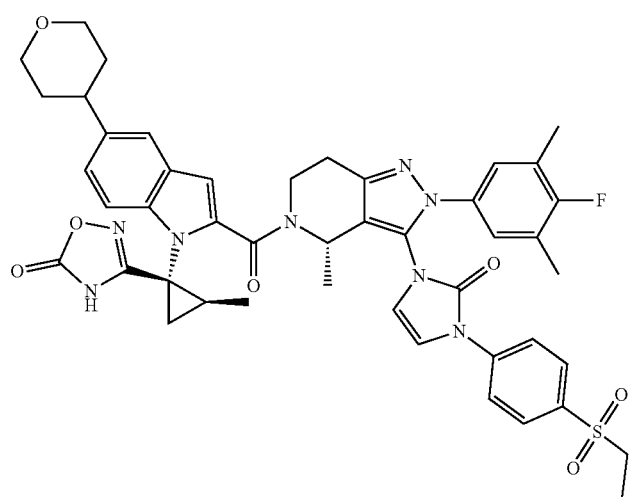 [SMILES: CCS(=O)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1] | EC$_{50}$: 22 pM<br>Caco-2 Perm (nm/s): 1.26<br>Efflux: 51.7<br>Solubility (FaSSIF, μM): 4.0 |
| C-2 | 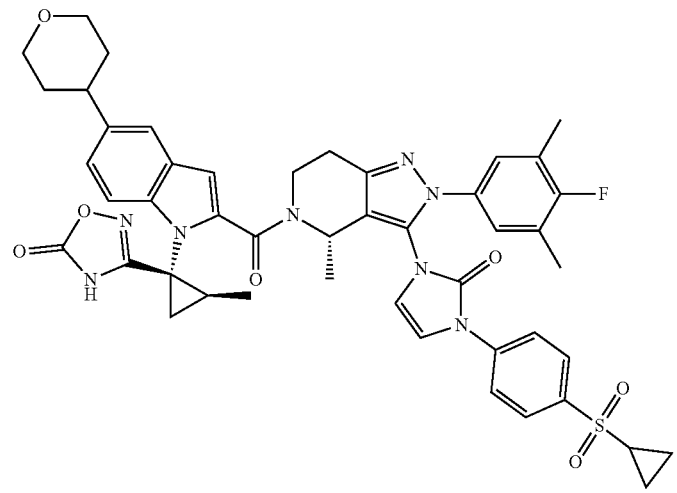 [SMILES: Cc1cc(-n2nc3c(c2-n2ccn(-c4ccc(S(=O)(=O)C5CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] | EC$_{50}$: 43 pM<br>Caco-2 Perm (nm/s): <0.5<br>Efflux: >62.6<br>Solubility (FaSSIF, μM): 9.3 |

TABLE 4-continued

| Compound No. | Structure | Data |
|---|---|---|
| C-3 | 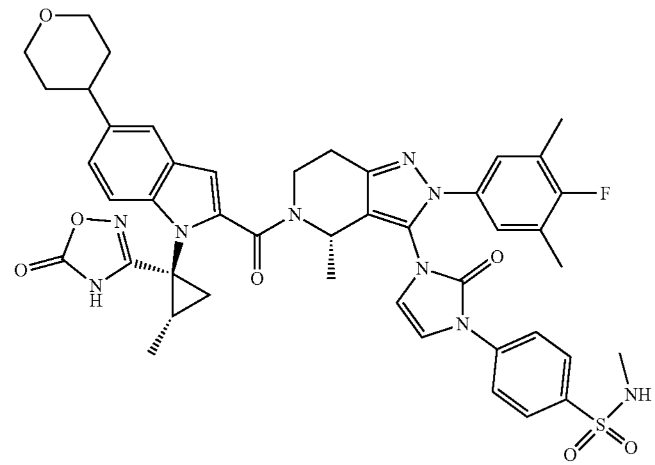 [SMILES: CNS(=O)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1] | EC$_{50}$: 81 pM<br>Caco-2 Perm (nm/s): 0.5<br>Efflux: 78.1<br>Solubility (FaSSIF, μM): 6.45 |
| C-4 | 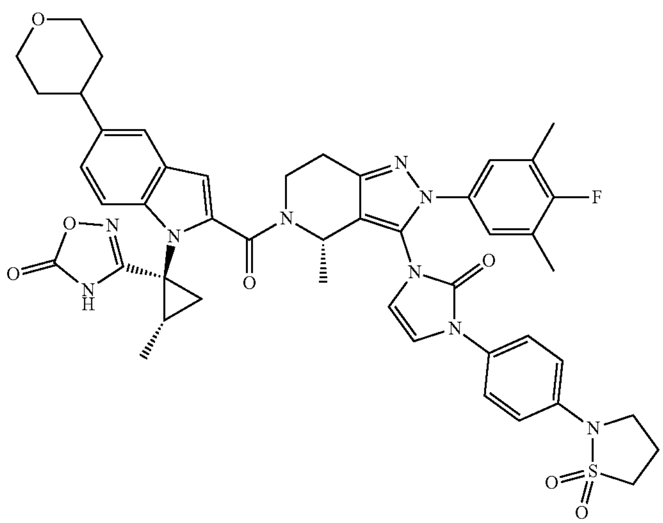 [SMILES: Cc1cc(-n2nc3c(c2-n2ccn(-c4ccc(N5CCCS5(=O)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] | EC$_{50}$: 140 pM<br>Caco-2 Perm (nm/s): 1.8<br>Efflux: 16.7<br>Solubility (FaSSIF, μM): 5.38 |
| C-5 | 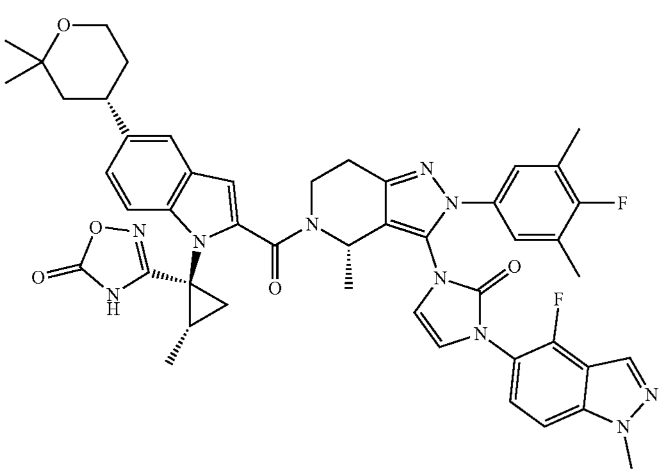 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F] | EC$_{50}$: 33 pM (n =12)<br>Caco-2 Perm (nm/s): 2.1<br>Efflux: 7.4<br>Solubility (FaSSIF, μM): 0.4 |

TABLE 4-continued

| Compound No. | Structure | Data |
|---|---|---|
| C-6 | 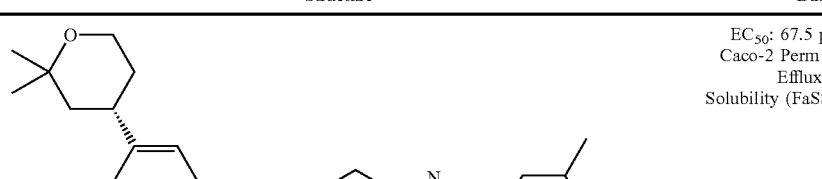 | $EC_{50}$: 67.5 pM (n =6)<br>Caco-2 Perm (nm/s): 1.6<br>Efflux: 26<br>Solubility (FaSSIF, μM): 4.5 |

Rat IV/PO PK Study Protocol, Method A:

Pharmacokinetics (PK) study was conducted on male Sprague Dawley (SD) rats by two delivery routes intravenous (IV) and/or oral gavage (PO). Rats in IV route (n=3) were free access to food and water. Rats in PO route (n=3) were fasted overnight and fed at 4 hrs post dosing. Test article was formulated in solution (10% solutol HS 15 in saline) for IV route and solution or suspension (10% solutol HS 15 in saline/water) for PO route, respectively. On the day of experiment, test article was administered via vein (e.g. foot dorsal vein) injection (commonly at 1 mg/kg and 5 mL/kg) for IV route or via oral gavage (commonly at 2 or 5 mg/kg and 5 mL/kg) for PO route, respectively. Blood samples were collected via serial bleeding at ~8 time points from 0.083 to 24 hrs post dose. Approximate 150 μL of blood/time point was collected into $K_2$EDTA tube via tail vein or jugular vein. Blood samples were put on wet ice and centrifuged to obtain plasma samples and plasma samples were submitted to LC-MS/MS for sample analysis. Pharmacokinetics parameters, including elimination half life ($t_1/2$) (IV), area under the curve (AUC) and oral bioavailability (F %), etc. were calculated by non-compartmental model using WinNonlin.

Data for select compounds are shown in Table 5A.

TABLE 5A

| Compound No. | Bioavailablility (% F) | $t_{1/2}$ (hr) | AUC (ng · h/mL)_free form/dose |
|---|---|---|---|
| C-5 | 36% | 8.1 | 4,398/2 mpk |
| C-6 | 47% | 3.1 | 4,276/5 mpk |
| 149 | 32% | 1.6 | 4,276/5 mpk |
| 180 | 28% | 3.0 | 4,954/5 mpk |
| 181 | 30% | 1.66 | 6,097/5 mpk |
| 164 | 29.4% | 2.4 | 6,094/5 mpk |
| 195 | 14% | 4.3 | 9,545/5 mpk |
| 238 | 25.5% | 4.78 | 4,997/5 mpk |

Rat PO PK Study Protocol, Method B:

Pharmacokinetics (PK) study was conducted on male Sprague Dawley (SD) rats by oral gavage (PO). Rats in PO route (n=3) were free access to food and water. Test article was formulated in solution or suspension (10% solutol HS 15 in saline/water). On the day of experiment, test article was administered via oral gavage (commonly at 10, 30, or 100 mg/kg, with dose volume as 10 mL/kg). Blood samples were collected via serial bleeding at ~8 time points from 0.25 to 24 hrs post dose. Approximate 150 μL of blood/time point was collected into KzEDTA tube via tail vein or jugular vein. Blood samples were put on wet ice and centrifuged to obtain plasma samples and plasma samples were submitted to LC-MS/MS for sample analysis. Pharmiacokinetics parameters, including $C_{max}$, and area under the curve (AUC), etc. were calculated by non-compartmental model using WinNonlin.

Data for select compounds are shown in Table 5B.

TABLE 5B

| Compound No. | Dose (mg/kg) | Cmax (ng/mL) | AUC (ng · h/mL) |
|---|---|---|---|
| C-5 | 2* | 573 | 4,398 |
| | 10 | 1,250 | 14,491 |
| | 30 | 1,012 | 13,023 |
| C-6 | 5* | 744 | 4,276 |
| | 30 | 7,543 | 58,799 |
| | 100 | 7,480 | 86,039 |
| 164 | 5* | 1,880 | 9,545 |
| | 30# | 5,403 | 66,166 |
| | 100# | 11,200 | 172,912 |
| 180 | 5* | 1,793 | 6,097 |
| | 30 | 8,340 | 97,026 |
| | 100 | 13,267 | 166,937 |
| 195 | 5* | 774 | 4,997 |
| | 30 | 3,907 | 51,065 |
| | 100 | 7,690 | 102,420 |
| 238 | 5* | 1,065 | 7,426 |
| | 30# | 4,713 | 67,518 |
| | 100# | 8,677 | 124,394 |

*obtained under method 3A
used 20% solutol HS 15 in water

Under the same formulation using free form of the compounds, the rat PK exposure of C-5 is plateaued at 10 mg/kg, while C-7 is less proportional to dose from 30 to 100 mg/kg. In contrast, compounds 164, 180, 195 and 238 demonstrate good rat PK dose proportionality from 5 to 100 mg/kg and achieve higher exposure than C-5 and C-6.

The invention claimed is:
1. A compound selected from:
121
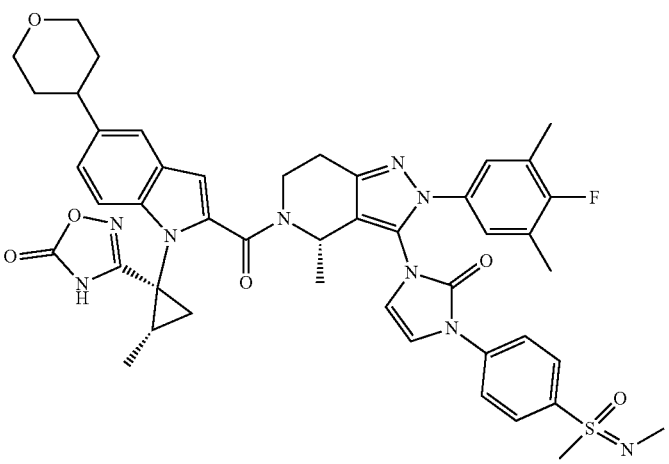
Enantiomer 2
142
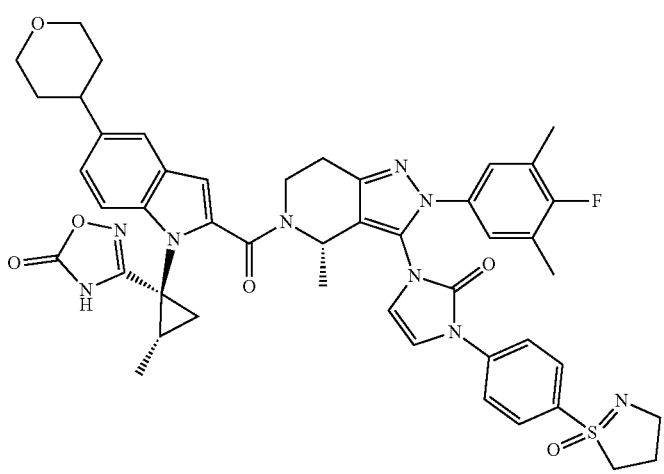 [SMILES: Cc1cc(-n2nc3c(c2-n2ccn(-c4ccc(S5(=O)=NCCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
Enantiomer 1
143
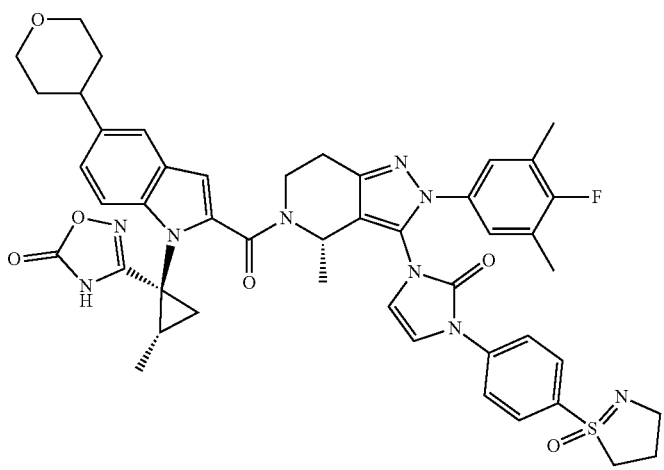 [SMILES: Cc1cc(-n2nc3c(c2-n2ccn(-c4ccc(S5(=O)=NCCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F]
Enantiomer 2

144
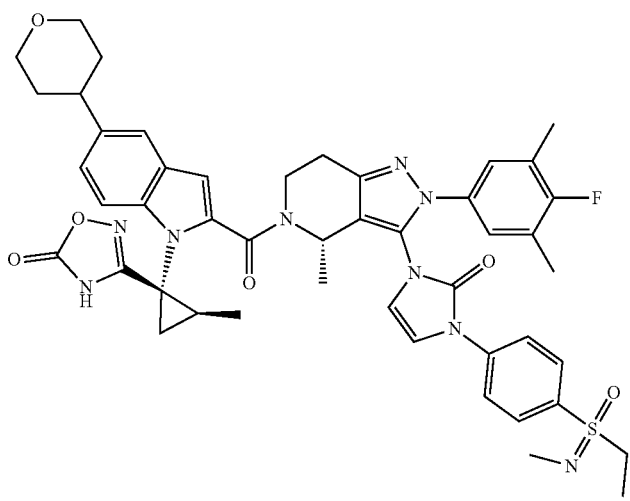 [SMILES: CCS(=O)(=NC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]
Single unknown enantiomer
149
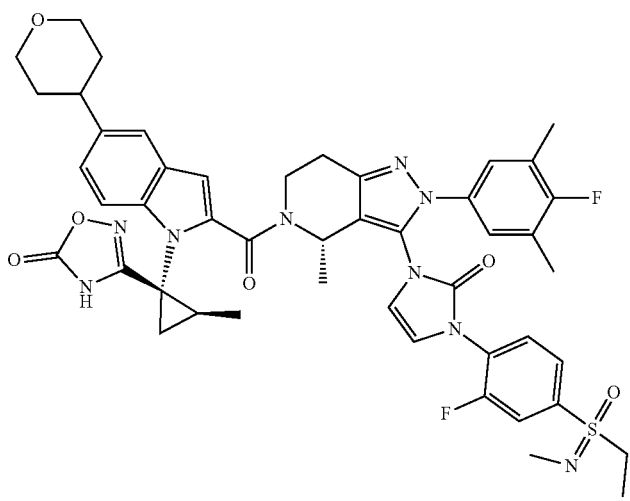 [SMILES: CCS(=O)(=NC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(F)c1]
Enantiomer 1
151
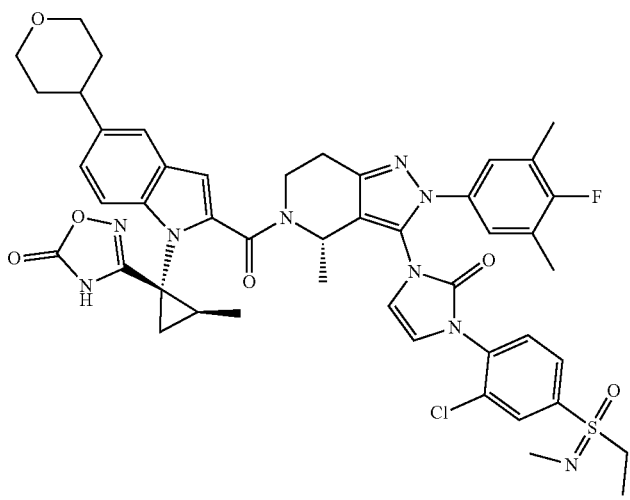 [SMILES: CCS(=O)(=NC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(Cl)c1]
Enantiomer 1

164
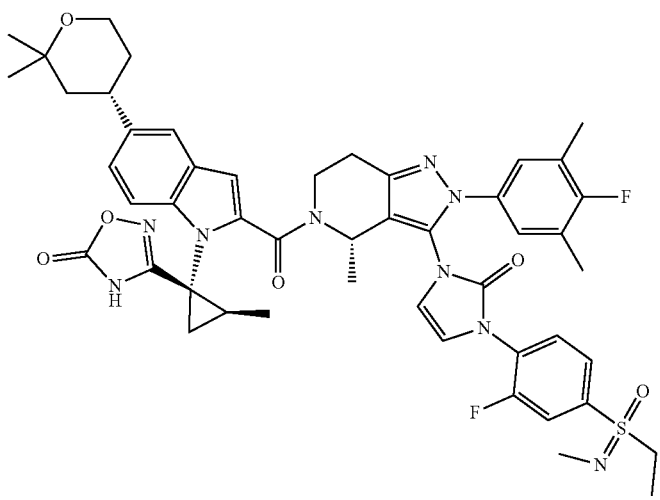 [SMILES: CCS(=O)(=NC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1]
Single unknown enantiomer
168
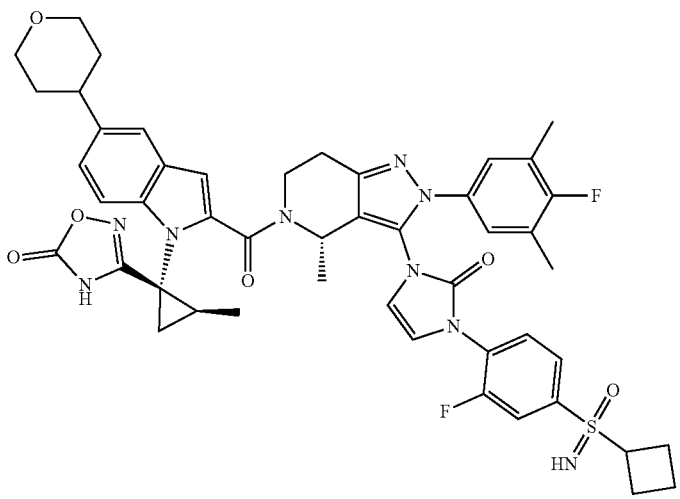 [SMILES: Cc1cc(-n2nc3c(c2-n2ccn(-c4ccc(S(=N)(=O)C5CCC5)cc4F)c2=O)[C@H](C)N(C(=O)c2cc4cc(C5CCOCC5)ccc4n2[C@@]2(c4noc(=O)[nH]4)C[C@@H]2C)CC3)cc(C)c1F]
Enantiomer 1
180
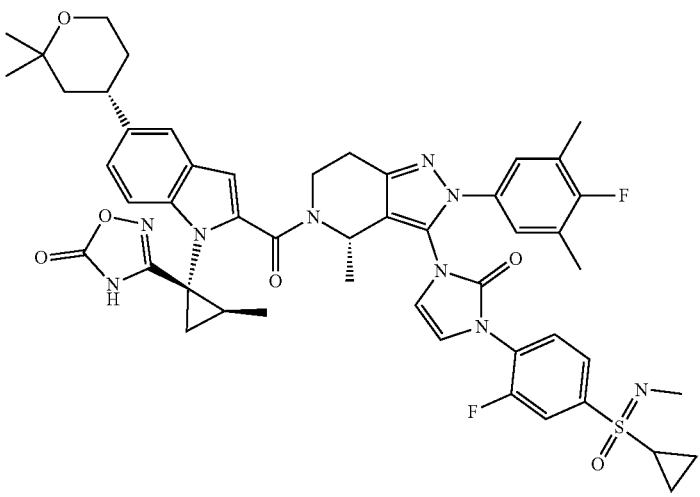 [SMILES: CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1)C1CC1]
Single unknown enantiomer

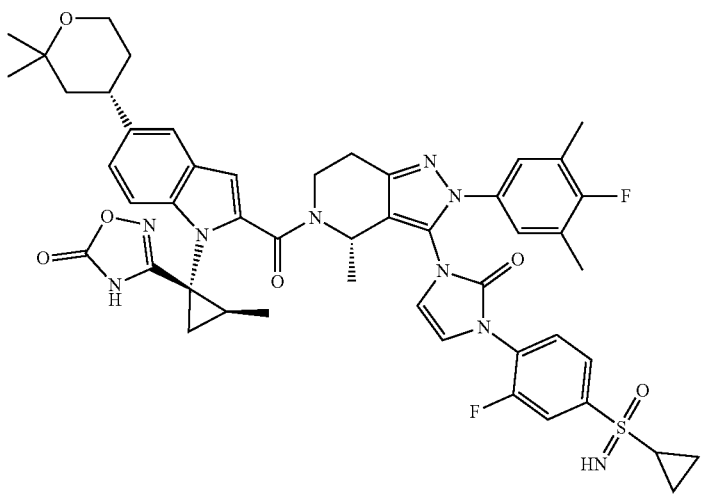 [SMILES: Cc1cc(-n2nc3c(c2-n2ccn(-c4ccc(S(=N)(=O)C5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
181
Single unknown enantiomer
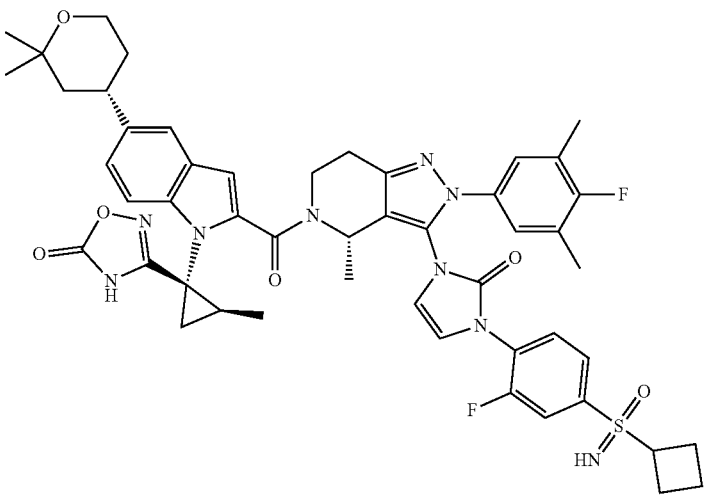
183
Single unknown enantiomer
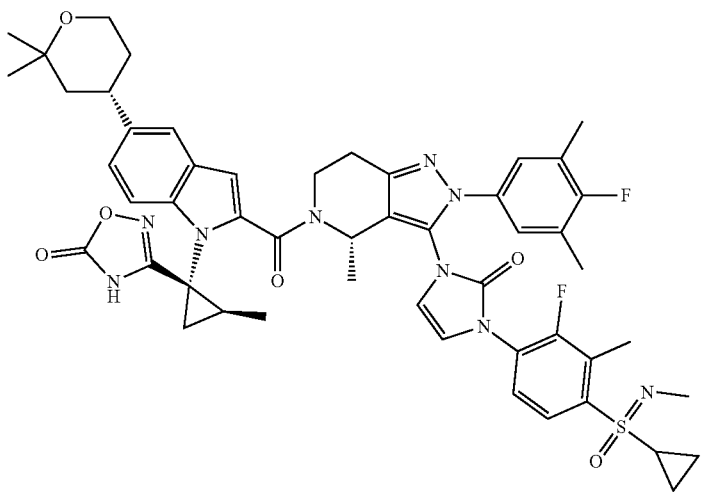 [SMILES: CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1Cl)C1CC1]
195
Enantiomer 1

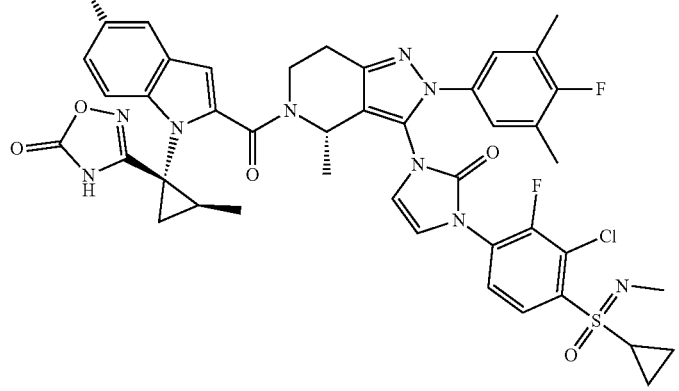
Enantiomer 1
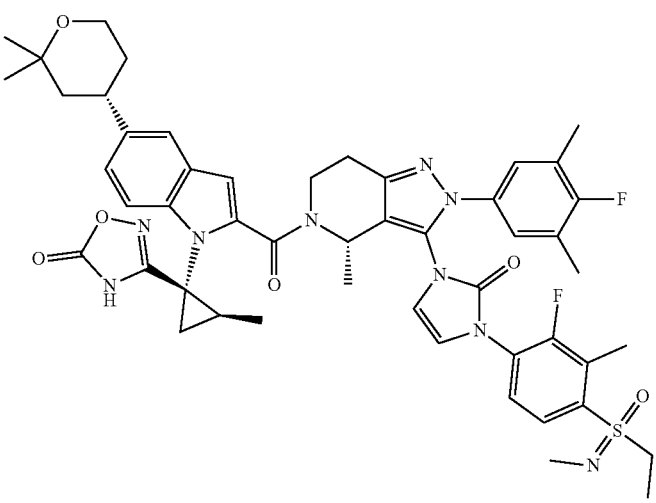
Single unknown enantiomer
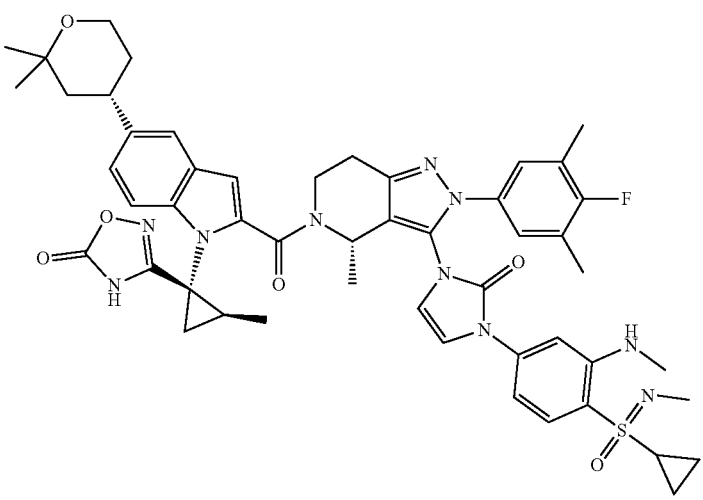
Single unknown enantiomer 221 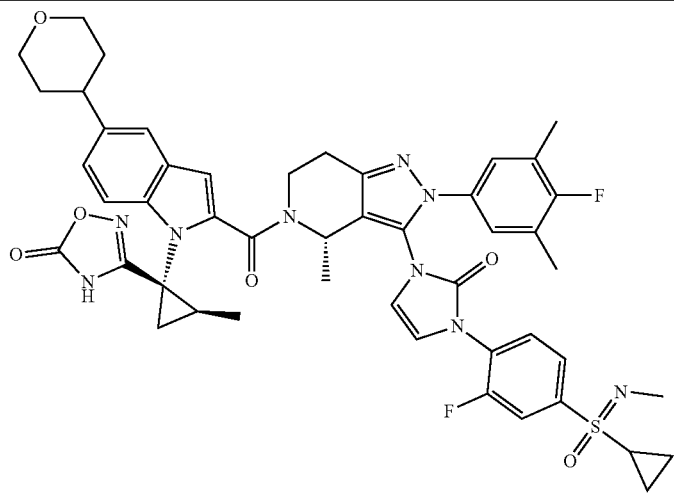
Enantiomer 1
and
238 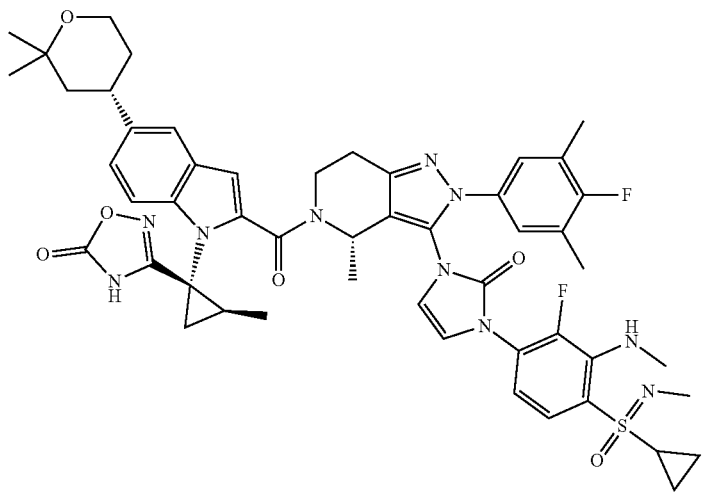
Single unknown enantiomer
or a pharmaceutically acceptable salt, stereoisomer, or mixture of stereoisomers thereof.

2. A compound selected from:
164
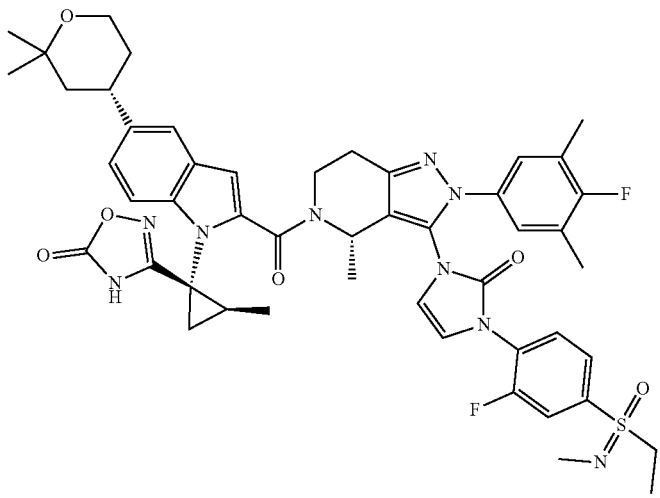 [SMILES: CCS(=O)(=NC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1]
Single unknown enantiomer
180
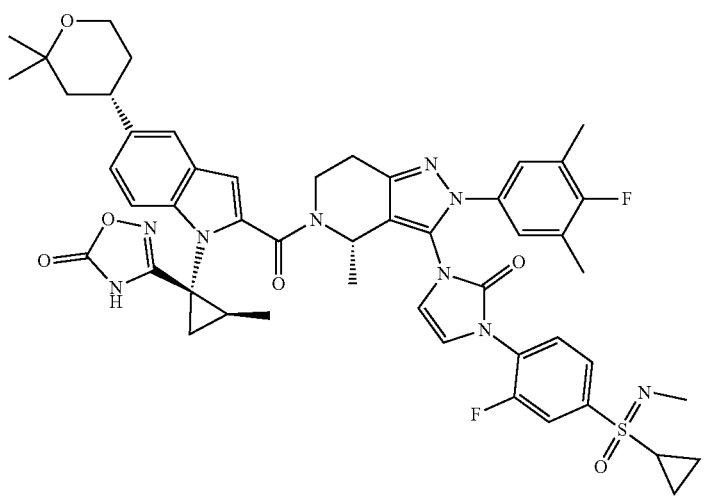 [SMILES: CN=S(=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1)C1CC1]
Single unknown enantiomer
181
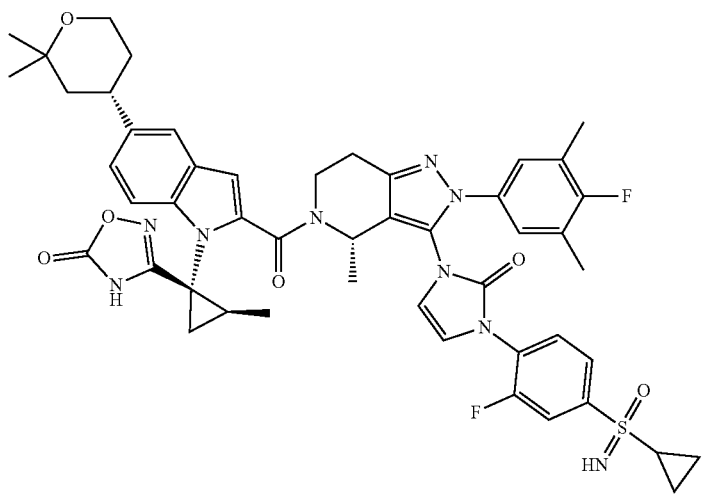 [SMILES: Cc1cc(-n2nc3c(c2-n2ccn(-c4ccc(S(=N)(=O)C5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
Single unknown enantiomer 195
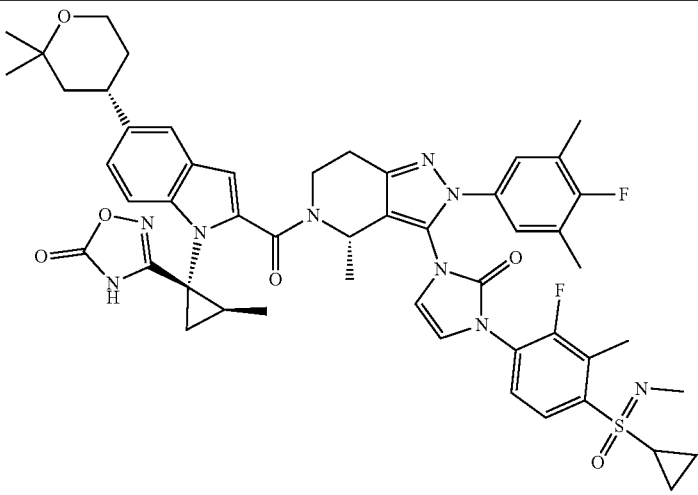
Enantiomer 1
and
238
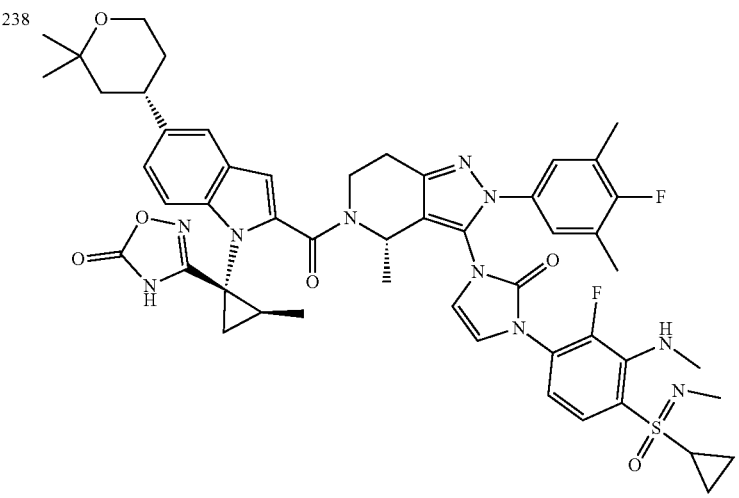
Single unknown enantiomer
or a pharmaceutically acceptable salt thereof.

3. A compound selected from:
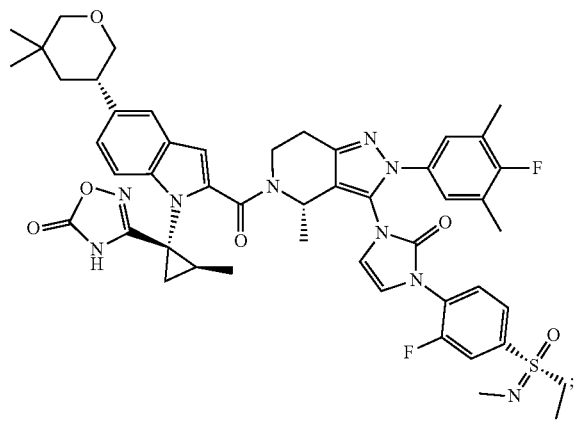
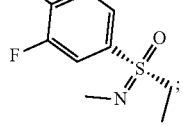
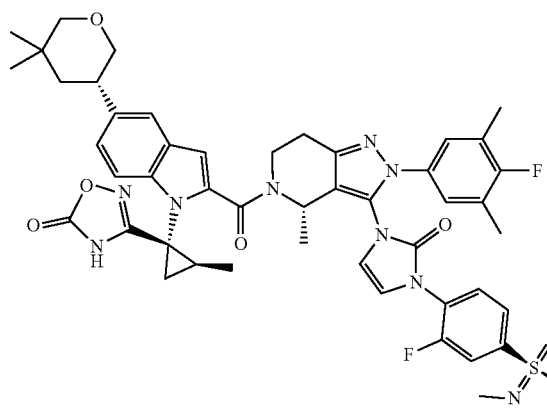
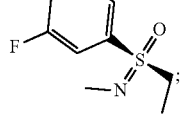
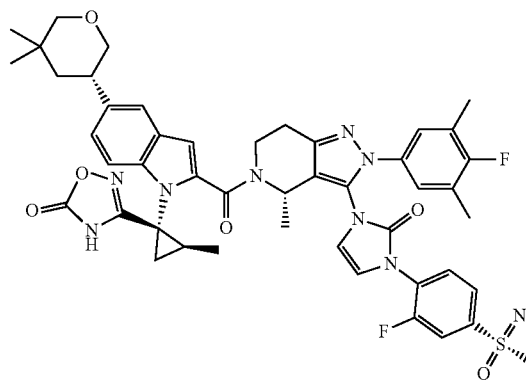
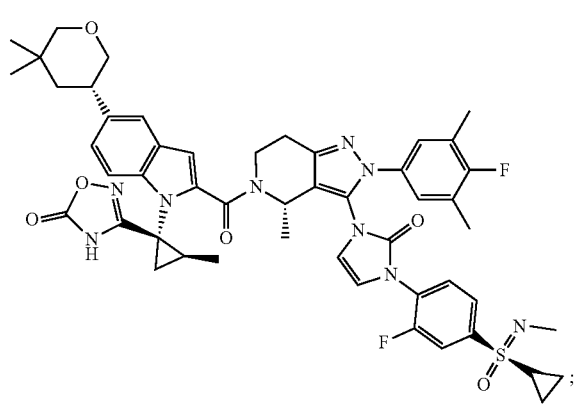
-continued
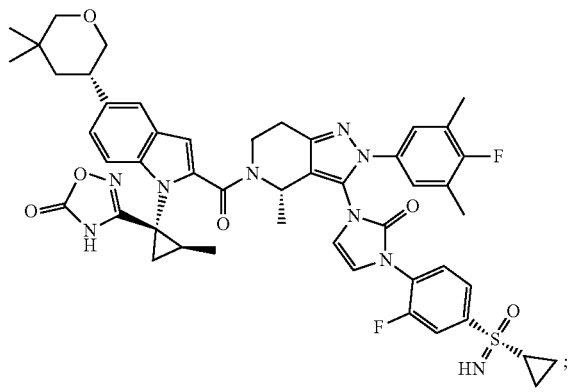
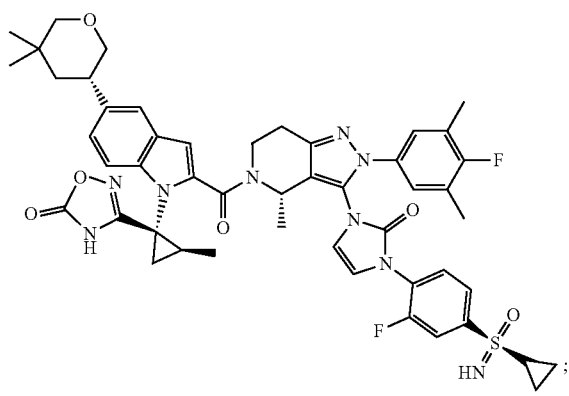
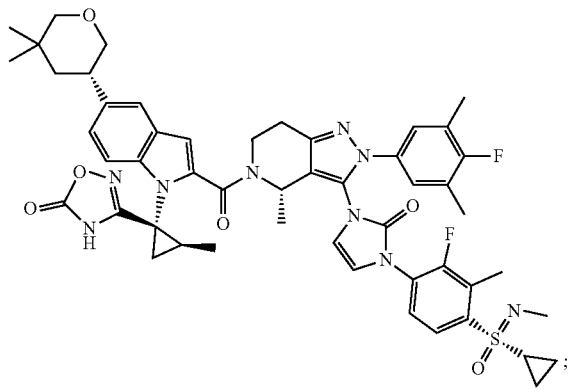
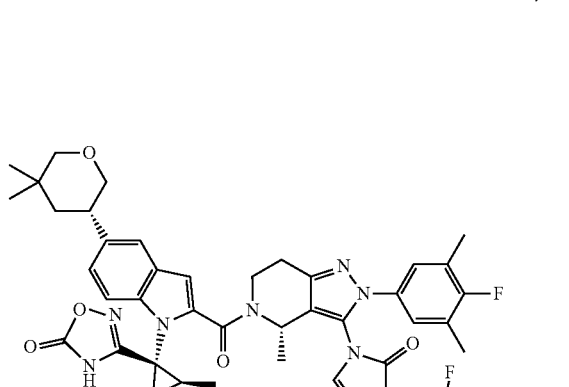

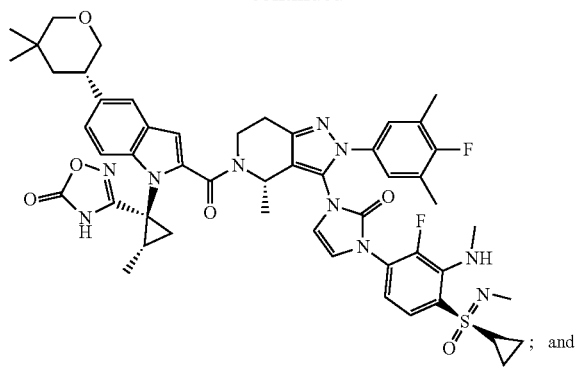
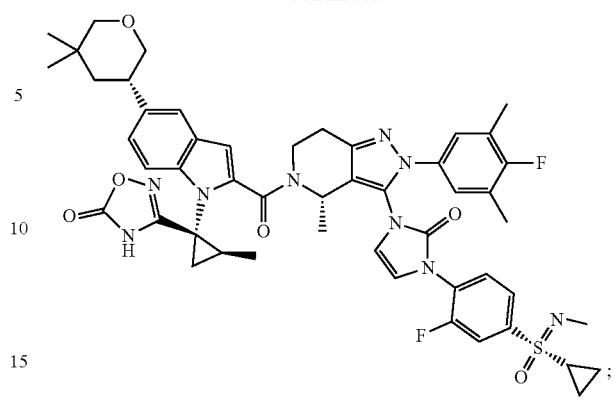
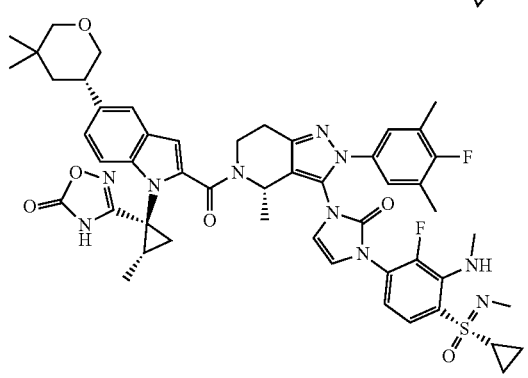
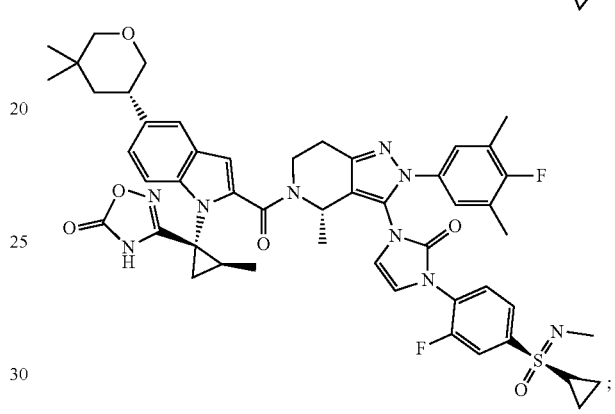
or a pharmaceutically acceptable salt thereof.
4. A compound selected from:
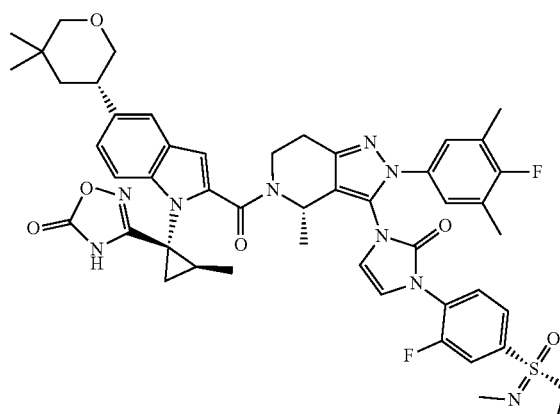
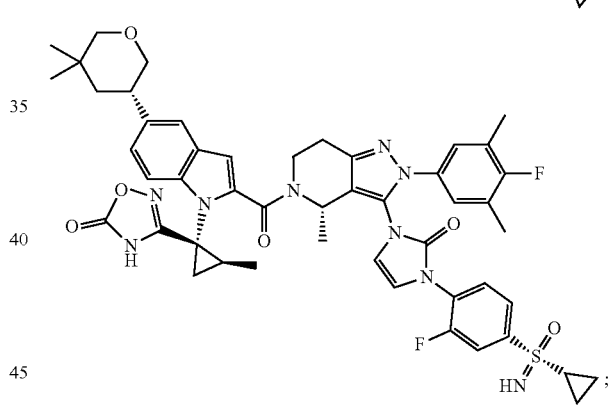
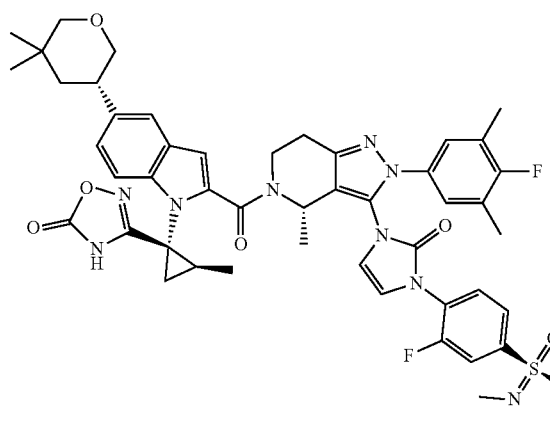
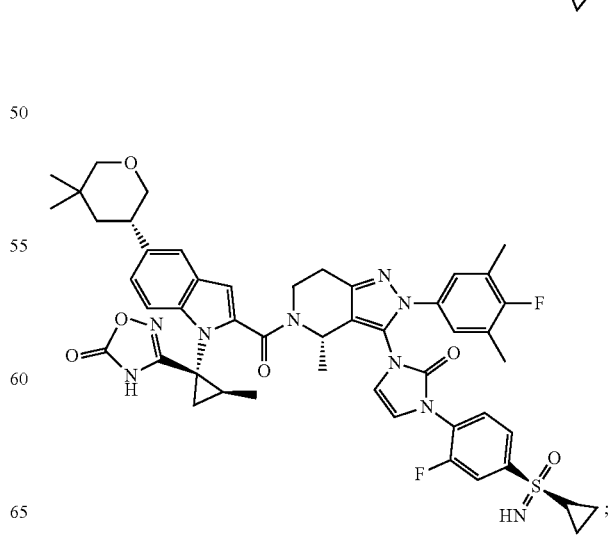

-continued

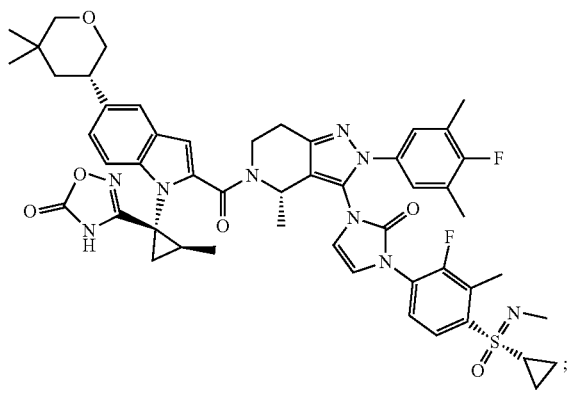

;

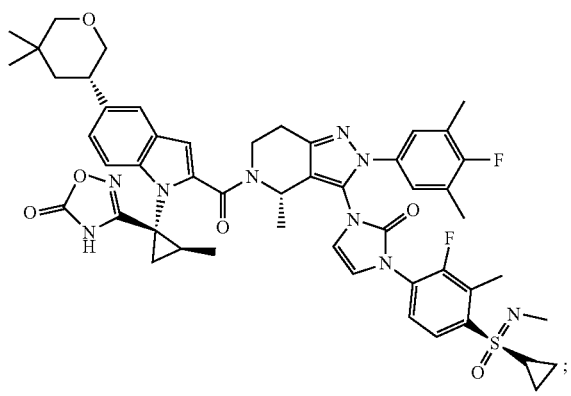

;

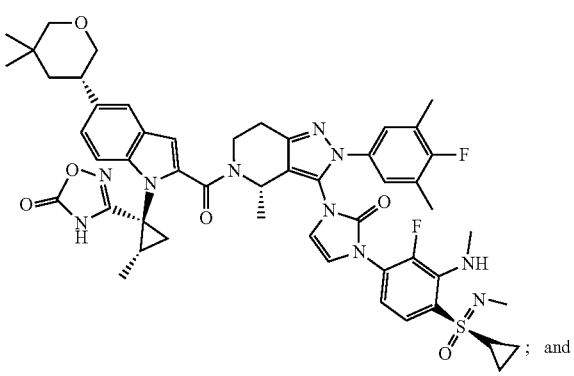

; and

5. A pharmaceutical composition comprising a compound of claim 1, or a pharmaceutically acceptable salt, stereoisomer, or mixture of stereoisomers thereof, and a pharmaceutically acceptable excipient.

6. A pharmaceutical composition comprising a compound of claim 2, or a pharmaceutically acceptable salt thereof, and a pharmaceutically acceptable excipient.

7. A pharmaceutical composition comprising a compound of claim 3, or a pharmaceutically acceptable salt thereof, and a pharmaceutically acceptable excipient.

8. A pharmaceutical composition comprising a compound of claim 7, and a pharmaceutically acceptable excipient.

9. A compound which is:

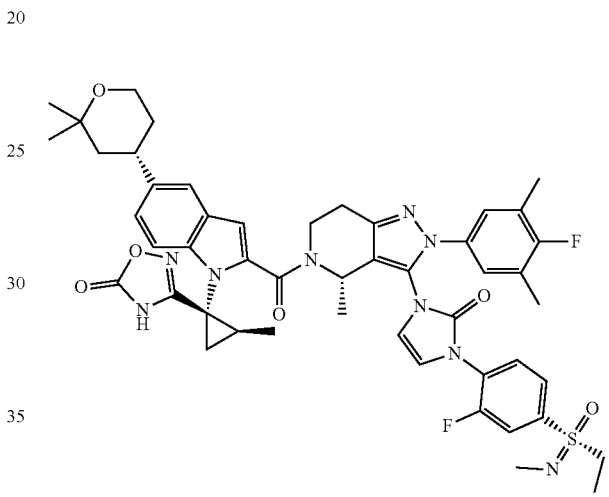

or a pharmaceutically acceptable salt thereof.

10. The compound of claim 9, wherein the compound is:

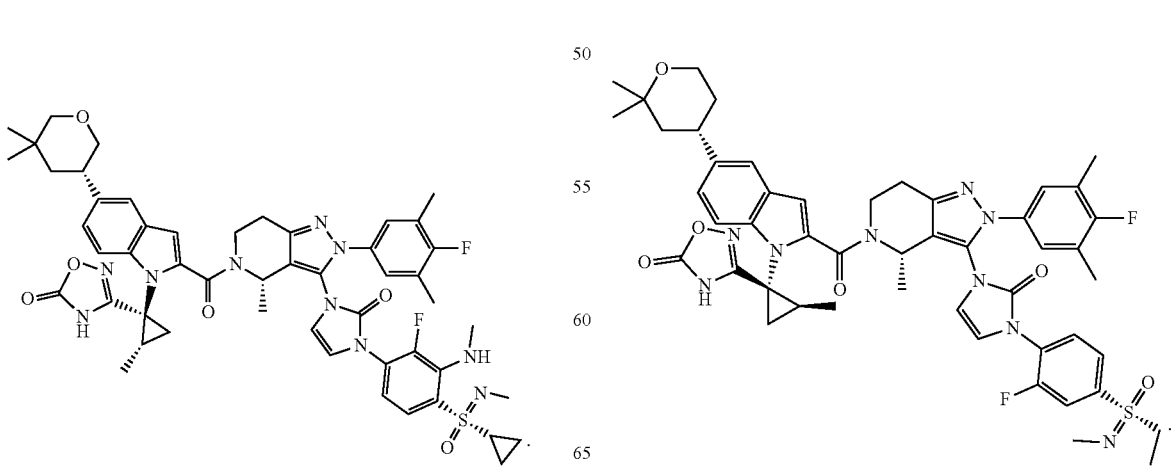

11. A compound which is:
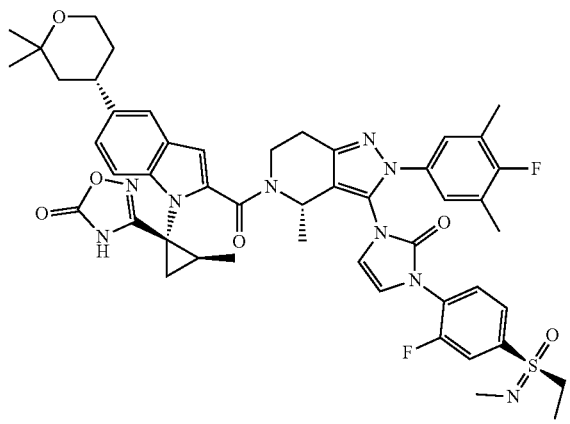 [SMILES: CC[S@@](=O)(=NC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1]
or a pharmaceutically acceptable salt thereof.
12. The compound of claim 11, wherein the compound is:
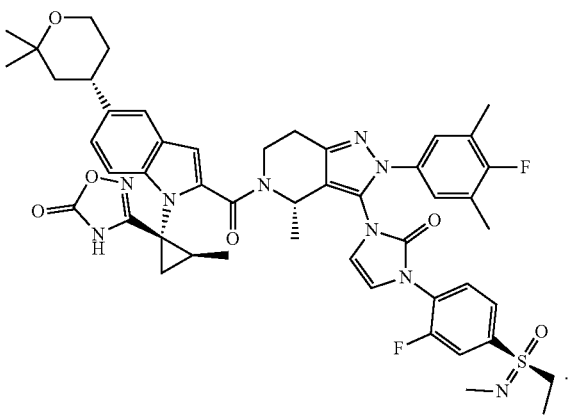 [SMILES: CC[S@@](=O)(=NC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1]
13. A compound which is:
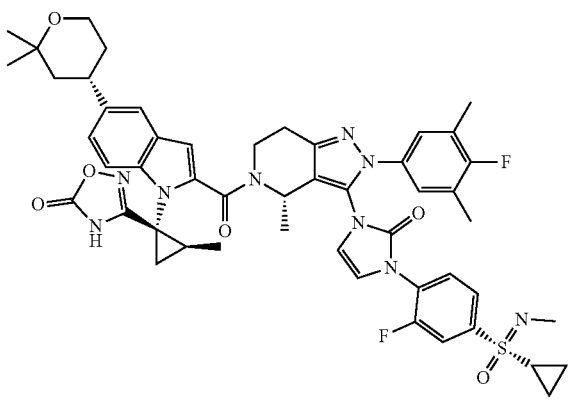 [SMILES: CN=[S@@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1)C1CC1]
or a pharmaceutically acceptable salt thereof.
14. The compound of claim 13, wherein the compound is:
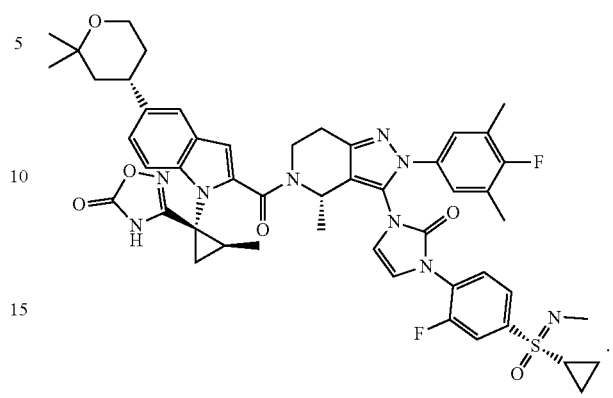
15. A compound which is:
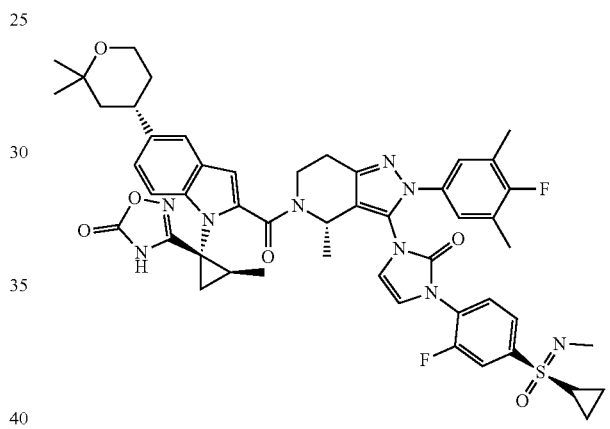
or a pharmaceutically acceptable salt thereof.
16. The compound of claim 15, wherein the compound is:
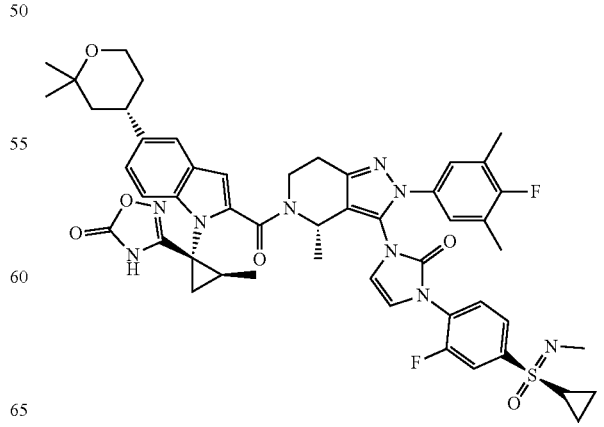

17. A compound which is:
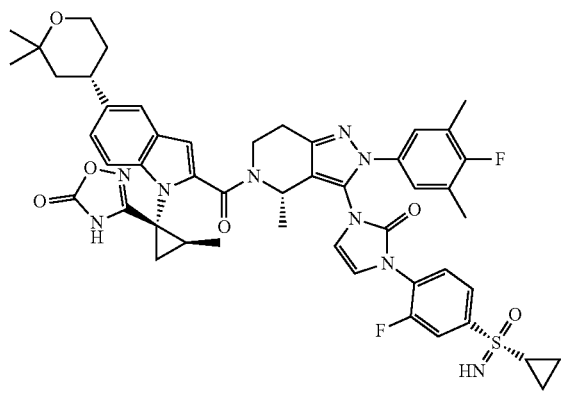 [SMILES: Cc1cc(-n2nc3c(c2-n2ccn(-c4ccc([S@](=N)(=O)C5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
or a pharmaceutically acceptable salt thereof.
18. The compound of claim 17, wherein the compound is:
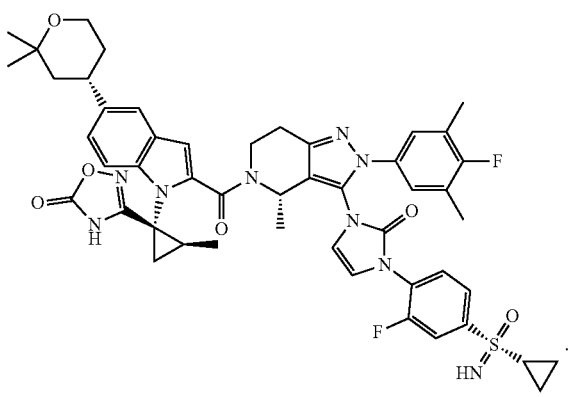 [SMILES: Cc1cc(-n2nc3c(c2-n2ccn(-c4ccc([S@](=N)(=O)C5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
19. A compound which is:
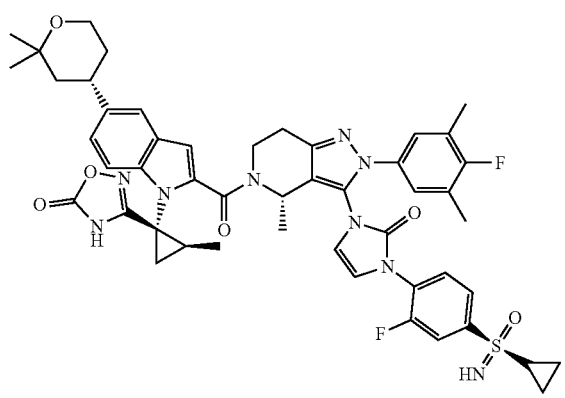 [SMILES: Cc1cc(-n2nc3c(c2-n2ccn(-c4ccc([S@@](=N)(=O)C5CC5)cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]
or a pharmaceutically acceptable salt thereof.
20. The compound of claim 19, wherein the compound is:
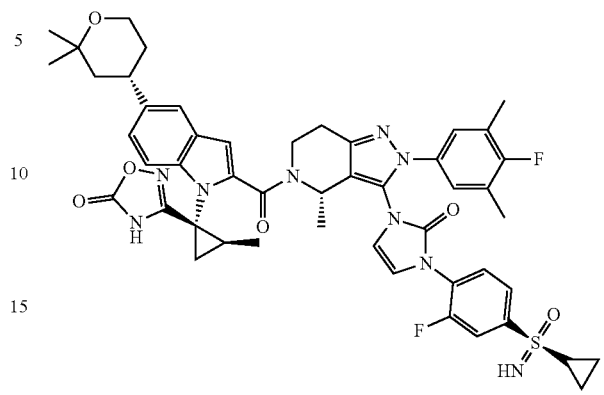
21. A compound which is:
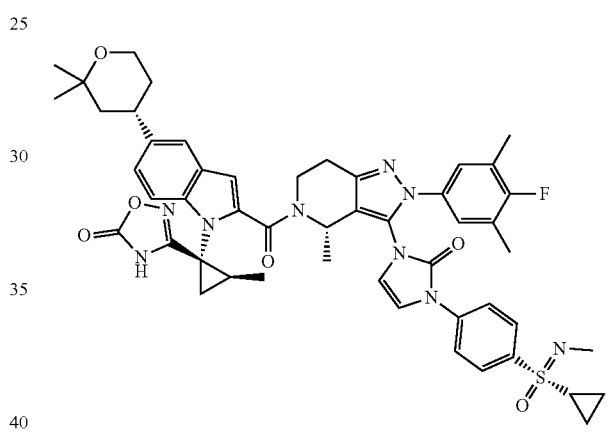
or a pharmaceutically acceptable salt thereof.
22. The compound of claim 21, wherein the compound is:
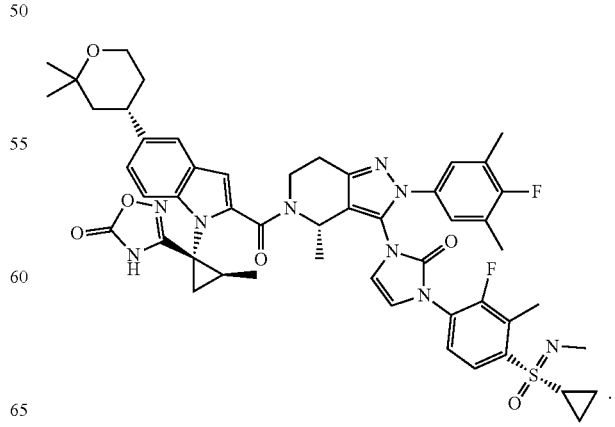

23. A compound which is:
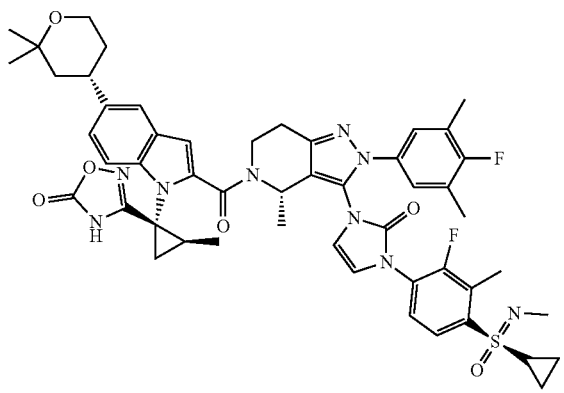 [SMILES: CN=[S@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1C)C1CC1]
or a pharmaceutically acceptable salt thereof.
24. The compound of claim 23, wherein the compound is:
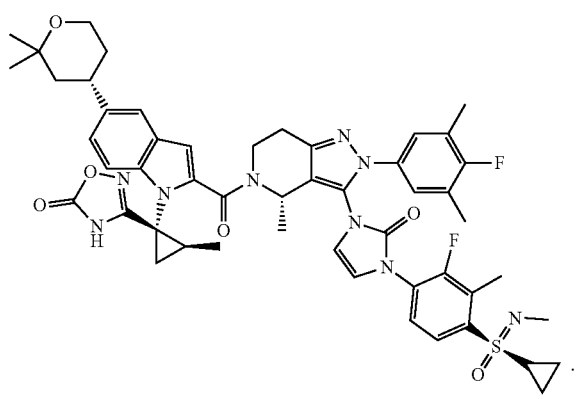 [SMILES: CN=[S@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1C)C1CC1]
25. A compound which is:
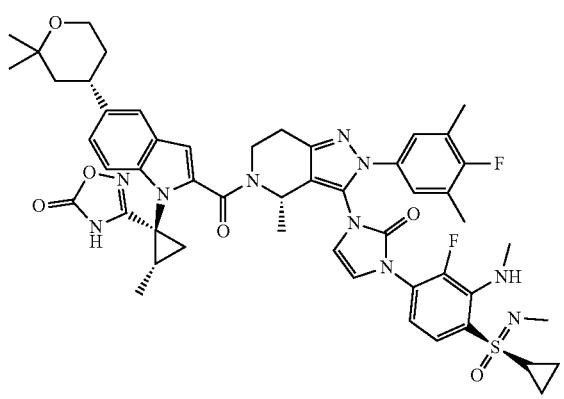 [SMILES: CN=[S@](=O)(c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)c(F)c1NC)C1CC1]
or a pharmaceutically acceptable salt thereof.
26. The compound of claim 25, wherein the compound is:
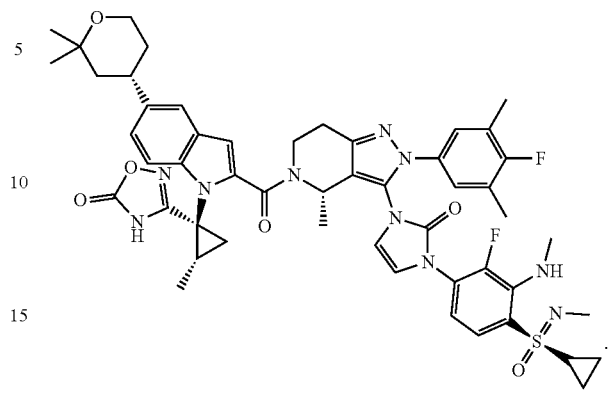
27. A compound which is:
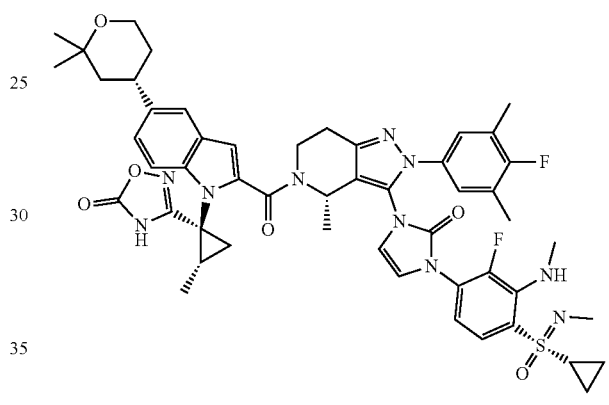
or a pharmaceutically acceptable salt thereof.
28. The compound of claim 27, wherein the compound is:
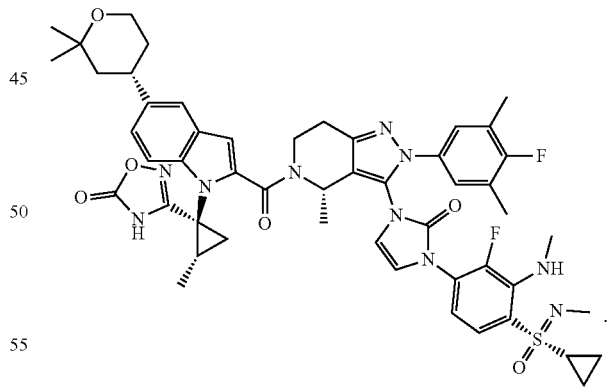
\* \* \* \* \*